(12) United States Patent
Lombana et al.

(10) Patent No.: US 11,555,076 B2
(45) Date of Patent: Jan. 17, 2023

(54) ANTI-MIC ANTIBODIES AND METHODS OF USE

(71) Applicant: Genentech, Inc., South San Francisco, CA (US)

(72) Inventors: Twyla Noelle Lombana, South San Francisco, CA (US); Christoph Spiess, South San Francisco, CA (US); Jeong Kim, San Francisco, CA (US); Evangeline Toy, South San Francisco, CA (US); Jill Schartner, South San Francisco, CA (US); Zhengmao Ye, South San Francisco, CA (US); Jack Bevers, III, San Mateo, CA (US); Ryan Cook, South San Francisco, CA (US); Marissa Matsumoto, South San Francisco, CA (US); Amy Berkley, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 535 days.

(21) Appl. No.: 16/345,619

(22) PCT Filed: Oct. 27, 2017

(86) PCT No.: PCT/US2017/058880
§ 371 (c)(1),
(2) Date: Apr. 26, 2019

(87) PCT Pub. No.: WO2018/081648
PCT Pub. Date: May 3, 2018

(65) Prior Publication Data
US 2020/0055939 A1 Feb. 20, 2020

Related U.S. Application Data

(60) Provisional application No. 62/414,670, filed on Oct. 29, 2016.

(51) Int. Cl.
| | | |
|---|---|---|
| *C07K 16/28* | (2006.01) | |
| *A61K 47/68* | (2017.01) | |
| *A61P 35/00* | (2006.01) | |
| *A61K 39/00* | (2006.01) | |

(52) U.S. Cl.
CPC ...... *C07K 16/2833* (2013.01); *A61K 47/6849* (2017.08); *A61P 35/00* (2018.01); *A61K 2039/505* (2013.01); *C07K 2317/24* (2013.01); *C07K 2317/34* (2013.01); *C07K 2317/41* (2013.01); *C07K 2317/55* (2013.01); *C07K 2317/56* (2013.01); *C07K 2317/567* (2013.01); *C07K 2317/76* (2013.01); *C07K 2317/92* (2013.01); *C07K 2317/94* (2013.01)

(58) Field of Classification Search
CPC ............ C07K 16/2833; C07K 2317/24; C07K 2317/34; C07K 2317/41; C07K 2317/55; C07K 2317/56; C07K 2317/567; C07K 2317/76; C07K 2317/92; C07K 2317/94; C07K 16/08; A61K 47/6849; A61K 2039/505; A61P 35/00; A61P 35/02
See application file for complete search history.

(56) References Cited

U.S. PATENT DOCUMENTS

2014/0004112 A1* 1/2014 Wucherpfennig ...... A61P 43/00
424/133.1

FOREIGN PATENT DOCUMENTS

| JP | 2012530487 A | 12/2012 |
|---|---|---|
| WO | 2010146550 A1 | 12/2010 |
| WO | WO2013117647 A1 | 8/2013 |
| WO | WO2015085210 A1 | 6/2015 |

OTHER PUBLICATIONS

Dranoff et al. (PNAS, 103(24): 9190-9195, 2006).*
Caragea, C. et al. (Nov. 9, 2007). "Glycosylation Site Prediction Using Ensembles of Support Vector Machine Classifiers," BMC Bioinformatics 8(1):438:1-13.
Eggink, D. et al. (Jan. 2014, e-pub. Oct. 23, 2013). "Guiding the Immune Response against Influenza Virus Hemagglutin Toward the Conserved Stalk Domain by Hyperglycosylation of the Globular Head Domain," J. Virol. 88(1):699-704.
Fraczkiewicz, R. et al. (1998). "Exact and Efficient Analytical Calculation of the Accessible Surface Areas and their Gradients for Macromolecules," J. Comp. Chem. 19(3):319-333.
Greenfield, N.J. et al. (2006) "Using Circular Dichroism Collected as a Function of Temperature to Determine the Thermodynamics of Protein Unfolding and Binding Interactions," Nat. Protoc. 1(6):2876-2890.
International Preliminary Report on Patentability dated Apr. 30, 2019, for PCT Application No. PCT/US2017/058880, filed on Oct. 27, 2017, 13 pages.
International Search Report dated Dec. 11, 2018, for PCT Application No. PCT/US2017/058880, filed on Oct. 27, 2017, 9 pages.
Invitation to Pay Additional Fees dated Oct. 30, 2018, for PCT Application No. PCT/US2017/058880, filed on Oct. 27, 2017, 13 pages.
Lam, P.V.N. et al. (2013, e-pub. Feb. 28, 2013). "Structure Based Comparative Analysis and Prediction of N-Linked Glycosylation Sites in Evolutionarily Distant Eukaryotes," Genomic Proteomics Bioinformatics 11(2):96-104.
Li, J. et al. (Feb. 21, 2017). "Mapping the Energetic Epitope of an Antibody/Interleukin-23 Interaction with Hydrogen/Deuterium Exchange, Fast Photochemical Oxidation of Proteins Mass Spectrometry, and Alanine Shave Mutagenesis," Anal. Chem. 89(4):2250-2258, 25 pages.
Makhatadze, G.I. (1998). "Characterization of Recombinant Proteins," Chapter 7 in Measuring Protein Thermostability by Differential Scanning Calorimetery, John Wiley & Sons, Inc., pp. 7.9.1-7.9.14.

(Continued)

*Primary Examiner* — Nelson B Moseley, II
(74) *Attorney, Agent, or Firm* — Morrison & Foerster LLP

(57) ABSTRACT

The invention provides anti-MIC antibodies and methods of using the same.

32 Claims, 110 Drawing Sheets
Specification includes a Sequence Listing.

(56) References Cited

OTHER PUBLICATIONS

Moremen, K.W. et al. (2012). "Vertebrate Protein Glycosylation: Diversity, Synthesis and Function," Nature Reviews Molecular Cell Biology 13(7):448-462, 32 pages.

Morris, G.E. (1996). "Epitope Mapping Protocols," Methods in Molecular Biology 66:1-12.

Niesen, F.H. et al. (2007, e-pub. Sep. 13, 2007). "The Use of Differential Scanning Fluorimetry to Detect Ligand Interactions that Promote Protein Stability," Nat. Protoc. 2(9):2212-2221.

Rotstein, D.L. et al. (Feb. 2015). "Evaluation of No Evidence of Disease Activity in a 7-year Longitudinal Multiple Sclerosis Cohort." JAMA Neurol. 72:152-158.

Stephens, H. et al. (Jul. 2001). "MICA and MICB Genes: Can the Enigma of their Polymorphism be Resolved?," Trends Immunol. 22(7):378-385.

Waldhauer, I. et al. (Aug. 1, 2008). "Tumor-Associated MICA is Shed by ADAM Proteases," Cancer Research 68(15):6368-6376.

Wang, X. et al. (Sep. 25, 2009). "An Six-Amino Acid Motif in the alpha3 Domain of MICA is the Cancer Therapeutic Target to Inhibit Shedding," BBRC 387(3):476-486, 12 pages.

Wong, A.W. et al. (Aug. 1, 2010). "Enhancement of DNA Uptake in FUT8-deleted CHO Cells for Transient Production of Afucosylated Antibodies," Biotechnol. Bioeng 106(5):751-763.

Written Opinion dated Dec. 11, 2018, for PCT Application No. PCT/US2017/058880, filed on Oct. 27, 2017, 12 pages.

Zhang, Y. et al. (2015). "An Improved Fast Photochemical Oxidation of Proteins (FPOP) Platform for Protein Therapeutics," J. Am. Soc, Mass Spectrom 26:526-529.

Zhang, Y. et al. (May 2017). "Mapping the Binding Interface of VEGF and a Monoclonal Antibody Fab-1 Fragment with Fast Photochemical Oxidation of Proteins (FPOP) and Mass Spectrometry," J. Am. Soc. Mass Spectrom 28(5):850-858.

Karsten, U. et al. (2004, e-pub. Apr. 28, 2004). "Binding Patterns of DTR-Specific Antibodies Reveal a Glycosylation-Conditioned Tumor-Specific Epitope of the Epithelial Mucin (MUC1)," Glycobiology 14(8):681-692.

\* cited by examiner

FIG. 1A: 3C9.10 Hypervariable Regions

CDR sequences according to Kabat definition are underlined

Light chain variable region (SEQ ID NO: 16)

```
Kabat number    1               10                  20                  30                  40
3C9.10          D I Q M T Q T T S S L S A S L G D R V T I S C S A S Q G I S N Y L N W Y Q Q K P D G
```

```
Kabat number    45          50                  60                  70                  80
3C9.10          T V K L L I Y Y T S S L H S G V P S R F S G S G T D Y S L T I S N L E P E D I A
```

```
Kabat number    85              90                  100         107
3C9.10          T Y Y C Q Q Y S K L P P T F G G G T K V E I K
```

Heavy chain variable region (SEQ ID NO: 15)

```
Kabat number    1               10                  20                  30                  40
3C9.10          Q V Q L K E S G P G L V A P S Q S L S I T C T V S G F S L T G S G V N W V R Q P
```

```
Kabat number    45          50              55              60      65              70              75          80
3C9.10          K G L E W L G M I W G D G N T D Y N S A L K S R L S I S K D N S K S Q V F L K M N
```

```
Kabat number    82a 82b 82c         85              90                  100     100a-f          110         113
3C9.10          L Q T D D T A R Y Y C A R G A Y Y G K R W Y F D V W G A G T T V T V S S
```

| Antibody | HVR L1 | HVR L2 | HVR L3 | HVR H1 | HVR H2 | HVR H3 |
|---|---|---|---|---|---|---|
| 3C9.10 | SASQGISNYLN (SEQ ID NO: 4) | YTSSLHS (SEQ ID NO: 5) | QQYSKLPPT (SEQ ID NO: 6) | GSGVN (SEQ ID NO: 1) | MIWGDGNTDYNSALKS (SEQ ID NO: 2) | GAYYGKRWYFDV (SEQ ID NO: 3) |

FIG. 1B: 9C9.5.6 Hypervariable Regions
Light chain variable region (SEQ ID NO: 96)
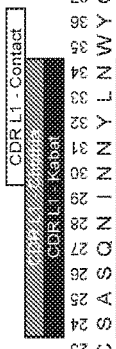
Heavy chain variable region (SEQ ID NO: 95)
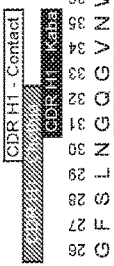
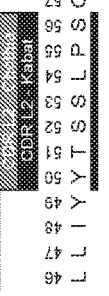
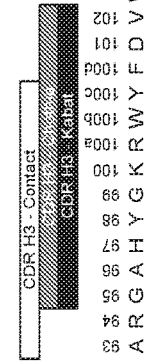
| Antibody | HVR L1 | HVR L2 | HVR L3 | HVR H1 | HVR H2 | HVR H3 |
|---|---|---|---|---|---|---|
| 9C9.5.6 | SASQNINNYLN (SEQ ID NO: 84) | YTSSLPS (SEQ ID NO: 85) | QQYSKLPPT (SEQ ID NO: 86) | GQGVN (SEQ ID NO: 81) | MIWGDGSTDYNSALKS (SEQ ID NO: 82) | GAHYGKRWYFDV (SEQ ID NO: 83) |

FIG. 1C: 1E6.1.3 Hypervariable Regions
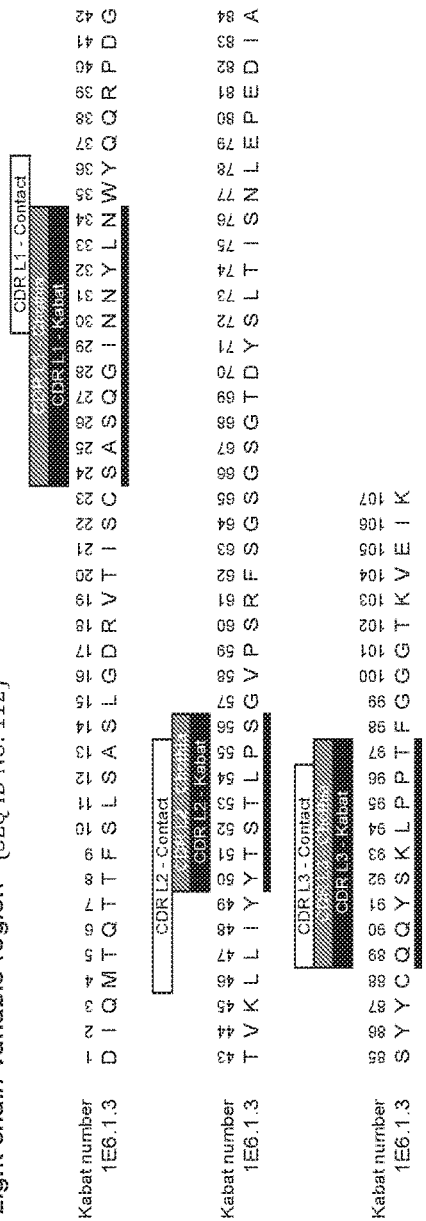
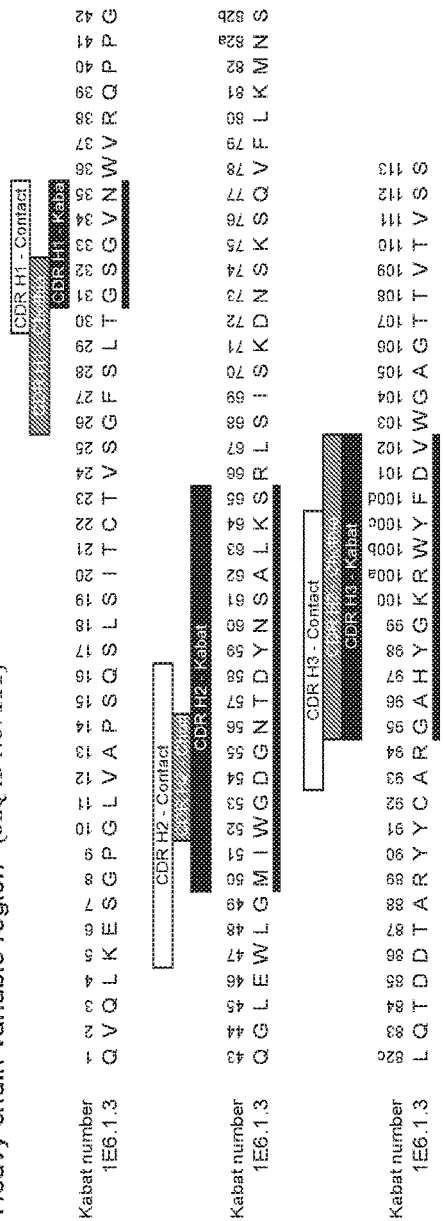
| Antibody | HVR L1 | HVR L2 | HVR L3 | HVR H1 | HVR H2 | HVR H3 |
|---|---|---|---|---|---|---|
| 1E6.1.3 | SASQGINNYLN (SEQ ID NO: 100) | YTSTLPS (SEQ ID NO: 101) | QQYSKLPPT (SEQ ID NO: 102) | GSGVN (SEQ ID NO: 97) | MIWGDGNTDYNSALKS (SEQ ID NO: 98) | GAHYGKRWYFDV (SEQ ID NO: 99) |

FIG. 1D: 7A3.1.9 Hypervariable Regions

Light chain variable region (SEQ ID NO: 128)

```
Kabat number  1  2  3  4  5  6  7  8  9 10 11 12 13 14 15 16 17 18 19 20 21 22 23 24 25 26 27 28 29 30 31 32 33 34 35 36 37 38 39 40 41 42
7A3.1.9       D  I  Q  M  T  Q  T  T  S  S  L  S  A  S  L  G  D  R  V  T  I  S  C  S  A  S  Q  G  I  N  N  Y  L  N  W  Y  Q  Q  K  P  D  G Kabat number 43 44 45 46 47 48 49 50 51 52 53 54 55 56 57 58 59 60 61 62 63 64 65 66 67 68 69 70 71 72 73 74 75 76 77 78 79 80 81 82 83 84
7A3.1.9       T  V  K  L  L  I  Y  Y  T  S  S  L  P  S  G  V  P  S  R  F  S  G  S  G  S  G  T  D  Y  S  L  T  I  S  N  L  E  P  E  D  I  A Kabat number 85 86 87 88 89 90 91 92 93 94 95 96 97 98 99 100 101 102 103 104 105 106 107
7A3.1.9       T  Y  Y  C  Q  Q  Y  S  K  L  P  P  T  F  G  G   G   T   K   V   E   I   K
```

Heavy chain variable region (SEQ ID NO: 127)

```
Kabat number  1  2  3  4  5  6  7  8  9 10 11 12 13 14 15 16 17 18 19 20 21 22 23 24 25 26 27 28 29 30 31 32 33 34 35 36 37 38 39 40 41 42
7A3.1.9       Q  V  Q  L  K  E  S  G  P  G  L  V  A  P  S  Q  S  L  S  I  T  C  T  V  S  G  F  A  L  T  G  S  G  V  N  W  V  R  Q  P  P  G Kabat number 43 44 45 46 47 48 49 50 51 52 53 54 55 56 57 58 59 60 61 62 63 64 65 66 67 68 69 70 71 72 73 74 75 76 77 78 79 80 81 82 82a 82b 82c
7A3.1.9       K  G  L  E  W  L  G  M  I  W  G  D  G  N  T  D  Y  N  S  A  L  K  S  R  L  S  I  S  K  D  N  S  K  S  Q  I  F  L  K  M  N  S   L   Q   T Kabat number 83 84 85 86 87 88 89 90 91 92 93 94 95 96 97 98 99 100 100a 100b 100c 100d 101 102 103 104 105 106 107 108 109 110 111 112 113
7A3.1.9       D  D  T  A  R  Y  Y  C  A  R  G  A  H  Y  G  K  R  W    Y    F    D    V   W   G   A   G   T   T   V   T   V   S   S
```

| Antibody | HVR L1 | HVR L2 | HVR L3 | HVR H1 | HVR H2 | HVR H3 |
|---|---|---|---|---|---|---|
| 7A3.1.9 | SASQGINNYLN (SEQ ID NO: 116) | YTSSLPS (SEQ ID NO: 117) | QQYSKLPPT (SEQ ID NO: 118) | GSGVN (SEQ ID NO: 113) | MIWGDGNTDYNSALKS (SEQ ID NO: 114) | GAHYGKRWYFDV (SEQ ID NO: 115) |

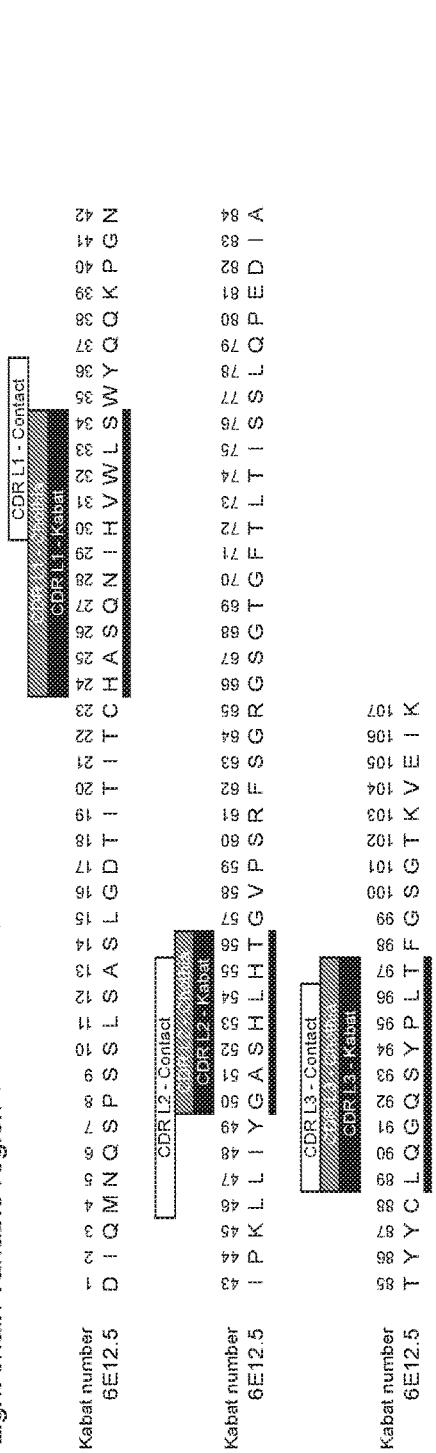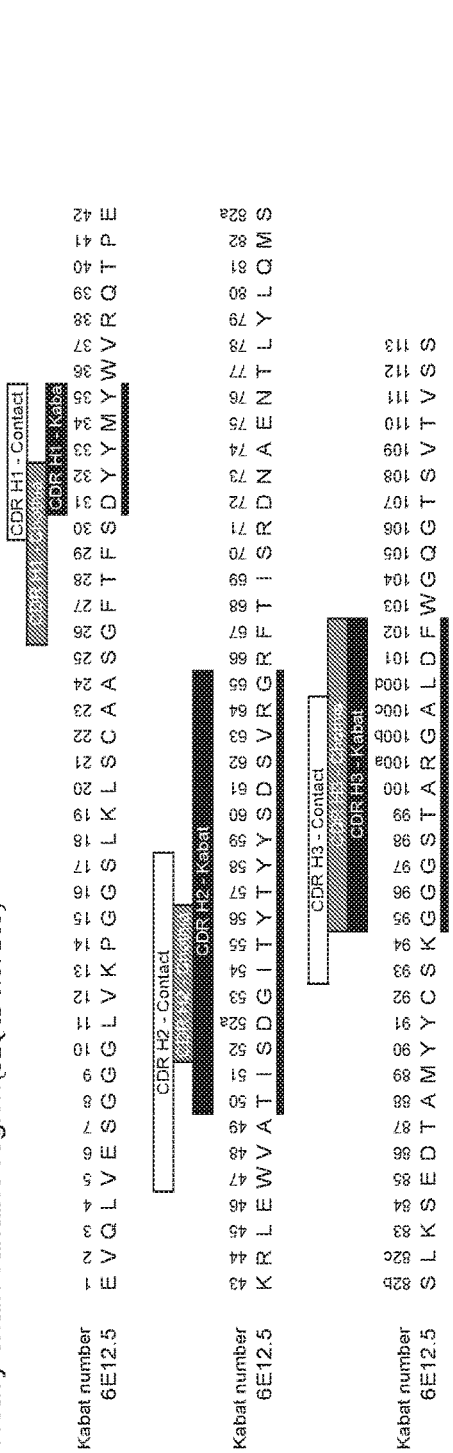
FIG. 1E: 6E12.5 Hypervariable Regions

FIG. 1F: 6E1.1.12 Hypervariable Regions
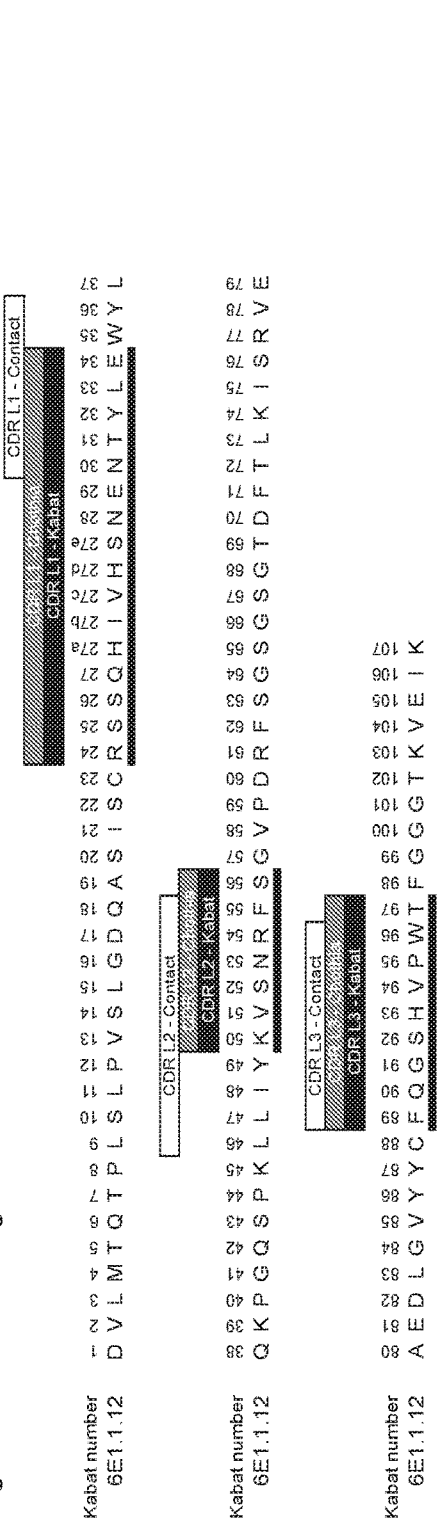
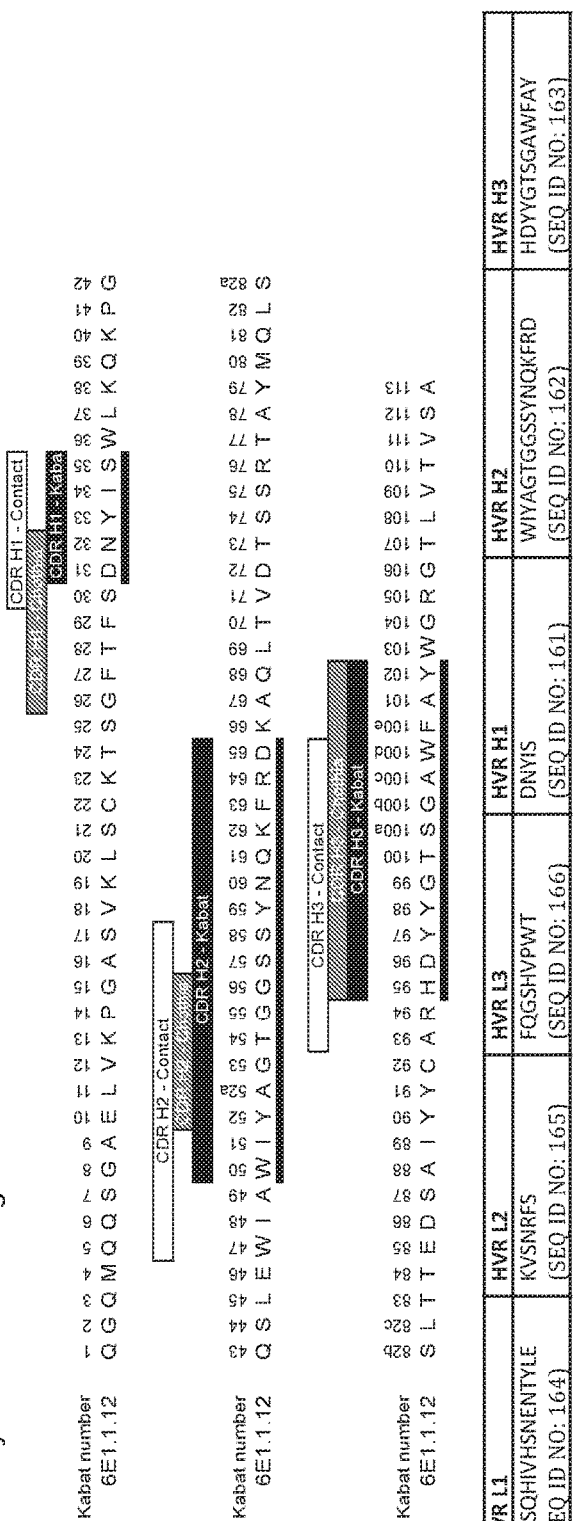

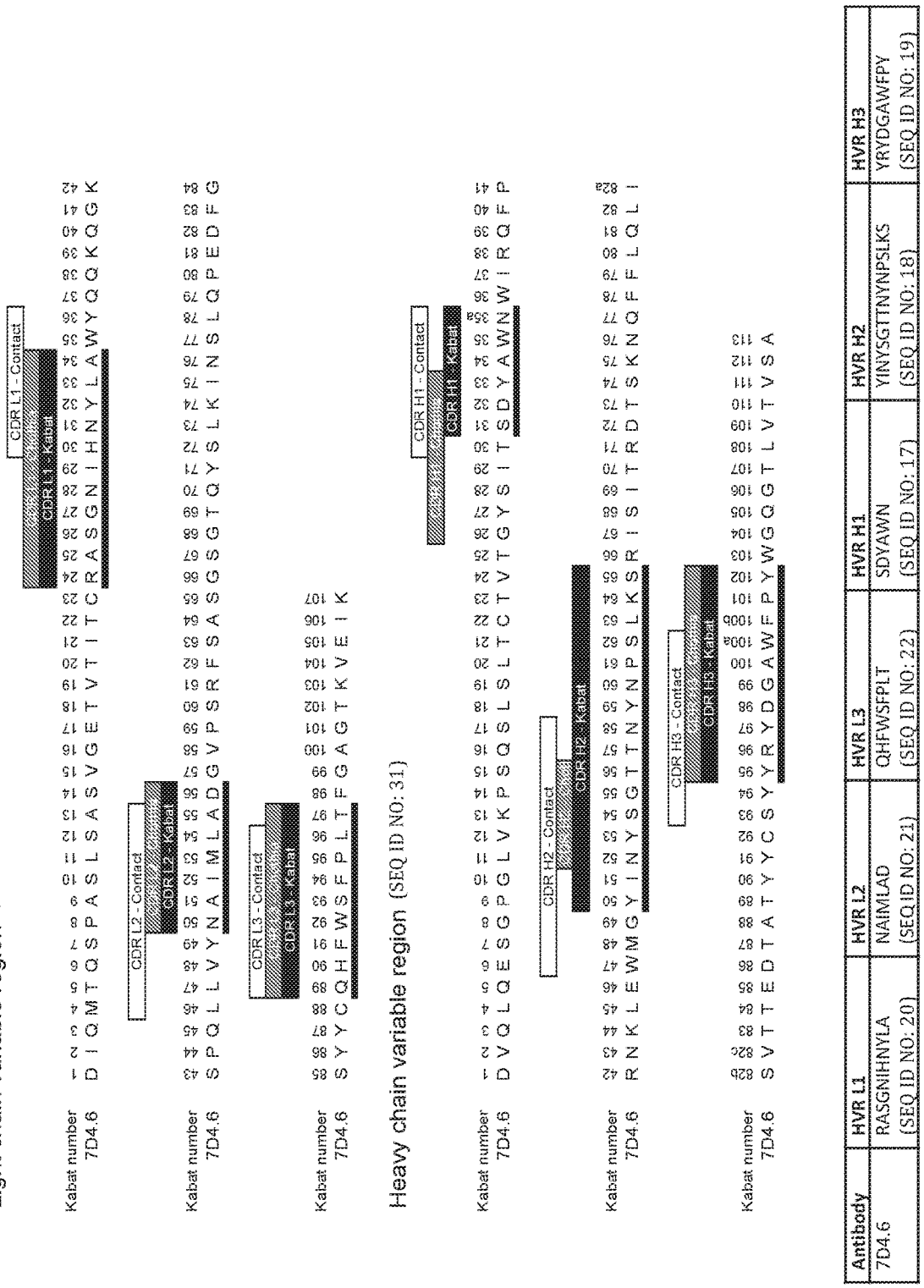

FIG. 1H: 2E5.2.3 Hypervariable Regions

Light chain variable region (SEQ ID NO: 176)

```
Kabat number   1  2  3  4  5  6  7  8  9 10 11 12 13 14 15 16 17 18 19 20 21 22 23 24 25 26 27 27a 27b 27c 27d 27e 28 29 30 31 32 33 34 35 36 37
2E5.2.3        D  V  L  M  T  Q  T  P  L  S  L  P  V  S  L  G  D  Q  A  S  L  S  C  R  S  S  Q  N   I   V   H   I   N  G  N  T  Y  L  E  W  Y  L Kabat number  38 39 40 41 42 43 44 45 46 47 48 49 50 51 52 53 54 55 56 57 58 59 60 61 62 63 64 65 66 67 68 69 70 71 72 73 74 75 76 77 78 79
2E5.2.3        Q  K  P  G  Q  S  P  K  L  L  I  Y  K  V  S  N  R  F  S  G  V  P  D  R  F  S  G  S  G  T  D  F  T  L  K  I  S  R  V  E Kabat number  80 81 82 83 84 85 86 87 88 89 90 91 92 93 94 95 96 97 98 99 100 101 102 103 104 105 106 107
2E5.2.3        A  E  D  L  G  V  Y  Y  C  F  Q  G  S  H  V  P  W  T  F  G  G   G   T   K   V   E   I   K
```

Heavy chain variable region (SEQ ID NO: 175)

```
Kabat number   1  2  3  4  5  6  7  8  9 10 11 12 13 14 15 16 17 18 19 20 21 22 23 24 25 26 27 28 29 30 31 32 33 34 35 36 37 38 39 40 41 42
2E5.2.3        Q  G  Q  M  Q  Q  S  G  A  E  L  V  K  P  G  A  S  V  K  L  S  C  K  T  S  G  F  T  F  S  D  N  Y  I  S  W  L  K  Q  K  P  G Kabat number  43 44 45 46 47 48 49 50 51 52 52a 53 54 55 56 57 58 59 60 61 62 63 64 65 66 67 68 69 70 71 72 73 74 75 76 77 78 79 80 81 82 82a
2E5.2.3        Q  S  L  E  W  I  A  W  I  Y  A   G  T  G  G  T  S  Y  N  Q  K  F  T  A  K  A  Q  L  T  V  D  T  S  S  S  T  A  Y  M  Q  F  S Kabat number  82b 82c 83 84 85 86 87 88 89 90 91 92 93 94 95 96 97 98 99 100 100a 100b 100c 100d 101 102 103 104 105 106 107 108 109 110 111 112 113
2E5.2.3        S   L   T  T  E  D  S  A  I  Y  Y  C  A  R  H  D  Y  Y  G   T    S    G    A    W    F   A   Y   W   G   Q   G   T   L   V   T   V   S   A
```

| Antibody | HVR L1 | HVR L2 | HVR L3 | HVR H1 | HVR H2 | HVR H3 |
|---|---|---|---|---|---|---|
| 2E5.2.3 | RSSQNIVHINGNTYLE (SEQ ID NO: 180) | KVSNRFS (SEQ ID NO: 181) | FQGSHVPWT (SEQ ID NO: 182) | DNYIS (SEQ ID NO: 177) | WIYAGTGGTSYNQKFTA (SEQ ID NO: 178) | HDYYGTSGAWFAY (SEQ ID NO: 179) |

FIG. 1-I: 20G11 Hypervariable Regions

Light chain variable region (SEQ ID NO: 192)

```
Kabat number    1  2  3  4  5  6  7  8  9 10 11 12 13 14 15 16 17 18 19 20 21 22 23 24 25 26 27 27a 28 29 30 31 32 33 34 35 36 37 38 39 40 41
20G11           Q  I  V  L  T  Q  S  P  A  I  M  S  A  S  L  G  E  R  V  T  M  T  C  T  A  T  S  G   V  S  S  S  Y  L  H  W  Y  Q  Q  K  P  G Kabat number   42 43 44 45 46 47 48 49 50 51 52 53 54 55 56 57 58 59 60 61 62 63 64 65 66 67 68 69 70 71 72 73 74 75 76 77 78 79 80 81 82 83
20G11           S  S  P  K  L  W  I  Y  S  S  S  N  L  A  S  G  V  P  A  R  F  S  G  S  G  S  G  T  S  Y  S  L  T  I  G  S  M  E  A  E  D  A Kabat number   84 85 86 87 88 89 90 91 92 93 94 95 96 97 98 99 100 101 102 103 104 105 106 107
20G11           A  T  Y  Y  C  H  Q  F  H  R  S  P  L  T  F  G  T   K   V   E   I   K
```

Heavy chain variable region (SEQ ID NO: 191)

```
Kabat number    1  2  3  4  5  6  7  8  9 10 11 12 13 14 15 16 17 18 19 20 21 22 23 24 25 26 27 28 29 30 31 32 33 34 35 36 37 38 39 40 41 42
20G11           D  V  Q  L  V  E  S  G  G  G  L  V  Q  P  G  G  S  R  K  L  S  C  A  A  S  G  F  T  F  S  T  F  G  I  H  W  V  R  Q  A  P  E Kabat number   43 44 45 46 47 48 49 50 51 52 52a 53 54 55 56 57 58 59 60 61 62 63 64 65 66 67 68 69 70 71 72 73 74 75 76 77 78 79 80 81 82 82a
20G11           K  G  L  E  W  V  A  Y  I  S  Y   D  S  R  T  I  Y  Y  A  D  T  V  K  G  R  F  T  I  S  R  D  N  P  K  N  T  L  F  L  Q  M  T Kabat number   82b 82c 83 84 85 86 87 88 89 90 91 92 93 94 95 96 97 98 99 100 100a 100b 100c 100d 101 102 103 104 105 106 107 108 109 110 111 112 113
20G11           S   L   R  S  E  D  T  A  M  Y  Y  C  A  R  W  A  Y  E  G  G   V    N    Y    F    D   N   W   G   Q   G   T   T   L   T   V   S   S
```

| Antibody | HVR L1 | HVR L2 | HVR L3 | HVR H1 | HVR H2 | HVR H3 |
|---|---|---|---|---|---|---|
| 20G11 | TATSGVSSSYLH (SEQ ID NO: 148) | SSSNLAS (SEQ ID NO: 149) | HQFHRSPLT (SEQ ID NO: 150) | TFGIH (SEQ ID NO: 145) | YISYDSRTIYYADTVKG (SEQ ID NO: 146) | WAYEGGVNYFDN (SEQ ID NO: 147) |

FIG. 1-J: 32D2 Hypervariable Regions
Light chain variable region (SEQ ID NO: 64)
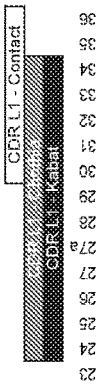
Heavy chain variable region (SEQ ID NO: 63)
| Antibody | HVR L1 | HVR L2 | HVR L3 | HVR H1 | HVR H2 | HVR H3 |
|---|---|---|---|---|---|---|
| 32D2 | TASSISSSYLH | TTSNLAS | HQHHRSPFT | TFGMN | YINSGSNTIYYADTVKG | WEPVTGGFSY |
| | (SEQ ID NO: 52) | (SEQ ID NO: 53) | (SEQ ID NO: 54) | (SEQ ID NO: 49) | (SEQ ID NO: 50) | (SEQ ID NO: 51) |

FIG. 1K: 3E11 Hypervariable Regions

Light chain variable region (SEQ ID NO: 80)

```
Kabat number    1  2  3  4  5  6  7  8  9  10 11 12 13 14 15 16 17 18 19 20 21 22 23 24 25 26 27 27a 27b 27c 27d 27e 28 29 30 31 32 33 34 35 36 37
3E11            D  I  L  M  T  Q  T  P  L  S  L  P  V  S  L  G  D  Q  A  S  I  S  C  R  S  S  Q  S   I   V   Y   T   N  G  N  T  N  L  E  W  Y  L
                                                       CDR L1 - Contact
                                                              CDR L1 - Kabat Kabat number    38 39 40 41 42 43 44 45 46 47 48 49 50 51 52 53 54 55 56 57 58 59 60 61 62 63 64 65 66 67 68 69 70 71 72 73 74 75 76 77 78 79
3E11            Q  K  P  G  Q  S  P  K  L  L  I  Y  K  V  S  N  R  F  S  G  V  P  D  R  F  S  G  S  G  S  G  T  D  F  T  L  K  I  S  R  V  E
                                        CDR L2 - Contact
                                            CDR L2 - Kabat Kabat number    80 81 82 83 84 85 86 87 88 89 90 91 92 93 94 95 96 97 98 99 100 101 102 103 104 105 106 107
3E11            A  E  D  L  G  V  Y  Y  C  F  Q  A  S  Y  V  P  F  T  F  G   G   T   K   V   E   I   K
                                        CDR L3 - Contact
                                            CDR L3 - Kabat
```

Heavy chain variable region (SEQ ID NO: 79)

```
Kabat number    1  2  3  4  5  6  7  8  9  10 11 12 13 14 15 16 17 18 19 20 21 22 23 24 25 26 27 28 29 30 31 32 33 34 35 36 37 38 39 40 41 42
3E11            E  I  Q  L  Q  Q  S  G  P  E  L  V  K  P  G  A  S  V  K  V  S  C  T  A  S  G  Y  A  F  T  K  Y  N  I  Y  W  V  K  Q  S  H  G
                                                                             CDR H1 - Contact
                                                                                   CDR H1 - Kabat Kabat number    43 44 45 46 47 48 49 50 51 52 52a 53 54 55 56 57 58 59 60 61 62 63 64 65 66 67 68 69 70 71 72 73 74 75 76 77 78 79 80 81 82 82a
3E11            K  S  L  E  W  I  G  Y  I  D  P   Y  T  G  G  T  I  S  N  Q  K  F  T  G  R  A  T  L  T  V  D  K  S  S  T  A  Y  L  H  L  T
                                  CDR H2 - Contact
                                      CDR H2 - Kabat Kabat number    82b 82c 83 84 85 86 87 88 89 90 91 92 93 94 95 96 97 98 99 100 100a 101 102 103 104 105 106 107 108 109 110 111 112 113
3E11            S   L   T  S  E  D  S  A  V  Y  Y  C  A  R  P  G  S  Y  W  Y   F    G   V   W   G   A   G   T   T   V   T   V   S   S
                                                     CDR H3 - Contact
                                                         CDR H3 - Kabat
```

| Antibody | HVR L1 | HVR L2 | HVR L3 | HVR H1 | HVR H2 | HVR H3 |
|---|---|---|---|---|---|---|
| 3E11 | RSSQSIVYTNGNTNLE (SEQ ID NO: 68) | KVSNRFS (SEQ ID NO: 69) | FQASYVPFT (SEQ ID NO: 70) | KYNIY (SEQ ID NO: 65) | YIDPYTGGTISNQKFTG (SEQ ID NO: 66) | PGSYWYFGV (SEQ ID NO: 67) |

FIG. 1L: 6F8.7 Hypervariable Regions

Light chain variable region (SEQ ID NO: 48)

```
Kabat number  1  2  3  4  5  6  7  8  9 10 11 12 13 14 15 16 17 18 19 20 21 22 23 24 25 26 27 28 29 30 31 32 33 34 35 36 37 38 39 40 41 42
6F8.7         D  I  Q  M  T  Q  S  P  A  S  L  S  A  S  V  G  E  T  V  T  I  T  C  R  A  S  G  N  I  H  N  Y  L  A  W  Y  Q  Q  K  Q  G  K
                                                                         |_____CDR L1 - Contact_____|
                                                                            |_____CDR L1 - Kabat_____|

Kabat number 43 44 45 46 47 48 49 50 51 52 53 54 55 56 57 58 59 60 61 62 63 64 65 66 67 68 69 70 71 72 73 74 75 76 77 78 79 80 81 82 83 84
6F8.7         S  P  Q  L  L  V  Y  D  A  I  T  L  A  D  G  V  P  S  R  F  S  G  S  G  S  G  T  Q  Y  S  L  K  I  N  S  L  Q  P  E  D  F  G
                       |___CDR L2 - Contact___|
                          |___CDR L2 - Kabat___|

Kabat number 85 86 87 88 89 90 91 92 93 94 95 96 97 98 99 100 101 102 103 104 105 106 107
6F8.7         S  V  T  T  E  D  T  A  T  Y  Y  C  Q  H  F  W   S   F   P   L   T   F   G   A   G   T   K   V   E   I   K
                                   |_____CDR L3 - Contact_____|
                                      |_____CDR L3 - Kabat_____|
```

Heavy chain variable region (SEQ ID NO: 47)

```
Kabat number  1  2  3  4  5  6  7  8  9 10 11 12 13 14 15 16 17 18 19 20 21 22 23 24 25 26 27 28 29 30 31 32 33 34 35 35a 36 37 38 39 40 41
6F8.7         D  V  Q  L  Q  G  S  G  P  G  L  V  K  P  S  Q  S  L  T  C  S  V  T  G  Y  S  I  T  N  D  Y  Y  W  N    W  I  R  Q  F  P
                                                                                     |___CDR H1 - Contact___|
                                                                                          |__CDR H1 - Kabat__|

Kabat number 42 43 44 45 46 47 48 49 50 51 52 52a 53 54 55 56 57 58 59 60 61 62 63 64 65 66 67 68 69 70 71 72 73 74 75 76 77 78 79 80 81 82 82a 82b 82c
6F8.7         G  N  K  L  E  W  M  G  F  I  S   F   G  G  S  N  N  Y  N  P  S  L  K  N  R  I  S  I  T  R  D  T  S  K  N  Q  F  F  L  K  L  S
                                      |____CDR H2 - Contact____|
                                         |_____CDR H2 - Kabat_____|

Kabat number 82c 83 84 85 86 87 88 89 90 91 92 93 94 95 96 97 98 99 100 100a 100b 101 102 103 104 105 106 107 108 109 110 111 112 113
6F8.7         S   V  T  T  E  D  T  A  T  Y  Y  C  A  R  Y  D  G  R  G   A    W    F   A   Y   W   A   Q   G   T   L   V   T   V   S   A
                                                      |_____CDR H3 - Contact_____|
                                                          |_____CDR H3 - Kabat_____|
```

| Antibody | HVR L1 | HVR L2 | HVR L3 | HVR H1 | HVR H2 | HVR H3 |
|---|---|---|---|---|---|---|
| 6F8.7 | RASGNIHNYLA (SEQ ID NO: 36) | DAITLAD (SEQ ID NO: 37) | QHFWSFPLT (SEQ ID NO: 38) | NDYYWN (SEQ ID NO: 33) | FISFGGSNNYNPSLKN (SEQ ID NO: 34) | YDGRGAWFAY (SEQ ID NO: 35) |

FIG. 2

MICA/B α3 domain alignment, % identity, % similarity

```
(SEQ ID NO: 443) MICA002.hu  1  TVPPMVNVTRSEASEGNITVTCRASGFYPWNITLSWRQDGVSLSHDTQQW
(SEQ ID NO: 441) MICA004.hu  1  RVPPMVNVTRSEASEGNITVTCRASSFYPRNIILTWRQDGVSLSHDTQQW
(SEQ ID NO: 199) MICA008.hu  1  TVPPMVNVTRSEASEGNITVTCRASSFYPRNIILTWRQDGVSLSHDTQQW
(SEQ ID NO: 442) MICB005.hu  1  TVPPMVNVTCSEVSEGNITVTCRASSFVPRNITLTWRQDGVSLSHNTQQW

MICA002.hu  51  GDVLPDGNGTYQTWVATRICQGEEQRFTCYMEHSGNHSTHPWPS  94
              MICA004.hu  51  GDVLPDGNGTYQTWVATRICQGEEQRFTCYMEHSGNHSTHPWPS  94
              MICA008.hu  51  GDVLPDGNGTYQTWVATRICRGEEQRFTCYMEHSGNHSTHPWPS  94
              MICB005.hu  51  GDVLPDGNGTYQTWVATRIRQGEEQRFTCYMEHSGNHGTHPWPS  94
```

Identity Percentage

|            | MICA002.hu | MICA004.hu | MICA008.hu | MICB005.hu |
|------------|------------|------------|------------|------------|
| MICA002.hu | 100.0      |            |            |            |
| MICA004.hu | 95.74      | 100.0      |            |            |
| MICA008.hu | 94.68      | 96.8       | 100.0      |            |
| MICB005.hu | 91.48      | 93.61      | 92.55      | 100.0      |

Similarity Percentage

|            | MICA002.hu | MICA004.hu | MICA008.hu | MICB005.hu |
|------------|------------|------------|------------|------------|
| MICA002.hu | 100.0      |            |            |            |
| MICA004.hu | 97.05      | 100.0      |            |            |
| MICA008.hu | 96.43      | 97.26      | 100.0      |            |
| MICB005.hu | 91.38      | 92.01      | 91.59      | 100.0      |

Bin 1 on MICA

Bin 2 on MICA

Bin 4 on MICA

Bin 3 on MICA

Bin 5 on MICA

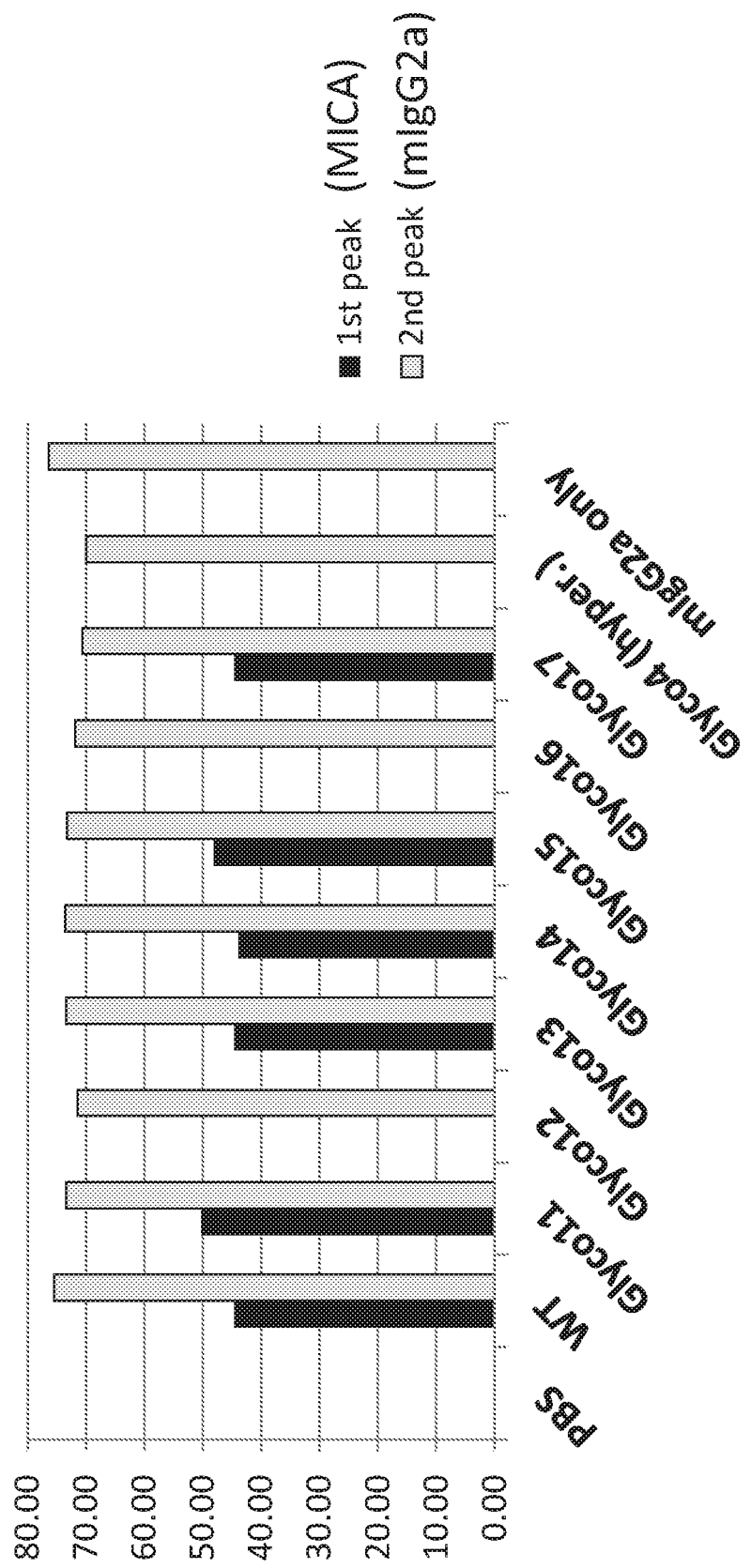

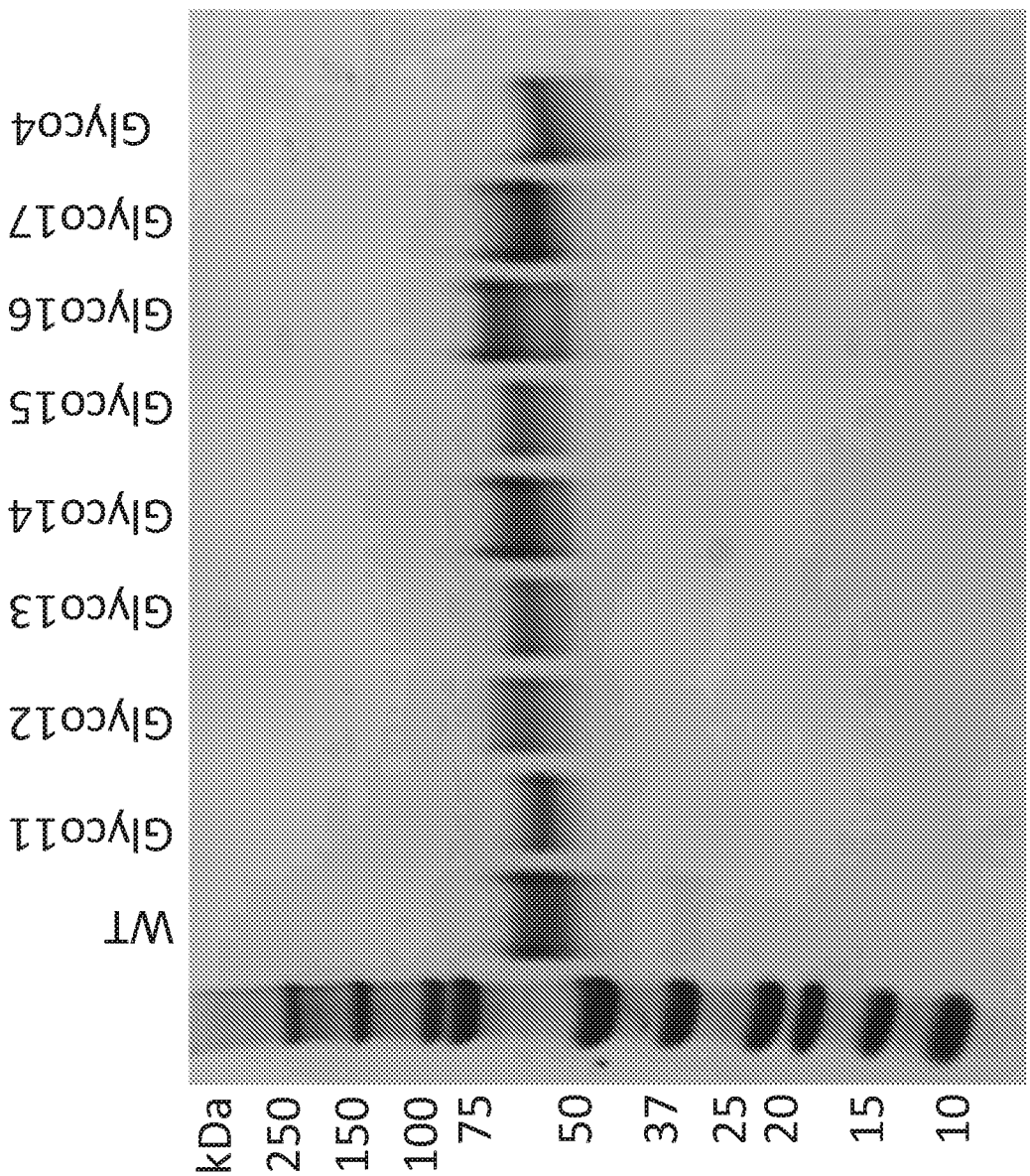
FIG. 6 Gel of Glyco variants

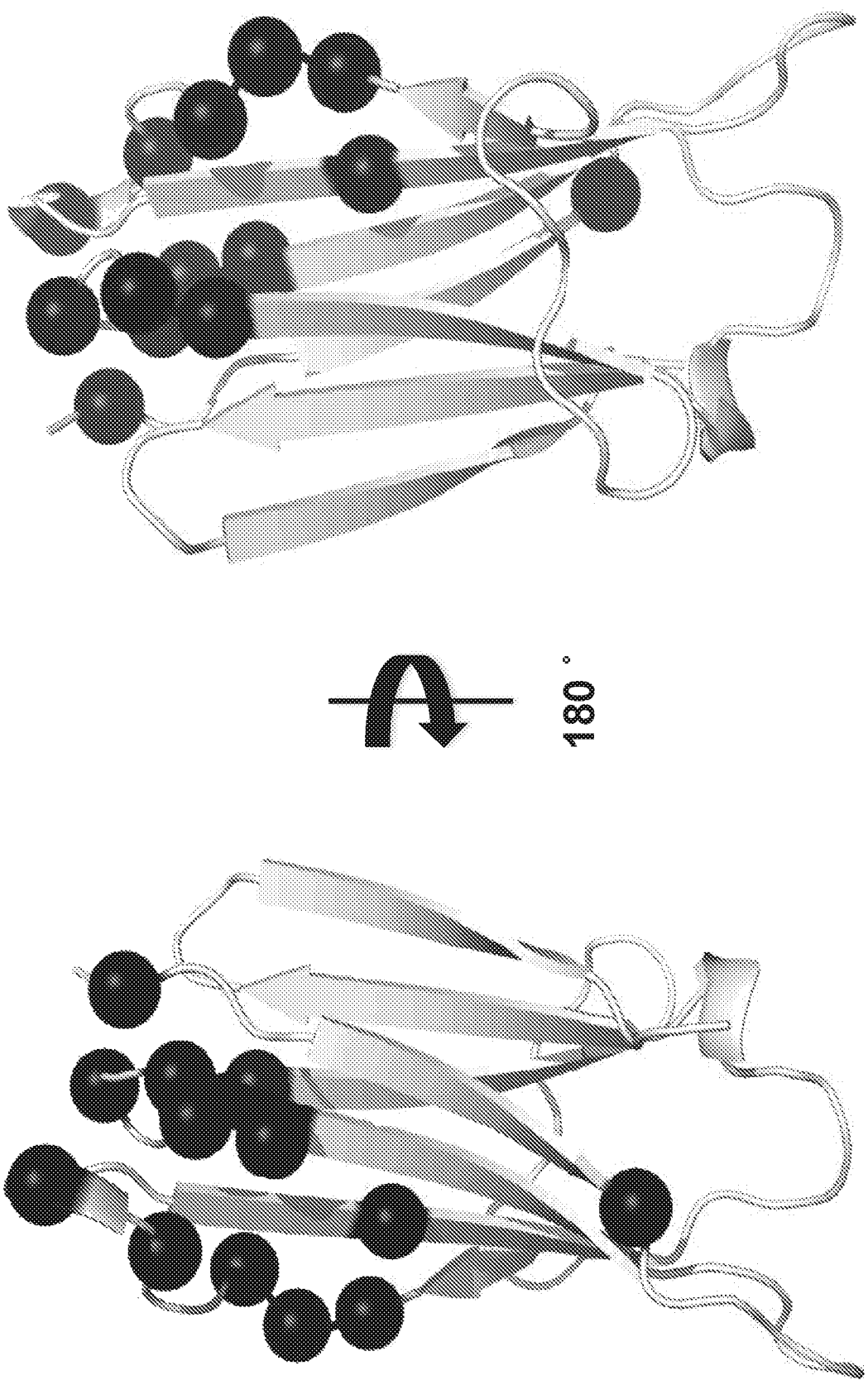
FIG. 7A: MICA *008 residues grafted on MILL

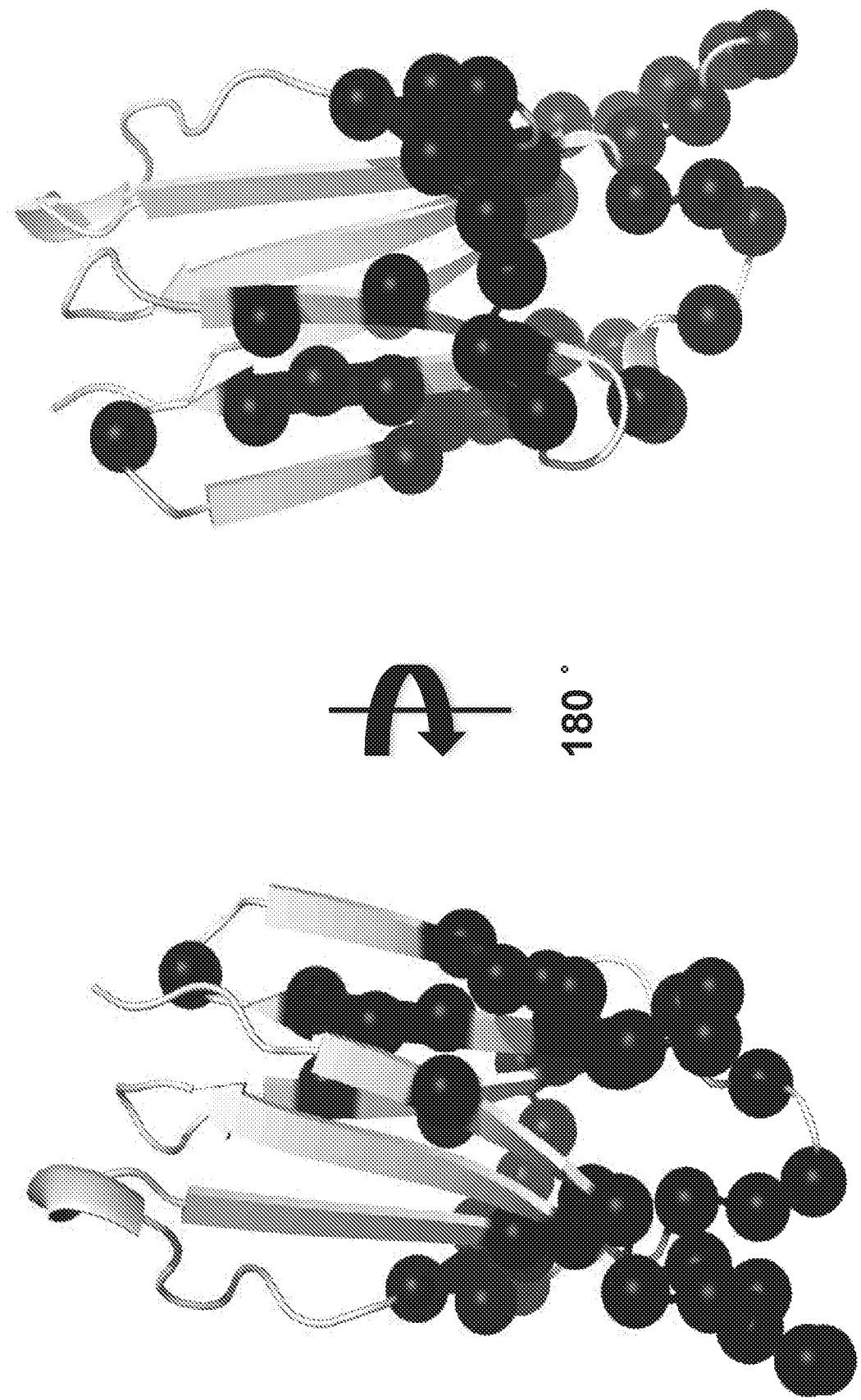
FIG. 7B: Non-MICA *008 residues in MILL chimera

6E1.1.12 (Final Bin 6) and 2E5.2.3 (Final Bin 7) on MILL1-MICA chimera

FIG. 9

| | 6F8 | 7D4 | 2E5.2.3 | 1D5 | % monomer |
|---|---|---|---|---|---|
| WT | 1 | 1 | 1 | 1 | 91.57 |
| I236A | 1.4 | 1.2 | 0.9 | 0.01 | 92.49 |
| T238A | 0.1 | 0.1 | 1.3 | 0.4 | 96 |
| R240A | 4.5 | 1499 | 1 | 18500 | 93.8 |
| Q241A | 1.1 | 0.4 | 1.1 | 9830 | 97.6 |
| V244A | 5.5 | 8.6 | 1 | 10400 | 97.6 |
| S245A | 1.2 | 1.6 | 1 | 13 | 93.96 |
| S247A | 0.9 | 0.8 | 1.1 | 0.2 | 94.87 |
| H248A | 0.6 | 0.6 | 1 | 16 | 92.05 |
| D249A | 0.8 | 0.7 | 1 | 3.5 | 86.64 |
| T250A | 0.5 | 0.6 | 1.2 | 8.8 | 91.61 |
| R274A | 1 | 0.9 | 1.1 | 3 | 94 |
| G275A | 4.6 | 3.1 | 1 | 0.03 | 98.9 |
| E276A | 4.3 | 0.7 | 1.2 | 22 | 86.14 |
| E277A | 2.7 | 1.3 | 1.1 | 1.9 | 81.58 |
| Q278A | 0.5 | 4.9 | 1 | 0.7 | 92.32 |
| R279A | 4.5 | 5.1 | 0.8 | 3950 | 95.2 |
| Y283A | 1.7 | 3.2 | 0.2 | 6260 | 92.7 |
| E285A | 3.9 | 7.9 | 0.9 | 1060 | 83.78 |
| S287A | 1.1 | 1.3 | 1 | 4.9 | 90.34 |
| G288A | 1 | 0.8 | 0.6 | 1 | 95.3 |
| N289A | 1.2 | 3.5 | 1.1 | 0.2 | 89.74 |
| H290A | 8.4 | 8.8 | 0.8 | 14400 | 90.37 |
| S291A | 2.7 | 2.7 | 1.1 | 1.1 | 83.21 |
| T292A | 1.7 | 2.1 | 1.3 | 3040 | 80.56 |
| P294A | 0.9 | 1 | 1 | 1 | 89.16 |
| P296A | 1 | 0.7 | 0.6 | 1.9 | 92.3 |
| S297A | 1 | 1.1 | 1.2 | 0.05 | 89.24 |

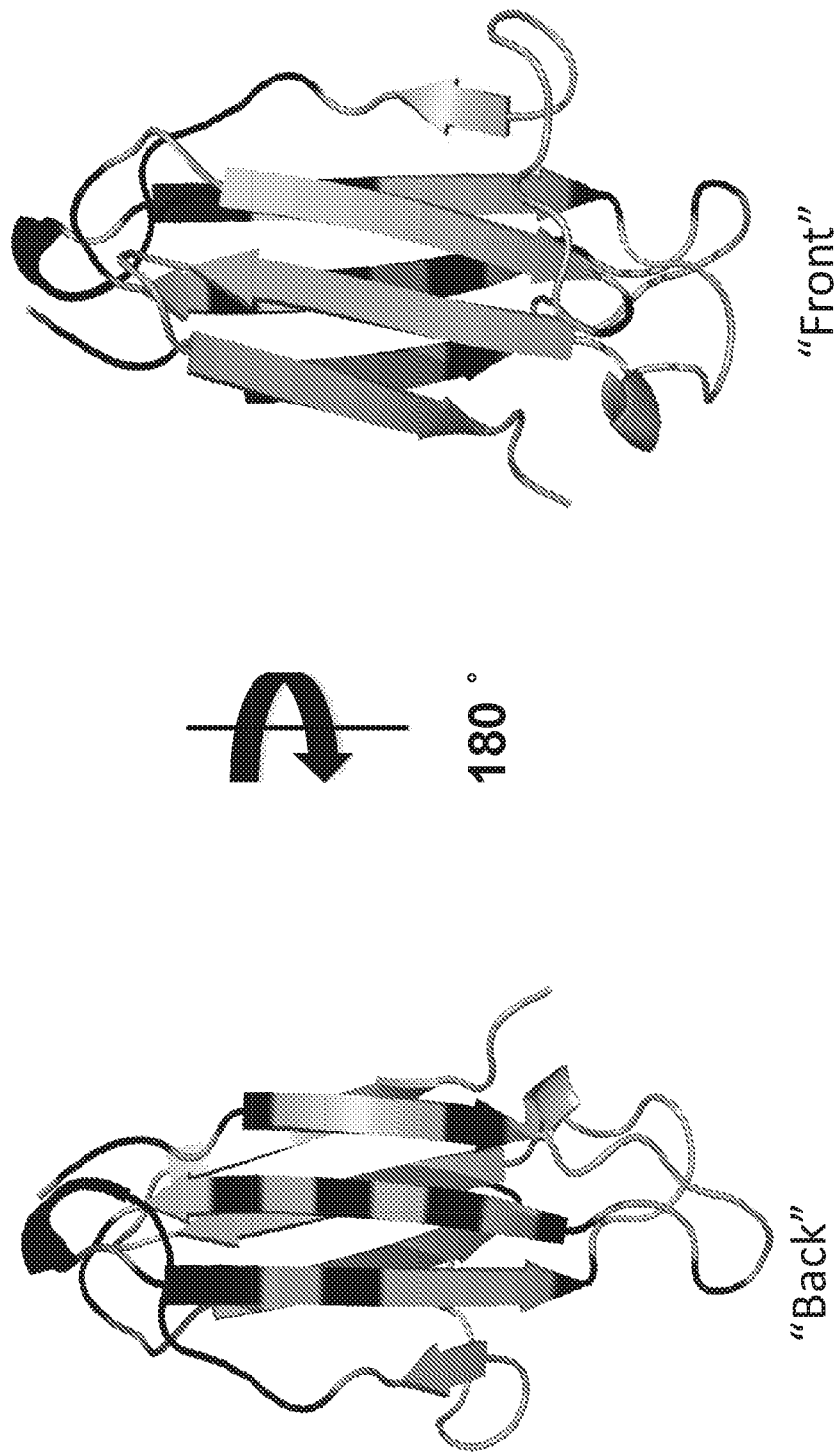
FIG. 10: 2E5.2.3 Epitope (Final Bin 7)

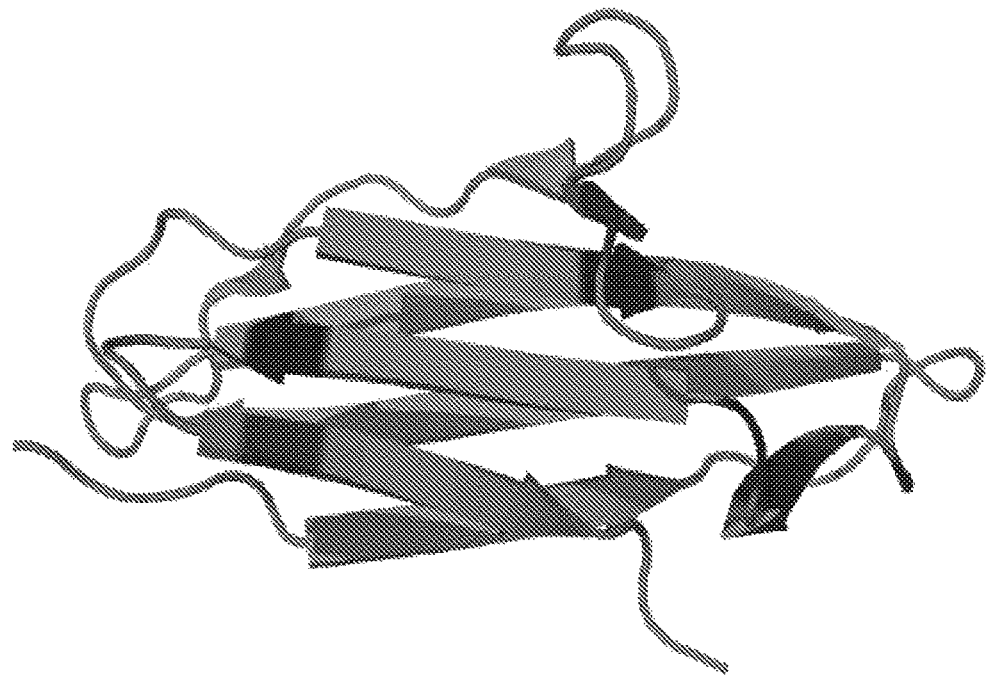
FIG. 11A: 6F8 Epitope
Epitope by Ala scan
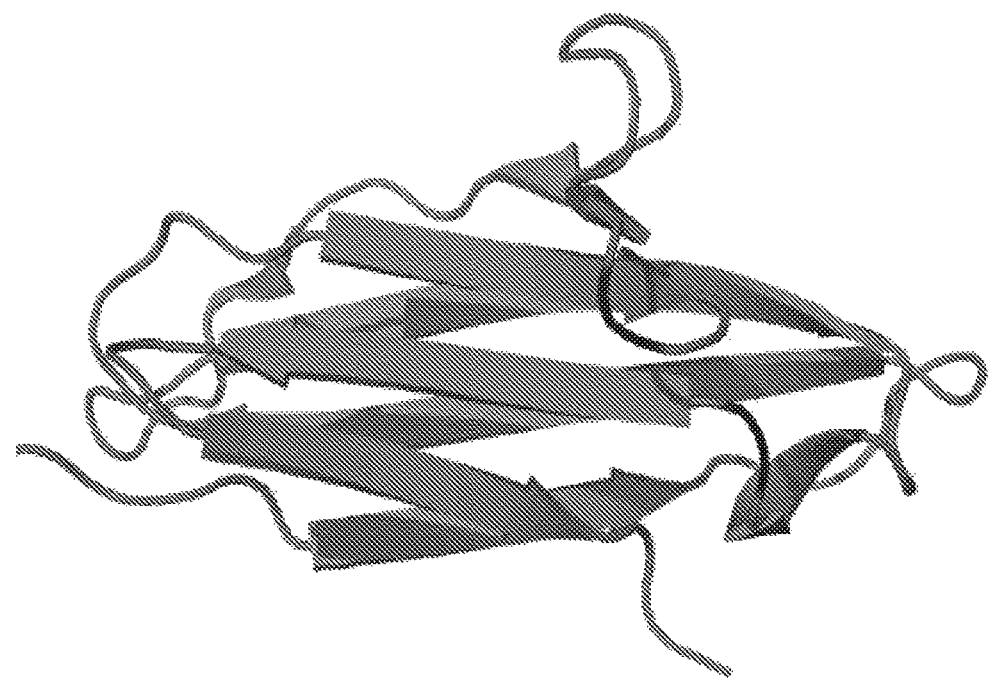
Epitope by Glyco mapping

FIG. 11B: 7D4 Epitope
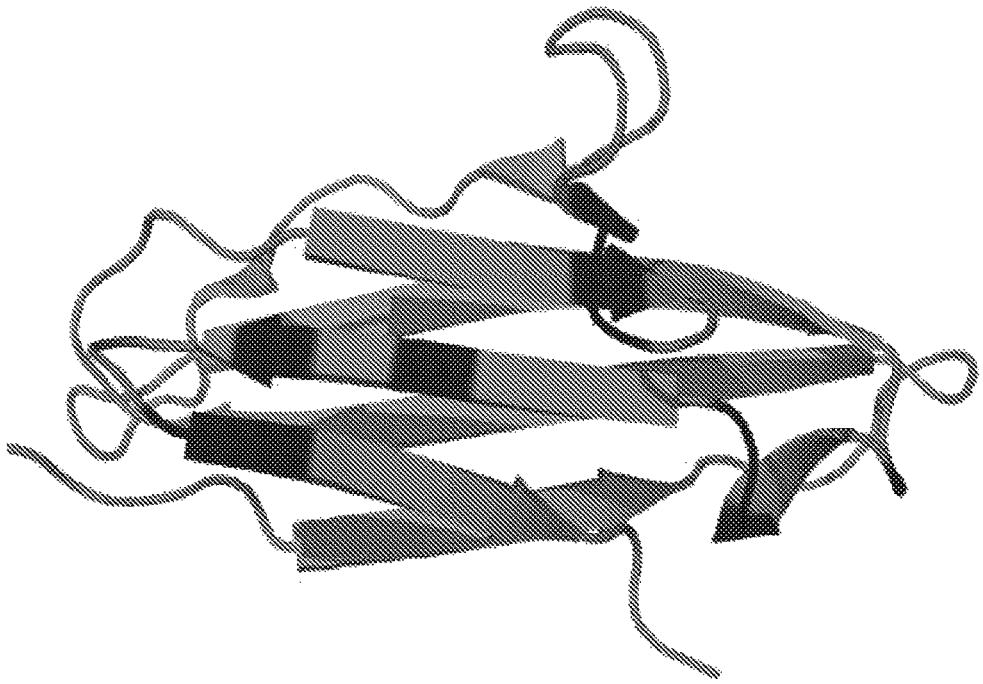
Epitope by Ala scan
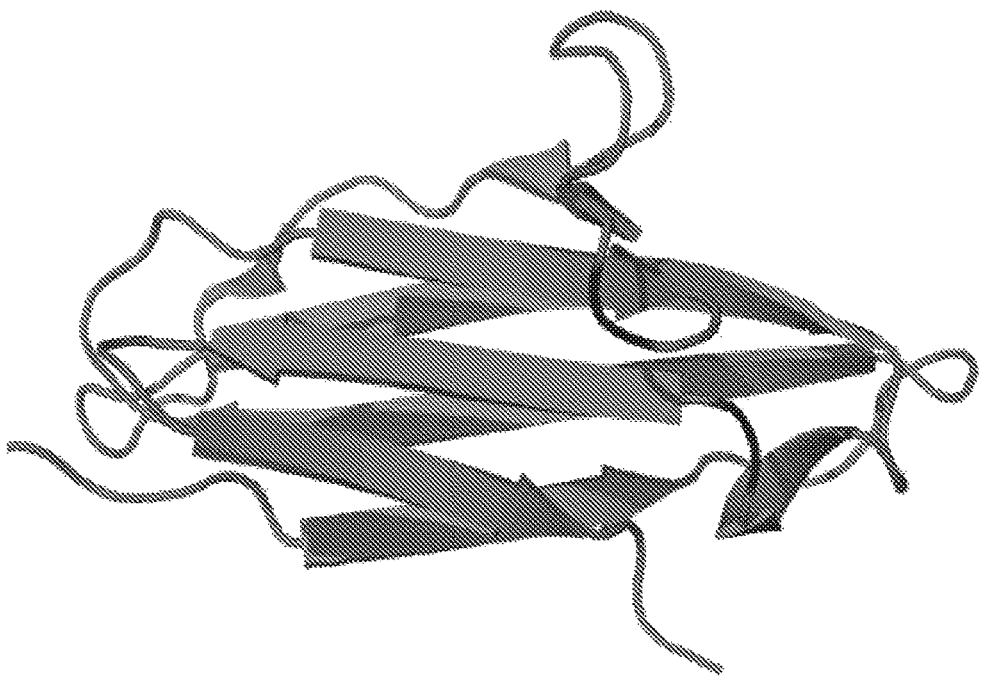
Epitope by Glyco mapping

FIG. 12

Overview of Sequence Identifiers (SEQ ID NOs:) for Anti-MICA Antibody Sequences

| Ab | HVR-H1 | HVR-H2 | HVR-H3 | HVR-L1 | HVR-L2 | HVR-L3 | FR-L1 | FR-L2 | FR-L3 | FR-L4 | FR-H1 | FR-H2 | FR-H3 | FR-H4 | VH | VL |
|---|---|---|---|---|---|---|---|---|---|---|---|---|---|---|---|---|
| 3C9.10 | 1 | 2 | 3 | 4 | 5 | 6 | 7 | 8 | 9 | 10 | 11 | 12 | 13 | 14 | 15 | 16 |
| 7D4.6 | 17 | 18 | 19 | 20 | 21 | 22 | 23 | 24 | 25 | 26 | 27 | 28 | 29 | 30 | 31 | 32 |
| 6F8.7 | 33 | 34 | 35 | 36 | 37 | 38 | 39 | 40 | 41 | 42 | 43 | 44 | 45 | 46 | 47 | 48 |
| 32D2 | 49 | 50 | 51 | 52 | 53 | 54 | 55 | 56 | 57 | 58 | 59 | 60 | 61 | 62 | 63 | 64 |
| 3E11 | 65 | 66 | 67 | 68 | 69 | 70 | 71 | 72 | 73 | 74 | 75 | 76 | 77 | 78 | 79 | 80 |
| 9C9.5.6 | 81 | 82 | 83 | 84 | 85 | 86 | 87 | 88 | 89 | 90 | 91 | 92 | 93 | 94 | 95 | 96 |
| 1E6.1.3 | 97 | 98 | 99 | 100 | 101 | 102 | 103 | 104 | 105 | 106 | 107 | 108 | 109 | 110 | 111 | 112 |
| 7A3.1.9 | 113 | 114 | 115 | 116 | 117 | 118 | 119 | 120 | 121 | 122 | 123 | 124 | 125 | 126 | 127 | 128 |
| 6E12.5 | 129 | 130 | 131 | 132 | 133 | 134 | 135 | 136 | 137 | 138 | 139 | 140 | 141 | 142 | 143 | 144 |
| 20G11 | 145 | 146 | 147 | 148 | 149 | 150 | 151 | 152 | 153 | 154 | 155 | 156 | 157 | 158 | 159 | 160 |
| 6E1.1.12 | 161 | 162 | 163 | 164 | 165 | 166 | 167 | 168 | 169 | 170 | 171 | 172 | 173 | 174 | 175 | 176 |
| 2E5.2.3 | 177 | 178 | 179 | 180 | 181 | 182 | 183 | 184 | 185 | 186 | 187 | 188 | 189 | 190 | 191 | 192 |

FIG. 13A

Inhibition

| 1D5 ug/mL > | | HCC1534 (MICA*004) | | | | | | |
|---|---|---|---|---|---|---|---|---|
| 13A9 ug/mL V | 10 | 2.5 | 0.625 | 0.15625 | 0.039063 | 0.009766 | 0.002441 | None |
| 10 | 52% | 53% | 55% | 55% | 57% | 57% | 59% | 58% |
| 2.5 | 54% | 57% | 57% | 53% | 50% | 53% | 51% | 47% |
| 0.625 | 60% | 58% | 59% | 57% | 52% | 42% | 38% | 34% |
| 0.15625 | 58% | 62% | 62% | 59% | 49% | 36% | 31% | 14% |
| 0.0390625 | 60% | 60% | 62% | 59% | 50% | 30% | 15% | 20% |
| 0.009765625 | 58% | 66% | 64% | 63% | 50% | 32% | 12% | 14% |
| 0.002441406 | 58% | 64% | 61% | 61% | 50% | 34% | 16% | 7% |
| None | 58% | 61% | 62% | 63% | 50% | 36% | 15% | -5% |

| 1D5 ug/mL > | 10 | 2.5 | 0.625 | 0.15625 | 0.039063 | 0.009766 | 0.002441 | None |
|---|---|---|---|---|---|---|---|---|
| 6E1 ug/mL V | | | | | | | | |
| 10 | 72% | 72% | 75% | 72% | 68% | 62% | 63% | 50% |
| 2.5 | 69% | 72% | 73% | 66% | 64% | 57% | 54% | 43% |
| 0.625 | 66% | 70% | 69% | 64% | 59% | 52% | 40% | 38% |
| 0.15625 | 63% | 65% | 68% | 66% | 50% | 45% | 29% | 25% |
| 0.0390625 | 61% | 61% | 63% | 61% | 47% | 25% | 19% | 10% |
| 0.009765625 | 63% | 61% | 60% | 56% | 42% | 23% | 9% | 4% |
| 0.002441406 | 58% | 59% | 58% | 55% | 40% | 19% | -4% | -9% |
| None | 58% | 56% | 56% | 48% | 40% | 13% | -5% | -17% |

| 13A9 ug/mL > | 10 | 2.5 | 0.625 | 0.15625 | 0.039063 | 0.009766 | 0.002441 | None |
|---|---|---|---|---|---|---|---|---|
| 6E1 ug/mL V | | | | | | | | |
| 10 | 66% | 61% | 59% | 57% | 55% | 53% | 49% | 50% |
| 2.5 | 62% | 60% | 58% | 53% | 52% | 50% | 52% | 52% |
| 0.625 | 61% | 58% | 51% | 54% | 50% | 41% | 42% | 39% |
| 0.15625 | 62% | 53% | 46% | 36% | 37% | 29% | 31% | 23% |
| 0.0390625 | 54% | 51% | 43% | 35% | 31% | 22% | 20% | 15% |
| 0.009765625 | 57% | 52% | 40% | 32% | 24% | 15% | 12% | 11% |
| 0.002441406 | 66% | 54% | 38% | 30% | 20% | 17% | 15% | -1% |
| None | 52% | 47% | 27% | 26% | 21% | 14% | 6% | -4% |

FIG. 13B

Inhibition

MEL-JUSO (MICA*008)

| 1D5 ug/mL > | 10 | 2.5 | 0.625 | 0.15625 | 0.0390063 | 0.009766 | 0.002441 | None |
|---|---|---|---|---|---|---|---|---|
| 13A9 ug/mL V | | | | | | | | |
| 10 | 65% | 66% | 62% | 55% | 51% | 45% | 44% | 38% |
| 2.5 | 70% | 70% | 70% | 66% | 55% | 48% | 46% | 39% |
| 0.625 | 69% | 75% | 73% | 73% | 62% | 45% | 40% | 27% |
| 0.15625 | 72% | 76% | 73% | 70% | 60% | 39% | 28% | 19% |
| 0.0390625 | 70% | 74% | 75% | 73% | 67% | 41% | 24% | 10% |
| 0.009765625 | 72% | 75% | 76% | 74% | 65% | 45% | 28% | 11% |
| 0.002441406 | 72% | 78% | 79% | 75% | 65% | 45% | 26% | 8% |
| None | 72% | 77% | 76% | 76% | 71% | 48% | 28% | 11% |

| 1D5 ug/mL > | 10 | 2.5 | 0.625 | 0.15625 | 0.0390063 | 0.009766 | 0.002441 | None |
|---|---|---|---|---|---|---|---|---|
| 6E1 ug/mL V | | | | | | | | |
| 10 | 81% | 82% | 84% | 82% | 75% | 64% | 57% | 48% |
| 2.5 | 79% | 81% | 82% | 79% | 71% | 59% | 52% | 44% |
| 0.625 | 76% | 79% | 80% | 77% | 68% | 52% | 45% | 36% |
| 0.15625 | 76% | 79% | 78% | 75% | 61% | 42% | 31% | 22% |
| 0.0390625 | 70% | 70% | 77% | 72% | 57% | 36% | 19% | 8% |
| 0.009765625 | 72% | 74% | 74% | 71% | 54% | 30% | 12% | 6% |
| 0.002441406 | 72% | 73% | 73% | 70% | 52% | 25% | 6% | -6% |
| None | 70% | 72% | 68% | 64% | 44% | 17% | -1% | -21% |

| 13A9 ug/mL > | 10 | 2.5 | 0.625 | 0.15625 | 0.0390063 | 0.009766 | 0.002441 | None |
|---|---|---|---|---|---|---|---|---|
| 6E1 ug/mL V | | | | | | | | |
| 10 | 40% | 29% | 27% | 32% | 31% | 32% | 32% | 29% |
| 2.5 | 37% | 36% | 31% | 37% | 38% | 36% | 40% | 35% |
| 0.625 | 40% | 41% | 34% | 33% | 28% | 31% | 30% | 29% |
| 0.15625 | 39% | 39% | 29% | 22% | 17% | 23% | 24% | 24% |
| 0.0390625 | 37% | 42% | 27% | 24% | 13% | 9% | 14% | 15% |
| 0.009765625 | 40% | 36% | 26% | 11% | 12% | 16% | 15% | 13% |
| 0.002441406 | 41% | 38% | 28% | 14% | 13% | 19% | 12% | 10% |
| None | 35% | 38% | 26% | 17% | 16% | 19% | 15% | 16% |

FIG. 13C

Inhibition

| 1D5 ug/mL > | 10 | 2.5 | 0.625 | 0.15625 | 0.039063 | 0.009766 | 0.002441 | None |
|---|---|---|---|---|---|---|---|---|
| 13A9 ug/mL V | | | | HCC1534 (MICB*005) | | | | |
| 10 | 53% | 58% | 66% | 73% | 73% | 74% | 75% | 75% |
| 2.5 | 47% | 57% | 63% | 69% | 70% | 74% | 76% | 77% |
| 0.625 | 53% | 53% | 58% | 61% | 65% | 68% | 70% | 68% |
| 0.15625 | 52% | 53% | 52% | 50% | 51% | 53% | 56% | 54% |
| 0.0390625 | 52% | 53% | 52% | 46% | 40% | 33% | 39% | 39% |
| 0.0097656256 | 52% | 53% | 55% | 48% | 38% | 31% | 31% | 27% |
| 0.002441406 | 52% | 57% | 53% | 46% | 38% | 32% | 25% | 13% |
| None | 48% | 51% | 51% | 48% | 40% | 29% | 15% | 7% |

| 1D5 ug/mL > | 10 | 2.5 | 0.625 | 0.15625 | 0.039063 | 0.009766 | 0.002441 | None |
|---|---|---|---|---|---|---|---|---|
| 6E1 ug/mL V | | | | | | | | |
| 10 | 78% | 77% | 76% | 76% | 71% | 67% | 63% | 57% |
| 2.5 | 76% | 77% | 78% | 73% | 70% | 64% | 60% | 52% |
| 0.625 | 72% | 75% | 74% | 71% | 65% | 60% | 54% | 46% |
| 0.15625 | 68% | 69% | 71% | 67% | 57% | 46% | 43% | 35% |
| 0.0390625 | 60% | 60% | 60% | 58% | 39% | 33% | 26% | 15% |
| 0.0097656256 | 56% | 57% | 54% | 49% | 34% | 21% | 11% | -1% |
| 0.002441406 | 56% | 51% | 52% | 48% | 36% | 17% | -3% | -11% |
| None | 53% | 51% | 52% | 43% | 25% | 7% | -9% | -15% |

| 13A9 ug/mL > | 10 | 2.5 | 0.625 | 0.15625 | 0.039063 | 0.009766 | 0.002441 | None |
|---|---|---|---|---|---|---|---|---|
| 6E1 ug/mL V | | | | | | | | |
| 10 | 78% | 70% | 68% | 65% | 61% | 51% | 43% | 43% |
| 2.5 | 75% | 75% | 71% | 65% | 64% | 58% | 50% | 48% |
| 0.625 | 78% | 76% | 71% | 68% | 63% | 56% | 51% | 42% |
| 0.15625 | 77% | 75% | 69% | 59% | 53% | 41% | 40% | 32% |
| 0.0390625 | 73% | 75% | 68% | 56% | 44% | 34% | 25% | 23% |
| 0.0097656256 | 74% | 75% | 67% | 53% | 41% | 29% | 31% | 10% |
| 0.002441406 | 75% | 74% | 68% | 56% | 39% | 25% | 19% | 2% |
| None | 73% | 74% | 65% | 54% | 39% | 27% | 9% | 2% |

FIG. 14A

CDR sequences according to Kabat definition are underlined
Heavy chain variable region

```
                               CDR H1 - Contact
                                CDR H1 - Kabat
              Kabat number  1  2  3  4  5  6  7  8  9 10 11 12 13 14 15 16 17 18 19 20 21 22 23 24 25 26 27 28 29 30 31 32 33 34 35 35a 36 37 38 39 40 41
(SEQ ID NO: 347)   1D5      E  I  Q  L  Q  Q  S  G  P  E  L  V  K  P  G  A  S  V  K  V  S  C  K  A  S  G  Y  A  F  T  S  Q  N  I  Y  .   W  V  K  Q  S  H
(SEQ ID NO: 349)   1D5v1    E  I  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 351)   1D5v2    E  V  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 353)   1D5v3    E  I  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 355)   1D5v4    E  V  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 357)   1D5v5    E  I  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 359)   1D5v6    E  V  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 361)   1D5v7    E  I  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 363)   1D5v8    E  V  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 365)   1D5v9    E  I  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 367)   1D5v10   E  V  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 369)   1D5v11   E  I  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 371)   1D5v12   E  V  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 373)   1D5v13   E  I  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 375)   1D5v14   E  V  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 377)   1D5v15   E  I  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 379)   1D5v16   E  V  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 381)   1D5v17   E  I  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 383)   1D5v18   E  I  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 385)   1D5v19   E  V  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 387)   1D5v20   E  I  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 389)   1D5v21   E  I  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 391)   1D5v22   E  I  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 393)   1D5v23   E  I  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 395)   1D5v24   E  V  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 397)   1D5v25   E  V  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 399)   1D5v26   E  V  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 401)   1D5v27   E  I  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 403)   1D5v28   E  I  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 405)   1D5v29   E  I  Q  L  V  Q  S  G  A  E  V  K  K  P  G  A  S  V  K  V  S  C  K  A  S  G  Y  A  F  T  S  Q  N  I  Y  .   W  V  R  Q  A  P
(SEQ ID NO: 407)   13A9     Q  V  Q  L  Q  Q  S  G  A  E  L  V  R  P  G  T  S  V  K  V  S  C  K  A  S  G  Y  A  F  T  N  Y  L  I  E  .   W  V  K  Q  R  P
(SEQ ID NO: 409)   13A9v1   E  V  Q  L  V  Q  S  G  A  E  V  K  K  P  G  A  S  V  K  V  S  C  K  A  S  G  Y  A  F  T  N  Y  L  I  E  .   W  V  R  Q  A  P
(SEQ ID NO: 411)   13A9v2   E  V  Q  L  V  Q  S  G  A  E  V  K  K  P  G  A  S  V  K  V  S  C  K  A  S  G  Y  A  F  T  N  Y  L  I  E  .   W  V  R  Q  A  P
(SEQ ID NO: 413)   13A9v3   E  V  Q  L  V  Q  S  G  A  E  V  K  K  P  G  A  S  V  K  V  S  C  K  A  S  G  Y  A  F  T  N  Y  L  I  E  .   W  V  R  Q  A  P
(SEQ ID NO: 415)   13A9v4   E  V  Q  L  V  Q  S  G  A  E  V  K  K  P  G  A  S  V  K  V  S  C  K  A  S  G  Y  A  F  T  N  Y  L  I  E  .   W  V  R  Q  A  P
(SEQ ID NO: 417)   13A9v5   E  V  Q  L  V  Q  S  G  A  E  V  K  K  P  G  S  S  V  K  V  S  C  K  A  S  G  Y  A  F  T  N  Y  L  I  E  .   W  V  R  Q  A  P
(SEQ ID NO: 419)   13A9v6   E  V  Q  L  V  Q  S  G  A  E  V  K  K  P  G  S  S  V  K  V  S  C  K  A  S  G  Y  A  F  T  N  Y  L  I  E  .   W  V  R  Q  A  P
(SEQ ID NO: 421)   15F11    E  I  Q  L  Q  Q  S  G  P  E  L  V  K  P  G  A  S  V  R  V  S  C  K  P  S  G  Y  A  F  T  S  N  N  I  Y  .   W  V  K  Q  S  R
(SEQ ID NO: 423)   15F11v1  E  V  Q  L  V  Q  S  G  A  E  V  K  K  P  G  A  S  V  K  V  S  C  K  A  S  G  Y  A  F  T  S  N  N  I  Y  .   W  V  R  Q  A  P
(SEQ ID NO: 425)   15F11v2  E  I  Q  L  V  Q  S  G  A  E  V  K  K  P  G  A  S  V  K  V  S  C  K  P  S  G  Y  A  F  T  S  N  N  I  Y  .   W  V  R  Q  A  P
(SEQ ID NO: 427)   15F11v3  E  V  Q  L  V  Q  S  G  A  E  V  K  K  P  G  A  S  V  K  V  S  C  K  A  S  G  Y  A  F  T  S  N  N  I  Y  .   W  V  R  Q  A  P
(SEQ ID NO: 429)   15F11v4  E  I  Q  L  V  Q  S  G  A  E  V  K  K  P  G  A  S  V  K  V  S  C  K  P  S  G  Y  A  F  T  S  N  N  I  Y  .   W  V  R  Q  A  P
(SEQ ID NO: 431)   15F11v5  E  I  Q  L  V  Q  S  G  A  E  V  K  K  P  G  S  S  V  K  V  S  C  K  P  S  G  Y  A  F  T  S  N  N  I  Y  .   W  V  R  Q  A  P
(SEQ ID NO: 433)   15F11v6  E  I  Q  L  V  Q  S  G  A  E  V  K  K  P  G  S  S  V  K  V  S  C  K  P  S  G  Y  A  F  T  S  N  N  I  Y  .   W  V  R  Q  A  P
(SEQ ID NO: 435)   6E1.1.12 Q  G  Q  M  Q  Q  S  G  A  E  L  V  K  P  G  A  S  V  K  L  S  C  K  T  S  G  F  T  F  S  D  N  Y  I  S  .   W  L  K  Q  K  P
(SEQ ID NO: 437)   18G3        V  Q  L  Q  E  S  G  P  G  L  V  K  P  S  Q  S  L  S  L  T  C  N  V  T  G  Y  S  I  T  G  D  Y  A  W  N  W  I  R  Q  F  P
(SEQ ID NO: 439)   12H10    D  V  Q  L  Q  E  S  G  P  G  L  V  K  P  S  Q  P  L  S  L  T  C  T  V  T  G  Y  S  I  T  S  N  Y  A  W  N  W  I  R  Q  F  P
```

FIG. 14B

```
                                    CDR H2 - Contact
                                    CDR H2 - Kabat
              Kabat number  4 4 4 4 4 4 4 4 5 5 5 5 5 5 5 5 5 5 5 6 6 6 6 6 6 6 6 6 6 7 7 7 7 7 7 7 7 7 7 8 8
                           2 3 4 5 6 7 8 9 0 1 2 2 2 3 4 5 6 7 8 9 0 1 2 3 4 5 6 7 8 9 0 1 2 3 4 5 6 7 8 9 0 1
                                              a b
(SEQ ID NO: 347)  1D5       G K S L E W I G Y I E P Y N V V P M Y   N P K F K G K A T L T V D K S S S S A Y I H
(SEQ ID NO: 349)  1D5v1     G Q G L E W I G Y I E P Y N V V P M Y   N P K F K G R A T L T V D K S T S T A Y M E
(SEQ ID NO: 351)  1D5v2     G Q G L E W M G Y I E P Y N V V P M Y   N P K F K G R V T M T D T S T S T A Y M E
(SEQ ID NO: 353)  1D5v3     G Q G L E W I G Y I E P Y N V V P M Y   N P K F K G R A T L T V D K S T S T A Y L E
(SEQ ID NO: 355)  1D5v4     G Q G L E W I G Y I E P Y N V V P M Y   N P K F K G R V T I T R D T S T S T A Y L E
(SEQ ID NO: 357)  1D5v5     G Q G L E W I G Y I E P Y N V V P M Y   N P K F K G R A T L T V D K S T S T A Y M E
(SEQ ID NO: 359)  1D5v6     G Q G L E W M G Y I E P Y N V V P M Y   N P K F K G R V T M T D T S T S T A Y M E
(SEQ ID NO: 361)  1D5v7     G Q G L E W I G Y I E P Y N V V P M Y   N P K F K G R A T L T V D K S T S T A Y L E
(SEQ ID NO: 363)  1D5v8     G Q G L E W I G Y I E P Y N V V P M Y   N P K F K G R V T I T R D T S T S T A Y L E
(SEQ ID NO: 365)  1D5v9     G Q G L E W I G Y I E P Y N V V P M Y   N P K F K G R A T L T V D K S T S T A Y M E
(SEQ ID NO: 367)  1D5v10    G Q G L E W M G Y I E P Y N V V P M Y   N P K F K G R V T M T D T S T S T A Y M E
(SEQ ID NO: 369)  1D5v11    G Q G L E W I G Y I E P Y N V V P M Y   N P K F K G R A T L T V D K S T S T A Y L E
(SEQ ID NO: 371)  1D5v12    G Q G L E W I G Y I E P Y N V V P M Y   N P K F K G R V T I T R D T S T S T A Y L E
(SEQ ID NO: 373)  1D5v13    G Q G L E W I G Y I E P Y N V V P M Y   N P K F K G R A T L T V D K S T S T A Y M E
(SEQ ID NO: 375)  1D5v14    G Q G L E W M G Y I E P Y N V V P M Y   N P K F K G R V T M T D T S T S T A Y M E
(SEQ ID NO: 377)  1D5v15    G Q G L E W I G Y I E P Y N V V P M Y   N P K F K G R A T L T V D K S T S T A Y L E
(SEQ ID NO: 379)  1D5v16    G Q G L E W I G Y I E P Y N V V P M Y   N P K F K G R V T I T R D T S T S T A Y L E
(SEQ ID NO: 381)  1D5v17    G Q G L E W I G Y I E P Y N V V P M Y   N P K F K G R A T L T V D K S T S T A Y L E
(SEQ ID NO: 383)  1D5v18    G Q G L E W I G Y I E P Y N V V P M Y   N P K F K G R A T L T V D K S T S T A Y L E
(SEQ ID NO: 385)  1D5v19    G Q G L E W I G Y I E P Y N V V P M Y   N P K F K G R A T L T V D K S T S T A Y L E
(SEQ ID NO: 387)  1D5v20    G Q G L E W I G Y I E P Y N V V P M Y   N P K F K G R V T L T V D K S T S T A Y L E
(SEQ ID NO: 389)  1D5v21    G Q G L E W I G Y I E P Y N V V P M Y   N P K F K G R A T I T V D K S T S T A Y L E
(SEQ ID NO: 391)  1D5v22    G Q G L E W I G Y I E P Y N V V P M Y   N P K F K G R A T L T R D K S T S T A Y L E
(SEQ ID NO: 393)  1D5v23    G Q G L E W I G Y I E P Y N V V P M Y   N P K F K G R A T L T V D T S T S T A Y L E
(SEQ ID NO: 395)  1D5v24    G Q G L E W I G Y I E P Y N V V P M Y   N P K F K G R V T I T V D K S T S T A Y L E
(SEQ ID NO: 397)  1D5v25    G Q G L E W I G Y I E P Y N V V P M Y   N P K F K G R V T I T V D T S T S T A Y L E
(SEQ ID NO: 399)  1D5v26    G Q G L E W I G Y I E P Y N V V P M Y   N P K F K G R V T I T R D K S T S T A Y L E
(SEQ ID NO: 401)  1D5v27    G Q G L E W I G Y I E P Y N V V P A Y   N P K F K G R A T L T V D K S T S T A Y L E
(SEQ ID NO: 403)  1D5v28    G Q G L E W I G Y I E P Y N V V P L Y   N P K F K G R A T L T V D K S T S T A Y L E
(SEQ ID NO: 405)  1D5v29    G Q G L E W I G Y I E P Y N V V P V Y   N P K F K G R A T L T V D K S T S T A Y L E
(SEQ ID NO: 407)  13A9      G Q G L E W I G A I N P G S G A T N Y   N E K F K D K A R L T A D K S S N T A Y L Q
(SEQ ID NO: 409)  13A9v1    G Q G L E W I G A I N P G S G A T N Y   N E K F K D R V T I T A D T S T S T A Y L E
(SEQ ID NO: 411)  13A9v2    G Q G L E W I G A I N P G S G A T N Y   N E K F K D R A T L T A D K S T N T A Y L E
(SEQ ID NO: 413)  13A9v3    G Q G L E W I G A I N P G S G A T N Y   N E K F K D R V T I T A D T S T S T A Y L E
(SEQ ID NO: 415)  13A9v4    G Q G L E W I G A I N P G S G A T N Y   N E K F K D R A T L T A D K S T N T A Y L E
(SEQ ID NO: 417)  13A9v5    G Q G L E W I G A I N P G S G A T N Y   N E K F K D R A T L T A D K S T N T A Y M E
(SEQ ID NO: 419)  13A9v6    G Q G L E W I G A I N P G S G A T N Y   N E K F K D R A T L T A D K S T N T A Y M E
(SEQ ID NO: 421)  15F11     R K S L E W I G Y I D P Y I G R I I Y   N Q Q F K D K A T L T V D K S S S T A Y M H
(SEQ ID NO: 423)  15F11v1   G Q G L E W I G Y I D P Y I G R I I Y   N Q Q F K D R V T I T A D T S T S T A Y L E
(SEQ ID NO: 425)  15F11v2   G Q G L E W I G Y I D P Y I G R I I Y   N Q Q F K D R A T L T V D K S T S T A Y L E
(SEQ ID NO: 427)  15F11v3   G Q G L E W I G Y I D P Y I G R I I Y   N Q Q F K D R V T I T A D T S T S T A Y L E
(SEQ ID NO: 429)  15F11v4   G Q G L E W I G Y I D P Y I G R I I Y   N Q Q F K D R A T L T V D K S T S T A Y L E
(SEQ ID NO: 431)  15F11v5   G Q G L E W I G Y I D P Y I G R I I Y   N Q Q F K D R A T L T V D K S T S T A Y M E
(SEQ ID NO: 433)  15F11v6   G Q G L E W I G Y I D P Y I G R I I Y   N Q Q F K D R A T L T V D K S T S T A Y M E
(SEQ ID NO: 435)  6E1.1.12  G Q S L E W I A W I Y A G T G G S S Y   N Q K F R D K A Q L T V D T S S R T A Y M Q
(SEQ ID NO: 437)  18G3      G N K L E W I G Y I G Y . T G S T T Y   N P S L K S R V S I T R D T S K N Q F F L Q
(SEQ ID NO: 439)  12H10     G D K L E W M G Y I S S . S G I T K S   N P S L K S R I S I T R D T S K N Q F F L Q
```

FIG. 14C

| SEQ ID NO | Name | Kabat 82-113 |
|---|---|---|
| (SEQ ID NO: 347) | 1D5 | L N S L T S E D S A I Y Y C A R S G S S N F . . . . . D Y W G Q G T T L T V S S |
| (SEQ ID NO: 349) | 1D5v1 | L R S L R S D D T A V Y Y C A R S G S S N F . . . . . D Y W G Q G T L V T V S S |
| (SEQ ID NO: 351) | 1D5v2 | L R S L R S D D T A V Y Y C A R S G S S N F . . . . . D Y W G Q G T L V T V S S |
| (SEQ ID NO: 353) | 1D5v3 | L S S L R S E D T A V Y Y C A R S G S S N F . . . . . D Y W G Q G T L V T V S S |
| (SEQ ID NO: 355) | 1D5v4 | L S S L R S E D T A V Y Y C A R S G S S N F . . . . . D Y W G Q G T L V T V S S |
| (SEQ ID NO: 357) | 1D5v5 | L R S L R S D D T A V Y Y C A R S G S S N F . . . . . D Y W G Q G T L V T V S S |
| (SEQ ID NO: 359) | 1D5v6 | L R S L R S D D T A V Y Y C A R S G S S N F . . . . . D Y W G Q G T L V T V S S |
| (SEQ ID NO: 361) | 1D5v7 | L S S L R S E D T A V Y Y C A R S G S S N F . . . . . D Y W G Q G T L V T V S S |
| (SEQ ID NO: 363) | 1D5v8 | L S S L R S E D T A V Y Y C A R S G S S N F . . . . . D Y W G Q G T L V T V S S |
| (SEQ ID NO: 365) | 1D5v9 | L R S L R S D D T A V Y Y C A R S G S S N F . . . . . D Y W G Q G T L V T V S S |
| (SEQ ID NO: 367) | 1D5v10 | L R S L R S D D T A V Y Y C A R S G S S N F . . . . . D Y W G Q G T L V T V S S |
| (SEQ ID NO: 369) | 1D5v11 | L S S L R S E D T A V Y Y C A R S G S S N F . . . . . D Y W G Q G T L V T V S S |
| (SEQ ID NO: 371) | 1D5v12 | L S S L R S E D T A V Y Y C A R S G S S N F . . . . . D Y W G Q G T L V T V S S |
| (SEQ ID NO: 373) | 1D5v13 | L R S L R S D D T A V Y Y C A R S G S S N F . . . . . D Y W G Q G T L V T V S S |
| (SEQ ID NO: 375) | 1D5v14 | L R S L R S D D T A V Y Y C A R S G S S N F . . . . . D Y W G Q G T L V T V S S |
| (SEQ ID NO: 377) | 1D5v15 | L S S L R S E D T A V Y Y C A R S G S S N F . . . . . D Y W G Q G T L V T V S S |
| (SEQ ID NO: 379) | 1D5v16 | L S S L R S E D T A V Y Y C A R S G S S N F . . . . . D Y W G Q G T L V T V S S |
| (SEQ ID NO: 381) | 1D5v17 | L S S L R S E D T A V Y Y C A R S G S S N F . . . . . D Y W G Q G T L V T V S S |
| (SEQ ID NO: 383) | 1D5v18 | L S S L R S E D T A V Y Y C A R S G S S N F . . . . . D Y W G Q G T L V T V S S |
| (SEQ ID NO: 385) | 1D5v19 | L S S L R S E D T A V Y Y C A R S G S S N F . . . . . D Y W G Q G T L V T V S S |
| (SEQ ID NO: 387) | 1D5v20 | L S S L R S E D T A V Y Y C A R S G S S N F . . . . . D Y W G Q G T L V T V S S |
| (SEQ ID NO: 389) | 1D5v21 | L S S L R S E D T A V Y Y C A R S G S S N F . . . . . D Y W G Q G T L V T V S S |
| (SEQ ID NO: 391) | 1D5v22 | L S S L R S E D T A V Y Y C A R S G S S N F . . . . . D Y W G Q G T L V T V S S |
| (SEQ ID NO: 393) | 1D5v23 | L S S L R S E D T A V Y Y C A R S G S S N F . . . . . D Y W G Q G T L V T V S S |
| (SEQ ID NO: 395) | 1D5v24 | L S S L R S E D T A V Y Y C A R S G S S N F . . . . . D Y W G Q G T L V T V S S |
| (SEQ ID NO: 397) | 1D5v25 | L S S L R S E D T A V Y Y C A R S G S S N F . . . . . D Y W G Q G T L V T V S S |
| (SEQ ID NO: 399) | 1D5v26 | L S S L R S E D T A V Y Y C A R S G S S N F . . . . . D Y W G Q G T L V T V S S |
| (SEQ ID NO: 401) | 1D5v27 | L S S L R S E D T A V Y Y C A R S G S S N F . . . . . D Y W G Q G T L V T V S S |
| (SEQ ID NO: 403) | 1D5v28 | L S S L R S E D T A V Y Y C A R S G S S N F . . . . . D Y W G Q G T L V T V S S |
| (SEQ ID NO: 405) | 1D5v29 | L S S L R S E D T A V Y Y C A R S G S S N F . . . . . D Y W G Q G T L V T V S S |
| (SEQ ID NO: 407) | 13A9 | F S S L T S D D S A V Y F C A R F L G N Y F . . . . . D N W G Q G A T L T V S S |
| (SEQ ID NO: 409) | 13A9v1 | L S S L R S E D T A V Y Y C A R F L G N Y F . . . . . D N W G Q G T L V T V S S |
| (SEQ ID NO: 411) | 13A9v2 | L S S L R S E D T A V Y F C A R F L G N Y F . . . . . D N W G Q G T L V T V S S |
| (SEQ ID NO: 413) | 13A9v3 | L S S L R S E D T A V Y Y C A R F L G N Y F . . . . . D N W G Q G T L V T V S S |
| (SEQ ID NO: 415) | 13A9v4 | L S S L R S E D T A V Y F C A R F L G N Y F . . . . . D N W G Q G T L V T V S S |
| (SEQ ID NO: 417) | 13A9v5 | L S S L R S E D T A V Y F C A R F L G N Y F . . . . . D N W G Q G T L V T V S S |
| (SEQ ID NO: 419) | 13A9v6 | L S S L R S E D T A V Y F C A R F L G N Y F . . . . . D N W G Q G T L V T V S S |
| (SEQ ID NO: 421) | 15F11 | L N S L T S E D S A V Y Y C S R S G E R S N F . . . . D Y W G Q G T T L T V S S |
| (SEQ ID NO: 423) | 15F11v1 | L S S L R S E D T A V Y Y C S R S G E R S N F . . . . D Y W G Q G T L V T V S S |
| (SEQ ID NO: 425) | 15F11v2 | L S S L R S E D T A V Y Y C S R S G E R S N F . . . . D Y W G Q G T L V T V S S |
| (SEQ ID NO: 427) | 15F11v3 | L S S L R S E D T A V Y Y C S R S G E R S N F . . . . D Y W G Q G T L V T V S S |
| (SEQ ID NO: 429) | 15F11v4 | L S S L R S E D T A V Y Y C S R S G E R S N F . . . . D Y W G Q G T L V T V S S |
| (SEQ ID NO: 431) | 15F11v5 | L S S L R S E D T A V Y Y C S R S G E R S N F . . . . D Y W G Q G T L V T V S S |
| (SEQ ID NO: 433) | 15F11v6 | L S S L R S E D T A V Y Y C S R S G E R S N F . . . . D Y W G Q G T L V T V S S |
| (SEQ ID NO: 435) | 6E1.1.12 | L S S L T T E D S A I Y Y C A R H D Y Y G T S G A W F A Y W G R G T L V T V S A |
| (SEQ ID NO: 437) | 18G3 | L N S V T P E D T A T Y Y C A R W R N W A M . . . . . D Y W G L G T S V T V S S |
| (SEQ ID NO: 439) | 12H10 | L N S L T T E D T A T Y Y C S R W S N W S F . . . . . D V W G A G T T V T V S S |

FIG. 14D

CDR sequences according to Kabat definition are underlined

Light chain variable region

| SEQ ID NO | Name | Sequence (positions 1-37, Kabat numbering) |
|---|---|---|
| 348 | 1D5 | E I I L T Q S P T T M A A S P G E K I T I T C S A S S S . . . . I S S H Y L H W Y Q |
| 350 | 1D5v1 | E I V L T Q S P D F Q S V T P K E K V T I T C S A S S S . . . . I S S H Y L H W Y Q |
| 352 | 1D5v2 | E I V L T Q S P D F Q S V T P K E K V T I T C S A S S S . . . . I S S H Y L H W Y Q |
| 354 | 1D5v3 | E I V L T Q S P D F Q S V T P K E K V T I T C S A S S S . . . . I S S H Y L H W Y Q |
| 356 | 1D5v4 | E I V L T Q S P D F Q S V T P K E K V T I T C S A S S S . . . . I S S H Y L H W Y Q |
| 358 | 1D5v5 | E I V L T Q S P D F Q S V T P K E K V T I T C S A S S S . . . . I S S H Y L H W Y Q |
| 360 | 1D5v6 | E I V L T Q S P D F Q S V T P K E K V T I T C S A S S S . . . . I S S H Y L H W Y Q |
| 362 | 1D5v7 | E I V L T Q S P D F Q S V T P K E K V T I T C S A S S S . . . . I S S H Y L H W Y Q |
| 364 | 1D5v8 | E I V L T Q S P D F Q S V T P K E K V T I T C S A S S S . . . . I S S H Y L H W Y Q |
| 366 | 1D5v9 | D I Q L T Q S P S S L S A S V G D R V T I T C S A S S S . . . . I S S H Y L H W Y Q |
| 368 | 1D5v10 | D I Q L T Q S P S S L S A S V G D R V T I T C S A S S S . . . . I S S H Y L H W Y Q |
| 370 | 1D5v11 | D I Q L T Q S P S S L S A S V G D R V T I T C S A S S S . . . . I S S H Y L H W Y Q |
| 372 | 1D5v12 | D I Q L T Q S P S S L S A S V G D R V T I T C S A S S S . . . . I S S H Y L H W Y Q |
| 374 | 1D5v13 | D I Q M T Q S P S S L S A S V G D R V T I T C S A S S S . . . . I S S H Y L H W Y Q |
| 376 | 1D5v14 | D I Q M T Q S P S S L S A S V G D R V T I T C S A S S S . . . . I S S H Y L H W Y Q |
| 378 | 1D5v15 | D I Q M T Q S P S S L S A S V G D R V T I T C S A S S S . . . . I S S H Y L H W Y Q |
| 380 | 1D5v16 | D I Q M T Q S P S S L S A S V G D R V T I T C S A S S S . . . . I S S H Y L H W Y Q |
| 382 | 1D5v17 | D I Q M T Q S P S S L S A S V G D R V T I T C S A S S S . . . . I S S H Y L H W Y Q |
| 384 | 1D5v18 | D I Q L T Q S P S S L S A S V G D R V T I T C S A S S S . . . . I S S H Y L H W Y Q |
| 386 | 1D5v19 | D I Q L T Q S P S S L S A S V G D R V T I T C S A S S S . . . . I S S H Y L H W Y Q |
| 388 | 1D5v20 | D I Q L T Q S P S S L S A S V G D R V T I T C S A S S S . . . . I S S H Y L H W Y Q |
| 390 | 1D5v21 | D I Q L T Q S P S S L S A S V G D R V T I T C S A S S S . . . . I S S H Y L H W Y Q |
| 392 | 1D5v22 | D I Q L T Q S P S S L S A S V G D R V T I T C S A S S S . . . . I S S H Y L H W Y Q |
| 394 | 1D5v23 | D I Q L T Q S P S S L S A S V G D R V T I T C S A S S S . . . . I S S H Y L H W Y Q |
| 396 | 1D5v24 | D I Q L T Q S P S S L S A S V G D R V T I T C S A S S S . . . . I S S H Y L H W Y Q |
| 398 | 1D5v25 | D I Q L T Q S P S S L S A S V G D R V T I T C S A S S S . . . . I S S H Y L H W Y Q |
| 400 | 1D5v26 | D I Q L T Q S P S S L S A S V G D R V T I T C S A S S S . . . . I S S H Y L H W Y Q |
| 402 | 1D5v27 | D I Q L T Q S P S S L S A S V G D R V T I T C S A S S S . . . . I S S H Y L H W Y Q |
| 404 | 1D5v28 | D I Q L T Q S P S S L S A S V G D R V T I T C S A S S S . . . . I S S H Y L H W Y Q |
| 406 | 1D5v29 | D I Q L T Q S P S S L S A S V G D R V T I T C S A S S S . . . . I S S H Y L H W Y Q |
| 408 | 13A9 | D I Q M T Q S P A S L S A S V G E T V T I T C R A S G . . . . . N I H S Y L A W Y Q |
| 410 | 13A9v1 | D I Q M T Q S P S S L S A S V G D R V T I T C R A S G . . . . . N I H S Y L A W Y Q |
| 412 | 13A9v2 | D I Q M T Q S P S S L S A S V G D R V T I T C R A S G . . . . . N I H S Y L A W Y Q |
| 414 | 13A9v3 | D I Q M T Q S P S S L S A S V G D R V T I T C R A S G . . . . . N I H S Y L A W Y Q |
| 416 | 13A9v4 | D I Q M T Q S P S S L S A S V G D R V T I T C R A S G . . . . . N I H S Y L A W Y Q |
| 418 | 13A9v5 | D I Q M T Q S P S S L S A S V G D R V T I T C R A S G . . . . . N I H S Y L A W Y Q |
| 420 | 13A9v6 | D I Q M T Q S P S S L S A S V G D R V T I T C R A S G . . . . . N I H S Y L A W Y Q |
| 422 | 15F11 | E I V L T Q S P T A M A A S P G E K I T I T C S A S S S . . . . I S S N Y L H W Y Q |
| 424 | 15F11v1 | E I V L T Q S P A T L S L S P G E R A T L S C S A S S S . . . . I S S N Y L H W Y Q |
| 426 | 15F11v2 | E I V L T Q S P A T L S L S P G E R A T L S C S A S S S . . . . I S S N Y L H W Y Q |
| 428 | 15F11v3 | E I V L T Q S P A T L S L S P G E R A T L S C S A S S S . . . . I S S N Y L H W Y Q |
| 430 | 15F11v4 | E I V L T Q S P A T L S L S P G E R A T L S C S A S S S . . . . I S S N Y L H W Y Q |
| 432 | 15F11v5 | E I V L T Q S P A T L S L S P G E R A T L S C S A S S S . . . . I S S N Y L H W Y Q |
| 434 | 15F11v6 | E I V L T Q S P A T L S L S P G E R A T L S C S A S S S . . . . I S S N Y L H W Y Q |
| 436 | 6E1.1.12 | D V L M T Q T P L S L P V S L G D Q A S I S C R S S Q H I V H S N E N T Y L E W Y L |
| 438 | 18G3 | D I Q M T Q T P S S L S A S L G D R V T I S C R A N Q . . . . . D I S H Y L N W Y Q |
| 440 | 12H10 | D I Q M T Q T P S S L S V S L G D R V T I N C R A S Q . . . . . D I H N Y F N W Y Q |

FIG. 14E

CDR L2 - Contact
CDR L2 - Kabat

Kabat number: 38 39 40 41 42 43 44 45 46 47 48 49 50 51 52 53 54 54a 55 56 57 58 59 60 61 62 63 64 65 66 67 68 69 70 71 72 73 74 75 76 77 78

| SEQ ID NO | Name | Sequence |
|---|---|---|
| 348 | 1D5 | Q K S G F S P K L L I Y R T S N L A S G V P   A R F S G S G S G T S Y S L T I G T M |
| 350 | 1D5v1 | Q K P D Q S P K L L I Y R T S N L A S G V P   S R F S G S G S G T D Y T L T I N S L |
| 352 | 1D5v2 | Q K P D Q S P K L L I Y R T S N L A S G V P   S R F S G S G S G T D Y T L T I N S L |
| 354 | 1D5v3 | Q K P D Q S P K L L I Y R T S N L A S G V P   S R F S G S G S G T D Y T L T I N S L |
| 356 | 1D5v4 | Q K P D Q S P K L L I Y R T S N L A S G V P   S R F S G S G S G T D Y T L T I N S L |
| 358 | 1D5v5 | Q K P D Q S P K L L I K R T S N L A S G V P   S R F S G S G S G T D F T L T I N S L |
| 360 | 1D5v6 | Q K P D Q S P K L L I K R T S N L A S G V P   S R F S G S G S G T D F T L T I N S L |
| 362 | 1D5v7 | Q K P D Q S P K L L I K R T S N L A S G V P   S R F S G S G S G T D F T L T I N S L |
| 364 | 1D5v8 | Q K P D Q S P K L L I K R T S N L A S G V P   S R F S G S G S G T D F T L T I N S L |
| 366 | 1D5v9 | Q K P G K S P K L L I Y R T S N L A S G V P   S R F S G S G S G T D Y T L T I S S L |
| 368 | 1D5v10 | Q K P G K S P K L L I Y R T S N L A S G V P   S R F S G S G S G T D Y T L T I S S L |
| 370 | 1D5v11 | Q K P G K S P K L L I Y R T S N L A S G V P   S R F S G S G S G T D Y T L T I S S L |
| 372 | 1D5v12 | Q K P G K S P K L L I Y R T S N L A S G V P   S R F S G S G S G T D Y T L T I S S L |
| 374 | 1D5v13 | Q K P G K A P K L L I Y R T S N L A S G V P   S R F S G S G S G T D F T L T I S S L |
| 376 | 1D5v14 | Q K P G K A P K L L I Y R T S N L A S G V P   S R F S G S G S G T D F T L T I S S L |
| 378 | 1D5v15 | Q K P G K A P K L L I Y R T S N L A S G V P   S R F S G S G S G T D F T L T I S S L |
| 380 | 1D5v16 | Q K P G K A P K L L I Y R T S N L A S G V P   S R F S G S G S G T D F T L T I S S L |
| 382 | 1D5v17 | Q K P G K S P K L L I Y R T S N L A S G V P   S R F S G S G S G T D Y T L T I S S L |
| 384 | 1D5v18 | Q K P G K S P K L L I Y R T S N L A S G V P   S R F S G S G S G T D F T L T I S S L |
| 386 | 1D5v19 | Q K P G K S P K L L I Y R T S N L A S G V P   S R F S G S G S G T D Y T L T I S S L |
| 388 | 1D5v20 | Q K P G K S P K L L I Y R T S N L A S G V P   S R F S G S G S G T D Y T L T I S S L |
| 390 | 1D5v21 | Q K P G K S P K L L I Y R T S N L A S G V P   S R F S G S G S G T D Y T L T I S S L |
| 392 | 1D5v22 | Q K P G K S P K L L I Y R T S N L A S G V P   S R F S G S G S G T D Y T L T I S S L |
| 394 | 1D5v23 | Q K P G K S P K L L I Y R T S N L A S G V P   S R F S G S G S G T D Y T L T I S S L |
| 396 | 1D5v24 | Q K P G K S P K L L I Y R T S N L A S G V P   S R F S G S G S G T D Y T L T I S S L |
| 398 | 1D5v25 | Q K P G K S P K L L I Y R T S N L A S G V P   S R F S G S G S G T D Y T L T I S S L |
| 400 | 1D5v26 | Q K P G K S P K L L I Y R T S N L A S G V P   S R F S G S G S G T D Y T L T I S S L |
| 402 | 1D5v27 | Q K P G K S P K L L I Y R T S N L A S G V P   S R F S G S G S G T D Y T L T I S S L |
| 404 | 1D5v28 | Q K P G K S P K L L I Y R T S N L A S G V P   S R F S G S G S G T D Y T L T I S S L |
| 406 | 1D5v29 | Q K P G K S P K L L I Y R T S N L A S G V P   S R F S G S G S G T D Y T L T I S S L |
| 408 | 13A9 | Q K Q G K S P Q L L V Y Y A E T L A D G V P S   R F S G R G S G T Q Y S L K I N S L |
| 410 | 13A9v1 | Q K P G K A P K L L I Y Y A E T L A D G V P S   R F S G S G S G T D F T L T I S S L |
| 412 | 13A9v2 | Q K P G K A P K L L I Y Y A E T L A D G V P S   R F S G S G S G T D F T L T I S S L |
| 414 | 13A9v3 | Q K P G K S P K L L V Y Y A E T L A D G V P S   R F S G S G S G T D Y T L T I S S L |
| 416 | 13A9v4 | Q K P G K S P K L L V Y Y A E T L A D G V P S   R F S G S G S G T D Y T L T I S S L |
| 418 | 13A9v5 | Q K P G K A P K L L I Y Y A E T L A D G V P S   R F S G S G S G T D F T L T I S S L |
| 420 | 13A9v6 | Q K P G K S P K L L V Y Y A E T L A D G V P S   R F S G S G S G T D Y T L T I S S L |
| 422 | 15F11 | Q K P G F S P K L L I Y R T S N L A S G V P   A R F S G S G S G T S Y S L T I G P M |
| 424 | 15F11v1 | Q K P G Q A P R L L I Y R T S N L A S G I P   A R F S G S G S G T D F T L T I S S L |
| 426 | 15F11v2 | Q K P G Q A P R L L I Y R T S N L A S G I P   A R F S G S G S G T D F T L T I S S L |
| 428 | 15F11v3 | Q K P G Q S P R L L I Y R T S N L A S G V P   A R F S G S G S G T D Y T L T I S S L |
| 430 | 15F11v4 | Q K P G Q S P R L L I Y R T S N L A S G V P   A R F S G S G S G T D Y T L T I S S L |
| 432 | 15F11v5 | Q K P G Q A P R L L I Y R T S N L A S G I P   A R F S G S G S G T D F T L T I S S L |
| 434 | 15F11v6 | Q K P G Q S P R L L I Y R T S N L A S G V P   A R F S G S G S G T D Y T L T I S S L |
| 436 | 6E1.1.12 | Q K P G Q S P K L L I Y K V S N R F   S G V P D R F S G S G S G T D F T L K I S R V |
| 438 | 18G3 | Q K P D G A V K L L I Y Y T S R I H S G V P S   R F S G S G S G T D Y S L T I A N L |
| 440 | 12H10 | Q K P D G T I K L L I Y Y T S R F H S G V P S   R F S G S G S G T D Y S L T I S N L |

FIG. 14F

|  | Kabat number | 79 80 81 82 83 84 85 86 87 88 89 90 91 92 93 94 95 96 97 98 99 100 101 102 103 104 105 106 107 |
|---|---|---|
| (SEQ ID NO: 348) | 1D5 | E A E D V A T Y Y C Q Q G S S L P L T F G A G T K V E I K |
| (SEQ ID NO: 350) | 1D5v1 | E A E D A A T Y Y C Q Q G S S L P L T F G Q G T K V E I K |
| (SEQ ID NO: 352) | 1D5v2 | E A E D A A T Y Y C Q Q G S S L P L T F G Q G T K V E I K |
| (SEQ ID NO: 354) | 1D5v3 | E A E D A A T Y Y C Q Q G S S L P L T F G Q G T K V E I K |
| (SEQ ID NO: 356) | 1D5v4 | E A E D A A T Y Y C Q Q G S S L P L T F G Q G T K V E I K |
| (SEQ ID NO: 358) | 1D5v5 | E A E D A A T Y Y C Q Q G S S L P L T F G Q G T K V E I K |
| (SEQ ID NO: 360) | 1D5v6 | E A E D A A T Y Y C Q Q G S S L P L T F G Q G T K V E I K |
| (SEQ ID NO: 362) | 1D5v7 | E A E D A A T Y Y C Q Q G S S L P L T F G Q G T K V E I K |
| (SEQ ID NO: 364) | 1D5v8 | E A E D A A T Y Y C Q Q G S S L P L T F G Q G T K V E I K |
| (SEQ ID NO: 366) | 1D5v9 | Q P E D F A T Y Y C Q Q G S S L P L T F G Q G T K V E I K |
| (SEQ ID NO: 368) | 1D5v10 | Q P E D F A T Y Y C Q Q G S S L P L T F G Q G T K V E I K |
| (SEQ ID NO: 370) | 1D5v11 | Q P E D F A T Y Y C Q Q G S S L P L T F G Q G T K V E I K |
| (SEQ ID NO: 372) | 1D5v12 | Q P E D F A T Y Y C Q Q G S S L P L T F G Q G T K V E I K |
| (SEQ ID NO: 374) | 1D5v13 | Q P E D F A T Y Y C Q Q G S S L P L T F G Q G T K V E I K |
| (SEQ ID NO: 376) | 1D5v14 | Q P E D F A T Y Y C Q Q G S S L P L T F G Q G T K V E I K |
| (SEQ ID NO: 378) | 1D5v15 | Q P E D F A T Y Y C Q Q G S S L P L T F G Q G T K V E I K |
| (SEQ ID NO: 380) | 1D5v16 | Q P E D F A T Y Y C Q Q G S S L P L T F G Q G T K V E I K |
| (SEQ ID NO: 382) | 1D5v17 | Q P E D F A T Y Y C Q Q G S S L P L T F G Q G T K V E I K |
| (SEQ ID NO: 384) | 1D5v18 | Q P E D F A T Y Y C Q Q G S S L P L T F G Q G T K V E I K |
| (SEQ ID NO: 386) | 1D5v19 | Q P E D F A T Y Y C Q Q G S S L P L T F G Q G T K V E I K |
| (SEQ ID NO: 388) | 1D5v20 | Q P E D F A T Y Y C Q Q G S S L P L T F G Q G T K V E I K |
| (SEQ ID NO: 390) | 1D5v21 | Q P E D F A T Y Y C Q Q G S S L P L T F G Q G T K V E I K |
| (SEQ ID NO: 392) | 1D5v22 | Q P E D F A T Y Y C Q Q G S S L P L T F G Q G T K V E I K |
| (SEQ ID NO: 394) | 1D5v23 | Q P E D F A T Y Y C Q Q G S S L P L T F G Q G T K V E I K |
| (SEQ ID NO: 396) | 1D5v24 | Q P E D F A T Y Y C Q Q G S S L P L T F G Q G T K V E I K |
| (SEQ ID NO: 398) | 1D5v25 | Q P E D F A T Y Y C Q Q G S S L P L T F G Q G T K V E I K |
| (SEQ ID NO: 400) | 1D5v26 | Q P E D F A T Y Y C Q Q G S S L P L T F G Q G T K V E I K |
| (SEQ ID NO: 402) | 1D5v27 | Q P E D F A T Y Y C Q Q G S S L P L T F G Q G T K V E I K |
| (SEQ ID NO: 404) | 1D5v28 | Q P E D F A T Y Y C Q Q G S S L P L T F G Q G T K V E I K |
| (SEQ ID NO: 406) | 1D5v29 | Q P E D F A T Y Y C Q Q G S S L P L T F G Q G T K V E I K |
| (SEQ ID NO: 408) | 13A9 | Q P E D F G S Y F C Q Q F W T T P Y T F G G G T K V E I K |
| (SEQ ID NO: 410) | 13A9v1 | Q P E D F A T Y Y C Q Q F W T T P Y T F G Q G T K V E I K |
| (SEQ ID NO: 412) | 13A9v2 | Q P E D F A T Y Y C Q Q F W T T P Y T F G Q G T K V E I K |
| (SEQ ID NO: 414) | 13A9v3 | Q P E D F A T Y F C Q Q F W T T P Y T F G Q G T K V E I K |
| (SEQ ID NO: 416) | 13A9v4 | Q P E D F A T Y F C Q Q F W T T P Y T F G Q G T K V E I K |
| (SEQ ID NO: 418) | 13A9v5 | Q P E D F A T Y Y C Q Q F W T T P Y T F G Q G T K V E I K |
| (SEQ ID NO: 420) | 13A9v6 | Q P E D F A T Y F C Q Q F W T T P Y T F G Q G T K V E I K |
| (SEQ ID NO: 422) | 15F11 | E A E D V A T Y Y C Q Q G G S L P L T F G A G T K V E I K |
| (SEQ ID NO: 424) | 15F11v1 | E P E D F A V Y Y C Q Q G G S L P L T F G Q G T K V E I K |
| (SEQ ID NO: 426) | 15F11v2 | E P E D F A V Y Y C Q Q G G S L P L T F G Q G T K V E I K |
| (SEQ ID NO: 428) | 15F11v3 | E P E D F A V Y Y C Q Q G G S L P L T F G Q G T K V E I K |
| (SEQ ID NO: 430) | 15F11v4 | E P E D F A V Y Y C Q Q G G S L P L T F G Q G T K V E I K |
| (SEQ ID NO: 432) | 15F11v5 | E P E D F A V Y Y C Q Q G G S L P L T F G Q G T K V E I K |
| (SEQ ID NO: 434) | 15F11v6 | E P E D F A V Y Y C Q Q G G S L P L T F G Q G T K V E I K |
| (SEQ ID NO: 436) | 6E1.1.12 | E A E D L G V Y Y C F Q G S H V P W T F G G G T K V E I K |
| (SEQ ID NO: 438) | 18G3 | E Q E D V A T Y F C Q Q G N T P P T F G G G T K V E I K |
| (SEQ ID NO: 440) | 12H10 | E E E D I A T Y F C Q Q G N S L P P T F G G G T K L E I K |

FIG. 16A

Interference — HCC1534 (MICA*004) (AMO1/8C5)

| 1D5 ug/mL \ 13A9 ug/mL | 10 | 2.5 | 0.625 | 0.15625 | 0.039063 | 0.009766 | 0.002441 | None |
|---|---|---|---|---|---|---|---|---|
| 10 | 27% | 28% | 29% | 33% | 31% | 27% | 22% | 23% |
| 2.5 | 26% | 31% | 34% | 36% | 33% | 31% | 28% | 22% |
| 0.625 | 18% | 30% | 30% | 33% | 36% | 30% | 26% | 23% |
| 0.15625 | 27% | 29% | 34% | 37% | 34% | 26% | 27% | 25% |
| 0.0390625 | 24% | 31% | 33% | 36% | 34% | 32% | 23% | 19% |
| 0.009765625 | 22% | 28% | 31% | 34% | 35% | 29% | 25% | 14% |
| 0.002441406 | 21% | 29% | 30% | 34% | 32% | 30% | 18% | 13% |
| None | 22% | 27% | 31% | 32% | 29% | 28% | 17% | 9% |

| 1D5 ug/mL \ 6E1 ug/mL | 10 | 2.5 | 0.625 | 0.15625 | 0.039063 | 0.009766 | 0.002441 | None |
|---|---|---|---|---|---|---|---|---|
| 10 | 34% | 36% | 45% | 42% | 38% | 31% | 26% | 13% |
| 2.5 | 32% | 33% | 36% | 37% | 36% | 33% | 21% | 14% |
| 0.625 | 25% | 35% | 31% | 34% | 31% | 25% | 22% | 6% |
| 0.15625 | 23% | 24% | 29% | 30% | 24% | 15% | 12% | 0% |
| 0.0390625 | 23% | 17% | 19% | 20% | 18% | 14% | 6% | -7% |
| 0.009765625 | 10% | 17% | 16% | 16% | 15% | 3% | -8% | -8% |
| 0.002441406 | 12% | 21% | 17% | 24% | 13% | 8% | -4% | -4% |
| None | 9% | 15% | 14% | 12% | 7% | 6% | -12% | -13% |

| 13A9 ug/mL \ 6E1 ug/mL | 10 | 2.5 | 0.625 | 0.15625 | 0.039063 | 0.009766 | 0.002441 | None |
|---|---|---|---|---|---|---|---|---|
| 10 | 34% | 39% | 30% | 30% | 26% | 16% | 13% | 22% |
| 2.5 | 31% | 35% | 42% | 33% | 21% | 18% | 29% | 19% |
| 0.625 | 27% | 35% | 29% | 27% | 24% | 19% | 20% | 13% |
| 0.15625 | 24% | 20% | 28% | 19% | 19% | 13% | 10% | 14% |
| 0.0390625 | 18% | 21% | 25% | 24% | 17% | 14% | 12% | 11% |
| 0.009765625 | 17% | 30% | 21% | 25% | 21% | 17% | 16% | 8% |
| 0.002441406 | 11% | 20% | 18% | 24% | 22% | 27% | 15% | 12% |
| None | 19% | 20% | 23% | 19% | 17% | 13% | 10% | 7% |

FIG. 16B

Interference

MEL-JUSO (MICA*008) (AMO18C5)

| 1D5 ug/mL > | 10 | 2.5 | 0.625 | 0.15625 | 0.039063 | 0.009766 | 0.002441 | None |
|---|---|---|---|---|---|---|---|---|
| 13A9 ug/mL V | | | | | | | | |
| 10 | -8% | -1% | -4% | 4% | 15% | 17% | 12% | 20% |
| 2.5 | 2% | -3% | 14% | 10% | 11% | 20% | 24% | 15% |
| 0.625 | -2% | 9% | 11% | 8% | 15% | 20% | 20% | 14% |
| 0.15625 | 4% | 3% | 18% | 15% | 9% | 8% | 15% | 12% |
| 0.0390625 | 0% | 7% | 8% | 11% | 14% | 11% | 14% | 10% |
| 0.009765625 | 5% | 12% | 8% | 13% | 15% | 16% | 12% | 10% |
| 0.002441406 | -1% | 10% | 7% | 7% | 16% | 21% | 12% | 11% |
| None | 14% | 11% | 8% | 7% | 13% | 14% | 14% | 6% |

| 1D5 ug/mL > | 10 | 2.5 | 0.625 | 0.15625 | 0.039063 | 0.009766 | 0.002441 | None |
|---|---|---|---|---|---|---|---|---|
| 6E1 ug/mL V | | | | | | | | |
| 10 | 11% | 17% | N/A | 14% | 13% | 15% | 12% | 8% |
| 2.5 | 13% | 13% | 6% | 14% | 15% | 19% | 16% | 9% |
| 0.625 | 7% | 12% | 15% | 14% | 16% | 17% | 20% | 6% |
| 0.15625 | 14% | 6% | 11% | 12% | 8% | 7% | 11% | 1% |
| 0.0390625 | 14% | 9% | 3% | 13% | 8% | 5% | 3% | 6% |
| 0.009765625 | -2% | 9% | 1% | 3% | 19% | 6% | 1% | 6% |
| 0.002441406 | -10% | 14% | 20% | 22% | 28% | 11% | 10% | 9% |
| None | 12% | 32% | 7% | 4% | 4% | 9% | -10% | -6% |

| 13A9 ug/mL > | 10 | 2.5 | 0.625 | 0.15625 | 0.039063 | 0.009766 | 0.002441 | None |
|---|---|---|---|---|---|---|---|---|
| 6E1 ug/mL V | | | | | | | | |
| 10 | 13% | -3% | 15% | 7% | 5% | 9% | 8% | 6% |
| 2.5 | 6% | 3% | 7% | 4% | 9% | 15% | 13% | 7% |
| 0.625 | 13% | 12% | 10% | 16% | 21% | 19% | 13% | 9% |
| 0.15625 | 4% | 11% | 10% | 19% | 13% | 16% | 10% | 11% |
| 0.0390625 | 6% | 18% | 16% | 17% | 25% | 22% | 15% | 7% |
| 0.009765625 | 2% | 9% | 17% | 21% | 20% | 21% | 20% | 13% |
| 0.002441406 | 1% | 15% | 19% | 20% | 24% | 24% | 15% | 11% |
| None | 11% | 14% | 17% | 19% | 20% | 23% | 14% | 8% |

FIG. 16C

Interference

| 1D5 ug/mL> | HCC1534 (MICB*005) (236511/7E3) | | | | | | | |
|---|---|---|---|---|---|---|---|---|
| 13A9 ug/mL V | 10 | 2.5 | 0.625 | 0.15625 | 0.039063 | 0.009766 | 0.002441 | None |
| 10 | 18% | 28% | 18% | 33% | 35% | 38% | 31% | 36% |
| 2.5 | 20% | 18% | 34% | 32% | 36% | 41% | 46% | 28% |
| 0.625 | 13% | 30% | 25% | 35% | 38% | 33% | 46% | 36% |
| 0.15625 | 26% | 25% | 33% | 35% | 33% | 33% | 37% | 41% |
| 0.0390625 | 31% | 33% | 32% | 26% | 34% | 29% | 36% | 35% |
| 0.009765625 | 29% | 30% | 18% | 34% | 32% | 39% | 32% | 23% |
| 0.002441406 | 15% | 31% | 35% | 31% | 27% | 31% | 25% | 22% |
| None | 25% | 28% | 33% | 34% | 31% | 25% | 24% | 15% |

| 1D5 ug/mL> | | | | | | | | |
|---|---|---|---|---|---|---|---|---|
| 6E1 ug/mL V | 10 | 2.5 | 0.625 | 0.15625 | 0.039063 | 0.009766 | 0.002441 | None |
| 10 | 41% | 38% | 29% | 49% | 43% | 33% | 31% | 24% |
| 2.5 | 44% | 43% | 40% | 43% | 44% | 41% | 29% | 14% |
| 0.625 | 39% | 43% | 39% | 42% | 43% | 24% | 35% | 25% |
| 0.15625 | 35% | 37% | 36% | 36% | 30% | 15% | 17% | 5% |
| 0.0390625 | 31% | 31% | 12% | 36% | 14% | 12% | 4% | 7% |
| 0.009765625 | 28% | 17% | 27% | 27% | 27% | 13% | -1% | -2% |
| 0.002441406 | 8% | 20% | 24% | 24% | 30% | 13% | 8% | -2% |
| None | 14% | 16% | 17% | 5% | 11% | 1% | -8% | -14% |

| 13A9 ug/mL> | | | | | | | | |
|---|---|---|---|---|---|---|---|---|
| 6E1 ug/mL V | 10 | 2.5 | 0.625 | 0.15625 | 0.039063 | 0.009766 | 0.002441 | None |
| 10 | 31% | 31% | 31% | 37% | 36% | 27% | 25% | 28% |
| 2.5 | 32% | 23% | 26% | 32% | 33% | 38% | 32% | 22% |
| 0.625 | 25% | 28% | 29% | 28% | 30% | 26% | 28% | 20% |
| 0.15625 | 29% | 25% | 24% | 30% | 30% | 24% | 22% | 19% |
| 0.0390625 | 27% | 31% | 31% | 26% | 31% | 19% | 22% | 10% |
| 0.009765625 | 18% | 23% | 28% | 33% | 29% | 26% | 19% | 13% |
| 0.002441406 | 23% | 26% | 27% | 28% | 29% | 17% | 15% | 7% |
| None | 21% | 28% | 30% | 33% | 31% | 23% | 15% | 8% |

FIG. 17

| Clone ID | MICA*008 kD (nM) |
|---|---|
| 12H10 | 1.9 |
| 18G3 | 2.6 |
| 1D5 | 0.5 |
| 1G3 | 0.75 |
| 20G11 | 3.8 |
| 2E5.2.3 | 1.8 |
| 32D2 | 4 |
| 3E11 | 2.5 |
| 6E1.1.12 | 6.8 |
| 6F8.7 | 8.4 |
| 7D4.6 | 10 |
| HZ.10A2 | 4.7 |
| HZ.10B4 | 4.6 |
| HZ.10G11 | 0.57 |
| HZ.10G12 | 6 |
| HZ.11H3 | 4.2 |
| HZ.12G2 | 1.2 |
| HZ.13A9 | 3.1 |
| HZ.13G6 | 0.62 |
| HZ.14C1 | 4.9 |
| HZ.15D2 | 1.6 |
| HZ.15E12 | 1.5 |
| HZ.15F11 | 2.1 |
| HZ.15G6 | 1.3 |
| HZ.16E2 | 3.2 |
| HZ.16F11 | 4.8 |

| Clone ID | MICA*008 kD (nM) |
|---|---|
| HZ.18B6 | 1.7 |
| HZ.19E8 | 0.89 |
| HZ.19H3 | 3.6 |
| HZ.20B2 | 4.8 |
| HZ.2C11 | 1.7 |
| HZ.2D10 | 1 |
| HZ.2H4 | 0.47 |
| HZ.2H7 | 1.7 |
| HZ.3B1 | 1.6 |
| HZ.3B10 | 0.52 |
| HZ.3B4 | 2.1 |
| HZ.3C9 | 3.9 |
| HZ.3E8 | 1.8 |
| HZ.3F2 | 2.5 |
| HZ.3F7 | 1.8 |
| HZ.3G4 | 1.9 |
| HZ.3H5 | 1.8 |
| HZ.4H6 | 2.4 |
| HZ.5C5 | 3.5 |
| HZ.6A11 | 2.8 |
| HZ.6A7 | 1.3 |
| HZ.6G2 | 2.1 |
| HZ.7A6 | 4.6 |
| HZ.7A9 | 4.4 |
| HZ.7G11 | 3.5 |
| HZ.9H10 | 6.2 |

FIG. 19A

| Clone ID | Bin 1 (1D5-like) | Bin2 | Bin 3 (6E1-like) |
|---|---|---|---|
| 12H10 | ▨ | | |
| 18G3 | ▨ | | |
| 1D5 | ▨ | | |
| 1G3 | ▨ | | |
| 20G11 | ▨ | | |
| 32D2 | ▨ | | |
| 3E11 | ▨ | | |
| 6F8.7 | ▨ | | |
| HZ.10G11 | ▨ | | |
| HZ.10G12 | ▨ | | |
| HZ.12G2 | ▨ | | |
| HZ.13A9 | ▨ | | |
| HZ.15E12 | ▨ | | |
| HZ.15F11 | ▨ | | |
| HZ.18B6 | ▨ | | |
| HZ.19E8 | ▨ | | |
| HZ.20B2 | ▨ | | |
| HZ.2C11 | ▨ | | |
| HZ.2D10 | ▨ | | |
| HZ.2H7 | ▨ | | |
| HZ.3B1 | ▨ | | |
| HZ.3B10 | ▨ | | |
| HZ.3E8 | ▨ | | |
| HZ.3F2 | ▨ | | |
| HZ.3F7 | ▨ | | |
| HZ.3G4 | ▨ | | |
| HZ.3H5 | ▨ | | |
| HZ.5C5 | ▨ | | |
| HZ.6A11 | ▨ | | |
| HZ.6G2 | ▨ | | |
| HZ.7A6 | ▨ | | |
| HZ.7G11 | ▨ | | |
| HZ.9H10 | ▨ | | |
| 7D4.6 | | ■ | |
| HZ.10B4 | | ■ | |
| HZ.3B4 | | ■ | |
| HZ.4H6 | | ■ | |
| 2E5.2.3 | | | ■ |
| 6E1.1.12 | | | ■ |
| HZ.10A2 | | | ■ |
| HZ.11H3 | | | ■ |
| HZ.13G6 | | | ■ |
| HZ.14C1 | | | ■ |
| HZ.15D2 | | | ■ |
| HZ.15G6 | | | ■ |
| HZ.16E2 | | | ■ |
| HZ.16F11 | | | ■ |
| HZ.19H3 | | | ■ |
| HZ.2H4 | | | ■ |
| HZ.3C9 | | | ■ |
| HZ.6A7 | | | ■ |
| HZ.7A9 | | | ■ |

FIG. 20

Antigen → Create N-linked glycosylation site (N-X-S/T) → Glyco-14 (GVS→NVS)

+ Antibody

ELISA or Biacore → Binding to each glyco-engineered antigen variant

| 11 | 12 | 13 | 14 | 15 | 16 | 17 |
|----|----|----|----|----|----|----|
| +  | +  | +  | -  | +  | -  | +  |

→ Epitope is defined as site(s) that cannot be bound when masked by glycosylation MICA α3 domain shows Glyco11-Glyco17, the 7 distinct and individually engineered glycosites

FIG. 21B

| | Sample | | | | | | | | Tryptic Peptide | |
|---|---|---|---|---|---|---|---|---|---|---|
| | WT | 11 | 12 | 13 | 14 | 15 | 16 | 17 | | |
| Site | | N3 | | | | | | | GSNR (sample 11) | (SEQ ID NO: 444) |
| % Fucosylation | | | | | | | | | | |
| % Afucosylation | | N/C | | | | | | | | |
| Total Glycosylation | | | | | | | | | | |
| Site | N9 | N11 | N9 | N9 | N9 | N9 | N9 | N9 | TVPPMVNVTR (all samples) | (SEQ ID NO: 445) |
| % Fucosylation | 59% | 64% | 48% | 65% | 75% | 64% | 64% | 75% | | |
| % Afucosylation | 20% | 36% | 55% | 31% | 25% | 36% | 36% | 25% | | |
| Total Glycosylation | 79% | >99% | 98% | 96% | >99% | >99% | >99% | >99% | | |
| Site | N19 | N21 | N14,N19 | N19 | N19 | N19 | N19 | N19 | SNASEGNTYTCR (sample 12) | (SEQ ID NO: 446) |
| % Fucosylation | 82% | 91% | 55% | 85% | 83% | 83% | 54% | 94% | SEASEGNTYTCR (all other samples) | (SEQ ID NO: 447) |
| % Afucosylation | 15% | 8% | 43% | 14% | 16% | 17% | 45% | 6% | | |
| Total Glycosylation | 98% | >99% | >99% | >99% | >99% | >99% | >99% | >99% | | |
| Site | | | | N33 | | | | | NTLTNR (sample 13) | (SEQ ID NO: 448) |
| % Fucosylation | | | | 73% | | | | | | |
| % Afucosylation | | | | 27% | | | | | | |
| Total Glycosylation | | | | >99% | | | | | | |
| Site | N60 | N62 | N61 | N60 | N48,N60 | N47,N60 | N61 | N61 | QDNYFSLSHTQQWGDVLPDGNGTYQTNWATR (sample 14) | (SEQ ID NO: 449) |
| % Fucosylation | | | | | | | | | QDSCSLSHTQQWGDVLPDGNGTYQTNWATR (sample 15) | (SEQ ID NO: 450) |
| % Afucosylation | N/C | N/C | N/C | N/C | N/C | N/C | N/C | N/C | QDSCSLSHTQQWGDVLPDGNGTYQTNWATR (all other samples) | (SEQ ID NO: 451) |
| Total Glycosylation | | | | | | | | | | |
| Site | N86 | N90 | N83 | N88 | N86 | N88 | N78,N86 | N38,N97 | GEEQNFTCYMEHSGNHSTHPVPSGNSR (sample 16) | (SEQ ID NO: 452) |
| % Fucosylation | 49% | 80% | 79% | 65% | 77% | 75% | | 77% | FTCYMEHSGNHSTHPVPSNGSGNSR (sample 17) | (SEQ ID NO: 453) |
| % Afucosylation | 18% | 17% | 19% | 22% | 17% | 19% | N/C | 9% | FTCYMEHSGNHSTHPVPSGNSR (all other samples) | (SEQ ID NO: 454) |
| Total Glycosylation | 68% | 97% | 98% | 87% | 94% | 94% | | 86% | | |
| Site | N191 | N193 | N161 | N191 | N191 | N191 | N191 | N194 | EDYNSTLR (all samples) | (SEQ ID NO: 455) |
| % Fucosylation | 59% | 86% | 94% | 65% | 94% | 75% | 94% | 93% | | |
| % Afucosylation | 26% | 12% | 6% | 26% | 6% | 25% | 6% | 7% | | |
| Total Glycosylation | 85% | >99% | >99% | 95% | >99% | 98% | >99% | >99% | | |

N/C = No coverage
▨ = Glyco-variant site

FIG. 21C

ELISA with Glyco-engineered variants of MICA*008

| | 11 | 12 | 13 | 14 | 15 | 16 | 17 | # Abs in each Bin | >70% shedding inhibition |
|---|---|---|---|---|---|---|---|---|---|
| Bin1 | | | | | | | | 1 | |
| Bin2 | | | | | | | | 21 | 4 |
| Bin3 | | | | | | | | 2 | |
| Bin4 | | | | | | | | 1 | |
| Bin5 | | | | | | | | 17 | 1 |
| Bin6 | | | | | | | | 34 | |
| Bin7 | | | | | | | | 4 | 2 |
| Bin8 | | | | | | | | 5 | |
| Bin9 | | | | | | | | 7 | |
| Bin10 | | | | | | | | 3 | |
| Bin11 | | | | | | | | 1 | |

FIG. 21D

Other glyco-engineered variants

Glyco11 Nterm
Glyco13 I236T
Glyco15 H248N
Glyco14 G243N
Glyco16 R279N
Glyco17 Cterm MICA*008 epitopes that when blocked by an antibody allow the best shedding inhibition 1D5 crystal structure

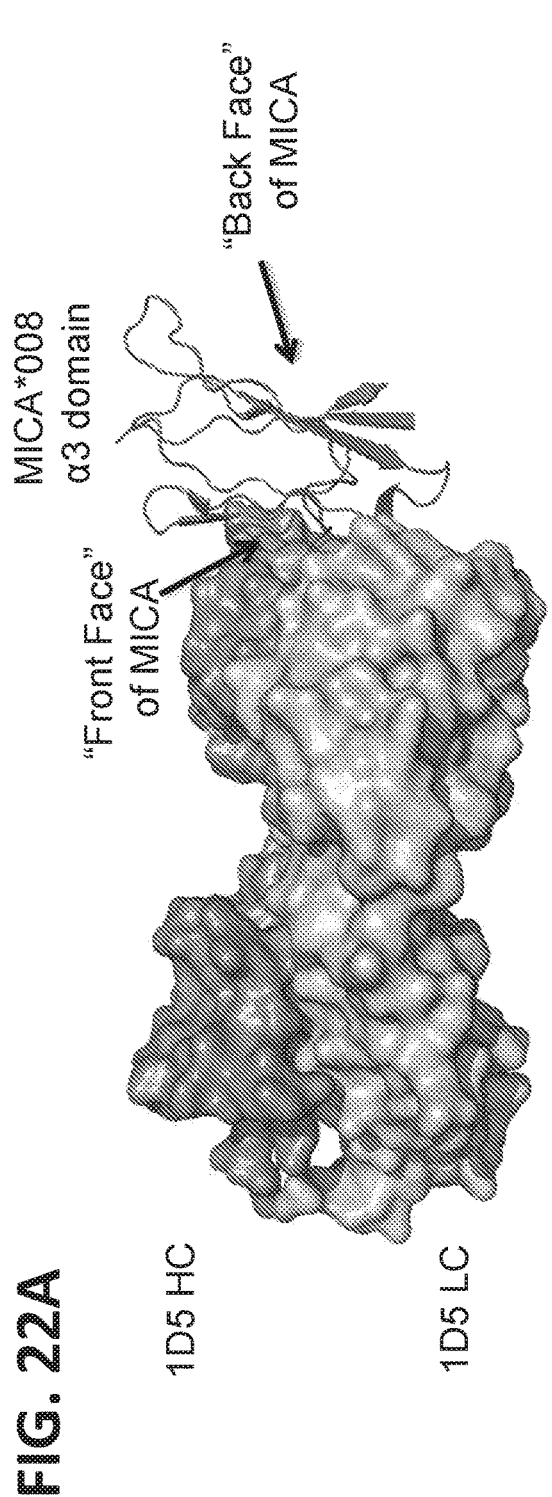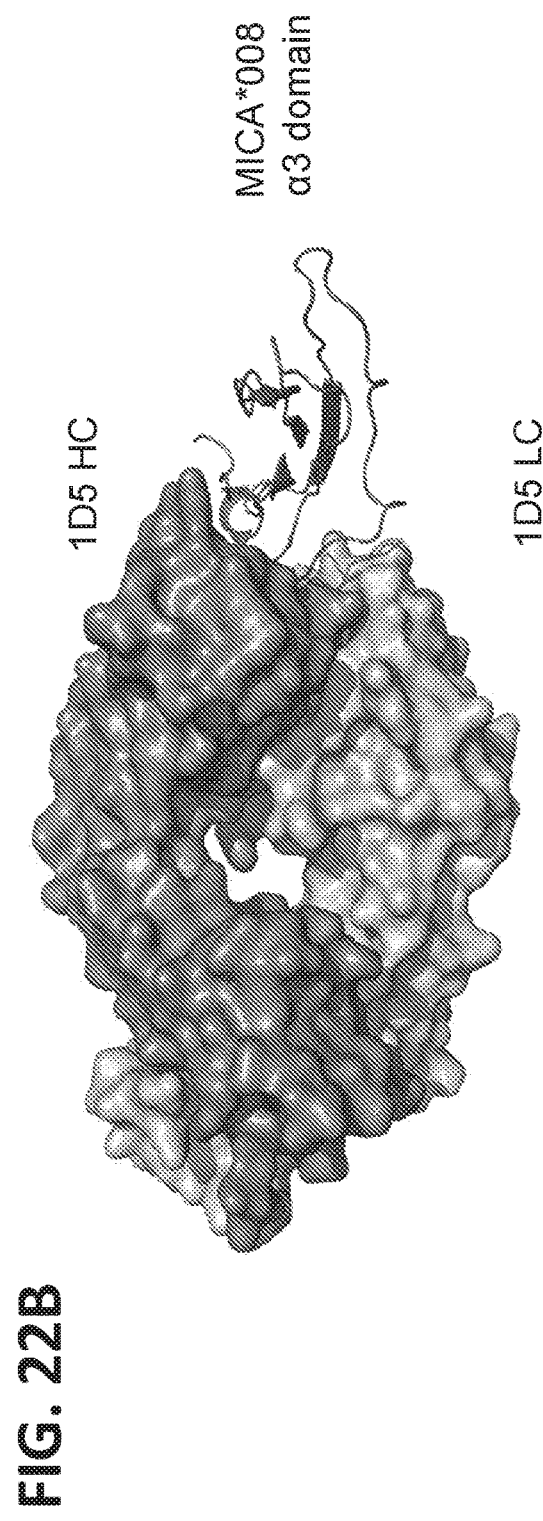

MICA*008 α3 domain

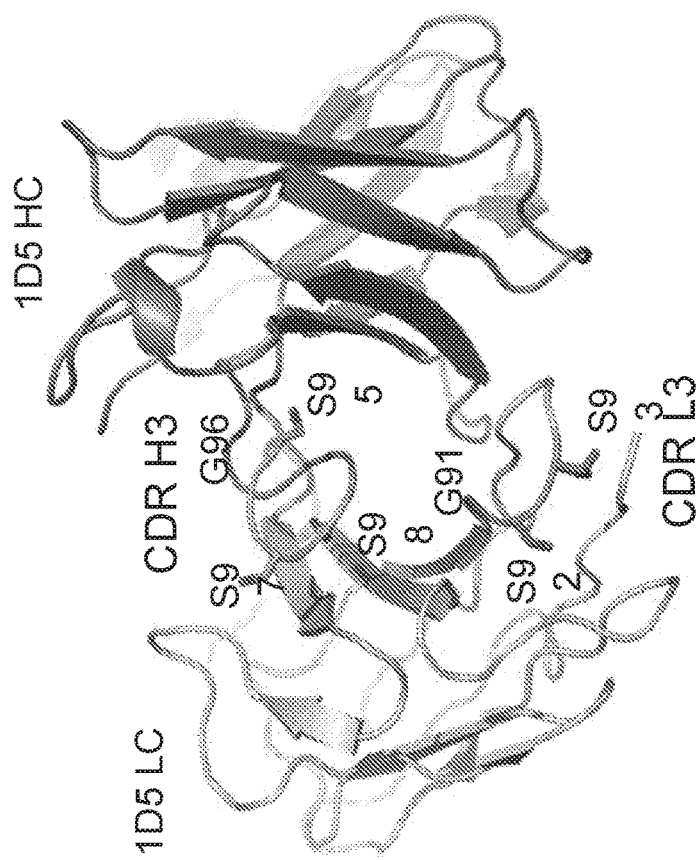
FIG. 27C
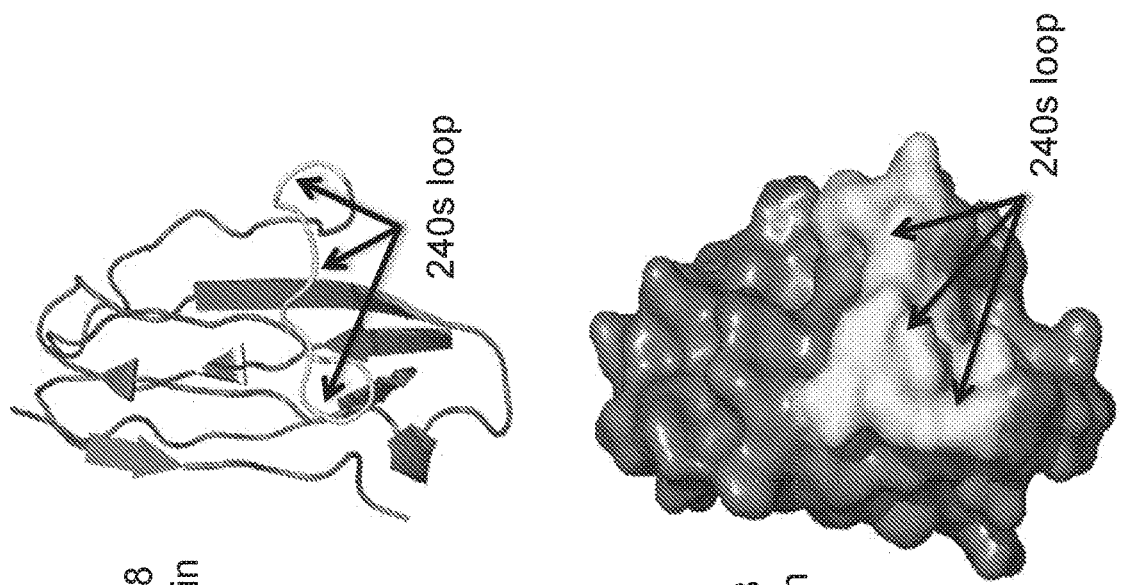
FIG. 27A
MICA*008
α3 domain
FIG. 27B
MICA*008
α3 domain

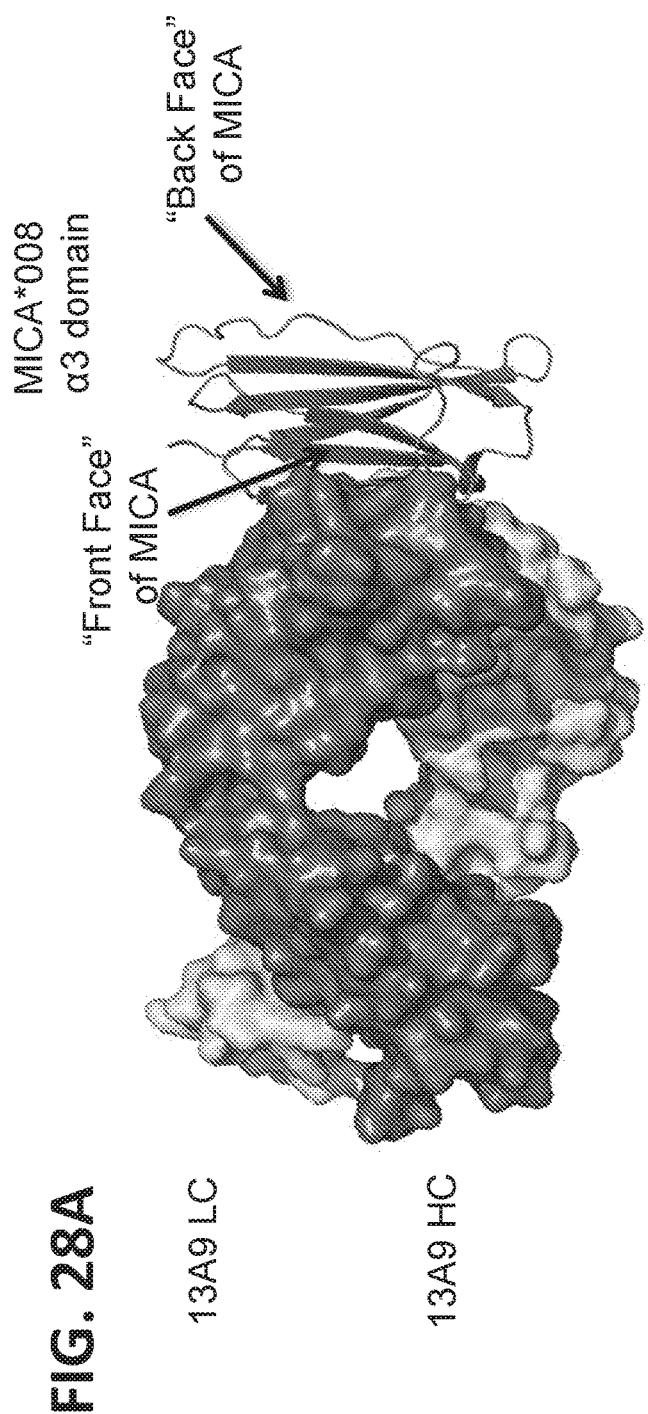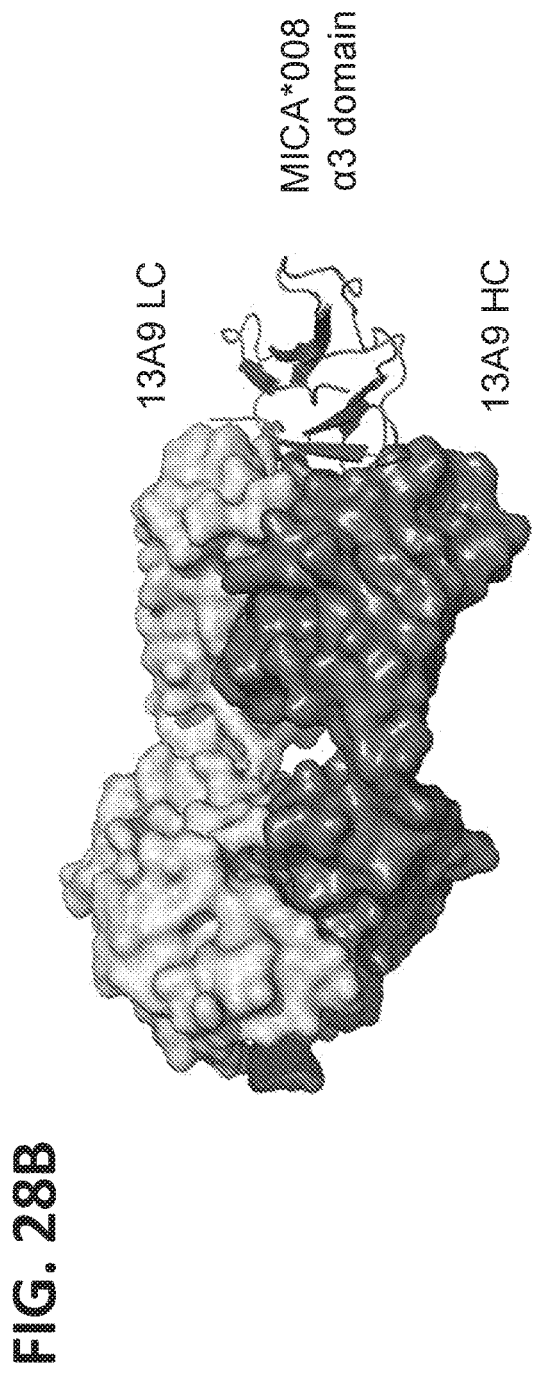
FIG. 28A
FIG. 28B

MICA*008
α3 domain

MICA*008
α3 domain

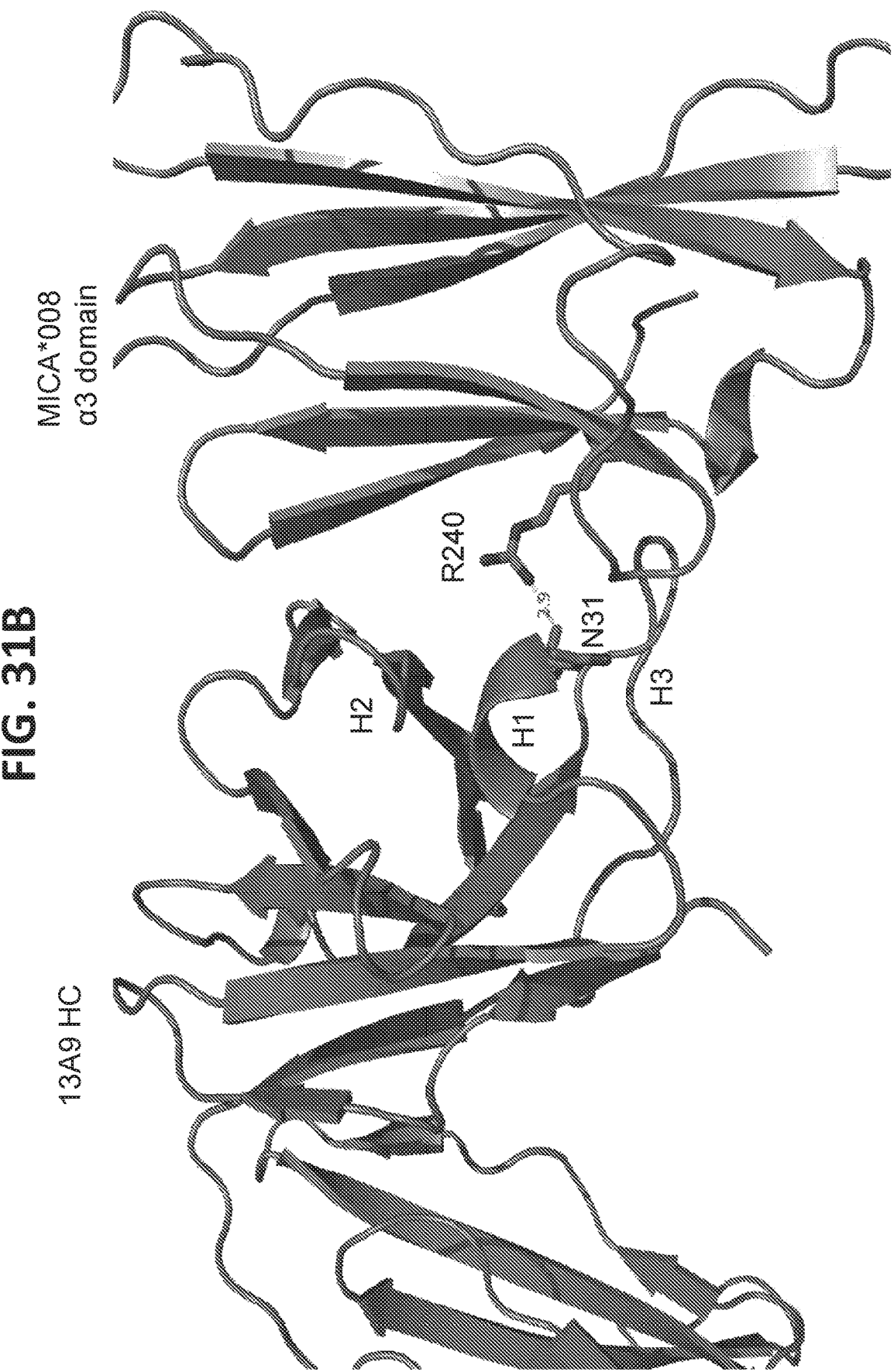

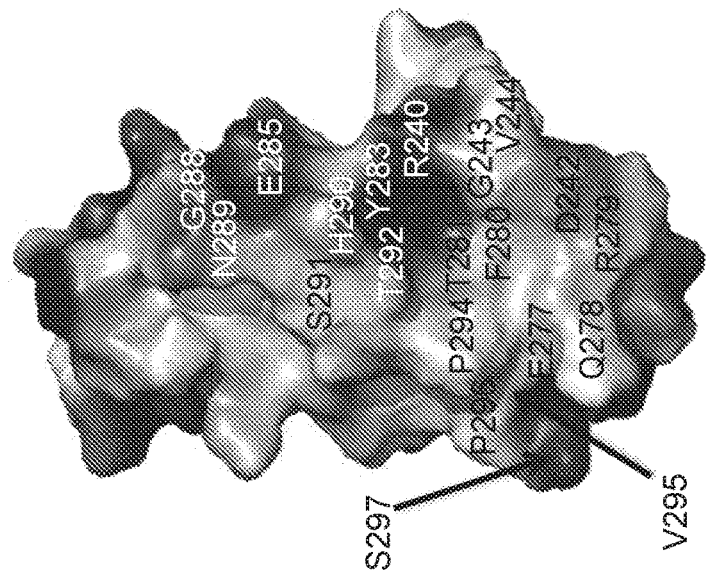
FIG. 32B
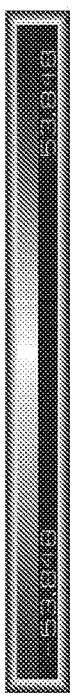
MICA*008 α3 domain viewed from "front face"
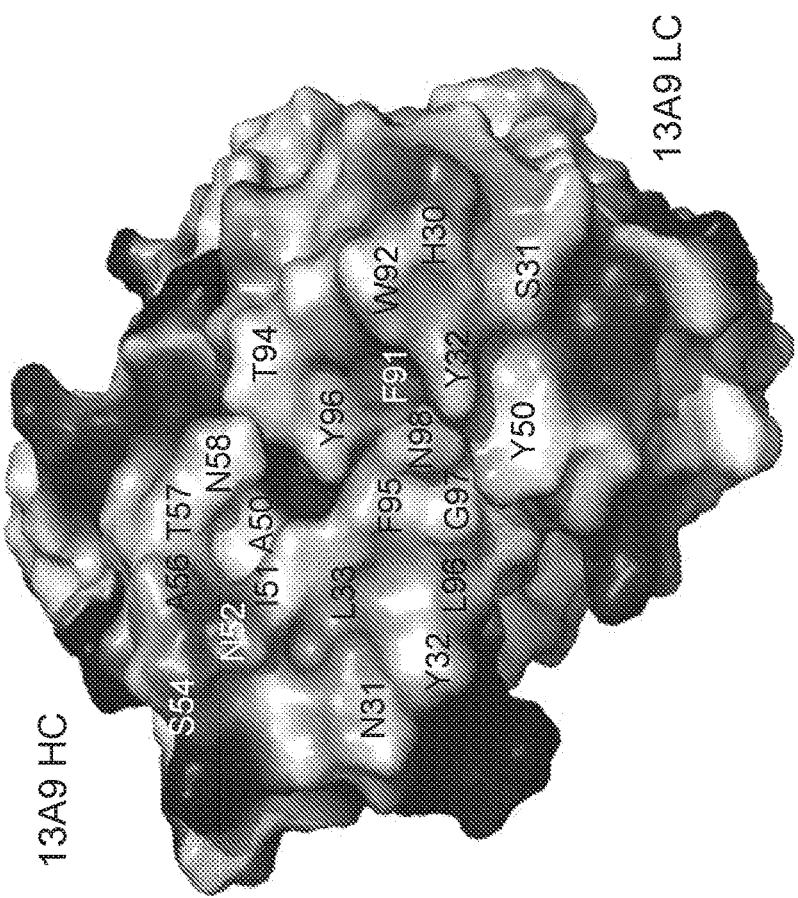
FIG. 32A
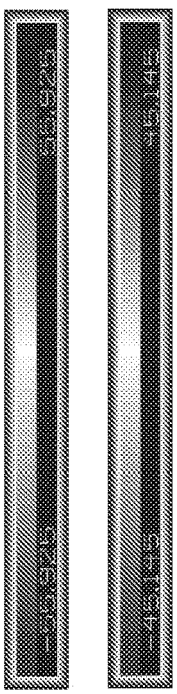
LC
HC MICA*008 α3 domain
288-297
240-245
277-279

MICA*008 α3 domain
288-297
240-245
277-279

MICA*008 α3 domain
H1, H2, H3
L1, L2, L3
13A9 HC
13A9 LC

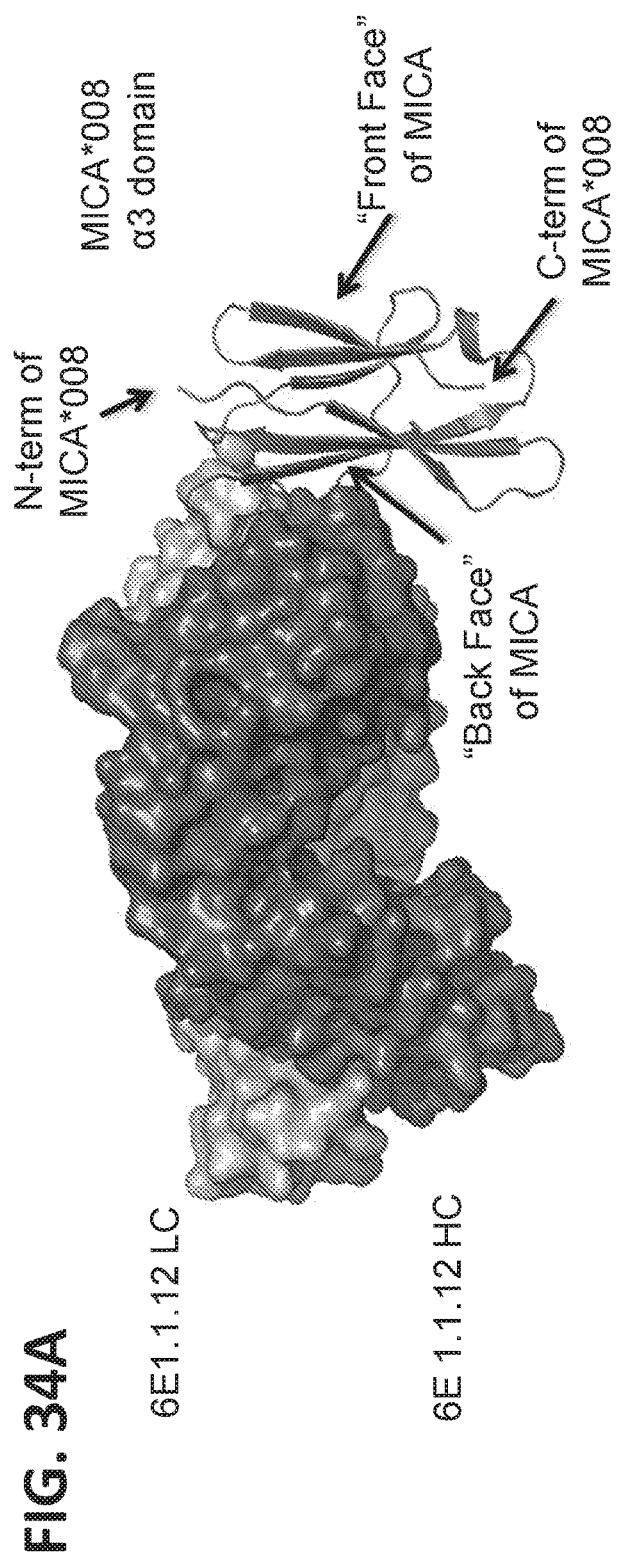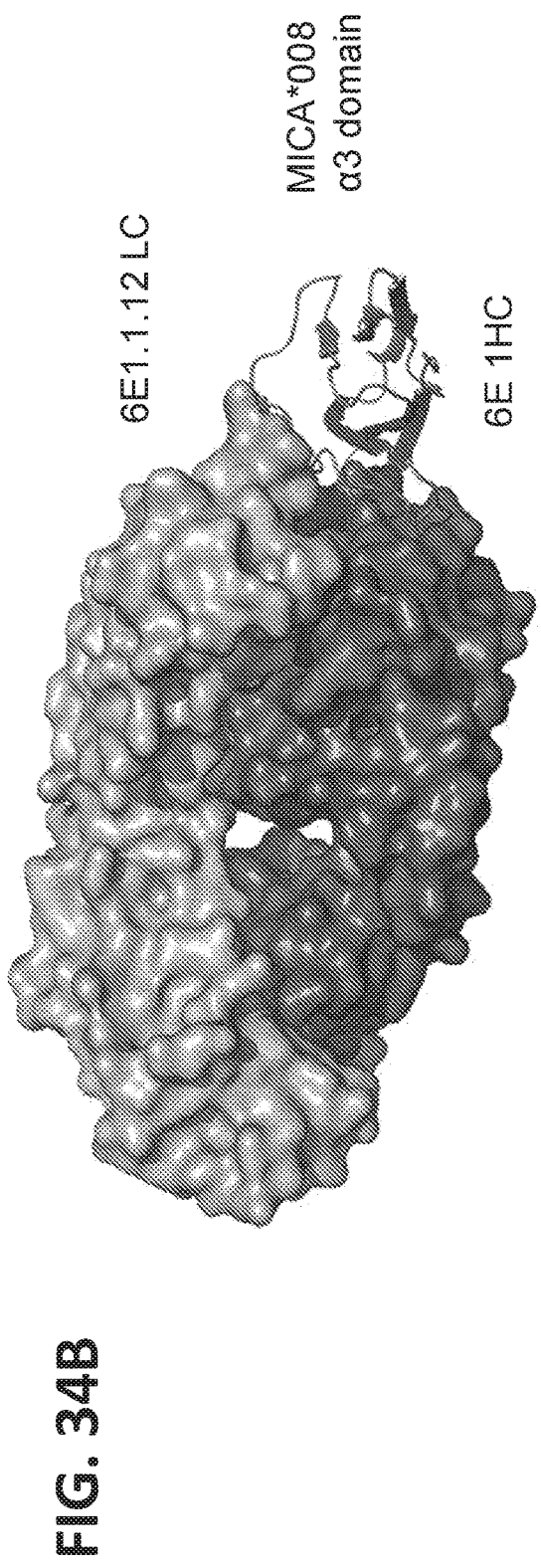
FIG. 34A
FIG. 34B

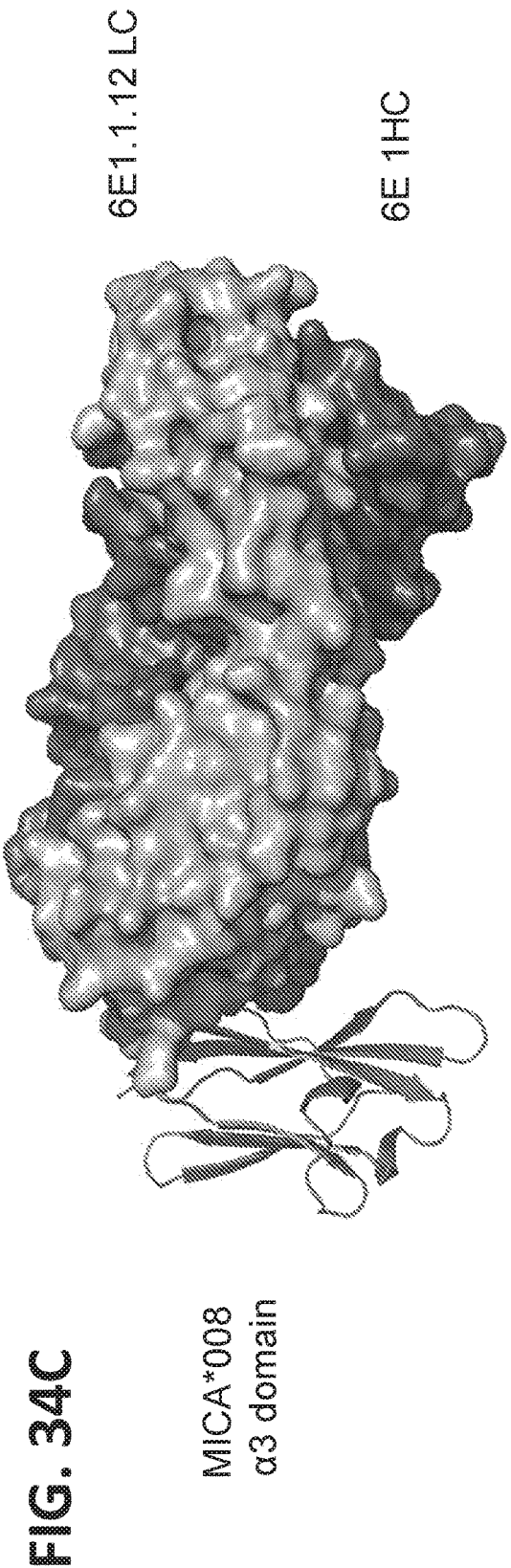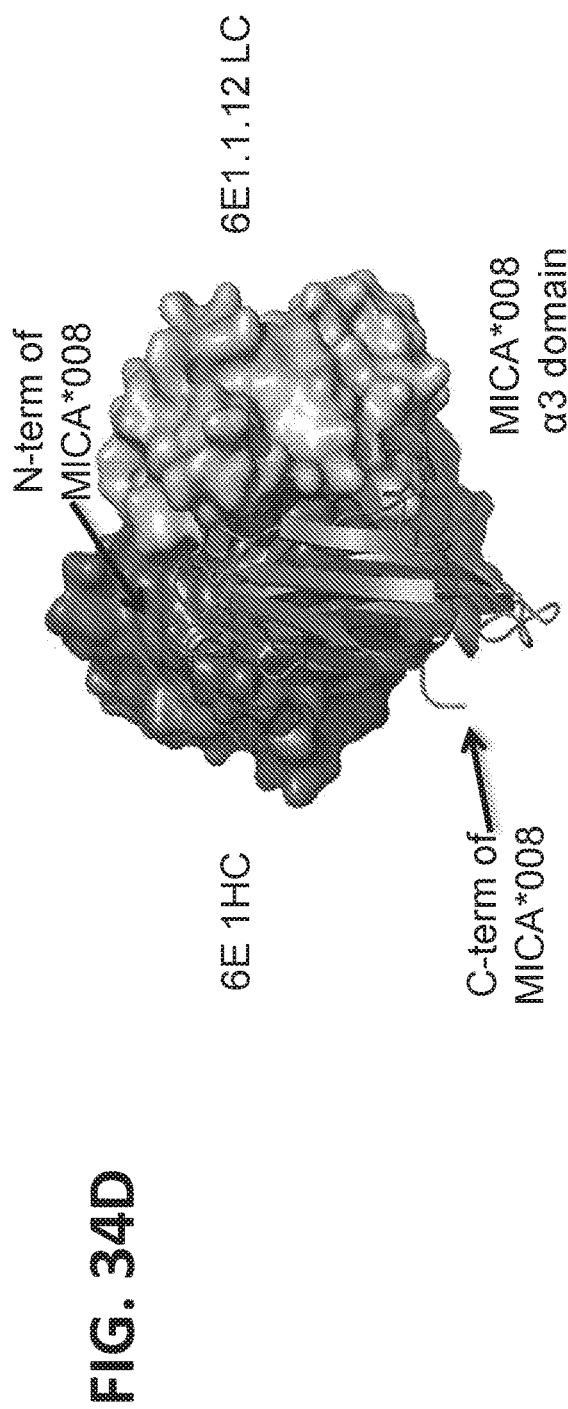
FIG. 34C
FIG. 34D

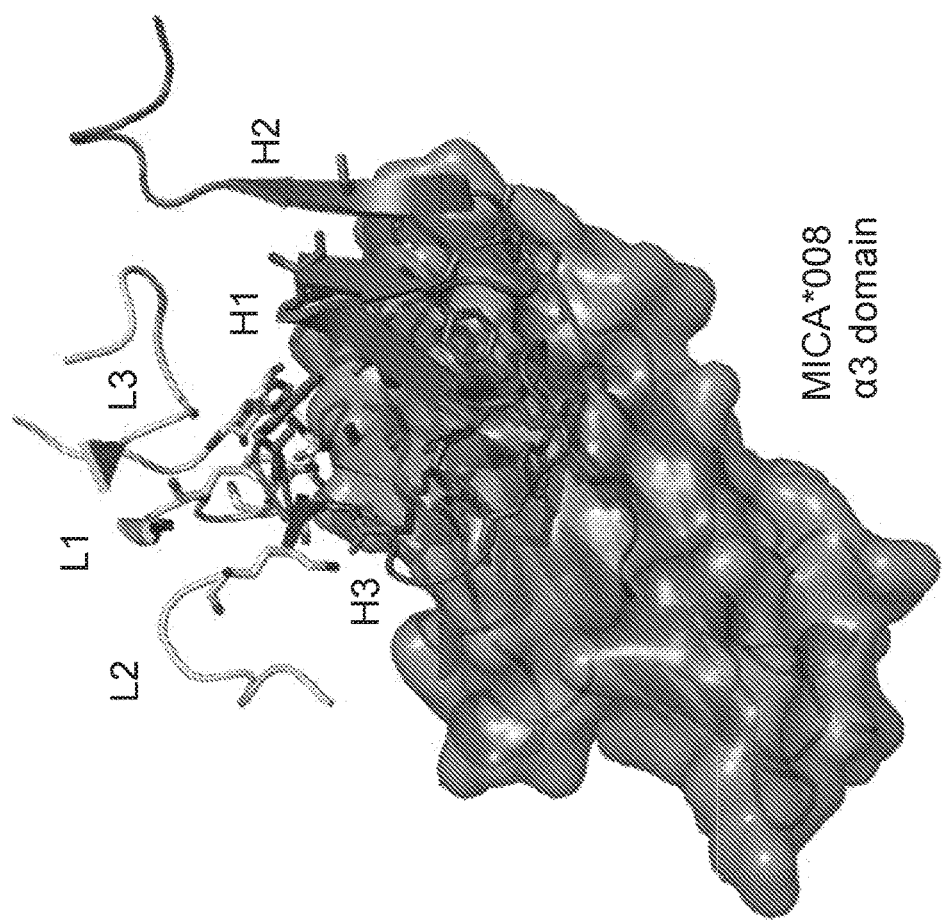
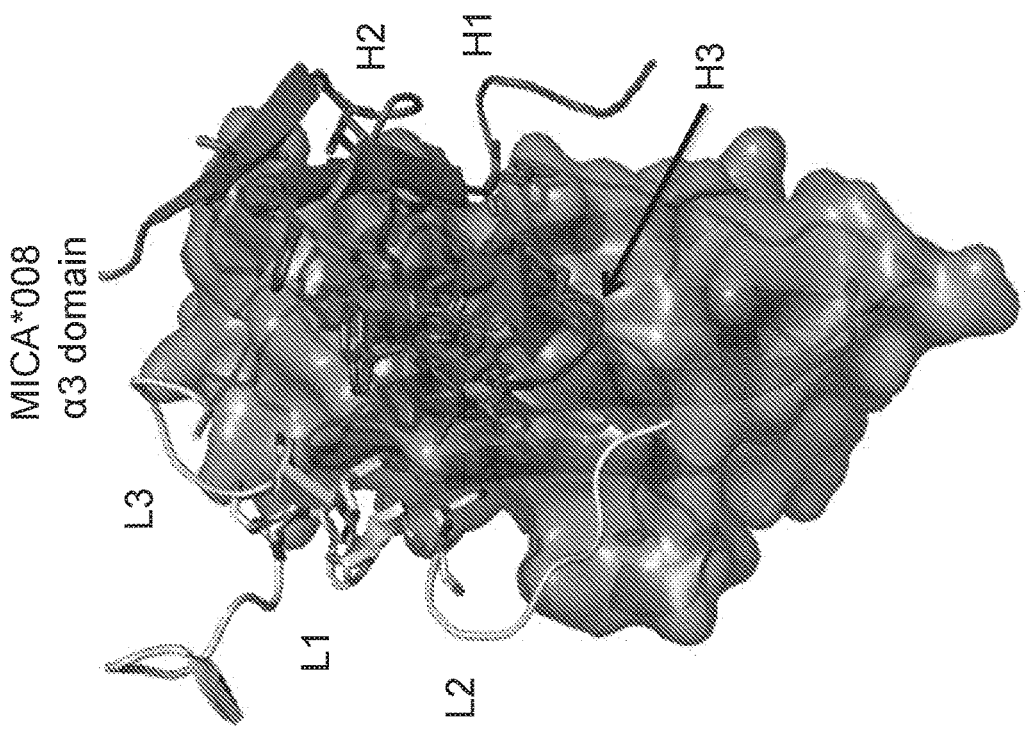
FIG. 35A
FIG. 35B

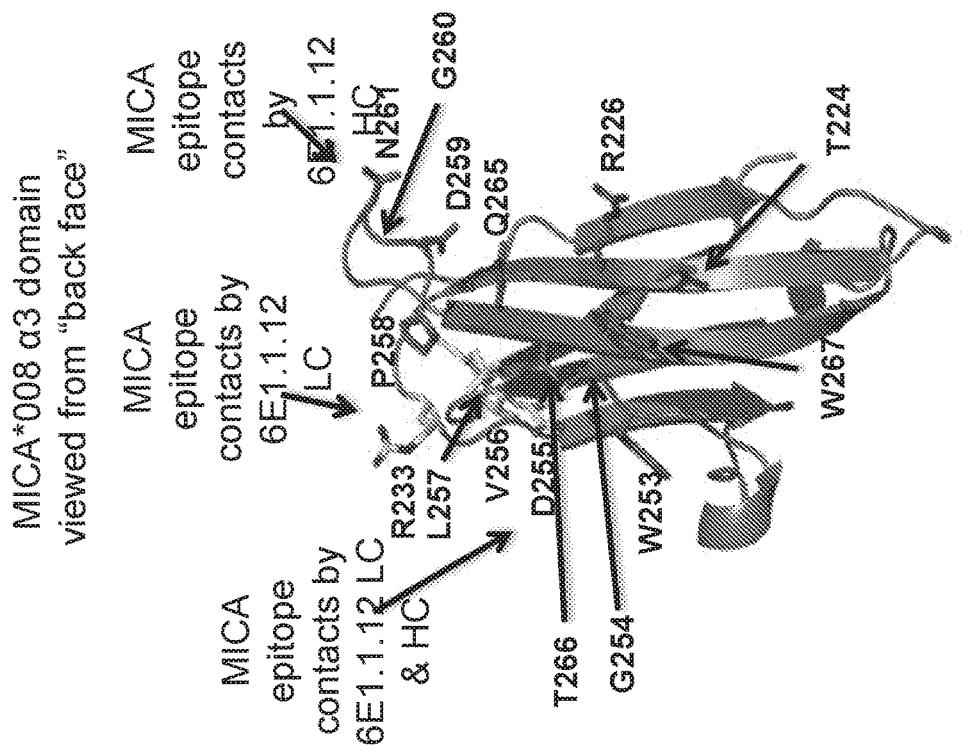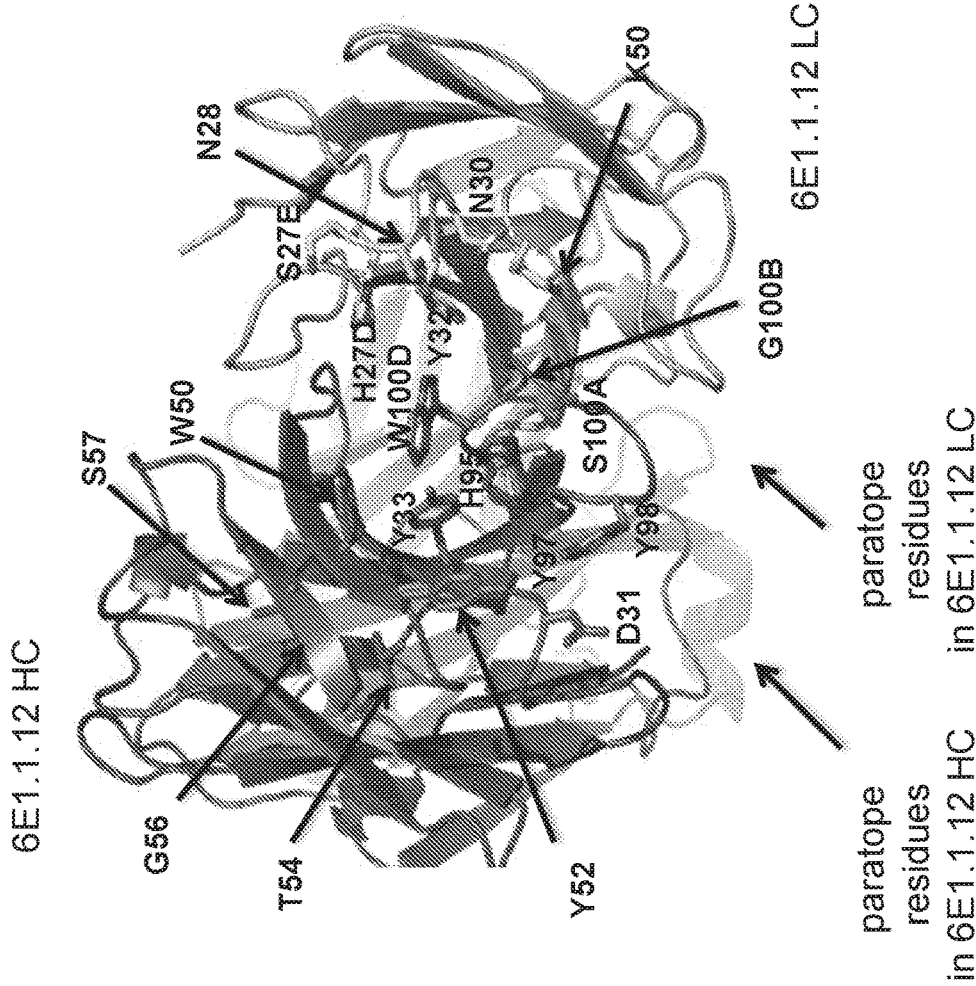

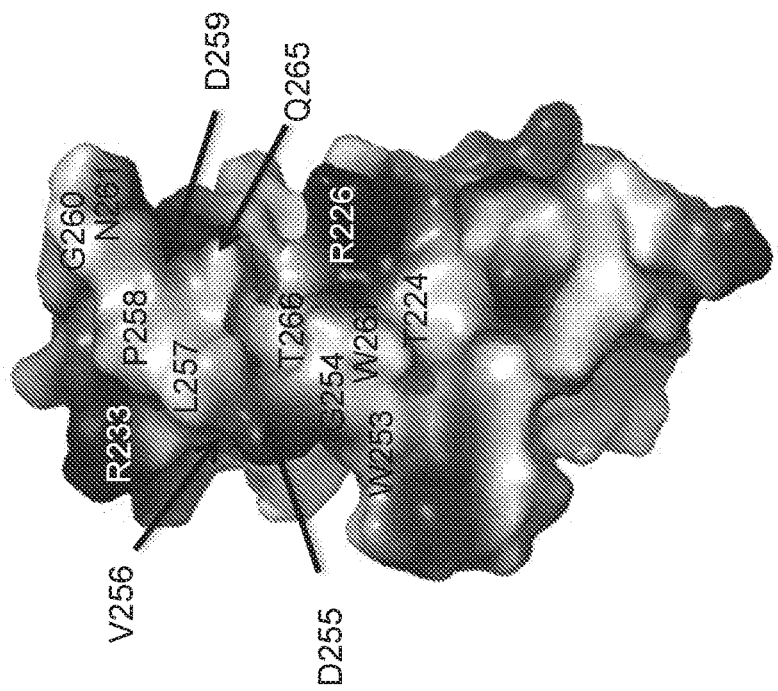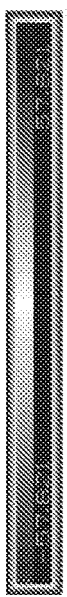
FIG. 38B
MICA*008 α3 domain viewed from "back face"
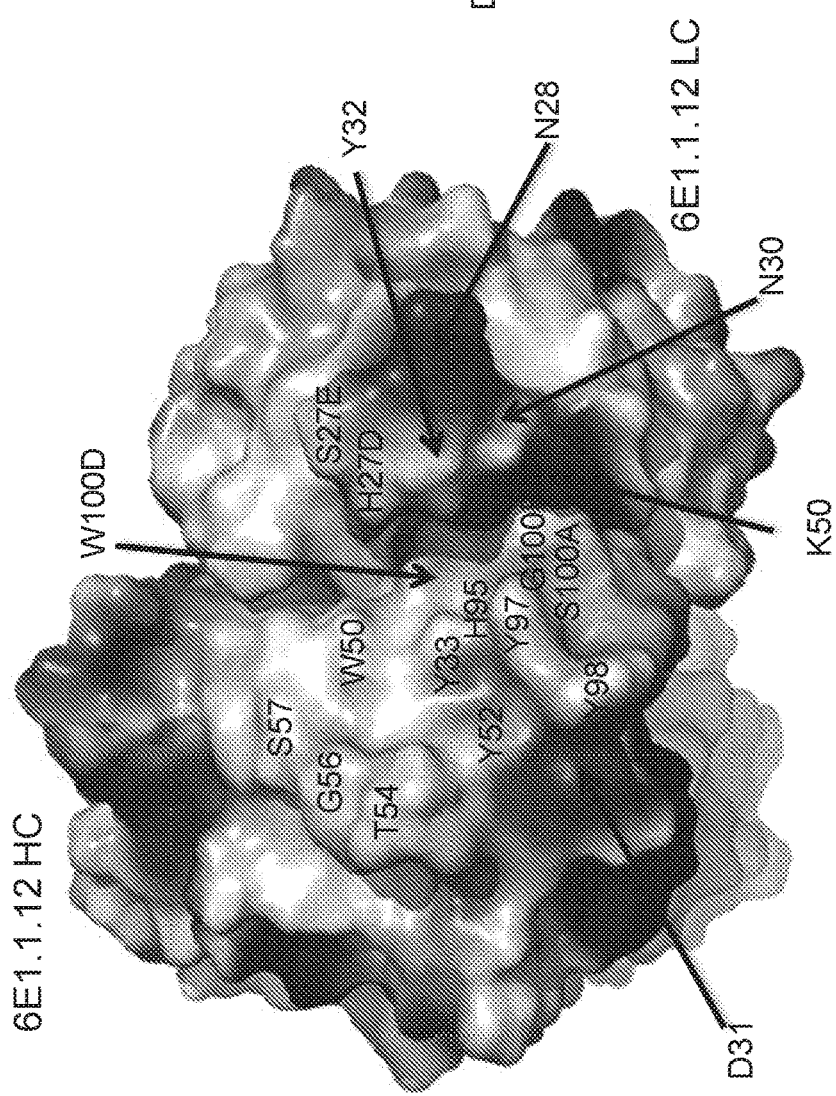
FIG. 38A MICA*008 α3 domain viewed from "back face"

MICA*008 α3 domain viewed from "back face"

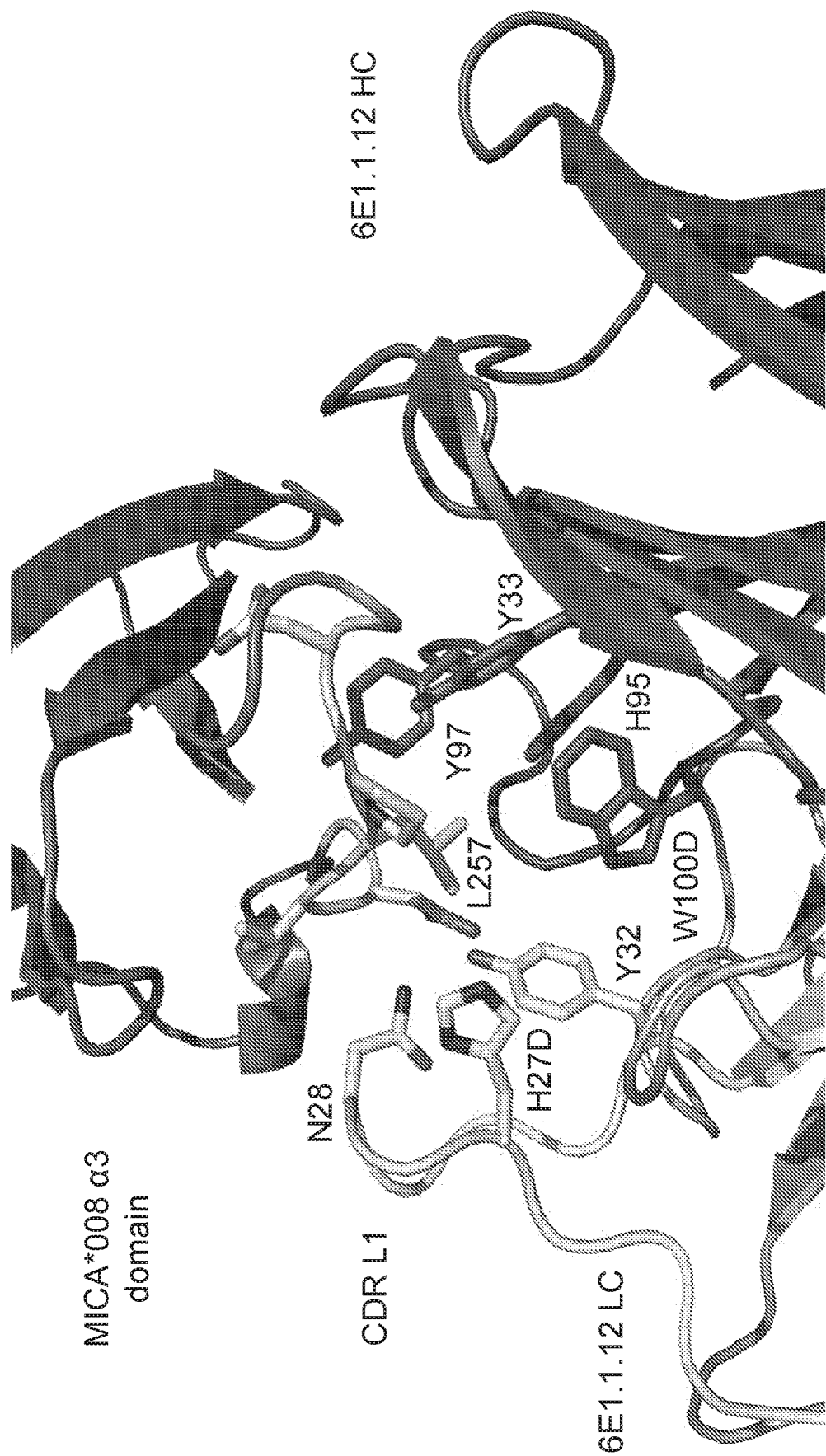

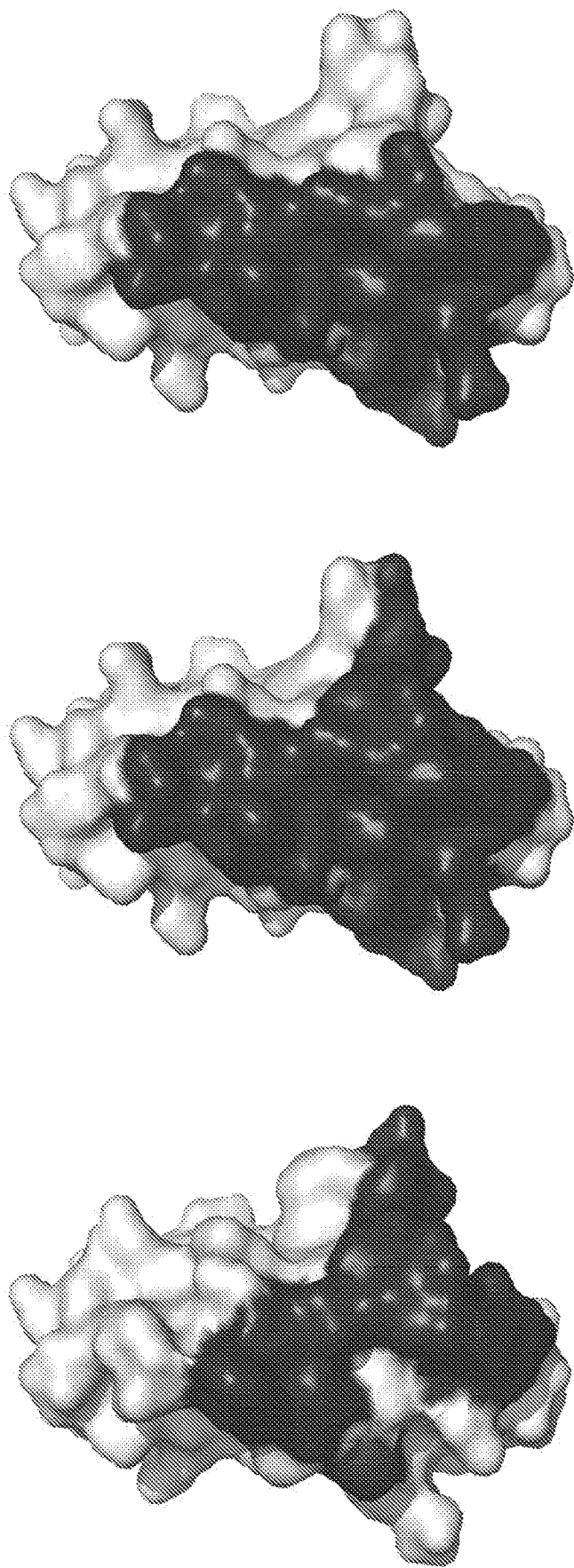

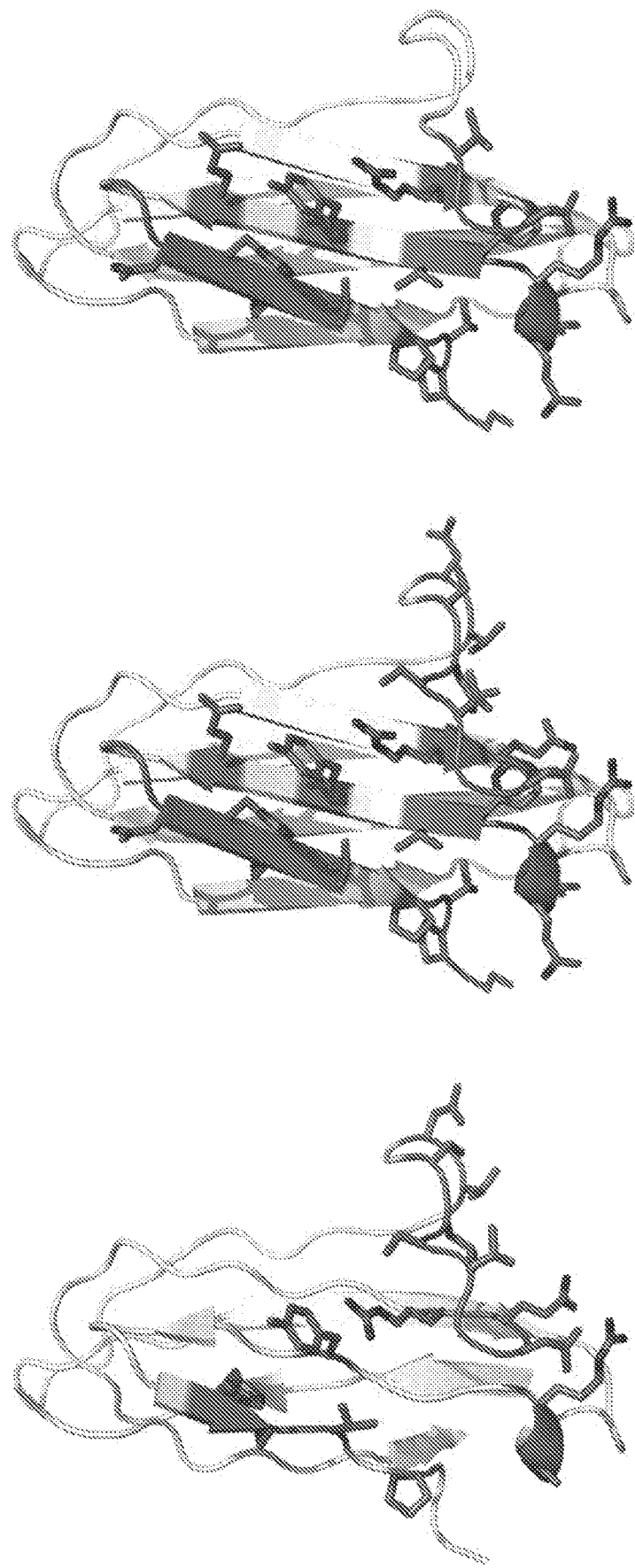

FIG. 41B
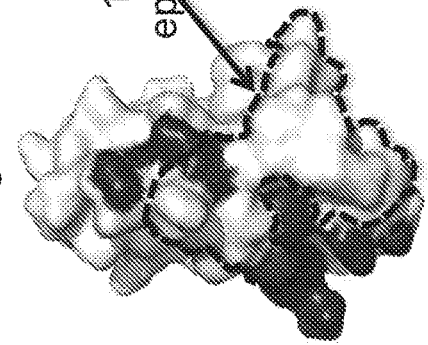
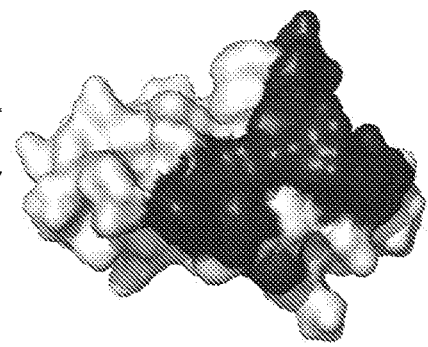
Front Face of MICA*008 α3 Domain
1D5 epitope — Cleavage sites — 1D5 epitope
13A9 epitope — Cleavage sites — 13A9 epitope
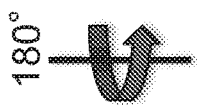 180°
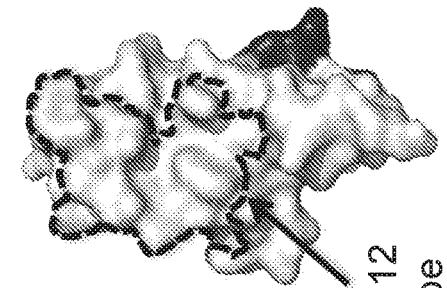
*Epitopes defined as residues within 4.5 Å of Fab, cleavage sites from *Cancer Res* (2008) 68: 6368; *BBRC* (2009) 387: 476
Back Face of MICA*008 α3 Domain
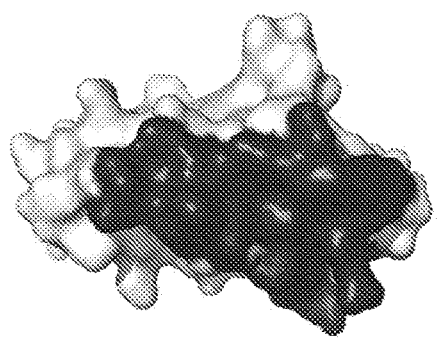
6E1.1.12 epitope — Cleavage sites — 6E1.1.12 epitope FIG. 46A
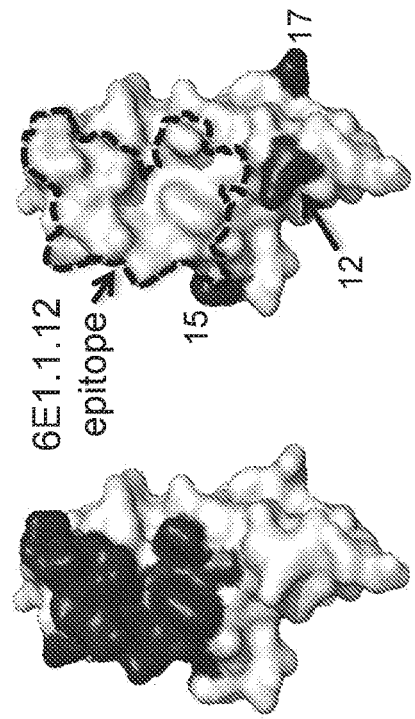
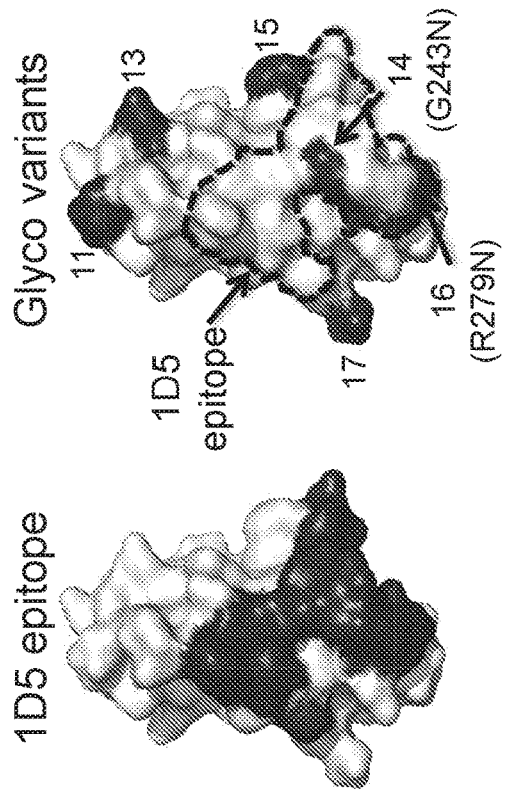
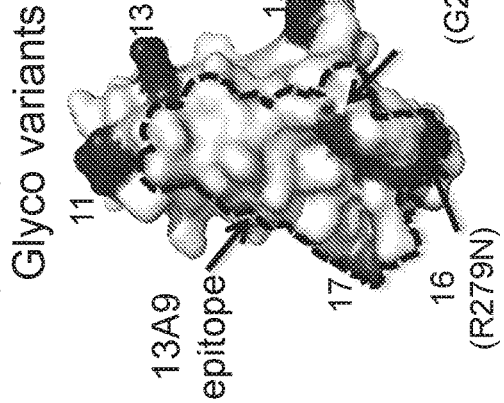

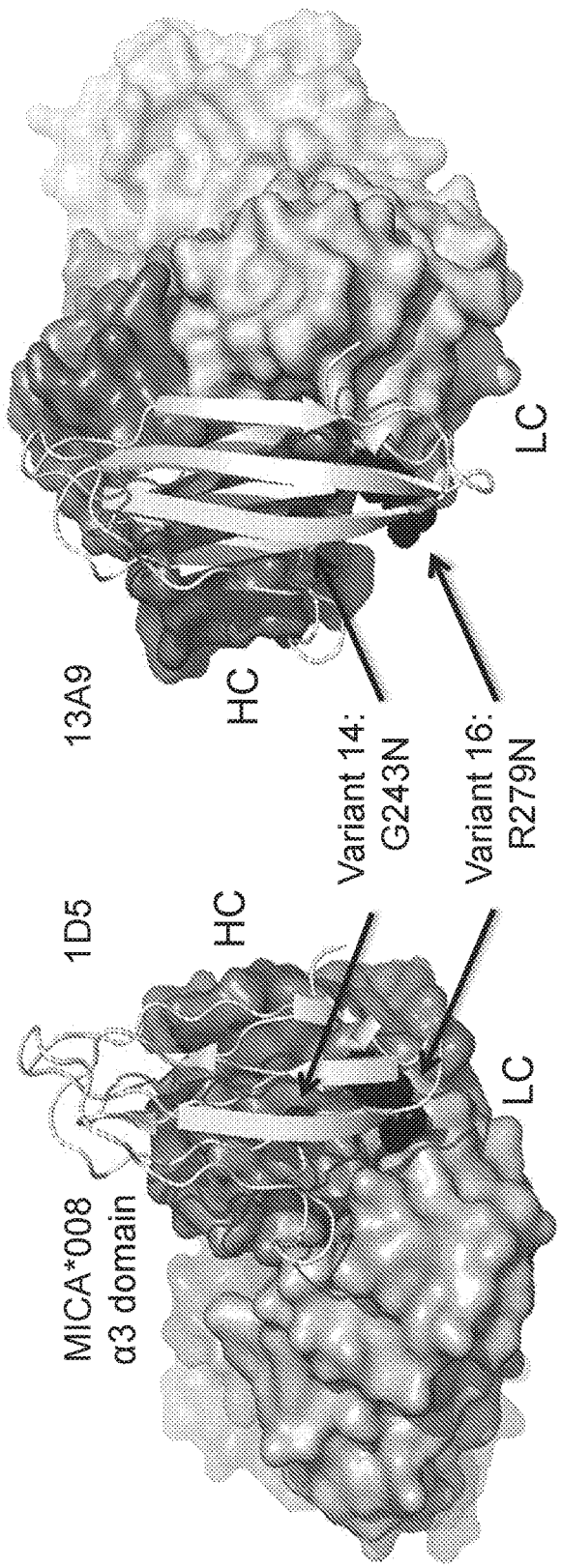

SEQUENCE LISTING

<160> NUMBER OF SEQ ID NOS: 457

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

```
<400> SEQUENCE: 1

Gly Ser Gly Val Asn
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic Construct

<400> SEQUENCE: 2

Met Ile Trp Gly Asp Gly Asn Thr Asp Tyr Asn Ser Ala Leu Lys Ser
1               5                   10                  15

<210> SEQ ID NO 3
<211> LENGTH: 12
<212> TYPE: PRT
<213> ORGANISM: Artificial Sequence
<220> FEATURE:
<223> OTHER INFORMATION: Synthetic Construct

<400> SEQUENCE: 3

Gly Ala Tyr Tyr Gly Lys Arg Trp Tyr Phe Asp Val
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Construct

<400> SEQUENCE: 4

Ser Ala Ser Gln Gly Ile Ser Asn Tyr Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Tyr Thr Ser Ser Leu His Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gln Gln Tyr Ser Lys Leu Pro Pro Thr
1               5

<210> SEQ ID NO 7
<211> LENGTH: 23
<212> TYPE: PRT
<213> ORGANISM: Artificial Sequence
<220> FEATURE:
<223> OTHER INFORMATION: Synthetic Construct
```

-continued

```
<400> SEQUENCE: 7

Asp Ile Gln Met Thr Gln Thr Thr Ser Ser Leu Ser Ala Ser Leu Gly
1               5                   10                  15

Asp Arg Val Thr Ile Ser Cys
            20

<210> SEQ ID NO 8
<211> LENGTH: 15
<212> TYPE: PRT
<213> ORGANISM: Artificial Sequence
<220> FEATURE:
<223> OTHER INFORMATION: Synthetic Construct

<400> SEQUENCE: 8

Trp Tyr Gln Gln Lys Pro Asp Gly Thr Val Lys Leu Leu Ile Tyr
1               5                   10                  15

<210> SEQ ID NO 9
<211> LENGTH: 32
<212> TYPE: PRT
<213> ORGANISM: Artificial Sequence
<220> FEATURE:
<223> OTHER INFORMATION: Synthetic Construct

<400> SEQUENCE: 9

Gly Val Pro Ser Arg Phe Ser Gly Ser Gly Ser Gly Thr Asp Tyr Ser
1               5                   10                  15

Leu Thr Ile Ser Asn Leu Glu Pro Glu Asp Ile Ala Thr Tyr Tyr Cys
            20                  25                  30

<210> SEQ ID NO 10
<211> LENGTH: 10
<212> TYPE: PRT
<213> ORGANISM: Artificial Sequence
<220> FEATURE:
<223> OTHER INFORMATION: Synthetic Construct

<400> SEQUENCE: 10

Phe Gly Gly Gly Thr Lys Val Glu Ile Lys
1               5                   10

<210> SEQ ID NO 11
<211> LENGTH: 30
<212> TYPE: PRT
<213> ORGANISM: Artificial Sequence
<220> FEATURE:
<223> OTHER INFORMATION: Synthetic Construct

<400> SEQUENCE: 11

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr
            20                  25                  30

<210> SEQ ID NO 12
<211> LENGTH: 14
<212> TYPE: PRT
<213> ORGANISM: Artificial Sequence
<220> FEATURE:
<223> OTHER INFORMATION: Synthetic Construct

<400> SEQUENCE: 12

Trp Val Arg Gln Pro Pro Gly Lys Gly Leu Glu Trp Leu Gly
1               5                   10
```

<210> SEQ ID NO 13
<211> LENGTH: 32
<212> TYPE: PRT
<213> ORGANISM: Artificial Sequence
<220> FEATURE:
<223> OTHER INFORMATION: Synthetic Construct

<400> SEQUENCE: 13

Arg Leu Ser Ile Ser Lys Asp Asn Ser Lys Ser Gln Ile Phe Leu Lys
1               5                   10                  15

Met Asn Ser Leu Gln Thr Asp Asp Thr Ala Arg Tyr Tyr Cys Ala Arg
            20                  25                  30

<210> SEQ ID NO 14
<211> LENGTH: 11
<212> TYPE: PRT
<213> ORGANISM: Artificial Sequence
<220> FEATURE:
<223> OTHER INFORMATION: Synthetic Construct

<400> SEQUENCE: 14

Trp Gly Ala Gly Thr Thr Val Thr Val Ser Ser
1               5                   10

<210> SEQ ID NO 15
<211> LENGTH: 120
<212> TYPE: PRT
<213> ORGANISM: Artificial Sequence
<220> FEATURE:
<223> OTHER INFORMATION: Synthetic Construct

<400> SEQUENCE: 15

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Ser
            20                  25                  30

Gly Val Asn Trp Val Arg Gln Pro Pro Gly Lys Gly Leu Glu Trp Leu
        35                  40                  45

Gly Met Ile Trp Gly Asp Gly Asn Thr Asp Tyr Asn Ser Ala Leu Lys
    50                  55                  60

Ser Arg Leu Ser Ile Ser Lys Asp Asn Ser Lys Ser Gln Ile Phe Leu
65                  70                  75                  80

Lys Met Asn Ser Leu Gln Thr Asp Asp Thr Ala Arg Tyr Tyr Cys Ala
                85                  90                  95

Arg Gly Ala Tyr Tyr Gly Lys Arg Trp Tyr Phe Asp Val Trp Gly Ala
            100                 105                 110

Gly Thr Thr Val Thr Val Ser Ser
        115                 120

<210> SEQ ID NO 16
<211> LENGTH: 107
<212> TYPE: PRT
<213> ORGANISM: Artificial Sequence
<220> FEATURE:
<223> OTHER INFORMATION: Synthetic Construct

<400> SEQUENCE: 16

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

```
Leu Asn Trp Tyr Gln Gln Lys Pro Asp Gly Thr Val Lys Leu Leu Ile
             35                  40                  45

Tyr Tyr Thr Ser Ser Leu His Ser Gly Val Pro Ser Arg Phe Ser Gly
 50                  55                  60

Ser Gly Ser Gly Thr Asp Tyr Ser Leu Thr Ile Ser Asn Leu Glu Pro
 65                  70                  75                  80

Glu Asp Ile Ala Thr Tyr Tyr Cys Gln Gln Tyr Ser Lys Leu Pro Pro
                 85                  90                  95

Thr Phe Gly Gly Gly Thr Lys Val Glu Ile Lys
            100                 105

<210> SEQ ID NO 17
<211> LENGTH: 6
<212> TYPE: PRT
<213> ORGANISM: Artificial Sequence
<220> FEATURE:
<223> OTHER INFORMATION: Synthetic Construct

<400> SEQUENCE: 17

Ser Asp Tyr Ala Trp Asn
1               5

<210> SEQ ID NO 18
<211> LENGTH: 16
<212> TYPE: PRT
<213> ORGANISM: Artificial Sequence
<220> FEATURE:
<223> OTHER INFORMATION: Synthetic Construct

<400> SEQUENCE: 18

Tyr Ile Asn Tyr Ser Gly Thr Thr Asn Tyr Asn Pro Ser Leu Lys Ser
1               5                   10                  15

<210> SEQ ID NO 19
<211> LENGTH: 10
<212> TYPE: PRT
<213> ORGANISM: Artificial Sequence
<220> FEATURE:
<223> OTHER INFORMATION: Synthetic Construct

<400> SEQUENCE: 19

Tyr Arg Tyr Asp Gly Ala Trp Phe Pro Tyr
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic Construct

<400> SEQUENCE: 20

Arg Ala Ser Gly Asn Ile His Asn Tyr Leu Ala
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic Construct

<400> SEQUENCE: 21

Asn Ala Ile Met Leu Ala Asp
1               5
```

<210> SEQ ID NO 22
<211> LENGTH: 9
<212> TYPE: PRT
<213> ORGANISM: Artificial Sequence
<220> FEATURE:
<223> OTHER INFORMATION: Synthetic Construct

<400> SEQUENCE: 22

Gln His Phe Trp Ser Phe Pro Leu Thr
1               5

<210> SEQ ID NO 23
<211> LENGTH: 23
<212> TYPE: PRT
<213> ORGANISM: Artificial Sequence
<220> FEATURE:
<223> OTHER INFORMATION: Synthetic Construct

<400> SEQUENCE: 23

Asp Ile Gln Met Thr Gln Ser Pro Ala Ser Leu Ser Ala Ser Val Gly
1               5                   10                  15

Glu Thr Val Thr Ile Thr Cys
            20

<210> SEQ ID NO 24
<211> LENGTH: 15
<212> TYPE: PRT
<213> ORGANISM: Artificial Sequence
<220> FEATURE:
<223> OTHER INFORMATION: Synthetic Construct

<400> SEQUENCE: 24

Trp Tyr Gln Gln Lys Gln Gly Lys Ser Pro Gln Leu Leu Val Tyr
1               5                   10                  15

<210> SEQ ID NO 25
<211> LENGTH: 32
<212> TYPE: PRT
<213> ORGANISM: Artificial Sequence
<220> FEATURE:
<223> OTHER INFORMATION: Synthetic Construct

<400> SEQUENCE: 25

Gly Val Pro Ser Arg Phe Ser Ala Ser Gly Ser Gly Thr Gln Tyr Ser
1               5                   10                  15

Leu Lys Ile Asn Ser Leu Gln Pro Glu Asp Phe Gly Ser Tyr Tyr Cys
            20                  25                  30

<210> SEQ ID NO 26
<211> LENGTH: 10
<212> TYPE: PRT
<213> ORGANISM: Artificial Sequence
<220> FEATURE:
<223> OTHER INFORMATION: Synthetic Construct

<400> SEQUENCE: 26

Phe Gly Ala Gly Thr Lys Val Glu Ile Lys
1               5                   10

<210> SEQ ID NO 27
<211> LENGTH: 30
<212> TYPE: PRT
<213> ORGANISM: Artificial Sequence
<220> FEATURE:
<223> OTHER INFORMATION: Synthetic Construct

<400> SEQUENCE: 27

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr
            20                  25                  30

<210> SEQ ID NO 28
<211> LENGTH: 14
<212> TYPE: PRT
<213> ORGANISM: Artificial Sequence
<220> FEATURE:
<223> OTHER INFORMATION: Synthetic Construct

<400> SEQUENCE: 28

Trp Ile Arg Gln Phe Pro Arg Asn Lys Leu Glu Trp Met Gly
1               5                   10

<210> SEQ ID NO 29
<211> LENGTH: 32
<212> TYPE: PRT
<213> ORGANISM: Artificial Sequence
<220> FEATURE:
<223> OTHER INFORMATION: Synthetic Construct

<400> SEQUENCE: 29

Arg Ile Ser Ile Thr Arg Asp Thr Ser Lys Asn Gln Phe Phe Leu Gln
1               5                   10                  15

Leu Ile Ser Val Thr Thr Glu Asp Thr Ala Thr Tyr Tyr Cys Ser Tyr
            20                  25                  30

<210> SEQ ID NO 30
<211> LENGTH: 11
<212> TYPE: PRT
<213> ORGANISM: Artificial Sequence
<220> FEATURE:
<223> OTHER INFORMATION: Synthetic Construct

<400> SEQUENCE: 30

Trp Gly Gln Gly Thr Leu Val Thr Val Ser Ala
1               5                   10

<210> SEQ ID NO 31
<211> LENGTH: 119
<212> TYPE: PRT
<213> ORGANISM: Artificial Sequence
<220> FEATURE:
<223> OTHER INFORMATION: Synthetic Construct

<400> SEQUENCE: 31

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Arg Asn Lys Leu Glu Trp
        35                  40                  45

Met Gly Tyr Ile Asn Tyr Ser Gly Thr Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Ile Ser Val Thr Thr Glu Asp Thr Ala Thr Tyr Tyr Cys
                85                  90                  95

Ser Tyr Tyr Arg Tyr Asp Gly Ala Trp Phe Pro Tyr Trp Gly Gln Gly
            100                 105                 110

Thr Leu Val Thr Val Ser Ala
        115

<210> SEQ ID NO 32
<211> LENGTH: 107
<212> TYPE: PRT
<213> ORGANISM: Artificial Sequence
<220> FEATURE:
<223> OTHER INFORMATION: Synthetic Construct

<400> SEQUENCE: 32

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Ile Met Leu Ala Asp Gly Val Pro Ser Arg Phe Ser Ala
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Phe Pro Leu
                85                  90                  95

Thr Phe Gly Ala Gly Thr Lys Val Glu Ile Lys
            100                 105

<210> SEQ ID NO 33
<211> LENGTH: 6
<212> TYPE: PRT
<213> ORGANISM: Artificial Sequence
<220> FEATURE:
<223> OTHER INFORMATION: Synthetic Construct

<400> SEQUENCE: 33

Asn Asp Tyr Tyr Trp Asn
1               5

<210> SEQ ID NO 34
<211> LENGTH: 16
<212> TYPE: PRT
<213> ORGANISM: Artificial Sequence
<220> FEATURE:
<223> OTHER INFORMATION: Synthetic Construct

<400> SEQUENCE: 34

Phe Ile Ser Phe Gly Gly Ser Asn Asn Tyr Asn Pro Ser Leu Lys Asn
1               5                   10                  15

<210> SEQ ID NO 35
<211> LENGTH: 10
<212> TYPE: PRT
<213> ORGANISM: Artificial Sequence
<220> FEATURE:
<223> OTHER INFORMATION: Synthetic Construct

<400> SEQUENCE: 35

Tyr Asp Gly Arg Gly Ala Trp Phe Ala Tyr
1               5                   10

<210> SEQ ID NO 36
<211> LENGTH: 11

```
<212> TYPE: PRT
<213> ORGANISM: Artificial Sequence
<220> FEATURE:
<223> OTHER INFORMATION: Synthetic Construct

<400> SEQUENCE: 36

Arg Ala Ser Gly Asn Ile His Asn Tyr Leu Ala
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Synthetic Construct

<400> SEQUENCE: 37

Asp Ala Ile Thr Leu Ala Asp
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Construct

<400> SEQUENCE: 38

Gln His Phe Trp Ser Phe Pro Leu Thr
1               5

<210> SEQ ID NO 39
<211> LENGTH: 23
<212> TYPE: PRT
<213> ORGANISM: Artificial Sequence
<220> FEATURE:
<223> OTHER INFORMATION: Synthetic Construct

<400> SEQUENCE: 39

Asp Ile Gln Met Thr Gln Ser Pro Ala Ser Leu Ser Ala Ser Val Gly
1               5                   10                  15

Glu Thr Val Thr Ile Thr Cys
            20

<210> SEQ ID NO 40
<211> LENGTH: 15
<212> TYPE: PRT
<213> ORGANISM: Artificial Sequence
<220> FEATURE:
<223> OTHER INFORMATION: Synthetic Construct

<400> SEQUENCE: 40

Trp Tyr Gln Gln Lys Gln Gly Lys Ser Pro Gln Leu Leu Val Tyr
1               5                   10                  15

<210> SEQ ID NO 41
<211> LENGTH: 32
<212> TYPE: PRT
<213> ORGANISM: Artificial Sequence
<220> FEATURE:
<223> OTHER INFORMATION: Synthetic Construct

<400> SEQUENCE: 41

Gly Val Pro Ser Arg Phe Ser Gly Ser Gly Ser Gly Thr Gln Tyr Ser
1               5                   10                  15
```

Leu Lys Ile Asn Ser Leu Gln Pro Glu Asp Phe Gly Asn Tyr Tyr Cys
            20                  25                  30

<210> SEQ ID NO 42
<211> LENGTH: 10
<212> TYPE: PRT
<213> ORGANISM: Artificial Sequence
<220> FEATURE:
<223> OTHER INFORMATION: Synthetic Construct

<400> SEQUENCE: 42

Phe Gly Ala Gly Thr Lys Val Glu Ile Lys
1               5                   10

<210> SEQ ID NO 43
<211> LENGTH: 30
<212> TYPE: PRT
<213> ORGANISM: Artificial Sequence
<220> FEATURE:
<223> OTHER INFORMATION: Synthetic Construct

<400> SEQUENCE: 43

Asp Val Gln Leu Gln Gly Ser Gly Pro Gly Leu Val Lys Pro Ser Gln
1               5                   10                  15

Ser Leu Ser Leu Thr Cys Ser Val Thr Gly Tyr Ser Ile Thr
            20                  25                  30

<210> SEQ ID NO 44
<211> LENGTH: 14
<212> TYPE: PRT
<213> ORGANISM: Artificial Sequence
<220> FEATURE:
<223> OTHER INFORMATION: Synthetic Construct

<400> SEQUENCE: 44

Trp Ile Arg Gln Phe Pro Gly Asn Lys Leu Glu Trp Met Gly
1               5                   10

<210> SEQ ID NO 45
<211> LENGTH: 32
<212> TYPE: PRT
<213> ORGANISM: Artificial Sequence
<220> FEATURE:
<223> OTHER INFORMATION: Synthetic Construct

<400> SEQUENCE: 45

Arg Ile Ser Ile Thr Arg Asp Thr Ser Lys Asn Gln Phe Phe Leu Lys
1               5                   10                  15

Leu Ser Ser Val Thr Thr Glu Asp Thr Ala Thr Tyr Tyr Cys Ala Arg
            20                  25                  30

<210> SEQ ID NO 46
<211> LENGTH: 11
<212> TYPE: PRT
<213> ORGANISM: Artificial Sequence
<220> FEATURE:
<223> OTHER INFORMATION: Synthetic Construct

<400> SEQUENCE: 46

Trp Ala Gln Gly Thr Leu Val Thr Val Ser Ala
1               5                   10

<210> SEQ ID NO 47
<211> LENGTH: 119
<212> TYPE: PRT

<213> ORGANISM: Artificial Sequence
<220> FEATURE:
<223> OTHER INFORMATION: Synthetic Construct

<400> SEQUENCE: 47

```
Asp Val Gln Leu Gln Gly Ser Gly Pro Gly Leu Val Lys Pro Ser Gln
1               5                   10                  15

Ser Leu Ser Leu Thr Cys Ser Val Thr Gly Tyr Ser Ile Thr Asn Asp
            20                  25                  30

Tyr Tyr Trp Asn Trp Ile Arg Gln Phe Pro Gly Asn Lys Leu Glu Trp
        35                  40                  45

Met Gly Phe Ile Ser Phe Gly Gly Ser Asn Asn Tyr Asn Pro Ser Leu
50                  55                  60

Lys Asn Arg Ile Ser Ile Thr Arg Asp Thr Ser Lys Asn Gln Phe Phe
65                  70                  75                  80

Leu Lys Leu Ser Ser Val Thr Thr Glu Asp Thr Ala Thr Tyr Tyr Cys
            85                  90                  95

Ala Arg Tyr Asp Gly Arg Gly Ala Trp Phe Ala Tyr Trp Ala Gln Gly
        100                 105                 110

Thr Leu Val Thr Val Ser Ala
        115
```

<210> SEQ ID NO 48
<211> LENGTH: 107
<212> TYPE: PRT
<213> ORGANISM: Artificial Sequence
<220> FEATURE:
<223> OTHER INFORMATION: Synthetic Construct

<400> SEQUENCE: 48

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asp Ala Ile Thr Leu Ala Asp Gly Val Pro Ser Arg Phe Ser Gly
50                  55                  60

Ser Gly Ser Gly Thr Gln Tyr Ser Leu Lys Ile Asn Ser Leu Gln Pro
65                  70                  75                  80

Glu Asp Phe Gly Asn Tyr Tyr Cys Gln His Phe Trp Ser Phe Pro Leu
            85                  90                  95

Thr Phe Gly Ala Gly Thr Lys Val Glu Ile Lys
        100                 105
```

<210> SEQ ID NO 49
<211> LENGTH: 5
<212> TYPE: PRT
<213> ORGANISM: Artificial Sequence
<220> FEATURE:
<223> OTHER INFORMATION: Synthetic Construct

<400> SEQUENCE: 49

```
Thr Phe Gly Met Asn
1               5
```

<210> SEQ ID NO 50
<211> LENGTH: 17
<212> TYPE: PRT
<213> ORGANISM: Artificial Sequence

```
<220> FEATURE:
<223> OTHER INFORMATION: Synthetic Construct

<400> SEQUENCE: 50

Tyr Ile Asn Ser Gly Ser Asn Thr Ile Tyr Tyr Ala Asp Thr Val Lys
1               5                   10                  15
Gly

<210> SEQ ID NO 51
<211> LENGTH: 10
<212> TYPE: PRT
<213> ORGANISM: Artificial Sequence
<220> FEATURE:
<223> OTHER INFORMATION: Synthetic Construct

<400> SEQUENCE: 51

Trp Glu Pro Val Thr Gly Gly Phe Ser Tyr
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic Construct

<400> SEQUENCE: 52

Thr Ala Ser Ser Ser Ile Ser Ser Ser Tyr Leu His
1               5                   10

<210> SEQ ID NO 53
<211> LENGTH: 7
<212> TYPE: PRT
<213> ORGANISM: Artificial Sequence
<220> FEATURE:
<223> OTHER INFORMATION: Synthetic Construct

<400> SEQUENCE: 53

Thr Thr Ser Asn Leu Ala Ser
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic Construct

<400> SEQUENCE: 54

His Gln His His Arg Ser Pro Phe Thr
1               5

<210> SEQ ID NO 55
<211> LENGTH: 23
<212> TYPE: PRT
<213> ORGANISM: Artificial Sequence
<220> FEATURE:
<223> OTHER INFORMATION: Synthetic Construct

<400> SEQUENCE: 55

Gln Ile Val Leu Thr Gln Ser Pro Ala Phe Lys Ser Ser Ser Leu Gly
1               5                   10                  15
Glu Arg Val Thr Met Thr Cys
            20
```

```
<210> SEQ ID NO 56
<211> LENGTH: 15
<212> TYPE: PRT
<213> ORGANISM: Artificial Sequence
<220> FEATURE:
<223> OTHER INFORMATION: Synthetic Construct

<400> SEQUENCE: 56

Trp Tyr Gln Gln Lys Pro Gly Ser Ser Pro Lys Leu Trp Ile Tyr
1               5                   10                  15

<210> SEQ ID NO 57
<211> LENGTH: 32
<212> TYPE: PRT
<213> ORGANISM: Artificial Sequence
<220> FEATURE:
<223> OTHER INFORMATION: Synthetic Construct

<400> SEQUENCE: 57

Gly Val Pro Ala Arg Phe Ser Gly Ser Gly Ser Gly Thr Ser Tyr Ser
1               5                   10                  15

Leu Thr Ile Ser Thr Met Glu Ala Glu Asp Ala Ala Thr Tyr Tyr Cys
            20                  25                  30

<210> SEQ ID NO 58
<211> LENGTH: 10
<212> TYPE: PRT
<213> ORGANISM: Artificial Sequence
<220> FEATURE:
<223> OTHER INFORMATION: Synthetic Construct

<400> SEQUENCE: 58

Phe Gly Ser Gly Thr Lys Val Glu Ile Lys
1               5                   10

<210> SEQ ID NO 59
<211> LENGTH: 30
<212> TYPE: PRT
<213> ORGANISM: Artificial Sequence
<220> FEATURE:
<223> OTHER INFORMATION: Synthetic Construct

<400> SEQUENCE: 59

Asp Val His Leu Val Glu Ser Gly Gly Gly Leu Val Gln Pro Gly Gly
1               5                   10                  15

Ser Arg Lys Leu Ser Cys Ala Ala Ser Gly Phe Thr Phe Asn
            20                  25                  30

<210> SEQ ID NO 60
<211> LENGTH: 14
<212> TYPE: PRT
<213> ORGANISM: Artificial Sequence
<220> FEATURE:
<223> OTHER INFORMATION: Synthetic Construct

<400> SEQUENCE: 60

Trp Val Arg Gln Ala Pro Glu Lys Gly Leu Glu Trp Val Ala
1               5                   10

<210> SEQ ID NO 61
<211> LENGTH: 32
<212> TYPE: PRT
<213> ORGANISM: Artificial Sequence
<220> FEATURE:
<223> OTHER INFORMATION: Synthetic Construct
```

<400> SEQUENCE: 61

Arg Phe Thr Ile Ser Arg Asp Asn Pro Lys Asn Thr Leu Phe Leu Gln
1               5                   10                  15

Met Thr Ser Leu Arg Ser Glu Asp Thr Ala Met Tyr Tyr Cys Thr Arg
            20                  25                  30

<210> SEQ ID NO 62
<211> LENGTH: 11
<212> TYPE: PRT
<213> ORGANISM: Artificial Sequence
<220> FEATURE:
<223> OTHER INFORMATION: Synthetic Construct

<400> SEQUENCE: 62

Trp Gly Gln Gly Thr Leu Val Thr Val Ser Ala
1               5                   10

<210> SEQ ID NO 63
<211> LENGTH: 119
<212> TYPE: PRT
<213> ORGANISM: Artificial Sequence
<220> FEATURE:
<223> OTHER INFORMATION: Synthetic Construct

<400> SEQUENCE: 63

Asp Val His Leu Val Glu Ser Gly Gly Leu Val Gln Pro Gly Gly
1               5                   10                  15

Ser Arg Lys Leu Ser Cys Ala Ala Ser Gly Phe Thr Phe Asn Thr Phe
            20                  25                  30

Gly Met Asn Trp Val Arg Gln Ala Pro Glu Lys Gly Leu Glu Trp Val
        35                  40                  45

Ala Tyr Ile Asn Ser Gly Ser Asn Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Thr Arg Trp Glu Pro Val Thr Gly Gly Phe Ser Tyr Trp Gly Gln Gly
            100                 105                 110

Thr Leu Val Thr Val Ser Ala
        115

<210> SEQ ID NO 64
<211> LENGTH: 108
<212> TYPE: PRT
<213> ORGANISM: Artificial Sequence
<220> FEATURE:
<223> OTHER INFORMATION: Synthetic Construct

<400> SEQUENCE: 64

Gln Ile Val Leu Thr Gln Ser Pro Ala Phe Lys Ser Ser Leu Gly
1               5                   10                  15

Glu Arg Val Thr Met Thr Cys Thr Ala Ser Ser Ser Ile Ser Ser Ser
            20                  25                  30

Tyr Leu His Trp Tyr Gln Gln Lys Pro Gly Ser Ser Pro Lys Leu Trp
        35                  40                  45

Ile Tyr Thr Thr Ser Asn Leu Ala Ser Gly Val Pro Ala Arg Phe Ser
    50                  55                  60

Gly Ser Gly Ser Gly Thr Ser Tyr Ser Leu Thr Ile Ser Thr Met Glu
65                  70                  75                  80

Ala Glu Asp Ala Ala Thr Tyr Tyr Cys His Gln His Arg Ser Pro
                85                  90                  95

Phe Thr Phe Gly Ser Gly Thr Lys Val Glu Ile Lys
            100                 105

<210> SEQ ID NO 65
<211> LENGTH: 5
<212> TYPE: PRT
<213> ORGANISM: Artificial Sequence
<220> FEATURE:
<223> OTHER INFORMATION: Synthetic Construct

<400> SEQUENCE: 65

Lys Tyr Asn Ile Tyr
1               5

<210> SEQ ID NO 66
<211> LENGTH: 17
<212> TYPE: PRT
<213> ORGANISM: Artificial Sequence
<220> FEATURE:
<223> OTHER INFORMATION: Synthetic Construct

<400> SEQUENCE: 66

Tyr Ile Asp Pro Tyr Thr Gly Gly Thr Ile Ser Asn Gln Lys Phe Thr
1               5                   10                  15

Gly

<210> SEQ ID NO 67
<211> LENGTH: 9
<212> TYPE: PRT
<213> ORGANISM: Artificial Sequence
<220> FEATURE:
<223> OTHER INFORMATION: Synthetic Construct

<400> SEQUENCE: 67

Pro Gly Ser Tyr Trp Tyr Phe Gly Val
1               5

<210> SEQ ID NO 68
<211> LENGTH: 16
<212> TYPE: PRT
<213> ORGANISM: Artificial Sequence
<220> FEATURE:
<223> OTHER INFORMATION: Synthetic Construct

<400> SEQUENCE: 68

Arg Ser Ser Gln Ser Ile Val Tyr Thr Asn Gly Asn Thr Asn Leu Glu
1               5                   10                  15

<210> SEQ ID NO 69
<211> LENGTH: 7
<212> TYPE: PRT
<213> ORGANISM: Artificial Sequence
<220> FEATURE:
<223> OTHER INFORMATION: Synthetic Construct

<400> SEQUENCE: 69

Lys Val Ser Asn Arg Phe Ser
1               5

<210> SEQ ID NO 70

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 70

Phe Gln Ala Ser Tyr Val Pro Phe Thr
1               5

<210> SEQ ID NO 71
<211> LENGTH: 23
<212> TYPE: PRT
<213> ORGANISM: Artificial Sequence
<220> FEATURE:
<223> OTHER INFORMATION: Synthetic Construct

<400> SEQUENCE: 71

Asp Ile Leu Met Thr Gln Thr Pro Leu Ser Leu Pro Val Ser Leu Gly
1               5                   10                  15

Asp Gln Ala Ser Ile Ser Cys
            20

<210> SEQ ID NO 72
<211> LENGTH: 15
<212> TYPE: PRT
<213> ORGANISM: Artificial Sequence
<220> FEATURE:
<223> OTHER INFORMATION: Synthetic Construct

<400> SEQUENCE: 72

Trp Tyr Leu Gln Lys Pro Gly Gln Ser Pro Lys Leu Leu Ile Tyr
1               5                   10                  15

<210> SEQ ID NO 73
<211> LENGTH: 32
<212> TYPE: PRT
<213> ORGANISM: Artificial Sequence
<220> FEATURE:
<223> OTHER INFORMATION: Synthetic Construct

<400> SEQUENCE: 73

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 74
<211> LENGTH: 10
<212> TYPE: PRT
<213> ORGANISM: Artificial Sequence
<220> FEATURE:
<223> OTHER INFORMATION: Synthetic Construct

<400> SEQUENCE: 74

Phe Gly Ser Gly Thr Lys Val Glu Ile Lys
1               5                   10

<210> SEQ ID NO 75
<211> LENGTH: 30
<212> TYPE: PRT
<213> ORGANISM: Artificial Sequence
<220> FEATURE:
<223> OTHER INFORMATION: Synthetic Construct

<400> SEQUENCE: 75
```

```
Glu Ile Gln Leu Gln Gln Ser Gly Pro Glu Leu Val Lys Pro Gly Ala
1               5                   10                  15

Ser Val Lys Val Ser Cys Thr Ala Ser Gly Tyr Ala Phe Thr
            20                  25                  30

<210> SEQ ID NO 76
<211> LENGTH: 14
<212> TYPE: PRT
<213> ORGANISM: Artificial Sequence
<220> FEATURE:
<223> OTHER INFORMATION: Synthetic Construct

<400> SEQUENCE: 76

Trp Val Lys Gln Ser His Gly Lys Ser Leu Glu Trp Ile Gly
1               5                   10

<210> SEQ ID NO 77
<211> LENGTH: 32
<212> TYPE: PRT
<213> ORGANISM: Artificial Sequence
<220> FEATURE:
<223> OTHER INFORMATION: Synthetic Construct

<400> SEQUENCE: 77

Arg Ala Thr Leu Thr Val Asp Lys Ser Ser Ser Thr Ala Tyr Leu His
1               5                   10                  15

Leu Asn Ser Leu Thr Ser Glu Asp Ser Ala Val Tyr Tyr Cys Ala Arg
            20                  25                  30

<210> SEQ ID NO 78
<211> LENGTH: 11
<212> TYPE: PRT
<213> ORGANISM: Artificial Sequence
<220> FEATURE:
<223> OTHER INFORMATION: Synthetic Construct

<400> SEQUENCE: 78

Trp Gly Ala Gly Thr Thr Val Thr Val Ser Ser
1               5                   10

<210> SEQ ID NO 79
<211> LENGTH: 118
<212> TYPE: PRT
<213> ORGANISM: Artificial Sequence
<220> FEATURE:
<223> OTHER INFORMATION: Synthetic Construct

<400> SEQUENCE: 79

Glu Ile Gln Leu Gln Gln Ser Gly Pro Glu Leu Val Lys Pro Gly Ala
1               5                   10                  15

Ser Val Lys Val Ser Cys Thr Ala Ser Gly Tyr Ala Phe Thr Lys Tyr
            20                  25                  30

Asn Ile Tyr Trp Val Lys Gln Ser His Gly Lys Ser Leu Glu Trp Ile
        35                  40                  45

Gly Tyr Ile Asp Pro Tyr Thr Gly Gly Thr Ile Ser Asn Gln Lys Phe
    50                  55                  60

Thr Gly Arg Ala Thr Leu Thr Val Asp Lys Ser Ser Ser Thr Ala Tyr
65                  70                  75                  80

Leu His Leu Asn Ser Leu Thr Ser Glu Asp Ser Ala Val Tyr Tyr Cys
                85                  90                  95

Ala Arg Pro Gly Ser Tyr Trp Tyr Phe Gly Val Trp Gly Ala Gly Thr
            100                 105                 110
```

Thr Val Thr Val Ser Ser
        115

<210> SEQ ID NO 80
<211> LENGTH: 112
<212> TYPE: PRT
<213> ORGANISM: Artificial Sequence
<220> FEATURE:
<223> OTHER INFORMATION: Synthetic Construct

<400> SEQUENCE: 80

Asp Ile Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Tyr Thr
            20                  25                  30

Asn Gly Asn Thr Asn Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ala
                85                  90                  95

Ser Tyr Val Pro Phe Thr Phe Gly Ser Gly Thr Lys Val Glu Ile Lys
            100                 105                 110

<210> SEQ ID NO 81
<211> LENGTH: 5
<212> TYPE: PRT
<213> ORGANISM: Artificial Sequence
<220> FEATURE:
<223> OTHER INFORMATION: Synthetic Construct

<400> SEQUENCE: 81

Gly Gln Gly Val Asn
1               5

<210> SEQ ID NO 82
<211> LENGTH: 16
<212> TYPE: PRT
<213> ORGANISM: Artificial Sequence
<220> FEATURE:
<223> OTHER INFORMATION: Synthetic Construct

<400> SEQUENCE: 82

Met Ile Trp Gly Asp Gly Ser Thr Asp Tyr Asn Ser Ala Leu Lys Ser
1               5                   10                  15

<210> SEQ ID NO 83
<211> LENGTH: 12
<212> TYPE: PRT
<213> ORGANISM: Artificial Sequence
<220> FEATURE:
<223> OTHER INFORMATION: Synthetic Construct

<400> SEQUENCE: 83

Gly Ala His Tyr Gly Lys Arg Trp Tyr Phe Asp Val
1               5                   10

<210> SEQ ID NO 84
<211> LENGTH: 11
<212> TYPE: PRT
<213> ORGANISM: Artificial Sequence
<220> FEATURE:

```
<223> OTHER INFORMATION: Synthetic Construct

<400> SEQUENCE: 84

Ser Ala Ser Gln Asn Ile Asn Asn Tyr Leu Asn
1               5                   10

<210> SEQ ID NO 85
<211> LENGTH: 7
<212> TYPE: PRT
<213> ORGANISM: Artificial Sequence
<220> FEATURE:
<223> OTHER INFORMATION: Synthetic Construct

<400> SEQUENCE: 85

Tyr Thr Ser Ser Leu Pro Ser
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic Construct

<400> SEQUENCE: 86

Gln Gln Tyr Ser Lys Leu Pro Pro Thr
1               5

<210> SEQ ID NO 87
<211> LENGTH: 23
<212> TYPE: PRT
<213> ORGANISM: Artificial Sequence
<220> FEATURE:
<223> OTHER INFORMATION: Synthetic Construct

<400> SEQUENCE: 87

Asp Ile Gln Met Thr Gln Thr Thr Ser Ser Leu Ser Ala Ser Leu Gly
1               5                   10                  15

Asp Arg Val Thr Ile Ser Cys
            20

<210> SEQ ID NO 88
<211> LENGTH: 15
<212> TYPE: PRT
<213> ORGANISM: Artificial Sequence
<220> FEATURE:
<223> OTHER INFORMATION: Synthetic Construct

<400> SEQUENCE: 88

Trp Tyr Gln Gln Lys Pro His Gly Thr Val Lys Leu Leu Ile Tyr
1               5                   10                  15

<210> SEQ ID NO 89
<211> LENGTH: 32
<212> TYPE: PRT
<213> ORGANISM: Artificial Sequence
<220> FEATURE:
<223> OTHER INFORMATION: Synthetic Construct

<400> SEQUENCE: 89

Gly Val Pro Ser Arg Phe Ser Gly Ser Gly Ser Gly Thr Asp Tyr Ser
1               5                   10                  15

Leu Thr Ile Ser Asn Leu Glu Pro Glu Asp Ile Ala Ser Tyr Tyr Cys
            20                  25                  30
```

```
<210> SEQ ID NO 90
<211> LENGTH: 10
<212> TYPE: PRT
<213> ORGANISM: Artificial Sequence
<220> FEATURE:
<223> OTHER INFORMATION: Synthetic Construct

<400> SEQUENCE: 90

Phe Gly Gly Gly Thr Lys Val Glu Ile Lys
1               5                   10

<210> SEQ ID NO 91
<211> LENGTH: 30
<212> TYPE: PRT
<213> ORGANISM: Artificial Sequence
<220> FEATURE:
<223> OTHER INFORMATION: Synthetic Construct

<400> SEQUENCE: 91

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Asn
            20                  25                  30

<210> SEQ ID NO 92
<211> LENGTH: 14
<212> TYPE: PRT
<213> ORGANISM: Artificial Sequence
<220> FEATURE:
<223> OTHER INFORMATION: Synthetic Construct

<400> SEQUENCE: 92

Trp Val Arg Gln Pro Pro Gly Lys Gly Leu Glu Trp Leu Gly
1               5                   10

<210> SEQ ID NO 93
<211> LENGTH: 32
<212> TYPE: PRT
<213> ORGANISM: Artificial Sequence
<220> FEATURE:
<223> OTHER INFORMATION: Synthetic Construct

<400> SEQUENCE: 93

Arg Leu Ser Ile Ser Lys Asp Asn Ser Arg Ser Gln Val Phe Leu Lys
1               5                   10                  15

Met Asn Ser Leu Gln Thr Asp Asp Thr Ala Arg Tyr Tyr Cys Ala Arg
            20                  25                  30

<210> SEQ ID NO 94
<211> LENGTH: 11
<212> TYPE: PRT
<213> ORGANISM: Artificial Sequence
<220> FEATURE:
<223> OTHER INFORMATION: Synthetic Construct

<400> SEQUENCE: 94

Trp Gly Ala Gly Thr Thr Val Thr Val Ser Ser
1               5                   10

<210> SEQ ID NO 95
<211> LENGTH: 120
<212> TYPE: PRT
<213> ORGANISM: Artificial Sequence
<220> FEATURE:
<223> OTHER INFORMATION: Synthetic Construct
```

<400> SEQUENCE: 95

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Asn Gly Gln
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Ser Ile Ser Lys Asp Asn Ser Arg Ser Gln Val Phe Leu
65                  70                  75                  80

Lys Met Asn Ser Leu Gln Thr Asp Asp Thr Ala Arg Tyr Tyr Cys Ala
                85                  90                  95

Arg Gly Ala His Tyr Gly Lys Arg Trp Tyr Phe Asp Val Trp Gly Ala
            100                 105                 110

Gly Thr Thr Val Thr Val Ser Ser
            115                 120

<210> SEQ ID NO 96
<211> LENGTH: 107
<212> TYPE: PRT
<213> ORGANISM: Artificial Sequence
<220> FEATURE:
<223> OTHER INFORMATION: Synthetic Construct

<400> SEQUENCE: 96

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Asn Ile Asn Asn Tyr
            20                  25                  30

Leu Asn Trp Tyr Gln Gln Lys Pro His Gly Thr Val Lys Leu Leu Ile
        35                  40                  45

Tyr Tyr Thr Ser Ser Leu Pro Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Ser Tyr Tyr Cys Gln Gln Tyr Ser Lys Leu Pro Pro
                85                  90                  95

Thr Phe Gly Gly Gly Thr Lys Val Glu Ile Lys
            100                 105

<210> SEQ ID NO 97
<211> LENGTH: 5
<212> TYPE: PRT
<213> ORGANISM: Artificial Sequence
<220> FEATURE:
<223> OTHER INFORMATION: Synthetic Construct

<400> SEQUENCE: 97

Gly Ser Gly Val Asn
1               5

<210> SEQ ID NO 98
<211> LENGTH: 16
<212> TYPE: PRT
<213> ORGANISM: Artificial Sequence
<220> FEATURE:
<223> OTHER INFORMATION: Synthetic Construct

```
<400> SEQUENCE: 98

Met Ile Trp Gly Asp Gly Asn Thr Asp Tyr Asn Ser Ala Leu Lys Ser
1               5                   10                  15

<210> SEQ ID NO 99
<211> LENGTH: 12
<212> TYPE: PRT
<213> ORGANISM: Artificial Sequence
<220> FEATURE:
<223> OTHER INFORMATION: Synthetic Construct

<400> SEQUENCE: 99

Gly Ala His Tyr Gly Lys Arg Trp Tyr Phe Asp Val
1               5                   10

<210> SEQ ID NO 100
<211> LENGTH: 11
<212> TYPE: PRT
<213> ORGANISM: Artificial Sequence
<220> FEATURE:
<223> OTHER INFORMATION: Synthetic Construct

<400> SEQUENCE: 100

Ser Ala Ser Gln Gly Ile Asn Asn Tyr Leu Asn
1               5                   10

<210> SEQ ID NO 101
<211> LENGTH: 7
<212> TYPE: PRT
<213> ORGANISM: Artificial Sequence
<220> FEATURE:
<223> OTHER INFORMATION: Synthetic Construct

<400> SEQUENCE: 101

Tyr Thr Ser Thr Leu Pro Ser
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic Construct

<400> SEQUENCE: 102

Gln Gln Tyr Ser Lys Leu Pro Pro Thr
1               5

<210> SEQ ID NO 103
<211> LENGTH: 23
<212> TYPE: PRT
<213> ORGANISM: Artificial Sequence
<220> FEATURE:
<223> OTHER INFORMATION: Synthetic Construct

<400> SEQUENCE: 103

Asp Ile Gln Met Thr Gln Thr Thr Phe Ser Leu Ser Ala Ser Leu Gly
1               5                   10                  15

Asp Arg Val Thr Ile Ser Cys
            20

<210> SEQ ID NO 104
<211> LENGTH: 15
<212> TYPE: PRT
<213> ORGANISM: Artificial Sequence
<220> FEATURE:
```

```
<223> OTHER INFORMATION: Synthetic Construct

<400> SEQUENCE: 104

Trp Tyr Gln Gln Arg Pro Asp Gly Thr Val Lys Leu Leu Ile Tyr
1               5                   10                  15

<210> SEQ ID NO 105
<211> LENGTH: 32
<212> TYPE: PRT
<213> ORGANISM: Artificial Sequence
<220> FEATURE:
<223> OTHER INFORMATION: Synthetic Construct

<400> SEQUENCE: 105

Gly Val Pro Ser Arg Phe Ser Gly Ser Gly Ser Gly Thr Asp Tyr Ser
1               5                   10                  15

Leu Thr Ile Ser Asn Leu Glu Pro Glu Asp Ile Ala Ser Tyr Tyr Cys
            20                  25                  30

<210> SEQ ID NO 106
<211> LENGTH: 10
<212> TYPE: PRT
<213> ORGANISM: Artificial Sequence
<220> FEATURE:
<223> OTHER INFORMATION: Synthetic Construct

<400> SEQUENCE: 106

Phe Gly Gly Gly Thr Lys Val Glu Ile Lys
1               5                   10

<210> SEQ ID NO 107
<211> LENGTH: 30
<212> TYPE: PRT
<213> ORGANISM: Artificial Sequence
<220> FEATURE:
<223> OTHER INFORMATION: Synthetic Construct

<400> SEQUENCE: 107

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr
            20                  25                  30

<210> SEQ ID NO 108
<211> LENGTH: 14
<212> TYPE: PRT
<213> ORGANISM: Artificial Sequence
<220> FEATURE:
<223> OTHER INFORMATION: Synthetic Construct

<400> SEQUENCE: 108

Trp Val Arg Gln Pro Pro Gly Gln Gly Leu Glu Trp Leu Gly
1               5                   10

<210> SEQ ID NO 109
<211> LENGTH: 32
<212> TYPE: PRT
<213> ORGANISM: Artificial Sequence
<220> FEATURE:
<223> OTHER INFORMATION: Synthetic Construct

<400> SEQUENCE: 109

Arg Leu Ser Ile Ser Lys Asp Asn Ser Lys Ser Gln Val Phe Leu Lys
1               5                   10                  15
```

Met Asn Ser Leu Gln Thr Asp Asp Thr Ala Arg Tyr Tyr Cys Ala Arg
            20                  25                  30

<210> SEQ ID NO 110
<211> LENGTH: 11
<212> TYPE: PRT
<213> ORGANISM: Artificial Sequence
<220> FEATURE:
<223> OTHER INFORMATION: Synthetic Construct

<400> SEQUENCE: 110

Trp Gly Ala Gly Thr Thr Val Thr Val Ser Ser
1               5                   10

<210> SEQ ID NO 111
<211> LENGTH: 120
<212> TYPE: PRT
<213> ORGANISM: Artificial Sequence
<220> FEATURE:
<223> OTHER INFORMATION: Synthetic Construct

<400> SEQUENCE: 111

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Ser
            20                  25                  30

Gly Val Asn Trp Val Arg Gln Pro Pro Gly Gln Gly Leu Glu Trp Leu
        35                  40                  45

Gly Met Ile Trp Gly Asp Gly Asn Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Gly Ala His Tyr Gly Lys Arg Trp Tyr Phe Asp Val Trp Gly Ala
            100                 105                 110

Gly Thr Thr Val Thr Val Ser Ser
        115                 120

<210> SEQ ID NO 112
<211> LENGTH: 107
<212> TYPE: PRT
<213> ORGANISM: Artificial Sequence
<220> FEATURE:
<223> OTHER INFORMATION: Synthetic Construct

<400> SEQUENCE: 112

Asp Ile Gln Met Thr Gln Thr Thr Phe Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Arg Pro Asp Gly Thr Val Lys Leu Leu Ile
        35                  40                  45

Tyr Tyr Thr Ser Thr Leu Pro Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Ser Tyr Tyr Cys Gln Gln Tyr Ser Lys Leu Pro Pro
                85                  90                  95

Thr Phe Gly Gly Gly Thr Lys Val Glu Ile Lys
            100                 105

<210> SEQ ID NO 113
<211> LENGTH: 5
<212> TYPE: PRT
<213> ORGANISM: Artificial Sequence
<220> FEATURE:
<223> OTHER INFORMATION: Synthetic Construct

<400> SEQUENCE: 113

Gly Ser Gly Val Asn
1               5

<210> SEQ ID NO 114
<211> LENGTH: 16
<212> TYPE: PRT
<213> ORGANISM: Artificial Sequence
<220> FEATURE:
<223> OTHER INFORMATION: Synthetic Construct

<400> SEQUENCE: 114

Met Ile Trp Gly Asp Gly Asn Thr Asp Tyr Asn Ser Ala Leu Lys Ser
1               5                   10                  15

<210> SEQ ID NO 115
<211> LENGTH: 12
<212> TYPE: PRT
<213> ORGANISM: Artificial Sequence
<220> FEATURE:
<223> OTHER INFORMATION: Synthetic Construct

<400> SEQUENCE: 115

Gly Ala His Tyr Gly Lys Arg Trp Tyr Phe Asp Val
1               5                   10

<210> SEQ ID NO 116
<211> LENGTH: 11
<212> TYPE: PRT
<213> ORGANISM: Artificial Sequence
<220> FEATURE:
<223> OTHER INFORMATION: Synthetic Construct

<400> SEQUENCE: 116

Ser Ala Ser Gln Gly Ile Asn Asn Tyr Leu Asn
1               5                   10

<210> SEQ ID NO 117
<211> LENGTH: 7
<212> TYPE: PRT
<213> ORGANISM: Artificial Sequence
<220> FEATURE:
<223> OTHER INFORMATION: Synthetic Construct

<400> SEQUENCE: 117

Tyr Thr Ser Ser Leu Pro Ser
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic Construct -continued

<400> SEQUENCE: 118

Gln Gln Tyr Ser Lys Leu Pro Pro Thr
1               5

<210> SEQ ID NO 119
<211> LENGTH: 23
<212> TYPE: PRT
<213> ORGANISM: Artificial Sequence
<220> FEATURE:
<223> OTHER INFORMATION: Synthetic Construct

<400> SEQUENCE: 119

Asp Ile Gln Met Thr Gln Thr Thr Ser Ser Leu Ser Ala Ser Leu Gly
1               5                   10                  15

Asp Arg Val Thr Ile Ser Cys
            20

<210> SEQ ID NO 120
<211> LENGTH: 15
<212> TYPE: PRT
<213> ORGANISM: Artificial Sequence
<220> FEATURE:
<223> OTHER INFORMATION: Synthetic Construct

<400> SEQUENCE: 120

Trp Tyr Gln Gln Lys Pro Asp Gly Thr Val Lys Leu Leu Ile Tyr
1               5                   10                  15

<210> SEQ ID NO 121
<211> LENGTH: 32
<212> TYPE: PRT
<213> ORGANISM: Artificial Sequence
<220> FEATURE:
<223> OTHER INFORMATION: Synthetic Construct

<400> SEQUENCE: 121

Gly Val Pro Ser Arg Phe Ser Gly Ser Gly Ser Gly Thr Asp Tyr Ser
1               5                   10                  15

Leu Thr Ile Ser Asn Leu Glu Pro Glu Asp Ile Ala Thr Tyr Tyr Cys
            20                  25                  30

<210> SEQ ID NO 122
<211> LENGTH: 10
<212> TYPE: PRT
<213> ORGANISM: Artificial Sequence
<220> FEATURE:
<223> OTHER INFORMATION: Synthetic Construct

<400> SEQUENCE: 122

Phe Gly Gly Gly Thr Lys Val Glu Ile Lys
1               5                   10

<210> SEQ ID NO 123
<211> LENGTH: 30
<212> TYPE: PRT
<213> ORGANISM: Artificial Sequence
<220> FEATURE:
<223> OTHER INFORMATION: Synthetic Construct

<400> SEQUENCE: 123

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ala Leu Thr
            20                  25                  30

<210> SEQ ID NO 124
<211> LENGTH: 14
<212> TYPE: PRT
<213> ORGANISM: Artificial Sequence
<220> FEATURE:
<223> OTHER INFORMATION: Synthetic Construct

<400> SEQUENCE: 124

```
Trp Val Arg Gln Pro Pro Gly Lys Gly Leu Glu Trp Leu Gly
1               5                   10
```

<210> SEQ ID NO 125
<211> LENGTH: 32
<212> TYPE: PRT
<213> ORGANISM: Artificial Sequence
<220> FEATURE:
<223> OTHER INFORMATION: Synthetic Construct

<400> SEQUENCE: 125

```
Arg Leu Ser Ile Ser Lys Asp Asn Ser Lys Ser Gln Ile Phe Leu Lys
1               5                   10                  15

Met Asn Ser Leu Gln Thr Asp Asp Thr Ala Arg Tyr Tyr Cys Ala Arg
                20                  25                  30
```

<210> SEQ ID NO 126
<211> LENGTH: 11
<212> TYPE: PRT
<213> ORGANISM: Artificial Sequence
<220> FEATURE:
<223> OTHER INFORMATION: Synthetic Construct

<400> SEQUENCE: 126

```
Trp Gly Ala Gly Thr Thr Val Thr Val Ser Ser
1               5                   10
```

<210> SEQ ID NO 127
<211> LENGTH: 120
<212> TYPE: PRT
<213> ORGANISM: Artificial Sequence
<220> FEATURE:
<223> OTHER INFORMATION: Synthetic Construct

<400> SEQUENCE: 127

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ala Leu Thr Gly Ser
                20                  25                  30

Gly Val Asn Trp Val Arg Gln Pro Pro Gly Lys Gly Leu Glu Trp Leu
        35                  40                  45

Gly Met Ile Trp Gly Asp Gly Asn Thr Asp Tyr Asn Ser Ala Leu Lys
    50                  55                  60

Ser Arg Leu Ser Ile Ser Lys Asp Asn Ser Lys Ser Gln Ile Phe Leu
65                  70                  75                  80

Lys Met Asn Ser Leu Gln Thr Asp Asp Thr Ala Arg Tyr Tyr Cys Ala
                85                  90                  95

Arg Gly Ala His Tyr Gly Tyr Arg Trp Tyr Phe Asp Val Trp Gly Ala
                100                 105                 110

Gly Thr Thr Val Thr Val Ser Ser
        115                 120
```

<210> SEQ ID NO 128

<211> LENGTH: 107
<212> TYPE: PRT
<213> ORGANISM: Artificial Sequence
<220> FEATURE:
<223> OTHER INFORMATION: Synthetic Construct

<400> SEQUENCE: 128

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu Pro Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Pro
                85                  90                  95

Thr Phe Gly Gly Gly Thr Lys Val Glu Ile Lys
            100                 105

<210> SEQ ID NO 129
<211> LENGTH: 5
<212> TYPE: PRT
<213> ORGANISM: Artificial Sequence
<220> FEATURE:
<223> OTHER INFORMATION: Synthetic Construct

<400> SEQUENCE: 129

Asp Tyr Tyr Met Tyr
1               5

<210> SEQ ID NO 130
<211> LENGTH: 17
<212> TYPE: PRT
<213> ORGANISM: Artificial Sequence
<220> FEATURE:
<223> OTHER INFORMATION: Synthetic Construct

<400> SEQUENCE: 130

Thr Ile Ser Asp Gly Ile Thr Tyr Thr Tyr Tyr Ser Asp Ser Val Arg
1               5                   10                  15

Gly

<210> SEQ ID NO 131
<211> LENGTH: 12
<212> TYPE: PRT
<213> ORGANISM: Artificial Sequence
<220> FEATURE:
<223> OTHER INFORMATION: Synthetic Construct

<400> SEQUENCE: 131

Gly Gly Gly Ser Thr Ala Arg Gly Ala Leu Asp Phe
1               5                   10

<210> SEQ ID NO 132
<211> LENGTH: 11
<212> TYPE: PRT
<213> ORGANISM: Artificial Sequence
<220> FEATURE:
<223> OTHER INFORMATION: Synthetic Construct

<400> SEQUENCE: 132

His Ala Ser Gln Asn Ile His Val Trp Leu Ser
1               5                   10

<210> SEQ ID NO 133
<211> LENGTH: 7
<212> TYPE: PRT
<213> ORGANISM: Artificial Sequence
<220> FEATURE:
<223> OTHER INFORMATION: Synthetic Construct

<400> SEQUENCE: 133

Gly Ala Ser His Leu His Thr
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic Construct

<400> SEQUENCE: 134

Leu Gln Gly Gln Ser Tyr Pro Leu Thr
1               5

<210> SEQ ID NO 135
<211> LENGTH: 23
<212> TYPE: PRT
<213> ORGANISM: Artificial Sequence
<220> FEATURE:
<223> OTHER INFORMATION: Synthetic Construct

<400> SEQUENCE: 135

Asp Ile Gln Met Asn Gln Ser Pro Ser Ser Leu Ser Ala Ser Leu Gly
1               5                   10                  15

Asp Thr Ile Thr Ile Thr Cys
            20

<210> SEQ ID NO 136
<211> LENGTH: 15
<212> TYPE: PRT
<213> ORGANISM: Artificial Sequence
<220> FEATURE:
<223> OTHER INFORMATION: Synthetic Construct

<400> SEQUENCE: 136

Trp Tyr Gln Gln Lys Pro Gly Asn Ile Pro Lys Leu Leu Ile Tyr
1               5                   10                  15

<210> SEQ ID NO 137
<211> LENGTH: 32
<212> TYPE: PRT
<213> ORGANISM: Artificial Sequence
<220> FEATURE:
<223> OTHER INFORMATION: Synthetic Construct

<400> SEQUENCE: 137

Gly Val Pro Ser Arg Phe Ser Gly Arg Gly Ser Gly Thr Gly Phe Thr
1               5                   10                  15

Leu Thr Ile Ser Ser Leu Gln Pro Glu Asp Ile Ala Thr Tyr Tyr Cys
            20                  25                  30

<210> SEQ ID NO 138

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 138

Phe Gly Ser Gly Thr Lys Val Glu Ile Lys
1               5                   10

<210> SEQ ID NO 139
<211> LENGTH: 30
<212> TYPE: PRT
<213> ORGANISM: Artificial Sequence
<220> FEATURE:
<223> OTHER INFORMATION: Synthetic Construct

<400> SEQUENCE: 139

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser
            20                  25                  30

<210> SEQ ID NO 140
<211> LENGTH: 14
<212> TYPE: PRT
<213> ORGANISM: Artificial Sequence
<220> FEATURE:
<223> OTHER INFORMATION: Synthetic Construct

<400> SEQUENCE: 140

Trp Val Arg Gln Thr Pro Glu Lys Arg Leu Glu Trp Val Ala
1               5                   10

<210> SEQ ID NO 141
<211> LENGTH: 32
<212> TYPE: PRT
<213> ORGANISM: Artificial Sequence
<220> FEATURE:
<223> OTHER INFORMATION: Synthetic Construct

<400> SEQUENCE: 141

Arg Phe Thr Ile Ser Arg Asp Asn Ala Glu Asn Thr Leu Tyr Leu Gln
1               5                   10                  15

Met Ser Ser Leu Lys Ser Glu Asp Thr Ala Met Tyr Tyr Cys Ser Lys
            20                  25                  30

<210> SEQ ID NO 142
<211> LENGTH: 11
<212> TYPE: PRT
<213> ORGANISM: Artificial Sequence
<220> FEATURE:
<223> OTHER INFORMATION: Synthetic Construct

<400> SEQUENCE: 142

Trp Gly Gln Gly Thr Ser Val Thr Val Ser Ser
1               5                   10

<210> SEQ ID NO 143
<211> LENGTH: 121
<212> TYPE: PRT
<213> ORGANISM: Artificial Sequence
<220> FEATURE:
<223> OTHER INFORMATION: Synthetic Construct
```

<400> SEQUENCE: 143

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Thr Ile Ser Asp Gly Ile Thr Tyr Thr Tyr Tyr Ser Asp Ser Val
    50                  55                  60

Arg Gly Arg Phe Thr Ile Ser Arg Asp Asn Ala Glu Asn Thr Leu Tyr
65                  70                  75                  80

Leu Gln Met Ser Ser Leu Lys Ser Glu Asp Thr Ala Met Tyr Tyr Cys
                85                  90                  95

Ser Lys Gly Gly Gly Ser Thr Ala Arg Gly Ala Leu Asp Phe Trp Gly
            100                 105                 110

Gln Gly Thr Ser Val Thr Val Ser Ser
            115                 120

<210> SEQ ID NO 144
<211> LENGTH: 107
<212> TYPE: PRT
<213> ORGANISM: Artificial Sequence
<220> FEATURE:
<223> OTHER INFORMATION: Synthetic Construct

<400> SEQUENCE: 144

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile His Val Trp
            20                  25                  30

Leu Ser Trp Tyr Gln Gln Lys Pro Gly Asn Ile Pro Lys Leu Leu Ile
        35                  40                  45

Tyr Gly Ala Ser His Leu His Thr Gly Val Pro Ser Arg Phe Ser Gly
    50                  55                  60

Arg Gly Ser Gly Thr Gly Phe Thr Leu Thr Ile Ser Ser Leu Gln Pro
65                  70                  75                  80

Glu Asp Ile Ala Thr Tyr Tyr Cys Leu Gln Gly Gln Ser Tyr Pro Leu
                85                  90                  95

Thr Phe Gly Ser Gly Thr Lys Val Glu Ile Lys
            100                 105

<210> SEQ ID NO 145
<211> LENGTH: 5
<212> TYPE: PRT
<213> ORGANISM: Artificial Sequence
<220> FEATURE:
<223> OTHER INFORMATION: Synthetic Construct

<400> SEQUENCE: 145

Thr Phe Gly Ile His
1               5

<210> SEQ ID NO 146
<211> LENGTH: 17
<212> TYPE: PRT
<213> ORGANISM: Artificial Sequence
<220> FEATURE:
<223> OTHER INFORMATION: Synthetic Construct

<400> SEQUENCE: 146

Tyr Ile Ser Tyr Asp Ser Arg Thr Ile Tyr Tyr Ala Asp Thr Val Lys
1               5                   10                  15

Gly

<210> SEQ ID NO 147
<211> LENGTH: 12
<212> TYPE: PRT
<213> ORGANISM: Artificial Sequence
<220> FEATURE:
<223> OTHER INFORMATION: Synthetic Construct

<400> SEQUENCE: 147

Trp Ala Tyr Glu Gly Gly Val Asn Tyr Phe Asp Asn
1               5                   10

<210> SEQ ID NO 148
<211> LENGTH: 12
<212> TYPE: PRT
<213> ORGANISM: Artificial Sequence
<220> FEATURE:
<223> OTHER INFORMATION: Synthetic Construct

<400> SEQUENCE: 148

Thr Ala Thr Ser Gly Val Ser Ser Ser Tyr Leu His
1               5                   10

<210> SEQ ID NO 149
<211> LENGTH: 7
<212> TYPE: PRT
<213> ORGANISM: Artificial Sequence
<220> FEATURE:
<223> OTHER INFORMATION: Synthetic Construct

<400> SEQUENCE: 149

Ser Ser Ser Asn Leu Ala Ser
1               5

<210> SEQ ID NO 150
<211> LENGTH: 9
<212> TYPE: PRT
<213> ORGANISM: Artificial Sequence
<220> FEATURE:
<223> OTHER INFORMATION: Synthetic Construct

<400> SEQUENCE: 150

His Gln Phe His Arg Ser Pro Leu Thr
1               5

<210> SEQ ID NO 151
<211> LENGTH: 23
<212> TYPE: PRT
<213> ORGANISM: Artificial Sequence
<220> FEATURE:
<223> OTHER INFORMATION: Synthetic Construct

<400> SEQUENCE: 151

Gln Ile Val Leu Thr Gln Ser Pro Ala Ile Met Ser Ala Ser Leu Gly
1               5                   10                  15

Glu Arg Val Thr Met Thr Cys
            20

<210> SEQ ID NO 152
<211> LENGTH: 15
<212> TYPE: PRT

```
<213> ORGANISM: Artificial Sequence
<220> FEATURE:
<223> OTHER INFORMATION: Synthetic Construct

<400> SEQUENCE: 152

Trp Tyr Gln Gln Lys Pro Gly Ser Ser Pro Lys Leu Trp Ile Tyr
1               5                   10                  15

<210> SEQ ID NO 153
<211> LENGTH: 32
<212> TYPE: PRT
<213> ORGANISM: Artificial Sequence
<220> FEATURE:
<223> OTHER INFORMATION: Synthetic Construct

<400> SEQUENCE: 153

Gly Val Pro Ala Arg Phe Ser Gly Ser Gly Ser Gly Thr Ser Tyr Ser
1               5                   10                  15

Leu Thr Ile Gly Ser Met Glu Ala Glu Asp Ala Ala Thr Tyr Tyr Cys
                20                  25                  30

<210> SEQ ID NO 154
<211> LENGTH: 10
<212> TYPE: PRT
<213> ORGANISM: Artificial Sequence
<220> FEATURE:
<223> OTHER INFORMATION: Synthetic Construct

<400> SEQUENCE: 154

Phe Gly Thr Gly Thr Lys Val Glu Ile Lys
1               5                   10

<210> SEQ ID NO 155
<211> LENGTH: 30
<212> TYPE: PRT
<213> ORGANISM: Artificial Sequence
<220> FEATURE:
<223> OTHER INFORMATION: Synthetic Construct

<400> SEQUENCE: 155

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser
                20                  25                  30

<210> SEQ ID NO 156
<211> LENGTH: 14
<212> TYPE: PRT
<213> ORGANISM: Artificial Sequence
<220> FEATURE:
<223> OTHER INFORMATION: Synthetic Construct

<400> SEQUENCE: 156

Trp Val Arg Gln Ala Pro Glu Lys Gly Leu Glu Trp Val Ala
1               5                   10

<210> SEQ ID NO 157
<211> LENGTH: 32
<212> TYPE: PRT
<213> ORGANISM: Artificial Sequence
<220> FEATURE:
<223> OTHER INFORMATION: Synthetic Construct

<400> SEQUENCE: 157

Arg Phe Thr Ile Ser Arg Asp Asn Pro Lys Asn Thr Leu Phe Leu Gln
1               5                   10                  15
```

```
Met Thr Ser Leu Arg Ser Glu Asp Thr Ala Met Tyr Tyr Cys Ala Arg
            20                  25                  30
```

<210> SEQ ID NO 158
<211> LENGTH: 11
<212> TYPE: PRT
<213> ORGANISM: Artificial Sequence
<220> FEATURE:
<223> OTHER INFORMATION: Synthetic Construct

<400> SEQUENCE: 158

```
Trp Gly Gln Gly Thr Thr Leu Thr Val Ser Ser
1               5                   10
```

<210> SEQ ID NO 159
<211> LENGTH: 122
<212> TYPE: PRT
<213> ORGANISM: Artificial Sequence
<220> FEATURE:
<223> OTHER INFORMATION: Synthetic Construct

<400> SEQUENCE: 159

```
Gln Gly Gln Met Gln Gln Ser Gly Ala Glu Leu Val Lys Pro Gly Ala
1               5                   10                  15

Ser Val Lys Leu Ser Cys Lys Thr Ser Gly Phe Thr Phe Ser Asp Asn
            20                  25                  30

Tyr Ile Ser Trp Leu Lys Gln Lys Pro Gly Gln Ser Leu Glu Trp Ile
        35                  40                  45

Ala Trp Ile Tyr Ala Gly Thr Gly Gly Ser Ser Tyr Asn Gln Lys Phe
    50                  55                  60

Arg Asp Lys Ala Gln Leu Thr Val Asp Thr Ser Ser Arg Thr Ala Tyr
65                  70                  75                  80

Met Gln Leu Ser Ser Leu Thr Thr Glu Asp Ser Ala Ile Tyr Tyr Cys
                85                  90                  95

Ala Arg His Asp Tyr Tyr Gly Thr Ser Gly Ala Trp Phe Ala Tyr Trp
            100                 105                 110

Gly Arg Gly Thr Leu Val Thr Val Ser Ala
        115                 120
```

<210> SEQ ID NO 160
<211> LENGTH: 112
<212> TYPE: PRT
<213> ORGANISM: Artificial Sequence
<220> FEATURE:
<223> OTHER INFORMATION: Synthetic Construct

<400> SEQUENCE: 160

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln His Ile Val His Ser
            20                  25                  30

Asn Glu Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95
```

Ser His Val Pro Trp Thr Phe Gly Gly Gly Thr Lys Val Glu Ile Lys
            100                 105                 110

<210> SEQ ID NO 161
<211> LENGTH: 5
<212> TYPE: PRT
<213> ORGANISM: Artificial Sequence
<220> FEATURE:
<223> OTHER INFORMATION: Synthetic Construct

<400> SEQUENCE: 161

Asp Asn Tyr Ile Ser
1               5

<210> SEQ ID NO 162
<211> LENGTH: 17
<212> TYPE: PRT
<213> ORGANISM: Artificial Sequence
<220> FEATURE:
<223> OTHER INFORMATION: Synthetic Construct

<400> SEQUENCE: 162

Trp Ile Tyr Ala Gly Thr Gly Gly Ser Ser Tyr Asn Gln Lys Phe Arg
1               5                   10                  15

Asp

<210> SEQ ID NO 163
<211> LENGTH: 13
<212> TYPE: PRT
<213> ORGANISM: Artificial Sequence
<220> FEATURE:
<223> OTHER INFORMATION: Synthetic Construct

<400> SEQUENCE: 163

His Asp Tyr Tyr Gly Thr Ser Gly Ala Trp Phe Ala Tyr
1               5                   10

<210> SEQ ID NO 164
<211> LENGTH: 16
<212> TYPE: PRT
<213> ORGANISM: Artificial Sequence
<220> FEATURE:
<223> OTHER INFORMATION: Synthetic Construct

<400> SEQUENCE: 164

Arg Ser Ser Gln His Ile Val His Ser Asn Glu Asn Thr Tyr Leu Glu
1               5                   10                  15

<210> SEQ ID NO 165
<211> LENGTH: 7
<212> TYPE: PRT
<213> ORGANISM: Artificial Sequence
<220> FEATURE:
<223> OTHER INFORMATION: Synthetic Construct

<400> SEQUENCE: 165

Lys Val Ser Asn Arg Phe Ser
1               5

<210> SEQ ID NO 166
<211> LENGTH: 9
<212> TYPE: PRT
<213> ORGANISM: Artificial Sequence
<220> FEATURE:
<223> OTHER INFORMATION: Synthetic Construct

<400> SEQUENCE: 166

Phe Gln Gly Ser His Val Pro Trp Thr
1               5

<210> SEQ ID NO 167
<211> LENGTH: 23
<212> TYPE: PRT
<213> ORGANISM: Artificial Sequence
<220> FEATURE:
<223> OTHER INFORMATION: Synthetic Construct

<400> SEQUENCE: 167

Asp Val Leu Met Thr Gln Thr Pro Leu Ser Leu Pro Val Ser Leu Gly
1               5                   10                  15

Asp Gln Ala Ser Ile Ser Cys
            20

<210> SEQ ID NO 168
<211> LENGTH: 15
<212> TYPE: PRT
<213> ORGANISM: Artificial Sequence
<220> FEATURE:
<223> OTHER INFORMATION: Synthetic Construct

<400> SEQUENCE: 168

Trp Tyr Leu Gln Lys Pro Gly Gln Ser Pro Lys Leu Leu Ile Tyr
1               5                   10                  15

<210> SEQ ID NO 169
<211> LENGTH: 32
<212> TYPE: PRT
<213> ORGANISM: Artificial Sequence
<220> FEATURE:
<223> OTHER INFORMATION: Synthetic Construct

<400> SEQUENCE: 169

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 170
<211> LENGTH: 10
<212> TYPE: PRT
<213> ORGANISM: Artificial Sequence
<220> FEATURE:
<223> OTHER INFORMATION: Synthetic Construct

<400> SEQUENCE: 170

Phe Gly Gly Gly Thr Lys Val Glu Ile Lys
1               5                   10

<210> SEQ ID NO 171
<211> LENGTH: 30
<212> TYPE: PRT
<213> ORGANISM: Artificial Sequence
<220> FEATURE:
<223> OTHER INFORMATION: Synthetic Construct

<400> SEQUENCE: 171

Gln Gly Gln Met Gln Gln Ser Gly Ala Glu Leu Val Lys Pro Gly Ala
1               5                   10                  15

Ser Val Lys Leu Ser Cys Lys Thr Ser Gly Phe Thr Phe Ser
            20                  25                  30

<210> SEQ ID NO 172
<211> LENGTH: 14
<212> TYPE: PRT
<213> ORGANISM: Artificial Sequence
<220> FEATURE:
<223> OTHER INFORMATION: Synthetic Construct

<400> SEQUENCE: 172

Trp Leu Lys Gln Lys Pro Gly Gln Ser Leu Glu Trp Ile Ala
1               5                   10

<210> SEQ ID NO 173
<211> LENGTH: 32
<212> TYPE: PRT
<213> ORGANISM: Artificial Sequence
<220> FEATURE:
<223> OTHER INFORMATION: Synthetic Construct

<400> SEQUENCE: 173

Lys Ala Gln Leu Thr Val Asp Thr Ser Ser Arg Thr Ala Tyr Met Gln
1               5                   10                  15

Leu Ser Ser Leu Thr Thr Glu Asp Ser Ala Ile Tyr Tyr Cys Ala Arg
            20                  25                  30

<210> SEQ ID NO 174
<211> LENGTH: 11
<212> TYPE: PRT
<213> ORGANISM: Artificial Sequence
<220> FEATURE:
<223> OTHER INFORMATION: Synthetic Construct

<400> SEQUENCE: 174

Trp Gly Arg Gly Thr Leu Val Thr Val Ser Ala
1               5                   10

<210> SEQ ID NO 175
<211> LENGTH: 122
<212> TYPE: PRT
<213> ORGANISM: Artificial Sequence
<220> FEATURE:
<223> OTHER INFORMATION: Synthetic Construct

<400> SEQUENCE: 175

Gln Gly Gln Met Gln Gln Ser Gly Ala Glu Leu Val Lys Pro Gly Ala
1               5                   10                  15

Ser Val Lys Leu Ser Cys Lys Thr Ser Gly Phe Thr Phe Ser Asp Asn
            20                  25                  30

Tyr Ile Ser Trp Leu Lys Gln Lys Pro Gly Gln Ser Leu Glu Trp Ile
        35                  40                  45

Ala Trp Ile Tyr Ala Gly Thr Gly Gly Thr Ser Tyr Asn Gln Lys Phe
    50                  55                  60

Thr Ala Lys Ala Gln Leu Thr Val Asp Thr Ser Ser Ser Thr Ala Tyr
65                  70                  75                  80

Met Gln Phe Ser Ser Leu Thr Thr Glu Asp Ser Ala Ile Tyr Tyr Cys
                85                  90                  95

Ala Arg His Asp Tyr Tyr Gly Thr Ser Gly Ala Trp Phe Ala Tyr Trp
            100                 105                 110

Gly Gln Gly Thr Leu Val Thr Val Ser Ala
        115                 120

<210> SEQ ID NO 176
<211> LENGTH: 112
<212> TYPE: PRT
<213> ORGANISM: Artificial Sequence
<220> FEATURE:
<223> OTHER INFORMATION: Synthetic Construct

<400> SEQUENCE: 176

Asp Val Leu Met Thr Gln Thr Pro Leu Ser Leu Pro Val Ser Leu Gly
1               5                   10                  15

Asp Gln Ala Ser Leu Ser Cys Arg Ser Gln Asn Ile Val His Ile
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Val Glu Ile Lys
            100                 105                 110

<210> SEQ ID NO 177
<211> LENGTH: 5
<212> TYPE: PRT
<213> ORGANISM: Artificial Sequence
<220> FEATURE:
<223> OTHER INFORMATION: Synthetic Construct

<400> SEQUENCE: 177

Asp Asn Tyr Ile Ser
1               5

<210> SEQ ID NO 178
<211> LENGTH: 17
<212> TYPE: PRT
<213> ORGANISM: Artificial Sequence
<220> FEATURE:
<223> OTHER INFORMATION: Synthetic Construct

<400> SEQUENCE: 178

Trp Ile Tyr Ala Gly Thr Gly Gly Thr Ser Tyr Asn Gln Lys Phe Thr
1               5                   10                  15
Ala

<210> SEQ ID NO 179
<211> LENGTH: 13
<212> TYPE: PRT
<213> ORGANISM: Artificial Sequence
<220> FEATURE:
<223> OTHER INFORMATION: Synthetic Construct

<400> SEQUENCE: 179

His Asp Tyr Tyr Gly Thr Ser Gly Ala Trp Phe Ala Tyr
1               5                   10

<210> SEQ ID NO 180
<211> LENGTH: 16
<212> TYPE: PRT
<213> ORGANISM: Artificial Sequence
<220> FEATURE:

<223> OTHER INFORMATION: Synthetic Construct

<400> SEQUENCE: 180

Arg Ser Ser Gln Asn Ile Val His Ile Asn Gly Asn Thr Tyr Leu Glu
1               5                   10                  15

<210> SEQ ID NO 181
<211> LENGTH: 7
<212> TYPE: PRT
<213> ORGANISM: Artificial Sequence
<220> FEATURE:
<223> OTHER INFORMATION: Synthetic Construct

<400> SEQUENCE: 181

Lys Val Ser Asn Arg Phe Ser
1               5

<210> SEQ ID NO 182
<211> LENGTH: 9
<212> TYPE: PRT
<213> ORGANISM: Artificial Sequence
<220> FEATURE:
<223> OTHER INFORMATION: Synthetic Construct

<400> SEQUENCE: 182

Phe Gln Gly Ser His Val Pro Trp Thr
1               5

<210> SEQ ID NO 183
<211> LENGTH: 23
<212> TYPE: PRT
<213> ORGANISM: Artificial Sequence
<220> FEATURE:
<223> OTHER INFORMATION: Synthetic Construct

<400> SEQUENCE: 183

Asp Val Leu Met Thr Gln Thr Pro Leu Ser Leu Pro Val Ser Leu Gly
1               5                   10                  15

Asp Gln Ala Ser Leu Ser Cys
            20

<210> SEQ ID NO 184
<211> LENGTH: 15
<212> TYPE: PRT
<213> ORGANISM: Artificial Sequence
<220> FEATURE:
<223> OTHER INFORMATION: Synthetic Construct

<400> SEQUENCE: 184

Trp Tyr Leu Gln Lys Pro Gly Gln Ser Pro Lys Leu Leu Ile Tyr
1               5                   10                  15

<210> SEQ ID NO 185
<211> LENGTH: 32
<212> TYPE: PRT
<213> ORGANISM: Artificial Sequence
<220> FEATURE:
<223> OTHER INFORMATION: Synthetic Construct

<400> SEQUENCE: 185

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

```
<210> SEQ ID NO 186
<211> LENGTH: 10
<212> TYPE: PRT
<213> ORGANISM: Artificial Sequence
<220> FEATURE:
<223> OTHER INFORMATION: Synthetic Construct

<400> SEQUENCE: 186

Phe Gly Gly Gly Thr Lys Val Glu Ile Lys
1               5                   10

<210> SEQ ID NO 187
<211> LENGTH: 30
<212> TYPE: PRT
<213> ORGANISM: Artificial Sequence
<220> FEATURE:
<223> OTHER INFORMATION: Synthetic Construct

<400> SEQUENCE: 187

Gln Gly Gln Met Gln Gln Ser Gly Ala Glu Leu Val Lys Pro Gly Ala
1               5                   10                  15

Ser Val Lys Leu Ser Cys Lys Thr Ser Gly Phe Thr Phe Ser
            20                  25                  30

<210> SEQ ID NO 188
<211> LENGTH: 14
<212> TYPE: PRT
<213> ORGANISM: Artificial Sequence
<220> FEATURE:
<223> OTHER INFORMATION: Synthetic Construct

<400> SEQUENCE: 188

Trp Leu Lys Gln Lys Pro Gly Gln Ser Leu Glu Trp Ile Ala
1               5                   10

<210> SEQ ID NO 189
<211> LENGTH: 32
<212> TYPE: PRT
<213> ORGANISM: Artificial Sequence
<220> FEATURE:
<223> OTHER INFORMATION: Synthetic Construct

<400> SEQUENCE: 189

Lys Ala Gln Leu Thr Val Asp Thr Ser Ser Ser Thr Ala Tyr Met Gln
1               5                   10                  15

Phe Ser Ser Leu Thr Thr Glu Asp Ser Ala Ile Tyr Tyr Cys Ala Arg
            20                  25                  30

<210> SEQ ID NO 190
<211> LENGTH: 11
<212> TYPE: PRT
<213> ORGANISM: Artificial Sequence
<220> FEATURE:
<223> OTHER INFORMATION: Synthetic Construct

<400> SEQUENCE: 190

Trp Gly Gln Gly Thr Leu Val Thr Val Ser Ala
1               5                   10

<210> SEQ ID NO 191
<211> LENGTH: 121
<212> TYPE: PRT
<213> ORGANISM: Artificial Sequence
<220> FEATURE:
<223> OTHER INFORMATION: Synthetic Construct
```

<400> SEQUENCE: 191

Asp Val Gln Leu Val Glu Ser Gly Gly Leu Val Gln Pro Gly Gly
1               5                   10                  15

Ser Arg Lys Leu Ser Cys Ala Ala Ser Gly Phe Thr Phe Ser Thr Phe
            20                  25                  30

Gly Ile His Trp Val Arg Gln Ala Pro Glu Lys Gly Leu Glu Trp Val
        35                  40                  45

Ala Tyr Ile Ser Tyr Asp Ser Arg Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Trp Ala Tyr Glu Gly Gly Val Asn Tyr Phe Asp Asn Trp Gly
            100                 105                 110

Gln Gly Thr Thr Leu Thr Val Ser Ser
        115                 120

<210> SEQ ID NO 192
<211> LENGTH: 108
<212> TYPE: PRT
<213> ORGANISM: Artificial Sequence
<220> FEATURE:
<223> OTHER INFORMATION: Synthetic Construct

<400> SEQUENCE: 192

Gln Ile Val Leu Thr Gln Ser Pro Ala Ile Met Ser Ala Ser Leu Gly
1               5                   10                  15

Glu Arg Val Thr Met Thr Cys Thr Ala Thr Ser Gly Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Ser Ser Asn Leu Ala Ser Gly Val Pro Ala Arg Phe Ser
    50                  55                  60

Gly Ser Gly Ser Gly Thr Ser Tyr Ser Leu Thr Ile Gly Ser Met Glu
65                  70                  75                  80

Ala Glu Asp Ala Ala Thr Tyr Tyr Cys His Gln Phe His Arg Ser Pro
                85                  90                  95

Leu Thr Phe Gly Thr Gly Thr Lys Val Glu Ile Lys
            100                 105

<210> SEQ ID NO 193
<211> LENGTH: 332
<212> TYPE: PRT
<213> ORGANISM: Homo sapiens

<400> SEQUENCE: 193

Met Gly Leu Gly Pro Val Phe Leu Leu Leu Ala Gly Ile Phe Pro Phe
1               5                   10                  15

Ala Pro Pro Gly Ala Ala Ala Glu Pro His Ser Leu Arg Tyr Asn Leu
            20                  25                  30

Thr Val Leu Ser Trp Asp Gly Ser Val Gln Ser Gly Phe Leu Ala Glu
        35                  40                  45

Val His Leu Asp Gly Gln Pro Phe Leu Arg Tyr Asp Arg Gln Lys Cys
    50                  55                  60

```
Arg Ala Lys Pro Gln Gly Gln Trp Ala Glu Asp Val Leu Gly Asn Lys
 65                  70                  75                  80

Thr Trp Asp Arg Glu Thr Arg Asp Leu Thr Gly Asn Gly Lys Asp Leu
                 85                  90                  95

Arg Met Thr Leu Ala His Ile Lys Asp Gln Lys Glu Gly Leu His Ser
            100                 105                 110

Leu Gln Glu Ile Arg Val Cys Glu Ile His Glu Asp Asn Ser Thr Arg
        115                 120                 125

Ser Ser Gln His Phe Tyr Tyr Asp Gly Glu Leu Phe Leu Ser Gln Asn
130                 135                 140

Leu Glu Thr Glu Glu Trp Thr Val Pro Gln Ser Ser Arg Ala Gln Thr
145                 150                 155                 160

Leu Ala Met Asn Val Arg Asn Phe Leu Lys Glu Asp Ala Met Lys Thr
                165                 170                 175

Lys Thr His Tyr His Ala Met His Ala Asp Cys Leu Gln Glu Leu Arg
            180                 185                 190

Arg Tyr Leu Glu Ser Gly Val Val Leu Arg Arg Thr Val Pro Pro Met
        195                 200                 205

Val Asn Val Thr Arg Ser Glu Ala Ser Glu Gly Asn Ile Thr Val Thr
210                 215                 220

Cys Arg Ala Ser Ser Phe Tyr Pro Arg Asn Ile Ile Leu Thr Trp Arg
225                 230                 235                 240

Gln Asp Gly Val Ser Leu Ser His Asp Thr Gln Gln Trp Gly Asp Val
                245                 250                 255

Leu Pro Asp Gly Asn Gly Thr Tyr Gln Thr Trp Val Ala Thr Arg Ile
            260                 265                 270

Cys Arg Gly Glu Glu Gln Arg Phe Thr Cys Tyr Met Glu His Ser Gly
        275                 280                 285

Asn His Ser Thr His Pro Val Pro Ser Gly Lys Val Leu Val Leu Gln
290                 295                 300

Ser His Trp Gln Thr Phe His Val Ser Ala Val Ala Ala Gly Cys Cys
305                 310                 315                 320

Tyr Phe Cys Tyr Tyr Phe Leu Cys Pro Leu Leu
                325                 330

<210> SEQ ID NO 194
<211> LENGTH: 341
<212> TYPE: PRT
<213> ORGANISM: Homo sapiens

<400> SEQUENCE: 194

Gly Ser Thr Val Pro Pro Met Val Asn Val Thr Arg Ser Glu Ala Ser
 1               5                  10                  15

Glu Gly Asn Ile Thr Val Thr Cys Arg Ala Ser Ser Phe Tyr Pro Arg
             20                  25                  30

Asn Ile Ile Leu Thr Trp Arg Gln Asp Gly Val Ser Leu Ser His Asp
         35                  40                  45

Thr Gln Gln Trp Gly Asp Val Leu Pro Asp Gly Asn Gly Thr Tyr Gln
 50                  55                  60

Thr Trp Val Ala Thr Arg Ile Cys Arg Gly Glu Glu Gln Arg Phe Thr
 65                  70                  75                  80

Cys Tyr Met Glu His Ser Gly Asn His Ser Thr His Pro Val Pro Ser
                 85                  90                  95
```

```
Gly Asn Ser Arg Ala Gln Val Thr Asp Lys Lys Ile Glu Pro Arg Gly
                100                 105                 110

Pro Thr Ile Lys Pro Cys Pro Pro Cys Lys Cys Pro Ala Pro Asn Leu
            115                 120                 125

Leu Gly Gly Pro Ser Val Phe Ile Phe Pro Pro Lys Ile Lys Asp Val
        130                 135                 140

Leu Met Ile Ser Leu Ser Pro Ile Val Thr Cys Val Val Val Asp Val
145                 150                 155                 160

Ser Glu Asp Asp Pro Asp Val Gln Ile Ser Trp Phe Val Asn Asn Val
                165                 170                 175

Glu Val His Thr Ala Gln Thr Gln Thr His Arg Glu Asp Tyr Asn Ser
            180                 185                 190

Thr Leu Arg Val Val Ser Ala Leu Pro Ile Gln His Gln Asp Trp Met
        195                 200                 205

Ser Gly Lys Glu Phe Lys Cys Lys Val Asn Asn Lys Asp Leu Pro Ala
210                 215                 220

Pro Ile Glu Arg Thr Ile Ser Lys Pro Lys Gly Ser Val Arg Ala Pro
225                 230                 235                 240

Gln Val Tyr Val Leu Pro Pro Glu Glu Glu Met Thr Lys Lys Gln
                245                 250                 255

Val Thr Leu Thr Cys Met Val Thr Asp Phe Met Pro Glu Asp Ile Tyr
            260                 265                 270

Val Glu Trp Thr Asn Asn Gly Lys Thr Glu Leu Asn Tyr Lys Asn Thr
        275                 280                 285

Glu Pro Val Leu Asp Ser Asp Gly Ser Tyr Phe Met Tyr Ser Lys Leu
        290                 295                 300

Arg Val Glu Lys Lys Asn Trp Val Glu Arg Asn Ser Tyr Ser Cys Ser
305                 310                 315                 320

Val Val His Glu Gly Leu His Asn His His Thr Thr Lys Ser Phe Ser
                325                 330                 335

Arg Thr Pro Gly Lys
                340

<210> SEQ ID NO 195
<211> LENGTH: 107
<212> TYPE: PRT
<213> ORGANISM: Homo sapiens

<400> SEQUENCE: 195

Gly Ser Thr Val Pro Met Val Asn Val Thr Arg Ser Glu Ala Ser
1               5                   10                  15

Glu Gly Asn Ile Thr Val Thr Cys Arg Ala Ser Ser Phe Tyr Pro Arg
            20                  25                  30

Asn Ile Ile Leu Thr Trp Arg Gln Asp Gly Val Ser Leu Ser His Asp
        35                  40                  45

Thr Gln Gln Trp Gly Asp Val Leu Pro Asp Gly Asn Gly Thr Tyr Gln
    50                  55                  60

Thr Trp Val Ala Thr Arg Ile Cys Arg Gly Glu Glu Gln Arg Phe Thr
65                  70                  75                  80

Cys Tyr Met Glu His Ser Gly Asn His Ser Thr His Pro Val Pro Ser
                85                  90                  95

Gly Asn Ser His His His His His His
            100                 105
```

<210> SEQ ID NO 196
<211> LENGTH: 107
<212> TYPE: PRT
<213> ORGANISM: Homo sapiens

<400> SEQUENCE: 196

Gly Ser Thr Val Pro Pro Met Val Asn Val Thr Arg Ser Glu Ala Ser
1               5                   10                  15

Glu Gly Asn Ile Thr Val Thr Cys Arg Ala Ser Gly Phe Tyr Pro Trp
                20                  25                  30

Asn Ile Thr Leu Ser Trp Arg Gln Asp Gly Val Ser Leu Ser His Asp
            35                  40                  45

Thr Gln Gln Trp Gly Asp Val Leu Pro Asp Gly Asn Gly Thr Tyr Gln
    50                  55                  60

Thr Trp Val Ala Thr Arg Ile Cys Gln Gly Glu Glu Gln Arg Phe Thr
65                  70                  75                  80

Cys Tyr Met Glu His Ser Gly Asn His Ser Thr His Pro Val Pro Ser
                85                  90                  95

Gly Asn Ser His His His His His His His
            100                 105

<210> SEQ ID NO 197
<211> LENGTH: 106
<212> TYPE: PRT
<213> ORGANISM: Homo sapiens

<400> SEQUENCE: 197

Gly Ser Val Pro Pro Met Val Asn Val Thr Arg Ser Glu Ala Ser Glu
1               5                   10                  15

Gly Asn Ile Thr Val Thr Cys Arg Ala Ser Ser Phe Tyr Pro Arg Asn
                20                  25                  30

Ile Thr Leu Thr Trp Arg Gln Asp Gly Val Ser Leu Ser His Asp Thr
            35                  40                  45

Gln Gln Trp Gly Asp Val Leu Pro Asp Gly Asn Gly Thr Tyr Gln Thr
    50                  55                  60

Trp Val Ala Thr Arg Ile Cys Gln Gly Glu Glu Gln Arg Phe Thr Cys
65                  70                  75                  80

Tyr Met Glu His Ser Gly Asn His Ser Thr His Pro Val Pro Ser Gly
                85                  90                  95

Asn Ser His His His His His His His
            100                 105

<210> SEQ ID NO 198
<211> LENGTH: 107
<212> TYPE: PRT
<213> ORGANISM: Homo sapiens

<400> SEQUENCE: 198

Gly Ser Thr Val Pro Pro Met Val Asn Val Thr Cys Ser Glu Val Ser
1               5                   10                  15

Glu Gly Asn Ile Thr Val Thr Cys Arg Ala Ser Ser Phe Tyr Pro Arg
                20                  25                  30

Asn Ile Thr Leu Thr Trp Arg Gln Asp Gly Val Ser Leu Ser His Asn
            35                  40                  45

Thr Gln Gln Trp Gly Asp Val Leu Pro Asp Gly Asn Gly Thr Tyr Gln
    50                  55                  60

Thr Trp Val Ala Thr Arg Ile Arg Gln Gly Glu Glu Gln Arg Phe Thr
65                  70                  75                  80

```
Cys Tyr Met Glu His Ser Gly Asn His Gly Thr His Pro Val Pro Ser
                85                  90                  95

Gly Asn Ser His His His His His His
            100                 105
```

<210> SEQ ID NO 199
<211> LENGTH: 94
<212> TYPE: PRT
<213> ORGANISM: Homo sapiens

<400> SEQUENCE: 199

```
Thr Val Pro Pro Met Val Asn Val Thr Arg Ser Glu Ala Ser Glu Gly
1               5                   10                  15

Asn Ile Thr Val Thr Cys Arg Ala Ser Ser Phe Tyr Pro Arg Asn Ile
            20                  25                  30

Ile Leu Thr Trp Arg Gln Asp Gly Val Ser Leu Ser His Asp Thr Gln
        35                  40                  45

Gln Trp Gly Asp Val Leu Pro Asp Gly Asn Gly Thr Tyr Gln Thr Trp
    50                  55                  60

Val Ala Thr Arg Ile Cys Arg Gly Glu Glu Gln Arg Phe Thr Cys Tyr
65                  70                  75                  80

Met Glu His Ser Gly Asn His Ser Thr His Pro Val Pro Ser
                85                  90
```

<210> SEQ ID NO 200
<211> LENGTH: 97
<212> TYPE: PRT
<213> ORGANISM: Artificial Sequence
<220> FEATURE:
<223> OTHER INFORMATION: Synthetic Construct

<400> SEQUENCE: 200

```
Thr Val Pro Pro Met Val Asn Val Thr Arg Ser Asn Ala Ser Glu Gly
1               5                   10                  15

Asn Ile Thr Val Thr Cys Arg Ala Ser Ser Phe Tyr Pro Arg Asn Ile
            20                  25                  30

Ile Leu Thr Trp Arg Gln Asp Asn Val Ser Leu Ser Asn Asp Thr Gln
        35                  40                  45

Gln Trp Gly Asp Val Leu Pro Asp Gly Asn Gly Thr Tyr Gln Thr Trp
    50                  55                  60

Val Ala Thr Arg Ile Cys Arg Gly Glu Glu Gln Asn Phe Thr Cys Tyr
65                  70                  75                  80

Met Glu His Ser Gly Asn His Ser Thr His Pro Val Pro Ser Asn Gly
                85                  90                  95

Ser
```

<210> SEQ ID NO 201
<211> LENGTH: 96
<212> TYPE: PRT
<213> ORGANISM: Artificial Sequence
<220> FEATURE:
<223> OTHER INFORMATION: Synthetic Construct

<400> SEQUENCE: 201

```
Asn Arg Thr Val Pro Pro Met Val Asn Val Thr Arg Ser Glu Ala Ser
1               5                   10                  15

Glu Gly Asn Ile Thr Val Thr Cys Arg Ala Ser Ser Phe Tyr Pro Arg
            20                  25                  30
```

Asn Ile Ile Leu Thr Trp Arg Gln Asp Gly Val Ser Leu Ser His Asp
            35                  40                  45

Thr Gln Gln Trp Gly Asp Val Leu Pro Asp Gly Asn Gly Thr Tyr Gln
    50                  55                  60

Thr Trp Val Ala Thr Arg Ile Cys Arg Gly Glu Glu Gln Arg Phe Thr
65                  70                  75                  80

Cys Tyr Met Glu His Ser Gly Asn His Ser Thr His Pro Val Pro Ser
                85                  90                  95

<210> SEQ ID NO 202
<211> LENGTH: 94
<212> TYPE: PRT
<213> ORGANISM: Artificial Sequence
<220> FEATURE:
<223> OTHER INFORMATION: Synthetic Construct

<400> SEQUENCE: 202

Thr Val Pro Pro Met Val Asn Val Thr Arg Ser Asn Ala Ser Glu Gly
1               5                   10                  15

Asn Ile Thr Val Thr Cys Arg Ala Ser Ser Phe Tyr Pro Arg Asn Ile
            20                  25                  30

Ile Leu Thr Trp Arg Gln Asp Gly Val Ser Leu Ser His Asp Thr Gln
            35                  40                  45

Gln Trp Gly Asp Val Leu Pro Asp Gly Asn Gly Thr Tyr Gln Thr Trp
    50                  55                  60

Val Ala Thr Arg Ile Cys Arg Gly Glu Glu Gln Arg Phe Thr Cys Tyr
65                  70                  75                  80

Met Glu His Ser Gly Asn His Ser Thr His Pro Val Pro Ser
                85                  90

<210> SEQ ID NO 203
<211> LENGTH: 94
<212> TYPE: PRT
<213> ORGANISM: Artificial Sequence
<220> FEATURE:
<223> OTHER INFORMATION: Synthetic Construct

<400> SEQUENCE: 203

Thr Val Pro Pro Met Val Asn Val Thr Arg Ser Glu Ala Ser Glu Gly
1               5                   10                  15

Asn Ile Thr Val Thr Cys Arg Ala Ser Ser Phe Tyr Pro Arg Asn Ile
            20                  25                  30

Thr Leu Thr Trp Arg Gln Asp Gly Val Ser Leu Ser His Asp Thr Gln
            35                  40                  45

Gln Trp Gly Asp Val Leu Pro Asp Gly Asn Gly Thr Tyr Gln Thr Trp
    50                  55                  60

Val Ala Thr Arg Ile Cys Arg Gly Glu Glu Gln Arg Phe Thr Cys Tyr
65                  70                  75                  80

Met Glu His Ser Gly Asn His Ser Thr His Pro Val Pro Ser
                85                  90

<210> SEQ ID NO 204
<211> LENGTH: 94
<212> TYPE: PRT
<213> ORGANISM: Artificial Sequence
<220> FEATURE:
<223> OTHER INFORMATION: Synthetic Construct

<400> SEQUENCE: 204

Thr Val Pro Pro Met Val Asn Val Thr Arg Ser Glu Ala Ser Glu Gly
1               5                   10                  15

Asn Ile Thr Val Thr Cys Arg Ala Ser Ser Phe Tyr Pro Arg Asn Ile
            20                  25                  30

Ile Leu Thr Trp Arg Gln Asp Asn Val Ser Leu Ser His Asp Thr Gln
        35                  40                  45

Gln Trp Gly Asp Val Leu Pro Asp Gly Asn Gly Thr Tyr Gln Thr Trp
    50                  55                  60

Val Ala Thr Arg Ile Cys Arg Gly Glu Glu Gln Arg Phe Thr Cys Tyr
65                  70                  75                  80

Met Glu His Ser Gly Asn His Ser Thr His Pro Val Pro Ser
                85                  90

<210> SEQ ID NO 205
<211> LENGTH: 94
<212> TYPE: PRT
<213> ORGANISM: Artificial Sequence
<220> FEATURE:
<223> OTHER INFORMATION: Synthetic Construct

<400> SEQUENCE: 205

Thr Val Pro Pro Met Val Asn Val Thr Arg Ser Glu Ala Ser Glu Gly
1               5                   10                  15

Asn Ile Thr Val Thr Cys Arg Ala Ser Ser Phe Tyr Pro Arg Asn Ile
            20                  25                  30

Ile Leu Thr Trp Arg Gln Asp Gly Val Ser Leu Ser Asn Asp Thr Gln
        35                  40                  45

Gln Trp Gly Asp Val Leu Pro Asp Gly Asn Gly Thr Tyr Gln Thr Trp
    50                  55                  60

Val Ala Thr Arg Ile Cys Arg Gly Glu Glu Gln Arg Phe Thr Cys Tyr
65                  70                  75                  80

Met Glu His Ser Gly Asn His Ser Thr His Pro Val Pro Ser
                85                  90

<210> SEQ ID NO 206
<211> LENGTH: 94
<212> TYPE: PRT
<213> ORGANISM: Artificial Sequence
<220> FEATURE:
<223> OTHER INFORMATION: Synthetic Construct

<400> SEQUENCE: 206

Thr Val Pro Pro Met Val Asn Val Thr Arg Ser Glu Ala Ser Glu Gly
1               5                   10                  15

Asn Ile Thr Val Thr Cys Arg Ala Ser Ser Phe Tyr Pro Arg Asn Ile
            20                  25                  30

Ile Leu Thr Trp Arg Gln Asp Gly Val Ser Leu Ser His Asp Thr Gln
        35                  40                  45

Gln Trp Gly Asp Val Leu Pro Asp Gly Asn Gly Thr Tyr Gln Thr Trp
    50                  55                  60

Val Ala Thr Arg Ile Cys Arg Gly Glu Glu Gln Asn Phe Thr Cys Tyr
65                  70                  75                  80

Met Glu His Ser Gly Asn His Ser Thr His Pro Val Pro Ser
                85                  90

<210> SEQ ID NO 207

<211> LENGTH: 97
<212> TYPE: PRT
<213> ORGANISM: Artificial Sequence
<220> FEATURE:
<223> OTHER INFORMATION: Synthetic Construct

<400> SEQUENCE: 207

```
Thr Val Pro Pro Met Val Asn Val Thr Arg Ser Glu Ala Ser Glu Gly
1               5                   10                  15

Asn Ile Thr Val Thr Cys Arg Ala Ser Ser Phe Tyr Pro Arg Asn Ile
            20                  25                  30

Ile Leu Thr Trp Arg Gln Asp Gly Val Ser Leu Ser His Asp Thr Gln
        35                  40                  45

Gln Trp Gly Asp Val Leu Pro Asp Gly Asn Gly Thr Tyr Gln Thr Trp
    50                  55                  60

Val Ala Thr Arg Ile Cys Arg Gly Glu Glu Gln Arg Phe Thr Cys Tyr
65                  70                  75                  80

Met Glu His Ser Gly Asn His Ser Thr His Pro Val Pro Ser Asn Gly
                85                  90                  95

Ser
```

<210> SEQ ID NO 208
<211> LENGTH: 340
<212> TYPE: PRT
<213> ORGANISM: Artificial Sequence
<220> FEATURE:
<223> OTHER INFORMATION: Synthetic Construct

<400> SEQUENCE: 208

```
Gly Ser Thr Val Pro Pro Met Val Thr Val Thr Ser Arg Asn Tyr Pro
1               5                   10                  15

Val Gly Arg Val Thr Leu Thr Cys Arg Ala Ser Ser Pro Tyr Pro Arg
            20                  25                  30

Asn Ile Thr Leu Val Trp Leu Gln Asp Gly Lys Pro Val Gln Gln Lys
        35                  40                  45

Thr Phe Arg Ser Gly Asp Val Leu Pro Asp Gly Asn Gly Thr Tyr Gln
    50                  55                  60

Thr Trp Val Ser Ile Arg Val Leu Pro Gly Gln Glu Pro Gln Phe Ser
65                  70                  75                  80

Cys Asn Leu Arg His Gly Asn His Ser Ile Met Gln Thr Ala Val Gly
                85                  90                  95

Asn Ser Arg Ala Gln Val Thr Asp Lys Lys Ile Glu Pro Arg Gly Pro
            100                 105                 110

Thr Ile Lys Pro Cys Pro Pro Cys Lys Cys Pro Ala Pro Asn Leu Leu
        115                 120                 125

Gly Gly Pro Ser Val Phe Ile Phe Pro Pro Lys Ile Lys Asp Val Leu
    130                 135                 140

Met Ile Ser Leu Ser Pro Ile Val Thr Cys Val Val Val Asp Val Ser
145                 150                 155                 160

Glu Asp Asp Pro Asp Val Gln Ile Ser Trp Phe Val Asn Asn Val Glu
                165                 170                 175

Val His Thr Ala Gln Thr Gln Thr His Arg Glu Asp Tyr Asn Ser Thr
            180                 185                 190

Leu Arg Val Val Ser Ala Leu Pro Ile Gln His Gln Asp Trp Met Ser
        195                 200                 205

Gly Lys Glu Phe Lys Cys Lys Val Asn Asn Lys Asp Leu Pro Ala Pro
    210                 215                 220
```

```
Ile Glu Arg Thr Ile Ser Lys Pro Lys Gly Ser Val Arg Ala Pro Gln
225                 230                 235                 240

Val Tyr Val Leu Pro Pro Glu Glu Glu Met Thr Lys Lys Gln Val
                245                 250                 255

Thr Leu Thr Cys Met Val Thr Asp Phe Met Pro Glu Asp Ile Tyr Val
            260                 265                 270

Glu Trp Thr Asn Asn Gly Lys Thr Glu Leu Asn Tyr Lys Asn Thr Glu
        275                 280                 285

Pro Val Leu Asp Ser Asp Gly Ser Tyr Phe Met Tyr Ser Lys Leu Arg
    290                 295                 300

Val Glu Lys Lys Asn Trp Val Glu Arg Asn Ser Tyr Ser Cys Ser Val
305                 310                 315                 320

Val His Glu Gly Leu His Asn His His Thr Thr Lys Ser Phe Ser Arg
                325                 330                 335

Thr Pro Gly Lys
            340

<210> SEQ ID NO 209
<211> LENGTH: 5
<212> TYPE: PRT
<213> ORGANISM: Artificial Sequence
<220> FEATURE:
<223> OTHER INFORMATION: Synthetic Construct

<400> SEQUENCE: 209

Ser Gln Asn Ile Tyr
1               5

<210> SEQ ID NO 210
<211> LENGTH: 17
<212> TYPE: PRT
<213> ORGANISM: Artificial Sequence
<220> FEATURE:
<223> OTHER INFORMATION: Synthetic Construct

<400> SEQUENCE: 210

Tyr Ile Glu Pro Tyr Asn Val Val Pro Met Tyr Asn Pro Lys Phe Lys
1               5                   10                  15

Gly

<210> SEQ ID NO 211
<211> LENGTH: 8
<212> TYPE: PRT
<213> ORGANISM: Artificial Sequence
<220> FEATURE:
<223> OTHER INFORMATION: Synthetic Construct

<400> SEQUENCE: 211

Ser Gly Ser Ser Asn Phe Asp Tyr
1               5

<210> SEQ ID NO 212
<211> LENGTH: 12
<212> TYPE: PRT
<213> ORGANISM: Artificial Sequence
<220> FEATURE:
<223> OTHER INFORMATION: Synthetic Construct

<400> SEQUENCE: 212

Ser Ala Ser Ser Ser Ile Ser Ser His Tyr Leu His
1               5                   10
```

```
<210> SEQ ID NO 213
<211> LENGTH: 8
<212> TYPE: PRT
<213> ORGANISM: Artificial Sequence
<220> FEATURE:
<223> OTHER INFORMATION: Synthetic Construct

<400> SEQUENCE: 213

Arg Thr Ser Asn Leu Ala Ser Gly
1               5

<210> SEQ ID NO 214
<211> LENGTH: 9
<212> TYPE: PRT
<213> ORGANISM: Artificial Sequence
<220> FEATURE:
<223> OTHER INFORMATION: Synthetic Construct

<400> SEQUENCE: 214

Gln Gln Gly Ser Ser Leu Pro Leu Thr
1               5

<210> SEQ ID NO 215
<211> LENGTH: 17
<212> TYPE: PRT
<213> ORGANISM: Artificial Sequence
<220> FEATURE:
<223> OTHER INFORMATION: Synthetic Construct

<400> SEQUENCE: 215

Tyr Ile Glu Pro Tyr Asn Val Val Pro Ala Tyr Asn Pro Lys Phe Lys
1               5                   10                  15

Gly

<210> SEQ ID NO 216
<211> LENGTH: 17
<212> TYPE: PRT
<213> ORGANISM: Artificial Sequence
<220> FEATURE:
<223> OTHER INFORMATION: Synthetic Construct

<400> SEQUENCE: 216

Tyr Ile Glu Pro Tyr Asn Val Val Pro Leu Tyr Asn Pro Lys Phe Lys
1               5                   10                  15

Gly

<210> SEQ ID NO 217
<211> LENGTH: 17
<212> TYPE: PRT
<213> ORGANISM: Artificial Sequence
<220> FEATURE:
<223> OTHER INFORMATION: Synthetic Construct

<400> SEQUENCE: 217

Tyr Ile Glu Pro Tyr Asn Val Val Pro Val Tyr Asn Pro Lys Phe Lys
1               5                   10                  15

Gly

<210> SEQ ID NO 218
<211> LENGTH: 5
<212> TYPE: PRT
<213> ORGANISM: Artificial Sequence
<220> FEATURE:
<223> OTHER INFORMATION: Synthetic Construct
```

```
<400> SEQUENCE: 218

Asn Tyr Leu Ile Glu
1               5

<210> SEQ ID NO 219
<211> LENGTH: 17
<212> TYPE: PRT
<213> ORGANISM: Artificial Sequence
<220> FEATURE:
<223> OTHER INFORMATION: Synthetic Construct

<400> SEQUENCE: 219

Ala Ile Asn Pro Gly Ser Gly Ala Thr Asn Tyr Asn Glu Lys Phe Lys
1               5                   10                  15

Asp

<210> SEQ ID NO 220
<211> LENGTH: 8
<212> TYPE: PRT
<213> ORGANISM: Artificial Sequence
<220> FEATURE:
<223> OTHER INFORMATION: Synthetic Construct

<400> SEQUENCE: 220

Phe Leu Gly Asn Tyr Phe Asp Asn
1               5

<210> SEQ ID NO 221
<211> LENGTH: 11
<212> TYPE: PRT
<213> ORGANISM: Artificial Sequence
<220> FEATURE:
<223> OTHER INFORMATION: Synthetic Construct

<400> SEQUENCE: 221

Arg Ala Ser Gly Asn Ile His Ser Tyr Leu Ala
1               5                   10

<210> SEQ ID NO 222
<211> LENGTH: 8
<212> TYPE: PRT
<213> ORGANISM: Artificial Sequence
<220> FEATURE:
<223> OTHER INFORMATION: Synthetic Construct

<400> SEQUENCE: 222

Tyr Ala Glu Thr Leu Ala Asp Gly
1               5

<210> SEQ ID NO 223
<211> LENGTH: 9
<212> TYPE: PRT
<213> ORGANISM: Artificial Sequence
<220> FEATURE:
<223> OTHER INFORMATION: Synthetic Construct

<400> SEQUENCE: 223

Gln Gln Phe Trp Thr Thr Pro Tyr Thr
1               5

<210> SEQ ID NO 224
<211> LENGTH: 5
<212> TYPE: PRT
<213> ORGANISM: Artificial Sequence
<220> FEATURE:
<223> OTHER INFORMATION: Synthetic Construct
```

<400> SEQUENCE: 224

Ser Asn Asn Ile Tyr
1               5

<210> SEQ ID NO 225
<211> LENGTH: 17
<212> TYPE: PRT
<213> ORGANISM: Artificial Sequence
<220> FEATURE:
<223> OTHER INFORMATION: Synthetic Construct

<400> SEQUENCE: 225

Tyr Ile Asp Pro Tyr Ile Gly Arg Ile Ile Tyr Asn Gln Gln Phe Lys
1               5                   10                  15

Asp

<210> SEQ ID NO 226
<211> LENGTH: 9
<212> TYPE: PRT
<213> ORGANISM: Artificial Sequence
<220> FEATURE:
<223> OTHER INFORMATION: Synthetic Construct

<400> SEQUENCE: 226

Ser Gly Glu Arg Ser Asn Phe Asp Tyr
1               5

<210> SEQ ID NO 227
<211> LENGTH: 12
<212> TYPE: PRT
<213> ORGANISM: Artificial Sequence
<220> FEATURE:
<223> OTHER INFORMATION: Synthetic Construct

<400> SEQUENCE: 227

Ser Ala Ser Ser Ser Ile Ser Ser Asn Tyr Leu His
1               5                   10

<210> SEQ ID NO 228
<211> LENGTH: 8
<212> TYPE: PRT
<213> ORGANISM: Artificial Sequence
<220> FEATURE:
<223> OTHER INFORMATION: Synthetic Construct

<400> SEQUENCE: 228

Arg Thr Ser Asn Leu Ala Ser Gly
1               5

<210> SEQ ID NO 229
<211> LENGTH: 9
<212> TYPE: PRT
<213> ORGANISM: Artificial Sequence
<220> FEATURE:
<223> OTHER INFORMATION: Synthetic Construct

<400> SEQUENCE: 229

Gln Gln Gly Gly Ser Leu Pro Leu Thr
1               5

<210> SEQ ID NO 230
<211> LENGTH: 5
<212> TYPE: PRT
<213> ORGANISM: Artificial Sequence
<220> FEATURE:

<223> OTHER INFORMATION: Synthetic Construct

<400> SEQUENCE: 230

Asp Asn Tyr Ile Ser
1               5

<210> SEQ ID NO 231
<211> LENGTH: 17
<212> TYPE: PRT
<213> ORGANISM: Artificial Sequence
<220> FEATURE:
<223> OTHER INFORMATION: Synthetic Construct

<400> SEQUENCE: 231

Trp Ile Tyr Ala Gly Thr Gly Gly Ser Ser Tyr Asn Gln Lys Phe Arg
1               5                   10                  15

Asp

<210> SEQ ID NO 232
<211> LENGTH: 13
<212> TYPE: PRT
<213> ORGANISM: Artificial Sequence
<220> FEATURE:
<223> OTHER INFORMATION: Synthetic Construct

<400> SEQUENCE: 232

His Asp Tyr Tyr Gly Thr Ser Gly Ala Trp Phe Ala Tyr
1               5                   10

<210> SEQ ID NO 233
<211> LENGTH: 16
<212> TYPE: PRT
<213> ORGANISM: Artificial Sequence
<220> FEATURE:
<223> OTHER INFORMATION: Synthetic Construct

<400> SEQUENCE: 233

Arg Ser Ser Gln His Ile Val His Ser Asn Glu Asn Thr Tyr Leu Glu
1               5                   10                  15

<210> SEQ ID NO 234
<211> LENGTH: 7
<212> TYPE: PRT
<213> ORGANISM: Artificial Sequence
<220> FEATURE:
<223> OTHER INFORMATION: Synthetic Construct

<400> SEQUENCE: 234

Lys Val Ser Asn Arg Phe Ser
1               5

<210> SEQ ID NO 235
<211> LENGTH: 9
<212> TYPE: PRT
<213> ORGANISM: Artificial Sequence
<220> FEATURE:
<223> OTHER INFORMATION: Synthetic Construct

<400> SEQUENCE: 235

Phe Gln Gly Ser His Val Pro Trp Thr
1               5

<210> SEQ ID NO 236
<211> LENGTH: 6
<212> TYPE: PRT
<213> ORGANISM: Artificial Sequence

```
<220> FEATURE:
<223> OTHER INFORMATION: Synthetic Construct

<400> SEQUENCE: 236

Gly Asp Tyr Ala Trp Asn
1               5

<210> SEQ ID NO 237
<211> LENGTH: 16
<212> TYPE: PRT
<213> ORGANISM: Artificial Sequence
<220> FEATURE:
<223> OTHER INFORMATION: Synthetic Construct

<400> SEQUENCE: 237

Tyr Ile Gly Tyr Thr Gly Ser Thr Thr Tyr Asn Pro Ser Leu Lys Ser
1               5                   10                  15

<210> SEQ ID NO 238
<211> LENGTH: 8
<212> TYPE: PRT
<213> ORGANISM: Artificial Sequence
<220> FEATURE:
<223> OTHER INFORMATION: Synthetic Construct

<400> SEQUENCE: 238

Trp Arg Asn Trp Ala Met Asp Tyr
1               5

<210> SEQ ID NO 239
<211> LENGTH: 11
<212> TYPE: PRT
<213> ORGANISM: Artificial Sequence
<220> FEATURE:
<223> OTHER INFORMATION: Synthetic Construct

<400> SEQUENCE: 239

Arg Ala Asn Gln Asp Ile Ser His Tyr Leu Asn
1               5                   10

<210> SEQ ID NO 240
<211> LENGTH: 8
<212> TYPE: PRT
<213> ORGANISM: Artificial Sequence
<220> FEATURE:
<223> OTHER INFORMATION: Synthetic Construct

<400> SEQUENCE: 240

Tyr Thr Ser Arg Ile His Ser Gly
1               5

<210> SEQ ID NO 241
<211> LENGTH: 9
<212> TYPE: PRT
<213> ORGANISM: Artificial Sequence
<220> FEATURE:
<223> OTHER INFORMATION: Synthetic Construct

<400> SEQUENCE: 241

Gln Gln Gly Asn Thr Pro Pro Thr Thr
1               5

<210> SEQ ID NO 242
<211> LENGTH: 6
<212> TYPE: PRT
<213> ORGANISM: Artificial Sequence
<220> FEATURE:
```

```
<223> OTHER INFORMATION: Synthetic Construct

<400> SEQUENCE: 242

Ser Asn Tyr Ala Trp Asn
1               5

<210> SEQ ID NO 243
<211> LENGTH: 16
<212> TYPE: PRT
<213> ORGANISM: Artificial Sequence
<220> FEATURE:
<223> OTHER INFORMATION: Synthetic Construct

<400> SEQUENCE: 243

Tyr Ile Ser Ser Ser Gly Ile Thr Lys Ser Asn Pro Ser Leu Lys Ser
1               5                   10                  15

<210> SEQ ID NO 244
<211> LENGTH: 8
<212> TYPE: PRT
<213> ORGANISM: Artificial Sequence
<220> FEATURE:
<223> OTHER INFORMATION: Synthetic Construct

<400> SEQUENCE: 244

Trp Ser Asn Trp Ser Phe Asp Val
1               5

<210> SEQ ID NO 245
<211> LENGTH: 11
<212> TYPE: PRT
<213> ORGANISM: Artificial Sequence
<220> FEATURE:
<223> OTHER INFORMATION: Synthetic Construct

<400> SEQUENCE: 245

Arg Ala Ser Gln Asp Ile His Asn Tyr Phe Asn
1               5                   10

<210> SEQ ID NO 246
<211> LENGTH: 8
<212> TYPE: PRT
<213> ORGANISM: Artificial Sequence
<220> FEATURE:
<223> OTHER INFORMATION: Synthetic Construct

<400> SEQUENCE: 246

Tyr Thr Ser Arg Phe His Ser Gly
1               5

<210> SEQ ID NO 247
<211> LENGTH: 9
<212> TYPE: PRT
<213> ORGANISM: Artificial Sequence
<220> FEATURE:
<223> OTHER INFORMATION: Synthetic Construct

<400> SEQUENCE: 247

Gln Gln Gly Asn Ser Leu Pro Pro Thr
1               5

<210> SEQ ID NO 248
<211> LENGTH: 23
<212> TYPE: PRT
<213> ORGANISM: Artificial Sequence
<220> FEATURE:
<223> OTHER INFORMATION: Synthetic Construct
```

```
<400> SEQUENCE: 248

Glu Ile Ile Leu Thr Gln Ser Pro Thr Thr Met Ala Ala Ser Pro Gly
1               5                   10                  15

Glu Lys Ile Thr Ile Thr Cys
            20

<210> SEQ ID NO 249
<211> LENGTH: 15
<212> TYPE: PRT
<213> ORGANISM: Artificial Sequence
<220> FEATURE:
<223> OTHER INFORMATION: Synthetic Construct

<400> SEQUENCE: 249

Trp Tyr Gln Gln Lys Ser Gly Phe Ser Pro Lys Leu Leu Ile Tyr
1               5                   10                  15

<210> SEQ ID NO 250
<211> LENGTH: 31
<212> TYPE: PRT
<213> ORGANISM: Artificial Sequence
<220> FEATURE:
<223> OTHER INFORMATION: Synthetic Construct

<400> SEQUENCE: 250

Val Pro Ala Arg Phe Ser Gly Ser Gly Ser Gly Thr Ser Tyr Ser Leu
1               5                   10                  15

Thr Ile Gly Thr Met Glu Ala Glu Asp Val Ala Thr Tyr Tyr Cys
            20                  25                  30

<210> SEQ ID NO 251
<211> LENGTH: 10
<212> TYPE: PRT
<213> ORGANISM: Artificial Sequence
<220> FEATURE:
<223> OTHER INFORMATION: Synthetic Construct

<400> SEQUENCE: 251

Phe Gly Ala Gly Thr Lys Val Glu Ile Lys
1               5                   10

<210> SEQ ID NO 252
<211> LENGTH: 23
<212> TYPE: PRT
<213> ORGANISM: Artificial Sequence
<220> FEATURE:
<223> OTHER INFORMATION: Synthetic Construct

<400> SEQUENCE: 252

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 253
<211> LENGTH: 15
<212> TYPE: PRT
<213> ORGANISM: Artificial Sequence
<220> FEATURE:
<223> OTHER INFORMATION: Synthetic Construct

<400> SEQUENCE: 253

Trp Tyr Gln Gln Lys Pro Asp Gln Ser Pro Lys Leu Leu Ile Tyr
1               5                   10                  15
```

```
<210> SEQ ID NO 254
<211> LENGTH: 31
<212> TYPE: PRT
<213> ORGANISM: Artificial Sequence
<220> FEATURE:
<223> OTHER INFORMATION: Synthetic Construct

<400> SEQUENCE: 254

Val Pro Ser Arg Phe Ser Gly Ser Gly Ser Gly Thr Asp Tyr Thr Leu
1               5                   10                  15

Thr Ile Asn Ser Leu Glu Ala Glu Asp Ala Ala Thr Tyr Tyr Cys
            20                  25                  30

<210> SEQ ID NO 255
<211> LENGTH: 10
<212> TYPE: PRT
<213> ORGANISM: Artificial Sequence
<220> FEATURE:
<223> OTHER INFORMATION: Synthetic Construct

<400> SEQUENCE: 255

Phe Gly Gln Gly Thr Lys Val Glu Ile Lys
1               5                   10

<210> SEQ ID NO 256
<211> LENGTH: 15
<212> TYPE: PRT
<213> ORGANISM: Artificial Sequence
<220> FEATURE:
<223> OTHER INFORMATION: Synthetic Construct

<400> SEQUENCE: 256

Trp Tyr Gln Gln Lys Pro Asp Gln Ser Pro Lys Leu Leu Ile Lys
1               5                   10                  15

<210> SEQ ID NO 257
<211> LENGTH: 31
<212> TYPE: PRT
<213> ORGANISM: Artificial Sequence
<220> FEATURE:
<223> OTHER INFORMATION: Synthetic Construct

<400> SEQUENCE: 257

Val Pro Ser Arg Phe Ser Gly Ser Gly Ser Gly Thr Asp Phe Thr Leu
1               5                   10                  15

Thr Ile Asn Ser Leu Glu Ala Glu Asp Ala Ala Thr Tyr Tyr Cys
            20                  25                  30

<210> SEQ ID NO 258
<211> LENGTH: 23
<212> TYPE: PRT
<213> ORGANISM: Artificial Sequence
<220> FEATURE:
<223> OTHER INFORMATION: Synthetic Construct

<400> SEQUENCE: 258

Asp Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 259
<211> LENGTH: 15
<212> TYPE: PRT
```

<213> ORGANISM: Artificial Sequence
<220> FEATURE:
<223> OTHER INFORMATION: Synthetic Construct

<400> SEQUENCE: 259

Trp Tyr Gln Gln Lys Pro Gly Lys Ser Pro Lys Leu Leu Ile Tyr
1               5                   10                  15

<210> SEQ ID NO 260
<211> LENGTH: 31
<212> TYPE: PRT
<213> ORGANISM: Artificial Sequence
<220> FEATURE:
<223> OTHER INFORMATION: Synthetic Construct

<400> SEQUENCE: 260

Val Pro Ser Arg Phe Ser Gly Ser Gly Ser Gly Thr Asp Tyr Thr Leu
1               5                   10                  15

Thr Ile Ser Ser Leu Gln Pro Glu Asp Phe Ala Thr Tyr Tyr Cys
            20                  25                  30

<210> SEQ ID NO 261
<211> LENGTH: 23
<212> TYPE: PRT
<213> ORGANISM: Artificial Sequence
<220> FEATURE:
<223> OTHER INFORMATION: Synthetic Construct

<400> SEQUENCE: 261

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 262
<211> LENGTH: 15
<212> TYPE: PRT
<213> ORGANISM: Artificial Sequence
<220> FEATURE:
<223> OTHER INFORMATION: Synthetic Construct

<400> SEQUENCE: 262

Trp Tyr Gln Gln Lys Pro Gly Lys Ala Pro Lys Leu Leu Ile Tyr
1               5                   10                  15

<210> SEQ ID NO 263
<211> LENGTH: 31
<212> TYPE: PRT
<213> ORGANISM: Artificial Sequence
<220> FEATURE:
<223> OTHER INFORMATION: Synthetic Construct

<400> SEQUENCE: 263

Val Pro Ser Arg Phe Ser Gly Ser Gly Ser Gly Thr Asp Phe Thr Leu
1               5                   10                  15

Thr Ile Ser Ser Leu Gln Pro Glu Asp Phe Ala Thr Tyr Tyr Cys
            20                  25                  30

<210> SEQ ID NO 264
<211> LENGTH: 15
<212> TYPE: PRT
<213> ORGANISM: Artificial Sequence
<220> FEATURE:
<223> OTHER INFORMATION: Synthetic Construct

<400> SEQUENCE: 264

Trp Tyr Gln Gln Lys Pro Gly Lys Ser Pro Lys Leu Leu Ile Tyr
1               5                   10                  15

<210> SEQ ID NO 265
<211> LENGTH: 31
<212> TYPE: PRT
<213> ORGANISM: Artificial Sequence
<220> FEATURE:
<223> OTHER INFORMATION: Synthetic Construct

<400> SEQUENCE: 265

Val Pro Ser Arg Phe Ser Gly Ser Gly Ser Gly Thr Asp Tyr Thr Leu
1               5                   10                  15

Thr Ile Ser Ser Leu Gln Pro Glu Asp Phe Ala Thr Tyr Tyr Cys
            20                  25                  30

<210> SEQ ID NO 266
<211> LENGTH: 23
<212> TYPE: PRT
<213> ORGANISM: Artificial Sequence
<220> FEATURE:
<223> OTHER INFORMATION: Synthetic Construct

<400> SEQUENCE: 266

Asp Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 267
<211> LENGTH: 31
<212> TYPE: PRT
<213> ORGANISM: Artificial Sequence
<220> FEATURE:
<223> OTHER INFORMATION: Synthetic Construct

<400> SEQUENCE: 267

Val Pro Ser Arg Phe Ser Gly Ser Gly Ser Gly Thr Asp Phe Thr Leu
1               5                   10                  15

Thr Ile Ser Ser Leu Gln Pro Glu Asp Phe Ala Thr Tyr Tyr Cys
            20                  25                  30

<210> SEQ ID NO 268
<211> LENGTH: 23
<212> TYPE: PRT
<213> ORGANISM: Artificial Sequence
<220> FEATURE:
<223> OTHER INFORMATION: Synthetic Construct

<400> SEQUENCE: 268

Asp Ile Gln Met Thr Gln Ser Pro Ala Ser Leu Ser Ala Ser Val Gly
1               5                   10                  15

Glu Thr Val Thr Ile Thr Cys
            20

<210> SEQ ID NO 269
<211> LENGTH: 15
<212> TYPE: PRT
<213> ORGANISM: Artificial Sequence
<220> FEATURE:
<223> OTHER INFORMATION: Synthetic Construct

<400> SEQUENCE: 269

Trp Tyr Gln Gln Lys Gln Gly Lys Ser Pro Gln Leu Leu Val Tyr
1               5                   10                  15

<210> SEQ ID NO 270
<211> LENGTH: 31
<212> TYPE: PRT
<213> ORGANISM: Artificial Sequence
<220> FEATURE:
<223> OTHER INFORMATION: Synthetic Construct

<400> SEQUENCE: 270

Val Pro Ser Arg Phe Ser Gly Arg Gly Ser Gly Thr Gln Tyr Ser Leu
1               5                   10                  15

Lys Ile Asn Ser Leu Gln Pro Glu Asp Phe Gly Ser Tyr Phe Cys
            20                  25                  30

<210> SEQ ID NO 271
<211> LENGTH: 10
<212> TYPE: PRT
<213> ORGANISM: Artificial Sequence
<220> FEATURE:
<223> OTHER INFORMATION: Synthetic Construct

<400> SEQUENCE: 271

Phe Gly Gly Gly Thr Lys Val Glu Ile Lys
1               5                   10

<210> SEQ ID NO 272
<211> LENGTH: 23
<212> TYPE: PRT
<213> ORGANISM: Artificial Sequence
<220> FEATURE:
<223> OTHER INFORMATION: Synthetic Construct

<400> SEQUENCE: 272

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 273
<211> LENGTH: 15
<212> TYPE: PRT
<213> ORGANISM: Artificial Sequence
<220> FEATURE:
<223> OTHER INFORMATION: Synthetic Construct

<400> SEQUENCE: 273

Trp Tyr Gln Gln Lys Pro Gly Lys Ala Pro Lys Leu Leu Ile Tyr
1               5                   10                  15

<210> SEQ ID NO 274
<211> LENGTH: 31
<212> TYPE: PRT
<213> ORGANISM: Artificial Sequence
<220> FEATURE:
<223> OTHER INFORMATION: Synthetic Construct

<400> SEQUENCE: 274

Val Pro Ser Arg Phe Ser Gly Ser Gly Ser Gly Thr Asp Phe Thr Leu
1               5                   10                  15

Thr Ile Ser Ser Leu Gln Pro Glu Asp Phe Ala Thr Tyr Tyr Cys
            20                  25                  30

<210> SEQ ID NO 275
<211> LENGTH: 15
<212> TYPE: PRT
<213> ORGANISM: Artificial Sequence
<220> FEATURE:
<223> OTHER INFORMATION: Synthetic Construct

<400> SEQUENCE: 275

Trp Tyr Gln Gln Lys Pro Gly Lys Ser Pro Lys Leu Leu Val Tyr
1               5                   10                  15

<210> SEQ ID NO 276
<211> LENGTH: 31
<212> TYPE: PRT
<213> ORGANISM: Artificial Sequence
<220> FEATURE:
<223> OTHER INFORMATION: Synthetic Construct

<400> SEQUENCE: 276

Val Pro Ser Arg Phe Ser Gly Ser Gly Ser Gly Thr Asp Tyr Thr Leu
1               5                   10                  15

Thr Ile Ser Ser Leu Gln Pro Glu Asp Phe Ala Thr Tyr Phe Cys
            20                  25                  30

<210> SEQ ID NO 277
<211> LENGTH: 23
<212> TYPE: PRT
<213> ORGANISM: Artificial Sequence
<220> FEATURE:
<223> OTHER INFORMATION: Synthetic Construct

<400> SEQUENCE: 277

Glu Ile Val Leu Thr Gln Ser Pro Thr Ala Met Ala Ala Ser Pro Gly
1               5                   10                  15

Glu Lys Ile Thr Ile Thr Cys
            20

<210> SEQ ID NO 278
<211> LENGTH: 15
<212> TYPE: PRT
<213> ORGANISM: Artificial Sequence
<220> FEATURE:
<223> OTHER INFORMATION: Synthetic Construct

<400> SEQUENCE: 278

Trp Tyr Gln Gln Lys Pro Gly Phe Ser Pro Lys Leu Leu Ile Tyr
1               5                   10                  15

<210> SEQ ID NO 279
<211> LENGTH: 31
<212> TYPE: PRT
<213> ORGANISM: Artificial Sequence
<220> FEATURE:
<223> OTHER INFORMATION: Synthetic Construct

<400> SEQUENCE: 279

Val Pro Ala Arg Phe Ser Gly Ser Gly Ser Gly Thr Ser Tyr Ser Leu
1               5                   10                  15

Thr Ile Gly Pro Met Glu Ala Glu Asp Val Ala Thr Tyr Tyr Cys
            20                  25                  30

<210> SEQ ID NO 280
<211> LENGTH: 23
<212> TYPE: PRT

```
<213> ORGANISM: Artificial Sequence
<220> FEATURE:
<223> OTHER INFORMATION: Synthetic Construct

<400> SEQUENCE: 280

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 281
<211> LENGTH: 15
<212> TYPE: PRT
<213> ORGANISM: Artificial Sequence
<220> FEATURE:
<223> OTHER INFORMATION: Synthetic Construct

<400> SEQUENCE: 281

Trp Tyr Gln Gln Lys Pro Gly Gln Ala Pro Arg Leu Leu Ile Tyr
1               5                   10                  15

<210> SEQ ID NO 282
<211> LENGTH: 31
<212> TYPE: PRT
<213> ORGANISM: Artificial Sequence
<220> FEATURE:
<223> OTHER INFORMATION: Synthetic Construct

<400> SEQUENCE: 282

Ile Pro Ala Arg Phe Ser Gly Ser Gly Ser Gly Thr Asp Phe Thr Leu
1               5                   10                  15

Thr Ile Ser Ser Leu Glu Pro Glu Asp Phe Ala Val Tyr Tyr Cys
            20                  25                  30

<210> SEQ ID NO 283
<211> LENGTH: 15
<212> TYPE: PRT
<213> ORGANISM: Artificial Sequence
<220> FEATURE:
<223> OTHER INFORMATION: Synthetic Construct

<400> SEQUENCE: 283

Trp Tyr Gln Gln Lys Pro Gly Gln Ser Pro Arg Leu Leu Ile Tyr
1               5                   10                  15

<210> SEQ ID NO 284
<211> LENGTH: 31
<212> TYPE: PRT
<213> ORGANISM: Artificial Sequence
<220> FEATURE:
<223> OTHER INFORMATION: Synthetic Construct

<400> SEQUENCE: 284

Val Pro Ala Arg Phe Ser Gly Ser Gly Ser Gly Thr Asp Tyr Thr Leu
1               5                   10                  15

Thr Ile Ser Ser Leu Glu Pro Glu Asp Phe Ala Val Tyr Tyr Cys
            20                  25                  30

<210> SEQ ID NO 285
<211> LENGTH: 23
<212> TYPE: PRT
<213> ORGANISM: Artificial Sequence
<220> FEATURE:
<223> OTHER INFORMATION: Synthetic Construct
```

```
<400> SEQUENCE: 285

Asp Val Leu Met Thr Gln Thr Pro Leu Ser Leu Pro Val Ser Leu Gly
1               5                   10                  15

Asp Gln Ala Ser Ile Ser Cys
            20

<210> SEQ ID NO 286
<211> LENGTH: 15
<212> TYPE: PRT
<213> ORGANISM: Artificial Sequence
<220> FEATURE:
<223> OTHER INFORMATION: Synthetic Construct

<400> SEQUENCE: 286

Trp Tyr Leu Gln Lys Pro Gly Gln Ser Pro Lys Leu Leu Ile Tyr
1               5                   10                  15

<210> SEQ ID NO 287
<211> LENGTH: 32
<212> TYPE: PRT
<213> ORGANISM: Artificial Sequence
<220> FEATURE:
<223> OTHER INFORMATION: Synthetic Construct

<400> SEQUENCE: 287

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 288
<211> LENGTH: 23
<212> TYPE: PRT
<213> ORGANISM: Artificial Sequence
<220> FEATURE:
<223> OTHER INFORMATION: Synthetic Construct

<400> SEQUENCE: 288

Asp Ile Gln Met Thr Gln Thr Pro Ser Ser Leu Ser Ala Ser Leu Gly
1               5                   10                  15

Asp Arg Val Thr Ile Ser Cys
            20

<210> SEQ ID NO 289
<211> LENGTH: 15
<212> TYPE: PRT
<213> ORGANISM: Artificial Sequence
<220> FEATURE:
<223> OTHER INFORMATION: Synthetic Construct

<400> SEQUENCE: 289

Trp Tyr Gln Gln Lys Pro Asp Gly Ala Val Lys Leu Leu Ile Tyr
1               5                   10                  15

<210> SEQ ID NO 290
<211> LENGTH: 31
<212> TYPE: PRT
<213> ORGANISM: Artificial Sequence
<220> FEATURE:
<223> OTHER INFORMATION: Synthetic Construct

<400> SEQUENCE: 290

Val Pro Ser Arg Phe Ser Gly Ser Gly Ser Gly Thr Asp Tyr Ser Leu
1               5                   10                  15
```

```
Thr Ile Ala Asn Leu Glu Gln Glu Asp Val Ala Thr Tyr Phe Cys
            20                  25                  30

<210> SEQ ID NO 291
<211> LENGTH: 23
<212> TYPE: PRT
<213> ORGANISM: Artificial Sequence
<220> FEATURE:
<223> OTHER INFORMATION: Synthetic Construct

<400> SEQUENCE: 291

Asp Ile Gln Met Thr Gln Thr Pro Ser Ser Leu Ser Val Ser Leu Gly
1               5                   10                  15

Asp Arg Val Thr Ile Asn Cys
            20

<210> SEQ ID NO 292
<211> LENGTH: 15
<212> TYPE: PRT
<213> ORGANISM: Artificial Sequence
<220> FEATURE:
<223> OTHER INFORMATION: Synthetic Construct

<400> SEQUENCE: 292

Trp Tyr Gln Gln Lys Pro Asp Gly Thr Ile Lys Leu Leu Ile Tyr
1               5                   10                  15

<210> SEQ ID NO 293
<211> LENGTH: 31
<212> TYPE: PRT
<213> ORGANISM: Artificial Sequence
<220> FEATURE:
<223> OTHER INFORMATION: Synthetic Construct

<400> SEQUENCE: 293

Val Pro Ser Arg Phe Ser Gly Ser Gly Ser Gly Thr Asp Tyr Ser Leu
1               5                   10                  15

Thr Ile Ser Asn Leu Glu Gln Glu Asp Ile Ala Thr Tyr Phe Cys
            20                  25                  30

<210> SEQ ID NO 294
<211> LENGTH: 10
<212> TYPE: PRT
<213> ORGANISM: Artificial Sequence
<220> FEATURE:
<223> OTHER INFORMATION: Synthetic Construct

<400> SEQUENCE: 294

Phe Gly Gly Gly Thr Lys Leu Glu Ile Lys
1               5                   10

<210> SEQ ID NO 295
<211> LENGTH: 30
<212> TYPE: PRT
<213> ORGANISM: Artificial Sequence
<220> FEATURE:
<223> OTHER INFORMATION: Synthetic Construct

<400> SEQUENCE: 295

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr
            20                  25                  30
```

```
<210> SEQ ID NO 296
<211> LENGTH: 14
<212> TYPE: PRT
<213> ORGANISM: Artificial Sequence
<220> FEATURE:
<223> OTHER INFORMATION: Synthetic Construct

<400> SEQUENCE: 296

Trp Val Lys Gln Ser His Gly Lys Ser Leu Glu Trp Ile Gly
1               5                   10

<210> SEQ ID NO 297
<211> LENGTH: 32
<212> TYPE: PRT
<213> ORGANISM: Artificial Sequence
<220> FEATURE:
<223> OTHER INFORMATION: Synthetic Construct

<400> SEQUENCE: 297

Lys Ala Thr Leu Thr Val Asp Lys Ser Ser Ser Ser Ala Tyr Ile His
1               5                   10                  15

Leu Asn Ser Leu Thr Ser Glu Asp Ser Ala Ile Tyr Tyr Cys Ala Arg
            20                  25                  30

<210> SEQ ID NO 298
<211> LENGTH: 11
<212> TYPE: PRT
<213> ORGANISM: Artificial Sequence
<220> FEATURE:
<223> OTHER INFORMATION: Synthetic Construct

<400> SEQUENCE: 298

Trp Gly Gln Gly Thr Thr Leu Thr Val Ser Ser
1               5                   10

<210> SEQ ID NO 299
<211> LENGTH: 30
<212> TYPE: PRT
<213> ORGANISM: Artificial Sequence
<220> FEATURE:
<223> OTHER INFORMATION: Synthetic Construct

<400> SEQUENCE: 299

Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr
            20                  25                  30

<210> SEQ ID NO 300
<211> LENGTH: 14
<212> TYPE: PRT
<213> ORGANISM: Artificial Sequence
<220> FEATURE:
<223> OTHER INFORMATION: Synthetic Construct

<400> SEQUENCE: 300

Trp Val Arg Gln Ala Pro Gly Gln Gly Leu Glu Trp Ile Gly
1               5                   10

<210> SEQ ID NO 301
<211> LENGTH: 32
<212> TYPE: PRT
<213> ORGANISM: Artificial Sequence
<220> FEATURE:
<223> OTHER INFORMATION: Synthetic Construct
```

```
<400> SEQUENCE: 301

Arg Ala Thr Leu Thr Val Asp Lys Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 302
<211> LENGTH: 11
<212> TYPE: PRT
<213> ORGANISM: Artificial Sequence
<220> FEATURE:
<223> OTHER INFORMATION: Synthetic Construct

<400> SEQUENCE: 302

Trp Gly Gln Gly Thr Leu Val Thr Val Ser Ser
1               5                   10

<210> SEQ ID NO 303
<211> LENGTH: 30
<212> TYPE: PRT
<213> ORGANISM: Artificial Sequence
<220> FEATURE:
<223> OTHER INFORMATION: Synthetic Construct

<400> SEQUENCE: 303

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr
            20                  25                  30

<210> SEQ ID NO 304
<211> LENGTH: 14
<212> TYPE: PRT
<213> ORGANISM: Artificial Sequence
<220> FEATURE:
<223> OTHER INFORMATION: Synthetic Construct

<400> SEQUENCE: 304

Trp Val Arg Gln Ala Pro Gly Gln Gly Leu Glu Trp Met Gly
1               5                   10

<210> SEQ ID NO 305
<211> LENGTH: 32
<212> TYPE: PRT
<213> ORGANISM: Artificial Sequence
<220> FEATURE:
<223> OTHER INFORMATION: Synthetic Construct

<400> SEQUENCE: 305

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 306
<211> LENGTH: 32
<212> TYPE: PRT
<213> ORGANISM: Artificial Sequence
<220> FEATURE:
<223> OTHER INFORMATION: Synthetic Construct

<400> SEQUENCE: 306

Arg Ala Thr Leu Thr Val Asp Lys Ser Thr Ser Thr Ala Tyr Leu Glu
1               5                   10                  15
```

```
Leu Ser Ser Leu Arg Ser Glu Asp Thr Ala Val Tyr Tyr Cys Ala Arg
            20                  25                  30
```

<210> SEQ ID NO 307
<211> LENGTH: 32
<212> TYPE: PRT
<213> ORGANISM: Artificial Sequence
<220> FEATURE:
<223> OTHER INFORMATION: Synthetic Construct

<400> SEQUENCE: 307

```
Arg Val Thr Ile Thr Arg Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30
```

<210> SEQ ID NO 308
<211> LENGTH: 32
<212> TYPE: PRT
<213> ORGANISM: Artificial Sequence
<220> FEATURE:
<223> OTHER INFORMATION: Synthetic Construct

<400> SEQUENCE: 308

```
Arg Val Thr Leu Thr Val Asp Lys Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30
```

<210> SEQ ID NO 309
<211> LENGTH: 32
<212> TYPE: PRT
<213> ORGANISM: Artificial Sequence
<220> FEATURE:
<223> OTHER INFORMATION: Synthetic Construct

<400> SEQUENCE: 309

```
Arg Ala Thr Ile Thr Val Asp Lys Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30
```

<210> SEQ ID NO 310
<211> LENGTH: 32
<212> TYPE: PRT
<213> ORGANISM: Artificial Sequence
<220> FEATURE:
<223> OTHER INFORMATION: Synthetic Construct

<400> SEQUENCE: 310

```
Arg Ala Thr Leu Thr Arg Asp Lys Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30
```

<210> SEQ ID NO 311
<211> LENGTH: 32
<212> TYPE: PRT
<213> ORGANISM: Artificial Sequence
<220> FEATURE:
<223> OTHER INFORMATION: Synthetic Construct

<400> SEQUENCE: 311

Arg Ala Thr Leu Thr Val Asp Thr Ser Thr Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 312
<211> LENGTH: 32
<212> TYPE: PRT
<213> ORGANISM: Artificial Sequence
<220> FEATURE:
<223> OTHER INFORMATION: Synthetic Construct

<400> SEQUENCE: 312

Arg Val Thr Ile Thr Val Asp Lys Ser Thr Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 313
<211> LENGTH: 32
<212> TYPE: PRT
<213> ORGANISM: Artificial Sequence
<220> FEATURE:
<223> OTHER INFORMATION: Synthetic Construct

<400> SEQUENCE: 313

Arg Val Thr Ile Thr Val Asp Thr Ser Thr Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 314
<211> LENGTH: 32
<212> TYPE: PRT
<213> ORGANISM: Artificial Sequence
<220> FEATURE:
<223> OTHER INFORMATION: Synthetic Construct

<400> SEQUENCE: 314

Arg Val Thr Ile Thr Arg Asp Lys Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 315
<211> LENGTH: 30
<212> TYPE: PRT
<213> ORGANISM: Artificial Sequence
<220> FEATURE:
<223> OTHER INFORMATION: Synthetic Construct

<400> SEQUENCE: 315

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr
            20                  25                  30

<210> SEQ ID NO 316
<211> LENGTH: 14
<212> TYPE: PRT
<213> ORGANISM: Artificial Sequence
<220> FEATURE:

<223> OTHER INFORMATION: Synthetic Construct

<400> SEQUENCE: 316

Trp Val Lys Gln Arg Pro Gly Gln Gly Leu Glu Trp Ile Gly
1               5                   10

<210> SEQ ID NO 317
<211> LENGTH: 32
<212> TYPE: PRT
<213> ORGANISM: Artificial Sequence
<220> FEATURE:
<223> OTHER INFORMATION: Synthetic Construct

<400> SEQUENCE: 317

Lys Ala Arg Leu Thr Ala Asp Lys Ser Ser Asn Thr Ala Tyr Leu Gln
1               5                   10                  15

Phe Ser Ser Leu Thr Ser Asp Asp Ser Ala Val Tyr Phe Cys Ala Arg
            20                  25                  30

<210> SEQ ID NO 318
<211> LENGTH: 11
<212> TYPE: PRT
<213> ORGANISM: Artificial Sequence
<220> FEATURE:
<223> OTHER INFORMATION: Synthetic Construct

<400> SEQUENCE: 318

Trp Gly Gln Gly Ala Thr Leu Thr Val Ser Ser
1               5                   10

<210> SEQ ID NO 319
<211> LENGTH: 30
<212> TYPE: PRT
<213> ORGANISM: Artificial Sequence
<220> FEATURE:
<223> OTHER INFORMATION: Synthetic Construct

<400> SEQUENCE: 319

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr
            20                  25                  30

<210> SEQ ID NO 320
<211> LENGTH: 14
<212> TYPE: PRT
<213> ORGANISM: Artificial Sequence
<220> FEATURE:
<223> OTHER INFORMATION: Synthetic Construct

<400> SEQUENCE: 320

Trp Val Arg Gln Ala Pro Gly Gln Gly Leu Glu Trp Ile Gly
1               5                   10

<210> SEQ ID NO 321
<211> LENGTH: 32
<212> TYPE: PRT
<213> ORGANISM: Artificial Sequence
<220> FEATURE:
<223> OTHER INFORMATION: Synthetic Construct

<400> SEQUENCE: 321

Arg Val Thr Ile Thr Ala Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 322
<211> LENGTH: 32
<212> TYPE: PRT
<213> ORGANISM: Artificial Sequence
<220> FEATURE:
<223> OTHER INFORMATION: Synthetic Construct

<400> SEQUENCE: 322

Arg Ala Thr Leu Thr Ala Asp Lys Ser Thr Asn Thr Ala Tyr Leu Glu
1               5                   10                  15

Leu Ser Ser Leu Arg Ser Glu Asp Thr Ala Val Tyr Phe Cys Ala Arg
            20                  25                  30

<210> SEQ ID NO 323
<211> LENGTH: 30
<212> TYPE: PRT
<213> ORGANISM: Artificial Sequence
<220> FEATURE:
<223> OTHER INFORMATION: Synthetic Construct

<400> SEQUENCE: 323

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr
            20                  25                  30

<210> SEQ ID NO 324
<211> LENGTH: 32
<212> TYPE: PRT
<213> ORGANISM: Artificial Sequence
<220> FEATURE:
<223> OTHER INFORMATION: Synthetic Construct

<400> SEQUENCE: 324

Arg Ala Thr Leu Thr Ala Asp Lys Ser Thr Asn Thr Ala Tyr Met Glu
1               5                   10                  15

Leu Ser Ser Leu Arg Ser Glu Asp Thr Ala Val Tyr Phe Cys Ala Arg
            20                  25                  30

<210> SEQ ID NO 325
<211> LENGTH: 30
<212> TYPE: PRT
<213> ORGANISM: Artificial Sequence
<220> FEATURE:
<223> OTHER INFORMATION: Synthetic Construct

<400> SEQUENCE: 325

Glu Ile Gln Leu Gln Gln Ser Gly Pro Glu Leu Val Lys Pro Gly Ala
1               5                   10                  15

Ser Val Arg Val Ser Cys Lys Pro Ser Gly Tyr Ala Phe Thr
            20                  25                  30

<210> SEQ ID NO 326
<211> LENGTH: 14
<212> TYPE: PRT
<213> ORGANISM: Artificial Sequence
<220> FEATURE:
<223> OTHER INFORMATION: Synthetic Construct

```
<400> SEQUENCE: 326

Trp Val Lys Gln Ser Arg Arg Lys Ser Leu Glu Trp Ile Gly
1               5                   10

<210> SEQ ID NO 327
<211> LENGTH: 32
<212> TYPE: PRT
<213> ORGANISM: Artificial Sequence
<220> FEATURE:
<223> OTHER INFORMATION: Synthetic Construct

<400> SEQUENCE: 327

Lys Ala Thr Leu Thr Val Asp Lys Ser Ser Thr Ala Tyr Met His
1               5                   10                  15

Leu Asn Ser Leu Thr Ser Glu Asp Ser Ala Val Tyr Tyr Cys Ser Arg
                20                  25                  30

<210> SEQ ID NO 328
<211> LENGTH: 11
<212> TYPE: PRT
<213> ORGANISM: Artificial Sequence
<220> FEATURE:
<223> OTHER INFORMATION: Synthetic Construct

<400> SEQUENCE: 328

Trp Gly Gln Gly Thr Thr Leu Thr Val Ser Ser
1               5                   10

<210> SEQ ID NO 329
<211> LENGTH: 30
<212> TYPE: PRT
<213> ORGANISM: Artificial Sequence
<220> FEATURE:
<223> OTHER INFORMATION: Synthetic Construct

<400> SEQUENCE: 329

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr
                20                  25                  30

<210> SEQ ID NO 330
<211> LENGTH: 32
<212> TYPE: PRT
<213> ORGANISM: Artificial Sequence
<220> FEATURE:
<223> OTHER INFORMATION: Synthetic Construct

<400> SEQUENCE: 330

Arg Val Thr Ile Thr Ala Asp Thr Ser Thr Ser Thr Ala Tyr Leu Glu
1               5                   10                  15

Leu Ser Ser Leu Arg Ser Glu Asp Thr Ala Val Tyr Tyr Cys Ser Arg
                20                  25                  30

<210> SEQ ID NO 331
<211> LENGTH: 30
<212> TYPE: PRT
<213> ORGANISM: Artificial Sequence
<220> FEATURE:
<223> OTHER INFORMATION: Synthetic Construct

<400> SEQUENCE: 331

Glu Ile Gln Leu Val Gln Ser Gly Ala Glu Val Lys Lys Pro Gly Ala
1               5                   10                  15
```

Ser Val Lys Val Ser Cys Lys Pro Ser Gly Tyr Ala Phe Thr
            20                  25                  30

<210> SEQ ID NO 332
<211> LENGTH: 32
<212> TYPE: PRT
<213> ORGANISM: Artificial Sequence
<220> FEATURE:
<223> OTHER INFORMATION: Synthetic Construct

<400> SEQUENCE: 332

Arg Ala Thr Leu Thr Val Asp Lys Ser Thr Ser Thr Ala Tyr Leu Glu
1               5                   10                  15

Leu Ser Ser Leu Arg Ser Glu Asp Thr Ala Val Tyr Tyr Cys Ser Arg
            20                  25                  30

<210> SEQ ID NO 333
<211> LENGTH: 30
<212> TYPE: PRT
<213> ORGANISM: Artificial Sequence
<220> FEATURE:
<223> OTHER INFORMATION: Synthetic Construct

<400> SEQUENCE: 333

Glu Ile Gln Leu Val Gln Ser Gly Ala Glu Val Lys Lys Pro Gly Ser
1               5                   10                  15

Ser Val Lys Val Ser Cys Lys Pro Ser Gly Tyr Ala Phe Thr
            20                  25                  30

<210> SEQ ID NO 334
<211> LENGTH: 32
<212> TYPE: PRT
<213> ORGANISM: Artificial Sequence
<220> FEATURE:
<223> OTHER INFORMATION: Synthetic Construct

<400> SEQUENCE: 334

Arg Ala Thr Leu Thr Val Asp Lys Ser Thr Ser Thr Ala Tyr Met Glu
1               5                   10                  15

Leu Ser Ser Leu Arg Ser Glu Asp Thr Ala Val Tyr Tyr Cys Ser Arg
            20                  25                  30

<210> SEQ ID NO 335
<211> LENGTH: 30
<212> TYPE: PRT
<213> ORGANISM: Artificial Sequence
<220> FEATURE:
<223> OTHER INFORMATION: Synthetic Construct

<400> SEQUENCE: 335

Gln Gly Gln Met Gln Gln Ser Gly Ala Glu Leu Val Lys Pro Gly Ala
1               5                   10                  15

Ser Val Lys Leu Ser Cys Lys Thr Ser Gly Phe Thr Phe Ser
            20                  25                  30

<210> SEQ ID NO 336
<211> LENGTH: 14
<212> TYPE: PRT
<213> ORGANISM: Artificial Sequence
<220> FEATURE:
<223> OTHER INFORMATION: Synthetic Construct

<400> SEQUENCE: 336

Trp Leu Lys Gln Lys Pro Gly Gln Ser Leu Glu Trp Ile Ala
1               5                   10

<210> SEQ ID NO 337
<211> LENGTH: 32
<212> TYPE: PRT
<213> ORGANISM: Artificial Sequence
<220> FEATURE:
<223> OTHER INFORMATION: Synthetic Construct

<400> SEQUENCE: 337

Lys Ala Gln Leu Thr Val Asp Thr Ser Ser Arg Thr Ala Tyr Met Gln
1               5                   10                  15

Leu Ser Ser Leu Thr Thr Glu Asp Ser Ala Ile Tyr Tyr Cys Ala Arg
            20                  25                  30

<210> SEQ ID NO 338
<211> LENGTH: 11
<212> TYPE: PRT
<213> ORGANISM: Artificial Sequence
<220> FEATURE:
<223> OTHER INFORMATION: Synthetic Construct

<400> SEQUENCE: 338

Trp Gly Arg Gly Thr Leu Val Thr Val Ser Ala
1               5                   10

<210> SEQ ID NO 339
<211> LENGTH: 29
<212> TYPE: PRT
<213> ORGANISM: Artificial Sequence
<220> FEATURE:
<223> OTHER INFORMATION: Synthetic Construct

<400> SEQUENCE: 339

Val Gln Leu Gln Glu Ser Gly Pro Gly Leu Val Lys Pro Ser Gln Ser
1               5                   10                  15

Leu Ser Leu Thr Cys Asn Val Thr Gly Tyr Ser Ile Thr
            20                  25

<210> SEQ ID NO 340
<211> LENGTH: 14
<212> TYPE: PRT
<213> ORGANISM: Artificial Sequence
<220> FEATURE:
<223> OTHER INFORMATION: Synthetic Construct

<400> SEQUENCE: 340

Trp Ile Arg Gln Phe Pro Gly Asn Lys Leu Glu Trp Ile Gly
1               5                   10

<210> SEQ ID NO 341
<211> LENGTH: 32
<212> TYPE: PRT
<213> ORGANISM: Artificial Sequence
<220> FEATURE:
<223> OTHER INFORMATION: Synthetic Construct

<400> SEQUENCE: 341

Arg Val Ser Ile Thr Arg Asp Thr Ser Lys Asn Gln Phe Phe Leu Gln
1               5                   10                  15

Leu Asn Ser Val Thr Pro Glu Asp Thr Ala Thr Tyr Tyr Cys Ala Arg
            20                  25                  30

<210> SEQ ID NO 342
<211> LENGTH: 11
<212> TYPE: PRT
<213> ORGANISM: Artificial Sequence
<220> FEATURE:
<223> OTHER INFORMATION: Synthetic Construct

<400> SEQUENCE: 342

Trp Gly Leu Gly Thr Ser Val Thr Val Ser Ser
1               5                   10

<210> SEQ ID NO 343
<211> LENGTH: 30
<212> TYPE: PRT
<213> ORGANISM: Artificial Sequence
<220> FEATURE:
<223> OTHER INFORMATION: Synthetic Construct

<400> SEQUENCE: 343

Asp Val Gln Leu Gln Glu Ser Gly Pro Gly Leu Val Lys Pro Ser Gln
1               5                   10                  15

Pro Leu Ser Leu Thr Cys Thr Val Thr Gly Tyr Ser Ile Thr
            20                  25                  30

<210> SEQ ID NO 344
<211> LENGTH: 14
<212> TYPE: PRT
<213> ORGANISM: Artificial Sequence
<220> FEATURE:
<223> OTHER INFORMATION: Synthetic Construct

<400> SEQUENCE: 344

Trp Ile Arg Gln Phe Pro Gly Asp Lys Leu Glu Trp Met Gly
1               5                   10

<210> SEQ ID NO 345
<211> LENGTH: 32
<212> TYPE: PRT
<213> ORGANISM: Artificial Sequence
<220> FEATURE:
<223> OTHER INFORMATION: Synthetic Construct

<400> SEQUENCE: 345

Arg Ile Ser Ile Thr Arg Asp Thr Ser Lys Asn Gln Phe Phe Leu Gln
1               5                   10                  15

Leu Asn Ser Leu Thr Thr Glu Asp Thr Ala Thr Tyr Tyr Cys Ser Arg
            20                  25                  30

<210> SEQ ID NO 346
<211> LENGTH: 11
<212> TYPE: PRT
<213> ORGANISM: Artificial Sequence
<220> FEATURE:
<223> OTHER INFORMATION: Synthetic Construct

<400> SEQUENCE: 346

Trp Gly Ala Gly Thr Thr Val Thr Val Ser Ser
1               5                   10

<210> SEQ ID NO 347
<211> LENGTH: 117
<212> TYPE: PRT
<213> ORGANISM: Artificial Sequence
<220> FEATURE:
<223> OTHER INFORMATION: Synthetic Construct

<400> SEQUENCE: 347

```
Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Gln
            20                  25                  30

Asn Ile Tyr Trp Val Lys Gln Ser His Gly Lys Ser Leu Glu Trp Ile
        35                  40                  45

Gly Tyr Ile Glu Pro Tyr Asn Val Val Pro Met Tyr Asn Pro Lys Phe
50                  55                  60

Lys Gly Lys Ala Thr Leu Thr Val Asp Lys Ser Ser Ser Ser Ala Tyr
65                  70                  75                  80

Ile His Leu Asn Ser Leu Thr Ser Glu Asp Ser Ala Ile Tyr Tyr Cys
                85                  90                  95

Ala Arg Ser Gly Ser Ser Asn Phe Asp Tyr Trp Gly Gln Gly Thr Thr
            100                 105                 110

Leu Thr Val Ser Ser
        115
```

<210> SEQ ID NO 348
<211> LENGTH: 108
<212> TYPE: PRT
<213> ORGANISM: Artificial Sequence
<220> FEATURE:
<223> OTHER INFORMATION: Synthetic Construct

<400> SEQUENCE: 348

```
Glu Ile Ile Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser His
            20                  25                  30

Tyr Leu His Trp Tyr Gln Gln Lys Ser Gly Phe Ser Pro Lys Leu Leu
        35                  40                  45

Ile Tyr Arg Thr Ser Asn Leu Ala Ser Gly Val Pro Ala Arg Phe Ser
50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Ser Leu Pro
                85                  90                  95

Leu Thr Phe Gly Ala Gly Thr Lys Val Glu Ile Lys
            100                 105
```

<210> SEQ ID NO 349
<211> LENGTH: 117
<212> TYPE: PRT
<213> ORGANISM: Artificial Sequence
<220> FEATURE:
<223> OTHER INFORMATION: Synthetic Construct

<400> SEQUENCE: 349

```
Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
            20                  25                  30

Asn Ile Tyr Trp Val Arg Gln Ala Pro Gly Gln Gly Leu Glu Trp Ile
        35                  40                  45

Gly Tyr Ile Glu Pro Tyr Asn Val Val Pro Met Tyr Asn Pro Lys Phe
50                  55                  60
```

```
Lys Gly Arg Ala Thr Leu Thr Val Asp Lys Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Ser Gly Ser Ser Asn Phe Asp Tyr Trp Gly Gln Gly Thr Leu
            100                 105                 110

Val Thr Val Ser Ser
            115

<210> SEQ ID NO 350
<211> LENGTH: 108
<212> TYPE: PRT
<213> ORGANISM: Artificial Sequence
<220> FEATURE:
<223> OTHER INFORMATION: Synthetic Construct

<400> SEQUENCE: 350

Glu Ile Val Leu Thr Gln Ser Pro Asp Phe Gln Ser Val Thr Pro Lys
 1               5                  10                  15

Glu Lys Val Thr Ile Thr Cys Ser Ala Ser Ser Ser Ile Ser Ser His
                20                  25                  30

Tyr Leu His Trp Tyr Gln Gln Lys Pro Asp Gln Ser Pro Lys Leu Leu
             35                  40                  45

Ile Tyr Arg Thr Ser Asn Leu Ala Ser Gly Val Pro Ser Arg Phe Ser
 50                  55                  60

Gly Ser Gly Ser Gly Thr Asp Tyr Thr Leu Thr Ile Asn Ser Leu Glu
 65                  70                  75                  80

Ala Glu Asp Ala Ala Thr Tyr Tyr Cys Gln Gln Gly Ser Ser Leu Pro
                 85                  90                  95

Leu Thr Phe Gly Gln Gly Thr Lys Val Glu Ile Lys
            100                 105

<210> SEQ ID NO 351
<211> LENGTH: 117
<212> TYPE: PRT
<213> ORGANISM: Artificial Sequence
<220> FEATURE:
<223> OTHER INFORMATION: Synthetic Construct

<400> SEQUENCE: 351

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Ser Gln
                20                  25                  30

Asn Ile Tyr Trp Val Arg Gln Ala Pro Gly Gln Gly Leu Glu Trp Met
             35                  40                  45

Gly Tyr Ile Glu Pro Tyr Asn Val Pro Met Tyr Asn Pro Lys Phe
 50                  55                  60

Lys Gly Arg Val Thr Met Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Ser Gly Ser Ser Asn Phe Asp Tyr Trp Gly Gln Gly Thr Leu
            100                 105                 110

Val Thr Val Ser Ser
            115
```

```
<210> SEQ ID NO 352
<211> LENGTH: 108
<212> TYPE: PRT
<213> ORGANISM: Artificial Sequence
<220> FEATURE:
<223> OTHER INFORMATION: Synthetic Construct

<400> SEQUENCE: 352

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Ile Ser Ser His
            20                  25                  30

Tyr Leu His Trp Tyr Gln Gln Lys Pro Asp Gln Ser Pro Lys Leu Leu
        35                  40                  45

Ile Tyr Arg Thr Ser Asn Leu Ala Ser Gly Val Pro Ser Arg Phe Ser
    50                  55                  60

Gly Ser Gly Ser Gly Thr Asp Tyr Thr Leu Thr Ile Asn Ser Leu Glu
65                  70                  75                  80

Ala Glu Asp Ala Ala Thr Tyr Tyr Cys Gln Gln Gly Ser Ser Leu Pro
                85                  90                  95

Leu Thr Phe Gly Gln Gly Thr Lys Val Glu Ile Lys
            100                 105

<210> SEQ ID NO 353
<211> LENGTH: 117
<212> TYPE: PRT
<213> ORGANISM: Artificial Sequence
<220> FEATURE:
<223> OTHER INFORMATION: Synthetic Construct

<400> SEQUENCE: 353

Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
            20                  25                  30

Asn Ile Tyr Trp Val Arg Gln Ala Pro Gly Gln Gly Leu Glu Trp Ile
        35                  40                  45

Gly Tyr Ile Glu Pro Tyr Asn Val Val Pro Met Tyr Asn Pro Lys Phe
    50                  55                  60

Lys Gly Arg Ala Thr Leu Thr Val Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Ser Ser Asn Phe Asp Tyr Trp Gly Gln Gly Thr Leu
            100                 105                 110

Val Thr Val Ser Ser
        115

<210> SEQ ID NO 354
<211> LENGTH: 108
<212> TYPE: PRT
<213> ORGANISM: Artificial Sequence
<220> FEATURE:
<223> OTHER INFORMATION: Synthetic Construct

<400> SEQUENCE: 354

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Ile Ser Ser His
            20                  25                  30
```

Tyr Leu His Trp Tyr Gln Gln Lys Pro Asp Gln Ser Pro Lys Leu Leu
            35                  40                  45

Ile Tyr Arg Thr Ser Asn Leu Ala Ser Gly Val Pro Ser Arg Phe Ser
 50                  55                  60

Gly Ser Gly Ser Gly Thr Asp Tyr Thr Leu Thr Ile Asn Ser Leu Glu
 65                  70                  75                  80

Ala Glu Asp Ala Ala Thr Tyr Tyr Cys Gln Gln Gly Ser Ser Leu Pro
                 85                  90                  95

Leu Thr Phe Gly Gln Gly Thr Lys Val Glu Ile Lys
            100                 105

<210> SEQ ID NO 355
<211> LENGTH: 117
<212> TYPE: PRT
<213> ORGANISM: Artificial Sequence
<220> FEATURE:
<223> OTHER INFORMATION: Synthetic Construct

<400> SEQUENCE: 355

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Ser Gln
                 20                  25                  30

Asn Ile Tyr Trp Val Arg Gln Ala Pro Gly Gln Gly Leu Glu Trp Ile
             35                  40                  45

Gly Tyr Ile Glu Pro Tyr Asn Val Val Pro Met Tyr Asn Pro Lys Phe
 50                  55                  60

Lys Gly Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Ser Gly Ser Ser Asn Phe Asp Tyr Trp Gly Gln Gly Thr Leu
                100                 105                 110

Val Thr Val Ser Ser
            115

<210> SEQ ID NO 356
<211> LENGTH: 108
<212> TYPE: PRT
<213> ORGANISM: Artificial Sequence
<220> FEATURE:
<223> OTHER INFORMATION: Synthetic Construct

<400> SEQUENCE: 356

Glu Ile Val Leu Thr Gln Ser Pro Asp Phe Gln Ser Val Thr Pro Lys
 1               5                  10                  15

Glu Lys Val Thr Ile Thr Cys Ser Ala Ser Ser Ser Ile Ser Ser His
                 20                  25                  30

Tyr Leu His Trp Tyr Gln Gln Lys Pro Asp Gln Ser Pro Lys Leu Leu
            35                  40                  45

Ile Tyr Arg Thr Ser Asn Leu Ala Ser Gly Val Pro Ser Arg Phe Ser
 50                  55                  60

Gly Ser Gly Ser Gly Thr Asp Tyr Thr Leu Thr Ile Asn Ser Leu Glu
 65                  70                  75                  80

Ala Glu Asp Ala Ala Thr Tyr Tyr Cys Gln Gln Gly Ser Ser Leu Pro
                85                  90                  95

Leu Thr Phe Gly Gln Gly Thr Lys Val Glu Ile Lys
            100                 105

<210> SEQ ID NO 357
<211> LENGTH: 117
<212> TYPE: PRT
<213> ORGANISM: Artificial Sequence
<220> FEATURE:
<223> OTHER INFORMATION: Synthetic Construct

<400> SEQUENCE: 357

Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
            20                  25                  30

Asn Ile Tyr Trp Val Arg Gln Ala Pro Gly Gln Gly Leu Glu Trp Ile
        35                  40                  45

Gly Tyr Ile Glu Pro Tyr Asn Val Val Pro Met Tyr Asn Pro Lys Phe
    50                  55                  60

Lys Gly Arg Ala Thr Leu Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Gly Ser Ser Asn Phe Asp Tyr Trp Gly Gln Gly Thr Leu
            100                 105                 110

Val Thr Val Ser Ser
        115

<210> SEQ ID NO 358
<211> LENGTH: 108
<212> TYPE: PRT
<213> ORGANISM: Artificial Sequence
<220> FEATURE:
<223> OTHER INFORMATION: Synthetic Construct

<400> SEQUENCE: 358

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Ile Ser Ser His
            20                  25                  30

Tyr Leu His Trp Tyr Gln Gln Lys Pro Asp Gln Ser Pro Lys Leu Leu
        35                  40                  45

Ile Lys Arg Thr Ser Asn Leu Ala Ser Gly Val Pro Ser Arg Phe Ser
    50                  55                  60

Gly Ser Gly Ser Gly Thr Asp Phe Thr Leu Thr Ile Asn Ser Leu Glu
65                  70                  75                  80

Ala Glu Asp Ala Ala Thr Tyr Tyr Cys Gln Gln Gly Ser Ser Leu Pro
                85                  90                  95

Leu Thr Phe Gly Gln Gly Thr Lys Val Glu Ile Lys
            100                 105

<210> SEQ ID NO 359
<211> LENGTH: 117
<212> TYPE: PRT
<213> ORGANISM: Artificial Sequence
<220> FEATURE:
<223> OTHER INFORMATION: Synthetic Construct

<400> SEQUENCE: 359

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
            20                  25                  30

Asn Ile Tyr Trp Val Arg Gln Ala Pro Gly Gln Gly Leu Glu Trp Met
        35                  40                  45

Gly Tyr Ile Glu Pro Tyr Asn Val Val Pro Met Tyr Asn Pro Lys Phe
50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Gly Ser Ser Asn Phe Asp Tyr Trp Gly Gln Gly Thr Leu
            100                 105                 110

Val Thr Val Ser Ser
            115
```

<210> SEQ ID NO 360
<211> LENGTH: 108
<212> TYPE: PRT
<213> ORGANISM: Artificial Sequence
<220> FEATURE:
<223> OTHER INFORMATION: Synthetic Construct

<400> SEQUENCE: 360

```
Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Ile Ser Ser His
            20                  25                  30

Tyr Leu His Trp Tyr Gln Gln Lys Pro Asp Gln Ser Pro Lys Leu Leu
        35                  40                  45

Ile Lys Arg Thr Ser Asn Leu Ala Ser Gly Val Pro Ser Arg Phe Ser
50                  55                  60

Gly Ser Gly Ser Gly Thr Asp Phe Thr Leu Thr Ile Asn Ser Leu Glu
65                  70                  75                  80

Ala Glu Asp Ala Ala Thr Tyr Tyr Cys Gln Gln Gly Ser Ser Leu Pro
                85                  90                  95

Leu Thr Phe Gly Gln Gly Thr Lys Val Glu Ile Lys
            100                 105
```

<210> SEQ ID NO 361
<211> LENGTH: 117
<212> TYPE: PRT
<213> ORGANISM: Artificial Sequence
<220> FEATURE:
<223> OTHER INFORMATION: Synthetic Construct

<400> SEQUENCE: 361

```
Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
            20                  25                  30

Asn Ile Tyr Trp Val Arg Gln Ala Pro Gly Gln Gly Leu Glu Trp Ile
        35                  40                  45

Gly Tyr Ile Glu Pro Tyr Asn Val Val Pro Met Tyr Asn Pro Lys Phe
50                  55                  60
```

```
Lys Gly Arg Ala Thr Leu Thr Val Asp Lys Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Ser Gly Ser Ser Asn Phe Asp Tyr Trp Gly Gln Gly Thr Leu
            100                 105                 110

Val Thr Val Ser Ser
            115

<210> SEQ ID NO 362
<211> LENGTH: 108
<212> TYPE: PRT
<213> ORGANISM: Artificial Sequence
<220> FEATURE:
<223> OTHER INFORMATION: Synthetic Construct

<400> SEQUENCE: 362

Glu Ile Val Leu Thr Gln Ser Pro Asp Phe Gln Ser Val Thr Pro Lys
 1               5                  10                  15

Glu Lys Val Thr Ile Thr Cys Ser Ala Ser Ser Ser Ile Ser Ser His
                20                  25                  30

Tyr Leu His Trp Tyr Gln Gln Lys Pro Asp Gln Ser Pro Lys Leu Leu
            35                  40                  45

Ile Lys Arg Thr Ser Asn Leu Ala Ser Gly Val Pro Ser Arg Phe Ser
 50                  55                  60

Gly Ser Gly Ser Gly Thr Asp Phe Thr Leu Thr Ile Asn Ser Leu Glu
 65                  70                  75                  80

Ala Glu Asp Ala Ala Thr Tyr Tyr Cys Gln Gln Gly Ser Ser Leu Pro
                 85                  90                  95

Leu Thr Phe Gly Gln Gly Thr Lys Val Glu Ile Lys
            100                 105

<210> SEQ ID NO 363
<211> LENGTH: 117
<212> TYPE: PRT
<213> ORGANISM: Artificial Sequence
<220> FEATURE:
<223> OTHER INFORMATION: Synthetic Construct

<400> SEQUENCE: 363

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Ser Gln
                20                  25                  30

Asn Ile Tyr Trp Val Arg Gln Ala Pro Gly Gln Gly Leu Glu Trp Ile
            35                  40                  45

Gly Tyr Ile Glu Pro Tyr Asn Val Val Pro Met Tyr Asn Pro Lys Phe
 50                  55                  60

Lys Gly Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Ser Gly Ser Ser Asn Phe Asp Tyr Trp Gly Gln Gly Thr Leu
            100                 105                 110

Val Thr Val Ser Ser
            115
```

<210> SEQ ID NO 364
<211> LENGTH: 108
<212> TYPE: PRT
<213> ORGANISM: Artificial Sequence
<220> FEATURE:
<223> OTHER INFORMATION: Synthetic Construct

<400> SEQUENCE: 364

```
Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Ile Ser Ser His
                20                  25                  30

Tyr Leu His Trp Tyr Gln Gln Lys Pro Asp Gln Ser Pro Lys Leu Leu
            35                  40                  45

Ile Lys Arg Thr Ser Asn Leu Ala Ser Gly Val Pro Ser Arg Phe Ser
    50                  55                  60

Gly Ser Gly Ser Gly Thr Asp Phe Thr Leu Thr Ile Asn Ser Leu Glu
65                  70                  75                  80

Ala Glu Asp Ala Ala Thr Tyr Tyr Cys Gln Gln Gly Ser Ser Leu Pro
                85                  90                  95

Leu Thr Phe Gly Gln Gly Thr Lys Val Glu Ile Lys
            100                 105
```

<210> SEQ ID NO 365
<211> LENGTH: 117
<212> TYPE: PRT
<213> ORGANISM: Artificial Sequence
<220> FEATURE:
<223> OTHER INFORMATION: Synthetic Construct

<400> SEQUENCE: 365

```
Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
                20                  25                  30

Asn Ile Tyr Trp Val Arg Gln Ala Pro Gly Gln Gly Leu Glu Trp Ile
            35                  40                  45

Gly Tyr Ile Glu Pro Tyr Asn Val Val Pro Met Tyr Asn Pro Lys Phe
    50                  55                  60

Lys Gly Arg Ala Thr Leu Thr Val Asp Lys Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Ser Gly Ser Ser Asn Phe Asp Tyr Trp Gly Gln Gly Thr Leu
            100                 105                 110

Val Thr Val Ser Ser
        115
```

<210> SEQ ID NO 366
<211> LENGTH: 108
<212> TYPE: PRT
<213> ORGANISM: Artificial Sequence
<220> FEATURE:
<223> OTHER INFORMATION: Synthetic Construct

<400> SEQUENCE: 366

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Ile Ser Ser His
                20                  25                  30
```

Tyr Leu His Trp Tyr Gln Gln Lys Pro Gly Lys Ser Pro Lys Leu Leu
        35                  40                  45

Ile Tyr Arg Thr Ser Asn Leu Ala Ser Gly Val Pro Ser Arg Phe Ser
 50                  55                  60

Gly Ser Gly Ser Gly Thr Asp Tyr Thr Leu Thr Ile Ser Ser Leu Gln
 65                  70                  75                  80

Pro Glu Asp Phe Ala Thr Tyr Tyr Cys Gln Gln Gly Ser Ser Leu Pro
                 85                  90                  95

Leu Thr Phe Gly Gln Gly Thr Lys Val Glu Ile Lys
                100                 105

<210> SEQ ID NO 367
<211> LENGTH: 117
<212> TYPE: PRT
<213> ORGANISM: Artificial Sequence
<220> FEATURE:
<223> OTHER INFORMATION: Synthetic Construct

<400> SEQUENCE: 367

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Ser Gln
                20                  25                  30

Asn Ile Tyr Trp Val Arg Gln Ala Pro Gly Gln Gly Leu Glu Trp Met
            35                  40                  45

Gly Tyr Ile Glu Pro Tyr Asn Val Val Pro Met Tyr Asn Pro Lys Phe
 50                  55                  60

Lys Gly Arg Val Thr Met Thr Thr Asp Thr Ser Thr Ser Thr Ala Tyr
 65                  70                  75                  80

Met Glu Leu Arg Ser Leu Arg Ser Asp Thr Ala Val Tyr Tyr Cys
                 85                  90                  95

Ala Arg Ser Gly Ser Ser Asn Phe Asp Tyr Trp Gly Gln Gly Thr Leu
                100                 105                 110

Val Thr Val Ser Ser
        115

<210> SEQ ID NO 368
<211> LENGTH: 108
<212> TYPE: PRT
<213> ORGANISM: Artificial Sequence
<220> FEATURE:
<223> OTHER INFORMATION: Synthetic Construct

<400> SEQUENCE: 368

Asp Ile Gln Leu Thr Gln Ser Pro Ser Ser Leu Ser Ala Ser Val Gly
 1               5                  10                  15

Asp Arg Val Thr Ile Thr Cys Ser Ala Ser Ser Ser Ile Ser Ser His
                20                  25                  30

Tyr Leu His Trp Tyr Gln Gln Lys Pro Gly Lys Ser Pro Lys Leu Leu
        35                  40                  45

Ile Tyr Arg Thr Ser Asn Leu Ala Ser Gly Val Pro Ser Arg Phe Ser
 50                  55                  60

Gly Ser Gly Ser Gly Thr Asp Tyr Thr Leu Thr Ile Ser Ser Leu Gln
 65                  70                  75                  80

Pro Glu Asp Phe Ala Thr Tyr Tyr Cys Gln Gln Gly Ser Ser Leu Pro
                 85                  90                  95

```
Leu Thr Phe Gly Gln Gly Thr Lys Val Glu Ile Lys
            100                 105

<210> SEQ ID NO 369
<211> LENGTH: 117
<212> TYPE: PRT
<213> ORGANISM: Artificial Sequence
<220> FEATURE:
<223> OTHER INFORMATION: Synthetic Construct

<400> SEQUENCE: 369

Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
                20                  25                  30

Asn Ile Tyr Trp Val Arg Gln Ala Pro Gly Gln Gly Leu Glu Trp Ile
            35                  40                  45

Gly Tyr Ile Glu Pro Tyr Asn Val Val Pro Met Tyr Asn Pro Lys Phe
    50                  55                  60

Lys Gly Arg Ala Thr Leu Thr Val Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Ser Ser Asn Phe Asp Tyr Trp Gly Gln Gly Thr Leu
            100                 105                 110

Val Thr Val Ser Ser
        115

<210> SEQ ID NO 370
<211> LENGTH: 108
<212> TYPE: PRT
<213> ORGANISM: Artificial Sequence
<220> FEATURE:
<223> OTHER INFORMATION: Synthetic Construct

<400> SEQUENCE: 370

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Ile Ser Ser His
                20                  25                  30

Tyr Leu His Trp Tyr Gln Gln Lys Pro Gly Lys Ser Pro Lys Leu Leu
            35                  40                  45

Ile Tyr Arg Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Ser Ser Leu Pro
                85                  90                  95

Leu Thr Phe Gly Gln Gly Thr Lys Val Glu Ile Lys
            100                 105

<210> SEQ ID NO 371
<211> LENGTH: 117
<212> TYPE: PRT
<213> ORGANISM: Artificial Sequence
<220> FEATURE:
<223> OTHER INFORMATION: Synthetic Construct
```

<400> SEQUENCE: 371

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
            20                  25                  30

Asn Ile Tyr Trp Val Arg Gln Ala Pro Gly Gln Gly Leu Glu Trp Ile
        35                  40                  45

Gly Tyr Ile Glu Pro Tyr Asn Val Val Pro Met Tyr Asn Pro Lys Phe
50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Ser Ser Asn Phe Asp Tyr Trp Gly Gln Gly Thr Leu
            100                 105                 110

Val Thr Val Ser Ser
            115

<210> SEQ ID NO 372
<211> LENGTH: 108
<212> TYPE: PRT
<213> ORGANISM: Artificial Sequence
<220> FEATURE:
<223> OTHER INFORMATION: Synthetic Construct

<400> SEQUENCE: 372

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Ile Ser Ser His
            20                  25                  30

Tyr Leu His Trp Tyr Gln Gln Lys Pro Gly Lys Ser Pro Lys Leu Leu
        35                  40                  45

Ile Tyr Arg Thr Ser Asn Leu Ala Ser Gly Val Pro Ser Arg Phe Ser
50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Ser Ser Leu Pro
                85                  90                  95

Leu Thr Phe Gly Gln Gly Thr Lys Val Glu Ile Lys
            100                 105

<210> SEQ ID NO 373
<211> LENGTH: 117
<212> TYPE: PRT
<213> ORGANISM: Artificial Sequence
<220> FEATURE:
<223> OTHER INFORMATION: Synthetic Construct

<400> SEQUENCE: 373

Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
            20                  25                  30

Asn Ile Tyr Trp Val Arg Gln Ala Pro Gly Gln Gly Leu Glu Trp Ile
        35                  40                  45

Gly Tyr Ile Glu Pro Tyr Asn Val Val Pro Met Tyr Asn Pro Lys Phe
50                  55                  60

```
Lys Gly Arg Ala Thr Leu Thr Val Asp Lys Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Ser Gly Ser Ser Asn Phe Asp Tyr Trp Gly Gln Gly Thr Leu
            100                 105                 110

Val Thr Val Ser Ser
            115

<210> SEQ ID NO 374
<211> LENGTH: 108
<212> TYPE: PRT
<213> ORGANISM: Artificial Sequence
<220> FEATURE:
<223> OTHER INFORMATION: Synthetic Construct

<400> SEQUENCE: 374

Asp Ile Gln Met Thr Gln Ser Pro Ser Ser Leu Ser Ala Ser Val Gly
 1               5                  10                  15

Asp Arg Val Thr Ile Thr Cys Ser Ala Ser Ser Ser Ile Ser Ser His
                 20                  25                  30

Tyr Leu His Trp Tyr Gln Gln Lys Pro Gly Lys Ala Pro Lys Leu Leu
             35                  40                  45

Ile Tyr Arg Thr Ser Asn Leu Ala Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Gly Ser Ser Leu Pro
                 85                  90                  95

Leu Thr Phe Gly Gln Gly Thr Lys Val Glu Ile Lys
            100                 105

<210> SEQ ID NO 375
<211> LENGTH: 117
<212> TYPE: PRT
<213> ORGANISM: Artificial Sequence
<220> FEATURE:
<223> OTHER INFORMATION: Synthetic Construct

<400> SEQUENCE: 375

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Ser Gln
                 20                  25                  30

Asn Ile Tyr Trp Val Arg Gln Ala Pro Gly Gln Gly Leu Glu Trp Met
             35                  40                  45

Gly Tyr Ile Glu Pro Tyr Asn Val Val Pro Met Tyr Asn Pro Lys Phe
 50                  55                  60

Lys Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Ser Gly Ser Ser Asn Phe Asp Tyr Trp Gly Gln Gly Thr Leu
            100                 105                 110

Val Thr Val Ser Ser
            115
```

```
<210> SEQ ID NO 376
<211> LENGTH: 108
<212> TYPE: PRT
<213> ORGANISM: Artificial Sequence
<220> FEATURE:
<223> OTHER INFORMATION: Synthetic Construct

<400> SEQUENCE: 376

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Ile Ser Ser His
            20                  25                  30

Tyr Leu His Trp Tyr Gln Gln Lys Pro Gly Lys Ala Pro Lys Leu Leu
        35                  40                  45

Ile Tyr Arg Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Gly Ser Ser Leu Pro
                85                  90                  95

Leu Thr Phe Gly Gln Gly Thr Lys Val Glu Ile Lys
            100                 105

<210> SEQ ID NO 377
<211> LENGTH: 117
<212> TYPE: PRT
<213> ORGANISM: Artificial Sequence
<220> FEATURE:
<223> OTHER INFORMATION: Synthetic Construct

<400> SEQUENCE: 377

Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
            20                  25                  30

Asn Ile Tyr Trp Val Arg Gln Ala Pro Gly Gln Gly Leu Glu Trp Ile
        35                  40                  45

Gly Tyr Ile Glu Pro Tyr Asn Val Val Pro Met Tyr Asn Pro Lys Phe
    50                  55                  60

Lys Gly Arg Ala Thr Leu Thr Val Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Ser Ser Asn Phe Asp Tyr Trp Gly Gln Gly Thr Leu
            100                 105                 110

Val Thr Val Ser Ser
        115

<210> SEQ ID NO 378
<211> LENGTH: 108
<212> TYPE: PRT
<213> ORGANISM: Artificial Sequence
<220> FEATURE:
<223> OTHER INFORMATION: Synthetic Construct

<400> SEQUENCE: 378

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Ile Ser Ser His
            20                  25                  30
```

Tyr Leu His Trp Tyr Gln Gln Lys Pro Gly Lys Ala Pro Lys Leu Leu
        35                  40                  45

Ile Tyr Arg Thr Ser Asn Leu Ala Ser Gly Val Pro Ser Arg Phe Ser
 50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Gly Ser Ser Leu Pro
                85                  90                  95

Leu Thr Phe Gly Gln Gly Thr Lys Val Glu Ile Lys
            100                 105

<210> SEQ ID NO 379
<211> LENGTH: 117
<212> TYPE: PRT
<213> ORGANISM: Artificial Sequence
<220> FEATURE:
<223> OTHER INFORMATION: Synthetic Construct

<400> SEQUENCE: 379

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
                20                  25                  30

Asn Ile Tyr Trp Val Arg Gln Ala Pro Gly Gln Gly Leu Glu Trp Ile
            35                  40                  45

Gly Tyr Ile Glu Pro Tyr Asn Val Val Pro Met Tyr Asn Pro Lys Phe
 50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Ser Ser Asn Phe Asp Tyr Trp Gly Gln Gly Thr Leu
            100                 105                 110

Val Thr Val Ser Ser
        115

<210> SEQ ID NO 380
<211> LENGTH: 108
<212> TYPE: PRT
<213> ORGANISM: Artificial Sequence
<220> FEATURE:
<223> OTHER INFORMATION: Synthetic Construct

<400> SEQUENCE: 380

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Ile Ser Ser His
                20                  25                  30

Tyr Leu His Trp Tyr Gln Gln Lys Pro Gly Lys Ala Pro Lys Leu Leu
            35                  40                  45

Ile Tyr Arg Thr Ser Asn Leu Ala Ser Gly Val Pro Ser Arg Phe Ser
 50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Gly Ser Ser Leu Pro
                85                  90                  95

Leu Thr Phe Gly Gln Gly Thr Lys Val Glu Ile Lys
        100                 105

<210> SEQ ID NO 381
<211> LENGTH: 117
<212> TYPE: PRT
<213> ORGANISM: Artificial Sequence
<220> FEATURE:
<223> OTHER INFORMATION: Synthetic Construct

<400> SEQUENCE: 381

Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
            20                  25                  30

Asn Ile Tyr Trp Val Arg Gln Ala Pro Gly Gln Gly Leu Glu Trp Ile
        35                  40                  45

Gly Tyr Ile Glu Pro Tyr Asn Val Val Pro Met Tyr Asn Pro Lys Phe
    50                  55                  60

Lys Gly Arg Ala Thr Leu Thr Val Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Ser Ser Asn Phe Asp Tyr Trp Gly Gln Gly Thr Leu
            100                 105                 110

Val Thr Val Ser Ser
        115

<210> SEQ ID NO 382
<211> LENGTH: 108
<212> TYPE: PRT
<213> ORGANISM: Artificial Sequence
<220> FEATURE:
<223> OTHER INFORMATION: Synthetic Construct

<400> SEQUENCE: 382

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Ile Ser Ser His
            20                  25                  30

Tyr Leu His Trp Tyr Gln Gln Lys Pro Gly Lys Ser Pro Lys Leu Leu
        35                  40                  45

Ile Tyr Arg Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Ser Ser Leu Pro
                85                  90                  95

Leu Thr Phe Gly Gln Gly Thr Lys Val Glu Ile Lys
        100                 105

<210> SEQ ID NO 383
<211> LENGTH: 117
<212> TYPE: PRT
<213> ORGANISM: Artificial Sequence
<220> FEATURE:
<223> OTHER INFORMATION: Synthetic Construct

<400> SEQUENCE: 383

Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
            20                  25                  30

Asn Ile Tyr Trp Val Arg Gln Ala Pro Gly Gln Gly Leu Glu Trp Ile
        35                  40                  45

Gly Tyr Ile Glu Pro Tyr Asn Val Val Pro Met Tyr Asn Pro Lys Phe
    50                  55                  60

Lys Gly Arg Ala Thr Leu Thr Val Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Ser Ser Asn Phe Asp Tyr Trp Gly Gln Gly Thr Leu
            100                 105                 110

Val Thr Val Ser Ser
        115

<210> SEQ ID NO 384
<211> LENGTH: 108
<212> TYPE: PRT
<213> ORGANISM: Artificial Sequence
<220> FEATURE:
<223> OTHER INFORMATION: Synthetic Construct

<400> SEQUENCE: 384

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Ile Ser Ser His
            20                  25                  30

Tyr Leu His Trp Tyr Gln Gln Lys Pro Gly Lys Ser Pro Lys Leu Leu
        35                  40                  45

Ile Tyr Arg Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Gly Ser Ser Leu Pro
                85                  90                  95

Leu Thr Phe Gly Gln Gly Thr Lys Val Glu Ile Lys
            100                 105

<210> SEQ ID NO 385
<211> LENGTH: 117
<212> TYPE: PRT
<213> ORGANISM: Artificial Sequence
<220> FEATURE:
<223> OTHER INFORMATION: Synthetic Construct

<400> SEQUENCE: 385

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
            20                  25                  30

Asn Ile Tyr Trp Val Arg Gln Ala Pro Gly Gln Gly Leu Glu Trp Ile
        35                  40                  45

Gly Tyr Ile Glu Pro Tyr Asn Val Val Pro Met Tyr Asn Pro Lys Phe
    50                  55                  60

```
Lys Gly Arg Ala Thr Leu Thr Val Asp Lys Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Ser Gly Ser Ser Asn Phe Asp Tyr Trp Gly Gln Gly Thr Leu
            100                 105                 110

Val Thr Val Ser Ser
        115

<210> SEQ ID NO 386
<211> LENGTH: 108
<212> TYPE: PRT
<213> ORGANISM: Artificial Sequence
<220> FEATURE:
<223> OTHER INFORMATION: Synthetic Construct

<400> SEQUENCE: 386

Asp Ile Gln Leu Thr Gln Ser Pro Ser Ser Leu Ser Ala Ser Val Gly
 1               5                  10                  15

Asp Arg Val Thr Ile Thr Cys Ser Ala Ser Ser Ser Ile Ser Ser His
            20                  25                  30

Tyr Leu His Trp Tyr Gln Gln Lys Pro Gly Lys Ser Pro Lys Leu Leu
        35                  40                  45

Ile Tyr Arg Thr Ser Asn Leu Ala Ser Gly Val Pro Ser Arg Phe Ser
 50                  55                  60

Gly Ser Gly Ser Gly Thr Asp Tyr Thr Leu Thr Ile Ser Ser Leu Gln
 65                  70                  75                  80

Pro Glu Asp Phe Ala Thr Tyr Tyr Cys Gln Gln Gly Ser Ser Leu Pro
                 85                  90                  95

Leu Thr Phe Gly Gln Gly Thr Lys Val Glu Ile Lys
            100                 105

<210> SEQ ID NO 387
<211> LENGTH: 117
<212> TYPE: PRT
<213> ORGANISM: Artificial Sequence
<220> FEATURE:
<223> OTHER INFORMATION: Synthetic Construct

<400> SEQUENCE: 387

Glu Ile Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Ser Gln
            20                  25                  30

Asn Ile Tyr Trp Val Arg Gln Ala Pro Gly Gln Gly Leu Glu Trp Ile
        35                  40                  45

Gly Tyr Ile Glu Pro Tyr Asn Val Val Pro Met Tyr Asn Pro Lys Phe
 50                  55                  60

Lys Gly Arg Val Thr Leu Thr Val Asp Lys Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Ser Gly Ser Ser Asn Phe Asp Tyr Trp Gly Gln Gly Thr Leu
            100                 105                 110

Val Thr Val Ser Ser
        115
```

```
<210> SEQ ID NO 388
<211> LENGTH: 108
<212> TYPE: PRT
<213> ORGANISM: Artificial Sequence
<220> FEATURE:
<223> OTHER INFORMATION: Synthetic Construct

<400> SEQUENCE: 388
```

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ile Ser Ser His
            20                  25                  30

Tyr Leu His Trp Tyr Gln Gln Lys Pro Gly Lys Ser Pro Lys Leu Leu
            35                  40                  45

Ile Tyr Arg Thr Ser Asn Leu Ala Ser Gly Val Pro Ser Arg Phe Ser
        50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Ser Ser Leu Pro
                85                  90                  95

Leu Thr Phe Gly Gln Gly Thr Lys Val Glu Ile Lys
            100                 105

```
<210> SEQ ID NO 389
<211> LENGTH: 117
<212> TYPE: PRT
<213> ORGANISM: Artificial Sequence
<220> FEATURE:
<223> OTHER INFORMATION: Synthetic Construct

<400> SEQUENCE: 389
```

Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
            20                  25                  30

Asn Ile Tyr Trp Val Arg Gln Ala Pro Gly Gln Gly Leu Glu Trp Ile
        35                  40                  45

Gly Tyr Ile Glu Pro Tyr Asn Val Val Pro Met Tyr Asn Pro Lys Phe
    50                  55                  60

Lys Gly Arg Ala Thr Ile Thr Val Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Ser Ser Asn Phe Asp Tyr Trp Gly Gln Gly Thr Leu
            100                 105                 110

Val Thr Val Ser Ser
        115

```
<210> SEQ ID NO 390
<211> LENGTH: 108
<212> TYPE: PRT
<213> ORGANISM: Artificial Sequence
<220> FEATURE:
<223> OTHER INFORMATION: Synthetic Construct

<400> SEQUENCE: 390
```

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ile Ser Ser His
            20                  25                  30

Tyr Leu His Trp Tyr Gln Gln Lys Pro Gly Lys Ser Pro Lys Leu Leu
            35                  40                  45

Ile Tyr Arg Thr Ser Asn Leu Ala Ser Gly Val Pro Ser Arg Phe Ser
        50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Ser Ser Leu Pro
                85                  90                  95

Leu Thr Phe Gly Gln Gly Thr Lys Val Glu Ile Lys
            100                 105

<210> SEQ ID NO 391
<211> LENGTH: 117
<212> TYPE: PRT
<213> ORGANISM: Artificial Sequence
<220> FEATURE:
<223> OTHER INFORMATION: Synthetic Construct

<400> SEQUENCE: 391

Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
            20                  25                  30

Asn Ile Tyr Trp Val Arg Gln Ala Pro Gly Gln Gly Leu Glu Trp Ile
        35                  40                  45

Gly Tyr Ile Glu Pro Tyr Asn Val Val Pro Met Tyr Asn Pro Lys Phe
    50                  55                  60

Lys Gly Arg Ala Thr Leu Thr Arg Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Ser Ser Asn Phe Asp Tyr Trp Gly Gln Gly Thr Leu
            100                 105                 110

Val Thr Val Ser Ser
        115

<210> SEQ ID NO 392
<211> LENGTH: 108
<212> TYPE: PRT
<213> ORGANISM: Artificial Sequence
<220> FEATURE:
<223> OTHER INFORMATION: Synthetic Construct

<400> SEQUENCE: 392

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Ile Ser Ser His
            20                  25                  30

Tyr Leu His Trp Tyr Gln Gln Lys Pro Gly Lys Ser Pro Lys Leu Leu
        35                  40                  45

Ile Tyr Arg Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Ser Ser Leu Pro
                85                  90                  95

Leu Thr Phe Gly Gln Gly Thr Lys Val Glu Ile Lys
        100                 105

<210> SEQ ID NO 393
<211> LENGTH: 117
<212> TYPE: PRT
<213> ORGANISM: Artificial Sequence
<220> FEATURE:
<223> OTHER INFORMATION: Synthetic Construct

<400> SEQUENCE: 393

Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
            20                  25                  30

Asn Ile Tyr Trp Val Arg Gln Ala Pro Gly Gln Gly Leu Glu Trp Ile
        35                  40                  45

Gly Tyr Ile Glu Pro Tyr Asn Val Val Pro Met Tyr Asn Pro Lys Phe
    50                  55                  60

Lys Gly Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Ser Ser Asn Phe Asp Tyr Trp Gly Gln Gly Thr Leu
            100                 105                 110

Val Thr Val Ser Ser
        115

<210> SEQ ID NO 394
<211> LENGTH: 108
<212> TYPE: PRT
<213> ORGANISM: Artificial Sequence
<220> FEATURE:
<223> OTHER INFORMATION: Synthetic Construct

<400> SEQUENCE: 394

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Ile Ser Ser His
            20                  25                  30

Tyr Leu His Trp Tyr Gln Gln Lys Pro Gly Lys Ser Pro Lys Leu Leu
        35                  40                  45

Ile Tyr Arg Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Ser Ser Leu Pro
                85                  90                  95

Leu Thr Phe Gly Gln Gly Thr Lys Val Glu Ile Lys
            100                 105

<210> SEQ ID NO 395
<211> LENGTH: 117
<212> TYPE: PRT
<213> ORGANISM: Artificial Sequence
<220> FEATURE:
<223> OTHER INFORMATION: Synthetic Construct

<400> SEQUENCE: 395

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
            20                  25                  30

Asn Ile Tyr Trp Val Arg Gln Ala Pro Gly Gln Gly Leu Glu Trp Ile
        35                  40                  45

Gly Tyr Ile Glu Pro Tyr Asn Val Val Pro Met Tyr Asn Pro Lys Phe
50                  55                  60

Lys Gly Arg Val Thr Ile Thr Val Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Ser Ser Asn Phe Asp Tyr Trp Gly Gln Gly Thr Leu
            100                 105                 110

Val Thr Val Ser Ser
            115

<210> SEQ ID NO 396
<211> LENGTH: 108
<212> TYPE: PRT
<213> ORGANISM: Artificial Sequence
<220> FEATURE:
<223> OTHER INFORMATION: Synthetic Construct

<400> SEQUENCE: 396

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Ile Ser Ser His
            20                  25                  30

Tyr Leu His Trp Tyr Gln Gln Lys Pro Gly Lys Ser Pro Lys Leu Leu
        35                  40                  45

Ile Tyr Arg Thr Ser Asn Leu Ala Ser Gly Val Pro Ser Arg Phe Ser
50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Ser Ser Leu Pro
                85                  90                  95

Leu Thr Phe Gly Gln Gly Thr Lys Val Glu Ile Lys
            100                 105

<210> SEQ ID NO 397
<211> LENGTH: 117
<212> TYPE: PRT
<213> ORGANISM: Artificial Sequence
<220> FEATURE:
<223> OTHER INFORMATION: Synthetic Construct

<400> SEQUENCE: 397

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
            20                  25                  30

Asn Ile Tyr Trp Val Arg Gln Ala Pro Gly Gln Gly Leu Glu Trp Ile
        35                  40                  45

Gly Tyr Ile Glu Pro Tyr Asn Val Val Pro Met Tyr Asn Pro Lys Phe
50                  55                  60

```
Lys Gly Arg Val Thr Ile Thr Val Asp Thr Ser Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Ser Gly Ser Ser Asn Phe Asp Tyr Trp Gly Gln Gly Thr Leu
            100                 105                 110

Val Thr Val Ser Ser
            115

<210> SEQ ID NO 398
<211> LENGTH: 108
<212> TYPE: PRT
<213> ORGANISM: Artificial Sequence
<220> FEATURE:
<223> OTHER INFORMATION: Synthetic Construct

<400> SEQUENCE: 398

Asp Ile Gln Leu Thr Gln Ser Pro Ser Ser Leu Ser Ala Ser Val Gly
  1               5                  10                  15

Asp Arg Val Thr Ile Thr Cys Ser Ala Ser Ser Ser Ile Ser Ser His
                 20                  25                  30

Tyr Leu His Trp Tyr Gln Gln Lys Pro Gly Lys Ser Pro Lys Leu Leu
             35                  40                  45

Ile Tyr Arg Thr Ser Asn Leu Ala Ser Gly Val Pro Ser Arg Phe Ser
 50                  55                  60

Gly Ser Gly Ser Gly Thr Asp Tyr Thr Leu Thr Ile Ser Ser Leu Gln
 65                  70                  75                  80

Pro Glu Asp Phe Ala Thr Tyr Tyr Cys Gln Gln Gly Ser Ser Leu Pro
                 85                  90                  95

Leu Thr Phe Gly Gln Gly Thr Lys Val Glu Ile Lys
            100                 105

<210> SEQ ID NO 399
<211> LENGTH: 117
<212> TYPE: PRT
<213> ORGANISM: Artificial Sequence
<220> FEATURE:
<223> OTHER INFORMATION: Synthetic Construct

<400> SEQUENCE: 399

Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Ala Phe Thr Ser Gln
                 20                  25                  30

Asn Ile Tyr Trp Val Arg Gln Ala Pro Gly Gln Gly Leu Glu Trp Ile
             35                  40                  45

Gly Tyr Ile Glu Pro Tyr Asn Val Val Pro Met Tyr Asn Pro Lys Phe
 50                  55                  60

Lys Gly Arg Val Thr Ile Thr Arg Asp Lys Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Ser Gly Ser Ser Asn Phe Asp Tyr Trp Gly Gln Gly Thr Leu
            100                 105                 110

Val Thr Val Ser Ser
            115
```

<210> SEQ ID NO 400
<211> LENGTH: 108
<212> TYPE: PRT
<213> ORGANISM: Artificial Sequence
<220> FEATURE:
<223> OTHER INFORMATION: Synthetic Construct

<400> SEQUENCE: 400

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Ile Ser Ser His
            20                  25                  30

Tyr Leu His Trp Tyr Gln Gln Lys Pro Gly Lys Ser Pro Lys Leu Leu
        35                  40                  45

Ile Tyr Arg Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Ser Ser Leu Pro
                85                  90                  95

Leu Thr Phe Gly Gln Gly Thr Lys Val Glu Ile Lys
            100                 105

<210> SEQ ID NO 401
<211> LENGTH: 117
<212> TYPE: PRT
<213> ORGANISM: Artificial Sequence
<220> FEATURE:
<223> OTHER INFORMATION: Synthetic Construct

<400> SEQUENCE: 401

Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
            20                  25                  30

Asn Ile Tyr Trp Val Arg Gln Ala Pro Gly Gln Gly Leu Glu Trp Ile
        35                  40                  45

Gly Tyr Ile Glu Pro Tyr Asn Val Val Pro Ala Tyr Asn Pro Lys Phe
    50                  55                  60

Lys Gly Arg Ala Thr Leu Thr Val Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Ser Ser Asn Phe Asp Tyr Trp Gly Gln Gly Thr Leu
            100                 105                 110

Val Thr Val Ser Ser
        115

<210> SEQ ID NO 402
<211> LENGTH: 108
<212> TYPE: PRT
<213> ORGANISM: Artificial Sequence
<220> FEATURE:
<223> OTHER INFORMATION: Synthetic Construct

<400> SEQUENCE: 402

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Ile Ser Ser His
            20                  25                  30

```
Tyr Leu His Trp Tyr Gln Gln Lys Pro Gly Lys Ser Pro Lys Leu Leu
        35                  40                  45

Ile Tyr Arg Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Ser Ser Leu Pro
                85                  90                  95

Leu Thr Phe Gly Gln Gly Thr Lys Val Glu Ile Lys
            100                 105

<210> SEQ ID NO 403
<211> LENGTH: 117
<212> TYPE: PRT
<213> ORGANISM: Artificial Sequence
<220> FEATURE:
<223> OTHER INFORMATION: Synthetic Construct

<400> SEQUENCE: 403

Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
                20                  25                  30

Asn Ile Tyr Trp Val Arg Gln Ala Pro Gly Gln Gly Leu Glu Trp Ile
            35                  40                  45

Gly Tyr Ile Glu Pro Tyr Asn Val Val Pro Leu Tyr Asn Pro Lys Phe
        50                  55                  60

Lys Gly Arg Ala Thr Leu Thr Val Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Ser Ser Asn Phe Asp Tyr Trp Gly Gln Gly Thr Leu
            100                 105                 110

Val Thr Val Ser Ser
        115

<210> SEQ ID NO 404
<211> LENGTH: 108
<212> TYPE: PRT
<213> ORGANISM: Artificial Sequence
<220> FEATURE:
<223> OTHER INFORMATION: Synthetic Construct

<400> SEQUENCE: 404

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Ile Ser Ser His
                20                  25                  30

Tyr Leu His Trp Tyr Gln Gln Lys Pro Gly Lys Ser Pro Lys Leu Leu
            35                  40                  45

Ile Tyr Arg Thr Ser Asn Leu Ala Ser Gly Val Pro Ser Arg Phe Ser
        50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Ser Ser Leu Pro
                85                  90                  95
```

Leu Thr Phe Gly Gln Gly Thr Lys Val Glu Ile Lys
            100                 105

<210> SEQ ID NO 405
<211> LENGTH: 117
<212> TYPE: PRT
<213> ORGANISM: Artificial Sequence
<220> FEATURE:
<223> OTHER INFORMATION: Synthetic Construct

<400> SEQUENCE: 405

Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
            20                  25                  30

Asn Ile Tyr Trp Val Arg Gln Ala Pro Gly Gln Gly Leu Glu Trp Ile
        35                  40                  45

Gly Tyr Ile Glu Pro Tyr Asn Val Val Pro Val Tyr Asn Pro Lys Phe
    50                  55                  60

Lys Gly Arg Ala Thr Leu Thr Val Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Ser Ser Asn Phe Asp Tyr Trp Gly Gln Gly Thr Leu
            100                 105                 110

Val Thr Val Ser Ser
        115

<210> SEQ ID NO 406
<211> LENGTH: 108
<212> TYPE: PRT
<213> ORGANISM: Artificial Sequence
<220> FEATURE:
<223> OTHER INFORMATION: Synthetic Construct

<400> SEQUENCE: 406

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Ile Ser Ser His
            20                  25                  30

Tyr Leu His Trp Tyr Gln Gln Lys Pro Gly Lys Ser Pro Lys Leu Leu
        35                  40                  45

Ile Tyr Arg Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Ser Ser Leu Pro
                85                  90                  95

Leu Thr Phe Gly Gln Gly Thr Lys Val Glu Ile Lys
            100                 105

<210> SEQ ID NO 407
<211> LENGTH: 117
<212> TYPE: PRT
<213> ORGANISM: Artificial Sequence
<220> FEATURE:
<223> OTHER INFORMATION: Synthetic Construct

<400> SEQUENCE: 407

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Ala Ile Asn Pro Gly Ser Gly Ala Thr Asn Tyr Asn Glu Lys Phe
    50                  55                  60

Lys Asp Lys Ala Arg Leu Thr Ala Asp Lys Ser Ser Asn Thr Ala Tyr
65                  70                  75                  80

Leu Gln Phe Ser Ser Leu Thr Ser Asp Asp Ser Ala Val Tyr Phe Cys
                85                  90                  95

Ala Arg Phe Leu Gly Asn Tyr Phe Asp Asn Trp Gly Gln Gly Ala Thr
            100                 105                 110

Leu Thr Val Ser Ser
        115

<210> SEQ ID NO 408
<211> LENGTH: 107
<212> TYPE: PRT
<213> ORGANISM: Artificial Sequence
<220> FEATURE:
<223> OTHER INFORMATION: Synthetic Construct

<400> SEQUENCE: 408

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Ser Tyr
            20                  25                  30

Leu Ala Trp Tyr Gln Gln Lys Gln Gly Lys Ser Pro Gln Leu Leu Val
        35                  40                  45

Tyr Tyr Ala Glu Thr Leu Ala Asp Gly Val Pro Ser Arg Phe Ser Gly
    50                  55                  60

Arg Gly Ser Gly Thr Gln Tyr Ser Leu Lys Ile Asn Ser Leu Gln Pro
65                  70                  75                  80

Glu Asp Phe Gly Ser Tyr Phe Cys Gln Gln Phe Trp Thr Thr Pro Tyr
                85                  90                  95

Thr Phe Gly Gly Gly Thr Lys Val Glu Ile Lys
            100                 105

<210> SEQ ID NO 409
<211> LENGTH: 117
<212> TYPE: PRT
<213> ORGANISM: Artificial Sequence
<220> FEATURE:
<223> OTHER INFORMATION: Synthetic Construct

<400> SEQUENCE: 409

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Ala Ile Asn Pro Gly Ser Gly Ala Thr Asn Tyr Asn Glu Lys Phe
    50                  55                  60

```
Lys Asp Arg Val Thr Ile Thr Ala Asp Thr Ser Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Phe Leu Gly Asn Tyr Phe Asp Asn Trp Gly Gln Gly Thr Leu
            100                 105                 110

Val Thr Val Ser Ser
        115
```

<210> SEQ ID NO 410
<211> LENGTH: 107
<212> TYPE: PRT
<213> ORGANISM: Artificial Sequence
<220> FEATURE:
<223> OTHER INFORMATION: Synthetic Construct

<400> SEQUENCE: 410

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gly Asn Ile His Ser Tyr
             20                  25                  30

Leu Ala Trp Tyr Gln Gln Lys Pro Gly Lys Ala Pro Lys Leu Leu Ile
         35                  40                  45

Tyr Tyr Ala Glu Thr Leu Ala Asp Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Trp Thr Thr Pro Tyr
                 85                  90                  95

Thr Phe Gly Gln Gly Thr Lys Val Glu Ile Lys
            100                 105
```

<210> SEQ ID NO 411
<211> LENGTH: 117
<212> TYPE: PRT
<213> ORGANISM: Artificial Sequence
<220> FEATURE:
<223> OTHER INFORMATION: Synthetic Construct

<400> SEQUENCE: 411

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Asn Tyr
             20                  25                  30

Leu Ile Glu Trp Val Arg Gln Ala Pro Gly Gln Gly Leu Glu Trp Ile
         35                  40                  45

Gly Ala Ile Asn Pro Gly Ser Gly Ala Thr Asn Tyr Asn Glu Lys Phe
 50                  55                  60

Lys Asp Arg Ala Thr Leu Thr Ala Asp Lys Ser Thr Asn Thr Ala Tyr
 65                  70                  75                  80

Leu Glu Leu Ser Ser Leu Arg Ser Glu Asp Thr Ala Val Tyr Phe Cys
                 85                  90                  95

Ala Arg Phe Leu Gly Asn Tyr Phe Asp Asn Trp Gly Gln Gly Thr Leu
            100                 105                 110

Val Thr Val Ser Ser
        115
```

```
<210> SEQ ID NO 412
<211> LENGTH: 107
<212> TYPE: PRT
<213> ORGANISM: Artificial Sequence
<220> FEATURE:
<223> OTHER INFORMATION: Synthetic Construct

<400> SEQUENCE: 412

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Ser Tyr
            20                  25                  30

Leu Ala Trp Tyr Gln Gln Lys Pro Gly Lys Ala Pro Lys Leu Leu Ile
        35                  40                  45

Tyr Tyr Ala Glu Thr Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Trp Thr Thr Pro Tyr
                85                  90                  95

Thr Phe Gly Gln Gly Thr Lys Val Glu Ile Lys
            100                 105

<210> SEQ ID NO 413
<211> LENGTH: 117
<212> TYPE: PRT
<213> ORGANISM: Artificial Sequence
<220> FEATURE:
<223> OTHER INFORMATION: Synthetic Construct

<400> SEQUENCE: 413

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Ala Ile Asn Pro Gly Ser Gly Ala Thr Asn Tyr Asn Glu Lys Phe
    50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Phe Leu Gly Asn Tyr Phe Asp Asn Trp Gly Gln Gly Thr Leu
            100                 105                 110

Val Thr Val Ser Ser
        115

<210> SEQ ID NO 414
<211> LENGTH: 107
<212> TYPE: PRT
<213> ORGANISM: Artificial Sequence
<220> FEATURE:
<223> OTHER INFORMATION: Synthetic Construct

<400> SEQUENCE: 414

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Ser Tyr
            20                  25                  30
```

Leu Ala Trp Tyr Gln Gln Lys Pro Gly Lys Ser Pro Lys Leu Leu Val
            35                  40                  45

Tyr Tyr Ala Glu Thr Leu Ala Asp Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Phe Trp Thr Thr Pro Tyr
                85                  90                  95

Thr Phe Gly Gln Gly Thr Lys Val Glu Ile Lys
                100                 105

<210> SEQ ID NO 415
<211> LENGTH: 117
<212> TYPE: PRT
<213> ORGANISM: Artificial Sequence
<220> FEATURE:
<223> OTHER INFORMATION: Synthetic Construct

<400> SEQUENCE: 415

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Ile
            35                  40                  45

Gly Ala Ile Asn Pro Gly Ser Gly Ala Thr Asn Tyr Asn Glu Lys Phe
        50                  55                  60

Lys Asp Arg Ala Thr Leu Thr Ala Asp Lys Ser Thr Asn Thr Ala Tyr
65                  70                  75                  80

Leu Glu Leu Ser Ser Leu Arg Ser Glu Asp Thr Ala Val Tyr Phe Cys
                85                  90                  95

Ala Arg Phe Leu Gly Asn Tyr Phe Asp Asn Trp Gly Gln Gly Thr Leu
                100                 105                 110

Val Thr Val Ser Ser
            115

<210> SEQ ID NO 416
<211> LENGTH: 107
<212> TYPE: PRT
<213> ORGANISM: Artificial Sequence
<220> FEATURE:
<223> OTHER INFORMATION: Synthetic Construct

<400> SEQUENCE: 416

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Ser Tyr
                20                  25                  30

Leu Ala Trp Tyr Gln Gln Lys Pro Gly Lys Ser Pro Lys Leu Leu Val
            35                  40                  45

Tyr Tyr Ala Glu Thr Leu Ala Asp Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Phe Trp Thr Thr Pro Tyr
                85                  90                  95

```
Thr Phe Gly Gln Gly Thr Lys Val Glu Ile Lys
            100                 105
```

<210> SEQ ID NO 417
<211> LENGTH: 117
<212> TYPE: PRT
<213> ORGANISM: Artificial Sequence
<220> FEATURE:
<223> OTHER INFORMATION: Synthetic Construct

<400> SEQUENCE: 417

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Ala Ile Asn Pro Gly Ser Gly Ala Thr Asn Tyr Asn Glu Lys Phe
    50                  55                  60

Lys Asp Arg Ala Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Phe Cys
                85                  90                  95

Ala Arg Phe Leu Gly Asn Tyr Phe Asp Asn Trp Gly Gln Gly Thr Leu
            100                 105                 110

Val Thr Val Ser Ser
        115
```

<210> SEQ ID NO 418
<211> LENGTH: 107
<212> TYPE: PRT
<213> ORGANISM: Artificial Sequence
<220> FEATURE:
<223> OTHER INFORMATION: Synthetic Construct

<400> SEQUENCE: 418

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Ser Tyr
            20                  25                  30

Leu Ala Trp Tyr Gln Gln Lys Pro Gly Lys Ala Pro Lys Leu Leu Ile
        35                  40                  45

Tyr Tyr Ala Glu Thr Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Trp Thr Thr Pro Tyr
                85                  90                  95

Thr Phe Gly Gln Gly Thr Lys Val Glu Ile Lys
            100                 105
```

<210> SEQ ID NO 419
<211> LENGTH: 117
<212> TYPE: PRT
<213> ORGANISM: Artificial Sequence
<220> FEATURE:
<223> OTHER INFORMATION: Synthetic Construct

<400> SEQUENCE: 419

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Ala Ile Asn Pro Gly Ser Gly Ala Thr Asn Tyr Asn Glu Lys Phe
    50                  55                  60

Lys Asp Arg Ala Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Phe Cys
                85                  90                  95

Ala Arg Phe Leu Gly Asn Tyr Phe Asp Asn Trp Gly Gln Gly Thr Leu
            100                 105                 110

Val Thr Val Ser Ser
        115

<210> SEQ ID NO 420
<211> LENGTH: 107
<212> TYPE: PRT
<213> ORGANISM: Artificial Sequence
<220> FEATURE:
<223> OTHER INFORMATION: Synthetic Construct

<400> SEQUENCE: 420

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Ser Tyr
            20                  25                  30

Leu Ala Trp Tyr Gln Gln Lys Pro Gly Lys Ser Pro Lys Leu Leu Val
        35                  40                  45

Tyr Tyr Ala Glu Thr Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Phe Trp Thr Thr Pro Tyr
                85                  90                  95

Thr Phe Gly Gln Gly Thr Lys Val Glu Ile Lys
            100                 105

<210> SEQ ID NO 421
<211> LENGTH: 118
<212> TYPE: PRT
<213> ORGANISM: Artificial Sequence
<220> FEATURE:
<223> OTHER INFORMATION: Synthetic Construct

<400> SEQUENCE: 421

Glu Ile Gln Leu Gln Gln Ser Gly Pro Glu Leu Val Lys Pro Gly Ala
1               5                   10                  15

Ser Val Arg Val Ser Cys Lys Pro Ser Gly Tyr Ala Phe Thr Ser Asn
            20                  25                  30

Asn Ile Tyr Trp Val Lys Gln Ser Arg Arg Lys Ser Leu Glu Trp Ile
        35                  40                  45

Gly Tyr Ile Asp Pro Tyr Ile Gly Arg Ile Ile Tyr Asn Gln Gln Phe
    50                  55                  60

```
Lys Asp Lys Ala Thr Leu Thr Val Asp Lys Ser Ser Thr Ala Tyr
 65                  70                  75                  80

Met His Leu Asn Ser Leu Thr Ser Glu Asp Ser Ala Val Tyr Tyr Cys
                 85                  90                  95

Ser Arg Ser Gly Glu Arg Ser Asn Phe Asp Tyr Trp Gly Gln Gly Thr
                100                 105                 110

Thr Leu Thr Val Ser Ser
            115
```

<210> SEQ ID NO 422
<211> LENGTH: 108
<212> TYPE: PRT
<213> ORGANISM: Artificial Sequence
<220> FEATURE:
<223> OTHER INFORMATION: Synthetic Construct

<400> SEQUENCE: 422

```
Glu Ile Val Leu Thr Gln Ser Pro Thr Ala Met Ala Ala Ser Pro Gly
  1               5                  10                  15

Glu Lys Ile Thr Ile Thr Cys Ser Ala Ser Ser Ser Ile Ser Ser Asn
             20                  25                  30

Tyr Leu His Trp Tyr Gln Gln Lys Pro Gly Phe Ser Pro Lys Leu Leu
             35                  40                  45

Ile Tyr Arg Thr Ser Asn Leu Ala Ser Gly Val Pro Ala Arg Phe Ser
 50                  55                  60

Gly Ser Gly Ser Gly Thr Ser Tyr Ser Leu Thr Ile Gly Pro Met Glu
 65                  70                  75                  80

Ala Glu Asp Val Ala Thr Tyr Tyr Cys Gln Gln Gly Gly Ser Leu Pro
                 85                  90                  95

Leu Thr Phe Gly Ala Gly Thr Lys Val Glu Ile Lys
            100                 105
```

<210> SEQ ID NO 423
<211> LENGTH: 118
<212> TYPE: PRT
<213> ORGANISM: Artificial Sequence
<220> FEATURE:
<223> OTHER INFORMATION: Synthetic Construct

<400> SEQUENCE: 423

```
Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Ala Phe Thr Ser Asn
             20                  25                  30

Asn Ile Tyr Trp Val Arg Gln Ala Pro Gly Gln Gly Leu Glu Trp Ile
             35                  40                  45

Gly Tyr Ile Asp Pro Tyr Ile Gly Arg Ile Ile Tyr Asn Gln Gln Phe
 50                  55                  60

Lys Asp Arg Val Thr Ile Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ser Arg Ser Gly Glu Arg Ser Asn Phe Asp Tyr Trp Gly Gln Gly Thr
                100                 105                 110

Leu Val Thr Val Ser Ser
            115
```

<210> SEQ ID NO 424
<211> LENGTH: 108
<212> TYPE: PRT
<213> ORGANISM: Artificial Sequence
<220> FEATURE:
<223> OTHER INFORMATION: Synthetic Construct

<400> SEQUENCE: 424

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Ser Ser Asn
            20                  25                  30

Tyr Leu His Trp Tyr Gln Gln Lys Pro Gly Gln Ala Pro Arg Leu Leu
        35                  40                  45

Ile Tyr Arg Thr Ser Asn Leu Ala Ser Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Gly Ser Leu Pro
                85                  90                  95

Leu Thr Phe Gly Gln Gly Thr Lys Val Glu Ile Lys
            100                 105
```

<210> SEQ ID NO 425
<211> LENGTH: 118
<212> TYPE: PRT
<213> ORGANISM: Artificial Sequence
<220> FEATURE:
<223> OTHER INFORMATION: Synthetic Construct

<400> SEQUENCE: 425

```
Glu Ile Gln Leu Val Gln Ser Gly Ala Glu Val Lys Lys Pro Gly Ala
1               5                   10                  15

Ser Val Lys Val Ser Cys Lys Pro Ser Gly Tyr Ala Phe Thr Ser Asn
            20                  25                  30

Asn Ile Tyr Trp Val Arg Gln Ala Pro Gly Gln Gly Leu Glu Trp Ile
        35                  40                  45

Gly Tyr Ile Asp Pro Tyr Ile Gly Arg Ile Ile Tyr Asn Gln Gln Phe
    50                  55                  60

Lys Asp Arg Ala Thr Leu Thr Val Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ser Arg Ser Gly Glu Arg Ser Asn Phe Asp Tyr Trp Gly Gln Gly Thr
            100                 105                 110

Leu Val Thr Val Ser Ser
        115
```

<210> SEQ ID NO 426
<211> LENGTH: 108
<212> TYPE: PRT
<213> ORGANISM: Artificial Sequence
<220> FEATURE:
<223> OTHER INFORMATION: Synthetic Construct

<400> SEQUENCE: 426

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Ser Ser Asn
            20                  25                  30
```

```
Tyr Leu His Trp Tyr Gln Gln Lys Pro Gly Gln Ala Pro Arg Leu Leu
            35                  40                  45

Ile Tyr Arg Thr Ser Asn Leu Ala Ser Gly Ile Pro Ala Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Gly Gly Ser Leu Pro
                 85                  90                  95

Leu Thr Phe Gly Gln Gly Thr Lys Val Glu Ile Lys
            100                 105

<210> SEQ ID NO 427
<211> LENGTH: 118
<212> TYPE: PRT
<213> ORGANISM: Artificial Sequence
<220> FEATURE:
<223> OTHER INFORMATION: Synthetic Construct

<400> SEQUENCE: 427

Glu Val Gln Leu Val Gln Ser Gly Ala Glu Val Lys Lys Pro Gly Ala
 1               5                   10                  15

Ser Val Lys Val Ser Cys Lys Ala Ser Gly Tyr Ala Phe Thr Ser Asn
                 20                  25                  30

Asn Ile Tyr Trp Val Arg Gln Ala Pro Gly Gln Gly Leu Glu Trp Ile
            35                  40                  45

Gly Tyr Ile Asp Pro Tyr Ile Gly Arg Ile Ile Tyr Asn Gln Gln Phe
 50                  55                  60

Lys Asp Arg Val Thr Ile Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ser Arg Ser Gly Glu Arg Ser Asn Phe Asp Tyr Trp Gly Gln Gly Thr
            100                 105                 110

Leu Val Thr Val Ser Ser
        115

<210> SEQ ID NO 428
<211> LENGTH: 108
<212> TYPE: PRT
<213> ORGANISM: Artificial Sequence
<220> FEATURE:
<223> OTHER INFORMATION: Synthetic Construct

<400> SEQUENCE: 428

Glu Ile Val Leu Thr Gln Ser Pro Ala Thr Leu Ser Leu Ser Pro Gly
 1               5                   10                  15

Glu Arg Ala Thr Leu Ser Cys Ser Ala Ser Ser Ile Ser Ser Asn
                 20                  25                  30

Tyr Leu His Trp Tyr Gln Gln Lys Pro Gly Gln Ser Pro Arg Leu Leu
            35                  40                  45

Ile Tyr Arg Thr Ser Asn Leu Ala Ser Gly Val Pro Ala Arg Phe Ser
 50                  55                  60

Gly Ser Gly Ser Gly Thr Asp Tyr Thr Leu Thr Ile Ser Ser Leu Glu
 65                  70                  75                  80

Pro Glu Asp Phe Ala Val Tyr Tyr Cys Gln Gln Gly Gly Ser Leu Pro
                 85                  90                  95
```

Leu Thr Phe Gly Gln Gly Thr Lys Val Glu Ile Lys
            100                 105

<210> SEQ ID NO 429
<211> LENGTH: 118
<212> TYPE: PRT
<213> ORGANISM: Artificial Sequence
<220> FEATURE:
<223> OTHER INFORMATION: Synthetic Construct

<400> SEQUENCE: 429

Glu Ile Gln Leu Val Gln Ser Gly Ala Glu Val Lys Lys Pro Gly Ala
1               5                   10                  15

Ser Val Lys Val Ser Cys Lys Pro Ser Gly Tyr Ala Phe Thr Ser Asn
            20                  25                  30

Asn Ile Tyr Trp Val Arg Gln Ala Pro Gly Gln Gly Leu Glu Trp Ile
        35                  40                  45

Gly Tyr Ile Asp Pro Tyr Ile Gly Arg Ile Ile Tyr Asn Gln Gln Phe
    50                  55                  60

Lys Asp Arg Ala Thr Leu Thr Val Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ser Arg Ser Gly Glu Arg Ser Asn Phe Asp Tyr Trp Gly Gln Gly Thr
            100                 105                 110

Leu Val Thr Val Ser Ser
        115

<210> SEQ ID NO 430
<211> LENGTH: 108
<212> TYPE: PRT
<213> ORGANISM: Artificial Sequence
<220> FEATURE:
<223> OTHER INFORMATION: Synthetic Construct

<400> SEQUENCE: 430

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Ser Ser Asn
            20                  25                  30

Tyr Leu His Trp Tyr Gln Gln Lys Pro Gly Gln Ser Pro Arg Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Asp Tyr Thr Leu Thr Ile Ser Ser Leu Glu
65                  70                  75                  80

Pro Glu Asp Phe Ala Val Tyr Tyr Cys Gln Gln Gly Gly Ser Leu Pro
                85                  90                  95

Leu Thr Phe Gly Gln Gly Thr Lys Val Glu Ile Lys
            100                 105

<210> SEQ ID NO 431
<211> LENGTH: 118
<212> TYPE: PRT
<213> ORGANISM: Artificial Sequence
<220> FEATURE:
<223> OTHER INFORMATION: Synthetic Construct

<400> SEQUENCE: 431

Glu Ile Gln Leu Val Gln Ser Gly Ala Glu Val Lys Lys Pro Gly Ser
1               5                   10                  15

Ser Val Lys Val Ser Cys Lys Pro Ser Gly Tyr Ala Phe Thr Ser Asn
            20                  25                  30

Asn Ile Tyr Trp Val Arg Gln Ala Pro Gly Gln Gly Leu Glu Trp Ile
        35                  40                  45

Gly Tyr Ile Asp Pro Tyr Ile Gly Arg Ile Ile Tyr Asn Gln Gln Phe
50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Ser Gly Glu Arg Ser Asn Phe Asp Tyr Trp Gly Gln Gly Thr
            100                 105                 110

Leu Val Thr Val Ser Ser
            115

<210> SEQ ID NO 432
<211> LENGTH: 108
<212> TYPE: PRT
<213> ORGANISM: Artificial Sequence
<220> FEATURE:
<223> OTHER INFORMATION: Synthetic Construct

<400> SEQUENCE: 432

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Ser Ser Asn
            20                  25                  30

Tyr Leu His Trp Tyr Gln Gln Lys Pro Gly Gln Ala Pro Arg Leu Leu
        35                  40                  45

Ile Tyr Arg Thr Ser Asn Leu Ala Ser Gly Ile Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Gly Gly Ser Leu Pro
                85                  90                  95

Leu Thr Phe Gly Gln Gly Thr Lys Val Glu Ile Lys
            100                 105

<210> SEQ ID NO 433
<211> LENGTH: 118
<212> TYPE: PRT
<213> ORGANISM: Artificial Sequence
<220> FEATURE:
<223> OTHER INFORMATION: Synthetic Construct

<400> SEQUENCE: 433

Glu Ile Gln Leu Val Gln Ser Gly Ala Glu Val Lys Lys Pro Gly Ser
1               5                   10                  15

Ser Val Lys Val Ser Cys Lys Pro Ser Gly Tyr Ala Phe Thr Ser Asn
            20                  25                  30

Asn Ile Tyr Trp Val Arg Gln Ala Pro Gly Gln Gly Leu Glu Trp Ile
        35                  40                  45

Gly Tyr Ile Asp Pro Tyr Ile Gly Arg Ile Ile Tyr Asn Gln Gln Phe
50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Ser Gly Glu Arg Ser Asn Phe Asp Tyr Trp Gly Gln Gly Thr
            100                 105                 110

Leu Val Thr Val Ser Ser
        115

<210> SEQ ID NO 434
<211> LENGTH: 108
<212> TYPE: PRT
<213> ORGANISM: Artificial Sequence
<220> FEATURE:
<223> OTHER INFORMATION: Synthetic Construct

<400> SEQUENCE: 434

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Ser Ser Asn
            20                  25                  30

Tyr Leu His Trp Tyr Gln Gln Lys Pro Gly Gln Ser Pro Arg Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Asp Tyr Thr Leu Thr Ile Ser Ser Leu Glu
65                  70                  75                  80

Pro Glu Asp Phe Ala Val Tyr Tyr Cys Gln Gln Gly Gly Ser Leu Pro
                85                  90                  95

Leu Thr Phe Gly Gln Gly Thr Lys Val Glu Ile Lys
            100                 105

<210> SEQ ID NO 435
<211> LENGTH: 122
<212> TYPE: PRT
<213> ORGANISM: Artificial Sequence
<220> FEATURE:
<223> OTHER INFORMATION: Synthetic Construct

<400> SEQUENCE: 435

Gln Gly Gln Met Gln Gln Ser Gly Ala Glu Leu Val Lys Pro Gly Ala
1               5                   10                  15

Ser Val Lys Leu Ser Cys Lys Thr Ser Gly Phe Thr Phe Ser Asp Asn
            20                  25                  30

Tyr Ile Ser Trp Leu Lys Gln Lys Pro Gly Gln Ser Leu Glu Trp Ile
        35                  40                  45

Ala Trp Ile Tyr Ala Gly Thr Gly Gly Ser Ser Tyr Asn Gln Lys Phe
    50                  55                  60

Arg Asp Lys Ala Gln Leu Thr Val Asp Thr Ser Arg Thr Ala Tyr
65                  70                  75                  80

Met Gln Leu Ser Ser Leu Thr Thr Glu Asp Ser Ala Ile Tyr Tyr Cys
                85                  90                  95

Ala Arg His Asp Tyr Tyr Gly Thr Ser Gly Ala Trp Phe Ala Tyr Trp
            100                 105                 110

Gly Arg Gly Thr Leu Val Thr Val Ser Ala
        115                 120

<210> SEQ ID NO 436
<211> LENGTH: 112
<212> TYPE: PRT
<213> ORGANISM: Artificial Sequence
<220> FEATURE:
<223> OTHER INFORMATION: Synthetic Construct

<400> SEQUENCE: 436

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln His Ile Val His Ser
            20                  25                  30

Asn Glu Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Val Glu Ile Lys
            100                 105                 110
```

<210> SEQ ID NO 437
<211> LENGTH: 116
<212> TYPE: PRT
<213> ORGANISM: Artificial Sequence
<220> FEATURE:
<223> OTHER INFORMATION: Synthetic Construct

<400> SEQUENCE: 437

```
Val Gln Leu Gln Glu Ser Gly Pro Gly Leu Val Lys Pro Ser Gln Ser
1               5                   10                  15

Leu Ser Leu Thr Cys Asn Val Thr Gly Tyr Ser Ile Thr Gly Asp Tyr
            20                  25                  30

Ala Trp Asn Trp Ile Arg Gln Phe Pro Gly Asn Lys Leu Glu Trp Ile
        35                  40                  45

Gly Tyr Ile Gly Tyr Thr Gly Ser Thr Thr Tyr Asn Pro Ser Leu Lys
    50                  55                  60

Ser Arg Val Ser Ile Thr Arg Asp Thr Ser Lys Asn Gln Phe Phe Leu
65                  70                  75                  80

Gln Leu Asn Ser Val Thr Pro Glu Asp Thr Ala Thr Tyr Tyr Cys Ala
                85                  90                  95

Arg Trp Arg Asn Trp Ala Met Asp Tyr Trp Gly Leu Gly Thr Ser Val
            100                 105                 110

Thr Val Ser Ser
        115
```

<210> SEQ ID NO 438
<211> LENGTH: 107
<212> TYPE: PRT
<213> ORGANISM: Artificial Sequence
<220> FEATURE:
<223> OTHER INFORMATION: Synthetic Construct

<400> SEQUENCE: 438

```
Asp Ile Gln Met Thr Gln Thr Pro Ser Ser Leu Ser Ala Ser Leu Gly
1               5                   10                  15

Asp Arg Val Thr Ile Ser Cys Arg Ala Asn Gln Asp Ile Ser His Tyr
            20                  25                  30
```

Leu Asn Trp Tyr Gln Gln Lys Pro Asp Gly Ala Val Lys Leu Leu Ile
            35                  40                  45

Tyr Tyr Thr Ser Arg Ile His Ser Gly Val Pro Ser Arg Phe Ser Gly
    50                  55                  60

Ser Gly Ser Gly Thr Asp Tyr Ser Leu Thr Ile Ala Asn Leu Glu Gln
65                  70                  75                  80

Glu Asp Val Ala Thr Tyr Phe Cys Gln Gln Gly Asn Thr Pro Pro Thr
                85                  90                  95

Thr Phe Gly Gly Gly Thr Lys Val Glu Ile Lys
            100                 105

<210> SEQ ID NO 439
<211> LENGTH: 117
<212> TYPE: PRT
<213> ORGANISM: Artificial Sequence
<220> FEATURE:
<223> OTHER INFORMATION: Synthetic Construct

<400> SEQUENCE: 439

Asp Val Gln Leu Gln Glu Ser Gly Pro Gly Leu Val Lys Pro Ser Gln
1               5                   10                  15

Pro Leu Ser Leu Thr Cys Thr Val Thr Gly Tyr Ser Ile Thr Ser Asn
                20                  25                  30

Tyr Ala Trp Asn Trp Ile Arg Gln Phe Pro Gly Asp Lys Leu Glu Trp
            35                  40                  45

Met Gly Tyr Ile Ser Ser Ser Gly Ile Thr Lys Ser Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Leu Thr Thr Glu Asp Thr Ala Thr Tyr Tyr Cys
                85                  90                  95

Ser Arg Trp Ser Asn Trp Ser Phe Asp Val Trp Gly Ala Gly Thr Thr
            100                 105                 110

Val Thr Val Ser Ser
        115

<210> SEQ ID NO 440
<211> LENGTH: 107
<212> TYPE: PRT
<213> ORGANISM: Artificial Sequence
<220> FEATURE:
<223> OTHER INFORMATION: Synthetic Construct

<400> SEQUENCE: 440

Asp Ile Gln Met Thr Gln Thr Pro Ser Ser Leu Ser Val Ser Leu Gly
1               5                   10                  15

Asp Arg Val Thr Ile Asn Cys Arg Ala Ser Gln Asp Ile His Asn Tyr
                20                  25                  30

Phe Asn Trp Tyr Gln Gln Lys Pro Asp Gly Thr Ile Lys Leu Leu Ile
            35                  40                  45

Tyr Tyr Thr Ser Arg Phe His Ser Gly Val Pro Ser Arg Phe Ser Gly
            50                  55                  60

Ser Gly Ser Gly Thr Asp Tyr Ser Leu Thr Ile Ser Asn Leu Glu Glu
65                  70                  75                  80

Glu Asp Ile Ala Thr Tyr Phe Cys Gln Gln Gly Asn Ser Leu Pro Pro
                85                  90                  95

Thr Phe Gly Gly Gly Thr Lys Leu Glu Ile Lys
            100                 105

<210> SEQ ID NO 441
<211> LENGTH: 94
<212> TYPE: PRT
<213> ORGANISM: Homo sapiens

<400> SEQUENCE: 441

Arg Val Pro Pro Met Val Asn Val Thr Arg Ser Glu Ala Ser Glu Gly
1               5                   10                  15

Asn Ile Thr Val Thr Cys Arg Ala Ser Ser Phe Tyr Pro Arg Asn Ile
            20                  25                  30

Thr Leu Thr Trp Arg Gln Asp Gly Val Ser Leu Ser His Asp Thr Gln
        35                  40                  45

Gln Trp Gly Asp Val Leu Pro Asp Gly Asn Gly Thr Tyr Gln Thr Trp
    50                  55                  60

Val Ala Thr Arg Ile Cys Gln Gly Glu Glu Gln Arg Phe Thr Cys Tyr
65                  70                  75                  80

Met Glu His Ser Gly Asn His Ser Thr His Pro Val Pro Ser
                85                  90

<210> SEQ ID NO 442
<211> LENGTH: 94
<212> TYPE: PRT
<213> ORGANISM: Homo sapiens

<400> SEQUENCE: 442

Thr Val Pro Pro Met Val Asn Val Thr Cys Ser Glu Val Ser Glu Gly
1               5                   10                  15

Asn Ile Thr Val Thr Cys Arg Ala Ser Ser Phe Tyr Pro Arg Asn Ile
            20                  25                  30

Thr Leu Thr Trp Arg Gln Asp Gly Val Ser Leu Ser His Asn Thr Gln
        35                  40                  45

Gln Trp Gly Asp Val Leu Pro Asp Gly Asn Gly Thr Tyr Gln Thr Trp
    50                  55                  60

Val Ala Thr Arg Ile Arg Gln Gly Glu Glu Gln Arg Phe Thr Cys Tyr
65                  70                  75                  80

Met Glu His Ser Gly Asn His Gly Thr His Pro Val Pro Ser
                85                  90

<210> SEQ ID NO 443
<211> LENGTH: 94
<212> TYPE: PRT
<213> ORGANISM: Homo sapiens

<400> SEQUENCE: 443

Thr Val Pro Pro Met Val Asn Val Thr Arg Ser Glu Ala Ser Glu Gly
1               5                   10                  15

Asn Ile Thr Val Thr Cys Arg Ala Ser Ser Phe Tyr Pro Arg Asn Ile
            20                  25                  30

Ile Leu Thr Trp Arg Gln Asp Gly Val Ser Leu Ser His Asp Thr Gln
        35                  40                  45

Gln Trp Gly Asp Val Leu Pro Asp Gly Asn Gly Thr Tyr Gln Thr Trp
    50                  55                  60

Val Ala Thr Arg Ile Cys Arg Gly Glu Glu Gln Arg Phe Thr Cys Tyr
65                  70                  75                  80

```
Met Glu His Ser Gly Asn His Ser Thr His Pro Val Pro Ser
                85                  90
```

<210> SEQ ID NO 444
<211> LENGTH: 4
<212> TYPE: PRT
<213> ORGANISM: Artificial Sequence
<220> FEATURE:
<223> OTHER INFORMATION: Synthetic Construct

<400> SEQUENCE: 444

```
Gly Ser Asn Arg
1
```

<210> SEQ ID NO 445
<211> LENGTH: 10
<212> TYPE: PRT
<213> ORGANISM: Artificial Sequence
<220> FEATURE:
<223> OTHER INFORMATION: Synthetic Construct

<400> SEQUENCE: 445

```
Thr Val Pro Pro Met Val Asn Val Thr Arg
1               5                   10
```

<210> SEQ ID NO 446
<211> LENGTH: 13
<212> TYPE: PRT
<213> ORGANISM: Artificial Sequence
<220> FEATURE:
<223> OTHER INFORMATION: Synthetic Construct

<400> SEQUENCE: 446

```
Ser Asn Ala Ser Glu Gly Asn Ile Thr Val Thr Cys Arg
1               5                   10
```

<210> SEQ ID NO 447
<211> LENGTH: 13
<212> TYPE: PRT
<213> ORGANISM: Artificial Sequence
<220> FEATURE:
<223> OTHER INFORMATION: Synthetic Construct

<400> SEQUENCE: 447

```
Ser Glu Ala Ser Glu Gly Asn Ile Thr Val Thr Cys Arg
1               5                   10
```

<210> SEQ ID NO 448
<211> LENGTH: 7
<212> TYPE: PRT
<213> ORGANISM: Artificial Sequence
<220> FEATURE:
<223> OTHER INFORMATION: Synthetic Construct

<400> SEQUENCE: 448

```
Asn Ile Thr Leu Thr Trp Arg
1               5
```

<210> SEQ ID NO 449
<211> LENGTH: 31
<212> TYPE: PRT
<213> ORGANISM: Artificial Sequence
<220> FEATURE:
<223> OTHER INFORMATION: Synthetic Construct

<400> SEQUENCE: 449

Gln Asp Asn Val Ser Leu Ser His Asp Thr Gln Gln Trp Gly Asp Val
1               5                   10                  15

Leu Pro Asp Gly Asn Gly Thr Tyr Gln Thr Trp Val Ala Thr Arg
            20                  25                  30

<210> SEQ ID NO 450
<211> LENGTH: 31
<212> TYPE: PRT
<213> ORGANISM: Artificial Sequence
<220> FEATURE:
<223> OTHER INFORMATION: Synthetic Construct

<400> SEQUENCE: 450

Gln Asp Gly Val Ser Leu Ser Asn Asp Thr Gln Gln Trp Gly Asp Val
1               5                   10                  15

Leu Pro Asp Gly Asn Gly Thr Tyr Gln Thr Trp Val Ala Thr Arg
            20                  25                  30

<210> SEQ ID NO 451
<211> LENGTH: 31
<212> TYPE: PRT
<213> ORGANISM: Artificial Sequence
<220> FEATURE:
<223> OTHER INFORMATION: Synthetic Construct

<400> SEQUENCE: 451

Gln Asp Gly Val Ser Leu Ser His Asp Thr Gln Gln Trp Gly Asp Val
1               5                   10                  15

Leu Pro Asp Gly Asn Gly Thr Tyr Gln Thr Trp Val Ala Thr Arg
            20                  25                  30

<210> SEQ ID NO 452
<211> LENGTH: 27
<212> TYPE: PRT
<213> ORGANISM: Artificial Sequence
<220> FEATURE:
<223> OTHER INFORMATION: Synthetic Construct

<400> SEQUENCE: 452

Gly Glu Glu Gln Asn Phe Thr Cys Tyr Met Glu His Ser Gly Asn His
1               5                   10                  15

Ser Thr His Pro Val Pro Ser Gly Asn Ser Arg
            20                  25

<210> SEQ ID NO 453
<211> LENGTH: 25
<212> TYPE: PRT
<213> ORGANISM: Artificial Sequence
<220> FEATURE:
<223> OTHER INFORMATION: Synthetic Construct

<400> SEQUENCE: 453

Phe Thr Cys Tyr Met Glu His Ser Gly Asn His Ser Thr His Pro Val
1               5                   10                  15

Pro Ser Asn Gly Ser Gly Asn Ser Arg
            20                  25

<210> SEQ ID NO 454
<211> LENGTH: 22
<212> TYPE: PRT
<213> ORGANISM: Artificial Sequence
<220> FEATURE:

<223> OTHER INFORMATION: Synthetic Construct

<400> SEQUENCE: 454

Phe Thr Cys Tyr Met Glu His Ser Gly Asn His Ser Thr His Pro Val
1               5                   10                  15
Pro Ser Gly Asn Ser Arg
            20

<210> SEQ ID NO 455
<211> LENGTH: 8
<212> TYPE: PRT
<213> ORGANISM: Artificial Sequence
<220> FEATURE:
<223> OTHER INFORMATION: Synthetic Construct

<400> SEQUENCE: 455

Glu Asp Tyr Asn Ser Thr Leu Arg
1               5

<210> SEQ ID NO 456
<211> LENGTH: 109
<212> TYPE: PRT
<213> ORGANISM: Homo sapiens

<400> SEQUENCE: 456

Thr Val Pro Pro Met Val Asn Val Thr Arg Ser Glu Ala Ser Glu Gly
1               5                   10                  15
Asn Ile Thr Val Thr Cys Arg Ala Ser Gly Phe Tyr Pro Trp Asn Ile
            20                  25                  30
Thr Leu Ser Trp Arg Gln Asp Gly Val Ser Leu Ser His Asp Thr Gln
        35                  40                  45
Trp Gly Asp Val Leu Pro Asp Gly Asn Gly Thr Tyr Gln Thr Trp Val
    50                  55                  60
Ala Thr Arg Ile Cys Gln Gly Glu Gln Arg Phe Thr Cys Tyr Met
65                  70                  75                  80
Glu His Ser Gly Asn His Ser Thr His Pro Val Pro Ser Gly Lys Val
                85                  90                  95
Leu Val Leu Gln Ser His Trp Gln Thr Phe His Val Ser
            100                 105

<210> SEQ ID NO 457
<211> LENGTH: 94
<212> TYPE: PRT
<213> ORGANISM: Homo sapiens

<400> SEQUENCE: 457

Thr Val Pro Pro Met Val Asn Val Thr Arg Ser Glu Ala Ser Glu Gly
1               5                   10                  15
Asn Ile Thr Val Thr Cys Arg Ala Ser Ser Phe Tyr Pro Arg Asn Ile
            20                  25                  30
Ile Leu Thr Trp Arg Gln Asp Gly Val Ser Ile Ser His Asp Thr Gln
        35                  40                  45
Gln Trp Gly Asp Val Leu Pro Asp Gly Asn Gly Thr Tyr Gln Thr Trp
    50                  55                  60
Val Ala Thr Arg Ile Cys Arg Gly Glu Glu Gln Arg Phe Thr Cys Tyr
65                  70                  75                  80
Met Glu His Ser Gly Asn His Ser Thr His Pro Val Pro Ser
                85                  90

ANTI-MIC ANTIBODIES AND METHODS OF USE

CROSS REFERENCE TO RELATED APPLICATIONS

This application claims the benefit of U.S. Provisional Application No. 62/414,670, which is hereby incorporated by reference in its entirety.

STATEMENT REGARDING FEDERALLY SPONSORED RESEARCH

Not applicable. (N/A)

PARTIES TO A JOINT RESEARCH AGREEMENT

Not applicable. (N/A)

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392034740SEQLIST.txt, date recorded: Oct. 26, 2017, size: 226 KB).

FIELD OF THE INVENTION

The present invention relates to anti-MIC antibodies, methods of using the same, and methods for mapping epitopes.

BACKGROUND OF THE INVENTION

MIC (e.g., MICA, MICB) is a ligand for NKG2D, a receptor that is expressed on most human NK cells, γδ T cells, and CD8+ T cells. While NKG2D ligands are not usually found on healthy tissues, various forms of cellular stress, including DNA damage, upregulate ligand expression, resulting in their frequent detection in multiple solid and hematologic malignancies, including melanoma. Upon binding to MIC, NKG2D activates perforin-dependent cytolysis by NK cells and provides co-stimulation of T cells, resulting in killing of the NKG2D-expressing cells, e.g., tumor cells. However, despite this mechanism, many MIC positive tumors have been identified. Studies have shown that immune escape of tumors is achieved by the shedding of MIC from these tumor cells. Soluble MIC triggers internalization and downregulation of surface NKG2D receptors and impaired function of cytotoxic lymphocytes. Soluble MIC may also stimulate the expansion of regulatory NKG2D+CD4+Foxp3-T cells that may antagonize anti-tumor cytotoxicity through Fas ligand, IL-10, and TGF-β. Sera from cancer patients typically contain elevated levels of the soluble form (sMICA).

It is clear that there continues to be a need for agents that have clinical attributes that are optimal for development as therapeutic agents. The antibodies described herein meet this need and provide other benefits.

Mapping the epitope is a critical aspect of characterizing antibodies. Knowledge of the epitope helps to guide design, selection and/or identification of other antibodies with similar properties. Identification of the epitope may also provide insight into the mechanism of binding for an antibody. Existing methods for mapping include x-ray crystallography, array-based oligopeptide screening, the use of synthetic peptides or proteolytic fragments of the antigen in ELISA or competition assays, site directed mutagenesis, phage display libraries of random peptide or antigen fragment sequences, proteolysis of antigens in the presence or absence of antibody with mass spectral analysis of either binding or non-binding fragments, and Shotgun Mutagenesis by Integral Molecular. Many of these methods are expensive and time consuming, requiring many steps before meaningful results are available. Thus there remains a need for improved methods of epitope mapping.

All references cited herein, including patent applications, patent publications, and UniProtKB/Swiss-Prot Accession numbers are herein incorporated by reference in their entirety, as if each individual reference were specifically and individually indicated to be incorporated by reference.

SUMMARY OF THE INVENTION

The invention provides anti-MIC antibodies and methods of using the same. The invention also provides methods for epitope mapping. The epitope mapping methods described herein provide several advantages over methods existing in the art. For example, the methods described herein enable epitope mapping of antibodies using properly folded polypeptide, while other methods map epitopes using short polypeptide fragments that are likely to be misfolded or unfolded. Furthermore, the addition of glycans can be stabilizing to a polypeptide, whereas substitution with alanines frequently disrupts polypeptide structure, causing aggregation and rendering the polypeptide unusable. Moreover, the methods described herein permit faster scanning of a large surface or the entire surface of an antigen and use a fewer number of constructs than in an alanine scan.

In one aspect, provided herein are antibodies that specifically bind to human MICA*008, wherein the antibody binds to an epitope on human MICA*008 comprising one or more amino acid residues selected from the group consisting of Glu215, Gly243, His248, and Arg279 of human MICA*008. In some embodiments, the antibodies bind to an epitope on human MICA*008 comprising amino acid residues Glu215, His248, and Arg279 of human MICA*008. In other embodiments, the antibodies bind to an epitope on human MICA*008 comprising amino acid residues Gly243 and Arg279 of human MICA*008. In other embodiments, the antibodies bind to an epitope on human MICA*008 comprising amino acid residues His248 and Arg279 of human MICA*008. In other embodiments, the antibodies bind to an epitope on human MICA*008 comprising amino acid residue His248 of human MICA*008. In other embodiments, the antibodies bind to an epitope on human MICA*008 comprising amino acid residues Arg279 of human MICA*008.

In another aspect, provided herein are antibodies that specifically bind to human MICA*008, wherein the antibody comprises the following six hypervariable regions (HVRs): a HVR-H1 comprising the amino acid sequence of SEQ ID NO: 1; a HVR-H2 comprising the amino acid sequence of SEQ ID NO: 2; a HVR-H3 comprising the amino acid sequence of SEQ ID NO: 3; a HVR-L1 comprising the amino acid sequence of SEQ ID NO: 4; a HVR-L2 comprising the amino acid sequence of SEQ ID NO: 5; and a HVR-L3 comprising the amino acid sequence of SEQ ID NO: 6. In some embodiments, the antibodies further comprise the following light chain variable region framework regions (FRs): a FR-L1 comprising the amino acid sequence of SEQ ID NO: 7; a FR-L2 comprising the amino acid sequence of SEQ ID NO: 8; a FR-L3 comprising the amino acid sequence of SEQ ID NO: 9; and a FR-L4 comprising the amino acid sequence of SEQ ID NO: 10. In other embodiments, the antibodies further comprise the following heavy chain variable region FRs: a FR-H1 comprising the amino acid sequence of SEQ ID NO: 11, a FR-H2 comprising the amino acid sequence of SEQ ID NO: 12; a FR-H3 comprising the amino acid sequence of SEQ ID NO: 13; and a FR-H4 comprising the amino acid sequence of SEQ ID NO: 14.

In another aspect, provided herein are antibodies that specifically bind to human MICA*008, wherein the antibody binds to an epitope on human MICA*008 comprising one or more amino acid residues selected from the group consisting of Glu215, Gly243, His248, and Arg279 of human MICA*008 and that comprise (a) a VH sequence having at least 95% sequence identity to the amino acid sequence of SEQ ID NO: 15; (b) a VL sequence having at least 95% sequence identity to the amino acid sequence of SEQ ID NO: 16; or (c) a VH sequence as in (a) and a VL sequence as in (b). In some embodiments, the antibodies comprise a VH sequence of SEQ ID NO: 15. In other embodiments, the antibodies comprise a VL sequence of SEQ ID NO: 16.

In another aspect, provided herein are antibodies comprising a VH sequence of SEQ ID NO: 15 and a VL sequence of SEQ ID NO: 16.

In another aspect, provided herein are antibodies that specifically bind to human MICA*008, wherein the antibody comprises the following six hypervariable regions (HVRs): a HVR-H1 comprising the amino acid sequence of SEQ ID NO: 17; a HVR-H2 comprising the amino acid sequence of SEQ ID NO: 18; a HVR-H3 comprising the amino acid sequence of SEQ ID NO: 19; a HVR-L1 comprising the amino acid sequence of SEQ ID NO: 20; a HVR-L2 comprising the amino acid sequence of SEQ ID NO: 21; and a HVR-L3 comprising the amino acid sequence of SEQ ID NO: 22. In some embodiments, the antibodies further comprise the following light chain variable region framework regions (FRs): a FR-L1 comprising the amino acid sequence of SEQ ID NO: 23; a FR-L2 comprising the amino acid sequence of SEQ ID NO: 24; a FR-L3 comprising the amino acid sequence of SEQ ID NO: 25; and a FR-L4 comprising the amino acid sequence of SEQ ID NO: 26. In other embodiments, the antibodies further comprise the following heavy chain variable region FRs: a FR-H1 comprising the amino acid sequence of SEQ ID NO: 27, a FR-H2 comprising the amino acid sequence of SEQ ID NO: 28; a FR-H3 comprising the amino acid sequence of SEQ ID NO: 29; and a FR-H4 comprising the amino acid sequence of SEQ ID NO: 30.

In another aspect, provided herein are antibodies that specifically bind to human MICA*008, wherein the antibody binds to an epitope on human MICA*008 comprising one or more amino acid residues selected from the group consisting of Glu215, Gly243, His248, and Arg279 of human MICA*008 and that comprise (a) a VH sequence having at least 95% sequence identity to the amino acid sequence of SEQ ID NO: 31; (b) a VL sequence having at least 95% sequence identity to the amino acid sequence of SEQ ID NO: 32; or (c) a VH sequence as in (a) and a VL sequence as in (b). In some embodiments, the antibodies comprise a VH sequence of SEQ ID NO: 31. In other embodiments, the antibodies comprise a VL sequence of SEQ ID NO: 32.

In another aspect, provided herein are antibodies comprising a VH sequence of SEQ ID NO: 31 and a VL sequence of SEQ ID NO: 32.

In another aspect, provided herein are antibodies that specifically bind to human MICA*008, wherein the antibody comprises the following six hypervariable regions (HVRs): a HVR-H1 comprising the amino acid sequence of SEQ ID NO: 33; a HVR-H2 comprising the amino acid sequence of SEQ ID NO: 34; a HVR-H3 comprising the amino acid sequence of SEQ ID NO: 35; a HVR-L1 comprising the amino acid sequence of SEQ ID NO: 36; a HVR-L2 comprising the amino acid sequence of SEQ ID NO: 37; and a HVR-L3 comprising the amino acid sequence of SEQ ID NO: 38. In some embodiments, the antibodies further comprise the following light chain variable region framework regions (FRs): a FR-L1 comprising the amino acid sequence of SEQ ID NO: 39; a FR-L2 comprising the amino acid sequence of SEQ ID NO: 40; a FR-L3 comprising the amino acid sequence of SEQ ID NO: 41; and a FR-L4 comprising the amino acid sequence of SEQ ID NO: 42. In other embodiments, the antibodies further comprise the following heavy chain variable region FRs: a FR-H1 comprising the amino acid sequence of SEQ ID NO: 43, a FR-H2 comprising the amino acid sequence of SEQ ID NO: 44; a FR-H3 comprising the amino acid sequence of SEQ ID NO: 45; and a FR-H4 comprising the amino acid sequence of SEQ ID NO: 46.

In another aspect, provided are antibodies that specifically bind to human MICA*008, wherein the antibody binds to an epitope on human MICA*008 comprising one or more amino acid residues selected from the group consisting of Glu215, Gly243, His248, and Arg279 of human MICA*008 and that comprise (a) a VH sequence having at least 95% sequence identity to the amino acid sequence of SEQ ID NO: 47; (b) a VL sequence having at least 95% sequence identity to the amino acid sequence of SEQ ID NO: 48; or (c) a VH sequence as in (a) and a VL sequence as in (b). In some embodiments, the antibodies comprise a VH sequence of SEQ ID NO: 47. In other embodiments, the antibodies comprise a VL sequence of SEQ ID NO: 48.

In another aspect, provided are antibodies comprising a VH sequence of SEQ ID NO: 47 and a VL sequence of SEQ ID NO: 48.

In another aspect, provided herein are antibodies that specifically bind to human MICA*008, wherein the antibody comprises the following six hypervariable regions (HVRs): a HVR-H1 comprising the amino acid sequence of SEQ ID NO: 49; a HVR-H2 comprising the amino acid sequence of SEQ ID NO: 50; a HVR-H3 comprising the amino acid sequence of SEQ ID NO: 51; a HVR-L1 comprising the amino acid sequence of SEQ ID NO: 52; a HVR-L2 comprising the amino acid sequence of SEQ ID NO: 53; and a HVR-L3 comprising the amino acid sequence of SEQ ID NO: 54. In some embodiments, the antibodies further comprise the following light chain variable region framework regions (FRs): a FR-L1 comprising the amino acid sequence of SEQ ID NO: 55; a FR-L2 comprising the amino acid sequence of SEQ ID NO: 56; a FR-L3 comprising the amino acid sequence of SEQ ID NO: 57; and a FR-L4 comprising the amino acid sequence of SEQ ID NO: 58. In other embodiments, the antibodies further comprise the following heavy chain variable region FRs: a FR-H1 comprising the amino acid sequence of SEQ ID NO: 59, a FR-H2 comprising the amino acid sequence of SEQ ID NO: 60; a FR-H3 comprising the amino acid sequence of SEQ ID NO: 61; and a FR-H4 comprising the amino acid sequence of SEQ ID NO: 62.

In another aspect, provided are antibodies that specifically bind to human MICA*008, wherein the antibody binds to an epitope on human MICA*008 comprising one or more amino acid residues selected from the group consisting of Glu215, Gly243, His248, and Arg279 of human MICA*008 and that comprise (a) a VH sequence having at least 95% sequence identity to the amino acid sequence of SEQ ID NO: 63; (b) a VL sequence having at least 95% sequence identity to the amino acid sequence of SEQ ID NO: 64; or (c) a VH sequence as in (a) and a VL sequence as in (b). In some embodiments, the antibodies comprise a VH sequence of SEQ ID NO: 63. In other embodiments, the antibodies comprise a VL sequence of SEQ ID NO: 64.

In another aspect, provided are antibodies comprising a VH sequence of SEQ ID NO: 63 and a VL sequence of SEQ ID NO: 64.

In another aspect, provided herein are antibodies that specifically bind to human MICA*008, wherein the antibody comprises the following six hypervariable regions (HVRs): a HVR-H1 comprising the amino acid sequence of SEQ ID NO: 65; a HVR-H2 comprising the amino acid sequence of SEQ ID NO: 66; a HVR-H3 comprising the amino acid sequence of SEQ ID NO: 67; a HVR-L1 comprising the amino acid sequence of SEQ ID NO: 68; a HVR-L2 comprising the amino acid sequence of SEQ ID NO: 69; and a HVR-L3 comprising the amino acid sequence of SEQ ID NO: 70. In some embodiments, the antibodies further comprise the following light chain variable region framework regions (FRs): a FR-L1 comprising the amino acid sequence of SEQ ID NO: 71; a FR-L2 comprising the amino acid sequence of SEQ ID NO: 72; a FR-L3 comprising the amino acid sequence of SEQ ID NO: 73; and a FR-L4 comprising the amino acid sequence of SEQ ID NO: 74. In other embodiments, the antibodies further comprise the following heavy chain variable region FRs: a FR-H1 comprising the amino acid sequence of SEQ ID NO: 75, a FR-H2 comprising the amino acid sequence of SEQ ID NO: 76; a FR-H3 comprising the amino acid sequence of SEQ ID NO: 77; and a FR-H4 comprising the amino acid sequence of SEQ ID NO: 78.

In another aspect, the antibodies that specifically bind to human MICA*008, wherein the antibody binds to an epitope on human MICA*008 comprising one or more amino acid residues selected from the group consisting of Glu215, Gly243, His248, and Arg279 of human MICA*008 and that comprise (a) a VH sequence having at least 95% sequence identity to the amino acid sequence of SEQ ID NO: 79; (b) a VL sequence having at least 95% sequence identity to the amino acid sequence of SEQ ID NO: 80; or (c) a VH sequence as in (a) and a VL sequence as in (b). In some embodiments, the antibodies comprise a VH sequence of SEQ ID NO: 79. In other embodiments, the antibodies comprise a VL sequence of SEQ ID NO: 80.

In another aspect, provided are antibodies comprising a VH sequence of SEQ ID NO: 79 and a VL sequence of SEQ ID NO: 80.

In another aspect, provided herein are antibodies that specifically bind to human MICA*008, wherein the antibody comprises the following six hypervariable regions (HVRs): a HVR-H1 comprising the amino acid sequence of SEQ ID NO: 81; a HVR-H2 comprising the amino acid sequence of SEQ ID NO: 82; a HVR-H3 comprising the amino acid sequence of SEQ ID NO: 83; a HVR-L1 comprising the amino acid sequence of SEQ ID NO: 84; a HVR-L2 comprising the amino acid sequence of SEQ ID NO: 85; and a HVR-L3 comprising the amino acid sequence of SEQ ID NO: 86. In some embodiments, the antibodies further comprise the following light chain variable region framework regions (FRs): a FR-L1 comprising the amino acid sequence of SEQ ID NO: 87; a FR-L2 comprising the amino acid sequence of SEQ ID NO: 88; a FR-L3 comprising the amino acid sequence of SEQ ID NO: 89; and a FR-L4 comprising the amino acid sequence of SEQ ID NO: 90. In other embodiments, the antibodies further comprise the following heavy chain variable region FRs: a FR-H1 comprising the amino acid sequence of SEQ ID NO: 91, a FR-H2 comprising the amino acid sequence of SEQ ID NO: 92; a FR-H3 comprising the amino acid sequence of SEQ ID NO: 93; and a FR-H4 comprising the amino acid sequence of SEQ ID NO: 94.

In another aspect, provided are antibodies that specifically bind to human MICA*008, wherein the antibody binds to an epitope on human MICA*008 comprising one or more amino acid residues selected from the group consisting of Glu215, Gly243, His248, and Arg279 of human MICA*008 and that comprise (a) a VH sequence having at least 95% sequence identity to the amino acid sequence of SEQ ID NO: 95; (b) a VL sequence having at least 95% sequence identity to the amino acid sequence of SEQ ID NO: 96; or (c) a VH sequence as in (a) and a VL sequence as in (b). In some embodiments, the antibody comprises a VH sequence of SEQ ID NO: 95. In other embodiments, the antibody comprises a VL sequence of SEQ ID NO: 96.

In another aspect, provided are antibodies comprising a VH sequence of SEQ ID NO: 95 and a VL sequence of SEQ ID NO: 96.

In another aspect, provided herein are antibodies that specifically bind to human MICA*008, wherein the antibody comprises the following six hypervariable regions (HVRs): a HVR-H1 comprising the amino acid sequence of SEQ ID NO: 97; a HVR-H2 comprising the amino acid sequence of SEQ ID NO: 98; a HVR-H3 comprising the amino acid sequence of SEQ ID NO: 99; a HVR-L1 comprising the amino acid sequence of SEQ ID NO: 100; a HVR-L2 comprising the amino acid sequence of SEQ ID NO: 101; and a HVR-L3 comprising the amino acid sequence of SEQ ID NO: 102. In some embodiments, the antibodies further comprise the following light chain variable region framework regions (FRs): a FR-L1 comprising the amino acid sequence of SEQ ID NO: 103; a FR-L2 comprising the amino acid sequence of SEQ ID NO: 104; a FR-L3 comprising the amino acid sequence of SEQ ID NO: 105; and a FR-L4 comprising the amino acid sequence of SEQ ID NO: 106. In other embodiments, the antibodies further comprise the following heavy chain variable region FRs: a FR-H1 comprising the amino acid sequence of SEQ ID NO: 107, a FR-H2 comprising the amino acid sequence of SEQ ID NO: 108; a FR-H3 comprising the amino acid sequence of SEQ ID NO: 109; and a FR-H4 comprising the amino acid sequence of SEQ ID NO: 110.

In another aspect, provided here antibodies that specifically bind to human MICA*008, wherein the antibody binds to an epitope on human MICA*008 comprising one or more amino acid residues selected from the group consisting of Glu215, Gly243, His248, and Arg279 of human MICA*008 and that comprise (a) a VH sequence having at least 95% sequence identity to the amino acid sequence of SEQ ID NO: 111; (b) a VL sequence having at least 95% sequence identity to the amino acid sequence of SEQ ID NO: 112; or (c) a VH sequence as in (a) and a VL sequence as in (b). In some embodiments, the antibodies comprise a VH sequence of SEQ ID NO: 111. In other embodiments, the antibodies comprise a VL sequence of SEQ ID NO: 112.

In another aspect, provided are antibodies comprising a VH sequence of SEQ ID NO: 111 and a VL sequence of SEQ ID NO: 112.

In another aspect, provided here are antibodies that specifically bind to human MICA*008, wherein the antibody comprises the following six hypervariable regions (HVRs): a HVR-H1 comprising the amino acid sequence of SEQ ID NO: 113; a HVR-H2 comprising the amino acid sequence of SEQ ID NO: 114; a HVR-H3 comprising the amino acid sequence of SEQ ID NO: 115; a HVR-L1 comprising the amino acid sequence of SEQ ID NO: 116; a HVR-L2 comprising the amino acid sequence of SEQ ID NO: 117; and a HVR-L3 comprising the amino acid sequence of SEQ ID NO: 118. In some embodiments, the antibodies further comprise the following light chain variable region framework regions (FRs): a FR-L1 comprising the amino acid sequence of SEQ ID NO: 119; a FR-L2 comprising the amino acid sequence of SEQ ID NO: 120; a FR-L3 comprising the amino acid sequence of SEQ ID NO: 121; and a FR-L4 comprising the amino acid sequence of SEQ ID NO: 122. In other embodiments, the antibodies further comprise the following heavy chain variable region FRs: a FR-H1 comprising the amino acid sequence of SEQ ID NO: 123, a FR-H2 comprising the amino acid sequence of SEQ ID NO: 124; a FR-H3 comprising the amino acid sequence of SEQ ID NO: 125; and a FR-H4 comprising the amino acid sequence of SEQ ID NO: 126.

In another aspect, provided are antibodies that specifically bind to human MICA*008, wherein the antibody binds to an epitope on human MICA*008 comprising one or more amino acid residues selected from the group consisting of Glu215, Gly243, His248, and Arg279 of human MICA*008 and that comprise (a) a VH sequence having at least 95% sequence identity to the amino acid sequence of SEQ ID NO: 127; (b) a VL sequence having at least 95% sequence identity to the amino acid sequence of SEQ ID NO: 128; or (c) a VH sequence as in (a) and a VL sequence as in (b). In some embodiments, the antibodies comprise a VH sequence of SEQ ID NO: 127. In other embodiments, the antibodies comprise a VL sequence of SEQ ID NO: 128.

In another aspect, provided are antibodies comprising a VH sequence of SEQ ID NO: 127 and a VL sequence of SEQ ID NO: 128.

In another aspect, provided here are antibodies that specifically bind to human MICA*008, wherein the antibody comprises the following six hypervariable regions (HVRs): a HVR-H1 comprising the amino acid sequence of SEQ ID NO: 129; a HVR-H2 comprising the amino acid sequence of SEQ ID NO: 130; a HVR-H3 comprising the amino acid sequence of SEQ ID NO: 131; a HVR-L1 comprising the amino acid sequence of SEQ ID NO: 132; a HVR-L2 comprising the amino acid sequence of SEQ ID NO: 133; and a HVR-L3 comprising the amino acid sequence of SEQ ID NO: 134. In some embodiments, the antibodies further comprise the following light chain variable region framework regions (FRs): a FR-L1 comprising the amino acid sequence of SEQ ID NO: 135; a FR-L2 comprising the amino acid sequence of SEQ ID NO: 136; a FR-L3 comprising the amino acid sequence of SEQ ID NO: 137; and a FR-L4 comprising the amino acid sequence of SEQ ID NO: 138. In other embodiments, the antibodies further comprise the following heavy chain variable region FRs: a FR-H1 comprising the amino acid sequence of SEQ ID NO: 139, a FR-H2 comprising the amino acid sequence of SEQ ID NO: 140; a FR-H3 comprising the amino acid sequence of SEQ ID NO: 141; and a FR-H4 comprising the amino acid sequence of SEQ ID NO: 142.

In another aspect, provided are antibodies that specifically bind to human MICA*008, wherein the antibody binds to an epitope on human MICA*008 comprising one or more amino acid residues selected from the group consisting of Glu215, Gly243, His248, and Arg279 of human MICA*008 and that comprise (a) a VH sequence having at least 95% sequence identity to the amino acid sequence of SEQ ID NO: 143; (b) a VL sequence having at least 95% sequence identity to the amino acid sequence of SEQ ID NO: 144; or (c) a VH sequence as in (a) and a VL sequence as in (b). In some embodiments, the antibodies comprise a VH sequence of SEQ ID NO: 143. In other embodiments, the antibodies comprise a VL sequence of SEQ ID NO: 144.

In another aspect, provided are antibodies that comprise a VH sequence of SEQ ID NO: 143 and a VL sequence of SEQ ID NO: 144.

In another aspect, provided herein are antibodies that specifically bind to human MICA*008, wherein the antibody comprises the following six hypervariable regions (HVRs): a HVR-H1 comprising the amino acid sequence of SEQ ID NO: 145; a HVR-H2 comprising the amino acid sequence of SEQ ID NO: 146; a HVR-H3 comprising the amino acid sequence of SEQ ID NO: 147; a HVR-L1 comprising the amino acid sequence of SEQ ID NO: 148; a HVR-L2 comprising the amino acid sequence of SEQ ID NO: 149; and a HVR-L3 comprising the amino acid sequence of SEQ ID NO: 150. In some embodiments, the antibodies further comprise the following light chain variable region framework regions (FRs): a FR-L1 comprising the amino acid sequence of SEQ ID NO: 151; a FR-L2 comprising the amino acid sequence of SEQ ID NO: 152; a FR-L3 comprising the amino acid sequence of SEQ ID NO: 153; and a FR-L4 comprising the amino acid sequence of SEQ ID NO: 154. In other embodiments, the antibodies further comprise the following heavy chain variable region FRs: a FR-H1 comprising the amino acid sequence of SEQ ID NO: 155, a FR-H2 comprising the amino acid sequence of SEQ ID NO: 156; a FR-H3 comprising the amino acid sequence of SEQ ID NO: 157; and a FR-H4 comprising the amino acid sequence of SEQ ID NO: 158.

In another aspect, provided are antibodies that specifically bind to human MICA*008, wherein the antibody binds to an epitope on human MICA*008 comprising one or more amino acid residues selected from the group consisting of Glu215, Gly243, His248, and Arg279 of human MICA*008 and that comprise (a) a VH sequence having at least 95% sequence identity to the amino acid sequence of SEQ ID NO: 159; (b) a VL sequence having at least 95% sequence identity to the amino acid sequence of SEQ ID NO: 160; or (c) a VH sequence as in (a) and a VL sequence as in (b). In some embodiments, the antibodies comprise a VH sequence of SEQ ID NO: 159. In other embodiments, the antibodies comprise a VL sequence of SEQ ID NO: 160.

In another aspect, provided are antibodies comprising a VH sequence of SEQ ID NO: 159 and a VL sequence of SEQ ID NO: 160.

In another aspect, provided herein are antibodies that specifically bind to human MICA*008, wherein the antibody comprises the following six hypervariable regions (HVRs): a HVR-H1 comprising the amino acid sequence of SEQ ID NO: 161; a HVR-H2 comprising the amino acid sequence of SEQ ID NO: 162; a HVR-H3 comprising the amino acid sequence of SEQ ID NO: 163; a HVR-L1 comprising the amino acid sequence of SEQ ID NO: 164; a HVR-L2 comprising the amino acid sequence of SEQ ID NO: 165; and a HVR-L3 comprising the amino acid sequence of SEQ ID NO: 166. In some embodiments, the antibodies further comprise the following light chain variable region framework regions (FRs): a FR-L1 comprising the amino acid sequence of SEQ ID NO: 167; a FR-L2 comprising the amino acid sequence of SEQ ID NO: 168; a FR-L3 comprising the amino acid sequence of SEQ ID NO: 169; and a FR-L4 comprising the amino acid sequence of SEQ ID NO: 170. In other embodiments, the antibodies further comprise the following heavy chain variable region FRs: a FR-H1 comprising the amino acid sequence of SEQ ID NO: 171, a FR-H2 comprising the amino acid sequence of SEQ ID NO: 172; a FR-H3 comprising the amino acid sequence of SEQ ID NO: 173; and a FR-H4 comprising the amino acid sequence of SEQ ID NO: 174.

In another aspect, provided are antibodies that specifically bind to human MICA*008, wherein the antibody binds to an epitope on human MICA*008 comprising one or more amino acid residues selected from the group consisting of Glu215, Gly243, His248, and Arg279 of human MICA*008 and that comprise (a) a VH sequence having at least 95% sequence identity to the amino acid sequence of SEQ ID NO: 175; (b) a VL sequence having at least 95% sequence identity to the amino acid sequence of SEQ ID NO: 176; or (c) a VH sequence as in (a) and a VL sequence as in (b). In some embodiments, the antibodies comprise a VH sequence of SEQ ID NO: 175. In other embodiments, the antibodies comprise a VL sequence of SEQ ID NO: 176.

In another aspect, provided are antibodies comprising a VH sequence of SEQ ID NO: 175 and a VL sequence of SEQ ID NO: 176.

In another aspect, provided herein are antibodies that specifically bind to human MICA*008, wherein the antibody comprises the following six hypervariable regions (HVRs): a HVR-H1 comprising the amino acid sequence of SEQ ID NO: 177; a HVR-H2 comprising the amino acid sequence of SEQ ID NO: 178; a HVR-H3 comprising the amino acid sequence of SEQ ID NO: 179; a HVR-L1 comprising the amino acid sequence of SEQ ID NO: 180; a HVR-L2 comprising the amino acid sequence of SEQ ID NO: 181; and a HVR-L3 comprising the amino acid sequence of SEQ ID NO: 182. In some embodiments, The antibodies further comprise the following light chain variable region framework regions (FRs): a FR-L1 comprising the amino acid sequence of SEQ ID NO: 183; a FR-L2 comprising the amino acid sequence of SEQ ID NO: 184; a FR-L3 comprising the amino acid sequence of SEQ ID NO: 185; and a FR-L4 comprising the amino acid sequence of SEQ ID NO: 186. In other embodiments, the antibodies further comprise the following heavy chain variable region FRs: a FR-H1 comprising the amino acid sequence of SEQ ID NO: 187, a FR-H2 comprising the amino acid sequence of SEQ ID NO: 188; a FR-H3 comprising the amino acid sequence of SEQ ID NO: 189; and a FR-H4 comprising the amino acid sequence of SEQ ID NO: 190.

In another aspect, provided are antibodies that specifically bind to human MICA*008, wherein the antibody binds to an epitope on human MICA*008 comprising one or more amino acid residues selected from the group consisting of Glu215, Gly243, His248, and Arg279 of human MICA*008 and that comprise (a) a VH sequence having at least 95% sequence identity to the amino acid sequence of SEQ ID NO: 191; (b) a VL sequence having at least 95% sequence identity to the amino acid sequence of SEQ ID NO: 192; or (c) a VH sequence as in (a) and a VL sequence as in (b). In some embodiments, the antibodies comprise a VH sequence of SEQ ID NO: 191. In other embodiments, the antibodies comprise a VL sequence of SEQ ID NO: 192.

In another aspect, provided are antibodies comprising a VH sequence of SEQ ID NO: 191 and a VL sequence of SEQ ID NO: 192.

In one aspect, provided herein are antibodies that specifically bind to human MICA*008, wherein the antibody binds to an epitope on human MICA*008 comprising amino acid residue Gly243 of human MICA*008. In some embodiments, the antibodies bind to an epitope on human MICA*008 comprising amino acid residues Gly243 and Arg279 of human MICA*008.

In another aspect, provided herein are antibodies that specifically bind to human MICA*008, wherein the antibody comprises the following six hypervariable regions (HVRs): a HVR-H1 comprising the amino acid sequence of SEQ ID NO: 209; a HVR-H2 comprising the amino acid sequence selected from the group consisting of: SEQ ID NO: 210, SEQ ID NO: 215, SEQ ID NO: 216, and SEQ ID NO: 217; a HVR-H3 comprising the amino acid sequence of SEQ ID NO: 211; a HVR-L1 comprising the amino acid sequence of SEQ ID NO: 212; a HVR-L2 comprising the amino acid sequence of SEQ ID NO: 213; and a HVR-L3 comprising the amino acid sequence of SEQ ID NO: 214. In some embodiments, the antibodies further comprise the following light chain variable region framework regions (FRs): a FR-L1 comprising the amino acid sequence selected from the group consisting of: SEQ ID NO: 248, SEQ ID NO: 252, SEQ ID NO: 258, SEQ ID NO: 261, and SEQ ID NO: 266; a FR-L2 comprising the amino acid sequence selected from the group consisting of: SEQ ID NO: 249, SEQ ID NO: 253, SEQ ID NO: 256, SEQ ID NO: 259, SEQ ID NO: 262, and SEQ ID NO: 264; a FR-L3 comprising the amino acid sequence selected from the group consisting of: SEQ ID NO: 250, SEQ ID NO: 254, SEQ ID NO: 257, SEQ ID NO: 260, SEQ ID NO: 263, SEQ ID NO: 265, and SEQ ID NO: 267; and a FR-L4 comprising the amino acid sequence of SEQ ID NO: 251 or SEQ ID NO: 255. In other embodiments, the antibodies further comprise the following heavy chain variable region FRs: a FR-H1 comprising the amino acid sequence selected from the group consisting of: SEQ ID NO: 295, SEQ ID NO: 299, and SEQ ID NO: 303; a FR-H2 comprising the amino acid sequence selected from the group consisting of: SEQ ID NO: 296, SEQ ID NO: 300, and SEQ ID NO: 304; a FR-H3 comprising the amino acid sequence selected from the group consisting of: SEQ ID NO: 297, SEQ ID NO: 301, SEQ ID NO: 305, SEQ ID NO: 306, SEQ ID NO: 307, SEQ ID NO: 308, SEQ ID NO: 309; SEQ ID NO: 310, SEQ ID NO: 311, SEQ ID NO: 312, SEQ ID NO: 313, and SEQ ID NO: 314; and a FR-H4 comprising the amino acid sequence of SEQ ID NO: 298 or SEQ ID NO: 302.

In another aspect, provided herein are antibodies that specifically bind to human MICA*008, wherein the antibody binds to an epitope on human MICA*008 comprising amino acid residue Gly243 of human MICA*008 and that comprise (a) a VH sequence having at least 95% sequence identity to the amino acid sequence of SEQ ID NO: 369; (b) a VL sequence having at least 95% sequence identity to the amino acid sequence of SEQ ID NO: 370; or (c) a VH sequence as in (a) and a VL sequence as in (b). In some embodiments, the antibodies comprise a VH sequence of SEQ ID NO: 369. In other embodiments, the antibodies comprise a VL sequence of SEQ ID NO: 370.

In another aspect, provided herein are antibodies comprising a VH sequence of SEQ ID NO: 369 and a VL sequence of SEQ ID NO: 370.

In another aspect, provided herein are antibodies that specifically bind to human MICA*008, wherein the antibody comprises the following six hypervariable regions (HVRs): a HVR-H1 comprising the amino acid sequence of SEQ ID NO: 218; a HVR-H2 comprising the amino acid sequence of SEQ ID NO: 219; a HVR-H3 comprising the amino acid sequence of SEQ ID NO: 220; a HVR-L1 comprising the amino acid sequence of SEQ ID NO: 221; a HVR-L2 comprising the amino acid sequence of SEQ ID NO: 222; and a HVR-L3 comprising the amino acid sequence of SEQ ID NO: 223. In some embodiments, the antibodies further comprise the following light chain variable region framework regions (FRs): a FR-L1 comprising the amino acid sequence of SEQ ID NO: 268 or SEQ ID NO: 272; a FR-L2 comprising the amino acid sequence selected from the group consisting of: SEQ ID NO: 269, SEQ ID NO: 273, and SEQ ID NO: 275; a FR-L3 comprising the amino acid sequence selected from the group consisting of: SEQ ID NO: 270, SEQ ID NO: 274, and SEQ ID NO: 276; and a FR-L4 comprising the amino acid sequence of SEQ ID NO: 255 or SEQ ID NO: 271. In other embodiments, the antibodies further comprise the following heavy chain variable region FRs: a FR-H1 comprising the amino acid sequence selected from the group consisting of: SEQ ID NO: 315, SEQ ID NO: 319, and SEQ ID NO: 323; a FR-H2 comprising the amino acid sequence of SEQ ID NO: 316 or SEQ ID NO: 320; a FR-H3 comprising the amino acid sequence selected from the group consisting of: SEQ ID NO: 317, SEQ ID NO: 321, SEQ ID NO: 322, and SEQ ID NO: 324; and a FR-H4 comprising the amino acid sequence of SEQ ID NO: 302 or SEQ ID NO: 318.

In another aspect, provided herein are antibodies that specifically bind to human MICA*008, wherein the antibody binds to an epitope on human MICA*008 comprising amino acid residue Gly243 of human MICA*008 and that comprise (a) a VH sequence having at least 95% sequence identity to the amino acid sequence of SEQ ID NO: 415; (b) a VL sequence having at least 95% sequence identity to the amino acid sequence of SEQ ID NO: 416; or (c) a VH sequence as in (a) and a VL sequence as in (b). In some embodiments, the antibodies comprise a VH sequence of SEQ ID NO: 415. In other embodiments, the antibodies comprise a VL sequence of SEQ ID NO: 416.

In another aspect, provided herein are antibodies comprising a VH sequence of SEQ ID NO: 415 and a VL sequence of SEQ ID NO: 416.

In another aspect, provided herein are antibodies that specifically bind to human MICA*008, wherein the antibody comprises the following six hypervariable regions (HVRs): a HVR-H1 comprising the amino acid sequence of SEQ ID NO: 224; a HVR-H2 comprising the amino acid sequence of SEQ ID NO: 225; a HVR-H3 comprising the amino acid sequence of SEQ ID NO: 226; a HVR-L1 comprising the amino acid sequence of SEQ ID NO: 227; a HVR-L2 comprising the amino acid sequence of SEQ ID NO: 228; and a HVR-L3 comprising the amino acid sequence of SEQ ID NO: 229. In some embodiments, the antibodies further comprise the following light chain variable region framework regions (FRs): a FR-L1 comprising the amino acid sequence of SEQ ID NO: 277 of SEQ ID NO: 280; a FR-L2 comprising the amino acid sequence selected from the group consisting of: SEQ ID NO: 278, SEQ ID NO: 281, and SEQ ID NO: 283; a FR-L3 comprising the amino acid sequence selected from the group consisting of: SEQ ID NO: 279, SEQ ID NO: 282, and SEQ ID NO: 284; and a FR-L4 comprising the amino acid sequence of SEQ ID NO: 251 or SEQ ID NO: 255. In other embodiments, the antibodies further comprise the following heavy chain variable region FRs: a FR-H1 comprising the amino acid sequence selected from the group consisting of: SEQ ID NO: 325, SEQ ID NO: 329, SEQ ID NO: 331, and SEQ ID NO: 333; a FR-H2 comprising the amino acid sequence of SEQ ID NO: 320 or SEQ ID NO: 326; a FR-H3 comprising the amino acid sequence selected from the group consisting of: SEQ ID NO: 327, SEQ ID NO: 330, SEQ ID NO: 332, and SEQ ID NO: 334; and a FR-H4 comprising the amino acid sequence of SEQ ID NO: 302 or SEQ ID NO: 328.

In another aspect, provided are antibodies that specifically bind to human MICA*008, wherein the antibody binds to an epitope on human MICA*008 comprising amino acid residue Gly243 of human MICA*008 and that comprise (a) a VH sequence having at least 95% sequence identity to the amino acid sequence of SEQ ID NO: 429; (b) a VL sequence having at least 95% sequence identity to the amino acid sequence of SEQ ID NO: 430; or (c) a VH sequence as in (a) and a VL sequence as in (b). In some embodiments, the antibodies comprise a VH sequence of SEQ ID NO: 429. In other embodiments, the antibodies comprise a VL sequence of SEQ ID NO: 430.

In another aspect, provided are antibodies comprising a VH sequence of SEQ ID NO: 429 and a VL sequence of SEQ ID NO: 430.

In another aspect, provided herein are antibodies that specifically bind to human MICA*008, wherein the antibody comprises the following six hypervariable regions (HVRs): a HVR-H1 comprising the amino acid sequence of SEQ ID NO: 236; a HVR-H2 comprising the amino acid sequence of SEQ ID NO: 237; a HVR-H3 comprising the amino acid sequence of SEQ ID NO: 238; a HVR-L1 comprising the amino acid sequence of SEQ ID NO: 239; a HVR-L2 comprising the amino acid sequence of SEQ ID NO: 240; and a HVR-L3 comprising the amino acid sequence of SEQ ID NO: 241. In some embodiments, the antibodies further comprise the following light chain variable region framework regions (FRs): a FR-L1 comprising the amino acid sequence of SEQ ID NO: 288; a FR-L2 comprising the amino acid sequence of SEQ ID NO: 289; a FR-L3 comprising the amino acid sequence of SEQ ID NO: 290; and a FR-L4 comprising the amino acid sequence of SEQ ID NO: 271. In other embodiments, the antibodies further comprise the following heavy chain variable region FRs: a FR-H1 comprising the amino acid sequence of SEQ ID NO: 339, a FR-H2 comprising the amino acid sequence of SEQ ID NO: 340; a FR-H3 comprising the amino acid sequence of SEQ ID NO: 341; and a FR-H4 comprising the amino acid sequence of SEQ ID NO: 342.

In another aspect, provided are antibodies that specifically bind to human MICA*008, wherein the antibody binds to an epitope on human MICA*008 comprising one or more amino acid residue Gly243 of human MICA*008 and that comprise (a) a VH sequence having at least 95% sequence identity to the amino acid sequence of SEQ ID NO: 437; (b) a VL sequence having at least 95% sequence identity to the amino acid sequence of SEQ ID NO: 438; or (c) a VH sequence as in (a) and a VL sequence as in (b). In some embodiments, the antibodies comprise a VH sequence of SEQ ID NO: 437. In other embodiments, the antibodies comprise a VL sequence of SEQ ID NO: 438.

In another aspect, provided are antibodies comprising a VH sequence of SEQ ID NO: 437 and a VL sequence of SEQ ID NO: 438.

In another aspect, provided herein are antibodies that specifically bind to human MICA*008, wherein the antibody comprises the following six hypervariable regions (HVRs): a HVR-H1 comprising the amino acid sequence of SEQ ID NO: 242; a HVR-H2 comprising the amino acid sequence of SEQ ID NO: 243; a HVR-H3 comprising the amino acid sequence of SEQ ID NO: 244; a HVR-L1 comprising the amino acid sequence of SEQ ID NO: 245; a HVR-L2 comprising the amino acid sequence of SEQ ID NO: 246; and a HVR-L3 comprising the amino acid sequence of SEQ ID NO: 247. In some embodiments, the antibodies further comprise the following light chain variable region framework regions (FRs): a FR-L1 comprising the amino acid sequence of SEQ ID NO: 291; a FR-L2 comprising the amino acid sequence of SEQ ID NO: 292; a FR-L3 comprising the amino acid sequence of SEQ ID NO: 293; and a FR-L4 comprising the amino acid sequence of SEQ ID NO: 294. In other embodiments, the antibodies further comprise the following heavy chain variable region FRs: a FR-H1 comprising the amino acid sequence of SEQ ID NO: 343, a FR-H2 comprising the amino acid sequence of SEQ ID NO: 344; a FR-H3 comprising the amino acid sequence of SEQ ID NO: 345; and a FR-H4 comprising the amino acid sequence of SEQ ID NO: 346.

In another aspect, the antibodies that specifically bind to human MICA*008, wherein the antibody binds to an epitope on human MICA*008 comprising amino acid residue Gly243 of human MICA*008 and that comprise (a) a VH sequence having at least 95% sequence identity to the amino acid sequence of SEQ ID NO: 439; (b) a VL sequence having at least 95% sequence identity to the amino acid sequence of SEQ ID NO: 440; or (c) a VH sequence as in (a) and a VL sequence as in (b). In some embodiments, the antibodies comprise a VH sequence of SEQ ID NO: 439. In other embodiments, the antibodies comprise a VL sequence of SEQ ID NO: 440.

In another aspect, provided are antibodies comprising a VH sequence of SEQ ID NO: 439 and a VL sequence of SEQ ID NO: 440.

In certain embodiments of antibodies of any one of the preceding aspects, the antibody binds to human MICA with a Kd of about 100 nM or lower.

In certain embodiments of antibodies of any one of the preceding aspects, the antibody is capable of binding to human MICA*002, human MICA*004 and human MICB*005.

In certain embodiments of antibodies of any one of the preceding aspects, the antibody is capable of binding to the extracellular domain of human MICA*008, human MICA*002, human MICA*004, human MICA*008 and human MICB*005.

In certain embodiments of antibodies of any one of the preceding aspects, the antibody is capable of binding to the alpha3 domain of human MICA*008, human MICA*002, human MICA*004, and human MICB*005.

In certain embodiments of antibodies of any one of the preceding aspects, the antibody is monoclonal.

In certain embodiments of antibodies of any one of the preceding aspects, the antibody is human, humanized, or chimeric.

In certain embodiments of antibodies of any one of the preceding aspects, at least a portion of the framework sequence is a human consensus framework sequence.

In certain embodiments of antibodies of any one of the preceding aspects, the antibody is a full-length antibody.

In certain embodiments of antibodies of any one of the preceding aspects, the antibody is a bispecific antibody.

In certain embodiments of antibodies of any one of the preceding aspects, the antibody is an antibody fragment that binds human MICA*008. In some embodiments, the antibody fragment is selected from the group consisting of Fab, Fab', Fab'-SH, Fv, single chain variable fragment (scFv), and (Fab')2 fragments.

In certain embodiments of antibodies of any one of the preceding aspects, the antibody is an IgG class antibody. In some embodiments, the IgG class antibody is an IgG1 subclass antibody. In some embodiments, the IgG class antibody is an IgG2 subclass antibody. In some embodiments, the IgG class antibody is an IgG4 subclass antibody.

In another aspect, provided herein are isolated nucleic acids encoding the antibodies of the preceding aspects.

In another aspect, provided herein are vectors comprising the nucleic acids of the preceding aspects.

In another aspect, provided herein are host cells comprising the vectors of the preceding aspects. In some embodiments, the host cell is prokaryotic, e.g., *Escherichia coli*. In other embodiments, the host cell is eukaryotic, e.g., a 293 cell, a CHO cell, a yeast cell, or a plant cell.

In another aspect, provided herein are methods of producing the antibody of any preceding aspects, the method comprising culturing the host cell of any of the preceding aspects in a culture medium. In some embodiments, the methods further comprise recovering the antibody from the host cell or culture medium.

In another aspect, provided herein are immunoconjugates comprising the antibody of any of the preceding aspects and a cytotoxic agent.

In another aspect, provided herein are compositions comprising the antibody of any of the preceding aspects. In some embodiments, the composition further comprises a pharmaceutically acceptable carrier, excipient, or diluent. In some embodiments, the composition is a pharmaceutical composition. In other embodiments, the composition further comprises a PD-1 axis binding antagonist or an additional therapeutic agent.

In another aspect, provided herein are antibodies of the preceding aspects for use in reducing shedding of MIC, for use in reducing levels of soluble MIC, and for use in reducing both shedding of MIC and levels of soluble MIC.

In another aspect, provided herein are antibodies of the preceding aspects for use as a medicament.

In another aspect, provided herein are antibodies of the preceding aspects for use in treating or delaying progression of a cancer in a subject in need thereof. In embodiments of this aspect, the cancer may be epithelial cancer, non-small cell lung cancer, small cell lung cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphomas, myelomas, mycoses fungoids, Merkel cell cancer, or other hematologic malignancies.

In another aspect, provided herein are antibodies of the preceding aspects for use in treating or delaying progression of an immune related disease in a subject in need thereof. In some embodiments of this aspect, the immune related disease is associated with a NKG2D ligand. In further embodiments, the NKG2D ligand is MIC. In other embodiments of this aspect, the immune related disease is selected from the group consisting of unresolved acute infection, chronic infection, and tumor immunity.

In another aspect, provided herein are antibodies of the preceding aspects for use in increasing, enhancing, or stimulating an immune response or function in a subject in need thereof.

In another aspect, provided herein are uses of the antibodies of any of the preceding aspects in the manufacture of a medicament for reducing shedding of MIC. In another aspect, provided herein are uses of the antibodies of the preceding aspects in the manufacture of a medicament for reducing levels of soluble MIC. In another aspect, provided herein are uses of the antibodies of the preceding aspects in the manufacture of a medicament for reducing shedding of MIC and levels of soluble MIC.

In another aspect, provided herein are uses of the antibodies of the preceding aspects in the manufacture of a medicament for treating or delaying progression of a cancer in a subject in need thereof. In embodiments of this aspect, the cancer may be epithelial cancer, non-small cell lung cancer, small cell lung cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphomas, myelomas, mycoses fungoids, Merkel cell cancer, or other hematologic malignancies.

In another aspect, provided herein are uses of the antibodies of the preceding aspects in the manufacture of a medicament for treating or delaying progression of an immune related disease in a subject in need thereof. In some embodiments of this aspect, the immune related disease is associated with a NKG2D ligand. In further embodiments, the NKG2D ligand is MIC. In other embodiments of this aspect, the immune related disease is selected from the group consisting of unresolved acute infection, chronic infection, and tumor immunity.

In another aspect, provided herein are uses of the antibodies of the preceding aspects in the manufacture of a medicament for increasing, enhancing, or stimulating an immune response or function in a subject in need thereof.

In another aspect, provided herein are methods of reducing shedding of MIC in an individual comprising administering to the individual an effective amount of the antibody of any of the preceding aspects to reduce shedding of MIC. In another aspect, provided herein are methods of reducing levels of soluble MIC in an individual comprising administering to the individual an effective amount of the antibody of any of the preceding aspects to reduce levels of soluble MIC. In another aspect, provided herein are methods of reducing shedding of MIC and reducing levels of soluble MIC in an individual comprising administering to the individual an effective amount of the antibody of any of the preceding aspects to reduce shedding of MIC and levels of soluble MIC.

In another aspect, provided herein are methods for treating or delaying progression of a cancer in a subject, the method comprising administering to the subject an effective amount of the antibody of any of the preceding aspects, thereby treating or delaying the progression of the cancer in the subject. In embodiments of this aspect, the cancer may be epithelial cancer, non-small cell lung cancer, small cell lung cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphomas, myelomas, mycoses fungoids, Merkel cell cancer, and other hematologic malignancies.

In another aspect, provided herein are methods for treating or delaying progression of an immune related disease in a subject, the method comprising administering to the subject an effective amount of the antibody of any of the preceding aspects, thereby treating or delaying the progression of the immune related disease in the subject. In some embodiments of this aspect, the immune related disease is associated with a NKG2D ligand. In further embodiments, the NKG2D ligand is MIC. In other embodiments of this aspect, the immune related disease is selected from the group consisting of unresolved acute infection, chronic infection, and tumor immunity.

In another aspect, provided herein are methods of increasing, enhancing, or stimulating an immune response or function in a subject, the comprising administering to the subject an effective amount of the antibody of any of the preceding aspects, thereby of increasing, enhancing, or stimulating an immune response or function in the subject.

In certain embodiments of the above methods for reducing shedding of MIC in an individual, treating or delaying progression of a cancer, treating or delaying progression of an immune related disease, or increasing, enhancing or stimulating an immune response of function in a subject, the methods further comprise administering to the subject a PD-1 axis binding antagonist. In some embodiments, the PD-1 axis binding antagonist is administered prior to or subsequent to the administration of the antibody. In other embodiments, the PD-1 axis binding antagonist is administered concurrently with the antibody. The PD-1 axis binding antagonist of these embodiments may be a PD-1 binding antagonist, a PD-L1 binding antagonist, or a PD-L2 binding antagonist.

In some embodiments, the PD-1 binding antagonist inhibits the binding of PD-1 to its ligand binding partners. The PD-1 binding antagonist may inhibit the binding of PD-1 to PD L1, inhibit the binding of PD-1 to PD L2, or inhibit the binding of PD-1 to both PD-L1 and PD-L2. In some embodiments, the PD-1 binding antagonist is an anti-PD-1 antibody, such as MDX 1106 (nivolumab), MK-3475 (pembrolizumab), CT-011 (pidilizumab), MEDI-0680 (AMP-514), PDR001, REGN2810, BGB-108, and BGB-A317.

In some embodiments, the PD-1 axis binding antagonist is a PD-L1 binding antagonist. The PD-L1 binding antagonist may inhibit the binding of PD-L1 to PD-1, inhibit the binding of PD-L1 to B7-1, or inhibit the binding of PD-L1 to both PD-1 and B7-1. In some embodiments, the PD-L1 binding antagonist is an anti-PD-L1 antibody, such as MPDL3280A (atezolizumab), YW243.55.S70, MDX-1105, MEDI4736 (durvalumab), and MSB0010718C (avelumab). In preferred embodiments, the anti-PD-L1 antibody is MPDL3280A.

In some embodiments, the PD-1 axis binding antagonist is a PD-L2 binding antagonist. IN some embodiments, the PD-L2 binding antagonist is anti-PD-L2 antibody. In other embodiments, the PD-L2 binding antagonist is an immunoadhesin.

In certain embodiments of the above methods for reducing shedding of MIC in an individual, treating or delaying progression of a cancer, treating or delaying progression of an immune related disease, or increasing, enhancing or stimulating an immune response of function in a subject, the methods further comprise administering to the subject an agent that decreases or inhibits one or more additional inhibitory co-stimulatory receptors. In some embodiments, the one or more additional inhibitory co-stimulatory receptor is selected from the group consisting of PD-1, CTLA-4, LAG3, TIM3, BTLA, VISTA, B7H4, and MM.

In certain embodiments of the above methods for reducing shedding of MIC in an individual, treating or delaying progression of a cancer, treating or delaying progression of an immune related disease, or increasing, enhancing or stimulating an immune response of function in a subject, the methods further comprise administering to the subject an additional therapeutic agent. In some embodiments, wherein the additional therapeutic agent is a chemotherapeutic agent.

In certain embodiments of the above methods for reducing shedding of MIC in an individual, treating or delaying progression of a cancer, treating or delaying progression of an immune related disease, or increasing, enhancing or stimulating an immune response of function in a subject, the antibody of the preceding aspects is administered parenterally, intrapulmonarily, intranasally, intramuscularly, intravenously, intraarterially, intraperitoneally, or subcutaneously.

In certain embodiments of the above methods for reducing shedding of MIC in an individual, treating or delaying progression of a cancer, treating or delaying progression of an immune related disease, or increasing, enhancing or stimulating an immune response of function in a subject, the subject is a human.

In another aspect, provided herein are kits comprising the antibody of any of the preceding aspects and a package insert comprising instructions for using the antibody for treating or delaying progression of a cancer in a subject. In another aspect, provided herein are kits comprising the antibody of any of the preceding aspects and a package insert comprising instructions for using the antibody for treating or delaying progression of an immune related disease in a subject. In another aspect, provided herein are kits comprising the antibody of any of the preceding aspect and a package insert comprising instructions for increasing, enhancing, or stimulating an immune response or function in a subject. In certain embodiments of the instructions of the kits of the preceding aspects, the subject is a human.

In another aspect, provided herein are methods of mapping an epitope of an antibody comprising substituting an unglycosylated amino acid of a polypeptide to generate a glycosylated polypeptide comprising a substituted glycosylated amino acid; determining whether the antibody binds to the glycosylated polypeptide; and identifying at least one of the unglycosylated amino acid or surface-exposed amino acids within 5 Angstroms of the unglycosylated amino acid as part of the epitope if binding of the antibody to the glycosylated polypeptide is reduced compared to binding of the antibody to the polypeptide without the substituted glycosylated amino acid.

In another aspect, provided herein are methods of mapping an epitope of an antibody comprising substituting an unglycosylated amino acid of a polypeptide to generate a glycosylated polypeptide comprising a substituted glycosylated amino acid; and determining whether the antibody binds to the glycosylated polypeptide, wherein at least one of the unglycosylated amino acid or surface-exposed amino acids within 5 Angstroms of the unglycosylated amino acid is identified as part of the epitope if binding of the antibody to the glycosylated polypeptide is reduced compared to binding of the antibody to the polypeptide without the substituted glycosylated amino acid.

In another aspect, provided herein are methods of mapping an epitope of an antibody comprising identifying at least one of an unglycosylated amino acid or surface-exposed amino acids within 5 Angstroms of the unglycosylated amino acid as part of the epitope if binding of the antibody to a glycosylated polypeptide comprising a substituted glycosylated amino acid is reduced compared to binding of the antibody to a polypeptide without the substituted glycosylated amino acid, wherein the glycosylated polypeptide is generated by substituting an unglycosylated amino acid of the polypeptide.

In some embodiments of the preceding methods for mapping an epitope, substituting an unglycosylated amino acid of a polypeptide comprises introducing a glycosylation site in the polypeptide. In some embodiments of any of the preceding methods for mapping an epitope, the epitope is a conformational epitope. In some embodiments of any of the preceding methods for mapping an epitope, the epitope is a linear epitope. In some embodiments of any of the preceding methods for mapping an epitope, the unglycosylated amino acid is on the surface of the polypeptide without the substituted glycosylated amino acid. In some embodiments of any of the preceding methods for mapping an epitope, the substituted glycosylated amino acid comprises an N-linked glycan. In some embodiments of any of the preceding methods for mapping an epitope, the polypeptide comprises a Fc domain. In some embodiments of any of the preceding methods for mapping an epitope, binding of antibody to the glycosylated polypeptide is detected by ELISA. In some embodiments of the method for mapping an epitope, binding of the antibody to the glycosylated polypeptide is reduced by at least 50% compared to binding of the antibody to the polypeptide without the substituted glycosylated amino acid.

In another aspect, provided herein are methods for binning antibodies comprising mapping the epitope of a first antibody by the preceding methods described herein; mapping the epitope of a second antibody by the methods described herein; and determining that the first antibody and the second antibody are in the same bin if they have the same epitope.

In another aspect, provided herein are methods for identifying the contact amino acids of an antibody comprising substituting an unglycosylated amino acid of a polypeptide to generate a glycosylated polypeptide comprising a substituted glycosylated amino acid; determining whether the antibody binds to the glycosylated polypeptide; and identifying at least one of the unglycosylated amino acid or surface-exposed amino acids within 5 Angstroms of the unglycosylated amino acid as one of the contact amino acids of the antibody if binding of the antibody to the glycosylated polypeptide is reduced compared to binding of the antibody to the polypeptide without the substituted glycosylated amino acid.

In another aspect, provided herein are methods for identifying the contact amino acids of an antibody comprising substituting an unglycosylated amino acid of a polypeptide to generate a glycosylated polypeptide comprising a substituted glycosylated amino acid; and determining whether the antibody binds to the glycosylated polypeptide, wherein at least one of the unglycosylated amino acid or surface-exposed amino acids within 5 Angstroms of the unglycosylated amino acid is identified as one of the contact amino acids of the antibody if binding of the antibody to the glycosylated polypeptide is reduced compared to binding of the antibody to the polypeptide without the substituted glycosylated amino acid.

In another aspect, provided herein are methods for identifying the contact amino acids of an antibody comprising identifying at least one of an unglycosylated amino acid or surface-exposed amino acids within 5 Angstroms of the unglycosylated amino acid as one of the contact amino acids of the antibody if binding of the antibody to a glycosylated polypeptide comprising a substituted glycosylated amino acid is reduced compared to binding of the antibody to a polypeptide without the substituted glycosylated amino acid, wherein the glycosylated polypeptide is generated by substituting an unglycosylated amino acid of the polypeptide.

In another aspect, provided herein are antibody of any of the preceding aspects, wherein the epitope is mapped by any of the methods of epitope mapping of the preceding aspects.

In another aspect, provided herein are antibodies that specifically binds to human MICA*008, wherein the antibody binds to an epitope on human MICA*008 comprising one or more amino acid residues selected from the group consisting of Glu215, Gly243, His248, Arg279, Arg213, Ser214, Ala216, Ser217, Asn220, Arg271, Arg240, Gln241, Asp242, Val244, Ser245, Thr281, Ser247, Asp249, Thr250, Trp253, Glu276, Glu277, and Gln278 of human MICA*008. In some embodiments, the antibody binds to an epitope on human MICA*008 comprising a first amino acid residue, a second amino acid residue, and a third amino acid residue; wherein the first amino acid residue is selected from the group consisting of Glu215, Arg213, Ser214, Ala216, Ser217, Asn220, and Arg271 of human MICA*008; the second amino acid residue is selected from the group consisting of His248, Ser247, Asp249, Thr250, and Trp253 of human MICA*008; and the third amino acid residue is selected from the group consisting of Arg279, Arg240, Gln241, Asp242, Gly243, Glu276, Glu277, Gln278, and Thr281 of human MICA*008. In some embodiments, the antibody binds to an epitope on human MICA*008 comprising a first amino acid residue and a second amino acid residue; wherein the first amino acid residue is selected from the group consisting of Gly243, Arg240, Gln241, Asp242, Val244, Ser245, Arg279, and Thr281 of human MICA*008; and the second amino acid residue is selected from the group consisting of Arg279, Arg240, Gln241, Asp242, Gly243, Glu276, Glu277, Gln278, and Thr281 of human MICA*008. In other embodiments, the antibody binds to an epitope on human MICA*008 comprising a first amino acid residue and a second amino acid residue; wherein the first amino acid residue is selected from the group consisting of His248, Ser247, Asp249, Thr250, or Trp253 of human MICA*008; and the second amino acid residue is selected from the group consisting of Arg279, Arg240, Gln241, Asp242, Gly243, Glu276, Glu277, Gln278, and Thr281 of human MICA*008. In still other embodiments, the antibody binds to an epitope on human MICA*008 comprising amino acid residues selected from the group consisting of His248, Ser247, Asp249, Thr250, and Trp253 of human MICA*008. In still other embodiments, the antibody binds to an epitope on human MICA*008 comprising amino acid residues selected from the group consisting of Arg279, Arg240, Gln241, Asp242, Gly243, Glu276, Glu277, Gln278, and Thr281 of human MICA*008.

In another aspect, provided herein are antibodies that specifically binds to human MICA*008, wherein the antibody binds to an epitope on human MICA*008 comprising one or more amino acid residues selected from the group consisting of Gly243, Arg240, Gln241, Asp242, Val244, Ser245, Arg 279, and Thr281 of human MICA*008.

In some embodiments, the antibody binds to an epitope on human MICA*008 comprising a first amino acid residue, and a second amino acid residue, wherein the first residue is selected from the group consisting of: Gly243, Arg240, Gln241, Asp242, Val244, Ser245, Arg 279, and Thr281 of human MICA*008, and the second residue is selected from the group consisting of Arg 279, Arg279, Arg240, Gln241, Asp242, Gly243, Glu276, Glu277, Gln278, and Thr281 of human MICA*008.

In another aspect, provided herein are antibodies that specifically binds to human MICA*008, wherein the antibody binds to an epitope on human MICA*008 comprising one or more amino acid residues selected from the group consisting of Arg240, Gln241, Val244, Ser245, His248, Glu276, Arg279, Tyr283, Glu285, His290, and Thr292 of human MICA*008.

In another aspect, provided herein are antibodies that specifically binds to human MICA*008, wherein the antibody binds to an epitope on human MICA*008 comprising one or more amino acid residues selected from the group consisting of Arg240, Gln241, Asp242, Gly243, Val244, Ser245, Leu246, Ser247, Asp249, Thr250, Arg279, Tyr283, His290, Ser291, Thr292, and Pro294 of human MICA*008.

In another aspect, provided herein are antibodies that specifically binds to human MICA*008, wherein the antibody binds to an epitope on human MICA*008 comprising one or more amino acid residues selected from the group consisting of Arg240, Asp242, Gly243, Val244, Glu277, Gln278, Arg279, Phe280, Thr281, Tyr283, Glu285, Gly288, Asn289, His290, Ser291, Thr292, Pro294, Val295, Pro296, and Ser297 of human MICA*008.

In another aspect, provided herein are antibodies that specifically binds to human MICA*008, wherein the antibody binds to an epitope on human MICA*008 comprising one or more amino acid residues selected from the group consisting of Asn234, Ile235, Ile236, Leu237, Thr238, Trp239, and Arg240 of human MICA*008.

In another aspect, provided herein are antibodies that specifically binds to human MICA*008, wherein the antibody binds to an epitope on human MICA*008 comprising one or more amino acid residues selected from the group consisting of Val268, Ala269, Thr270, Arg271, Ile272, Cys273, Arg274, Gly275, Glu276, Glu277, Gln278, Arg279, and Phe280 of human MICA*008.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE FIGURES

FIG. 1A-FIG. 1L: Amino acid sequences of variable regions of anti-MIC antibodies. Heavy chain HVR-H1, -H2, and -H3, and light chain HVR-L1, -L2, and -L3 sequences are marked Amino acid positions are numbered according to the Kabat numbering system as described herein. FIG. 1A: 3C9.10; FIG. 1B: 9C9.5.6; FIG. 1C: 1E6.1.3; FIG. 1D: 7A3.1.9; FIG. 1E: 6E12.5; FIG. 1F: 6E1.1.12; FIG. 1G: 7D4.6; FIG. 1H: 2E5.2.3; FIG. 1-I: 20G11; FIG. 1-J: 32D2; FIG. 1K: 3E11; FIG. 1L: 6F8.7.

FIG. 2 shows MICA/B alpha3 domain alignment, % identity, and % similarity.

FIG. 3A: Bin 1 (3C9.10) epitope maps to "bottom" of MICA. FIG. 3B: Bin 2 (6F8, 7D4, 32D2, and 3E11) epitope maps to "bottom and front" of MICA. FIG. 3C: Bin 3 (9C9.5.6, 1E6.1.3, 7A3.1.9) epitope maps to "bottom and side" of MICA. FIG. 3D: Bin 4 (6E12.5) epitope maps to "side" of MICA. FIG. 3E: Bin 5: 20G11 epitope maps to "front" of MICA.

FIG. 4A shows the fluorescence response (RFU) of all glycosylation variants. FIG. 4B shows the first derivative of the melt curves for all the glycosylation variants.

FIG. 5 shows the DSF melting temperature ($T_m$) values for MICA and mIgG2a.

FIG. 6 shows a gel confirming that the Glyco mutants are glycosylated.

FIG. 7A shows the human MICA*008 residues grafted on mouse MILL1. FIG. 7B shows the non-MICA*008 residues in the MILL1 chimera.

FIG. 9 shows the fold-decrease in affinity from alanine scanning. Fold-decrease greater than 3 is shaded.

FIG. 10 shows the 2E5.2.3 epitope with Ala scan data included. Residues in black are the epitope of 2E5.2.3, while residues in gray are not. Residues not included in the epitope are based on data from Alanine scanning, engineered glycosylation site mapping, allelic differences between MICA002, 004, 008 and MICB005, since 2E5.2.3 binds all four alleles, and residues in the MICA*001 structures (PDB codes 1B3J and 1HYR) predicted to be inward facing or not have any accessible surface area using the solvent accessibility calculation program GETAREA, as described in Fraczkiewicz, R. and Braun, W. (1998) "Exact and Efficient Analytical Calculation of the Accessible Surface Areas and Their Gradients for Macromolecules" *J. Comp. Chem.*, 19, 319-333. Supporting our hypothesis that 2E5.2.3 was predicted to bind the "back" and "top" of MICA, Ala scanning of residues on the "front" showed that 2E5.2.3 did not bind to any of these resdues. This reveals that the epitope for 2E5.2.3 is not on the "front" of MICA, and is on the "back" and "top" of MICA.

FIGS. 11A-FIG. 11B compare the epitope for antibodies mapped by glycosylation engineering and Ala scan. FIG. 11A: 6F8; FIG. 11B: 7D4.

FIG. 12 provides a summary of the sequence identifiers for the anti-MIC antibodies described herein.

FIG. 13A-FIG. 13C show percent reduction of soluble MIC (sMIC) shedding caused by inhibition by titrating combinations of anti-MIC antibodies 1D5, 13A9, and 6E1, added onto cells.

FIG. 14A-FIG. 14F: Amino acid sequences of variable regions of 1D5, 13A9, 15F11, 6E1 (also called 6E1.1.12), 18G3, and 12H10 anti-MIC antibodies. Heavy chain HVR-H1 (FIG. 14A), HVR-H2 (FIG. 14B), and HVR-H3 (FIG. 14C), and light chain HVR-L1 (FIG. 14D), HVR-L2 (FIG. 14E), and HVR-L3 (FIG. 14F) sequences are marked. Amino acid positions are numbered according to the Kabat numbering system as described herein.

FIG. 15A provides the results for the HCC1534 (MICA*004) cells. FIG. 15B provides the results for the MEL-JUSO cells (MICA*008).

FIG. 16A-FIG. 16C depict percent reduction of sMIC signal caused by antibody interference by titrating combinations of anti-MIC antibodies 1D5, 13A9, and 6E1, added onto conditioned media.

FIG. 17: 52 anti-MICA antibodies were selected from all the antibody campaigns that had the highest binding affinity to MICA*008 alpha-3 domain. Binding affinity values determined by biacore were less than or equal to 10 nM, with a range of 0.5 nM to 10 nM.

FIG. 20 depicts a Glyco-engineering Epitope Mapping (GEM) method. Single N-linked glycosylation sites are created by changing one or two residues in a protein antigen to achieve the N-X-S/T motif. Multiple antigen variants that each have a unique and newly created N-linked glycosylation site are then assessed for binding activity to an antibody panel using Elisa, Biacore or Wasatch. The epitope is then defined as any site that cannot be bound when glycosylation is present, thus masking the site.

FIG. 21A depicts the location of 7 individual and uniquely engineered N-linked glycosylation sites on the 'front' of MICA*008. Also shown is an analysis of total glycosylation (% fucosylation and % afucosylation) for each glyco-engineered MICA*008 variant (FIG. 21B). FIG. 21C depicts unique epitope bins identified by the Glyco-engineering Epitope Mapping (GEM) method based on the Elisa binding characteristics of the 7 glyco-engineered MICA*008 variants to 96 anti-MICA antibodies. FIG. 21D is the crystal structure of 1D5 indicating the epitopes of the glyco-engineered MICA variants on the 'front' and 'bottom' of MICA that when blocked by anti-MICA antibodies were most effective at blocking MICA*008 shedding. G243 (location of Glyco14's G243N mutation) and R279 (location of Glyco16's R279N mutation) were the epitopes that allow the best shedding inhibition of MICA*008 by anti-MICA antibodies.

FIG. 22A-FIG. 22D depict renderings of the crystal structure of the 1D5 Fab bound to the MICA*008 $\alpha3$ domain shown from different angles, with the Fab depicted as a surface and the MICA*008 $\alpha3$ domain as a ribbon diagram. The "front face" of the MICA*008 $\alpha3$ domain, defined as the beta sheet of the Ig domain containing the carboxy-terminal strand, and the "back face" of the MICA*008 $\alpha3$ domain, defined as the beta sheet of the Ig domain containing the amino-terminal strand, are highlighted along with the amino- (N-term) and carboxy-terminals (C-term).

FIG. 23A and FIG. 23B are renderings of the crystal structure of the 1D5 Fab CDRs bound to the MICA*008 $\alpha3$ domain, shown from different angles. The MICA*008 $\alpha3$ domain is depicted as a surface with the CDRs of the 1D5 Fab as ribbons. Residues defined as part of the 1D5 paratope (within 4.5 Å of the MICA*008 $\alpha3$ domain) have their side chains shown as sticks.

FIG. 24A and FIG. 24B are open book representations of the interface between the 1D5 Fab and the MICA*008 $\alpha3$ domain, respectively, shown as surfaces. Residues in the 1D5 paratope, defined as being within 4.5 Å of the MICA*008 α3 domain, are highlighted in FIG. 24A with their residue numbers. MICA*008 α3 domain residues in the 1D5 epitope, defined as being within 4.5 Å of the 1D5 Fab, are highlighted in FIG. 24B with their residue numbers.

FIG. 27A and FIG. 27B show the MICA*008 α3 domain structure depicted as a ribbon diagram or surface representation, respectively, with the 240s loop highlighted. FIG. 27C shows the 1D5 Fab structure as a ribbon diagram with the L3 and H3 CDRs highlighted, and small residues of these CDRs such as serine and glycine indicated by residue number. The side chains of these serines are shown as sticks.

respectively, shown from different angles. Only one chain of the Fab is depicted for simplicity of viewing. The 240s loop of the MICA*008 α3 domain is highlighted. Residues of either the LC or HC CDRs defined as part of the 1D5 paratope (within 4.5 Å of the MICA*008 α3 domain) have their side chains shown as sticks.

FIG. 28A-FIG. 28D are renderings of the crystal structure of the 13A9 Fab bound to MICA*008 α3 domain shown from different angles, with the Fab depicted as a surface and the MICA*008 α3 domain as a ribbon diagram. The "front face" of the MICA*008 α3 domain, defined as the beta sheet of the Ig domain containing the carboxy-terminal strand, and the "back face" of the MICA*008 α3 domain, defined as the beta sheet of the Ig domain containing the amino-terminal strand, are highlighted along with the amino- (N-term) and carboxy-termininals (C-term).

Figure 29B:
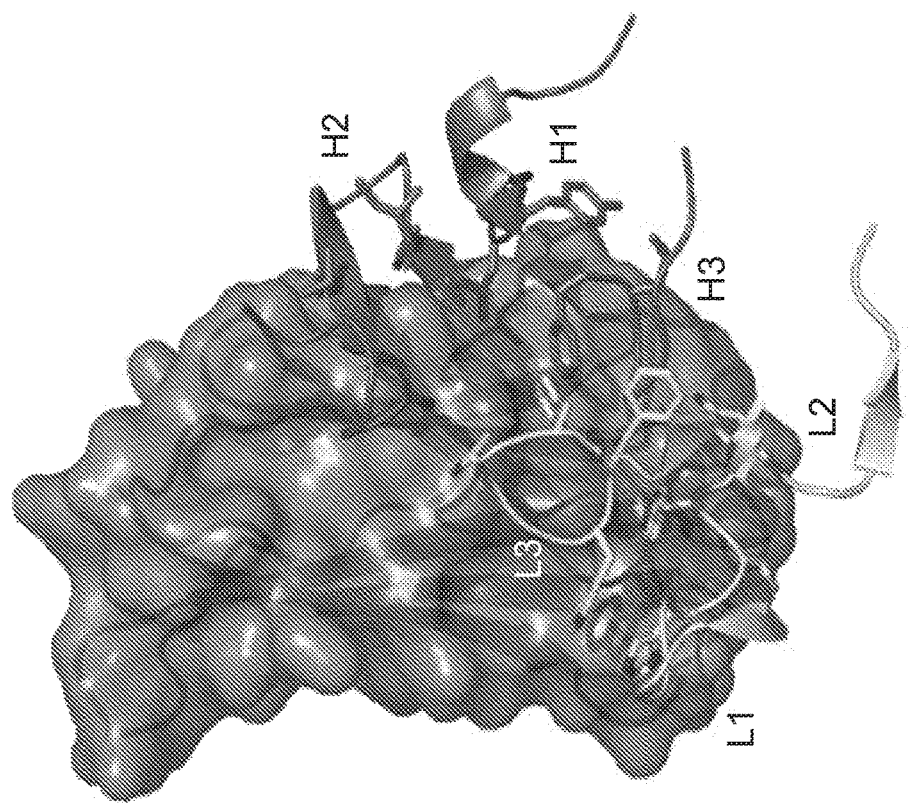
Figure 29A:
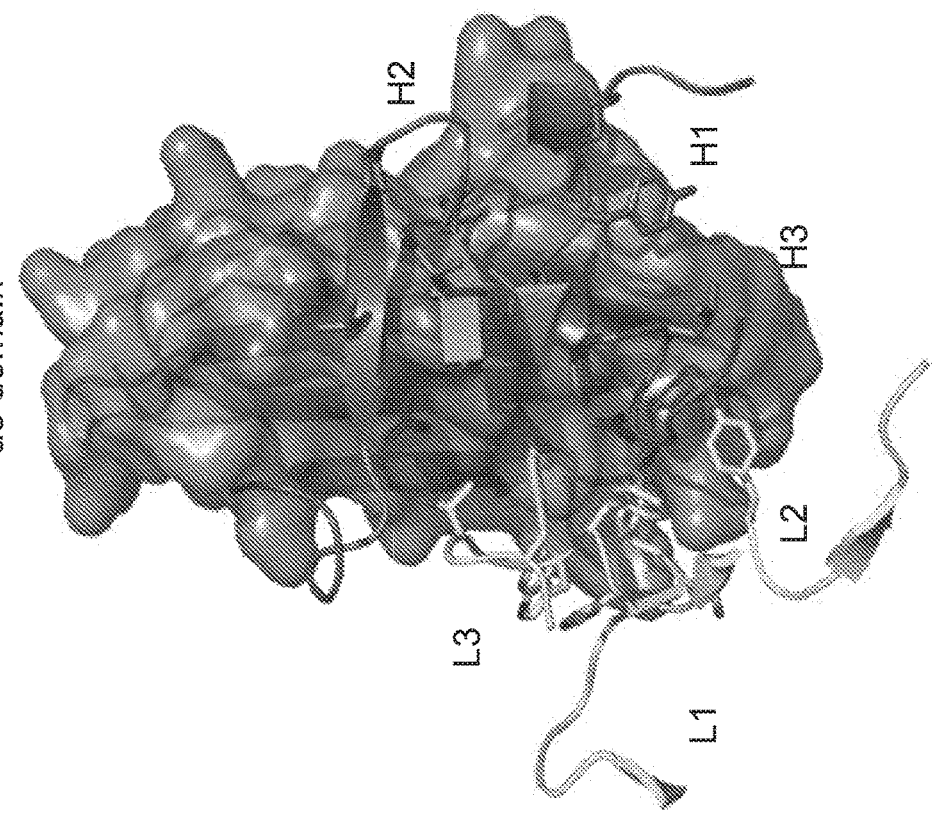

FIG. 29A and FIG. 29B are renderings of the crystal structure of the 13A9 Fab CDRs bound to the MICA*008 α3 domain, shown from different angles. The MICA*008 α3 domain is depicted as a surface with the CDRs of the 13A9 Fab as ribbon diagrams. Residues defined as part of the 13A9 paratope (within 4.5 Å of the MICA*008 α3 domain) have their side chains shown as sticks.

Figure 30A:
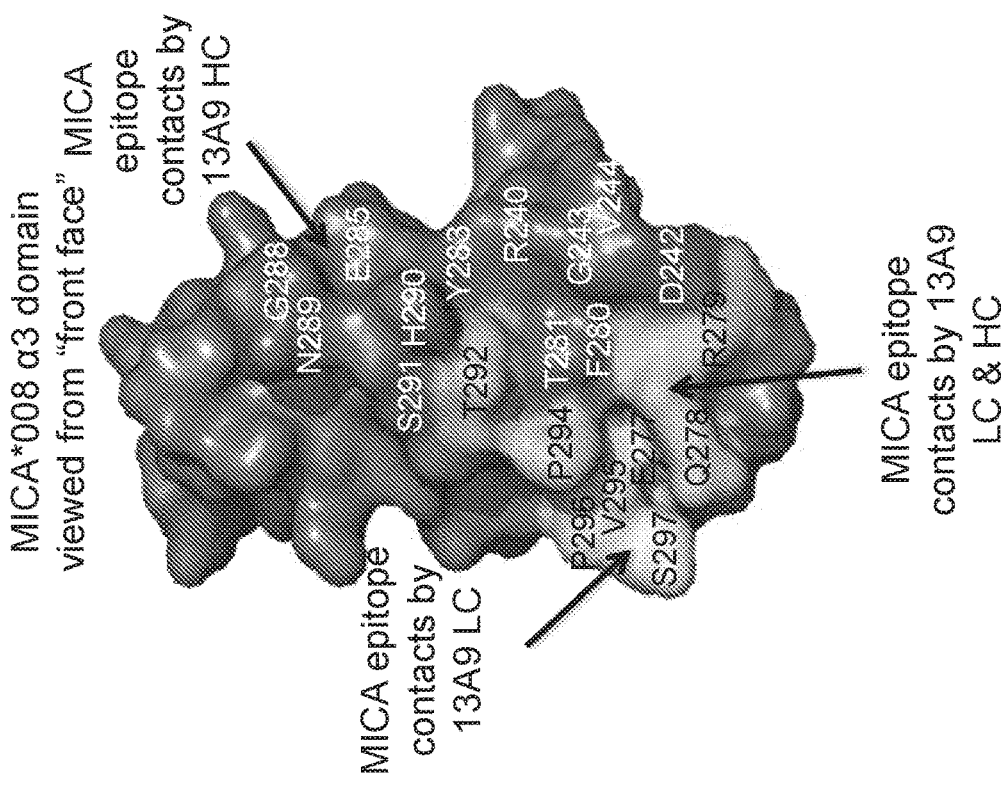
Figure 30B:
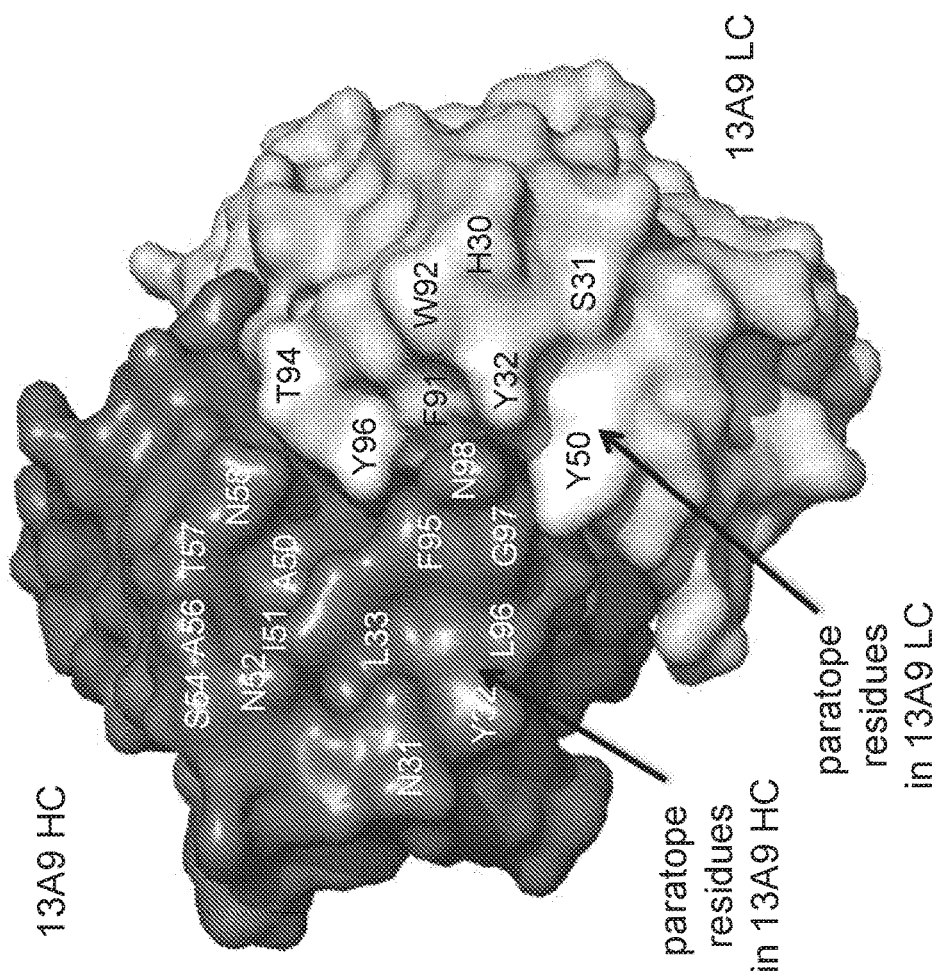
Figure 30D:
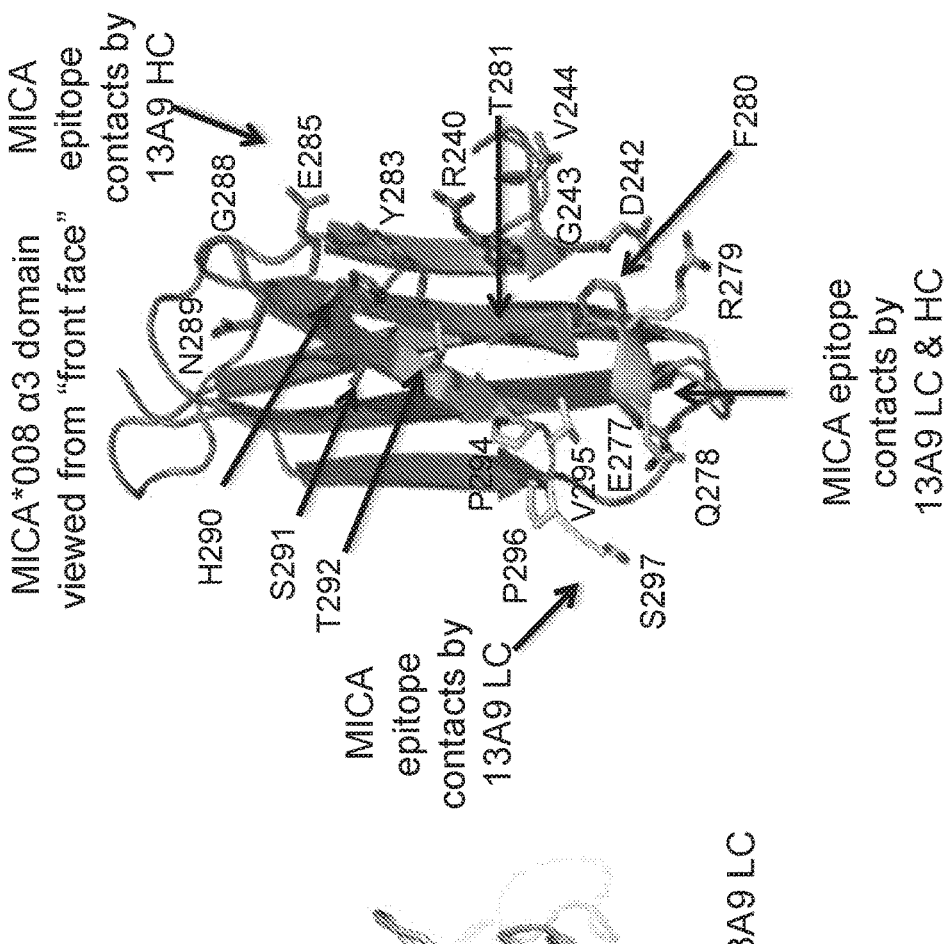
Figure 30C:
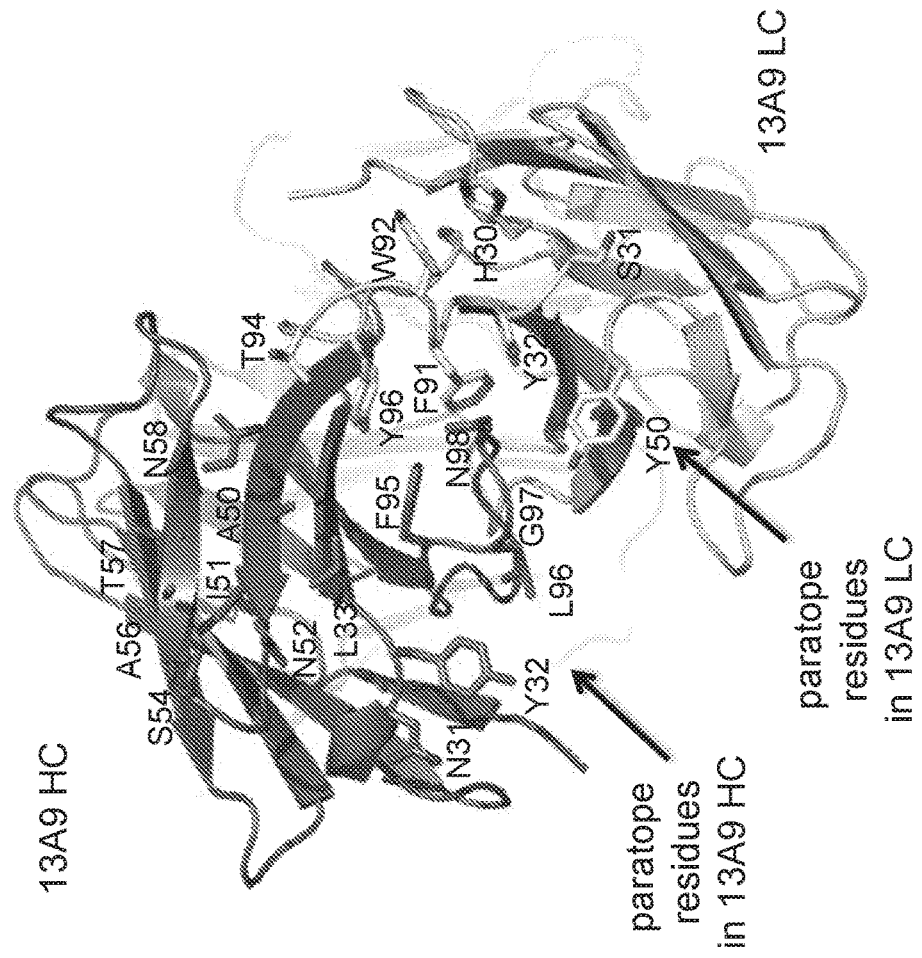

FIG. 30A-FIG. 30B are open book representations of the interface between the 13A9 Fab and the MICA*008 α3 domain, respectively, shown as surfaces. Residues in the 13A9 paratope, defined as being within 4.5 Å of the MICA*008 α3 domain, are highlighted in FIG. 30A with their residue numbers. MICA*008 α3 domain residues in the 13A9 epitope, defined as being within 4.5 Å of the 13A9 Fab, are highlighted in FIG. 30B with their residue numbers. FIG. 30C-FIG. 30D are open book representations of the interface between the 13A9 Fab and the MICA*008 α3 domain, respectively, shown as ribbon diagrams. Residues in the 13A9 paratope, defined as being within 4.5 Å of the MICA*008 α3 domain, are highlighted in FIG. 30C with their residue numbers and have their side chains shown as sticks. MICA*008 α3 domain residues in the 13A9 epitope, defined as being within 4.5 Å of the 13A9 Fab, are highlighted in FIG. 30D with their residue numbers and have their side chains shown as sticks.

Figure 31A:
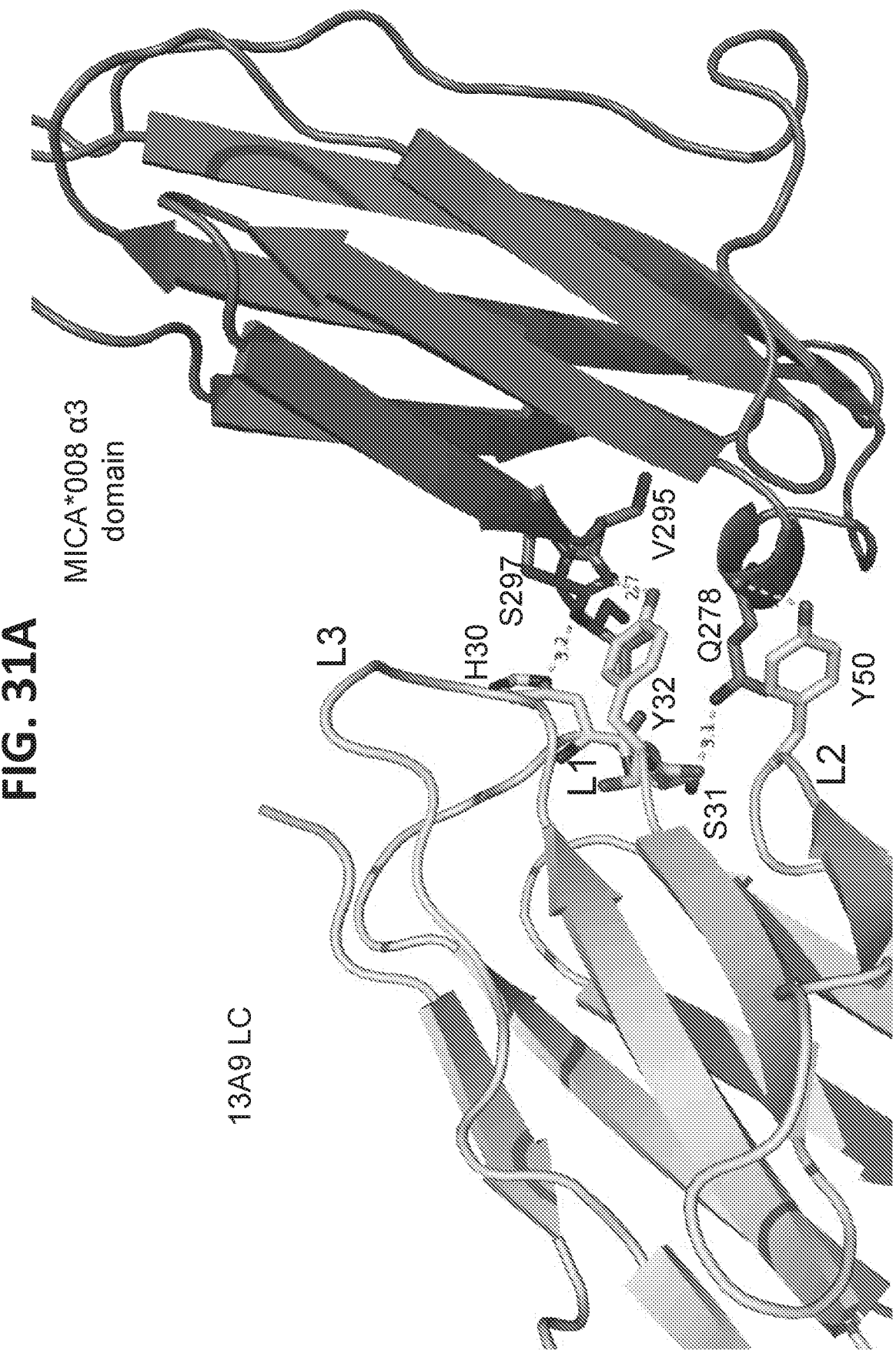
Figure 31C:
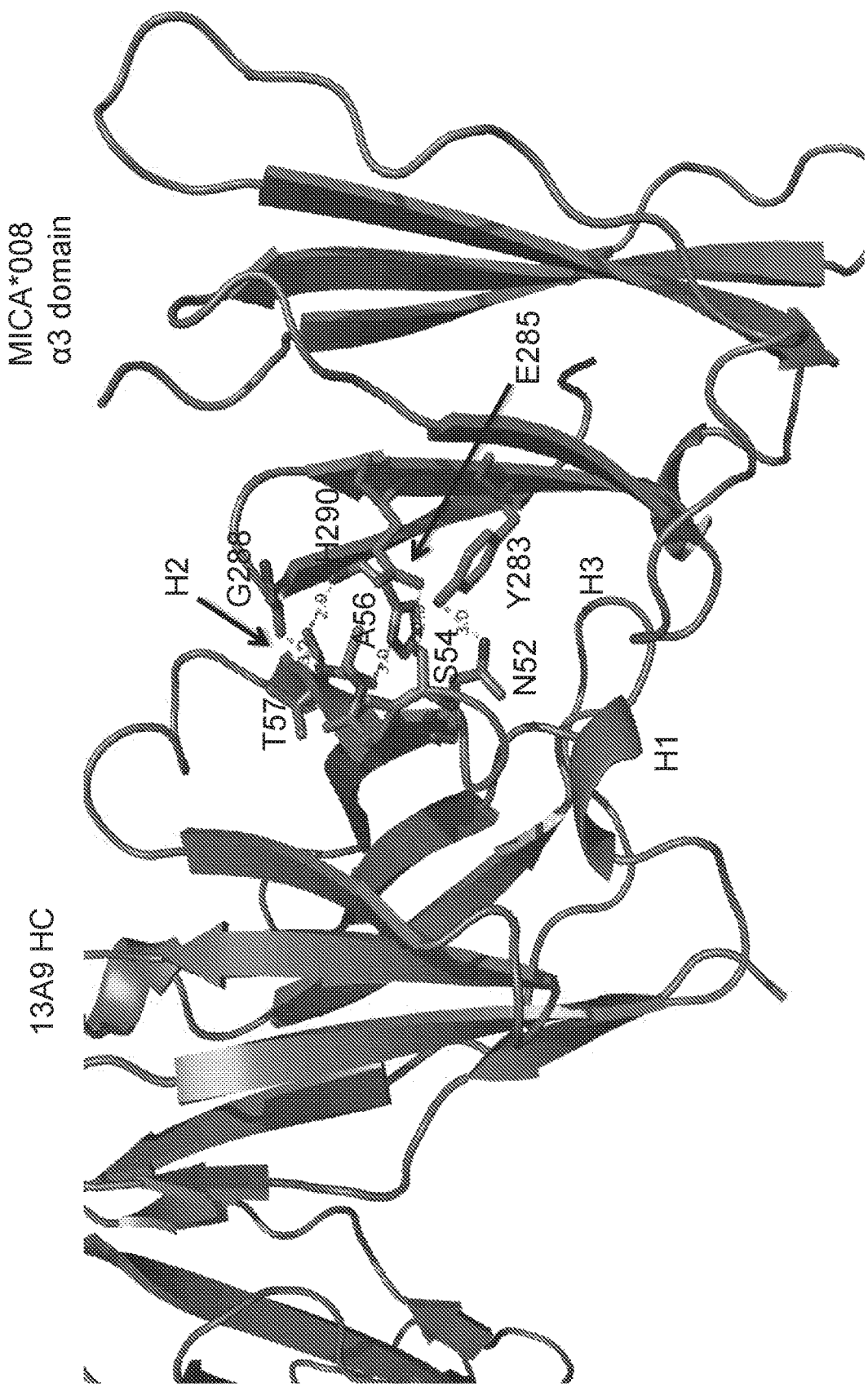
Figure 31D:
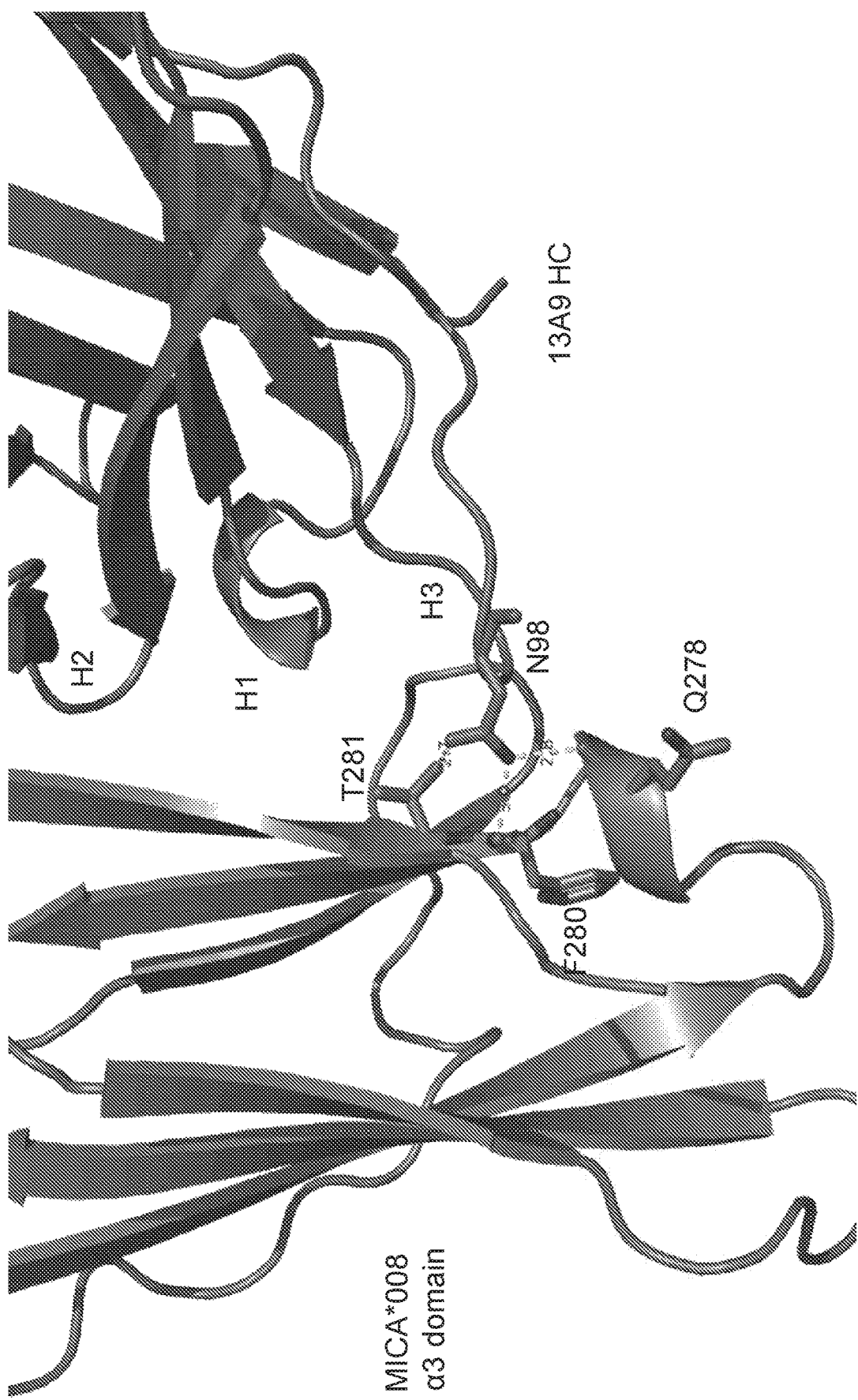

FIG. 31A highlights hydrogen bonds between residues of the LC of 13A9 and the MICA*008 α3 domain. The HC is not depicted for simplicity of viewing the LC interactions. FIG. 31B-FIG. 31D highlight hydrogen bonds between residues of the HC of 13A9 and the MICA*008 α3 domain. The LC is not depicted for simplicity of viewing the HC interactions.

FIG. 32A-FIG. 32B are open book representations of the interface between the 13A9 Fab and the MICA*008 α3 domain, respectively, shown as surfaces with electrostatic surface potentials colored as calculated in Pymol. Residues in the 13A9 paratope, defined as being within 4.5 Å of the MICA*008 α3 domain, are highlighted in FIG. 32A with their residue numbers. MICA*008 α3 domain residues in the 13A9 epitope, defined as being within 4.5 Å of the 13A9 Fab, are highlighted in FIG. 32B with their residue numbers.

Figure 33A:
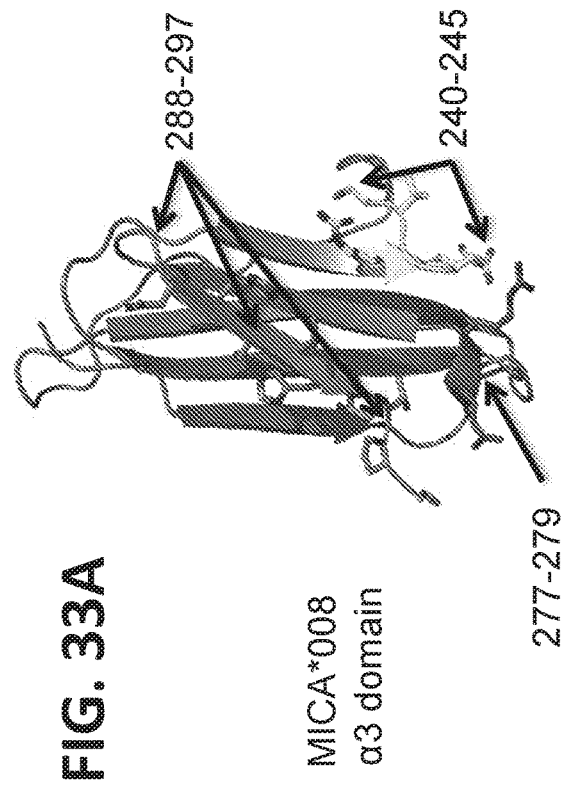
Figure 33B:
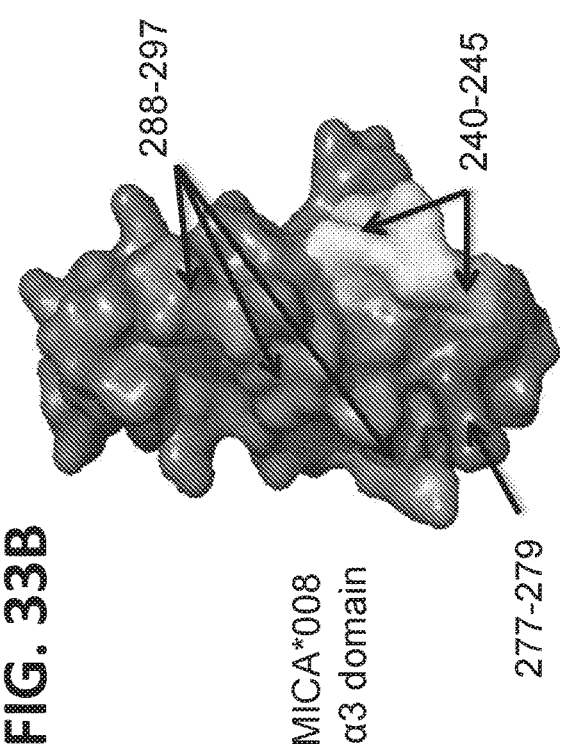
Figure 33C:
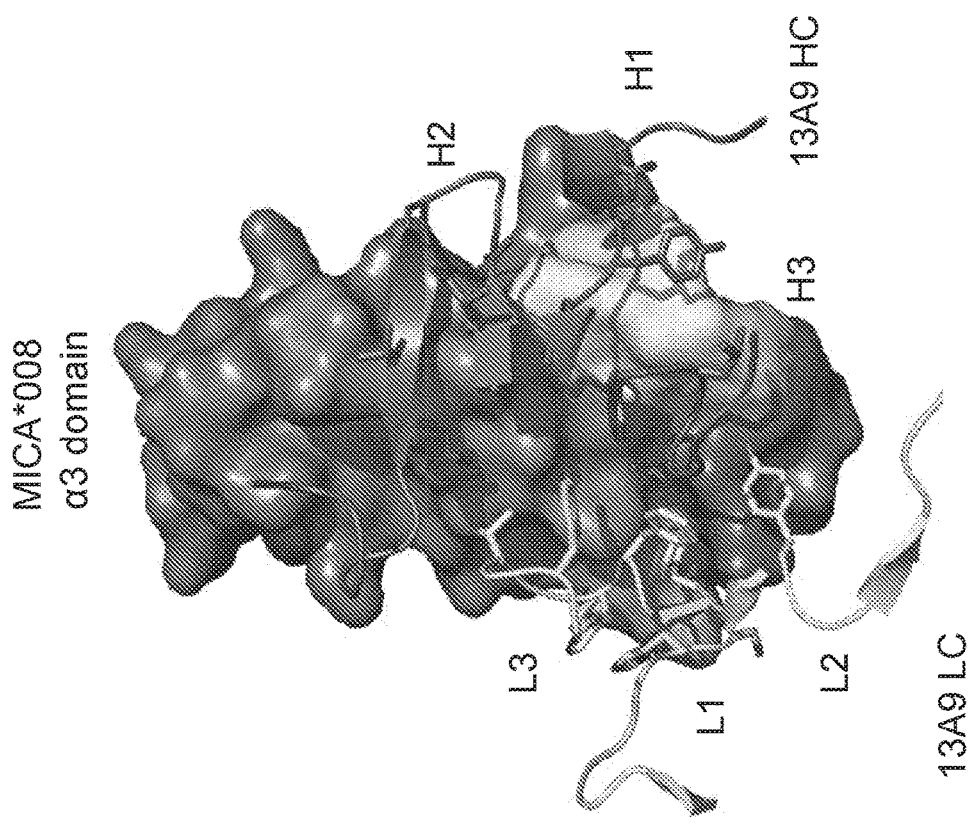
Figure 33E:
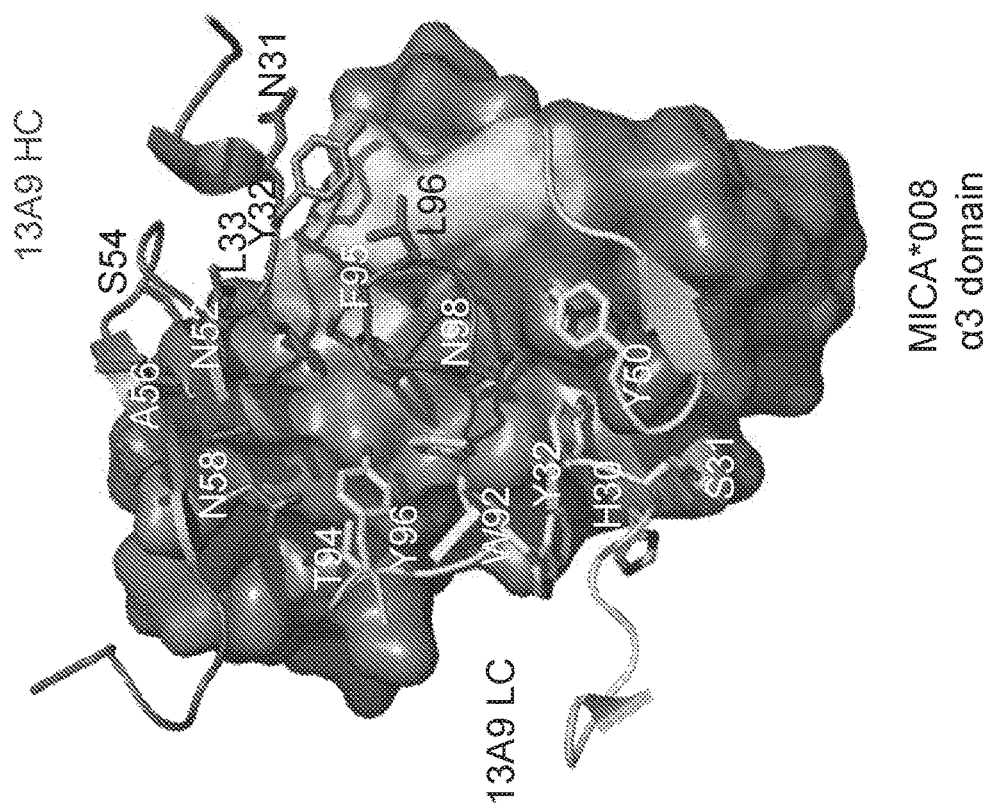
Figure 33D:
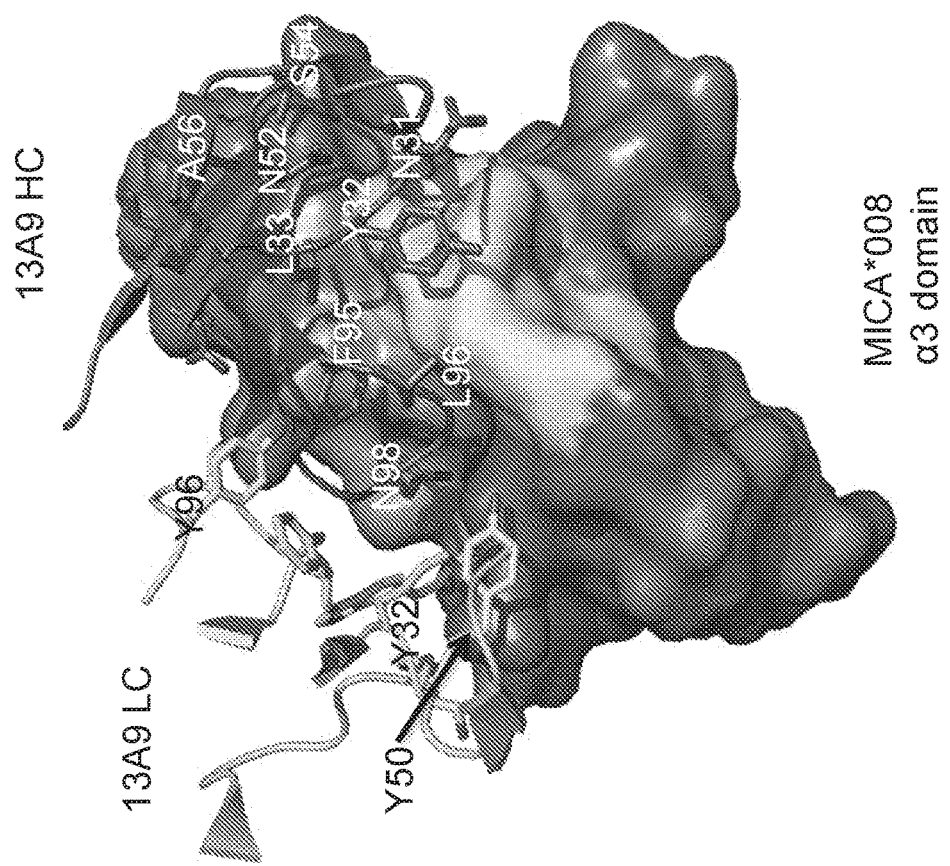

FIG. 33A and FIG. 33B show the MICA*008 α3 domain structure depicted as a ribbon diagram or surface representation, respectively, with residues 240-245, 277-279, and 288-297 highlighted to demonstrate the ridges and valley they create on the "front face" of the MICA*008 α3 domain. FIG. 33C is a rendering of the 13A9 Fab-MICA*008 α3 domain complex structure with the Fab CDRs shown as ribbon diagrams and the MICA*008 α3 domain as a surface. All six CDRs are highlighted with side chains of residues in the paratope (within 4.5 Å of the MICA*008 α3 domain) shown as sticks. Residues 240-245, 277-279, and 288-297 of the MICA*008 α3 domain are also highlighted on the MICA*008 surface to demonstrate that the 13A9 Fab binds across the ridges and valley created by these MICA*008 residues. FIG. 33D and FIG. 33E are renderings of the crystal structure of the 13A9 CDRs bound to the MICA*008 α3 domain, shown from different angles to demonstrate the shape complementarity of the ridges and valley of residues 240-245, 277-279, and 288-297 of the MICA*008 α3 domain and the side chains of the 13A9 Fab that fill the valley or span the ridges. Side chains of residues in the 13A9 paratope (within 4.5 Å of the MICA*008 α3 domain) are shown as sticks.

FIG. 34A-FIG. 34D are renderings of the crystal structure of the 6E1 (also called 6E1.1.12) Fab bound to the C273S MICA*008 α3 domain shown from different angles, with the Fab depicted as a surface and the MICA*008 α3 domain as a ribbon diagram. The "front face" of the MICA*008 α3 domain, defined as the beta sheet of the Ig domain containing the carboxy-terminal strand, and the "back face" of the MICA*008 α3 domain, defined as the beta sheet of the Ig domain containing the amino-terminal strand, are highlighted along with the amino- (N-term) and carboxy-terminals (C-term).

FIG. 35A and FIG. 35B are renderings of the crystal structure of the 6E1 Fab CDRs bound to the MICA*008 α3 domain, shown from different angles. The MICA*008 α3 domain is depicted as a surface with the CDRs of the 6E1 Fab as ribbon diagrams. Residues defined as part of the 6E1 paratope (within 4.5 Å of the MICA*008 α3 domain) have their side chains shown as sticks. It is noted that CDR L3 does not make any contact with the MICA*008 α3 domain.

Figure 36A:
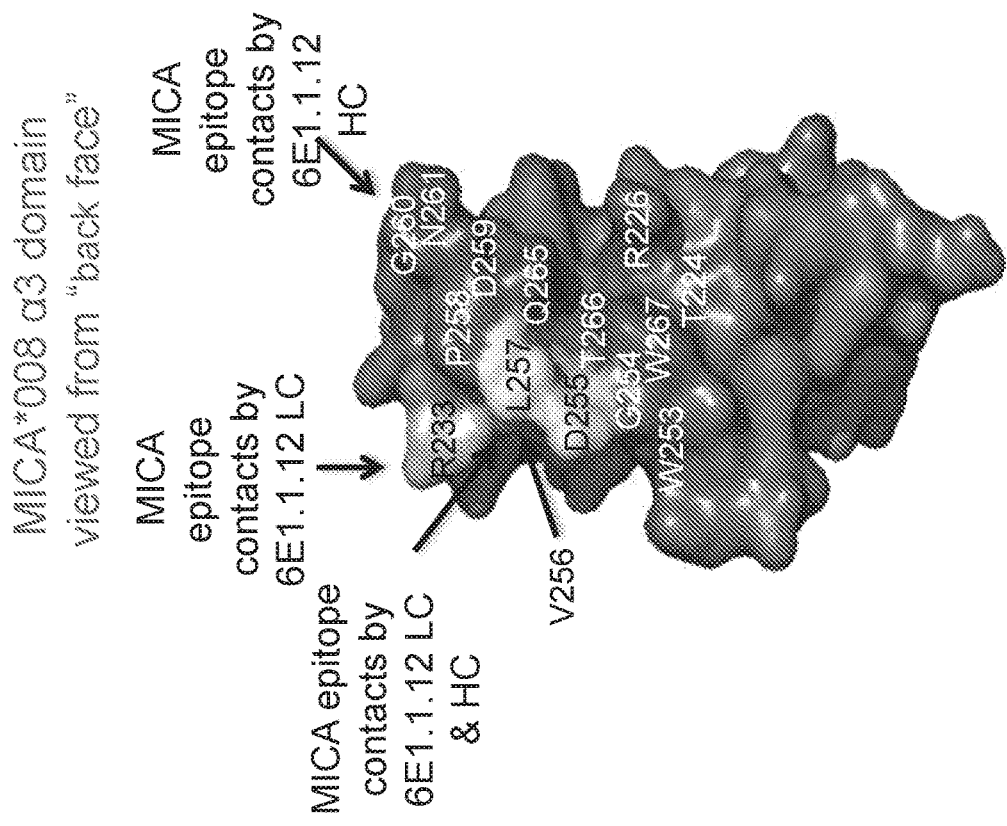
Figure 36B:
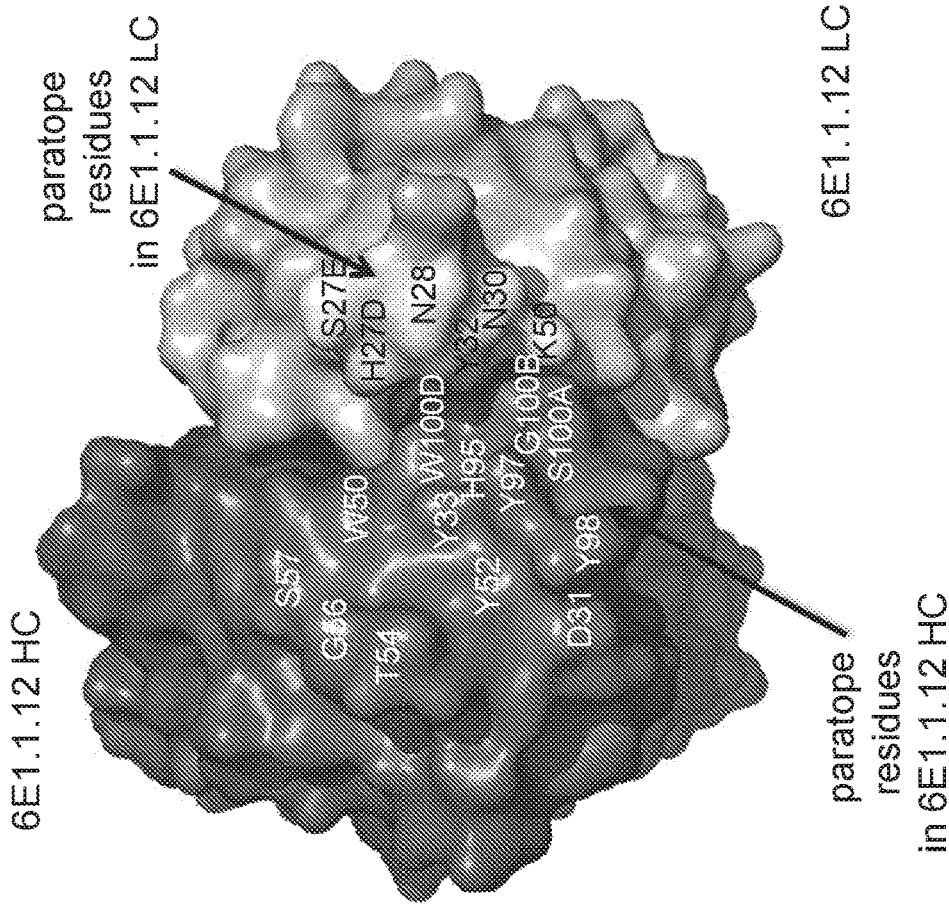

FIG. 36A and FIG. 36B are open book representations of the interface between the 6E1 Fab and the MICA*008 C273S α3 domain, respectively, shown as surfaces. Residues in the 6E1 paratope, defined as being within 4.5 Å of the MICA*008 C273S α3 domain, are highlighted in FIG. 36A with their residue numbers. MICA*008 C273S α3 domain residues in the 6E1 epitope, defined as being within 4.5 Å of the 6E1 Fab, are highlighted in FIG. 36B with their residue numbers. FIG. 36C and FIG. 36D are open book representations of the interface between the 6E1 Fab and the MICA*008 α3 domain, respectively, shown as ribbon diagrams. Residues in the 6E1 paratope, defined as being within 4.5 Å of the MICA*008 α3 domain, are highlighted in FIG. 36C with their residue numbers and have their side chains shown as sticks. MICA*008 α3 domain residues in the 6E1 epitope, defined as being within 4.5 Å of the 6E1 Fab, are highlighted in FIG. 36D with their residue numbers and have their side chains shown as sticks.

Figure 37A:
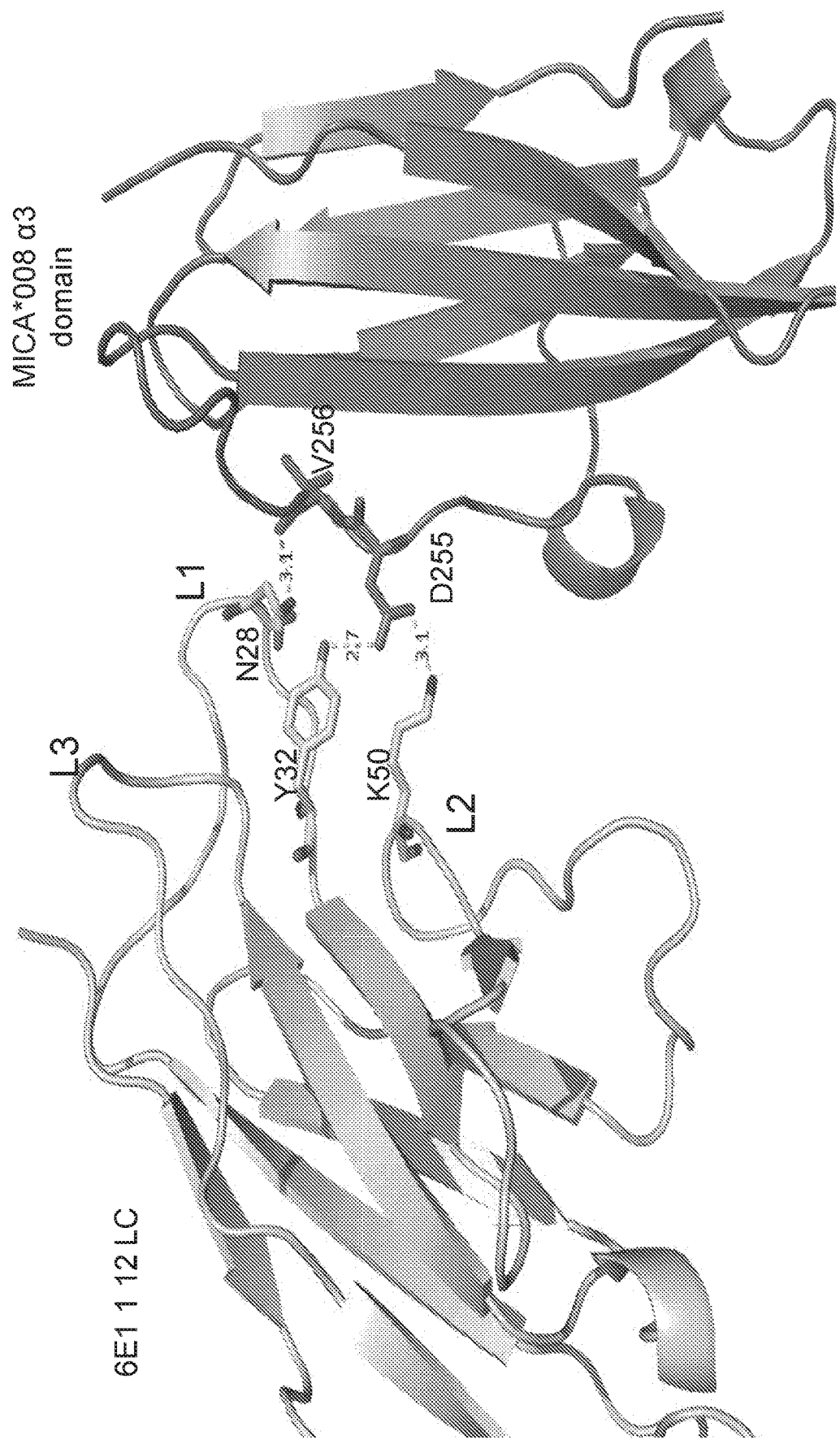
Figure 37B:
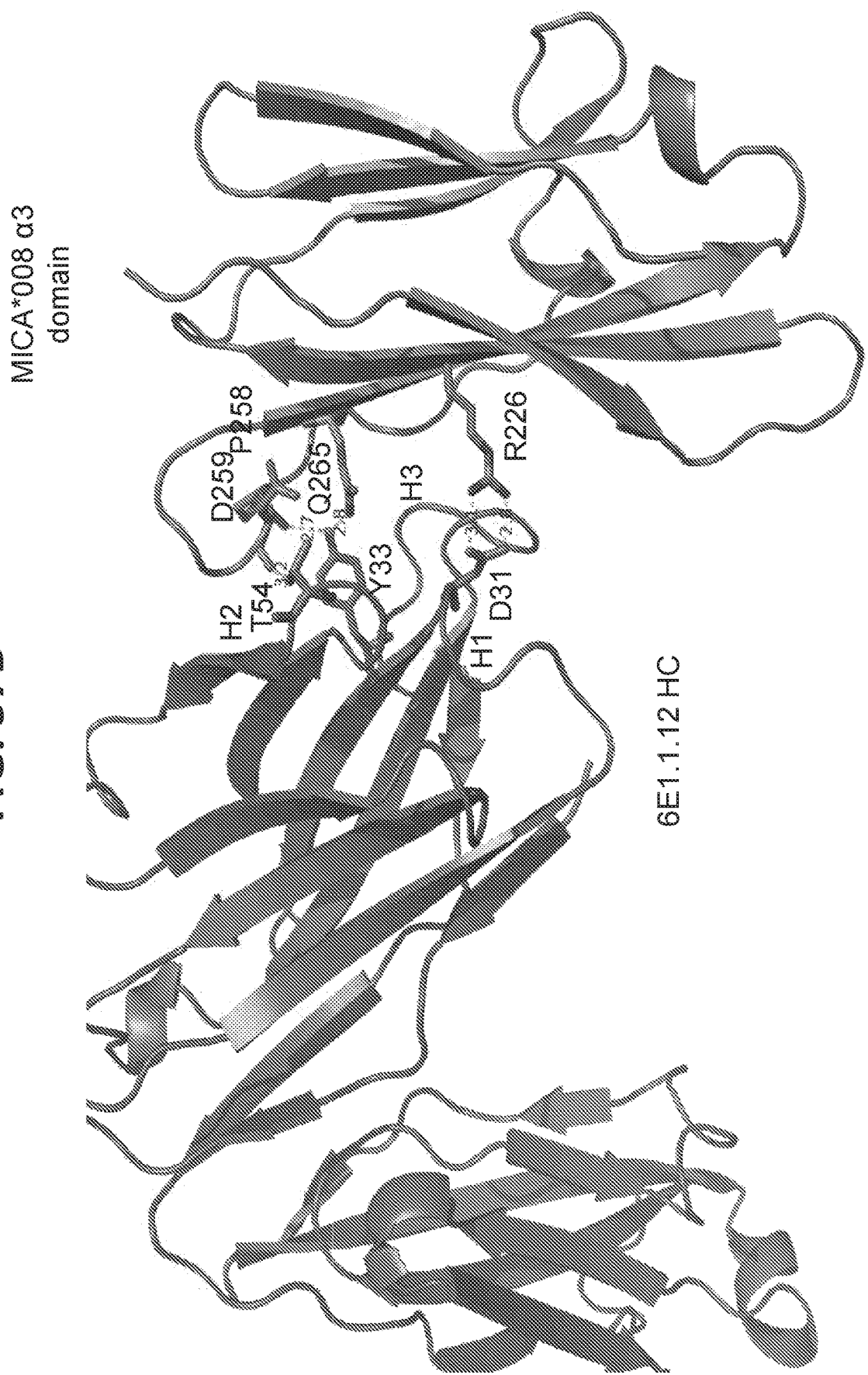
Figure 37C:

FIG. 37A highlights hydrogen bonds and salt bridges between residues of the LC of 6E1 and the MICA*008 C273S α3 domain. The HC is not depicted for simplicity of viewing the LC interactions. FIG. 37B and FIG. 37C highlight hydrogen bonds and salt bridges between residues of the HC of 6E1 and the MICA*008 C273S α3 domain. The LC is not depicted for simplicity of viewing the HC interactions.

FIG. 38A and FIG. 38B are open book representations of the interface between the 6E1 Fab and the MICA*008 C273S α3 domain, respectively, shown as surfaces with electrostatic surface potentials colored as calculated in Pymol. Residues in the 6E1 paratope, defined as being within 4.5 Å of the MICA*008 C273S α3 domain, are highlighted in 17A with their residue numbers. MICA*008 C273S α3 domain residues in the 6E1 epitope, defined as being within 4.5 Å of the 6E1 Fab, are highlighted in 17B with their residue numbers.

Figure 39B:
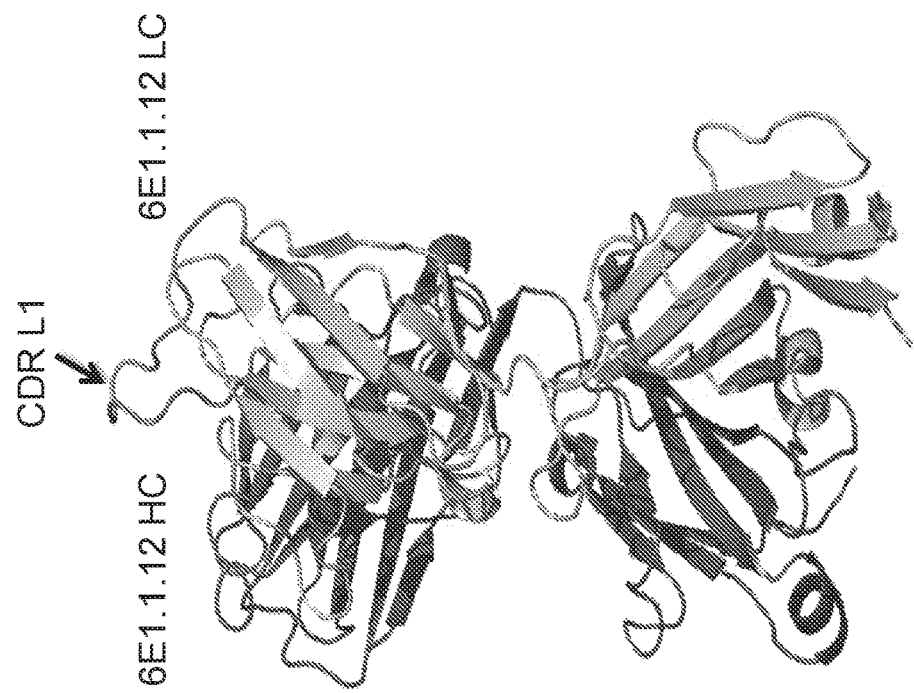
Figure 39A:
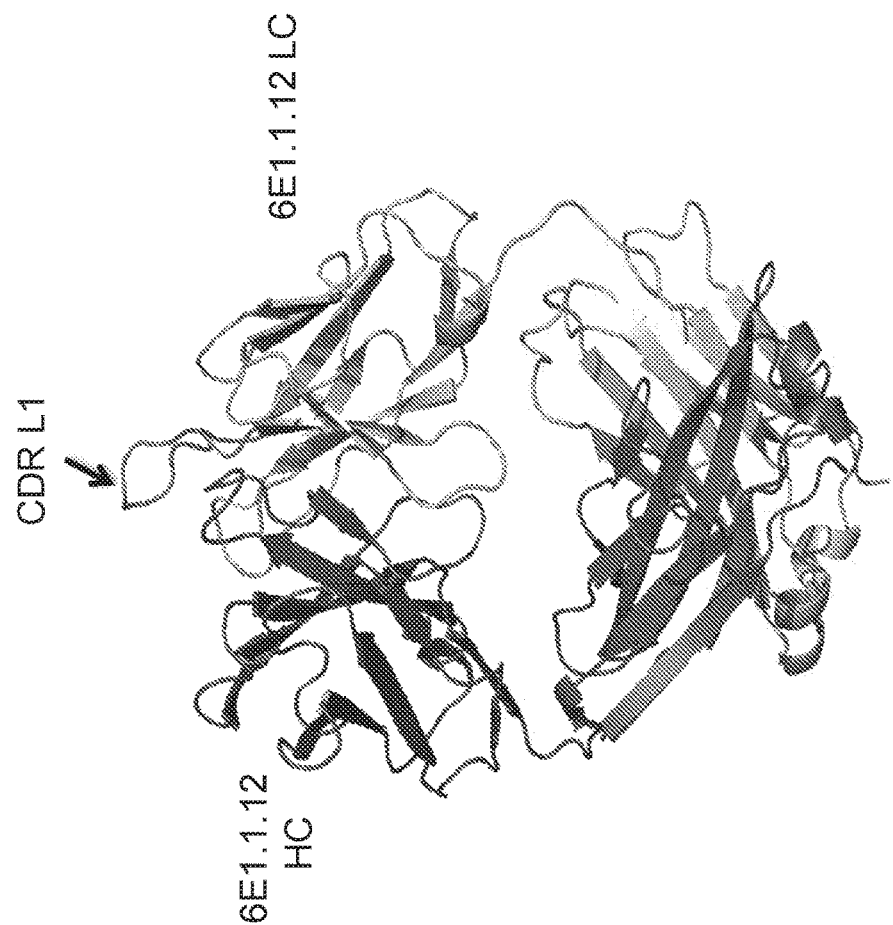
Figure 39C:
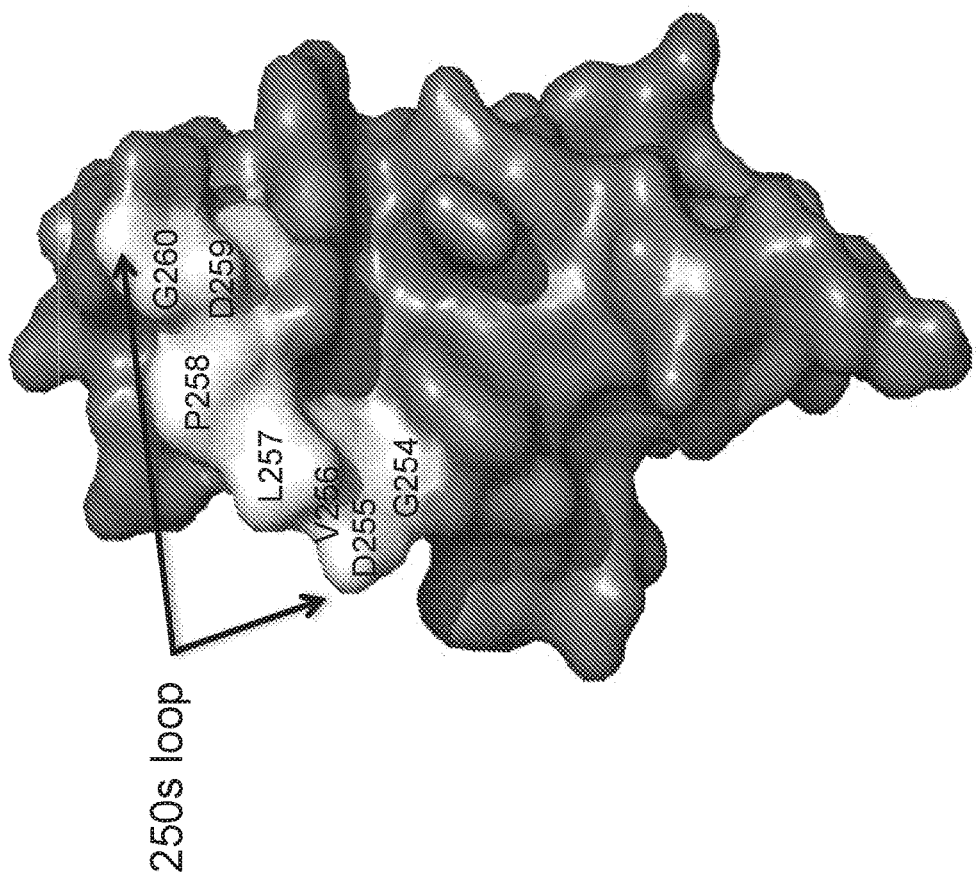
Figure 39D:
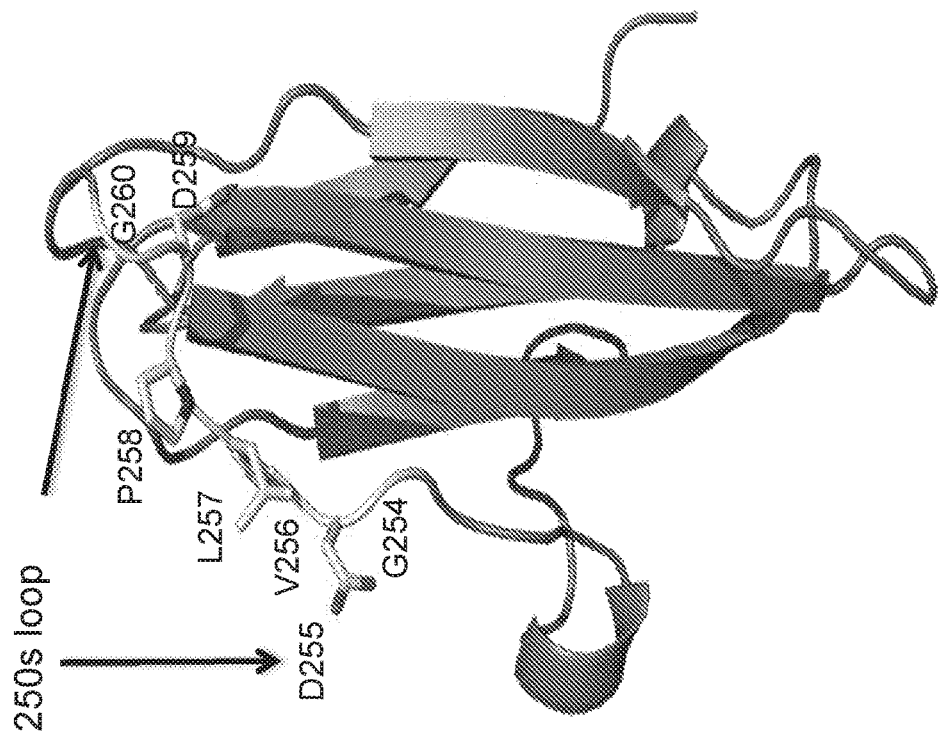
Figure 39E:
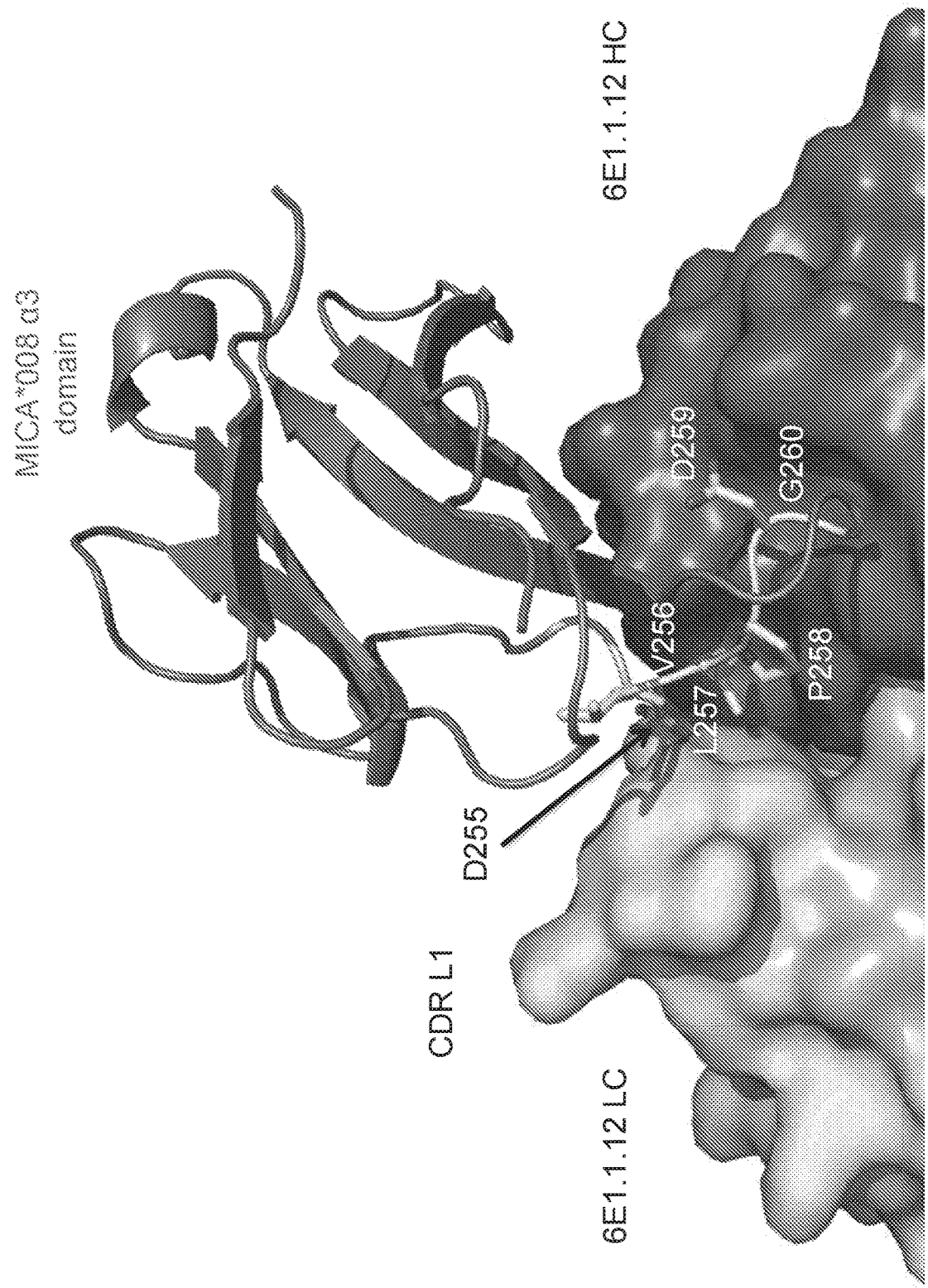
Figure 39F:
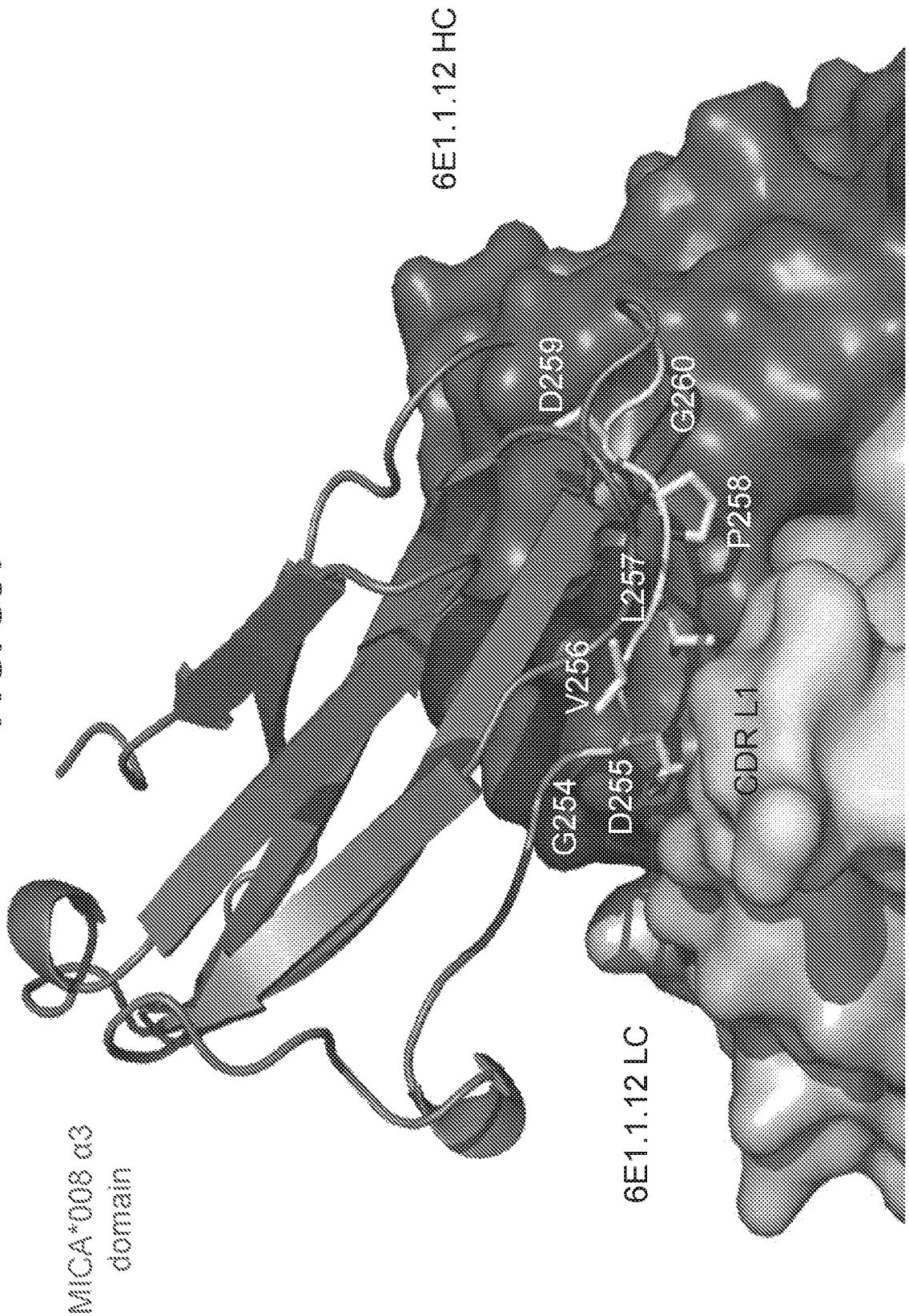
Figure 39H:
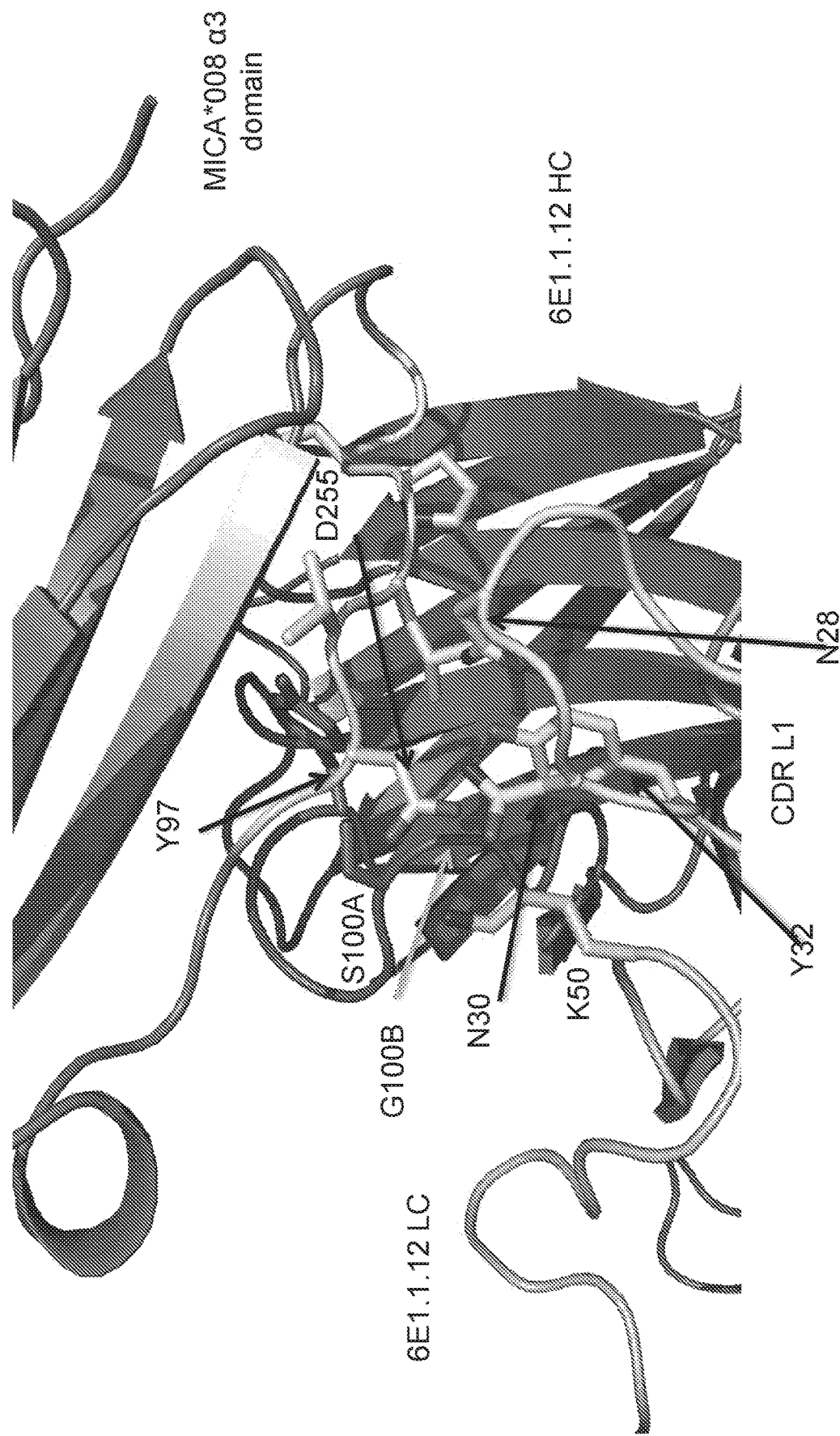

FIG. 39A and FIG. 39B show the 6E1 Fab depicted as a ribbon diagram representation in two different orientations, with CDR L1 highlighted to demonstrate the extended length of this CDR. FIG. 39C and FIG. 39D show the MICA*008 C273S α3 domain from the 6E1 Fab complex structure depicted as a ribbon diagram or surface representation, respectively, with the 250 s loop highlighted. FIG. 39E and FIG. 39F are renderings of the crystal structure of the 6E1 Fab shown as a surface bound to the MICA*008 C273S α3 domain depicted as a ribbon diagram. This interaction is shown from different angles to demonstrate binding of the 250 s loop of MICA*008 in the groove generated by the long CDR L1 of 6E1. Side chains of the residues in the 250 s loop are shown as sticks. FIG. 39G depicts the hydrophobic binding pocket of Leu257 in the 6E1 Fab peptide-binding groove. This pocket is composed of residues from CDRs L1, H1, and H3 of the 6E1 Fab and the side chains of these residues are shown as sticks. FIG. 39H depicts the hydrophillic binding pocket of Asp255 in the 6E1 Fab peptide-binding groove. This pocket is composed of residues from CDRs L1, L2, and H3 of the 6E1 Fab and the side chains of these residues are shown as sticks.

Figure 40A:
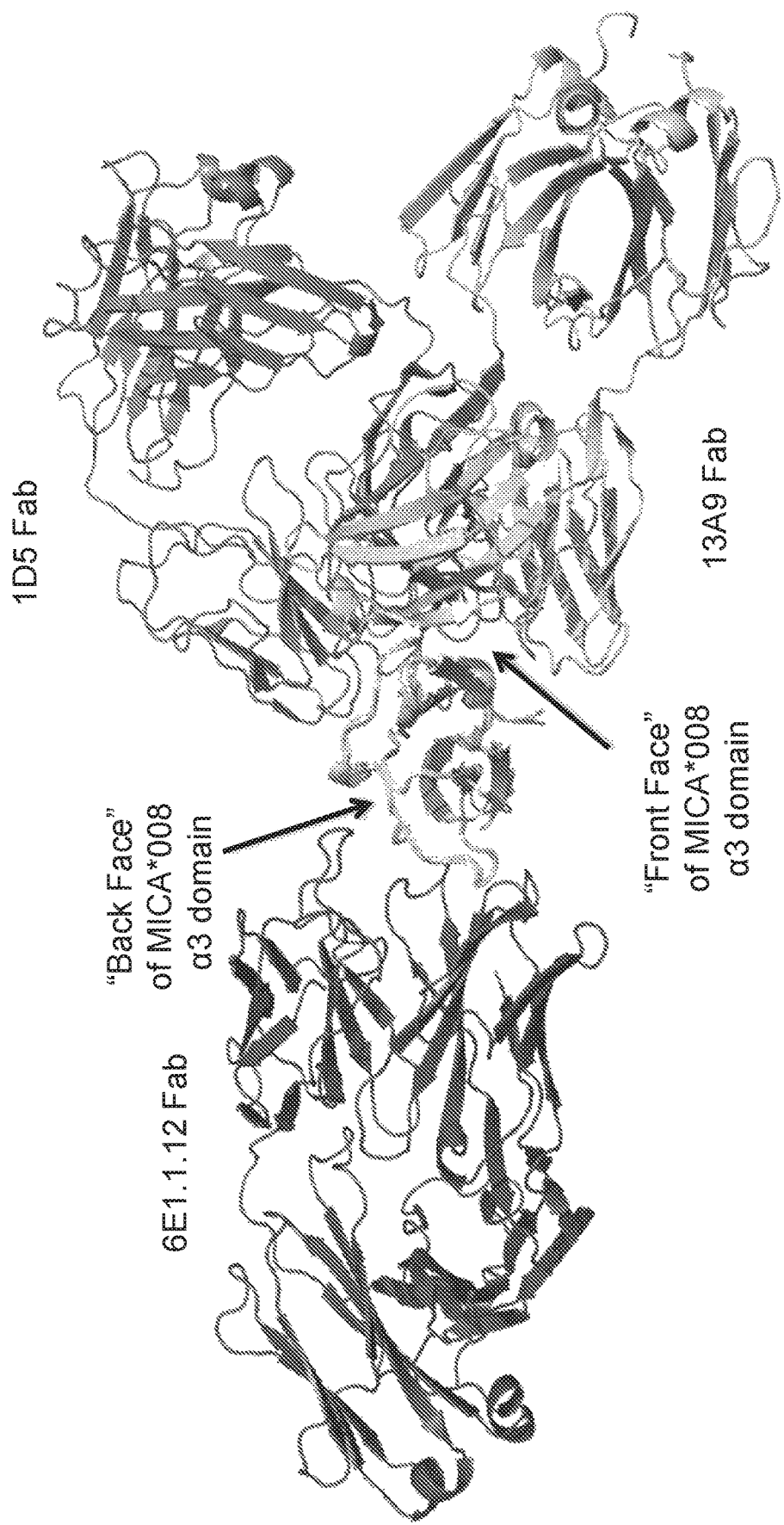

FIG. 40A is a rendering of the crystal structures of the 1D5 Fab-MICA*008 α3 domain complex, the 13A9 Fab-MICA*008 α3 domain complex, and 6E1 Fab-MICA*008 C273S α3 domain complex, superimposed on one another with respect to MICA, showing that 1D5 and 13A9 have overlapping epitopes on the "front face" of the MICA*008 α3 domain whereas 6E1 binds to the "back face" of the α3 domain. FIG. 40B is a surface representation of the MICA*008 α3 domain with the 1D5 Fab epitope (MICA*008 α3 domain residues within 4.5 Å of the 1D5 Fab), the 13A9 Fab epitope (MICA*008 α3 domain residues within 4.5 Å of the 13A9 Fab), and both the 1D5 and 13A9 epitopes combined, mapped onto the surface of the MICA*008 α3 domain highlighted in color. FIG. 40C is a ribbon diagram representation of the MICA*008 α3 domain with the 1D5 Fab epitope (MICA*008 α3 domain residues within 4.5 Å of the 1D5 Fab), the 13A9 Fab epitope (MICA*008 α3 domain residues within 4.5 Å of the 13A9 Fab), and both the 1D5 and 13A9 epitopes combined, mapped onto the ribbon diagram of the MICA*008 α3 domain. Side chains of residues in the defined epitopes are shown as sticks and colored.

Figure 41A:
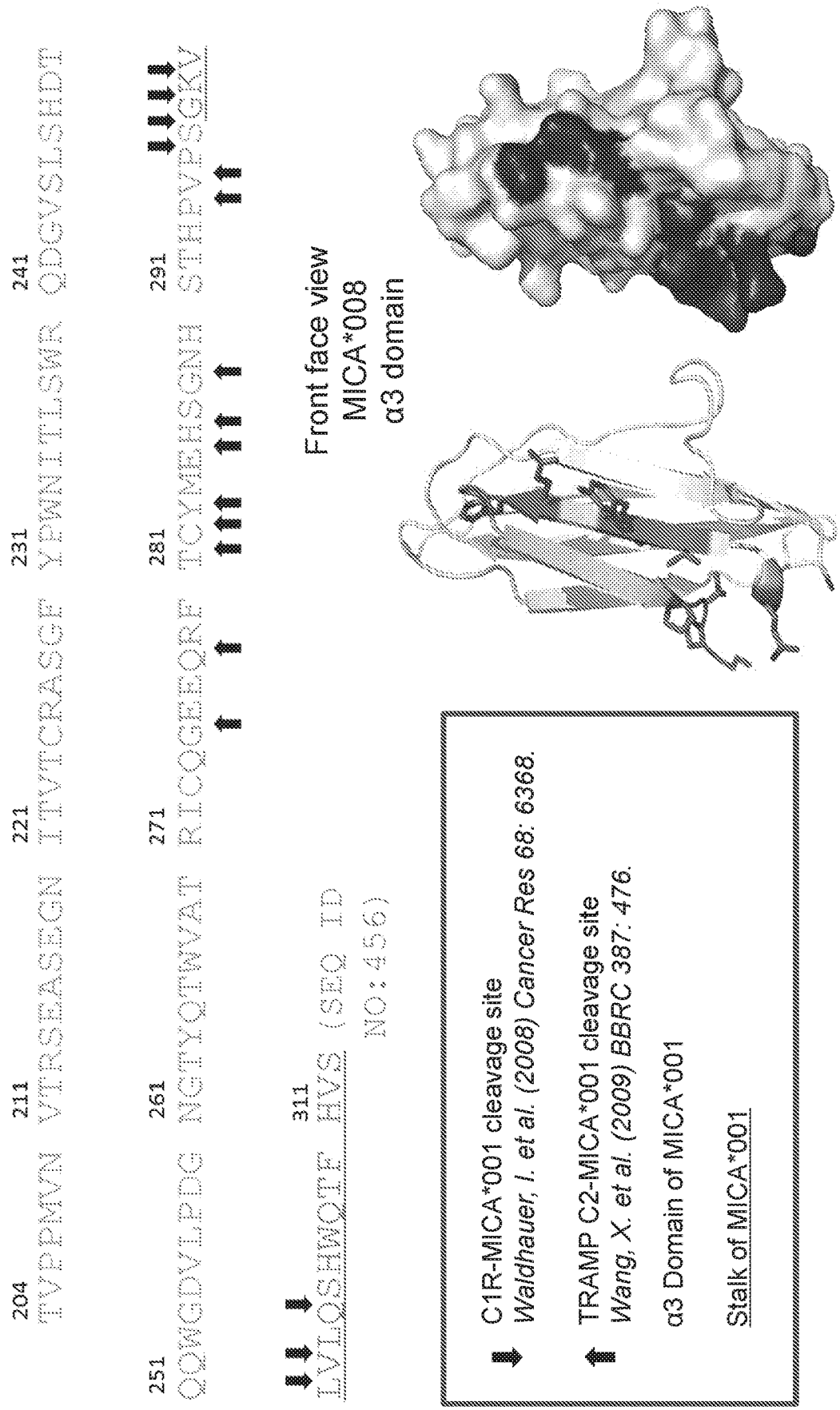

FIG. 41A depicts the sequence of the MICA*001 α3 domain (residues 204-297) and stalk region (residues 298-313, underlined). Reported MICA*001 cleavage sites from C1R cells (Waldhauer, I. et al., (2008) Cancer Research 68:6368) and TRAMP C2 cells (Wang, X. et al. (2009) BBRC 387:476) are indicated within the protein sequence by down- and up-pointing arrows, respectively. The homologous residues of these reported cleavage sites are mapped onto the crystal structure of the MICA*008 α3 domain (taken from the 13A9 Fab-MICA*008 α3 domain complex structure) rendered as either a ribbon diagram or surface representation. Cleavage sites are highlighted in color and the side chains are shown as sticks in the ribbon diagram. FIG. 41B shows a side-by-side comparison of the 1D5, 13A9, and 6E1 Fab epitopes mapped onto the surface of the MICA*008 α3 domain structure on the left with the reported cleavage sites mapped onto the surface of the MICA*008 α3 domain structure on the right. The boundaries of the 1D5, 13A9 and 6E1 Fab epitopes are also outlined with dashed lines on the MICA*008 α3 domain structures depicting the cleavage sites. The Fab epitopes were defined as MICA*008 α3 domain residues within 4.5 Å of the respective Fabs. The cleavages sites are those reported by Waldhauer, I. et al., (2008) Cancer Research 68:6368 and Wang, X. et al. (2009) BBRC 387:476.

Figure 42:
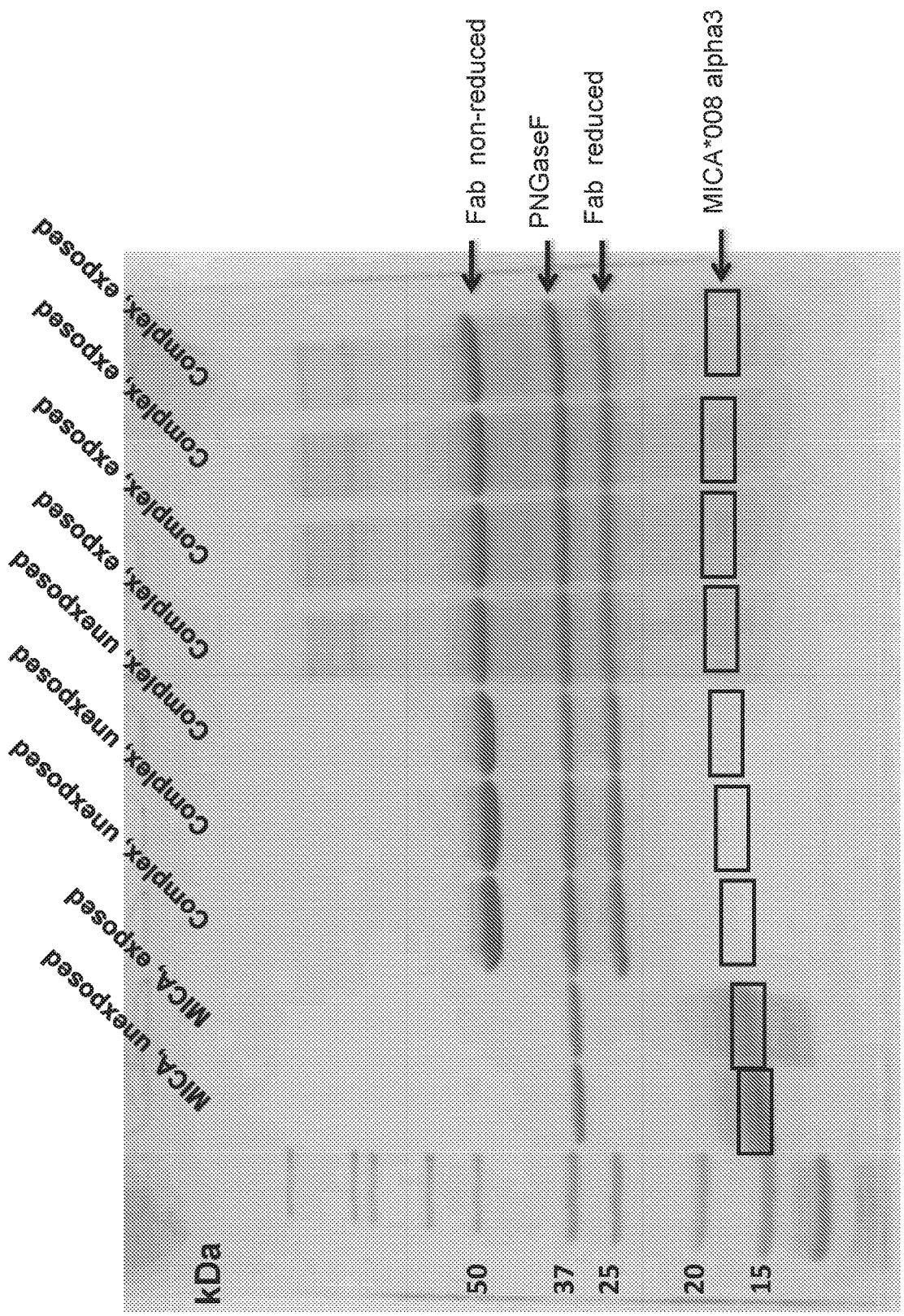

FIG. 42 depicts samples after reduction, deglycosylation, and alkylation from either MICA*008 α3 domain antigen alone unexposed to the laser (MICA, unexposed), MICA*008 α3 domain antigen alone exposed to the laser (MICA, exposed), MICA*008:1D5 Fab complex unexposed (Complex, unexposed) and MICA*008:1D5 Fab complex exposed (Complex, exposed) were run on a 4-20% Tris-Glycine gel. The boxed regions indicate the bands containing MICA*008 α3 domain that were excised for tryptic and chymotryptic digest and subsequent mass spectrometric analysis.

Figure 43A:
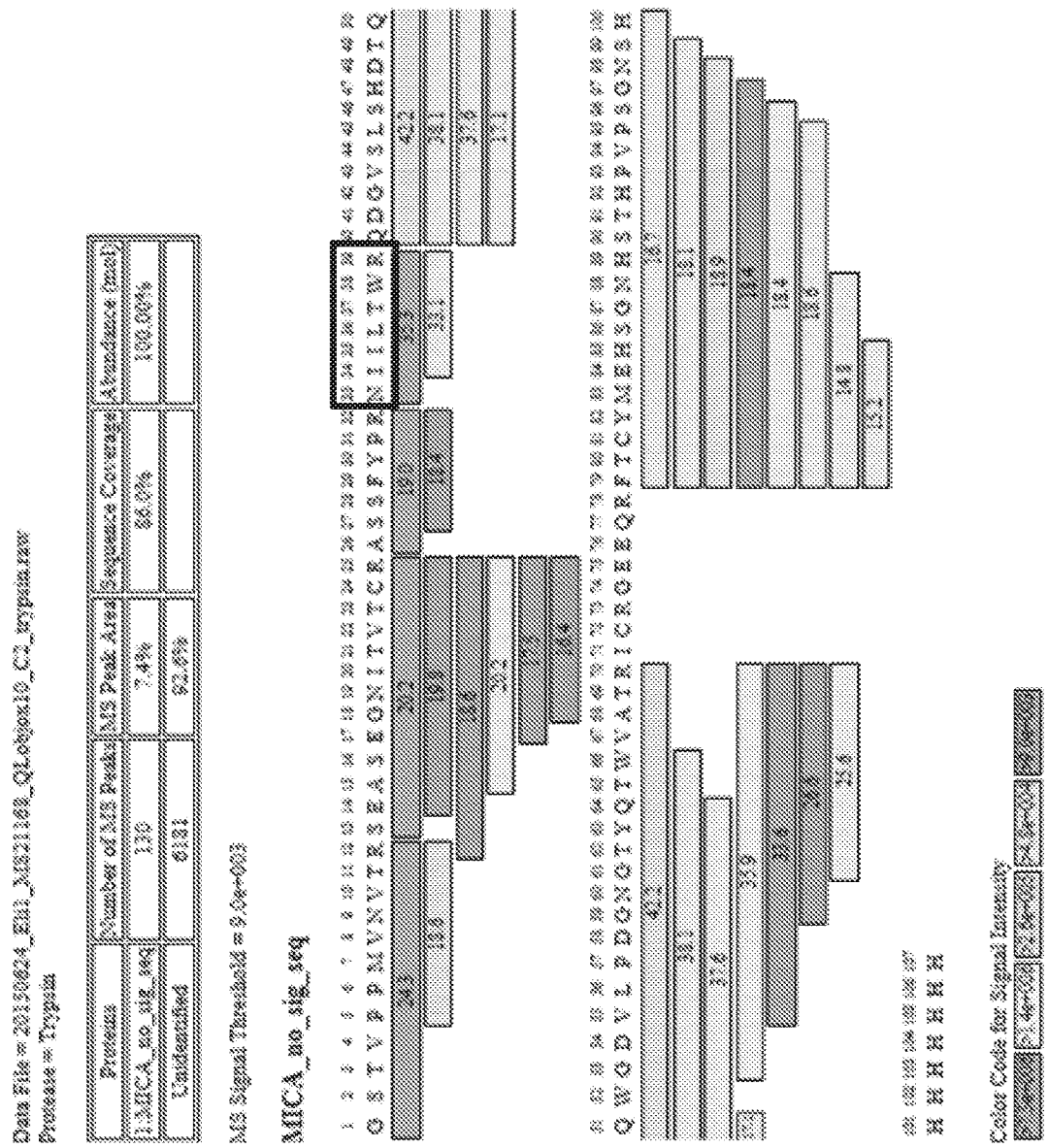
Figure 43B:
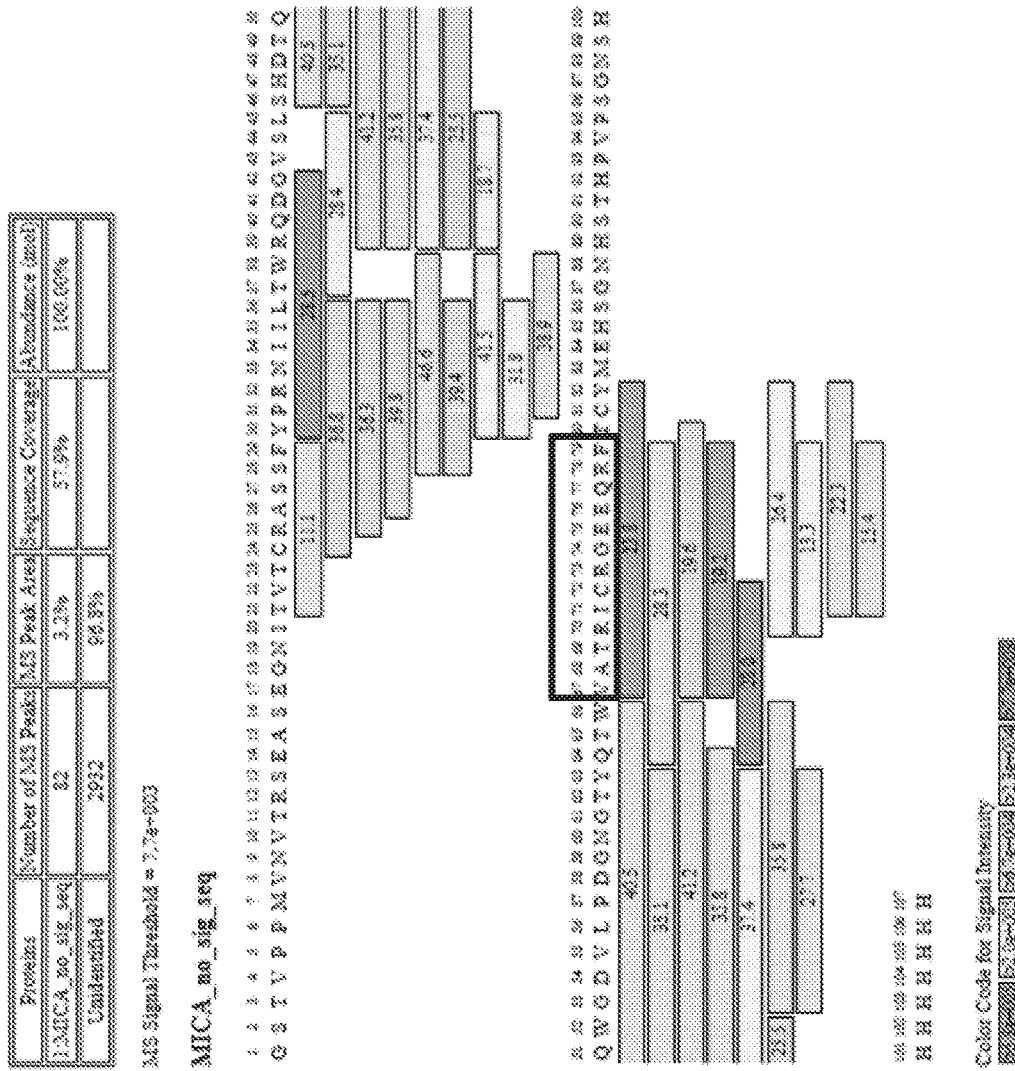

Sequence coverage obtained from tryptic (FIG. 43A) and chymotryptic (FIG. 43B) digest of the MICA*008 α3 domain (SEQ ID NO: 195) from the MICA*008:1D5 Fab complex, exposed sample is shown. Residue numbering starts at the beginning of the α3 domain construct where the first two residues G1 and S2 are cloning artifacts and the start of the α3 domain is at T3 corresponding to residue Thr204 of the full-length MICA*008 protein. The end of the α3 domain is S96 corresponding to residue Ser297 of the full-length MICA*008 protein. This is followed by residues G97-S99 (cloning artifacts) and H100-H107 (His8 purification tag). Peptide alignment to MicA sequence was performed using Byonic software (Protein Metrics, Palo Alto, Calif.). Peak intensity is denoted by the color scale shown in the figure.

Figure 44:
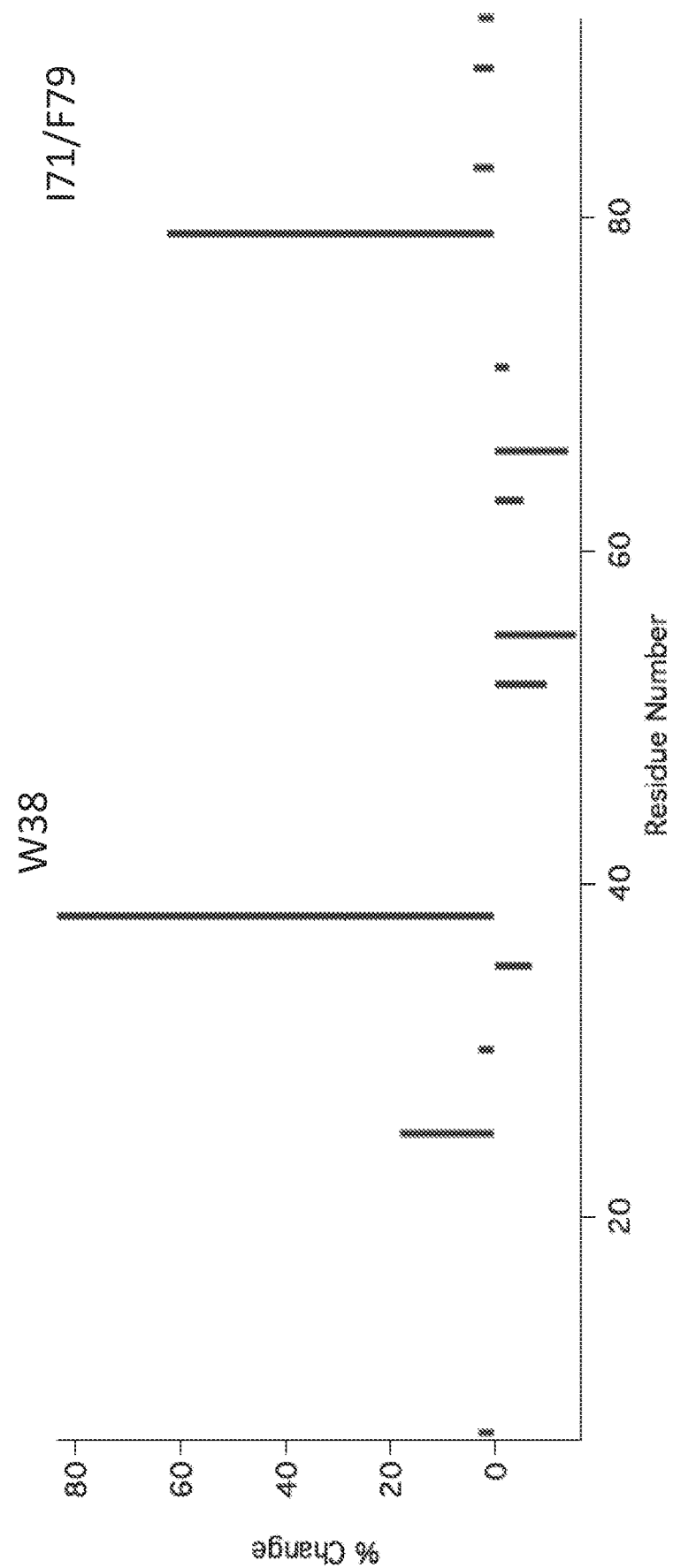

FIG. 44 shows percent change in oxidation when the MICA*008 α3 domain is bound in a complex with the 1D5 Fab relative to MICA*008 α3 domain alone is plotted against the MICA*008 α3 domain construct residue numbers. Residue numbering starts at the beginning of the α3 domain construct where the first two residues G1 and S2 are cloning artifacts and the start of the α3 domain is at T3 corresponding to residue Thr204 of the full-length MICA*008 protein. The end of the α3 domain is S96 corresponding to residue Ser297 of the full-length MICA*008 protein. The greatest change in oxidation is seen for residue W38 (Trp239 of the full-length MICA*008 protein) and Ile71 and Phe79 (Ile272 and Phe280 of the full-length MICA*008 protein).

Figure 45:
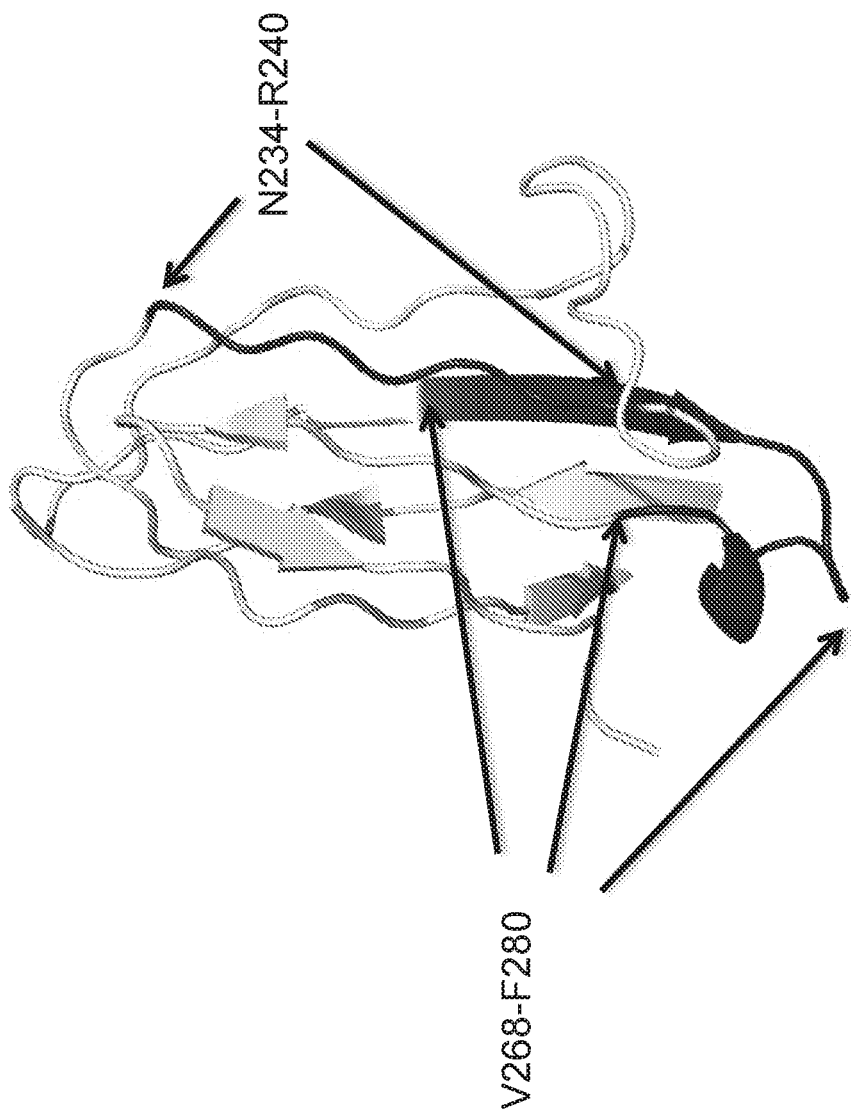

FIG. 45 depicts MICA*008 α3 domain peptides that showed significant change in oxidation protection in the presence of the bound 1D5 Fab compared to the MICA*008 α3 domain alone sample are mapped onto the crystal structure of the MICA*008 α3 domain determined above (from the complex of MICA*008 α3 domain bound to 1D5). These include N33-R39 (Asn234-Arg240 of the full-length MICA*008 protein) and V67-F79 (Val268-Phe280).

Figure 46C:
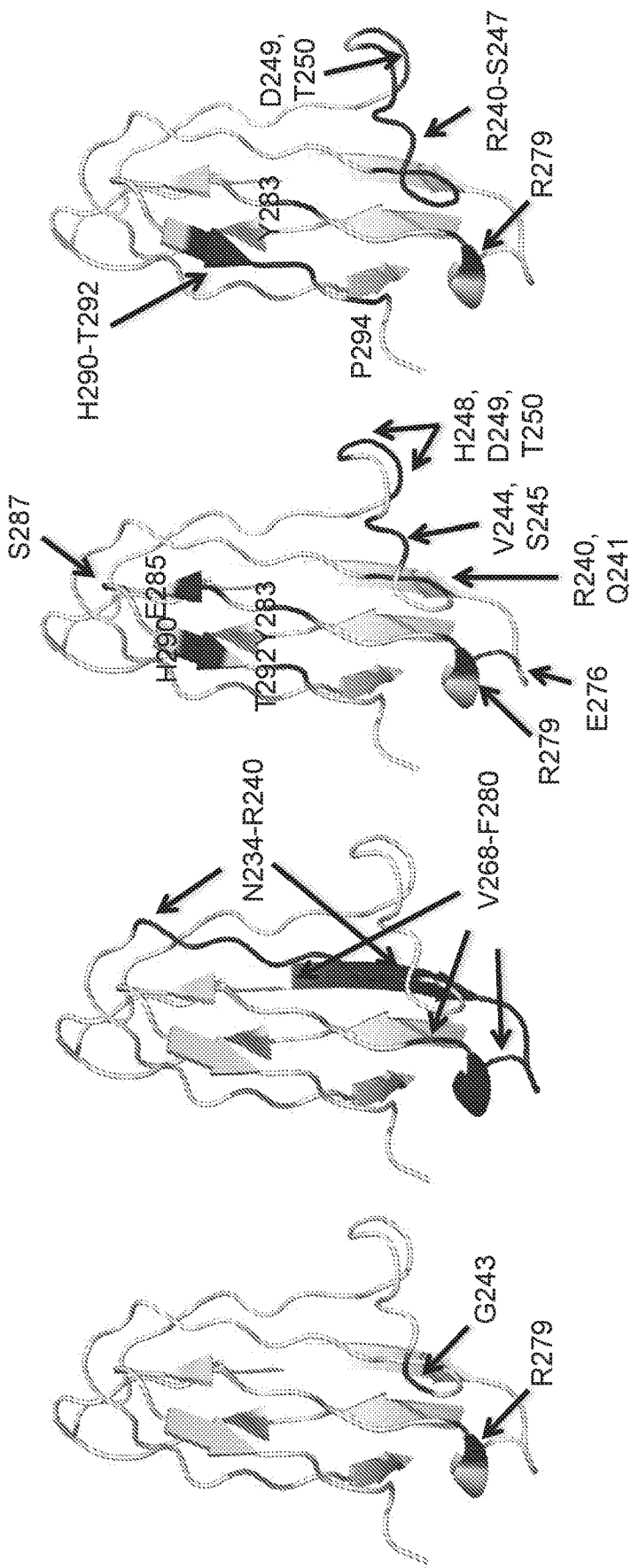

FIG. 46A shows a side-by-side comparison of the 1D5, 13A9, and 6E1 Fab epitopes mapped onto the surface of the MICA*008 α3 domain structure on the left with the glycoengineered variants mapped onto the surface of the MICA*008 α3 domain structure on the right. The boundaries of the 1D5, 13A9 and 6E1 Fab epitopes are also outlined with dashed lines on the MICA*008 α3 domain structures depicting the cleavage sites. The Fab epitopes were defined as MICA*008 α3 domain residues within 4.5 Å of the respective Fabs. The table shows the relative binding of the Fabs to the various glycoengineered variants with +indicating binding is unaffected, − indicating binding is completely lost, and +/− indicating binding is partially lost relative to the wild-type MICA*008 α3 domain. FIG. 46B is a rendering of the 1D5 Fab-MICA*008 α3 domain and 13A9 Fab-MICA*008 α3 domain complex structures shown from the same orientation with the Fabs depicted as surfaces and the MICA*008 α3 domains shown as ribbon diagrams. The table shows the relative binding of the Fabs to the various glycoengineered variants with +indicating binding is unaffected, − indicating binding is completely lost, and +/− indicating binding is partially lost relative to the wild-type MICA*008 α3 domain. The two mutations, Glyco14 (G243N) and Glyco16 (R279N), which affecting binding of the 1D5 and 13A9 Fabs to different degrees, are shown as spheres and highlighted with arrows. FIG. 46C depicts the 1D5 epitope determined by glycosylation engineering, FPOP, alanine scanning, and X-ray crystallography mapped onto the crystal structure of the MICA*008 α3 domain shown as a ribbon diagram. Residues identified as part of the epitope by each method are highlighted in color and the residue numbers are indicated. Epitope residues determined by glycosylation engineering of MICA*008 were defined as showing a loss in 1D5 binding upon mutation to Asn and introduction of an N-linked glycan, resulting in an ELISA $OD_{450}$ signal below 0.5. Epitope residues determined by FPOP were defined as showing decreased oxidation within a tryptic or chymotryptic peptide of MICA*008 upon 1D5 Fab binding, relative to the same MICA*008 peptides in the absence of the Fab. Epitope residues determined by alanine scanning of MICA*008 were defined as showing a 3-fold decrease in 1D5 binding affinity ($K_D$ measured by SPR) when mutated to alanine, relative to wild-type MICA*008. Epitope residues determined by X-ray crystallography were defined as being within 4.5 Å of the 1D5 Fab.

Figure 47A:
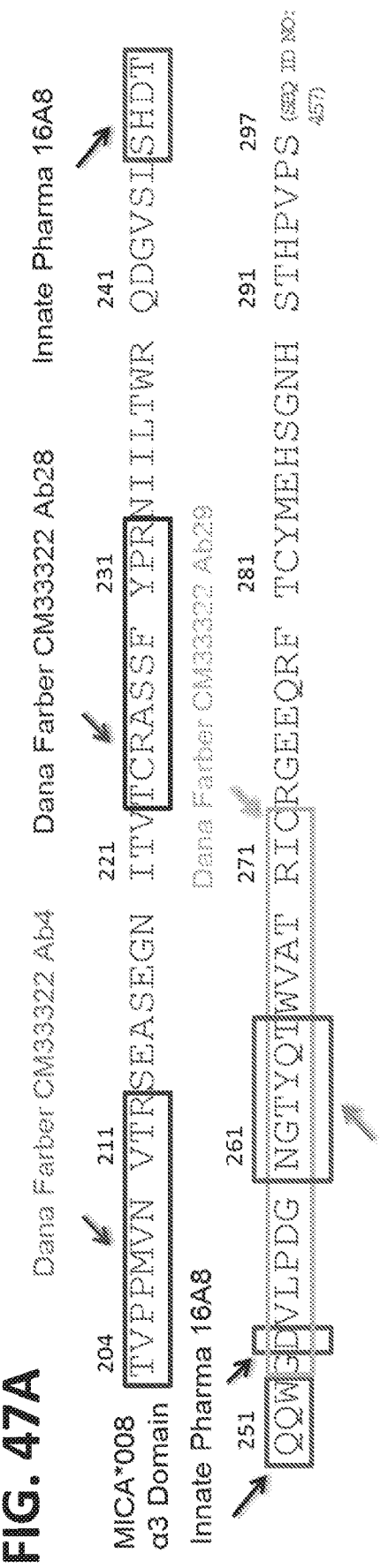
Figure 47B:
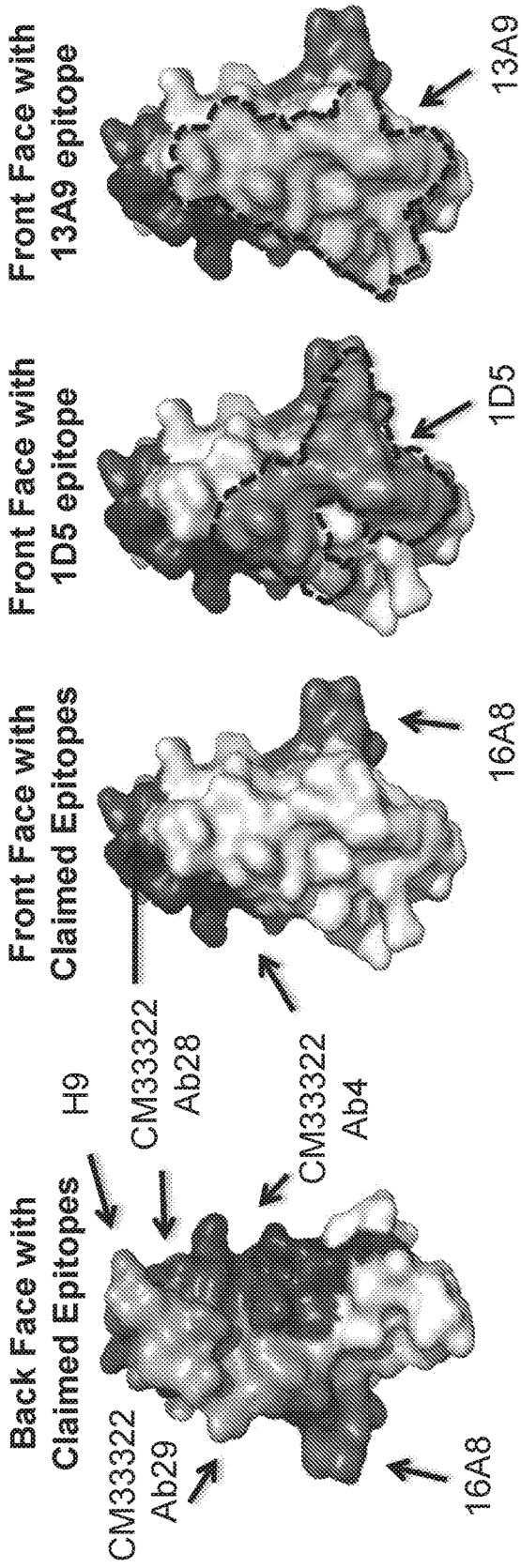

FIG. 47A depicts the epitopes of Dana Farber's CM33322 Ab4, CM33322 Ab28, and CM33322 Ab29, Innate Pharma's 16A8, and the University of Washington's H9 anti-MICA/B antibodies mapped on to the sequence (FIG. 47A) and structure (FIG. 47B) of the MICA*008 α3 domain. The epitopes of these previously described antibodies map predominantly to the "back face" of the MICA*008 α3 domain. In contrast, the epitopes of 1D5 and 13A9 map to the "front face" of the MICA*008 α3 domain.

Figure 48:
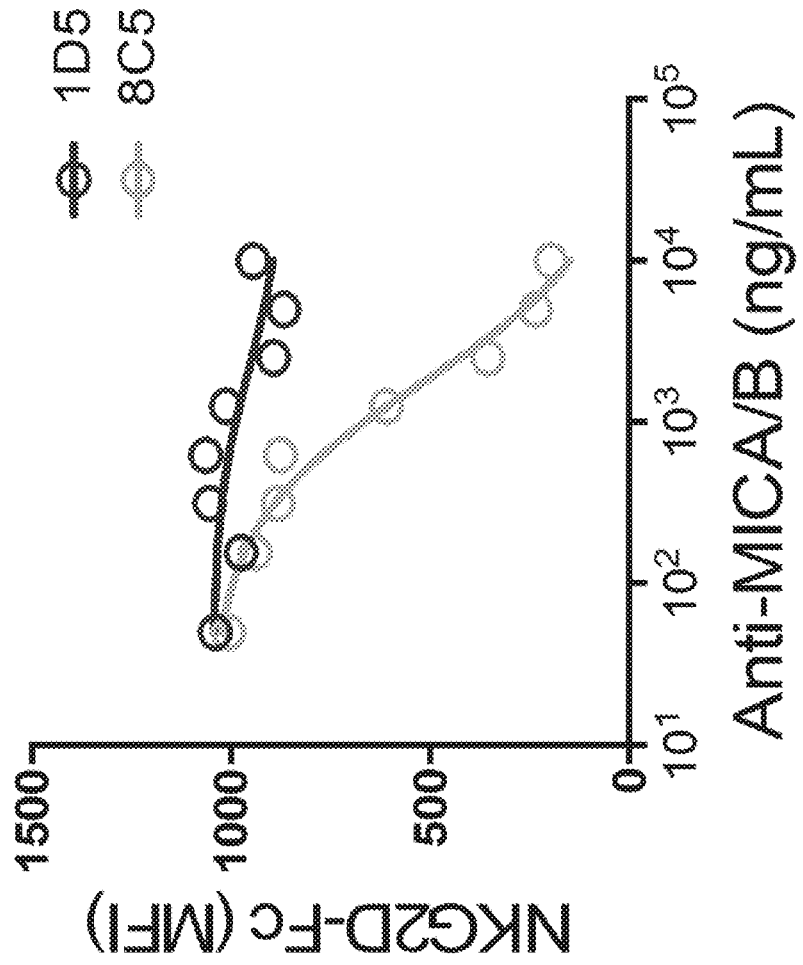

FIG. 48 depicts NKG2D-Fc vs. anti-MICA/B concentration, showing that antibody 1D5 does not interfere with MIC-NKG2D interactions.

Figure 49A:
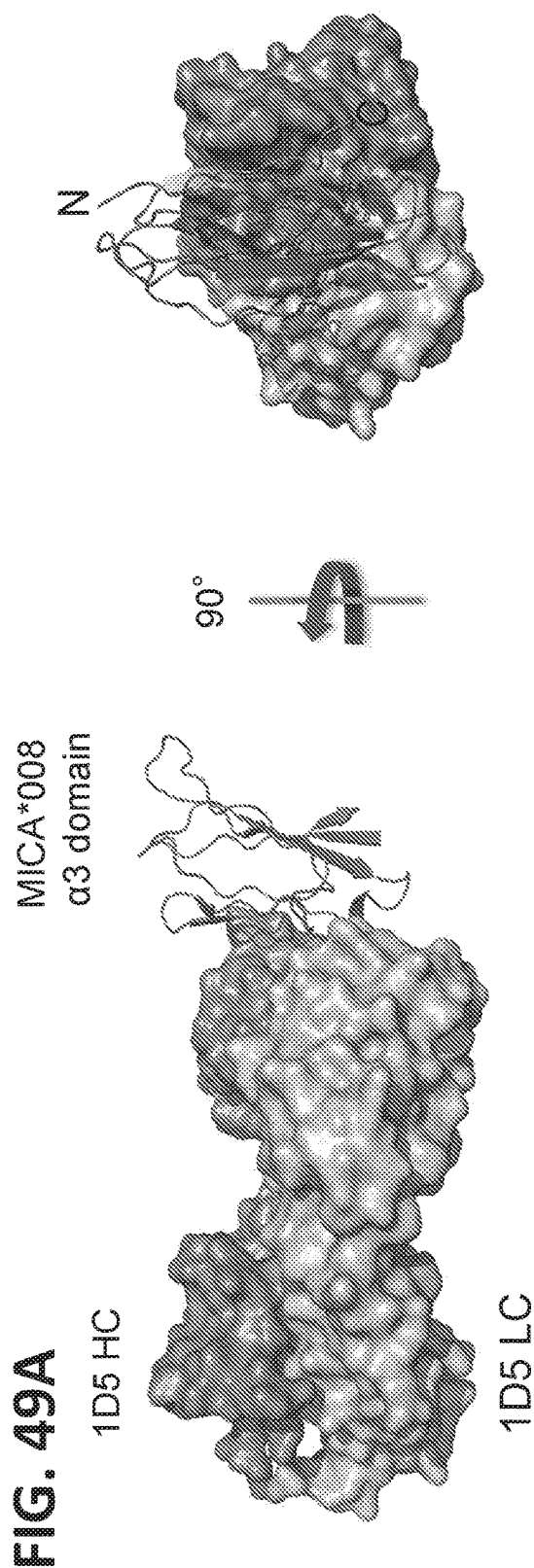
Figure 49B:
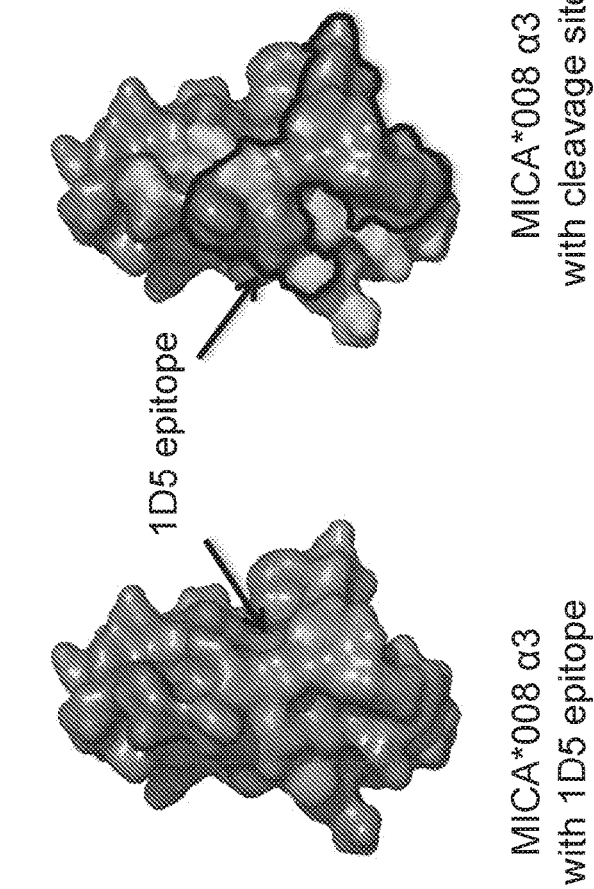

FIG. 49A depicts the crystal structure of the 1D5 Fab bound to the MICA*008 α3 domain determined at 1.3 Å resolution. 1D5 binds to the "front face" of the α3 domain containing the C-terminal beta strand. FIG. 49B depicts the epitope of 1D5, defined as MICA residues within 4.5 Å of the Fab, on the surface of the "front face" of the MICA*008 α3 domain. Reported cleavage sites are shown with the boundary of the 1D5 epitope also indicated.

Figure 50A:
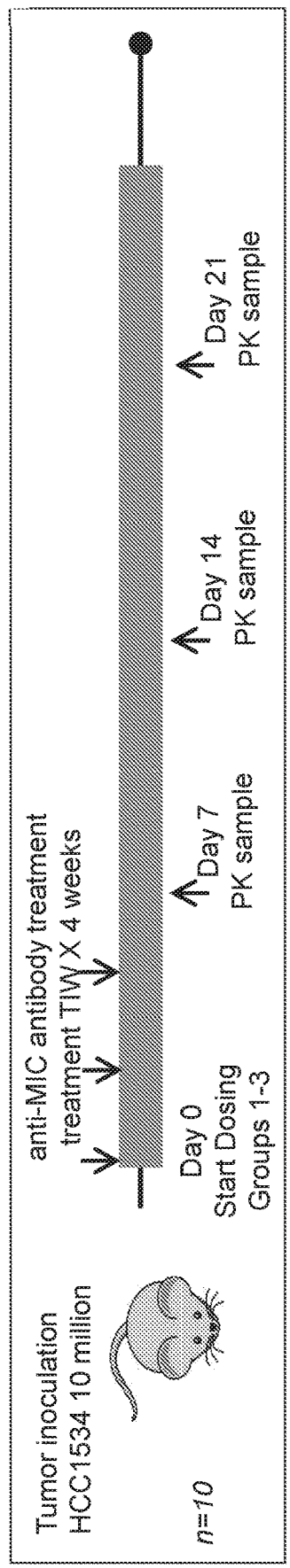
Figure 50B:
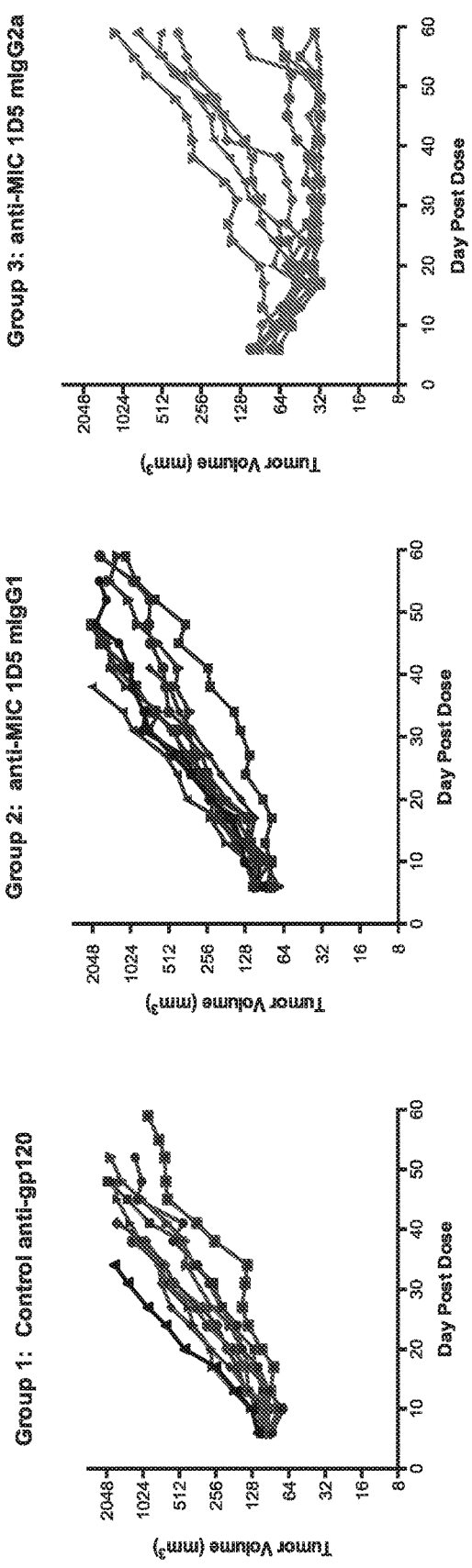
Figure 50D:
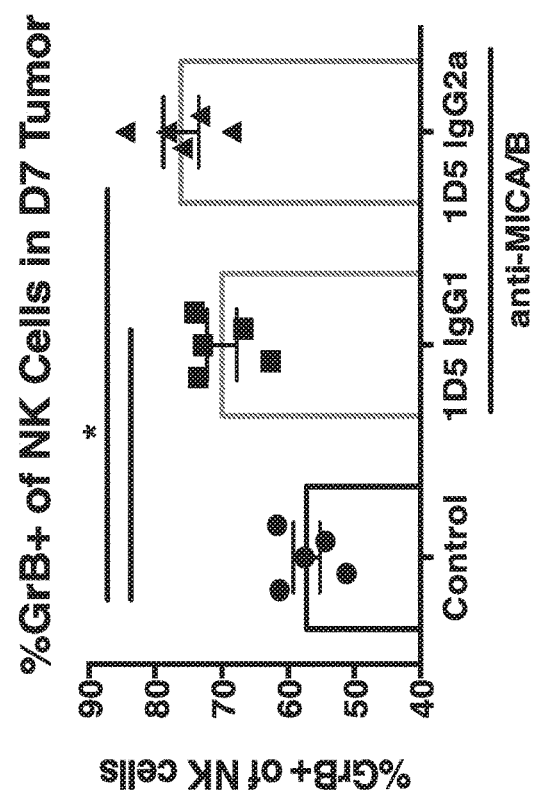
Figure 50C:
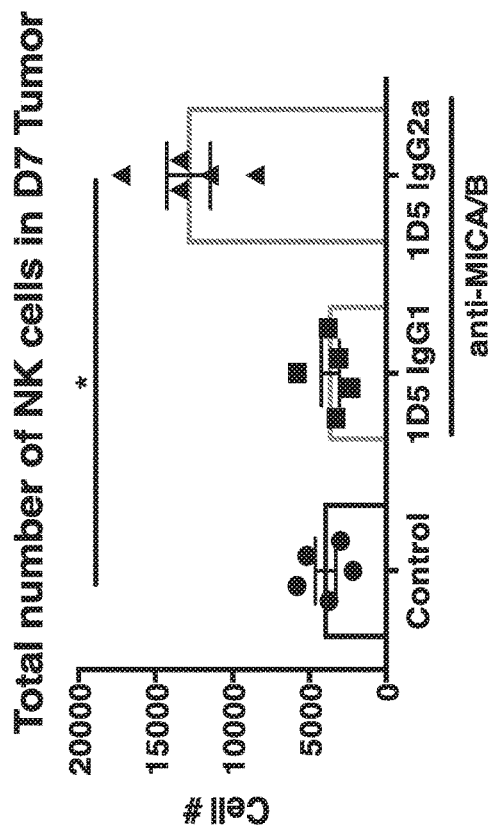

FIG. 50A illustrates the timeline of tumor inoculation in BALB/c SCID mice and dosing regimen of anti-MIC 1D5 antibody. FIG. 50B depicts tumor volumes by caliper measurement in various treatment groups. FIG. 50C and FIG. 50D depict the number of NK cells and the proportion of Granzyme B-positive NK cells, respectively, in harvested tumors following treatment with anti-MIC 1D5 antibody.

Figure 51A:
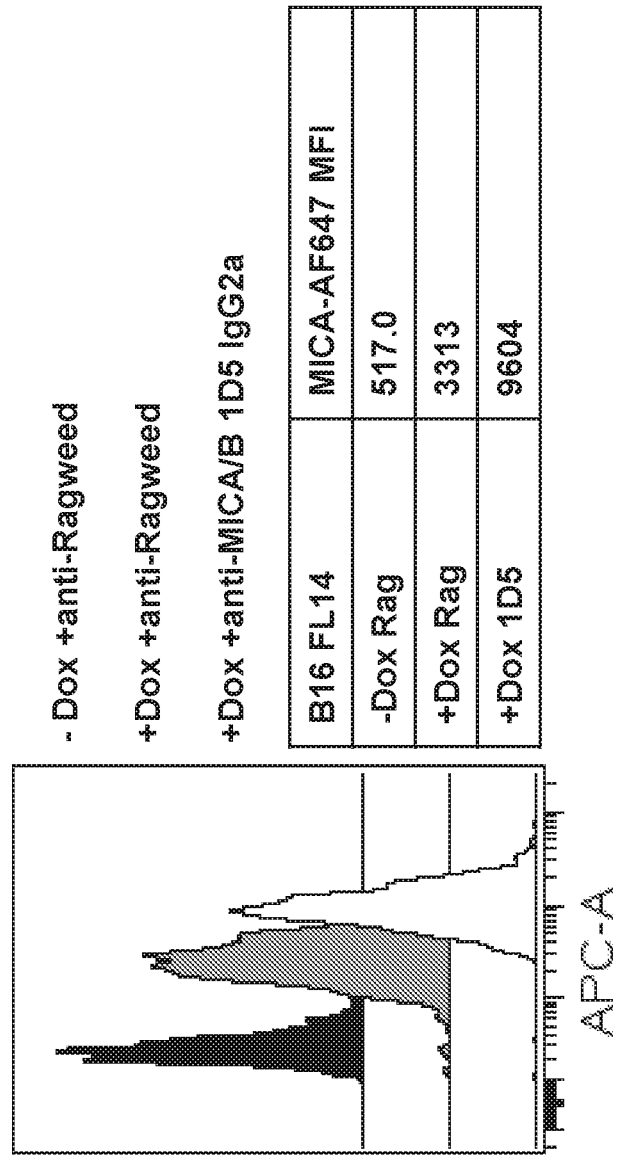

FIG. 51A shows that anti-MIC (1D5 antibody) treatment stabilized MICA surface expression in B16 cells engineered to express MICA (B16-MICA002) in a dox dependent manner. FIG. 52B depicts the anti-tumor response of a combination treatment of anti-MIC 1D5 and anti-PD-L1 in B16-MICA002.

DETAILED DESCRIPTION OF THE EMBODIMENTS OF THE INVENTION

I. Definitions

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

The term "MIC" as used herein, refers to any native MHC Class I related chain A or B from any vertebrate source, including mammals such as primates (e.g., humans) and rodents (e.g., mice and rats), unless otherwise indicated. The term encompasses "full-length," unprocessed MIC as well as any form of MIC that results from processing in the cell. The term also encompasses naturally occurring variants of MIC, for example, splice variants or allelic variants, including MICA alleles 002, 004, 008 and MICB allele 005. Other alleles of MICA encompassed by the term include MICA*001, MICA*005, MICA*006, MICA*007, MICA*009, MICA*010, MICA*011, MICA*012, MICA*013, MICA*014, MICA*015, MICA*016, MICA*017, MICA*018, MICA*019, MICA*020, MICA*022, MICA*023, MICA*024, MICA*025, MICA*026, MICA*027, MICA*028, MICA*029, MICA*030, MICA*031, MICA*032, MICA*033, MICA*034, MICA*035, MICA*036, MICA*037, MICA*038, MICA*039, MICA*040, MICA*041, MICA*042, MICA*043, MICA*044, MICA*045, MICA*046, MICA*047, MICA*048, MICA*049, MICA*050, MICA*051, MICA*052, MICA*053, MICA*054, MICA*055 and MICA*056. Other alleles of MICB encompassed by the term include MICB*001, MICB*002, MICB*003, MICB*004, MICB*006, MICB*007, MICB*008, MICB*009N, MICB*010, MICB*011, MICB*012, MICB*013, MICB*014, MICB*015, MICB*016, MICB*018, MICB*019, MICB*020, MICB*021N and MICB*022. A listing of alleles is available at hla.alleles/org/alleles/classo.html. The amino acid sequence of an exemplary human MICA allele 008 (including the signal sequence) is shown in SEQ ID NO: 193. All amino acid numbering in the application for MICA*008 is with respect to a human MICA*008 sequence including the signal sequence. Further description of MIC is provided in Stephens et al., Trends Immunol. 2001 July; 22(7):378-85. FIG. 2 shows MICA/B alpha3 domain alignment, percent identity, and percent similarity.

The terms "anti-MIC antibody", "an antibody that binds to MIC" and "an antibody that specifically binds to MIC" refer to an antibody that is capable of binding MIC with sufficient affinity such that the antibody is useful as a diagnostic and/or therapeutic agent in targeting MIC. In one embodiment, the extent of binding of an anti-MIC antibody to an unrelated, non-MIC protein is less than about 10% of the binding of the antibody to MIC as measured, e.g., by a radioimmunoassay (RIA). In certain embodiments, an antibody that binds to MIC has a dissociation constant (Kd) of ≤1 µM, ≤100 nM, ≤10 nM, ≤1 nM, ≤0.1 nM, ≤0.01 nM, or ≤0.001 nM (e.g., $10^{-8}$ M or less, e.g. from $10^{-8}$ M to $10^{-13}$ M, e.g., from $10^{-9}$ M to $10^{-13}$ M). In certain embodiments, an anti-MIC antibody binds to an epitope of MIC that is conserved among MIC from different species.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and µ, respectively.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1 (L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262:732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

In one embodiment, HVR residues comprise those identified in FIG. 1A-FIG. 1L or elsewhere in the specification.

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-MIC antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, diluent, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked Such vectors are referred to herein as "expression vectors."

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), ARO-MASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEU-VECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG1 λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., J. Biol. Chem. 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa 3 and membrane bound heterotrimer LTa1/β2 blockers such as Anti-lymphotoxin alpha (LTa); radioactive isotopes (e.g., At211, I131, I125, Y90, Re186, Re188, Sm153, Bi212, P32, Pb212 and radioactive isotopes of Lu); miscellaneous investigational agents such as thioplatin, PS-341, phenylbutyrate, ET-18-OCH3, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugswith analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

In some embodiments, an antigen binding polypeptide (e.g., antibody) or complex described herein may be administered in conjunction with a PARP inhibitor (e.g., Olaparanib, Rucaparib, Niraparib, Cediranib, BMN673, Veliparib), Trabectedin, nab-paclitaxel (albumen-bound paclitaxel, ABRAXANE), Trebananib, Pazopanib, Cediranib, Palbociclib, everolimus, fluoropyrimidine (e.g., FOLFOX, FOLFIRI), IFL, regorafenib, Reolysin, Alimta, Zykadia, Sutent, Torisel (temsirolimus), Inlyta (axitinib, Pfizer), Afinitor (everolimus, Novartis), Nexavar (sorafenib, Onyx/Bayer), Votrient, Pazopanib, axitinib, IMA-901, AGS-003, cabozantinib, Vinflunine, Hsp90 inhibitor (e.g., apatorsin), Ad-GM-CSF (CT-0070), Temazolomide, IL-2, IFNa, vinblastine, Thalomid, dacarbazine, cyclophosphamide, lenalidomide, azacytidine, lenalidomide, bortezomid (VELCADE), amrubicine, carfilzomib, pralatrexate, and/or enzastaurin.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing) As used herein, a PD-1 axis binding antagonist includes a PD-1 binding antagonist, a PD-L1 binding antagonist and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 (nivolumab) described herein. In another specific aspect, a PD-1 binding antagonist is MK-3475 (pembrolizumab) described herein. In another specific aspect, a PD-1 binding antagonist is CT-011 (pidilizumab) described herein. In another specific aspect, a PD-1 binding antagonist is AMP-224 described herein.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1105 described herein. In still another specific aspect, an anti-PD-L1 antibody is MPDL3280A described herein. In still another specific aspect, an anti-PD-L1 antibody is MEDI4736 described herein.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

The term "NKG2D ligand" refers to any molecule which is capable of binding to the NKG2D receptor and activating the receptor such that it triggers killing of the NKG2D-expressing cell. Exemplary NKG2D ligands include MICA, MICB, and related splice variants and alleles.

The term "reducing shedding of MIC" or grammatical variants thereof refer to a reduction in the release of membrane-bound MIC from MIC-expressing cells. In certain embodiments, the reduction in shedding of MIC reduces levels of soluble MIC such that there is a reduction in the effects of soluble MIC, including those that impair the immune system and permit cancer and other immune related diseases to develop and progress. In certain embodiments, the shedding of MIC is reduced by 10%, 15%, 20%, 25%, 30%, 35%, 40%, 45%. 50%, 55%, 60%, 65%, 70%, 75%, 80%, 85%, 90%, 95%, or 100% compared to shedding of MIC in the absence of antibodies described herein.

The term "reducing levels of soluble MIC" or grammatical variants thereof refers to reducing levels of non-membrane bound MIC. In certain embodiments, the reduction of soluble MIC is such that there is a reduction in the effects of soluble MIC, including those that impair the immune system and permit cancer and other immune related diseases to develop and progress. For example, the reduction of soluble MIC may reduce downregulation of NKG2D induced by soluble MIC. The reduction in levels of soluble MIC may arise from multiple mechanisms, including a reduction in shedding of MIC and/or binding of soluble MIC by an antibody described herein. In certain embodiments, the level of soluble MIC is reduced by 10%, 15%, 20%, 25%, 30%, 35%, 40%, 45%. 50%, 55%, 60%, 65%, 70%, 75%, 80%, 85%, 90%, 95%, or 100% compared to levels of soluble MIC in the absence of antibodies described herein.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

"Antibody-dependent cell-mediated cytotoxicity" or "ADCC" refers to a form of cytotoxicity in which secreted immunoglobulin bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 or 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. PNAS (USA) 95:652-656 (1998).

The term "biomarker" as used herein refers to an indicator, e.g., predictive, diagnostic, and/or prognostic, which can be detected in a sample. The biomarker may serve as an indicator of a particular subtype of a disease or disorder (e.g., cancer) characterized by certain, molecular, pathological, histological, and/or clinical features. In some embodiments, a biomarker is a gene. Biomarkers include, but are not limited to, polynucleotides (e.g., DNA, and/or RNA), polynucleotide copy number alterations (e.g., DNA copy numbers), polypeptides, polypeptide and polynucleotide modifications (e.g. posttranslational modifications), carbohydrates, and/or glycolipid-based molecular markers. The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include, but not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., J. Immunol. Methods 202:163 (1996), may be performed. Polypeptide variants with altered Fc region amino acid sequences (polypeptides with a variant Fc region) and increased or decreased C1q binding capability are described, e.g., in U.S. Pat. No. 6,194,551 B1 and WO 1999/51642. See also, e.g., Idusogie et al. J. Immunol. 164: 4178-4184 (2000).

The term "diagnosis" is used herein to refer to the identification or classification of a molecular or pathological state, disease or condition (e.g., cancer). For example, "diagnosis" may refer to identification of a particular type of cancer. "Diagnosis" may also refer to the classification of a particular subtype of cancer, e.g., by histopathological criteria, or by molecular features (e.g., a subtype characterized by expression of one or a combination of biomarkers (e.g., particular genes or proteins encoded by said genes)).

As used herein, "delaying progression of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Expression" generally refers to the process by which information (e.g., gene-encoded and/or epigenetic) is converted into the structures present and operating in the cell. Therefore, as used herein, "expression" may refer to transcription into a polynucleotide, translation into a polypeptide, or even polynucleotide and/or polypeptide modifications (e.g., posttranslational modification of a polypeptide). Fragments of the transcribed polynucleotide, the translated polypeptide, or polynucleotide and/or polypeptide modifications (e.g., posttranslational modification of a polypeptide) shall also be regarded as expressed whether they originate from a transcript generated by alternative splicing or a degraded transcript, or from a post-translational processing of the polypeptide, e.g., by proteolysis. "Expressed genes" include those that are transcribed into a polynucleotide as mRNA and then translated into a polypeptide, and also those that are transcribed into RNA but not translated into a polypeptide (for example, transfer and ribosomal RNAs).

A "growth inhibitory agent" when used herein refers to a compound or composition which inhibits growth of a cell either in vitro or in vivo. In one embodiment, growth inhibitory agent is growth inhibitory antibody that prevents or reduces proliferation of a cell expressing an antigen to which the antibody binds. In another embodiment, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W. B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

As used herein, "in conjunction with" refers to administration of one treatment modality in addition to another treatment modality. As such, "in conjunction with" refers to administration of one treatment modality before, during, or after administration of the other treatment modality to the individual.

The word "label" when used herein refers to a detectable compound or composition. The label is typically conjugated or fused directly or indirectly to a reagent, such as a polynucleotide probe or an antibody, and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which results in a detectable product.

The term "polynucleotide," when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

The term "sample," as used herein, refers to a composition that is obtained or derived from a subject and/or individual of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. Samples include, but are not limited to, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebrospinal fluid, saliva, sputum, tears, perspiration, mucus, tumor lysates, and tissue culture medium, tissue extracts such as homogenized tissue, tumor tissue, cellular extracts, and combinations thereof.

II. Compositions and Methods of Use

In one aspect, the invention is based, in part, on identification of anti-MIC antibodies that reduce shedding of MIC and or reduce levels of soluble MIC. In certain embodiments, antibodies that bind to MIC are provided. Antibodies of the invention are useful, e.g., for the diagnosis or treatment of cancer and immune related disease.

A. Exemplary Anti-MIC Antibodies

In one aspect, the invention provides isolated antibodies that bind to MIC. In certain embodiments, an anti-MIC antibody reduces shedding of MIC and/or levels of soluble MIC. In one aspect, the invention provides an anti-MIC antibody that binds to an epitope on human MICA*008 including, but not limited to Glu215, Gly243, His248, Arg279, Arg213, Ser214, Ala216, Ser217, Asn220, Arg271, Arg240, Gln241, Asp242, Val244, Ser245, Thr281, Ser247, Asp249, Thr250, Trp253, Glu276, Glu277, and/or Gln278 of human MICA*008.

In some embodiments, the antibody binds to an epitope on human MICA*008 including, but not limited to a first amino acid residue, a second amino acid residue, and a third amino acid residue; wherein the first amino acid residue is Glu215, Arg213, Ser214, Ala216, Ser217, Asn220, or Arg271; the second amino acid residue is His248, Ser247, Asp249, Thr250, or Trp253; and the third amino acid residue is Arg279, Arg240, Gln241, Asp242, Gly243, Glu276, Glu277, Gln278, or Thr281.

In other embodiments, the antibody binds to an epitope on human MICA*008 including, but not limited to a first amino acid residue and a second amino acid residue; wherein the first amino acid residue is Gly243, Arg240, Gln241, Asp242, Val244, Ser245, Arg279, or Thr281; and the second amino acid residue is Arg279, Arg240, Gln241, Asp242, Gly243, Glu276, Glu277, Gln278, or Thr281.

In still other embodiments, the antibody binds to an epitope on human MICA*008 including, but not limited to a first amino acid residue and a second amino acid residue; wherein the first amino acid residue is His248, Ser247, Asp249, Thr250, or Trp253; and the second amino acid residue is Arg279, Arg240, Gln241, Asp242, Gly243, Glu276, Glu277, Gln278, or Thr281.

In other embodiments, the antibody binds to an epitope on human MICA*008 including, but not limited to amino acid residue His248, Ser247, Asp249, Thr250, and/or Trp253.

In other embodiments, the antibody binds to an epitope on human MICA*008 including, but not limited to amino acid residues Arg279, Arg240, Gln241, Asp242, Gly243, Glu276, Glu277, Gln278, and/or Thr281.

In other embodiments, the antibody binds to an epitope on the "back and top" of MIC. In one embodiment, the antibody may bind to residues Val205, Pro206, Met208, Thr212, Gly219, Thr222, Thr224, Arg226, Ser228, Tyr231, Pro232, Gln241, Asp242, Thr250, any amino acid between Asp255 to Gly262, Tyr264, Gln265, Trp267, Arg271, Gly275, Glu277, Gly288, Asn289, and/or His290 of human MICA*008. In another embodiment, the antibody may bind to Val205, Pro206, Met208, Thr212, Gly219, Thr222, Thr224, Arg226, Ser228, Tyr231, Pro232, Asp242, any amino acid between Asp255 to Gly262, Tyr264, Gln265, Trp267, and/or Arg271 of human MICA*008.

In another aspect, the antibody binds to an epitope on human MICA*008 including, but not limited to amino acid residues Gly243, Arg240, Gln241, Asp242, Val244, Ser245, Arg 279, and/or Thr281.

In some embodiments, the antibody binds to an epitope on human MICA*008 including, but not limited to a first amino acid residue, and a second amino acid residue; wherein the first amino acid residue is Gly243, Arg240, Gln241, Asp242, Val244, Ser245, Arg 279, or Thr281; and the second amino acid residue is Arg 279, Arg279, Arg240, Gln241, Asp242, Gly243, Glu276, Glu277, Gln278, or Thr281.

In some embodiments, the antibody binds to an epitope on human MICA*008 including, but not limited to amino aid residue Gly243.

In some embodiments, the antibody binds to an epitope on human MICA*008 including, but not limited to amino aid residues Gly243, and Arg279.

In other embodiments, the antibody binds to an epitope on human MICA*008 including, but not limited to amino acid residues Arg240, Gln241, Val244, Ser245, His248, Glu276, Arg279, Tyr283, Glu285, His290, and/or Thr292.

In other embodiments, the antibody binds to an epitope on human MICA*008 including, but not limited to amino acid residues Arg240, Gln241, Asp242, Gly243, Val244, Ser245, Leu246, Ser247, Asp249, Thr250, Arg279, Tyr283, His290, Ser291, Thr292, and/or Pro294.

In other embodiments, the antibody binds to an epitope on human MICA*008 including, but not limited to amino acid residues Arg240, Asp242, Gly243, Val244, Glu277, Gln278, Arg279, Phe280, Thr281, Tyr283, Glu285, Gly288, Asn289, His290, Ser291, Thr292, Pro294, Val295, Pro296, and/or Ser297.

In other embodiments, the antibody binds to an epitope on human MICA*008 including, but not limited to amino acid residues Asn234, Ile235, Ile236, Leu237, Thr238, Trp239, and/or Arg240. In other embodiments, the antibody binds to an epitope on human MICA*008 including, but not limited to amino acid residues Val268, Ala269, Thr270, Arg271, Ile272, Cys273, Arg274, Gly275, Glu276, Glu277, Gln278, Arg279, and/or Phe280.

In another aspect, the invention provides an anti-MIC antibody comprising at least one, two, three, four, five, or six HVRs selected from (a) HVR-H1 comprising the amino acid sequence of SEQ ID NO: 1, 17, 33, 49, 65, 81, 97, 113, 129, 145, 161, or 177; (b) HVR-H2 comprising the amino acid sequence of SEQ ID NO: 2, 18, 34, 50, 66, 82, 98, 114, 130, 146, 162, or 178; (c) HVR-H3 comprising the amino acid sequence of SEQ ID NO: 3, 19, 35, 51, 67, 83, 99, 115, 131, 147, 163, or 179; (d) HVR-L1 comprising the amino acid sequence of SEQ ID NO: 4, 20, 36, 52, 68, 84, 100, 116, 132, 148, 164, or 180; (e) HVR-L2 comprising the amino acid sequence of SEQ ID NO: 5, 21, 37, 53, 69, 85, 101, 117, 133, 149, 165, or 181; and (f) HVR-L3 comprising the amino acid sequence of SEQ ID NO: 6, 22, 38, 54, 70, 86, 102, 118, 134, 150, 166, or 182.

In one aspect, the invention provides an antibody comprising at least one, at least two, or all three VH HVR sequences selected from (a) HVR-H1 comprising the amino acid sequence of SEQ ID NO: 1, 17, 33, 49, 65, 81, 97, 113, 129, 145, 161, or 177; (b) HVR-H2 comprising the amino acid sequence of SEQ ID NO: 2, 18, 34, 50, 66, 82, 98, 114, 130, 146, 162, or 178; and (c) HVR-H3 comprising the amino acid sequence of SEQ ID NO: 3, 19, 35, 51, 67, 83, 99, 115, 131, 147, 163, or 179. In one embodiment, the antibody comprises HVR-H3 comprising the amino acid sequence of SEQ ID NO: 3, 19, 35, 51, 67, 83, 99, 115, 131, 147, 163, or 179. In another embodiment, the antibody comprises HVR-H3 comprising the amino acid sequence of SEQ ID NO: 3, 19, 35, 51, 67, 83, 99, 115, 131, 147, 163, or 179 and HVR-L3 comprising the amino acid sequence of SEQ ID NO: 6, 22, 38, 54, 70, 86, 102, 118, 134, 150, 166, or 182. In a further embodiment, the antibody comprises HVR-H3 comprising the amino acid sequence of SEQ ID NO: 3, 19, 35, 51, 67, 83, 99, 115, 131, 147, 163, or 179; HVR-L3 comprising the amino acid sequence of SEQ ID NO: 6, 22, 38, 54, 70, 86, 102, 118, 134, 150, 166, or 182; and HVR-H2 comprising the amino acid sequence of SEQ ID NO: 2, 18, 34, 50, 66, 82, 98, 114, 130, 146, 162, or 178. In a further embodiment, the antibody comprises (a) HVR-H1 comprising the amino acid sequence of SEQ ID NO: 1, 17, 33, 49, 65, 81, 97, 113, 129, 145, 161, or 177; (b) HVR-H2 comprising the amino acid sequence of SEQ ID NO: 2, 18, 34, 50, 66, 82, 98, 114, 130, 146, 162, or 178; and (c) HVR-H3 comprising the amino acid sequence of SEQ ID NO: 3, 19, 35, 51, 67, 83, 99, 115, 131, 147, 163, or 179.

In another aspect, the invention provides an antibody comprising at least one, at least two, or all three VL HVR sequences selected from (a) HVR-L1 comprising the amino acid sequence of SEQ ID NO: 4, 20, 36, 52, 68, 84, 100, 116, 132, 148, 164, or 180; (b) HVR-L2 comprising the amino acid sequence of SEQ ID NO: 5, 21, 37, 53, 69, 85, 101, 117, 133, 149, 165, or 181; and (c) HVR-L3 comprising the amino acid sequence of SEQ ID NO: 6, 22, 38, 54, 70, 86, 102, 118, 134, 150, 166, or 182. In one embodiment, the antibody comprises (a) HVR-L1 comprising the amino acid sequence of SEQ ID NO: 4, 20, 36, 52, 68, 84, 100, 116, 132, 148, 164, or 180; (b) HVR-L2 comprising the amino acid sequence of SEQ ID NO: 5, 21, 37, 53, 69, 85, 101, 117, 133, 149, 165, or 181; and (c) HVR-L3 comprising the amino acid sequence of SEQ ID NO: 6, 22, 38, 54, 70, 86, 102, 118, 134, 150, 166, or 182.

In another aspect, an antibody of the invention comprises (a) a VH domain comprising at least one, at least two, or all three VH HVR sequences selected from (i) HVR-H1 comprising the amino acid sequence of SEQ ID NO: 1, 17, 33, 49, 65, 81, 97, 113, 129, 145, 161, or 177; (ii) HVR-H2 comprising the amino acid sequence of SEQ ID NO: 2, 18, 34, 50, 66, 82, 98, 114, 130, 146, 162, or 178; and (iii) HVR-H3 comprising the amino acid sequence of SEQ ID NO: 3, 19, 35, 51, 67, 83, 99, 115, 131, 147, 163, or 179; and (b) a VL domain comprising at least one, at least two, or all three VL HVR sequences selected from (i) HVR-L1 comprising the amino acid sequence of SEQ ID NO: 4, 20, 36, 52, 68, 84, 100, 116, 132, 148, 164, or 180; (ii) HVR-L2 comprising the amino acid sequence of SEQ ID NO: 5, 21, 37, 53, 69, 85, 101, 117, 133, 149, 165, or 181; and (iii) HVR-L3 comprising the amino acid sequence of SEQ ID NO: 6, 22, 38, 54, 70, 86, 102, 118, 134, 150, 166, or 182.

In another aspect, the invention provides an antibody comprising (a) HVR-H1 comprising the amino acid sequence of SEQ ID NO: 1, 17, 33, 49, 65, 81, 97, 113, 129, 145, 161, or 177; (b) HVR-H2 comprising the amino acid sequence of SEQ ID NO: 2, 18, 34, 50, 66, 82, 98, 114, 130, 146, 162, or 178; (c) HVR-H3 comprising the amino acid sequence of SEQ ID NO: 3, 19, 35, 51, 67, 83, 99, 115, 131, 147, 163, or 179; (d) HVR-L1 comprising the amino acid sequence of SEQ ID NO: 4, 20, 36, 52, 68, 84, 100, 116, 132, 148, 164, or 180; (e) HVR-L2 comprising the amino acid sequence of SEQ ID NO: 5, 21, 37, 53, 69, 85, 101, 117, 133, 149, 165, or 181; and (f) HVR-L3 comprising an amino acid sequence selected from SEQ ID NO: 6, 22, 38, 54, 70, 86, 102, 118, 134, 150, 166, or 182.

In another aspect, an anti-MIC antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 15, 31, 47, 63, 79, 95, 111, 127, 143, 159, 175, or 191. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-MIC antibody comprising that sequence retains the ability to bind to MIC. In certain embodiments, a total of 1 to 10 amino acids have been substituted, inserted and/or deleted in SEQ ID NO: 15, 31, 47, 63, 79, 95, 111, 127, 143, 159, 175, or 191. In certain embodiments, substitutions, insertions, or deletions occur in regions outside the HVRs (i.e., in the FRs). Optionally, the anti-MIC antibody comprises the VH sequence in SEQ ID NO: 15, 31, 47, 63, 79, 95, 111, 127, 143, 159, 175, or 191, including post-translational modifications of that sequence. In a particular embodiment, the VH comprises one, two or three HVRs selected from: (a) HVR-H1 comprising the amino acid sequence of SEQ ID NO: 1, 17, 33, 49, 65, 81, 97, 113, 129, 145, 161, or 177, (b) HVR-H2 comprising the amino acid sequence of SEQ ID NO: 2, 18, 34, 50, 66, 82, 98, 114, 130, 146, 162, or 178, and (c) HVR-H3 comprising the amino acid sequence of SEQ ID NO: 3, 19, 35, 51, 67, 83, 99, 115, 131, 147, 163, or 179.

In another aspect, an anti-MIC antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 16, 32, 48, 64, 80, 96, 112, 128, 144, 160, 176, or 192. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-MIC antibody comprising that sequence retains the ability to bind to MIC. In certain embodiments, a total of 1 to 10 amino acids have been substituted, inserted and/or deleted in SEQ ID NO: 16, 32, 48, 64, 80, 96, 112, 128, 144, 160, 176, or 192. In certain embodiments, the substitutions, insertions, or deletions occur in regions outside the HVRs (i.e., in the FRs). Optionally, the anti-MIC antibody comprises the VL sequence in SEQ ID NO: 16, 32, 48, 64, 80, 96, 112, 128, 144, 160, 176, or 192, including post-translational modifications of that sequence. In a particular embodiment, the VL comprises one, two or three HVRs selected from (a) HVR-L1 comprising the amino acid sequence of SEQ ID NO: 4, 20, 36, 52, 68, 84, 100, 116, 132, 148, 164, or 180; (b) HVR-L2 comprising the amino acid sequence of SEQ ID NO: 5, 21, 37, 53, 69, 85, 101, 117, 133, 149, 165, or 181; and (c) HVR-L3 comprising the amino acid sequence of SEQ ID NO: 6, 22, 38, 54, 70, 86, 102, 118, 134, 150, 166, or 182.

In another aspect, an anti-MIC antibody is provided, wherein the antibody comprises a VH as in any of the embodiments provided above, and a VL as in any of the embodiments provided above. In one embodiment, the antibody comprises the VH and VL sequences in SEQ ID NO: 15, 31, 47, 63, 79, 95, 111, 127, 143, 159, 175, or 191 and SEQ ID NO: 16, 32, 48, 64, 80, 96, 112, 128, 144, 160, 176, or 192, respectively, including post-translational modifications of those sequences.

In any of the above embodiments, an anti-MIC antibody is humanized. In one embodiment, an anti-MIC antibody comprises HVRs as in any of the above embodiments, and further comprises an acceptor human framework, e.g. a human immunoglobulin framework or a human consensus framework. In another embodiment, an anti-MIC antibody comprises HVRs as in any of the above embodiments, and further comprises a VH and/or VL comprising a FR sequence as disclosed in FIGS. 1A-1L. In some embodiments, the anti-MIC antibodies described above further comprise at least one, two, three or four light chain variable region framework regions (FRs) selected from (a) a FR-L1 comprising the amino acid sequence of SEQ ID NO: 7, 23, 39, 55, 71, 87, 103, 119, 135, 151, 167 or 183; (b) a FR-L2 comprising the amino acid sequence of SEQ ID NO: 8, 24, 40, 56, 72, 88, 104, 120, 136, 152, 168, or 184; (c) a FR-L3 comprising the amino acid sequence of SEQ ID NO: 9, 25, 41, 57, 73, 89, 105, 121, 137, 153, 169, or 185; and (d) a FR-L4 comprising the amino acid sequence of SEQ ID NO: 10, 26, 42, 58, 74, 90, 106, 122, 138, 154, 170, 186. In other embodiments, the anti-MIC antibodies decribed above further comprise the following heavy chain variable region FRs: a) a FR-H1 comprising the amino acid sequence of SEQ ID NO: 11, 27, 43, 59, 75, 91, 107, 123, 139, 155, 171, or 187; b) a FR-H2 comprising the amino acid sequence of SEQ ID NO: 12, 28, 44, 60, 76, 92, 108, 124, 140, 156, 172, or 188; c) a FR-H3 comprising the amino acid sequence of SEQ ID NO: 13, 29, 45, 61, 77, 93, 109, 125, 141, 157, 173 or 189; and d) a FR-H4 comprising the amino acid sequence of SEQ ID NO: 14, 30, 46, 62, 78, 94, 110, 126, 142, 158, 174, or 190.

Exemplary antibodies (3C9.10, 7D4.6, 6F8.7, 32D2, 3E11, 9C9.5.6, 1E6.1.3, 7A3.1.9, 6E12.5, 20G11, 6E1.1.12, and 2E5.2.3) are described in FIG. 1A-FIG. 1L, FIG. 12, the Examples and the Sequence section of the Detailed Description.

Exemplary antibody variants of 1D5, 13A9, 15F11, 6E1, 18G3, 12H10 are described in FIG. 14A-FIG. 14F, the Examples and the Sequence section of the Detailed Description.

In one aspect, the invention provides an anti-MIC antibody comprising at least one, two, three, four, five, or six HVRs selected from (a) HVR-H1 comprising the amino acid sequence of SEQ ID NO: 209, 218, 224, 236, or 242; (b) HVR-H2 comprising the amino acid sequence of SEQ ID NO: 210, 215, 216, 217, 219, 225, 237, or 243; (c) HVR-H3 comprising the amino acid sequence of SEQ ID NO: 211, 220, 226, 238, or 244; (d) HVR-L1 comprising the amino acid sequence of SEQ ID NO: 212, 221, 227, 239, or 245; (e) HVR-L2 comprising the amino acid sequence of SEQ ID NO: 213, 222, 228, 240, or 246; and (f) HVR-L3 comprising the amino acid sequence of SEQ ID NO: 214, 223, 229, 241, or 247.

In one aspect, the invention provides an antibody comprising at least one, at least two, or all three VH HVR sequences selected from (a) HVR-H1 comprising the amino acid sequence of SEQ ID NO: 209, 218, 224, 236, or 242; (b) HVR-H2 comprising the amino acid sequence of SEQ ID NO: 210, 215, 216, 217, 219, 225, 237, or 243; and (c) HVR-H3 comprising the amino acid sequence of SEQ ID NO: 211, 220, 226, 238, or 244. In one embodiment, the antibody comprises HVR-H3 comprising the amino acid sequence of SEQ ID NO: 211, 220, 226, 238, or 244. In another embodiment, the antibody comprises HVR-H3 comprising the amino acid sequence of SEQ ID NO: 211, 220, 226, 238, or 244 and HVR-L3 comprising the amino acid sequence of SEQ ID NO: 214, 223, 229, 241, or 247. In a further embodiment, the antibody comprises HVR-H3 comprising the amino acid sequence of SEQ ID NO: 211, 220, 226, 238, or 244; HVR-L3 comprising the amino acid sequence of SEQ ID NO: 214, 223, 229, 241, or 247; and HVR-H2 comprising the amino acid sequence of SEQ ID NO: 210, 215, 216, 217, 219, 225, 237, or 243. In a further embodiment, the antibody comprises (a) HVR-H1 comprising the amino acid sequence of SEQ ID NO: 209, 218, 224, 236, or 242; (b) HVR-H2 comprising the amino acid sequence of SEQ ID NO: 210, 215, 216, 217, 219, 225, 237, or 243; and (c) HVR-H3 comprising the amino acid sequence of SEQ ID NO: 211, 220, 226, 238, or 244.

In another aspect, the invention provides an antibody comprising at least one, at least two, or all three VL HVR sequences selected from (a) HVR-L1 comprising the amino acid sequence of SEQ ID NO: 212, 221, 227, 239, or 245; (b) HVR-L2 comprising the amino acid sequence of SEQ ID NO: 213, 222, 228, 240, or 246; and (c) HVR-L3 comprising the amino acid sequence of SEQ ID NO: 214, 223, 229, 241, or 247. In one embodiment, the antibody comprises (a) HVR-L1 comprising the amino acid sequence of SEQ ID NO: 212, 221, 227, 239, or 245; (b) HVR-L2 comprising the amino acid sequence of SEQ ID NO: 213, 222, 228, 240, or 246; and (c) HVR-L3 comprising the amino acid sequence of SEQ ID NO: SEQ ID NO: 214, 223, 229, 241, or 247.

In another aspect, an antibody of the invention comprises (a) a VH domain comprising at least one, at least two, or all three VH HVR sequences selected from (i) HVR-H1 comprising the amino acid sequence of SEQ ID NO: 209, 218, 224, 236, or 242; (ii) HVR-H2 comprising the amino acid sequence of SEQ ID NO: 210, 215, 216, 217, 219, 225, 237, or 243; and (iii) HVR-H3 comprising the amino acid sequence of SEQ ID NO: 211, 220, 226, 238, or 244; and (b) a VL domain comprising at least one, at least two, or all three VL HVR sequences selected from (i) HVR-L1 comprising the amino acid sequence of SEQ ID NO: 212, 221, 227, 239, or 245; (ii) HVR-L2 comprising the amino acid sequence of SEQ ID NO: 213, 222, 228, 240, or 246; and (iii) HVR-L3 comprising the amino acid sequence of SEQ ID NO: SEQ ID NO: 214, 223, 229, 241, or 247.

In another aspect, the invention provides an antibody comprising (a) HVR-H1 comprising the amino acid sequence of SEQ ID NO: 209, 218, 224, 236, or 242; (b) HVR-H2 comprising the amino acid sequence of SEQ ID NO: 210, 215, 216, 217, 219, 225, 237, or 243; (c) HVR-H3 comprising the amino acid sequence of SEQ ID NO: 211, 220, 226, 238, or 244; (d) HVR-L1 comprising the amino acid sequence of SEQ ID NO: 212, 221, 227, 239, or 245; (e) HVR-L2 comprising the amino acid sequence of SEQ ID NO: 213, 222, 228, 240, or 246; and (f) HVR-L3 comprising the amino acid sequence of SEQ ID NO: 214, 223, 229, 241, or 247.

In another aspect, an anti-MIC antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, or 439. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-MIC antibody comprising that sequence retains the ability to bind to MIC. In certain embodiments, a total of 1 to 10 amino acids have been substituted, inserted and/or deleted in SEQ ID NO: 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, or 439. In certain embodiments, substitutions, insertions, or deletions occur in regions outside the HVRs (i.e., in the FRs). Optionally, the anti-MIC antibody comprises the VH sequence in SEQ ID NO: 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, or 439, including post-translational modifications of that sequence. In a particular embodiment, the VH comprises one, two or three HVRs selected from: (a) HVR-H1 comprising the amino acid sequence of SEQ ID NO: 209, 218, 224, 236, or 242; (b) HVR-H2 comprising the amino acid sequence of SEQ ID NO: 210, 215, 216, 217, 219, 225, 237, or 243; and (c) HVR-H3 comprising the amino acid sequence of SEQ ID NO: 211, 220, 226, 238, or 244.

In another aspect, an anti-MIC antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, or 440. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-MIC antibody comprising that sequence retains the ability to bind to MIC. In certain embodiments, a total of 1 to 10 amino acids have been substituted, inserted and/or deleted in SEQ ID NO: 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, or 440. In certain embodiments, the substitutions, insertions, or deletions occur in regions outside the HVRs (i.e., in the FRs). Optionally, the anti-MIC antibody comprises the VL sequence in SEQ ID NO: 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, or 440, including post-translational modifications of that sequence. In a particular embodiment, the VL comprises one, two or three HVRs selected from (a) HVR-L1 comprising the amino acid sequence of SEQ ID NO: 212, 221, 227, 239, or 245; (b) HVR-L2 comprising the amino acid sequence of SEQ ID NO: 213, 222, 228, 240, or 246; and (c) HVR-L3 comprising the amino acid sequence of SEQ ID NO: 214, 223, 229, 241, or 247.

In another aspect, an anti-MIC antibody is provided, wherein the antibody comprises a VH as in any of the embodiments provided above, and a VL as in any of the embodiments provided above. In one embodiment, the antibody comprises the VH and VL sequences in SEQ ID NO:

347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, or 439 and SEQ ID NO: 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, or 440, respectively, including post-translational modifications of those sequences.

In any of the above embodiments, an anti-MIC antibody is humanized. In one embodiment, an anti-MIC antibody comprises HVRs as in any of the above embodiments, and further comprises an acceptor human framework, e.g. a human immunoglobulin framework or a human consensus framework. In another embodiment, an anti-MIC antibody comprises HVRs as in any of the above embodiments, and further comprises a VH and/or VL comprising a FR sequence as disclosed in FIG. 14A-FIG. 14F. In some embodiments, the anti-MIC antibodies described above further comprise at least one, two, three or four light chain variable region framework regions (FRs) selected from (a) a FR-L1 comprising the amino acid sequence of SEQ ID NO: 248, 252, 258, 261, 266, 268, 272, 277, 280, 288, or 291; (b) a FR-L2 comprising the amino acid sequence of SEQ ID NO: 249, 253, 256, 259, 262, 264, 269, 273, 275, 278, 281, 283, 289, or 292; (c) a FR-L3 comprising the amino acid sequence of SEQ ID NO: 250, 254, 257, 260, 263, 265, 267, 270, 274, 276, 279, 282, 284, 290, or 293; and (d) a FR-L4 comprising the amino acid sequence of SEQ ID NO: 251, 255, 271, or 294. In other embodiments, the anti-MIC antibodies decribed above further comprise the following heavy chain variable region FRs: a) a FR-H1 comprising the amino acid sequence of SEQ ID NO: 295, 299, 303, 315, 319, 323, 325, 329, 331, 333, 339, or 343; b) a FR-H2 comprising the amino acid sequence of SEQ ID NO: 296, 300, 304, 316, 320, 326, 340, or 344; c) a FR-H3 comprising the amino acid sequence of SEQ ID NO: 297, 301, 305, 306, 307, 308, 309, 310, 311, 312, 313, 314, 317, 321, 322, 324, 327, 330, 332, 334, 341, or 345; and d) a FR-H4 comprising the amino acid sequence of SEQ ID NO: 298, 302, 318, 328, 342, or 346.

In a further aspect, the anti-MIC antibody is capable of binding to human MICA*002, human MICA*004 and human MICB*005. In some embodiments, the anti-MIC antibody is capable of binding to the extracellular domain of human MICA*008, human MICA*002, human MICA*004 and human MICB*005. In some embodiments, the anti-MIC antibody is capable of binding to the alphaα3 domain of human MICA*008, human MICA*002, human MICA*004 and human MICB*005.

In a further aspect, the invention provides an antibody that binds to the same epitope as an anti-MIC antibody provided herein. For example, in certain embodiments, an antibody is provided that binds to the same epitope as an anti-MIC antibody provided herein.

In a further aspect of the invention, an anti-MIC antibody according to any of the above embodiments is a monoclonal antibody, including a chimeric, humanized or human antibody. In one embodiment, an anti-MIC antibody is an antibody fragment, e.g., a Fab, Fab', Fab'-SH, Fv, single chain variable fragment (scFv), and (Fab') fragment. In another embodiment, the antibody is a full length antibody, e.g., an intact IgG class antibody or IgG 1 isotype or other antibody class or isotype as defined herein.

In a further aspect, an anti-MIC antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BlAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates (kon) and dissociation rates (koff) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio koff/kon. See, e.g., Chen et al., *J. Mol. Biol.* 293:865-881 (1999). If the on-rate exceeds 106 M-1 s-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dalt'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. Proc. *Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006).

Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for MIC and the other is for any other antigen. In certain embodiments, bispecific antibodies may bind to two different epitopes of MIC. Bispecific antibodies may also be used to localize cytotoxic agents to cells which express MIC. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to MIC as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes Amino acid substitutions may be introduced into an antibody of interest and the products screened for a desired activity, e.g., retained/improved antigen binding, decreased immunogenicity, or improved ADCC or CDC.

TABLE 1

Amino Acid Substitutions.

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103: 2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-MIC antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-MIC antibody is provided, wherein the method comprises culturing a host cell comprising a nucleic acid encoding the antibody, as provided above, under in a culture medium conditions suitable for expression of the antibody, and optionally recovering the antibody from the host cell (or host cell culture medium).

For recombinant production of an anti-MIC antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, such as *Escherichia coli*, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology, Vol.* 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR⁻ CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-MIC antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with any of the anti-MIC antibodies described herein for binding to MIC. In certain embodiments, such a competing antibody binds to the same epitope (e.g., a linear or a conformational epitope) that is bound by any of the anti-MIC antibodies described herein. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized MIC is incubated in a solution comprising a first labeled antibody that binds to MIC (e.g., any of the anti-MIC antibodies described herein) and a second unlabeled antibody that is being tested for its ability to compete with the first antibody for binding to MIC. The second antibody may be present in a hybridoma supernatant. As a control, immobilized MIC is incubated in a solution comprising the first labeled antibody but not the second unlabeled antibody. After incubation under conditions permissive for binding of the first antibody to MIC, excess unbound antibody is removed, and the amount of label associated with immobilized MIC is measured. If the amount of label associated with immobilized MIC is substantially reduced in the test sample relative to the control sample, then that indicates that the second antibody is competing with the first antibody for binding to MIC. See Harlow and Lane (1988) *Antibodies: A Laboratory Manual* ch.14 (Cold Spring Harbor Laboratory, Cold Spring Harbor, N.Y.).

2. Activity Assays

In one aspect, assays are provided for identifying anti-MIC antibodies thereof having biological activity. Biological activity may include, e.g., reducing the shedding of MIC and/or reducing the level of soluble MIC. Antibodies having such biological activity in vivo and/or in vitro are also provided.

In certain embodiments, an antibody of the invention is tested for such biological activity. In some embodiments, the reduction in shedding of MIC is tested by assaying and comparing levels of surface MIC on MIC-expressing cells in the presence or absence of antibody. Levels of cell surface MIC can detected using either qualitative (e.g., immunohistochemistry) or quantitative (e.g., flow cytometry) methods known to those of skill for detecting surface polypeptides. An exemplary assay is described in Example 14 of WO2015/085210. In other embodiments, a reduction in the level of soluble MIC is tested by assaying and comparing levels of MIC found in the culture media of MIC-expressing cells in the presence or absence of antibody using, for example, an ELISA. An exemplary assay is described in the examples herein as well as Example 8 of WO2013/117647.

In certain embodiments, the shedding of MIC is reduced by 10%, 15%, 20%, 25%, 30%, 35%, 40%, 45%. 50%, 55%, 60%, 65%, 70%, 75%, 80%, 85%, 90%, 95%, or 100% compared to shedding of MIC in the absence of antibodies described herein.

In certain embodiments, the reduction in levels of soluble MIC is reduced by 10%, 15%, 20%, 25%, 30%, 35%, 40%, 45%., 50%, 55%, 60%, 65%, 70%, 75%, 80%, 85%, 90%, 95%, or 100% compared to the reduction in levels of soluble MIC in the absence of antibodies described herein.

Other biological activities of interest for the antibodies described herein include any that would enhance the antibody's efficacy for treating or delaying progression of cancer or an immune related disease and/or increasing, enhancing, or stimulating an immune response or function in a subject. Such biological activities may include enhancement of NK and T cell cytolytic function, inhibition of NKG2D downregulation, ability to reduce serum levels of MIC in vivo, and inhibition of tumor growth. Assays for these activities are well known in the art. Exemplary assays are described in WO2015/085210. In certain embodiments, the antibodies described herein enhance the biological activity by 10%, 15%, 20%, 25%, 30%, 35%, 40%, 45%. 50%, 55%, 60%, 65%, 70%, 75%, 80%, 85%, 90%, 95%, or 100% compared to the level of biological activity in the absence of antibodies described herein.

D. Immunoconjugates

The invention also provides immunoconjugates comprising an anti-MIC antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Rr^{186}$, $Re^{188}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate (HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-MIC antibodies provided herein is useful for detecting the presence of MIC in a biological sample. The term "detecting" as used herein encompasses quantitative or qualitative detection. In certain embodiments, a biological sample comprises a cell or tissue, such as a sample of a tumor from a biopsy, surgical specimen or a fine needle aspirate. In some embodiments, the biological sample is ascites, urine, blood, plasma or serum.

In one embodiment, an anti-MIC antibody for use in a method of diagnosis or detection is provided. In a further aspect, a method of detecting the presence of MIC in a biological sample is provided. In certain embodiments, the method comprises contacting the biological sample with an anti-MIC antibody as described herein under conditions permissive for binding of the anti-MIC antibody to MIC, and detecting whether a complex is formed between the anti-MIC antibody and MIC. Such method may be an in vitro or in vivo method. In one embodiment, an anti-MIC antibody is used to select subjects eligible for therapy with an anti-MIC antibody, e.g. where MIC is a biomarker for selection of patients. Exemplary disorders that may be diagnosed using an antibody of the invention include cancer, such as an epithelial cancer (e.g., melanoma).

In certain embodiments, labeled anti-MIC antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations and Compositions

Pharmaceutical formulations and compositions of an anti-MIC antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide an additional medicament (examples of which are provided herein). Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-MIC antibodies provided herein may be used in therapeutic methods.

In one aspect, an anti-MIC antibody for use as a medicament is provided. In further aspects, an anti-MIC antibody for use in treating or delaying progression of cancer or an immune related disease (e.g., immune related disease associated with a NKG2D ligand, unresolved acute infection, chronic infection, tumor immunity) or increasing, enhancing or stimulating an immune response or function is provided. In certain embodiments, an anti-MIC antibody for use in a method of treatment is provided. In certain embodiments, the invention provides an anti-MIC antibody for use in a method of treating an individual having cancer or an immune related disease (e.g., immune related disease associated with a NKG2D ligand, unresolved acute infection, chronic infection, tumor immunity or in need of increasing, enhancing or stimulating an immune response or function comprising administering to the individual an effective amount of the anti-MIC antibody. In one such embodiment, the method further comprises administering to the individual an effective amount of at least one additional therapeutic agent, e.g., as described below. In further embodiments, the invention provides an anti-MIC antibody for use in reducing shedding of MIC and/or reducing the level of soluble MIC. In certain embodiments, the invention provides an anti-MIC antibody for use in a method of reducing shedding of MIC and/or reducing the level of soluble MIC in an individual comprising administering to the individual an effective amount of the anti-MIC antibody to reducing shedding of MIC and/or reducing the level of soluble MIC. An "individual" according to any of the above embodiments is preferably a human.

In a further aspect, the invention provides for the use of an anti-MIC antibody in the manufacture or preparation of a medicament. In one embodiment, the medicament is for treating or delaying progression of cancer or an immune related disease (e.g., immune related disease associated with a NKG2D ligand, unresolved acute infection, chronic infection, tumor immunity) or increasing, enhancing or stimulating an immune response or function. In a further embodiment, the medicament is for use in a method of treating or delaying progression of cancer or an immune related disease (e.g., Immune related disease associated with NKG2D ligand, unresolved acute infection, chronic infection, tumor immunity) or increasing, enhancing or stimulating an immune response or function comprising administering to an individual having cancer or an immune related disease (e.g., immune related disease associated with NKG2D ligand, unresolved acute infection, chronic infection, tumor immunity) or in need of increasing, enhancing or stimulating an immune response or function an effective amount of the medicament. In one such embodiment, the method further comprises administering to the individual an effective amount of at least one additional therapeutic agent, e.g., as described below. In a further embodiment, the medicament is for reducing shedding of MIC and/or reducing the level of soluble MIC. In a further embodiment, the medicament is for use in a method of reducing shedding of MIC and/or reducing the level of soluble MIC. in an individual comprising administering to the individual an amount effective of the medicament to reducing shedding of MIC and/or reducing the level of soluble MIC. An "individual" according to any of the above embodiments may be a human.

In a further aspect, the invention provides a method for treating in treating or delaying progression of cancer or an immune related disease (e.g., immune related disease associated with NKG2D ligand, unresolved acute infection, chronic infection, tumor immunity) or increasing, enhancing or stimulating an immune response or function. In one embodiment, the method comprises administering to an individual having such cancer or an immune related disease (e.g., Immune related disease associated with NKG2D ligand, unresolved acute infection, chronic infection, tumor immunity) or in need of increasing, enhancing or stimulating an immune response or function an effective amount of an anti-MIC antibody. In one such embodiment, the method further comprises administering to the individual an effective amount of at least one additional therapeutic agent, as described below. An "individual" according to any of the above embodiments may be a human.

In a further aspect, the invention provides a method for reducing shedding of MIC and/or reducing the level of soluble MIC in an individual. In one embodiment, the method comprises administering to the individual an effective amount of an anti-MIC antibody reducing shedding of MIC and/or reducing the level of soluble MIC. In one embodiment, an "individual" is a human.

In embodiments of the therapeutic methods described above, the cancer is any epithelial cancer, non-small cell lung cancer, small cell lung cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphomas, myelomas, mycoses fungoids, Merkel cell cancer, or other hematologic malignancies.

In a further aspect, the invention provides pharmaceutical formulations comprising any of the anti-MIC antibodies provided herein, e.g., for use in any of the above therapeutic methods. In one embodiment, a pharmaceutical formulation comprises any of the anti-MIC antibodies provided herein and a pharmaceutically acceptable carrier. In another embodiment, a pharmaceutical formulation comprises any of the anti-MIC antibodies provided herein and at least one additional therapeutic agent, e.g., as described in the below Combination Therapies section.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-MIC antibody.

Combination Therapies

Antibodies of the invention can be used either alone or in combination with other agents in a therapy. For instance, an antibody of the invention may be co-administered with at least one additional therapeutic agent. Such combination therapies noted above encompass combined administration (where two or more therapeutic agents are included in the same or separate formulations), and separate administration, in which case, administration of the antibody of the invention can occur prior to, simultaneously, concurrently and/or following, administration of the additional therapeutic agent or agents. In one embodiment, administration of the anti-MIC antibody and administration of an additional therapeutic agent occur within about one month, or within about one, two or three weeks, or within about one, two, three, four, five, or six days, of each other. Antibodies of the invention can also be used in combination with radiation therapy.

In some embodiments, an antibody provided herein may be administered in conjunction with a chemotherapy or chemotherapeutic agent. In some embodiments, an antibody provided herein may be administered in conjunction with a radiation therapy or radiotherapeutic agent. In some embodiments, an antibody provided herein may be administered in conjunction with a targeted therapy or targeted therapeutic agent. In some embodiments, an antibody provided herein may be administered in conjunction with an immunotherapy or immunotherapeutic agent, for example a monoclonal antibody.

In some embodiments, an antibody provided herein may be administered in conjunction with a PD-1 axis binding antagonist. A PD-1 axis binding antagonist includes but is not limited to a PD-1 binding antagonist, a PD-L1 binding antagonist and a PD-L2 binding antagonist. Alternative names for "PD-1" include CD279 and SLEB2. Alternative names for "PD-L1" include B7-H1, B7-4, CD274, and B7-H. Alternative names for "PD-L2" include B7-DC, Btdc, and CD273. In some embodiments, PD-1, PD-L1, and PD-L2 are human PD-1, PD-L1 and PD-L2. In some embodiments, the PD-1 binding antagonist is a molecule that inhibits the binding of PD-1 to its ligand binding partners. In a specific aspect the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, the PD-L2 binding antagonist is a molecule that inhibits the binding of PD-L2 to its binding partners, such as an anti-PD-L2 antibody or immunoadhesin. In a specific aspect, a PD-L2 binding partner is PD-1. The antagonist may be an antibody, an antigen binding fragment thereof, an immunoadhesin, a fusion protein, or oligopeptide. In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of MDX-1106 (nivolumab, OPDIVO), Merck 3475 (MK-3475, pembrolizumab, KEYTRUDA), CT-011 (Pidilizumab), MEDI-0680 (AMP-514), PDR001, REGN2810, BGB-108, and BGB-A317. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 binding antagonist is AMP-224. In some embodiments, the PD-L1 binding antagonist is anti-PD-L1 antibody. In some embodiments, the anti-PD-L1 binding antagonist is selected from the group consisting of YW243.55.S70, MPDL3280A (atezolizumab), MEDI4736 (durvalumab), MDX-1105, and MSB0010718C (avelumab). MDX-1105, also known as BMS-936559, is an anti-PD-L1 antibody described in WO2007/005874. Antibody YW243.55.S70 (heavy and light chain variable region sequences shown in SEQ ID Nos. 20 and 21, respectively) is an anti-PD-L1 described in WO 2010/077634 A1. MDX-1106, also known as MDX-1106-04, ONO-4538, BMS-936558 or nivolumab, is an anti-PD-1 antibody described in WO2006/121168. Merck 3475, also known as MK-3475, SCH-900475 or pembrolizumab, is an anti-PD-1 antibody described in WO2009/114335. CT-011, also known as hBAT, hBAT-1 or pidilizumab, is an anti-PD-1 antibody described in WO2009/101611. AMP-224, also known as B7-DCIg, is a PD-L2-Fc fusion soluble receptor described in WO2010/027827 and WO2011/066342. In some embodiments, the anti-PD-1 antibody is MDX-1106. Alternative names for "MDX-1106" include MDX-1 106-04, ONO-4538, BMS-936558 or nivolumab. In some embodiments, the anti-PD-1 antibody is nivolumab (CAS Registry Number: 946414-94-4).

In some embodiments, an antibody provided herein may be administered in conjunction with an agonist directed against an activating co-stimulatory molecule. In some embodiments, an activating co-stimulatory molecule may include CD40, CD226, CD28, GITR, CD137, CD27, HVEM, or CD127. In some embodiments, the agonist directed against an activating co-stimulatory molecule is an agonist antibody that binds to CD40, CD226, CD28, OX40, GITR, CD137, CD27, HVEM, or CD127. In some embodiments, an antibody provided herein may be administered in conjunction with an antagonist directed against an inhibitory co-stimulatory molecule. In some embodiments, an inhibitory co-stimulatory molecule may include CTLA-4 (also known as CD152), PD-1, TIM-3, BTLA, VISTA, LAG-3, B7-H3, B7-H4, IDO, TIGIT, MICA/B, or arginase. In some embodiments, the antagonist directed against an inhibitory co-stimulatory molecule is an antagonist antibody that binds to CTLA-4, PD-1, TIM-3, BTLA, VISTA, LAG-3 (e.g., LAG-3-IgG fusion protein (IMP321)), B7-H3, B7-H4, IDO, TIGIT, MICA/B, or arginase.

In some embodiments, an antibody provided herein may be administered in conjunction with an antagonist directed against CTLA-4 (also known as CD152), e.g., a blocking antibody. In some embodiments, an antibody provided herein may be administered in conjunction with ipilimumab (also known as MDX-010, MDX-101, or Yervoy®). In some embodiments, an antibody provided herein may be administered in conjunction with tremelimumab (also known as ticilimumab or CP-675,206). In some embodiments, an antibody provided herein may be administered in conjunction with an antagonist directed against B7-H3 (also known as CD276), e.g., a blocking antibody. In some embodiments, an antibody provided herein may be administered in conjunction with MGA271. In some embodiments, an antibody provided herein may be administered in conjunction with an antagonist directed against a TGF beta, e.g., metelimumab (also known as CAT-192), fresolimumab (also known as GC1008), or LY2157299.

In some embodiments, an antibody provided herein may be administered in conjunction with a treatment comprising adoptive transfer of a T cell (e.g., a cytotoxic T cell or CTL) expressing a chimeric antigen receptor (CAR). In some embodiments, an antibody provided herein may be administered in conjunction with UCART19. In some embodiments, an antibody provided herein may be administered in conjunction with WT128z. In some embodiments, an antibody provided herein may be administered in conjunction with KTE-C19 (Kite). In some embodiments, an antibody provided herein may be administered in conjunction with CTL019 (Novartis). In some embodiments, an antibody provided herein may be administered in conjunction with a treatment comprising adoptive transfer of a T cell comprising a dominant-negative TGF beta receptor, e.g, a dominant-negative TGF beta type II receptor. In some embodiments, an antibody provided herein may be administered in conjunction with a treatment comprising a HERCREEM protocol (see, e.g., ClinicalTrials.gov Identifier NCT00889954).

In some embodiments, an antibody provided herein may be administered in conjunction with an antagonist directed against CD19. In some embodiments, an antibody provided herein may be administered in conjunction with MOR00208. In some embodiments, an antibody provided herein may be administered in conjunction with an antagonist directed against CD38. In some embodiments, an antibody provided herein may be administered in conjunction with daratumumab.

In some embodiments, an antibody provided herein may be administered in conjunction with an agonist directed against CD137 (also known as TNFRSF9, 4-1BB, or ILA), e.g., an activating antibody. In some embodiments, an antibody provided herein may be administered in conjunction with urelumab (also known as BMS-663513). In some embodiments, an antibody provided herein may be administered in conjunction with an agonist directed against CD40, e.g., an activating antibody. In some embodiments, an antibody provided herein may be administered in conjunction with CP-870893 or RO7009789. In some embodiments, an antibody provided herein may be administered in conjunction with an agonist directed against OX40 (also known as CD134), e.g., an activating antibody. In some embodiments, an antibody provided herein may be administered in conjunction with an agonist directed against CD27, e.g., an activating antibody. In some embodiments, an antibody provided herein may be administered in conjunction with CDX-1127 (also known as varlilumab). In some embodiments, an antibody provided herein may be administered in conjunction with an antagonist directed against indoleamine-2,3-dioxygenase (IDO). In some embodiments, with the IDO antagonist is 1-methyl-D-tryptophan (also known as 1-D-MT). In some embodiments, the IDO antagonist is an IDO antagonist shown in WO2010/005958 (the contents of which are expressly incorporated by record herein). In some embodiments the IDO antagonist is 4-({2-[(Aminosulfonyl)amino]ethyl}amino)-N-(3-bromo-4-fluorophenyl)-N'-hydroxy-1,2,5-oxadiazole-3-carboximidamide (e.g., as described in Example 23 of WO2010/005958). In some embodiments the IDO antagonist is

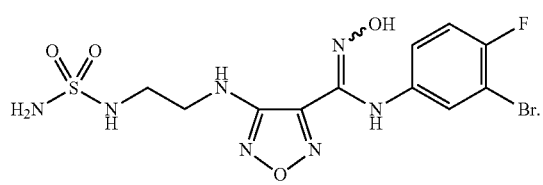 [SMILES: NS(=O)(=O)NCCNc1nonc1C(=NO)Nc1ccc(F)c(Br)c1]

In some embodiments, the IDO antagonist is INCB24360. In some embodiments, the IDO antagonist is Indoximod (the D isomer of 1-methyl-tryptophan). In some embodiments, an antibody provided herein may be administered in conjunction with an antibody-drug conjugate. In some embodiments, the antibody-drug conjugate comprises mertansine or monomethyl auristatin E (MMAE). In some embodiments, an antibody provided herein may be administered in conjunction with an anti-NaPi2b antibody-MMAE conjugate (also known as DNIB0600A, RG7599 or lifastuzumab vedotin). In some embodiments, an antibody provided herein may be administered in conjunction with trastuzumab emtansine (also known as T-DM1, ado-trastuzumab emtansine, or KADCYLA®, Genentech). In some embodiments, an antibody provided herein may be administered in conjunction with an anti-MUC16 antibody-MMAE conjugate, DMUC5754A. In some embodiments, an antibody provided herein may be administered in conjunction with an anti-MUC16 antibody-MMAE conjugate, DMUC4064A. In some embodiments, an antibody provided herein may be administered in conjunction with an antibody-drug conjugate targeting the endothelin B receptor (EDNBR), e.g., an antibody directed against EDNBR conjugated with MMAE. In some embodiments, an antibody provided herein may be administered in conjunction with an antibody-drug conjugate targeting the lymphocyte antigen 6 complex, locus E (Ly6E), e.g., an antibody directed against Ly6E conjugated with MMAE, (also known as DLYE5953A). In some embodiments, an antibody provided herein may be administered in conjunction with polatuzumab vedotin. In some embodiments, an antibody provided herein may be administered in conjunction with an antibody-drug conjugate targeting CD30. In some embodiments, an antibody provided herein may be administered in conjunction with ADCETRIS (also known as brentuximab vedotin). In some embodiments, an antibody provided herein may be administered in conjunction with polatuzumab vedotin.

In some embodiments, an antibody provided herein may be administered in conjunction with an angiogenesis inhibitor. In some embodiments, an antibody provided herein may be administered in conjunction with an antibody directed against a VEGF, e.g., VEGF-A. In some embodiments, an antibody provided herein may be administered in conjunction with bevacizumab (also known as AVASTIN®, Genentech). In some embodiments, an antibody provided herein may be administered in conjunction with an antibody directed against angiopoietin 2 (also known as Ang2). In some embodiments, an antibody provided herein may be administered in conjunction with MEDI3617. In some embodiments, an antibody provided herein may be administered in conjunction with an antibody directed against VEGFR2. In some embodiments, an antibody provided herein may be administered in conjunction with ramucirumab. In some embodiments, an antibody provided herein may be administered in conjunction with a VEGF Receptor fusion protein. In some embodiments, an antibody provided herein may be administered in conjunction with aflibercept. In some embodiments, an antibody provided herein may be administered in conjunction with ziv-aflibercept (also known as VEGF Trap or Zaltrap®). In some embodiments, an antibody provided herein may be administered in conjunction with a bispecific antibody directed against VEGF and Ang2. In some embodiments, an antibody provided herein may be administered in conjunction with RG7221 (also known as vanucizumab). In some embodiments, an antibody provided herein may be administered in conjunction with an angiogenesis inhibitor and in conjunction with a PD-1 axis binding antagonist (e.g., a PD-1 binding antagonist such as an anti-PD-1 antibody, a PD-L1 binding antagonist such as an anti-PD-L1 antibody, and a PD-L2 binding antagonist such as an anti-PD-L2 antibody). In some embodiments, an antibody provided herein may be administered in conjunction with bevacizumab and a PD-1 axis binding antagonist (e.g., a PD-1 binding antagonist such as an anti-PD-1 antibody, a PD-L1 binding antagonist such as an anti-PD-L1 antibody, and a PD-L2 binding antagonist such as an anti-PD-L2 antibody). In some embodiments, an antibody provided herein may be administered in conjunction with bevacizumab and MDX-1106 (nivolumab, OPDIVO). In some embodiments, an antibody provided herein may be administered in conjunction with bevacizumab and Merck 3475 (MK-3475, pembrolizumab, KEYTRUDA). In some embodiments, an antibody provided herein may be administered in conjunction with bevacizumab and CT-011 (Pidilizumab). In some embodiments, an antibody provided herein may be administered in conjunction with bevacizumab and MEDI-0680 (AMP-514). In some embodiments, an antibody provided herein may be administered in conjunction with bevacizumab and PDR001. In some embodiments, an antibody provided herein may be administered in conjunction with bevacizumab and REGN2810. In some embodiments, an antibody provided herein may be administered in conjunction with bevacizumab and BGB-108. In some embodiments, an antibody provided herein may be administered in conjunction with bevacizumab and BGB-A317. In some embodiments, an antibody provided herein may be administered in conjunction with bevacizumab and YW243.55.S70. In some embodiments, an antibody provided herein may be administered in conjunction with bevacizumab and MPDL3280A. In some embodiments, an antibody provided herein may be administered in conjunction with bevacizumab and MEDI4736. In some embodiments, an antibody provided herein may be administered in conjunction with bevacizumab and MDX-1105. In some embodiments, an antibody provided herein may be administered in conjunction with bevacizumab and MSB0010718C (avelumab).

In some embodiments, an antibody provided herein may be administered in conjunction with an antineoplastic agent. In some embodiments, an antibody provided herein may be administered in conjunction with an agent targeting CSF-1R (also known as M-CSFR or CD115). In some embodiments, an antibody provided herein may be administered in conjunction with anti-CSF-1R antibody (also known as IMC-CS4 or LY3022855) In some embodiments, an antibody provided herein may be administered in conjunction with anti-CSF-1R antibody, RG7155 (also known as R05509554 or emactuzumab). In some embodiments, an antibody provided herein may be administered in conjunction with an interferon, for example interferon alpha or interferon gamma. In some embodiments, an antibody provided herein may be administered in conjunction with Roferon-A (also known as recombinant Interferon alpha-2a). In some embodiments, an antibody provided herein may be administered in conjunction with GM-CSF (also known as recombinant human granulocyte macrophage colony stimulating factor, rhu GM-CSF, sargramostim, or Leukine®). In some embodiments, an antibody provided herein may be administered in conjunction with IL-2 (also known as aldesleukin or Proleukin®). In some embodiments, an antibody provided herein may be administered in conjunction with IL-12. In some embodiments, an antibody provided herein may be administered in conjunction with IL27. In some embodiments, an antibody provided herein may be administered in conjunction with IL-15. In some embodiments, an antibody provided herein may be administered in conjunction with ALT-803. In some embodiments, an antibody provided herein may be administered in conjunction with an antibody targeting CD20. In some embodiments, the antibody targeting CD20 is obinutuzumab (also known as GA101 or Gazyva®) or rituximab. In some embodiments, an antibody provided herein may be administered in conjunction with an antibody targeting GITR. In some embodiments, the antibody targeting GITR is TRX518. In some embodiments, the antibody targeting GITR is MK04166 (Merck).

In some embodiments, an antibody provided herein may be administered in conjunction with an inhibitor of Bruton's tyrosine kinase (BTK). In some embodiments, an antibody provided herein may be administered in conjunction with ibrutinib. In some embodiments, an antibody provided herein may be administered in conjunction with an inhibitor of Isocitrate dehydrogenase 1 (IDH1) and/or Isocitrate dehydrogenase 2 (IDH2). In some embodiments, an antibody provided herein may be administered in conjunction with AG-120 (Agios).

In some embodiments, an antibody provided herein may be administered in conjunction with obinutuzumab and a PD-1 axis binding antagonist (e.g., a PD-1 binding antagonist such as an anti-PD-1 antibody, a PD-L1 binding antagonist such as an anti-PD-L1 antibody, and a PD-L2 binding antagonist such as an anti-PD-L2 antibody).

In some embodiments, an antibody provided herein may be administered in conjunction with a cancer vaccine. In some embodiments, the cancer vaccine is a peptide cancer vaccine, which in some embodiments is a personalized peptide vaccine. In some embodiments the peptide cancer vaccine is a multivalent long peptide, a multi-peptide, a peptide cocktail, a hybrid peptide, or a peptide-pulsed dendritic cell vaccine (see, e.g., Yamada et al., Cancer Sci, 104:14-21, 2013). In some embodiments, an antibody provided herein may be administered in conjunction with an adjuvant. In some embodiments, an antibody provided herein may be administered in conjunction with a treatment comprising a TLR agonist, e.g., Poly-ICLC (also known as Hiltonol®), LPS, MPL, or CpG ODN. In some embodiments, an antibody provided herein may be administered in conjunction with tumor necrosis factor (TNF) alpha. In some embodiments, an antibody provided herein may be administered in conjunction with IL-1. In some embodiments, an antibody provided herein may be administered in conjunction with HMGB1. In some embodiments, an antibody provided herein may be administered in conjunction with an IL-10 antagonist. In some embodiments, an antibody provided herein may be administered in conjunction with an IL-4 antagonist. In some embodiments, an antibody provided herein may be administered in conjunction with an IL-13 antagonist. In some embodiments, an antibody provided herein may be administered in conjunction with an IL-17 antagonist. In some embodiments, an antibody provided herein may be administered in conjunction with an HVEM antagonist. In some embodiments, an antibody provided herein may be administered in conjunction with an ICOS agonist, e.g., by administration of ICOS-L, or an agonistic antibody directed against ICOS. In some embodiments, an antibody provided herein may be administered in conjunction with a treatment targeting CX3CL1. In some embodiments, an antibody provided herein may be administered in conjunction with a treatment targeting CXCL9. In some embodiments, an antibody provided herein may be administered in conjunction with a treatment targeting CXCL10. In some embodiments, an antibody provided herein may be administered in conjunction with a treatment targeting CCL5. In some embodiments, an antibody provided herein may be administered in conjunction with an LFA-1 or ICAM1 agonist. In some embodiments, an antibody provided herein may be administered in conjunction with a Selectin agonist.

In some embodiments, an antibody provided herein may be administered in conjunction with an inhibitor of B-Raf. In some embodiments, an antibody provided herein may be administered in conjunction with vemurafenib (also known as Zelboraf®). In some embodiments, an antibody provided herein may be administered in conjunction with dabrafenib (also known as Tafinlar®). In some embodiments, an antibody provided herein may be administered in conjunction with encorafenib (LGX818).

In some embodiments, an antibody provided herein may be administered in conjunction with an EGFR inhibitor. In some embodiments, an antibody provided herein may be administered in conjunction with erlotinib (also known as Tarceva®). In some embodiments, an antibody provided herein may be administered in conjunction with an inhibitor of EGFR-T790M. In some embodiments, an antibody provided herein may be administered in conjunction with gefitinib. In some embodiments, an antibody provided herein may be administered in conjunction with afatinib. In some embodiments, an antibody provided herein may be administered in conjunction with cetuximab (also known as Erbitux®). In some embodiments, an antibody provided herein may be administered in conjunction with panitumumab (also known as Vectibix®). In some embodiments, an antibody provided herein may be administered in conjunction with rociletinib. In some embodiments, an antibody provided herein may be administered in conjunction with AZD9291. In some embodiments, an antibody provided herein may be administered in conjunction with an inhibitor of a MEK, such as MEK1 (also known as MAP2K1) and/or MEK2 (also known as MAP2K2). In some embodiments, an antibody provided herein may be administered in conjunction with cobimetinib (also known as GDC-0973 or XL-518). In some embodiments, an antibody provided herein may be administered in conjunction with trametinib (also known as Mekinist®). In some embodiments, an antibody provided herein may be administered in conjunction with binimetinib.

In some embodiments, an antibody provided herein may be administered in conjunction an inhibitor of B-Raf (e.g., vemurafenib or dabrafenib) and an inhibitor of MEK (e.g., MEK1 and/or MEK2 (e.g., cobimetinib or trametinib). In some embodiments, an antibody provided herein may be administered in conjunction with an inhibitor of ERK (e.g., ERK1/2). In some embodiments, an antibody provided herein may be administered in conjunction with GDC-0994). In some embodiments, an antibody provided herein may be administered in conjunction with an inhibitor of B-Raf, an inhibitor of MEK, and an inhibitor of ERK1/2. In some embodiments, an antibody provided herein may be administered in conjunction with an inhibitor of EGFR, an inhibitor of MEK, and an inhibitor of ERK1/2. In some embodiments, an antibody provided herein may be administered in conjunction with one or more MAP kinase pathway inhibitor. In some embodiments, an antibody provided herein may be administered in conjunction with CK127. In some embodiments, an antibody provided herein may be administered in conjunction with an inhibitor of K-Ras.

In some embodiments, an antibody provided herein may be administered in conjunction with an inhibitor of c-Met. In some embodiments, an antibody provided herein may be administered in conjunction with onartuzumab (also known as MetMAb). In some embodiments, an antibody provided herein may be administered in conjunction with an inhibitor of anaplatic lymphoma kinase (ALK). In some embodiments, an antibody provided herein may be administered in conjunction with AF802 (also known as CH5424802 or alectinib). In some embodiments, an antibody provided herein may be administered in conjunction with crizotinib. In some embodiments, an antibody provided herein may be administered in conjunction with ceritinib. In some embodiments, an antibody provided herein may be administered in conjunction with an inhibitor of a phosphatidylinositol 3-kinase (PI3K). In some embodiments, an antibody provided herein may be administered in conjuction with buparlisib (BKM-120). In some embodiments, an antibody provided herein may be administered in conjunction with pictilisib (also known as GDC-0941). In some embodiments, an antibody provided herein may be administered in conjunction with buparlisib (also known as BKM-120). In some embodiments, an antibody provided herein may be administered in conjunction with perifosine (also known as KRX-0401). In some embodiments, an antibody provided herein may be administered in conjunction with a delta-selective inhibitor of a phosphatidylinositol 3-kinase (PI3K). In some embodiments, an antibody provided herein may be administered in conjunction with idelalisib (also known as GS-1101 or CAL-101). In some embodiments, an antibody provided herein may be administered in conjunction with taselisib (also known as GDC-0032). In some embodiments, an antibody provided herein may be administered in conjunction with BYL-719. In some embodiments, an antibody provided herein may be administered in conjunction with an inhibitor of an Akt. In some embodiments, an antibody provided herein may be administered in conjunction with MK2206. In some embodiments, an antibody provided herein may be administered in conjunction with GSK690693. In some embodiments, an antibody provided herein may be administered in conjunction with ipatasertib (also known as GDC-0068). In some embodiments, an antibody provided herein may be administered in conjunction with an inhibitor of mTOR. In some embodiments, an antibody provided herein may be administered in conjunction with sirolimus (also known as rapamycin). In some embodiments, an antibody provided herein may be administered in conjunction with temsirolimus (also known as CCI-779 or Torisel®). In some embodiments, an antibody provided herein may be administered in conjunction with everolimus (also known as RAD001). In some embodiments, an antibody provided herein may be administered in conjunction with ridaforolimus (also known as AP-23573, MK-8669, or deforolimus). In some embodiments, an antibody provided herein may be administered in conjunction with OSI-027. In some embodiments, an antibody provided herein may be administered in conjunction with AZD8055. In some embodiments, an antibody provided herein may be administered in conjunction with INK128. In some embodiments, an antibody provided herein may be administered in conjunction with a dual PI3K/mTOR inhibitor. In some embodiments, an antibody provided herein may be administered in conjunction with XL765. In some embodiments, an antibody provided herein may be administered in conjunction with GDC-0980. In some embodiments, an antibody provided herein may be administered in conjunction with BEZ235 (also known as NVP-BEZ235). In some embodiments, an antibody provided herein may be administered in conjunction with BGT226. In some embodiments, an antibody provided herein may be administered in conjunction with GSK2126458. In some embodiments, an antibody provided herein may be administered in conjunction with PF-04691502. In some embodiments, an antibody provided herein may be administered in conjunction with PF-05212384 (also known as PKI-587).

In some embodiments, an antibody provided herein may be administered in conjunction with an agent that selectively degrades the estrogen receptor. In some embodiments, an antibody provided herein may be administered in conjunction with GDC-0927. In some embodiments, an antibody provided herein may be administered in conjunction with an inhibitor of HER3. In some embodiments, an antibody provided herein may be administered in conjunction with duligotuzumab. In some embodiments, an antibody provided herein may be administered in conjunction with an inhibitor of LSD1. In some embodiments, an antibody provided herein may be administered in conjunction with an inhibitor of MDM2. In some embodiments, an antibody provided herein may be administered in conjunction with an inhibitor of BCL2. In some embodiments, an antibody provided herein may be administered in conjunction with venetoclax. In some embodiments, an antibody provided herein may be administered in conjunction with an inhibitor of CHK1. In some embodiments, an antibody provided herein may be administered in conjunction with GDC-0575. In some embodiments, an antibody provided herein may be administered in conjunction with an inhibitor of activated hedgehog signaling pathway. In some embodiments, an antibody provided herein may be administered in conjunction with ERIVEDGE.

In some embodiments, an antibody provided herein may be administered in conjunction with radiation therapy. In some embodiments, an antibody provided herein may be administered in conjunction with gemcitabine. In some embodiments, an antibody provided herein may be administered in conjunction with nab-paclitaxel (ABRAXANE). In some embodiments, an antibody provided herein may be administered in conjunction with trastuzumab. In some embodiments, an antibody provided herein may be administered in conjunction with TVEC. In some embodiments, an antibody provided herein may be administered in conjunction with IL27. In some embodiments, an antibody provided herein may be administered in conjunction with cyclophosphamide. In some embodiments, an antibody provided herein may be administered in conjunction with an agent that recruits T cells to the tumor. In some embodiments, an antibody provided herein may be administered in conjunction with lirilumab (IPH2102/BMS-986015). In some embodiments, an antibody provided herein may be administered in conjunction with Idelalisib. In some embodiments, an antibody provided herein may be administered in conjunction with an antibody that targets CD3 and CD20. In some embodiments, an antibody provided herein may be administered in conjunction with REGN1979. In some embodiments, an antibody provided herein may be administered in conjunction with an antibody that targets CD3 and CD19. In some embodiments, an antibody provided herein may be administered in conjunction with blinatumomab.

In some embodiments, an antibody provided herein may be administered in conjunction with an oncolytic virus. In some embodiments, an antibody provided herein may be administered in conjunction with carboplatin and nab-paclitaxel. In some embodiments, an antibody provided herein may be administered in conjunction with carboplatin and paclitaxel. In some embodiments, an antibody provided herein may be administered in conjunction with cisplatin and pemetrexed. In some embodiments, an antibody provided herein may be administered in conjunction with cisplatin and gemcitabine. In some embodiments, an antibody provided herein may be administered in conjunction with FOLFOX. In some embodiments, an antibody provided herein may be administered in conjunction with FOLFIRI.

Such combination therapies noted above encompass combined administration (where two or more therapeutic agents are included in the same or separate formulations), and separate administration, in which case, administration of the antibody provided herein can occur prior to, simultaneously, and/or following, administration of the additional therapeutic agent and/or adjuvant. Antibodies provided herein can also be used in combination with radiation therapy.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the conditions of choice described herein. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-MIC antibody.

III. Methods for Epitope Mapping

In one aspect, the invention is based on Applicants' discovery that introduction of glycosylation on an antigen can block antibody binding and provide information on the antigen epitope. Without wishing to be bound by theory, Applicants believe that glycosylation of specific amino acids of a polypeptide can disrupt antibody binding and accordingly, that reduced binding of an antibody to a glycosylated polypeptide compared to binding of the antibody to the polypeptide without the substituted glycosylated amino acid indicates that at least one of the previously unglycosylated amino acid or surface-exposed amino acids in its structural proximity, e.g., amino acids within 1, 2, 3, 4, or 5 Angstroms and accessible to antibodies, are a part of an epitope or a contact amino acid of the antibody. In some aspects, the methods described herein relate to mapping an epitope of an antibody. In other aspects, the methods described herein relate to identifying the contact amino acids of an antibody.

In some embodiments, the methods comprise (a) substituting an unglycosylated amino acid of a polypeptide to generate a glycosylated polypeptide comprising a substituted glycosylated amino acid; (b) determining whether the antibody binds to the glycosylated polypeptide; and (c) identifying at least one of the unglycosylated amino acid or surface-exposed amino acids within 5 Angstroms of the unglycosylated amino acid as part of the epitope or one of the contact amino acids of the antibody if binding of the antibody to the glycosylated polypeptide is reduced compared to binding of the antibody to the polypeptide without the substituted glycosylated amino acid.

In some embodiments, the methods comprise (a) substituting an unglycosylated amino acid of a polypeptide to generate a glycosylated polypeptide comprising a substituted glycosylated amino acid; and (b) determining whether the antibody binds to the glycosylated polypeptide, wherein at least one of the unglycosylated amino acid or surface-exposed amino acids within 5 Angstroms of the unglycosylated amino acid is identified as part of the epitope or one of the contact amino acids of the antibody if binding of the antibody to the glycosylated polypeptide is reduced compared to binding of the antibody to the polypeptide without the substituted glycosylated amino acid.

In some embodiments, the methods comprise identifying at least one of an unglycosylated amino acid or surface-exposed amino acids within 5 Angstroms of the unglycosylated amino acid as part of the epitope or one of the contact amino acids of the antibody if binding of the antibody to a glycosylated polypeptide comprising a substituted glycosylated amino acid is reduced compared to binding of the antibody to a polypeptide without the substituted glycosylated amino acid, wherein the glycosylated polypeptide is generated by substituting an unglycosylated amino acid of the polypeptide.

The methods described herein can be used to map the epitope or identify the contact amino acids for any polypeptide that can be expressed in a recombinant expression host with glycosylation machinery. The polypeptide may be a full-length protein, a fragment of a protein, and/or a protein fused to another domain to facilitate expression and folding, e.g., a Fc region. The epitope or contact amino acids to be mapped or identified may be linear or conformational.

In some embodiments, substitution of the unglycosylated amino acid of the polypeptide is accomplished by introducing or creating a glycosylation site in the polypeptide. The glycosylation site may be for any form of glycosylation, including, but not limited to, N-linked glycosylation, O-linked glycosylation, C-mannosylation, and glypiation. In eukaryotes, glycosylation sites for N-linked glycosylation are defined by a consensus sequence (N-X-S/T (standard sequons); N-X-C, N-G, N-X-V (non-standard sequons) (Moremen et al. *Nature Reviews Molecular Cell Biology* 13, 448-462 (2012)); X=any residue except P). For other types of glycosylation, bioinformatics software may be used to predict glycosylation sites e.g., Caragea et al. *BMC Bioinformatics* 8, 438 (2007). Methods for engineering glycosylation sites via site-directed mutagenesis are well known in the art. Introduction of N-linked glycosylation sites and confirmation of glycosylation by increased MW as measured by SDS-PAGE are described in Eggink et al. J. Virol. 88, 699-704 (2014). Methods are also described in Chandramouli et al. "Structure of HCMV glycoprotein B in the postfusion conformation bound to a broadly neutralizing human antibody" *Nature Communications*, in press. In some embodiments, to minimize the number of mutations needed for glycosylation, the glycosylation site is introduced at the site of a partial glycosylation motif. For N-linked glycosylation, a partial glycosylation motif in the primary sequence of the polypeptide is present when an asparagine residue is not followed by a proline, or when serine and threonine residues are not preceded by proline.

The substituted glycosylated amino acid in the methods described herein may comprise any type of glycan that can be linked to an amino acid and disrupts antibody binding. For example, a N-linked glycan, an O-linked glycan, a C-linked mannose, or a glycolipid.

In some embodiments, the unglycosylated amino acid is on the surface of the polypeptide without the substituted glycosylated amino acid. Any means of predicting or visualizing the structure of a polypeptide, such as a crystal structure or homology model, can be used to identify surface exposed positions to ensure properly folded material. Homology models can be created by modeling software such as SwissModel, MOE (CCG), Bioluminate (Schrödinger).

Binding of the antibody to the glycosylated polypeptide may be detected by any means known in the art to detect binding between antibodies and polypeptides, including ELISA and other methods described in the Assay section of this disclosure. Binding of the antibody to the glycosylated polypeptide may be reduced by 10%, 15%, 20%, 25%, 30%, 35%, 40%, 45%. 50%, 55%, 60%, 65%, 70%, 75%, 80%, 85%, 90%, 95%, or 100% compared to binding of the antibody to the polypeptide without the substituted glycosylated amino acid.

In some embodiments, the methods of epitope mapping and identifying contact amino acids of the antibody also include steps to ensure that the substitution of the unglycosylated amino acid with a substituted glycosylated amino acid does not alter the overall integrity or structure of the polypeptide. Exemplary steps include testing for binding of the glycosylated polypeptide to control antibodies that bind outside of the engineered glycosylation area. Other exemplary steps include performing biophysical techniques such as differential scanning fluorimetry (DSF) (Niesen et al. *Nat Protoc* 2, 2212-2221 (2007)), differential scanning calorimetry (DSC) Makhatadze, G. I. (1998) *Characterization of Recombinant Proteins, Chapter* 7: *Measuring Protein Thermostability by Differential Scanning Calorimetry,* 7.9.1-7.9.14. In *Current Protocols in Protein Science* by John Wiley & Sons, Inc. doi:10.1002/0471140864.ps0709s12/pdf, circular dichroism (CD) (Greenfield et al. *Nat Protoc* 1, 2876-2890 (2006)) to confirm the polypeptide still properly folds after substitution of the unglycosylated amino acid with a substituted glycosylated amino acid. In other embodiments, the methods of epitope mapping and identifying contact amino acids of the antibody also include steps to ensure that the substitution of the unglycosylated amino acid with a glycosylated amino acid is successful, for example, by mass-spectrometric assays, gel-shift assays or a Western.

In some embodiments, subsequent to mapping of the epitope or identifying contact amino acids, alanine scanning is used to fine map the epitope.

Methods for binning antibodies are also provided. The methods comprise mapping an epitope or identifying contact amino acids of a first antibody by any of the methods described above, mapping an epitope or identifying contact amino acids of a second antibody by any of the methods described above, and determining that the first antibody and the second antibody are in the same bin if they have the same epitope or contact amino acids.

Antibodies described herein, where the epitope is mapped by the above methods or the contact amino acids are identified by the above methods, are also provided.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1

Generation of Anti-MICAS Antibodies

This Example describes the strategies that were used to generate anti-MICA/B antibodies.

Legacy Immunization Protocol

A panel of antibodies that selectively bind human MICA were generated using MICA fused to Fc (in house) as an immunogen. Ten BALB/c mice were each injected at the footpad with MICA-Fc protein resuspended with 2-component Ribi in PBS. All subsequent boosts contained MICA-Fc protein resuspended with Ribi in PBS. Nine rounds of boosts followed every 3 to 4 days at footpad.

GH Immunization Protocol

A panel of antibodies that selectively bind human MICA were generated using MICA alpha 3 domains (alleles 002, 004, 008 and MICB 005) fused to murine IgG2a (in house) as an immunogen. Five BALB/c mice were each initially injected at the base of tail with 50 ug MICA protein (mixture of alleles) resuspended with Complete Freund's Adjuvant (CFA) in PBS. All subsequent boosts contained mixtures of MICA alleles resuspended with Incomplete Freund's Adjuvant (IFA) in PBS. Five rounds of boosts followed every two weeks at different sites (hock 16 ug/mouse, IP 8 ug/mouse, subcutaneous 8 ug/mouse, and/or base of tail 8 ug/mouse).

GG Immunization Protocol

A panel of antibodies that selectively bind human MICA were generated using MICA alpha 3 domains (allelles 002, 004, 008 and MICB 005) fused to murine IgG2a (in house) as an immunogen. Five BALB/c mice were each initially injected at the hock and IP with 6 and 3 ug of MICA002 alpha 3 domain fused to muIgG2a protein (mixture of alleles) resuspended with cocktail adjuvant (cocktail consisting of poly I:C+monophosphoryl lipid A (MBL)+R848+ CpG) in PBS per mouse respectively. All subsequent boosts contained sequential immunization of different MICA alpha 3 domains fused to muIgG2a (alleles 004, 008 and MICB005) resuspended with cocktail adjuvant in PBS. Fifteen rounds of boosts followed every 3-4 days at different sites (hock 6 ug/mouse, IP 3 ug/mouse, subcutaneous 3 ug/mouse, and/or base of tail 3 ug/mouse).

HZ Immunization Protocol

A panel of antibodies that bind human MICA were generated using MICA/B ECD domains (allelles 002, 004, 008 and MICB 005) with a Flag tag, (in house). Five BALB/c mice were each initially injected at the base of tail with 50 ug MICA/B protein (mixture of alleles) resuspended with cocktail adjuvant (poly I:C+monophosphoryl lipid A (MBL)+R848+CpG) in PBS. All subsequent boosts contained mixtures of MICA alleles resuspended with cocktail adjuvant in PBS. Mice were injected once a week at different sites (hock 16 ug/mouse, IP 8 ug/mouse subcutaneous 8 ug/mouse, and/or base of tail 8 ug/mouse).

Hybridoma Fusing And Development

For all of the above described immunizations, three days after the final boost, animals which showed positive serum titers by ELISA were sacrificed, and a single cell suspension of splenocytes was fused with the mouse myeloma cell line P3X63Ag.U.1 (American Type Culture Collection, Manassas, Va.) using electrofusion (Cyto Pulse Sciences, Inc., Glen Burnie, Md.). Fused hybridoma cells were selected from unfused splenic, popliteal node or myeloma cells using hypoxanthin-aminopterin-thymidine (HAT) selection in Medium D from the ClonaCell® hybridoma selection kit (StemCell Technologies, Inc., Vancouver, BC, Canada). Hybridoma cells were cultured in Medium E from the ClonaCell® hybridoma selection kit, and cell culture supernatants were used for further characterization and screening.

Example 2

Binding Assays

This Example describes identification of hybridoma clones that bind to human MICA/B alleles, as measured by ELISA. Antibodies that bind ELISA were further tested using Biacore.

ELISA

Enzyme-linked immunosorbent assays (ELISAs) were used to determine if hybridoma clones described as above were producing monoclonal antibodies that bound to human MICA/B alleles. Nunc Maxisorp plates were coated with human MICA alleles 002, 004, 008 or MICB 005 alpha 3 domain (in-house) at 2 ug/ml in 50 mM sodium carbonate buffer, pH 9.6 overnight at 4° C. Supernatants from mouse derived hybridomas were added to the plates after blocking for a hour with a 1×PBS buffer containing 0.5% BSA and 0.05% Tween 20. After incubation, plates were washed multiple times with wash buffer (1×PBS containing 0.05% Tween 20) and secondary antibody (goat anti-mouse IgG Fc conjugated to HRP, Sigma) was added. Plates were then washed multiple times with wash buffer again before adding either BioFX TMB Microwell 1 Component Peroxidase. After several minutes of incubation, the reaction was stopped with BioFX Stop Reagent for TMB Microwell. Plates were read on a Spectra MAX 340 plate reader (Molecular Devices; Sunnyvale, Calif.) at 630 nm.

The sequence of the MICA*008 alpha3 construct is provided below:

>MICA008.muIgG2a (a3 domain in bold).
Note: This was only used for the glyco variants.
(SEQ ID: 194)
GSTVPPMVNVTRSEASEGNITVTCRASSFYPRNIILTWRQDGVSLSHD

TQQWGDVLPDGNGTYQTWVATRICRGEEQRFTCYMEHSGNHSTHPVPS

GNSRAQVTDKKIEPRGPTIKPCPPCKCPAPNLLGGPSVFIFPPKIKDV

LMISLSPIVTCVVVDVSEDDPDVQISWFVNNVEVHTAQTQTHREDYNS

TLRVVSALPIQHQDWMSGKEFKCKVNNKDLPAPIERTISKPKGSVRAP

QVYVLPPPEEEMTKKQVTLTCMVTDFMPEDIYVEWTNNGKTELNYKNT

EPVLDSDGSYFMYSKLRVEKKNWVERNSYSCSVVHEGLHNHHTTKSFS

RTPGK

His-tagged MICA proteins used for ELISA and Biacore.

The sequence of the MICA*008 alpha3 construct is provided below:

>MICA008.His (a3 domain in bold)
(SEQ ID: 195)
GSTVPPMVNVTRSEASEGNITVTCRASSFYPRNIILTWRQDGVSLSHD

TQQWGDVLPDGNGTYQTWVATRICRGEEQRFTCYMEHSGNHSTHPVPS

GNSHHHHHHHH

The sequence of the MICA*002 alpha3 construct is provided below:

>MICA002.His (a3 domain in bold)
(SEQ ID: 196)
GSTVPPMVNVTRSEASEGNITVTCRASGFYPWNITLSWRQDGVSLSHD

TQQWGDVLPDGNGTYQTWVATRICQGEEQRFTCYMEHSGNHSTHPVPS

GNSHHHHHHHH

The sequence of the MICA*004 alpha3 construct is provided below:

>MICA004.His (a3 domain in bold)
(SEQ ID: 197)
GSVPPMVNVTRSEASEGNITVTCRASSFYPRNITLTWRQDGVSLSHDT

QQWGDVLPDGNGTYQTWVATRICQGEEQRFTCYMEHSGNHSTHPVPSG

NSHHHHHHHH

The sequence of the MICB*005 alpha3 construct is provided below:

>MICB005.His (a3 domain in bold)
(SEQ ID: 198)
GSTVPPMVNVTCSEVSEGNITVTCRASSFYPRNITLTWRQDGVSLSHN

TQQWGDVLPDGNGTYQTWVATRIRQGEEQRFTCYMEHSGNHGTHPVPS

GNSHHHHHHHH

TABLE 2

ELISA data for anti-MICA antibodies and binding to the alpha 3 domain of MICA alleles.

| | MICA*008 α3 | MICA*002 α3 | MICA*004 α3 | MICB*005 α3 |
|---|---|---|---|---|
| 3C9.10 | − | + | + | + |
| 7D4.6 | + | + | + | + |
| 6F8.7 | + | + | + | + |
| 32D2 | + | + | + | + |
| 3E11 | + | + | + | + |
| 9C9.5.6 | − | + | + | + |
| 1E6.1.3 | + | + | + | + |
| 7A3.1.9 | + | + | + | + |
| 6E12.5 | + | + | + | + |
| 20G11 | + | + | + | + |
| 6E1.1.12 | + | + | + | + |
| 2E5.2.3 | + | + | + | + |
| 1D5 | + | + | + | + |
| 15F11 | + | + | + | + |
| 13A9 | + | + | + | + |
| 12H10 | + | + | + | + |
| 18G3 | + | + | + | + |

Note:
ELISA values >0.5 are designated with a plus sign.
ELISA values <0.5 are designated with a minus sign.

Biacore

The binding kinetics of the anti-MICA/B antibodies were measured using surface plasmon resonance (SPR) on a Biacore T200 instrument (GE Healthcare). Anti-murine Fc or anti-human Fc (GE Healthcare) was immobilized on a CM5 sensor chip via amine-based coupling using manufacturer provided protocol. Anti-MICA/B antibody was captured by the anti-Fc and the MICA/B alleles were passed over. Antibody binding was measured to human MICA 002, 004, 008 and MICB 005 alpha 3 domains (His tagged, in-house). Sensograms for binding of MICA/B were recorded using an injection time of 2-3 minutes with a flow rate of 30 ml/min, at a temperature of 25° C., and with a running buffer of 10 mM HEPES, pH 7.4, 150 mM NaCl, and 0.005% Tween 20. After injection, disassociation of the alpha 3 domain from the antibody was monitored for 10 minutes in running buffer. The surface was regenerated between binding cycles with a 60 ul injection of 10 mM Glycine HCl pH 1.7. After subtraction of a blank which contained running buffer only, sensograms observed for MICA binding to anti-MICA/B antibody were analyzed using a 1:1 Langmuir binding model with software supplied by the manufacturer to calculate the kinetics and binding constants. The data was analyzed using a 1:1 binding model. Sensograms of MICA alleles binding to captured anti-MICA antibody were used to calculate the dissociation constant (Kd). Kinetic constants from these data are provided in Table 3. Final bin assignments for each clone are also shown (see Example 6 for further details regarding final bin assignments). FIG. 3A-FIG. 3E depict structural models showing where the epitopes for each bin are located on MICA.

TABLE 3

Kinetic Constants for Anti-MICA Antibodies Binding to its Ligands

| Clone | huMICA*002 alpha 3-his Kd (nM) | huMICA*004 alpha 3-his Kd (nM) | huMICA*008 alpha 3-his Kd (nM) | huMICB*005 alpha 3-his Kd (nM) | Final Bin |
|---|---|---|---|---|---|
| 3C9.10 | 81 | 60 | no binding | 45 | 1 |
| 9C9.5.6 | 16 | 18 | no binding | 11 | 3 |
| 1E6.1.3 | 24 | 37 | IC | 18 | 3 |
| 7A3.1.9 | 22 | 8.7 | IC | 16 | 3 |
| 6E12.5 | 4.5 | 3 | 15.1 | IC | 4 |
| 6E1.1.12 | 2.8 | 8.7 | 6.8 | 10 | 6 |
| 7D4.6 | 3.5 | 8.9 | 10 | 20 | 2 |
| 2E5.2.3 | 0.66 | 1.96 | 1.8 | 2.7 | 7 |
| 6F8.7 | 2.4 | 6.2 | 8.4 | 14.5 | 2 |
| 20G11 | 1.76 | 1.06 | 0.77 | 1.05 | 5 |
| 3E11 | 7.7 | 5 | 2.5 | 6.8 | 2 |
| 32D2 | 3.18 | 2.85 | 1.94 | 2.82 | 2 |
| 15F11 | 3.05 | 1.22 | 1.02 | 3.28 | 2 |
| 13A9 | 0.50 | 1.55 | 0.94 | 0.97 | 8 |
| 12H10 | 25.8 | 7.02 | 1.48 | 10.7 | 9 |
| 18G3 | 10.4 | 4.03 | 2.03 | 6.18 | 9 |
| 1D5 | 0.67 | 0.49 | 0.42 | 1.09 | 2 |

Note:
IC: inconclusive since weak binding was observed under experimental conditions despite good capture of monoclonal antibody

Example 3

Epitope Mapping by Octet Competition

Methods

Antibody epitope bins were determined using the Octet (Fortebio). MICA alpha 3 domain (allele 004, His tag) protein was biotinylated using EZ-LINK NHS-PEG4 Biotin (Pierce). Streptavidin biosensors tips (Fortebio) were used to capture biotinylated MICA protein (180 seconds in 10 ug/ml solution). Baseline was stabilized for 60 seconds before primary antibody (10 ug/ml) was allowed to associate for 300 seconds with captured protein. Panel of secondary antibodies at 5 ug/ml were then allowed to associate with the antigen and primary antibody complex for additional 300 seconds.

Results

Signals were recorded for each binding event and compared to determine antibody bins. No additional binding upon addition of second antibody indicated overlapping epitope bin. Additional binding upon addition of second antibody indicated separate epitope bin. The results show 3 bins.

TABLE 4

Epitope mapping by antibody competition with Octet shows 3 bins.

|        | Octet Bin |
|--------|-----------|
| 3C9.10 | 1         |
| 7D4.6  | 1         |
| 6F8.7  | 1         |
| 32D2   | N.D.      |
| 3E11   | N.D.      |
| 9C9.5.6| 1         |
| 1E6.1.3| 1         |
| 7A3.1.9| 1         |
| 6E12.5 | 1         |
| 20G11  | N.D.      |
| 6E1.1.12 | 3       |
| 15F11  | N.D.      |
| 13A9   | N.D.      |
| 12H10  | N.D.      |
| 18G3   | N.D.      |
| 1D5    | N.D.      |
| 2E5.2.3| 2         |

Note:
N.D. = not determined.

Example 4

Epitope Mapping by Glycosylation Site Engineering

This Example illustrates the use of single engineered N-linked glycosylation sites on an antigen to block antibody binding and give information on the antigen epitope. Specifically, this Example shows mapping of an epitope by substituting an unglycosylated amino acid of MICA*008 with a glycosylated asparagine or a threonine residue that introduces an N-linked glycosylation site and testing for antibody binding to a MICA*008 Fc fusion having the glycosylated asparagine. MICA*008 was engineered by introducing single or multiple N-linked glycosylation sites to mask different antigenic regions. These constructs were used to probe the MICA*008 antigen binding sites of various anti-MICA antibodies.

A comparative structural study of asparagines in human, mouse, fly, plant and yeast showed that a high percentage of asparagines in N-X-S/T, where W, motifs implicated in N-glycosylation are localized within a turn/loop and are solvent-exposed at the protein surface. The glycosylation site engineered variants were designed with this in mind and engineered into surface exposed residues in loops or near turns (Lam et al., "Structure-based Comparative Analysis and Prediction of N-linked Glycosylation Sites in Evolutionarily Distant Eukaryotes" Genomics Proteomics Bioinformatics (2013) 11(2):96-104).

Methods

Glycosylation Engineering

A single residue in MICA*008 was changed to Asn or Thr to introduce a new glycosylation site, which has a sequence motif of N-X-S/T, where X≠P. Seven constructs with individual mutations and a hyperglycosylated construct that contained five engineered N-linked glycosylation sites were made. Only residues that were surface exposed in the crystal structures of MICA*001 (Protein Data Bank structures 1B3J and 1HYR) were mutated. These MICA*008 engineered glycosylation site variants were expressed as murine IgG2a Fc fusions, expressed in 293S mammalian cells, and purified by MabSelect Sure.

The following variants were made (numbering is with respect to human MICA*008 sequence with signal sequence):

Glyco4: E215N.G243N.H248N.R279N

Glyco11: R202N

Glyco12: E215N

Glyco13: I236T

Glyco14: G243N

Glyco15: H248N

Glyco16: R279N

Glyco17: C-terminal insert of N298.G299.S300

Sequences of glycosylation-engineered sites on MICA*008.α3.murine IgG2a Fc fusion proteins are provided below. Only the MICA*008.α3 domain is shown with the mutations in bold and underlined, without the sequence for the murine IgG2a Fc fusion.

```
>MICA.008.a3.T204-S297.mIgG2a.Wild-type
                                           (SEQ ID: 199)
TVPPMVNVTRSEASEGNITVTCRASSFYPRNIILTWRQDGVSLSHDTQ

QWGDVLPDGNGTYQTWVATRICRGEEQRFTCYMEHSGNHSTHPVPS

>MICA.008.a3.T204-S297.E215N.G243N.H248N.R279N.
C-terminal insert of N298.G299.S300.mIgG2a.
Glyco4 (Hypergylcosylated)
                                           (SEQ ID: 200)
TVPPMVNVTRSNASEGNITVTCRASSFYPRNIILTWRQDNVSLSNDTQ

QWGDVLPDGNGTYQTWVATRICRGEEQNFTCYMEHSGNHSTHPVPSNG

S

>MICA.008.a3.R202-S297.R202N mIgG2a.Glyco11
                                           (SEQ ID: 201)
NRTVPPMVNVTRSEASEGNITVTCRASSFYPRNIILTWRQDGVSLSHD

TQQWGDVLPDGNGTYQTWVATRICRGEEQRFTCYMEHSGNHSTHPVPS

>MICA.008.a3.T204-S297.E215N.mIgG2a.Glyco12
                                           (SEQ ID: 202)
TVPPMVNVTRSNASEGNITVTCRASSFYPRNIILTWRQDGVSLSHDTQ

QWGDVLPDGNGTYQTWVATRICRGEEQRFTCYMEHSGNHSTHPVPS
```

-continued

>MICA.008.a3.T204-S297.I236T.mIgG2a.Glyco13
(SEQ ID: 203)
TVPPMVNVTRSEASEGNITVTCRASSFYPRNITLTWRQDGVSLSHDTQ

QWGDVLPDGNGTYQTWVATRICRGEEQRFTCYMEHSGNHSTHPVPS

>MICA.008.a3.T204-S297.G243N.mIgG2a.Glyco14
(SEQ ID: 204)
TVPPMVNVTRSEASEGNITVTCRASSFYPRNIILTWRQDNVSLSHDTQ

QWGDVLPDGNGTYQTWVATRICRGEEQRFTCYMEHSGNHSTHPVPS

>MICA.008.a3.T204-S297.H248N.mIgG2a.Glyco15
(SEQ ID: 205)
TVPPMVNVTRSEASEGNITVTCRASSFYPRNIILTWRQDGVSLSNDTQ

QWGDVLPDGNGTYQTWVATRICRGEEQRFTCYMEHSGNHSTHPVPS

>MICA.008.a3.T204-S297.R279N.mIgG2a.Glyco16
(SEQ ID: 206)
TVPPMVNVTRSEASEGNITVTCRASSFYPRNIILTWRQDGVSLSHDTQ

QWGDVLPDGNGTYQTWVATRICRGEEQNFTCYMEHSGNHSTHPVPS

>MICA.008.a3.T204-S297.C-terminal insert of
N298.G299.S300.mIgG2a.Glyco17
(SEQ ID: 207)
TVPPMVNVTRSEASEGNITVTCRASSFYPRNIILTWRQDGVSLSHDTQ

QWGDVLPDGNGTYQTWVATRICRGEEQRFTCYMEHSGNHSTHPVPS**NG
S**

Hybridoma derived clones binding to all four MICA/B alleles alpha 3 domains were tested by ELISA for binding to the MICA*008 alpha 3 glycosylation variants fused to murine IgG2a Fc fusion. Nunc maxisorp plates were coated with 2 ug/ml of glycosylation variants as previously described. Cloned and recombinantly expressed hybridoma monoclonal antibodies were added to the plates after blocking with a 1×PBS buffer containing 0.5% BSA and 0.05% Tween 20. After incubation, plates were washed multiple times with wash buffer (1×PBS containing 0.05% Tween 20) and secondary antibody (goat anti-human IgG Fc conjugated to HRP) was added. Plates were then washed multiple times with wash buffer again before adding either BioFX TMB Microwell 1 Component Peroxidase or tetramethylbenzidine (TMB) substrate (KPL; Gaithersburg, Md.). After several minutes of incubation, the reaction was stopped with BioFX stop solution or 1 N solution of HCl, respectively. Plates were read on a Spectra MAX 340 plate reader at either 630 or 450 nm respectively (Molecular Devices; Sunnyvale, Calif.).

Differential Scanning Fluorimetry (DSF)

Differential Scanning Fluorimetry (DSF) is a method used to measure the thermal stability of a protein. In this method, a SYPRO Orange fluorescent dye is combined with a protein and heated up slowly. When the protein unfolds, the exposed hydrophobic surface binds to the dye giving a fluorescent signal. The fluorescence signal is measured at every temperature during the heating process and the highest signals are correlated to a protein melt.

Protein stability measurements by differential scanning fluorimetry

Figure 3A:
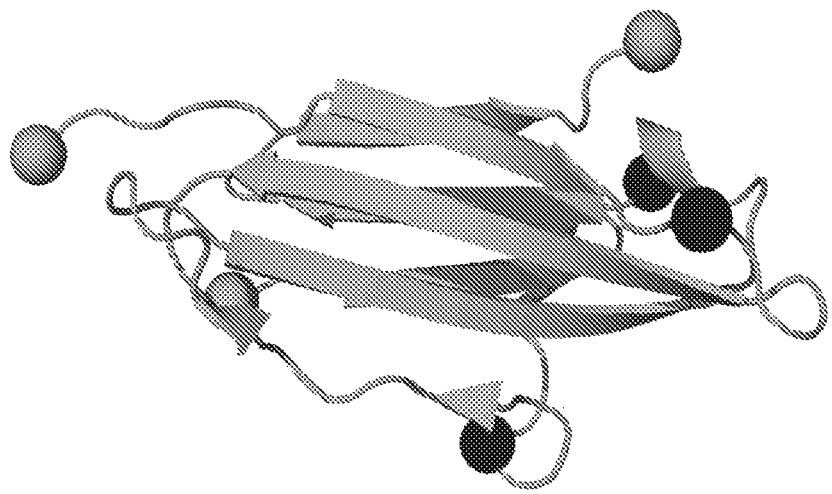
FIG. 3A-FIG. 3E: Black spheres indicate the engineered glycosylation site Asparagine that blocked antibody binding whereas grey spheres indicate engineered glycosylation sites that maintained antibody binding.
Figure 3B:
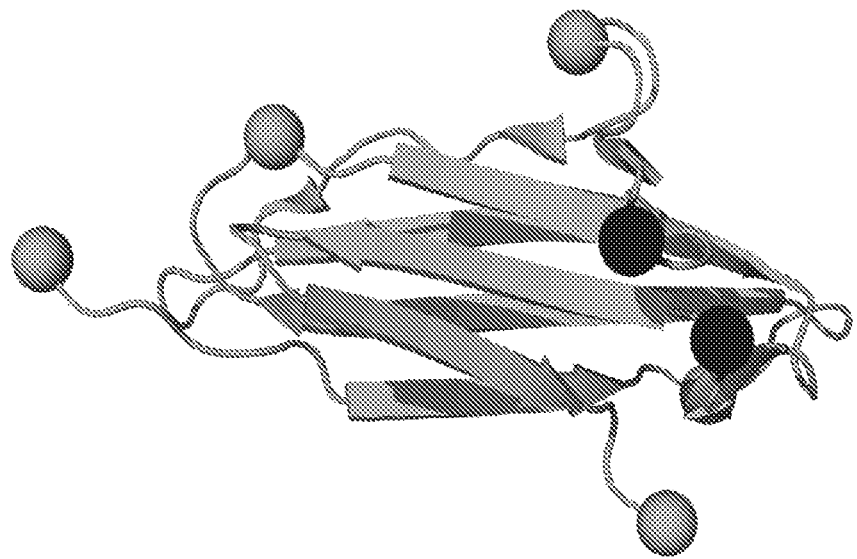
Figure 3D:
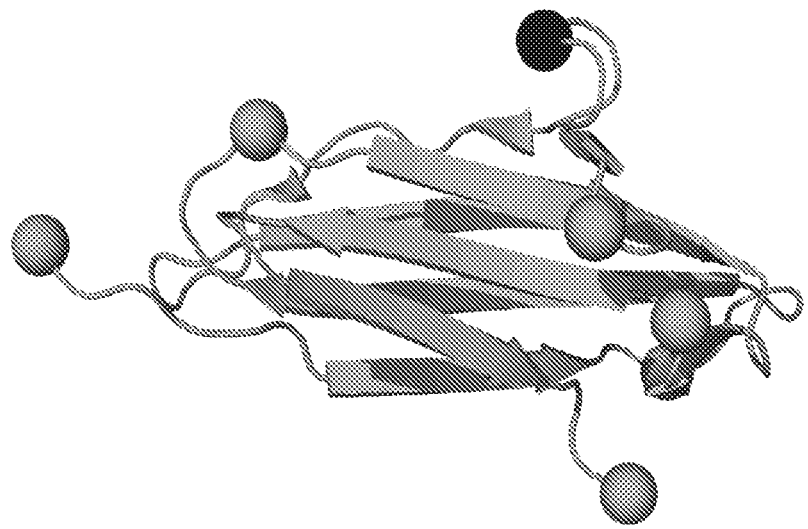
Figure 3C:
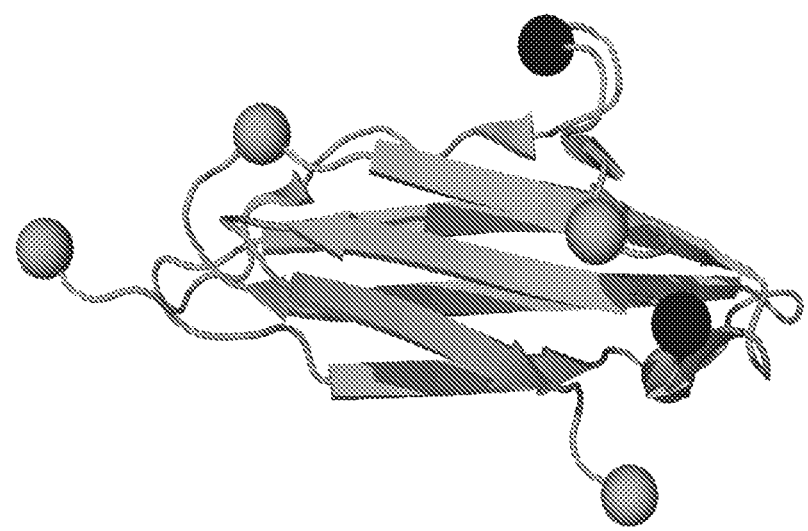
Figure 3E:
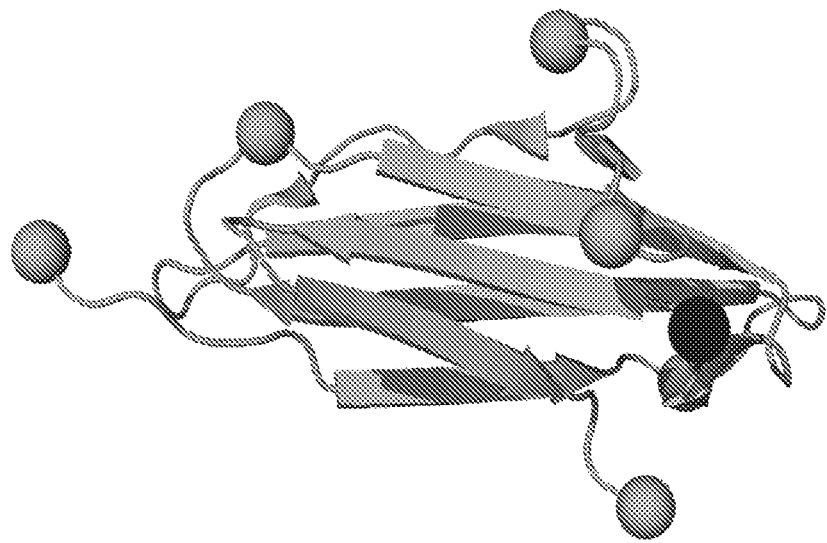
Figures 4A, 4B:
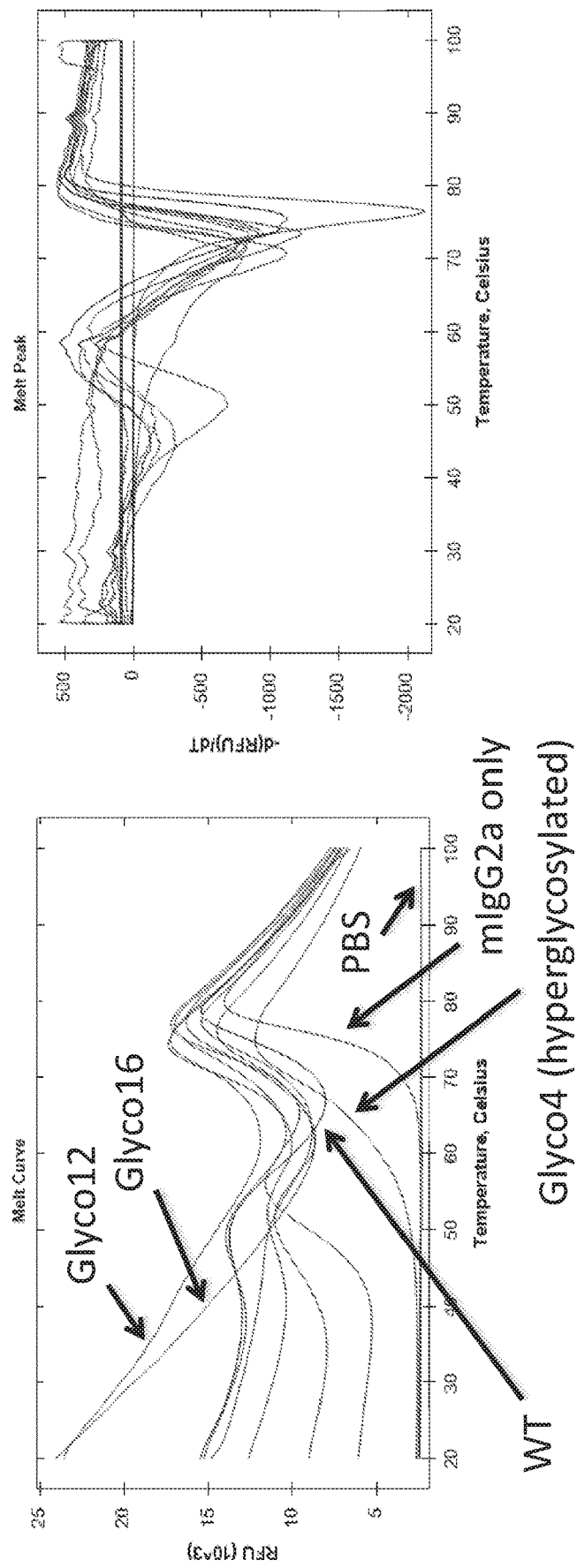
FIG. 4A-FIG. 4B show the melt curves from Differential Scanning Fluorimetry (DSF) for the Glyco variants.
Figure 8:
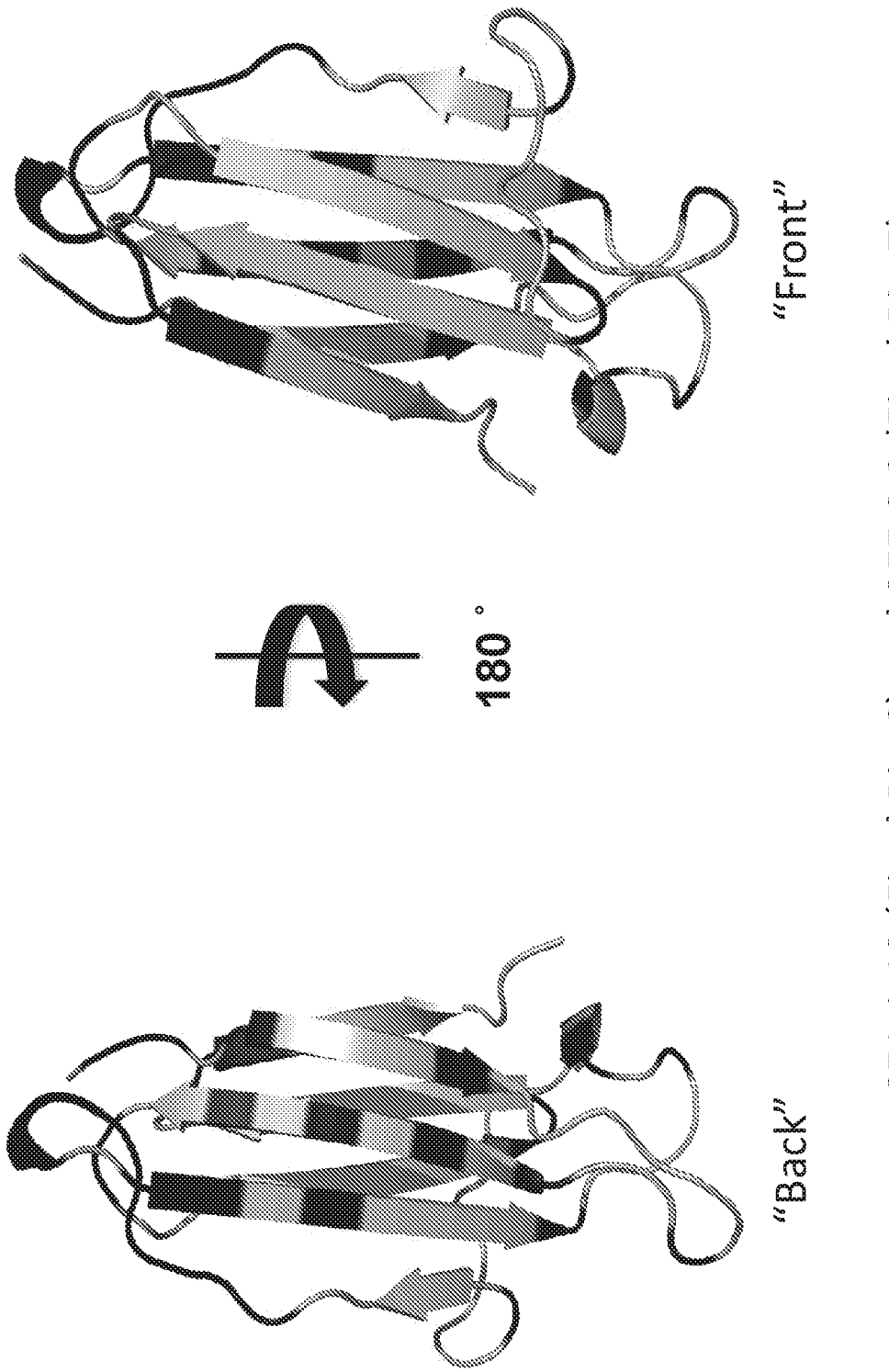
FIG. 8 shows that the Bin 6 and 7 (2E5.2.3 and 6E1.1.12, respectively) epitope maps to the"back and top" of MICA. Black indicates the possible epitope based upon these antibodies binding the MILL1-MICA chimera. Residues not included in the epitope are based on data from engineered glycosylation site mapping, allelic differences between MICA002, 004, 008 and MICB005, since Bin 6 and 7 antibodies bind all four alleles, and residues in the MICA*001 structures (PDB codes 1B3J and 1HYR) predicted to be inward facing or not have any accessible surface area using the solvent accessibility calculation program GETAREA, as described in Fraczkiewicz, R. and Braun, W. (1998) "Exact and Efficient Analytical Calculation of the Accessible Surface Areas and Their Gradients for Macromolecules" *J. Comp. Chem.*, 19, 319-333.

Protein stability was determined using a Biorad CFX96 Real-Time System (Biorad, USA) with a final dilution of 1:500 of the Sypro Orange dye stock (Molecular Probes, USA). Fluorescence of a 25 µL sample (0.5 mg/ml) in PBS was recorded from 20-100° C. (0.2° C. increments, 10 seconds hold per step). The muIgG2a melt corresponded to the second transition or peak seen with the MICA.mIgG2a Glyco variants (FIG. 4A, FIG. 5). The MICA melt was assigned to the first transition or peak (FIG. 4A, FIG. 5).

Gel Shift Assay 6 ug of each MICA.mIgG2a Glyco variant was run on a 4-12% Bis-Tris Gel (Life Technologies) using MES-SDS running buffer (50 mM MES, 50 mM TRIS Base pH 7.3, 0.1% SDS, 1 mM EDTA). Proteins bands were stained with GelCode Blue Safe Protein Stain (Thermo Fisher Scientific). The Glyco-engineered variants show shifts that are upward or distinct compared to wild-type (WT) MICA*008.mIgG2a indicating that they have differing glycosylation states.

Mass Spectrometry

5 µg of each protein sample were diluted with 50 mM ammonium bicarbonate pH 8, reduced with 10 mM dithiothreitol at 37° C. for 1 hour, and alkylated with 10 mM iodoacetamide at room temperature for 20 minutes. Each sample was separately digested overnight with trypsin (Promega) and chymotrypsin (Thermo Fisher Scientific) at 1:50 enzyme:substrate ratio at 37° C. Peptide digests were quenched with 2% trifluoroacetic acid and subjected to C18 stage-tip clean up. Samples were injected via an autosampler onto a 75 µm×100 mm column (BEH, 1.7 µm, Waters Corp) at a flow rate of 1 µL/min using a NanoAcquity UPLC (Waters). A gradient from 98% solvent A (water+ 0.1% formic acid) to 80% solvent B (acetonitrile+0.1% formic acid) was applied over 40 min. Samples were analyzed on-line via nanospray ionization into a hybrid LTQ-Orbitrap mass spectrometer (Thermo Fisher Scientific). Data was collected in data dependent mode with the parent ion being analyzed in the FTMS and the top 8 most abundant ions being selected for fragmentation and analysis in the LTQ. Tandem mass spectrometric data was analyzed using PepFinder software (Thermo Fisher Scientific). Fixed carbamidomethylation on cysteine and variable oxidation on methionine were included in the database search against the protein sequence with a precursor mass tolerance of 20 ppm and a fragment ion tolerance of 0.8 Da. A CHO N-linked glycan library within the software was also included in the database search for glycosylation site mapping and label-free quantitation.

Results

If reduced binding to a glycosylation variant was observed, then the potential epitope was presumed to include the glycosylated residue and residues that are structurally within 5 Angstroms of the glycosylated residue.

It is difficult to predict the size that one N-linked glycosylation can cover due to the varying widths and lengths seen for glycosylation, and the large amount of flexibility, which introduces more size uncertainty. For example, the size of the carbohydrate at each of six N-glycosylation sites in the plasma phospholipid transfer protein ranged from 3.14 to 4.2 kDa as measured by mass spectrometry (Albers et al., "Impact of site-specific N-glycosylation on cellular secretion, activity and specific activity of the plasma phospholipid transfer protein", Biochimica et Biophysica Acta (2001) 1814(7): 908-11.). However, the data with two antibodies comparing two glycosylation engineered variants and the Ala scanning data suggest that interactions structurally within 5 Angstroms of the Asn in the engineered glycosylation site could be valid epitopes. This is a structural prediction based on a small dataset and using the MICA*001 structure (PDB code 1HYR).

Listed below are the amino acid residues that are predicted to be within 5 Å of each glyco-engineered variant based on the 1HYR structure using Pymol. Residues that were predicted to not have any accessible surface area based upon both PDB structures 1HYR and 1B3J were not included. Mutation of amino acid positions of interest to Asn in the structural model did not alter the results of this analysis.

Glyco4 variant (E215N.G243N.H248N.R279N): Arg213, Ser214, Ala216, Ser217, Asn220, Arg240, Gln241, Asp242, Gly243, Val244, Ser245, Ser247, Asp249, Thr250, Trp253, Arg271, Glu276, Glu277, Gln278, Arg279, or Thr281.

Glyco12 variant (Glu215): Arg213, Ser214, Ala216, Ser217, Asn220, or Arg271.

Glyco14 variant (Gly243): Arg240, Gln241, Asp242, Val244, Ser245, Arg279, or Thr281.

Glyco15 variant (His248): Ser247, Asp249, Thr250, or Trp253.

Glyco16 variant (Arg279): Arg240, Gln241, Asp242, Gly243, Glu276, Glu277, Gln278, or Thr281.

Using this information, potential epitopes were identified. For example, if reduced binding to the Glyco12 variant was observed, then the epitope is presumed to include at least one of Glu215, Arg213, Ser214, Ala216, Ser217, Asn220, or Arg271.

Proper folding of glycosylation mutants was confirmed by Differential Scanning Fluorometry (DSF). FIG. 4A and FIG. 4B show melt curves and their derivatives for all glycosylation variants. Glyco12 and Glyco16 have a large amount of unfolded material at the start of DSF. The Glyco4 (hyperglycosylated) MICA peak shifts to the right suggesting that it is more stable and that the peak of the mIgG2a melt is masking the MICA melt. Additionally, it has the lowest amount of unfolded material at the start of DSF compared to the other Glyco variants. FIG. 5 shows the DSF melting temperature ($T_m$) values for MICA and mIgG2a. Glyco12 and Glyco16 likely have a combination of folded and unfolded species because we can see positive binding by ELISA, suggesting that some of the material is folded. Glyco4 (hyperglycosylated) is likely more stable than WT. Glycosylation of the MICA*008 Glyco variants is confirmed by gel shift in FIG. 6. All of the Glyco variants have shifts that are higher than or distinct from wild-type (WT) MICA*008.mIgG2a. Tryptic peptide mass spectrometry was performed to analyze glycosylation on the glycosylation variants of MICA*008 alphα3 domain. We did not have coverage of the tryptic peptides for the Glyco variants 11, 14, 15 or 16 (FIG. 3D). However, we did detect the tryptic peptides for Glyco12, 13 and 17, and they all showed increased N-linked glycosylation compared to their WT MICA*008 tryptic peptide counterpart (FIG. 3D). With the addition of the glycosylation site for Glyco12, we saw >99% total glycosylation on the tryptic peptide compared to the WT peptide that had 38% glycosylation and one native glycosylation site. Glyco13 introduced an N-linker glycosylation site in a peptide that had no other sites and went from 0 to 99% total glycosylation. With the addition of the glycosylation site for Glyco17, we saw 86% total glycosylation on the tryptic peptide compared to the WT peptide that had 68% glycosylation and one native glycosylation site.

Based on these experiments, antibodies were separated into 8 bins and the residues comprising the epitopes were determined. See Table 5, located after Example 5 and FIG. 3A-FIG. 3E, which are structural models showing where the epitopes for each bin are located on MICA. Bin 1 (3C9.10) epitope maps to “bottom” of MICA. Bin 2 (6F8, 7D4, 32D2, 3E11, 1D5, 15F11) epitope maps to “bottom and front” of MICA. Bin 3 (9C9.5.6, 1E6.1.3, 7A3.1.9) epitope maps to “bottom and side” of MICA. Bin 4 (6E12.5) epitope maps to “side” of MICA. Bin 5 (20G11) epitope maps to “front” of MICA. Bin 8 (12H10 and 18G3) epitope maps to “bottom and front” of MICA.

Example 5

Further Study of Epitopes for 6E1.1.12 and 2E5.2.3 Using the MILL1-MICA*008 Chimeras Methods MICA*008 alpha 3 domain was blasted against the non-redundant protein database using NCBI blast and the top hit was the murine MILL1 protein. The residues from MICA*008 surrounding the epitope NGTYQT on the “back” as well as residues in the interface where beta2 microglobulin binding site is found on MILL1 were grafted onto the murine MILL1 sequence. This was done as an alternative strategy to give information about the binding on the “back” of MICA.

The sequence of the MILL1-MICA*008 chimera.murine IgG2a Fc fusion protein is provided below:

```
>MILL1-MICA chimera.murine IgG2a Fc fusion
                                          (SEQ ID: 208)
GSTVPPMVTVTSRNYPVGRVTLTCRASSPYPRNITLVWLQDGKPVQQK

TFRSGDVLPDGNGTYQTWVSIRVLPGQEPQFSCNLRHGNHSIMQTAVG

NSRAQVTDKKIEPRGPTIKPCPPCKCPAPNLLGGPSVFIFPPKIKDVL

MISLSPIVTCVVVDVSEDDPDVQISWFVNNVEVHTAQTQTHREDYNST

LRVVSALPIQHQDWMSGKEFKCKVNNKDLPAPIERTISKPKGSVRAPQ

VYVLPPPEEEMTKKQVTLTCMVTDFMPEDIYVEWTNNGKTELNYKNTE

PVLDSDGSYFMYSKLRVEKKNWVERNSYSCSVVHEGLHNHHTTKSFSR

TPGK
```

FIG. 7A shows the MICA*008 residues grafted on MILL. FIG. 7B shows the non-MICA*008 residues of the MILL chimera.

Results

Two antibodies, 6E1.1.12 and 2E5.2.3, bind to the MILL1-MICA*008 chimera protein and all the glycosylation site engineered variants of MICA*008, indicating that they bind an epitope on the “back” of the antigen (Bin 6). See Table 5 below. FIG. 8 indicates in black the possible epitope based upon these antibodies binding the MILL1-MICA chimera. Darker grey regions indicate sites that are not the epitope. Such sites were identified based on the glycosylation site mapping. They were also identified based on the allelic differences between MICA002, 004, 008 and MICB005, since 6E1.1.12 and 2E5.2.3 bind to all four alleles. The model shows that the epitope for these antibodies is on the “back and top” of the antigen. The residues in black are Val205, Pro206, Met208, Thr212, Gly219, Thr222, Thr224, Arg226, Ser228, Tyr231, Pro232, Gln241, Asp242, Thr250, amino acids between Asp255 and Gly262, Tyr264, Gln265, Trp267, Arg271, Gly275, Glu277, Gly288, Asn289, and His290 of human MICA*008. The 13A9 antibody is unique in that it binds to the MILL1-MICA*008 chimera protein and all the glycosylation site engineered variants of MICA*008, except the hyperglycosylated variant Glyco4 (Bin 7). The Elisa value was 0.9 for Glyco14 suggesting that there is largely decreased binding at this region, even though the >0.65 Elisa cut-off catergorized this as positve binding. Additionally, the Elisa value of Glyco16 was 2.2, which is also suggests some decreased binding compared to the other Glyco variants that all had Elisa values of 3.8 or 3.9.

Therefore, the 13A9 antibody seems to share some binding on both the "front" and "back" of MICA*008.

TABLE 5

ELISA binding to glycosylation variants 4 and 11-17 and MILL1-MICA chimera.

| | 4 | 11 | 12 | 13 | 14 | 15 | 16 | 17 | Epitope | MILL1-MICA chimera | Glyco-engineering Bin |
|---|---|---|---|---|---|---|---|---|---|---|---|
| 3C9.10 | − | + | − | + | + | − | − | + | E215: R213, S214, A216, S217, N220, R271; H248: S247, D249, T250, W253; R279: R240, Q241, D242, G243, E276, E277, N278, T281 | − | 1 |
| 7D4.6 | − | + | + | + | − | + | − | + | G243: R240, Q241, D242, V244, S245, R279, T281; R279: R240, Q241, D242, G243, E276, E277, N278, T281 | − | 2 |
| 6F8.7 | − | + | + | + | − | + | − | + | G243: R240, Q241, D242, V244, S245, R279, T281; R279: R240, Q241, D242, G243, E276, E277, N278, T281 | − | 2 |
| 32D2 | − | + | + | + | − | + | − | + | G243: R240, Q241, D242, V244, S245, R279, T281; R279: R240, Q241, D242, G243, E276, E277, N278, T281 | − | 2 |
| 3E11 | − | + | + | + | − | + | − | + | G243: R240, Q241, D242, V244, S245, R279, T281; R279: R240, Q241, D242, G243, E276, E277, N278, T281 | − | 2 |
| 15F11 | − | + | + | + | − | + | − | + | G243: R240, Q241, D242, V244, S245, R279, T281; R279: R240, Q241, D242, G243, E276, E277, N278, T281 | − | 2 |
| 1D5 | − | + | + | + | − | + | − | + | G243: R240, Q241, D242, V244, S245, R279, T281; R279: R240, Q241, D242, G243, E276, E277, N278, T281 | − | 2 |
| 9C9.5.6 | − | + | + | + | + | | − | + | H248: S247, D249, T250, W253; R279: R240, Q241, D242, G243, E276, E277, N278, T281 | − | 3 |
| 1E6.1.3 | − | + | + | + | + | − | − | + | H248: S247, D249, T250, W253; R279: R240, Q241, D242, G243, E276, E277, N278, T281 | − | 3 |
| 7A3.1.9 | − | + | + | + | + | − | − | + | H248: S247, D249, T250, W253; R279: R240, Q241, D242, G243, E276, E277, N278, T281 | − | 3 |
| 6E12.5 | − | + | + | + | + | − | + | + | H248: S247, D249, T250, W253 | − | 4 |
| 20G11 | − | + | + | + | + | + | − | + | R279: R240, Q241, D242, G243, E276, E277, N278, T281 | − | 5 |
| 6E1.1.12 | + | + | + | + | + | + | + | + | 'back & top': V205, P206, M208, T212, G219, T222, T224, R226, S228, Y231, P232, Q241, D242, T250, D255-G262, Y264, Q265, W267, R271, G275, E277, G288, N289, H290 | + | 6 |
| 2E5.2.3 | + | + | + | + | + | + | + | + | 'back & top': V205, P206, M208, T212, G219, T222, T224, R226, S228, Y231, P232, Q241, D242, T250, D255-G262, Y264, Q265, W267, R271, G275, E277, G288, N289, H290 | + | 6 |

TABLE 5-continued

ELISA binding to glycosylation variants 4 and 11-17 and MILL1-MICA chimera.

| | 4 | 11 | 12 | 13 | 14 | 15 | 16 | 17 | Epitope | MILL1-MICA chimera | Glyco-engineering Bin |
|---|---|---|---|---|---|---|---|---|---|---|---|
| 13A9 | − | + | + | + | + | + | + | + | 'back & top': V205, P206, M208, T212, G219, T222, T224, R226, S228, Y231, P232, Q241, D242, T250, D255-G262, Y264, Q265, W267, R271, G275, E277, G288, N289, H290 | + | 7 |
| 12H10 | − | + | + | + | − | + | + | + | G243: R240, Q241, D242, V244, S245, R279, T281 | − | 8 |
| 18G3 | − | + | + | + | − | + | + | + | G243: R240, Q241, D242, V244, S245, R279, T281 | − | 8 |

In Table 5, ELISA values >0.65 are shown as positive binding. Final bin assignments are also shown. Residues in bold indicate glycosylation sites; non-bolded residues listed after the glycosylation site are within 5 Angstroms. Epitopes are presumed to comprise at least one of the glycosylated residues or one of the residues within 5 Angstroms of the glycosylated residue.

Example 6

Final Epitope Bin Assignments

Fina 1 bin assignment based on Octet competition and glycosylation site engineering shows 7 bins.

TABLE 6

Final bin assignment.

| | Octet Bin | Glycosylation Site Engineering Bin | Final Bin |
|---|---|---|---|
| 3C9.10 | 1 | 1 | 1 |
| 7D4.6 | 1 | 2 | 2 |
| 6F8.7 | 1 | 2 | 2 |
| 32D2 | N.D. | 2 | 2 |
| 3E11 | N.D. | 2 | 2 |
| 1D5 | N.D. | 2 | 2 |
| 15F11 | N.D. | 2 | 2 |
| 9C9.5.6 | 1 | 3 | 3 |
| 1E6.1.3 | 1 | 3 | 3 |
| 7A3.1.9 | 1 | 3 | 3 |
| 6E12.5 | 1 | 4 | 4 |
| 20G11 | N.D. | 5 | 5 |
| 6E1.1.12 | 3 | 6 | 6 |
| 2E5.2.3 | 2 | 6 | 7 |
| 13A9 | N.D. | 7 | 8 |
| 12H10 | N.D. | 8 | 9 |
| 15F11 | N.D. | 8 | 9 |

Note:
N.D. = not determined.
ELISA values >0.5 are shown.

Example 7

Alanine Scanning

This example maps the epitopes of 6F8.7 (Final Bin 2), 7D4.6 (Final Bin 2), 2E5.2.3 (Final Bin 7) and 1D5 (Final Bin 2) using alanine scanning of the MICA*008 allele.
Methods
The binding kinetics of the anti-MICA/B antibodies binding to the MICA alanine variants was measured using surface plasmon resonance (SPR) on a T200 instrument (GE Healthcare). Anti-murine Fc (GE Healthcare) was immobilized on a CM5 sensor chip via amine-based coupling using manufacturer provided protocol. MICA*008.mIgG2a alanine variants were captured by the anti-murine Fc and the anti-MICA/B antibodies as Fabs were passed over. Fab binding was measured to human MICA*008 alpha 3 domains (mIgG2a tagged, in-house). Sensograms for binding of anti-MICA/B Fabs were recorded using an injection time of 2 minutes with a flow rate of 30 µL/min, at a temperature of 25° C., and with a running buffer of 10 mM HEPES, pH 7.4, 150 mM NaCl, 3 mM EDTA and 0.005% Tween 20. After injection, disassociation of the Fab from the alpha 3 domain was monitored for 5 minutes in running buffer. The surface was regenerated between binding cycles with a 70 µL injection of 10 mM Glycine HCl pH 1.7. After subtraction of a blank which contained running buffer only, sensograms observed for anti-MICA/B Fab binding to MICA were analyzed using a 1:1 Langmuir binding model with software supplied by the manufacturer to calculate the kinetics and binding constants. Sensograms of anti-MICA/B antibody binding to captured MICA*008 alanine variants were used to calculate the dissociation constant (Kd). The Kd values were then normalized to wild-type MICA*008 and the data are reported as fold-decrease in affinity and provided in FIG. 9.
Results
FIG. 9 shows the fold-decrease in affinity from alanine scanning. Fold-decrease greater than 3-fold is shaded. The Ala scan of 2E5.2.3 (Final Bin 7) with the residues in the front confirms the MILL1-MIC chimera data suggesting that the antibody binds to the "back" and not the "front" of MIC. FIG. 10 shows the 2E5.2.3 epitope with Ala scan data included. The residues in black are Val205, Pro206, Met208, Thr212, Gly219, Thr222, Thr224, Arg226, Ser228, Tyr231, Pro232, Asp242, the amino acids between Asp255 and Gly262, Tyr264, Gln265, Trp267, and Arg271 of human MICA*008. FIG. 11A compares the epitope for 6F8 mapped by glycosylation engineering and Ala scan. FIG. 11B compares the epitope for 7D4 mapped by glycosylation engineering and Ala scan.
Discussion
The epitopes that were mapped by glycosylation engineering agreed very well with the results from the Ala scanning Biacore experiments for antibodies 6F8, 7D4 and 1D5. For both 6F8, 7D4 and 1D5, we identified Glyco engineered residues G243N (from Glyco14) and R279N (from Glyco16) as MICA epitopes. From Ala scanning, we identified 2 residues within 5 Å of G243 and 2 residues within 5 Å of R279 as epitopes for both 6F8, 7D4. For 1D5, we identified 4 residues within 5 Å of G243 and 1 residue within 5 Å of R279 as epitopes. We identified R279 as an epitope for 6F8, 7D4 and 1D5. However, G243A had a low Rmax in the Biacore experiment for the 2E5.2.3 control and the other antibodies suggesting that the protein was misfolded, so the Ala scan was not informative. Though we were able to identify R240 and V244, residues within 5 Å of G243, as epitopes for 6F8, 7D4 and 1D5. In addition to the alanine variant G243A, D242A, L246A, T281A, and H293A could not be assessed due to poorly folded MICA*008 protein.

Glyco engineering using an ELISA is a quick way to identify regions on the antigen surface that are important for binding. Although there may be limitations to the regions you can cover with glycosylation, it is a rapid and straightforward method to getting antigen epitope information. Ala scanning an antigen can give very detailed information about the epitope, but it requires many constructs, some of which may fold poorly, and takes more time using Biacore. This is especially cumbersome when mapping an epitope of a large or multi-domain protein. In this case, glycosylation engineering of an antigen would be particularly useful to identify the binding domain or region of the antigen without having to express all Ala variants or separate antigen domains. Once a binding domain or region is identified that is important for binding to the antibody, Ala scan could then be performed on a smaller subset of surface exposed residues.

Example 8

MICA Shedding Inhibition and Interference Assay

The anti-MIC antibodies were tested for MIC shedding inhibition from MICA*004 and MICA*008 shedding cell lines.
Methods
To analyze the MICA*004 and MICB*005 alleles, the lung cancer cell line HCC1534 (UTSW) was used. For the MICA*008, the melanoma cell line MEL-JUSO (DSMZ) was used. To examine bona fide cell shedding inhibition, samples reflecting both the effect of antibodies on cell secretion of MIC and samples reflecting antibody interference with the MIC ELISA assay were analyzed. Briefly, cells were cultured in RPMI1640 medium supplemented with 10% FBS and 2 mM Glutamax (Gibco) for at least 24 hours (post thaw) in T150 flasks (Corning). Cells were harvested when cell density reached 70-80% confluency and respuspended in culture media at the concentration of 250,000 cells/ml. Forty microliters of cell suspension (10,000 cells total) were added to each well of a 384-well polystyrene tissue culture plate (Greiner). Additional plates were seeded with the same number of cells to serve as supernatant (sup) for the interference assay.
Antibody Preparation for Combination Inhibition
Antibodies (mIgG2a, CHO-derived) were normalized to 40 ug/mL (4× concentration) in culture media for top concentration, and then serially diluted with a 4-fold, 7-point dilution scheme. Diluted 4× antibodies were combined in a checkerboard manner (horizontal/vertical) in a 1:1 ratio (final 20 ug/mL [2×] each Ab concentration).
Antibody Preparation for Concentration-Effect Analysis
Antibodies (hIgG1) were normalized to 20 ug/mL (2× concentration) in culture media for top concentration, and then serially diluted with a 4-fold, 8 point dilution scheme.

Establishment of Shedding Inhibition Assay
40 uL of 2× antibody samples were added to the cell culture plate containing 10,000 cells per well, yielding 80 uL of volume with a final top concentration of 10 ug/mL (1×). Any remaining wells had 40 uL of media added to serve as a control (80 uL final volume). Samples incubated at 37C/5% $CO_2$. After 24 hours incubation, the cell culture supernatant were harvested into a 384-well deep-well polypropylene block (Greiner) and frozen at −80C for future analysis (or analyzed the same day). For interference supernatant, cultured media was harvested into a reservoir to pool and was also frozen.
MIC ELISA Assay
ELISA plates were coated with either anti-MICA AMO1 (MBL) for MICA*004 and MICA*008 or anti-MICB 236511 (R&D) for MICB*005. Following overnight incubation, samples were washed 3 times and blocked using casein blocking buffer (Sigma). For inhibition sample analysis, sup samples were thawed the day of the assay (or used immediately after harvesting) and were then were then diluted in sample buffer (PBS 7.4 with 0.5% BSA, 10 ppm Proclin, 0.05% Tween20, 0.25% CHAPS, 5 mM EDTA, 0.35 M NaCl, 10 ppm Proclin) and added to the ELISA plate. For interference sample analysis, pooled conditioned media was spiked with testing antibody and incubated at room temperature for at least 1 hour with gentle agitation. The antibody-spiked media was then added to the ELISA plate. Serially diluted recombinant MIC proteins were also added to the plate (independent of sup) to establish a standard curve for sample quantification.

Figure 15A:
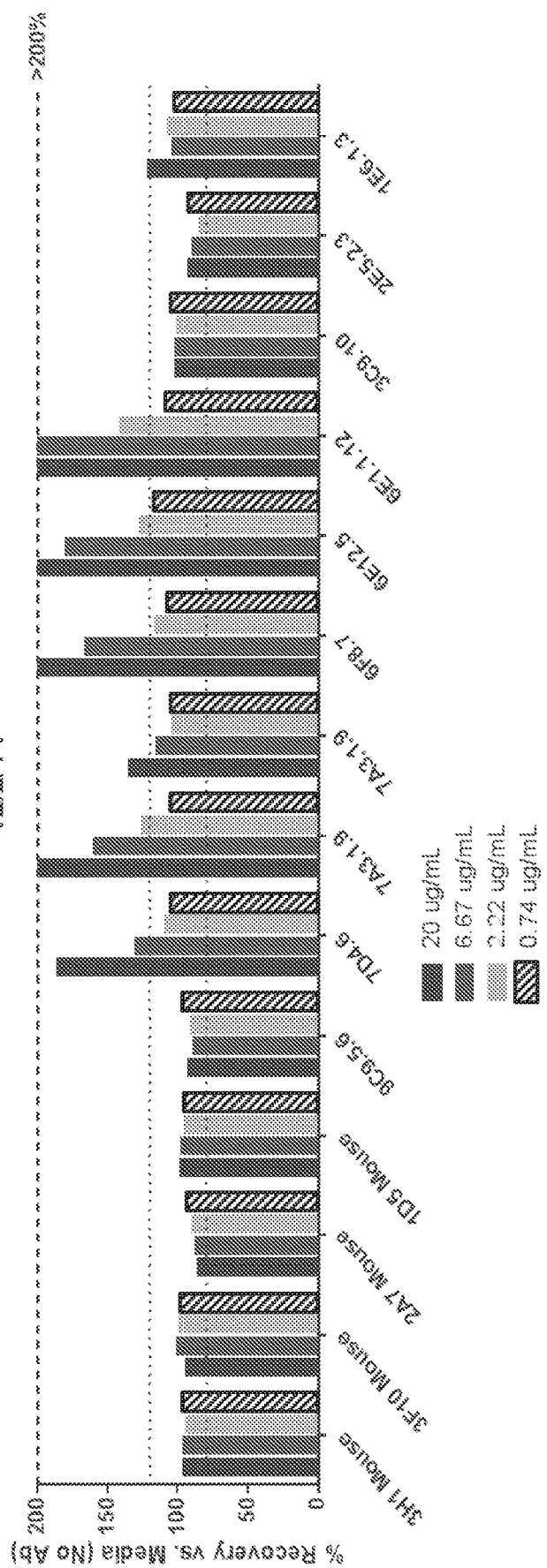
FIG. 15A-FIG. 15B provide the results of the experiments testing for antibody interference with the shedding inhibition assay.
Figure 15B:
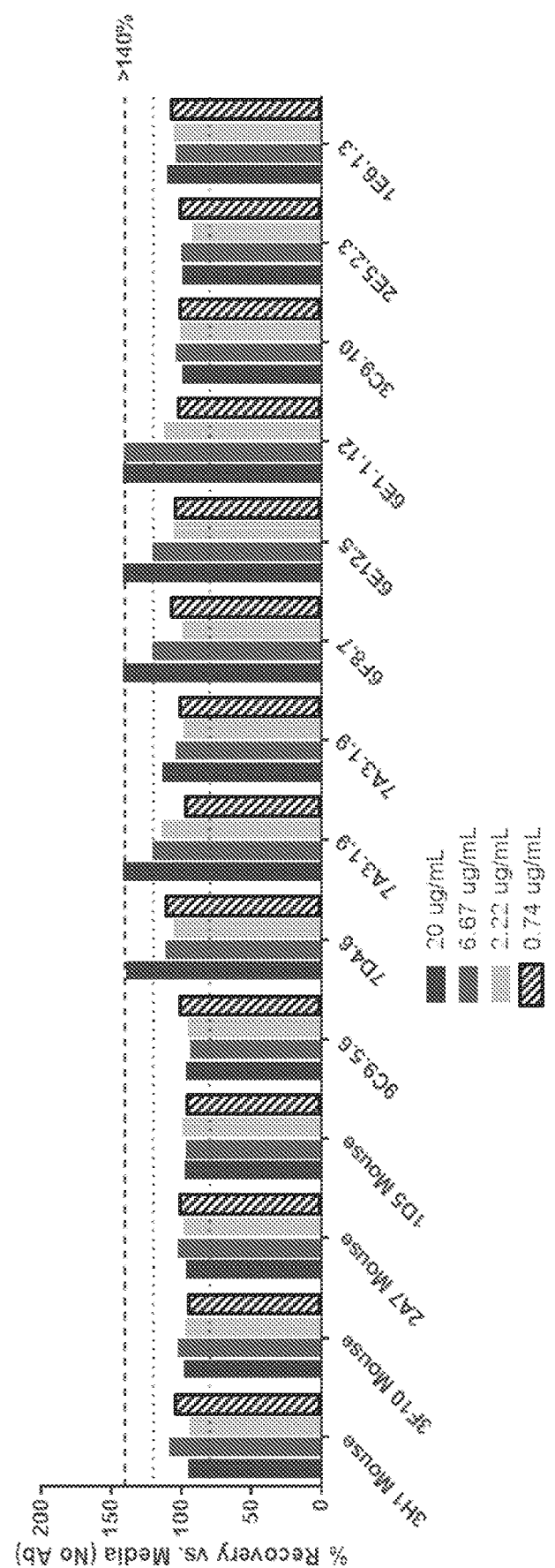

Plates were then sealed and incubated at room temperature for 2 hours with gentle agitation. The primary antibodies used were as follows: Bio-8C5.6 (in-house Genentech) for MICA: FIG. 13A-FIG. 13C; Bio-6D4 (MBL): FIG. 15A-FIG. 15B, and Table 7; Bio-8C5.6 (in-house Genentech) for MICA: FIG. 16A-FIG. 16C, and Table 8-Table 10; and Bio-7E3 (in-house Genentech) for MICB assay (FIG. 13A-FIG. 13C; FIG. 15A-FIG. 15C; FIG. 16A-FIG. 16C; and Table 8-Table 10. These antibodies were diluted in Assay Diluent (PBS pH7.4, 0.5% BSA, 0.05% Tween20, 10 ppm Proclin) and incubated with 50 ug/mL of non-specific mouse IgG (Equitech-Bio) for 1 hour at room temperature. After sample incubation, plates were washed 6 times, and 25 uL of primary antibody was added. Plates were then incubated for 1 hour at room temperature with gentle agitation. After incubation, Streptavidin Poly-HRP80 (Fitzgerald) was diluted in universal casein diluent (Fitzgerald) to 90 ng/mL. Plates were washed 6 times and 25 uL of diluted Streptavidin Poly-HRP80 were added to each well and incubated for 1 hour at room temperature with gentle agitation. After incubation, plates were washed 6 times and 25 uL of TMB (Moss) was added to each well, and incubated with gentle agitation for 15 minutes. 25 uL of 1M Phosphoric Acid was then added to each well and ELISA plates were read at 450/620 nm wavelength.
Data Analysis Method
ODs were processed using 5-parameter curve fitting (1/Y weighting) of the standard material to quantitate the amount of soluble MICA/B (sMIC) in each sample using the corresponding allele standard. Duplicate samples were averaged together, and all non-treated samples were averaged for that particular plate. Percent inhibition of each treated sample was defined as 1-(sMIC in treated sample)/(sMIC in untreated sample average).

Interference samples were processed in the same way. If the antibody interfered with the MICA/MICB quantification, the MICA/MICB concentration in the antibody spiked condition media would deviate significantly from the untreated condition media (control). If the MICA/MICB amount was higher than the control, it was defined as positive interference. If the MICA/MICB amount was lower than the control, it was defined as negative interference.

Results

Results are provided in Table 7. For the MICA 008 allele, antibodies in Final Bins 9 and 2 followed by Bin 5 and 7, have the highest % maximum inhibition values and the lowest EC50 values are seen in Bins 2 and 9. Antibodies in Final Bins 1 and 3, however, show poor inhibition of shedding for MICA 008 allele. This inability to block shedding could be due to the low affinity of the antibodies. For the MICA*004 allele, antibodies in Final Bins 2, 9, 5, 7, followed by Bins 8 and 6 show the highest % maximum inhibition values and the lowest EC50 values are seen for Bins 2 and 9. For MICB 005 allele, a smaller set of data is available however, Bin 8 followed by Bin 7 has the highest approximately 5-10% showing a minor additive/synergistic effect. Similarly, the combination of 13A9 and 6E1 showed a 5-10% increase in shedding inhibition.

MICB*005 shedding inhibition in HCC1534 cells is shown in FIG. 13C. Maximum inhibition of shedding by 1D5 alone was approximately 50%, while maximum inhibition by 13A9 reached 75%, and maximum inhibition of shedding by 6E1 was approximately 45-50%. The strong shedding inhibition activity of 13A9 was diminished by the addition of 1D5 as combining 1D5 and 13A9 at 10 ug/ml only showed 53% of shedding inhibition. In addition, there was no additive or synergistic effect in shedding inhibition. The combination of 1D5 and 6E1, however, significantly enhanced shedding inhibition by approximately 20-30% demonstrating an additive/synergistic effect. Combination of 6E1 to 13A9 did not show additive or synergistic effect.

TABLE 7

EC50 and Percent Maximum Inhibition Values.

| Name | MICA*008 MEL-JUSO EC50 (ug/mL) | MICA*008 MEL-JUSO % max inhibition | MICA*004 HCC1534 EC50 (ug/mL) | MICA*004 HCC1534 % max inhibition | MICB*005 HCC1534 EC50 (ug/mL) | MICB*005 HCC1534 % max inhibition | Final Bin |
|---|---|---|---|---|---|---|---|
| 3C9.10 | Inactive | <10 | 50 | 24 | N/A | N/A | 1 |
| 7D4.6 | Inactive | 26 | 0.185 | 63 | N/A | N/A | 2 |
| 6F8.7 | 0.163 | 47.5 | 0.251 | 70 | N/A | N/A | 2 |
| 3E11 | 0.265 | 70 | 0.309 | 55 | N/A | N/A | 2 |
| 9C9.5.6 | Inactive | <10 | 3.176 | 44 | N/A | N/A | 3 |
| 1E6.1.3 | Inactive | 20 | 0.681 | 46 | N/A | N/A | 3 |
| 7A3.1.9 | Inactive | <10 | 0.411 | 50 | N/A | N/A | 3 |
| 6E12.5 | 0.074 | 28 | 0.329 | 37 | N/A | N/A | 4 |
| 6E1.1.12 | 0.355 | 42.2 | 0.265 | 65 | N/A | N/A | 6 |
| 2E5.2.3 | 0.195 | 61 | 0.107 | 72 | N/A | N/A | 7 |
| 2E5.2.3 | 0.1122 | 60 | 0.2304 | 80% | 0.1067 | 60 | 7 |
| 6E1.1.12 | 0.0941 | 47 | 0.1565 | 73% | 0.0791 | 55 | 6 |
| 15F11 | 0.0165 | 74 | 0.0485 | 86% | 0.0736 | 59 | 2 |
| 32D2 | 0.0303 | 71 | 0.0592 | 76% | 0.0781 | 54 | 2 |
| 13A9 | 0.4888 | 47 | 0.1656 | 66% | 0.0530 | 79 | 8 |
| 18G3 | 0.0191 | 75 | 0.0120 | 74% | 0.0124 | 48 | 9 |
| 12H10 | 0.0103 | 81 | 0.0689 | 76% | 0.1394 | 54 | 9 |
| 20G11 | 0.0285 | 70 | 0.1234 | 69% | 0.0169 | 51 | 5 |
| 1D5 | 0.0087 | 77 | 0.0435 | 81% | 0.0128 | 54 | 2 |

Note:
Data highligted in bold was performed on a separate day, using anti-MICA antibodies purified from CHO instead of HEK293 cells.

% maximum inhibition values and the lowest EC50 values are seen in Bins 9, 2, 5 and 8.

MICA*004 shedding inhibition in HCC1534 cells is shown in FIG. 13A. Maximum inhibition of shedding by 1D5 or 13A9 alone was approximately 60%, while maximum inhibition of shedding by 6E1 was approximately 50%. Combining 1D5 with 13A9 did not show additive or synergistic effect. The combination of 1D5 and 6E1, however, further decreased the amount of sMIC in the samples by approximately 10% compared to backgound, indicating a minor additive/synergistic effect. Likewise, the combination of 13A9 and 6E1 also enhanced shedding inhibition.

MICA*008 shedding inhibition in MEL-JUSO cells is shown in FIG. 13B. Maximum inhibition of shedding by 1D5 alone was approximately 70-75%, while maximum inhibition of shedding by 13A9 alone was approximately 40%, and maximum inhibition of 6E1 was approximately 35-50%. There was no additive or synergistic effect in shedding inhibition when 1D5 and 13A9 were combined. The activity of 1D5 was generally maintained in the presence of 13A9. The combination of 1D5 and 6E1, however, further decreased the amount of sMIC in the samples by Assay interference was tested by diluting the antibody at different concentrations, then combining them and incubating for >1 hr with HCC1534 or MEL-JUSO cell culture supernatant, followed by quantification of shed MICA/MICB. If the antibody interfered with the MICA/MICB quantification, the MICA/MICB concentration would deviate significantly from the no antibody control. If the MICA/MICB amount was higher then the control, this would be positive interference (leading to a positive % recovery/negative % inhibition, possibly masking activity). If the MICA/MICB amount was lower than the control, this would be negative interference (leading to a positive % inhibition/false positive). Both positive and negative interference were observed to varying degrees (Table 8 and FIG. 15A-FIG. 15B). There was some positive interference at high concentrations for certain antibodies, potentially due to the presence of co-purified MICA from the HEK293 host cells (Table 8, FIG. 15A-FIG. 15B, and FIG. 16A-FIG. 16C). Thus, shedding inhibition activity from listed antibodies did not appear to be due to assay interference artifacts.

When anti-MICA antibodies purified from CHO were used, no co-purified MICA was present. As mIgG2a CHO-derived material was used, the only significant interference observed was negative, possibly leading to more potent activity than what was truly occurring in the biological mechanism. MICA*004 assay interference in HCC1534 cells is shown in FIG. 16A. For all antibodies, interference was lower than inhibition, therefore antibody actively inhibited shedding and results were not solely artifacts from assay interference. For the combination of 1D5 and 13A9, some interference (~25-35% above background) was observed across most samples, with a slight reduction at lower antibody concentrations. This interference was observed with single antibodies. For the combination of 1D5 and 6E1, there was some interference (~20-35% above background) at high amounts of 6E1 (highest with moderate amounts of 1D5), and this interference was diluted out with 6E1. This interference was not observed at significant levels with single antibodies. For the combination of 13A9 and 6E1, some antibody interference (~10-15% above background) was observed at high concentrations of 13A9 and 6E1, and seemed to dilute out, with 6E1 interference appearing to have a more significant impact than 13A9 in combination with 6E1.

MICA*008 assay interference in MEL-JUSO cells is shown in FIG. 16B. No significant antibody interference was observed on either allele by any antibodies, therefore, any effects were predominantly biological.

MICB*005 assay interference in HCC1534 cells is shown in FIG. 16C. There was some minor interference (20-30% inhibition) from 1D5 and 13A9. Interference was less at higher concentrations of combined antibodies. Therefore, most of 13A9's activity is biological, while much of 1D5's activity is interference. There was minimal interference from 1D5 or 6E1 alone, but when combined there was about 30-40% inhibition, therefore, some of the activity observed is partially due to interference. With the combination of 6E1 and 13A9, combination interference did not follow clear titration trends. Since most interference observed was around 25-30%, much of the activity was determined to be true inhibition.

TABLE 8

MICA/B Interference.

| Name | HCC1534 (MICA*004) Interference) | MEL-JUSO (MICA*008) Interference) | HCC1534 (MICB*005 Interference) |
|---|---|---|---|
| 3C9.10 | None | None | N/A |
| 7D4.6 | Positive Interference | None | N/A |
| 6F8.7 | Positive Interference | Positive Interference | N/A |
| 3E11 | None | N/A | N/A |
| 9C9.5.6 | None | None | N/A |
| 1E6.1.3 | None | None | N/A |
| 7A3.1.9 | Positive Interference | Positive Interference | N/A |
| 6E12.5 | Positive Interference | Positive Interference | N/A |
| 6E1.1.12 | Positive Interference | Positive Interference | N/A |
| 2E5.2.3 | None | None | N/A |
| 2E5.2.3 | 33% | No | 32% |
| 6E1.1.12 | 28% | No | 25% |
| 15F11 | 23% | No | 22% |
| 32D2 | N/A | No | N/A |
| 13A9 | 16% | No | 20% |
| 18G3 | 28% | No | 26% |
| 12H10 | 23% | No | 15% |
| 20G11 | 21% | No | 18% |
| 1D5 | 18% | No | 15% |

Note:
Data highlighted in bold was performed on a separate day, using anti-MICA antibodies purified from CHO instead of HEK293 cells.

Summary comparison of anti-MIC antibodies on sMIC shedding inhibition activity using low-interference assay formats (AMO1/8C5 for MICA and 236511/7E3 for MICB) are provided in Table 9.

TABLE 9

Shedding Inhibition of Anti-MIC Antibodies across MIC Alleles

| Ab | PANC-1 (MICA*002) | | HCC1534 (MICA*004) | | MEL-JUSO (MICA*008) | | HCC1534 (MICB*005) | |
|---|---|---|---|---|---|---|---|---|
| | Max % Inhibition | EC50 (ug/mL) | Max % Inhibition | EC50 (ug/mL) | Max % Inhibition | EC50 (ug/mL) | Max % Inhibition | EC50 (ug/mL) |
| 1D5 | 48% | 0.0342 | 65% | 0.0136 | 74% | 0.0207 | 59% | 0.0386 |
| 13A9 | 66% | 0.4180 | 56% | 0.5990 | 50% | 0.7945 | 76% | 0.0349 |
| 6E1 | 23% | Not possible | 52% | 0.3298 | 45% | 0.1050 | 58% | 0.0724 |
| 15F11 | 54% | 0.0752 | 64% | 0.0375 | 73% | 0.0255 | 60% | 0.1016 |

Summary comparison of anti-MIC antibodies' interference on conditioned media using low-interference assay formats (AMO1/8C5 for MICA and 236511/7E3 for MICB) are provided in Table 10.

TABLE 10

Interference of Anti-MIC Antibodies across MIC Alleles

| Ab | PANC-1 (MICA*002) % reduction due to interference at 10 ug/mL | HCC1534 (MICA*004) % reduction due to interference at 10 ug/mL | MEL-JUSO (MICA*008) % reduction due to interference at 10 ug/mL | HCC1534 (MICB*005) % reduction due to interference at 10 ug/mL |
|---|---|---|---|---|
| 1D5 | 24% | 26% | 14% | 31% |
| 13A9 | 24% | 21% | 6% | 33% |
| 6E1 | 26% | 23% | 13% | 17% |
| 15F11 | ND | 24% | 15% | 21% |

As shown in Table 9 and and Table 10, anti-MIC antibodies 1D5, 13A9, and 15F11 all demonstrate shedding inhibition activity above interference levels on PANC-1, HCC1534, and MEL-JUSO on all alleles. Anti-MIC antibody 6E1 demonstrates shedding inhibition activity above interference on HCC1534 and MEL-JUSO, but no non-interference activity on PANC-1. 1D5 & 15F11 demonstrated superior shedding inhibition activity on MICA*004 and MICB*008 alleles, while 13A9 demonstrated superior shedding inhibition on alleles MICA*002 and MICB*005.

Example 9

Affinity and Shedding Inhibition Properties of Anti-MICA/B Antibodies

This Example analyzes the relationship between MIC epitopes and affinity and shedding inhibition properties of anti-MICA/B clones. Anti-MICA/B clones binding to the alpha 3 domain from the HZ campaign and selected clones from earlier campaigns were tested for binding, antibody bins and inhibition of shedding. Bins were assigned based on this set of clones.

Wasatch Binning Method

A 96×96 array-based SPR imaging system (Carterra USA) was used to epitope bin a panel of monoclonal antibodies. Purified monoclonal hybridoma antibodies were diluted at 10 ug/ml in 10 nM sodium acetate buffer pH 4.5. Using amine coupling, antibodies were directly immobilized onto a SPR sensorprism CMD 200M chip (XanTec Bioanalytics, Germany) using a Continuous Flow Microspotter (Carterra, USA) to create an array of antibodies. For binning analysis, the IBIS MX96 SPRi (Carterra USA) was used to evaluate binding to the immobilized antibodies. The experiment was performed at 25° C. in a running buffer of 10 mM HEPES, pH 7.4, 150 mM NaCl, 3 mM EDTA, and 0.005% Tween 20 (HBS-TE). Antigen was first injected for 4 minutes at 100 nM and was followed by a second 4 minute injection of purified antibody at 10 ug/ml in a running buffer of HBS-TE. The surface was regenerated between cycles with 10 mM Glycine pH 2.0. The binding data was processed using the Wasatch binning software tool.

Results

Figure 18A:
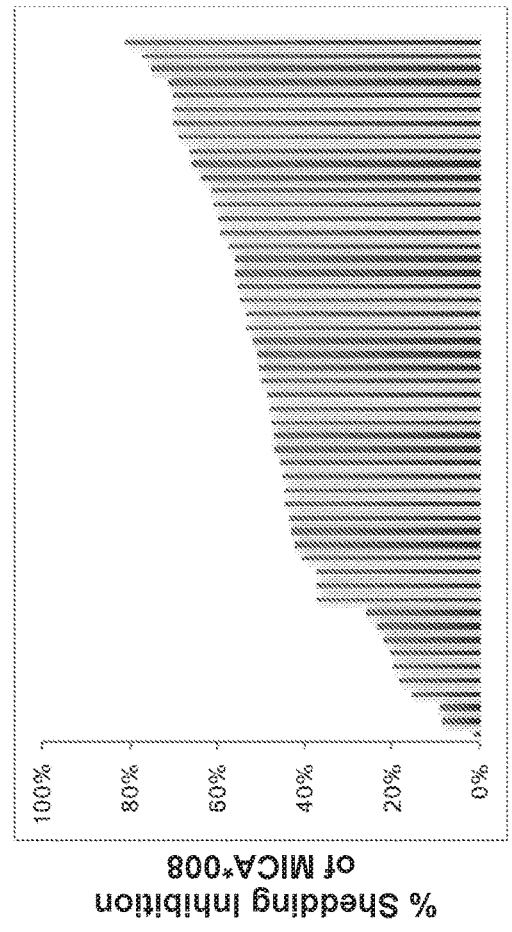
FIG. 18A and FIG. 18B: Waterfall plot showing percent shedding inhibition of MICA*008 (FIG. 18A) and binding affinity (KD) for MICA*008 alpha-3 domain vs. percent shedding inhibition of MICA*008 for the 52 anti-MICA antibodies with affinity less than or equal to 10 nM (FIG. 18B). The anti-MICA antibodies show an 80-fold range for percent shedding inhibition of MICA*008 from 1 to 81%.

A total of 96 anti-MICAS clones were found to bind ECD and alpha-3 domain of MICA alleles *002, *004 and 008, as well as MICB005 by an ELISA screen (data not shown). ELISA values of >0.5 were deemed as 'binding'. These clones were then tested for binding to alpha-3 domain versions of MICA and MICB by Biacore, and 52 clones selected that showed binding to MICA*008 alpha-3 domain with affinity values </=10 nM (FIG. 17). Next, these 52 anti-MICA/B antibodies were tested for % shedding inhibition of MICA*008 (FIG. 18A). Although these antibodies bind well to MICA*008 (</=, 10 nM), they inhibit shedding of MICA*008 from 1%-81%. Further dissecting this large range, 6 antibodies displayed 1-20% shedding inhibition of MICA*008, 7 antibodies from 21-40%, 26 antibodies from 41-60%, and 13 antibodies from 61-81%. Twenty-six anti-MICA antibodies inhibited MICA*008 shedding >/=50%, while 3 antibodies inhibited shedding >/=75%.

Figure 18B:
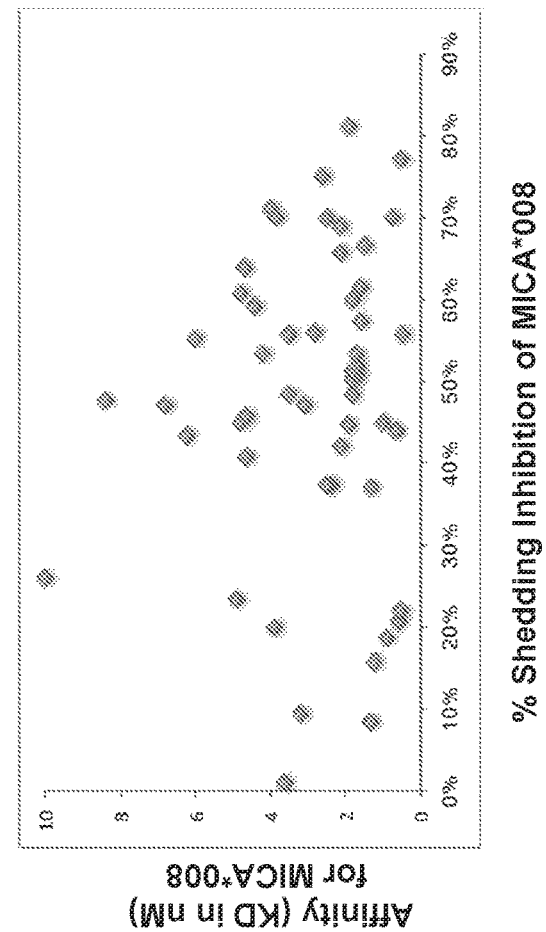

To understand the determinants responsible for better shedding inhibition properties of the anti-MICA antibodies, the correlation between shedding inhibition and affinity was analyzed. Affinity (KD) was plotted for MICA*008 and % shedding inhibition of MICA*008 for the 52 anti-MICA antibodies (FIG. 18B). This data showed no correlation between MICA*008 affinity and % shedding inhibition.

Figure 19B:
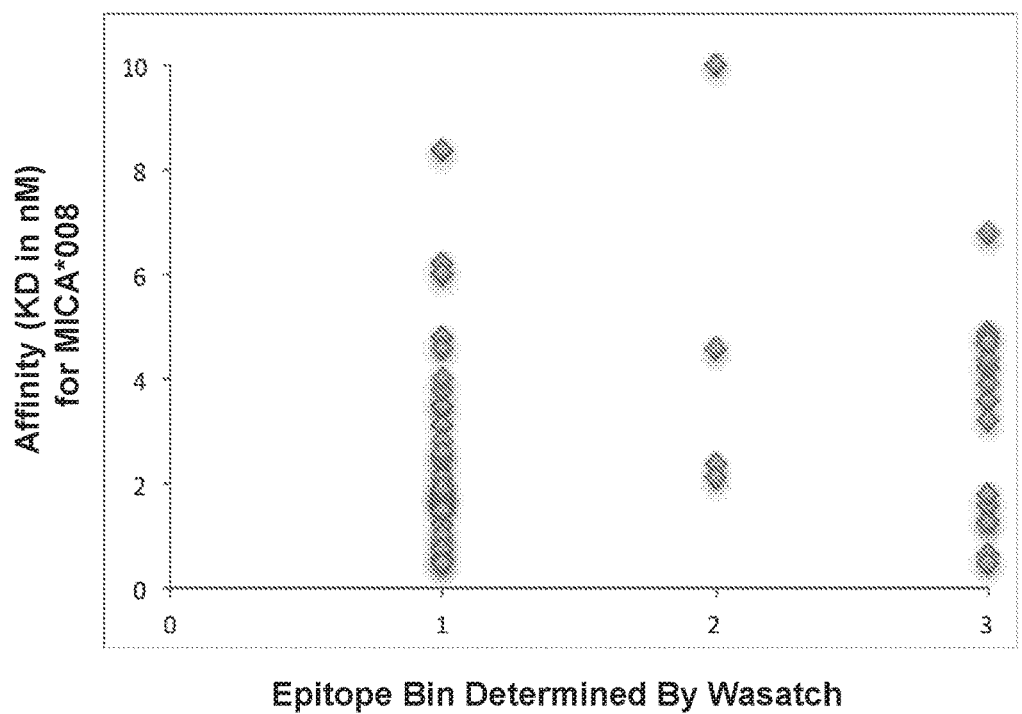
FIG. 19A shows three unique epitope bins for a set of 52 anti-MICA antibodies determined using Wasatch. Affinity for MICA*008 vs. Wasatch determined epitope bins (FIG. 19B) and percent shedding inhibition vs. Wasatch dertermined epitope bins (FIG. 19C) are also shown.

Next, the correlation between affinity and a particular epitope on MICA*008 was examined. A binning experiment was performed using Wasatch and three unique epitope bins for the set of 52 anti-MICA antibodies were determined (FIG. 19A). Bin 1 and Bin 3 were unique, while Bin 2 had some overlap with Bin 1 and Bin 3. Bin 1 contained antibodies that bound similarly to 1D5, while Bin 3 contained antibodies that had binding similar to 6E1.1.12. MICA*008 Wasatch epitope bins were plotted and compared to binding affinity for the MICA antibodies (FIG. 19B). Bin 1 had 33 anti-MICA antibodies with an affinity range of 0.5-8.4 nM, Bin 2 had 4 anti-MICA antibodies with an affinity range of 2.1 nM to 10 nM, while Bin 3 had 15 anti-MICA antibodies with an affinity range of 0.47-6.8 nM. Although Wasatch determined three distinct MICA*008 epitope bins, the affinity ranges within these bins (particularly Bins 1 and 3) were similar, indicating that there a lack of correlation between affinity and epitope bin.

Figure 19C:
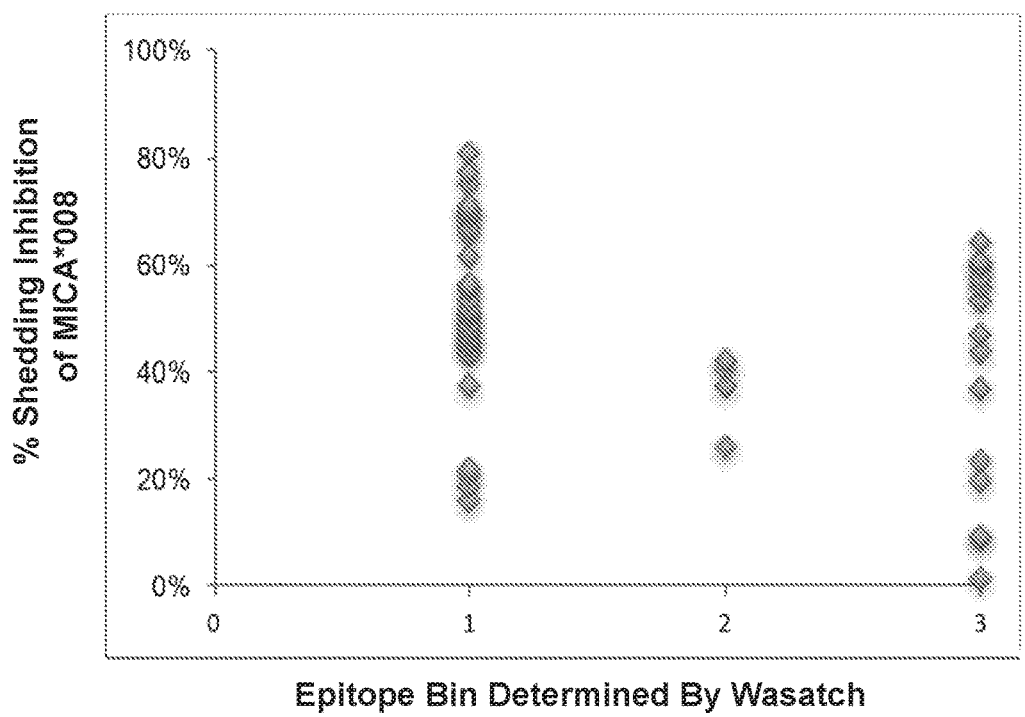

Finally, the correlation of shedding inhibition to a certain MICA*008 epitope for the 52 anti-MICA antibodies was analyzed. MICA*008 epitope bins by Wasatch and the percent (%) shedding inhibition were plotted (FIG. 19C). Bin 1 had 33 anti-MICA antibodies with a median % shedding inhibition of 51% and a range of 16-81%. Bin 2 had 4 anti-MICA antibodies with a % shedding inhibition median of 39% and a range of 26-42%. Bin 3 had 15 anti-MICA antibodies with a % shedding inhibition median of 47% and a range of 1-64%. The median % shedding inhibition values of Bin 1 and Bin 3 were similar and both had about a 65% range difference. However, a correlation between MICA*008 epitope to ability to inhibit shedding was found to exist. Bin 1 contained the 10 antibodies with the highest shedding inhibition values, while Bin 3 had the three antibodies with the lowest shedding inhibition ability (FIG. 19C). Due to the large range of percent shedding inhibition values in Bin 1, a higher resolution epitope mapping method was needed to identify the particular epitope that was correlated to the best shedding inhibition. This allowed screening of antibodies to select for the desired MICA epitope.

To address the need for a higher resolution and higher throughput epitope mapping method, a Glyco-engineering Epitope Mapping or GEM method was developed (FIG. 20). This method engineered protein antigen sequences to create a single N-linked glycosylation site (N-X-S/T, where X≠P). This was achieved by changing an N-X-X site to N-X-S/T or by changing a X-X-S/T site to N-X-S/T. Additionally, a few amino acids could be added to the N- or C-terminally to create a new N-linked glycosylation site. Once a panel of the glyco-engineered antigen variants was created and purified, they were screened for binding to antibodies using either ELISA or Biacore/Wasatch. Positive and negative binding was then established and the epitope was defined as the site or sites where no binding was observed due to the epitope being masked by glycosylation.

Figure 21A:
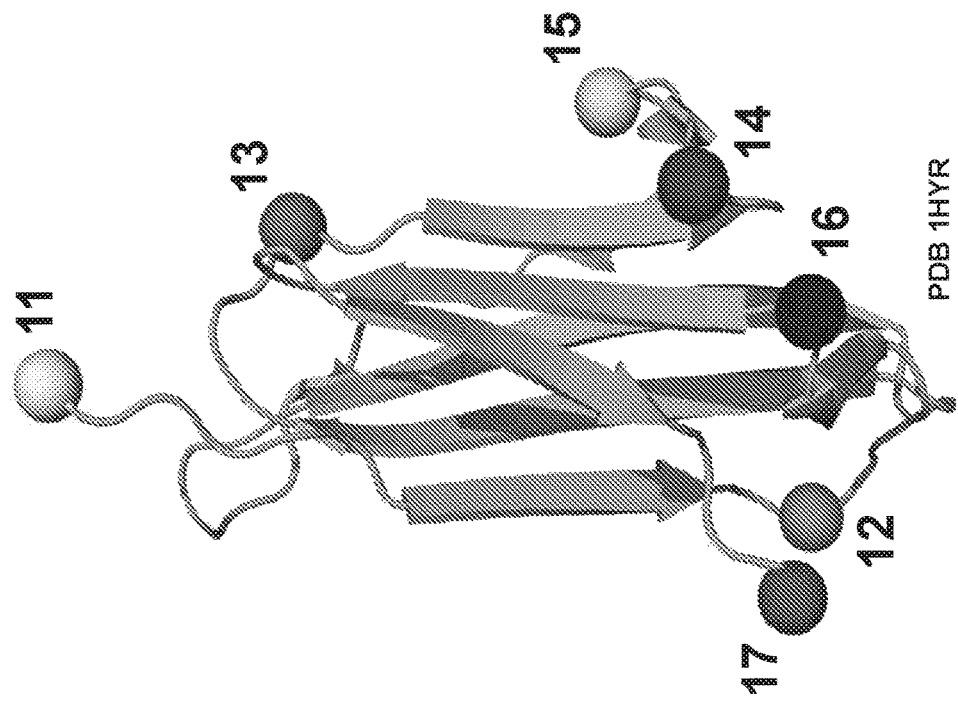
Figure 22C:
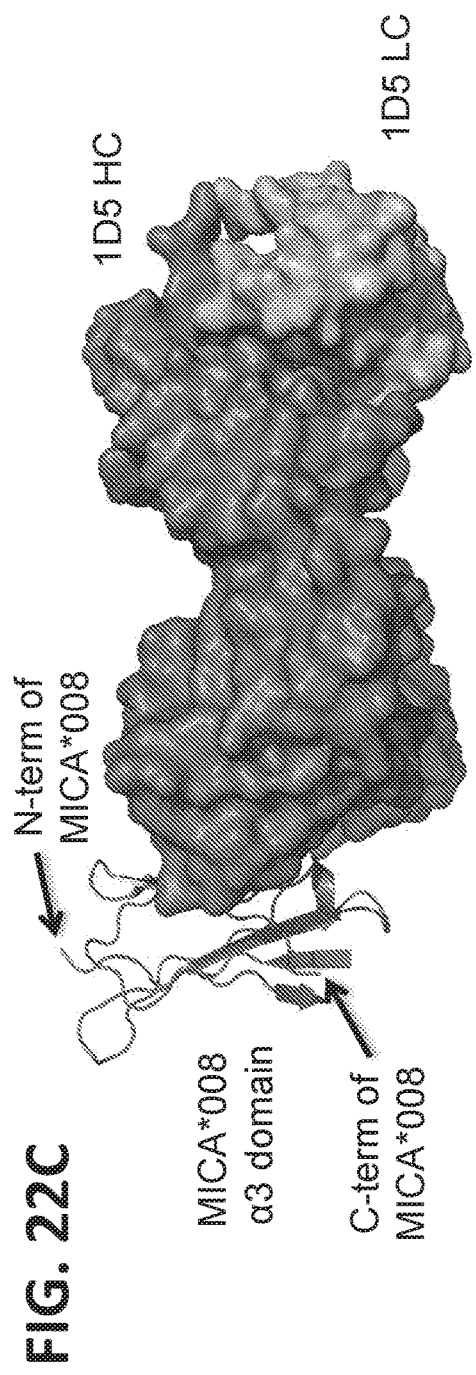
Figure 22D:
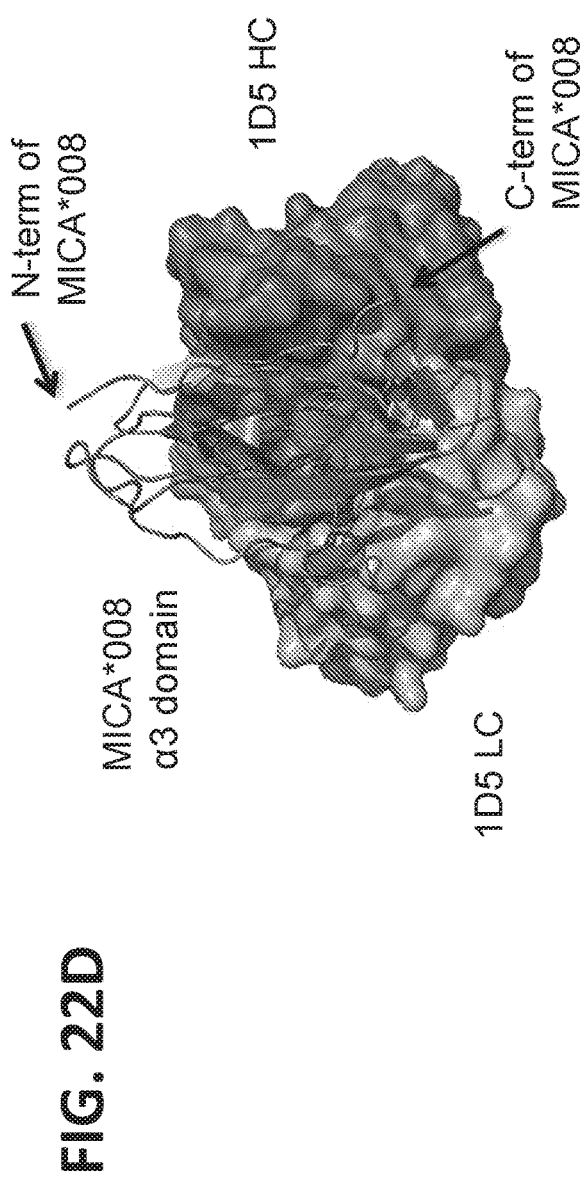

For MICA*008, single N-linked glycosylation sites on the 'front' of MICA*008 alphaα3 domain were introduced on 7 separate MICA*008 varaints (FIG. 21A). Such variants were designed based on the crystal structure of MICA*001 (Protein Data Bank structures 1B3J and 1HYR) and the 7 residues that were mutated were all surface exposed in the crystal structures. Mass spectrometry on the MICA*008 glyco-engineered variants was performed to analyze glycosylation (FIG. 21B). We did not have coverage of the tryptic peptides for the Glyco variants 11, 14, 15 or 16. However, we did detect the tryptic peptides for Glyco12, 13 and 17, and they all showed increased N-linked glycosylation compared to their WT MICA*008 tryptic peptide counterpart (FIG. 21B). With the addition of the glycosylation site for Glyco12, we saw >99% total glycosylation on the tryptic peptide compared to the WT peptide that had 38% glycosylation and one native glycosylation site. Glyco13 introduced an N-linked glycosylation site in a peptide that had no other sites and went from 0 to 99% total glycosylation. With the addition of the glycosylation site for Glyco17, we saw 86% total glycosylation on the tryptic peptide compared to the WT peptide that had 68% glycosylation and one native glycosylation site.

The binding of these 7 MICA glycosylation variants was tested with all 96 anti-MICA/B clones that bound all 4 MICA/B alleles by ELISA. 11 unique epitope bins were identified based on the binding characteristics to the 7 glyco-engineered variants (FIG. 21C). The highest number of antibodies were observed in Bin 6—not binding any of the glyco-engineered MICA variants, Bin 2—binding to glyco-engineered variants 14 and 16, and in Bin 5—binding to glyco-engineered variant 16. Further examination of the anti-MICA antibodies that inhibit shedding>70% showed that the top antibodies that block shedding fell into only 3 bins (FIG. 21C). These bins included epitopes with glyco-engineered variants Glyco14, Glyco16 or both Glyco14 and Glyco16. Therefore, antibodies that block epitopes on the 'front' and 'bottom' of MICA were most effective at blocking MICA*008 shedding (FIG. 21D).

Example 10

Crystallography for Anti-MIC Antibodies

This Example characterizes the crystal structures of anti-MIC 1D5, 13A9, and 6E1.1.12 antibodies.

Expression and Purification of Fabs

All Fabs were expressed in *E. coli* as chimeras containing murine variable domains and human kappa CL and human IgG1 CH1 constant domains. Cells were pelleted, resuspended in 25 mM Tris, pH 7.5, 150 mM NaCl, 5 mM EDTA, and lysed by passing twice through a microfluidizer. DNA was precipitated by the addition of 0.4% polyethyleneimine (PEI) and incubation for 1 hour to up to overnight at 4° C. with stirring. Lysates were cleared by centrifugation at 15,000×g for 1 hour followed by filtration through a 0.22 µm filter.

The 1D5 Fab was purified by affinity chromatography using GammaBind Plus Sepharose (GE Healthcare). After affinity capture, the column was washed with equilibration buffer (25 mM Tris, pH 7.5, 150 mM NaCl, 5 mM EDTA), equilibration buffer plus 0.1% Triton X-100+0.1% Triton X-114, equilibration buffer again, followed by low salt buffer (25 mM succinate, pH 6.0). The Fab was eluted with 150 mM acetic acid, pH 2.7 and immediately neutralized with 1/10 volume of 1 M Tris, pH 9.0. The 1D5 Fab was further purified by cation-exchange chromatography using an SP Sepharose High Performance column (GE Healthcare) pre-equilibrated in buffer A (20 mM sodium citrate, pH 5.0) and eluted with a 0-40% gradient of buffer B (20 mM sodium citrate, pH 5.0, 1 M NaCl) over 10 column volumes (CVs). After cation-exchange chromatography the 1D5 Fab was dialyzed into 25 mM Tris, pH 7.5, 150 mM NaCl prior to complex formation.

The 13A9 Fab was purified by affinity chromatography using GammaBind Plus Sepharose (GE Healthcare) as described above followed by size exclusion chromatography using a HiLoad Superdex 200 pg column (GE Healthcare). After size-exclusion chromatography the 13A9 Fab was dialyzed into 25 mM Tris, pH 7.5, 150 mM NaCl, prior to complex formation.

The 6E1.1.12 Fab was also purified by affinity chromatography using GammaBind Plus Sepharose (GE Healthcare) followed by cation-exchange chromatography as described above, except a 0-20% gradient of buffer B (20 mM sodium citrate, pH 5.0, 1 M NaCl) over 20 CVs was used for elution. Two peaks were observed upon elution from the SP Sepharose High Performance column. Mass spectrometry demonstrated that the major peak contained Fab with a light chain (LC) and heavy chain (HC) matching their respective theoretical masses. The minor peak contained the expected mass of the LC, however the HC was 17 Da smaller than the theoretical mass, suggesting formation of a pyroglutamate on the amino terminus of a fraction of the protein. The peak containing the pyroglutamate was a minor fraction of the total protein therefore the peak containing the glutamine at the amino terminus was used for crystallization. After cation-exchange chromatography the 6E1.1.12 Fab was dialyzed into 25 mM Tris, pH 7.5, 150 mM NaCl prior to complex formation.

Expression and Purification of the Human MICA*008 α3 Domain

Both the wild-type human MICA*008 α3 domain and a C273S mutant were generated. The C273S mutant was designed to remove the unpaired cysteine from the α3 domain and block covalent dimerization through disulfide bond formation that was observed with a small fraction of the wild-type protein.

The human MICA*008 α3 domain containing an amino-terminal, thrombin-cleavable His$_6$ tag was co-expressed with *Streptomyces plicatu* EndoH in *Trichoplusia ni* (*T. ni*) cells using a bacculovirus expression system. DNA encoding residues T204-S297 of human MICA*008 and residues F2-P313 of *Streptomyces plicatu* EndoH were cloned separately into a slightly modified version of pAcgp67 (BD Biosciences). Transfer vectors were co-transfected with BestBac linearized viral DNA (Expression Systems, LLC) into *Spodoptera frugiperda* (*Sf9*) cells using Cellfectin (Invitrogen) to produce recombinant baculovirus. Viruses were amplified twice to prepare the stocks used for protein expression. *T. ni* Pro cells were inoculated into 2 L of ESF921 serum-free, protein-free media (Expression Systems) at 2×10$^6$ cells/mL and infected with 20 mL of virus at a ratio of 1:1 MICA:EndoH. Kifunensine was dissolved in 10 mL of ESF921 media, sterile filtered, and added at infection to a final concentration of 1 mg/L to prevent complex N-linked glycan formation. Cells were grown in 5 L Thomson Optimum Growth™ flasks at 27° C. in a shaker with a 2 inch throw at 130 RPM. Forty-eight hours post infection cultures were adjusted with Tris and salts to a final concentration of 50 mM Tris, pH 8.0, 5 mM CaCl$_2$, 1 mM NiCl$_2$ and allowed to mix for 30 minutes to precipitate excess free amino acids in the media. Cells and precipitated amino acids were removed from the culture supernatant by centrifugation at 300 RCF for 15 minutes. The supernatant containing the secreted MICA*008 protein was filtered through a 0.2 µm filter and was adjusted to pH 7.0 prior to purification.

All MICA*008 purification steps were done at 4° C. The pH-adjusted supernatant was loaded over a Ni Sepharose Excel (GE Healthcare) column equilibrated in buffer A (50 mM sodium phosphate, pH 8.0, 300 mM NaCl). The column was washed with 2.5% buffer B (50 mM sodium phosphate, pH 8.0, 300 mM NaCl, 400 mM imidazole), Triton X-114 buffer (50 mM sodium phosphate, pH 8.0, 300 mM NaCl, 0.1% Triton X-114), followed by 2.5% buffer B. Protein was eluted with a step gradient of 100% buffer B and then dialyzed into 50 mM sodium phosphate, pH 8.0, 150 mM NaCl.

The $His_6$ tag was removed by cleavage with 15 units of thrombin (GE Healthcare) per mg of MICA*008 protein for 16 hours at room temperature with rotation and the cleavage reaction was monitored by mass spectrometry. An additional 5 units of thrombin per mg of MICA*008 was added and the reaction was allowed to proceed for an additional 24 hours at room temperature with rotation. The protein was filtered through a 0.22 µm filter to remove precipitation prior to further purification.

The untagged MICA*008 α3 domain was separated from any remaining tagged protein by reverse affinity purification using a Ni Sepharose Excel (GE Healthcare) column with collection of the flow through. The column was washed with 50 mM sodium phosphate, pH 8.0, 300 mM NaCl, 20 mM imidazole and the washes were also collected. Both the flow through and washes were further purified over a HiLoad Superdex 75 pg column (GE Healthcare) to remove thrombin and high molecular weigh aggregates.

A final polishing step over a Mono S GL column (GE Healthcare) with a 0-100% buffer B (20 mM sodium acetate, pH 5.0, 1 M NaCl) gradient over 30 CVs was performed to remove minor amounts of remaining $His_6$-tagged MICA*008. Fractions containing untagged MICA*008 α3 domain were pooled and dialyzed into 25 mM Tris, pH 7.5, 150 mM NaCl prior to complex formation.

Purification of Fab-MICA*008 α3 Domain Complexes

Fab-MICA*008 complexes were formed from a two-fold molar excess of the MICA*008 α3 domain incubated at 4° C. overnight with the various Fabs. Complexes containing the 1D5 or 13A9 Fab were formed with the wild type MICA*008 α3 domain, whereas the 6E1.1.12 complex was formed with the C273S mutant MICA*008 α3 domain. Complexes were purified from the excess MICA*008 α3 domain by size-exclusion chromatography using a HiLoad Superdex 75 pg column (GE Healthcare) in 25 mM Tris, pH 7.5, 150 mM NaCl. Fractions containing the complex were pooled and concentrated to 20 mg/mL for crystallization screening trials.

Crystallization and X-ray Data Collection of Fab-MICA*008 α3 Domain Complexes

Crystals of the 1D5 Fab-MICA*008 complex grew over 30 days at 4° C. in vapor diffusion hanging drops from a 1:1 mixture of protein (20 mg/mL in 25 mM Tris, pH 7.5, 150 mM NaCl) and well solution (0.1 M sodium acetate, pH 4.6, 25% PEG4000). Crystals were cryo-protected using well solution, flash frozen, and stored in liquid nitrogen. Diffraction data were collected under cryo-cooled conditions (100 K) at the Advanced Photon Source (APS) beamline SER-CAT 22-ID (Argonne National Laboratory, Ill.) at a wavelength of 1.00 Å (Table 11).

Crystals of the 13A9 Fab-MICA*008 complex grew overnight at 19° C. in vapor diffusion hanging drops from a 2:1 mixture of protein (20 mg/mL in 25 mM Tris, pH 7.5, 150 mM NaCl) and well solution (0.01 M $ZnSO_4$, 0.1 M MES, pH 6.5, 25% PEG 550 MME). These crystals were crushed with a Seed Bead kit (Hampton Research), diluted 1:500 in well solution and used for streak seeding into a 1:1 mixture of protein (20 mg/mL in 25 mM Tris, pH 7.5, 150 mM NaCl) and well solution containing a lower concentration of PEG 550 MME (0.01 M $ZnSO_4$, 0.1 M MES, pH 6.5, 16-18% PEG 550 MME). Seeded crystals grew over three days at 19° C. in vapor diffusion hanging drops. Crystals were cryo-protected in 25% glycerol, 0.01 M $ZnSO_4$, 0.1 M MES, pH 6.5, 15% PEG 550 MME, flash frozen, and stored in liquid nitrogen. Diffraction data were collected under cryo-cooled conditions (100 K) at the Advanced Light Source (ALS) beamline 5.0.2 (Lawrence Berkeley National Laboratory, Calif.) at a wavelength of 1.00 Å (Table 11).

Crystals of the 6E1.1.12 Fab-MICA*008 C273S complex grew over five days at 19° C. in vapor diffusion hanging drops from a 1:1 mixture of protein (20 mg/mL in 25 mM Tris, pH 7.5, 150 mM NaCl) and well solution (0.1 M tri-sodium citrate, 15% isopropanol, 15% PEG 4000). Crystals were cryo-protected using well solution with the addition of 25% glycerol, flash frozen, and stored in liquid nitrogen. Diffraction data were collected under cryo-cooled conditions (100 K) at the Stanford Synchrotron Radiation Lightsource (SSRL) beamline 12-2 (SLAC National Accelerator Laboratory, Calif.) at a wavelength of 0.97946 Å (Table 11).

TABLE 11

X-Ray Data Collection and Refinement Statistics

| Data Collection | 1D5 Fab-MICA*008 α3 | 13A9 Fab-MICA*008 α3 | 6E1.1.12 Fab-MICA*008 C273S α3 |
|---|---|---|---|
| Beamline | APS SER-CAT 22-ID | ALS 5.0.2 | SSRL 12-2 |
| Wavelength (Å) | 1.00 | 1.00 | 0.97946 |
| Detector | Rayonix 300HS | Pilatus 6M | Pilatus 6M |
| Space group | $P2_1$ | $P2_12_12_1$ | $P2_12_12_1$ |
| Cell dimensions | | | |
| a, b, c (Å) | 58.69, 50.18, 88.63 | 51.55, 61.83, 172.37 | 66.50, 89.79, 89.72 |
| α, β, γ (°) | 90.00, 90.85, 90.00 | 90.00, 90.00, 90.00 | 90.00, 90.00, 90.00 |
| Resolution (Å) | 35.00-1.30 | 35.00-1.90 | 35.00-2.21 |
|  | (1.32-1.30) | (1.93-1.90) | (2.26-2.21) |
| $R_{merge}$ | 0.059 (0.56) | 0.085 (0.49) | 0.090 (0.33) |
| <I/σI> | 23.9 (1.4) | 18.2 (2.2) | 10.5 (1.8) |
| CC1/2 (highest bin) | (0.793) | (0.724) | (0.591) |
| Completeness (%) | 99.6 (96.4) | 95.0 (74.6) | 76.0 (59.4) |
| Redundancy | 3.5 (2.9) | 5.2 (4.0) | 3.7 (1.7) |
| Observed reflections | 443,217 | 219,704 | 97,888 |
| Unique reflections | 126,363 | 42,120 | 26,155 |
| Refinement | | | |
| Resolution (Å) | 35.00-1.30 | 35.00-1.90 | 35.00-2.05 |
| Number of reflections | 120,157 | 40,023 | 24,785 |

TABLE 11-continued

X-Ray Data Collection and Refinement Statistics

| Data Collection | 1D5 Fab-MICA*008 α3 | 13A9 Fab-MICA*008 α3 | 6E1.1.12 Fab-MICA*008 C273S α3 |
|---|---|---|---|
| Reflections in $R_{free}$ set | 6,152 | 2,050 | 1,353 |
| Fab-MICA complexes in the ASU | 1 | 1 | 1 |
| $R_{work}/R_{free}$ (%) | 18.84/20.54 | 20.84/24.68 | 22.34/27.46 |
| Mean B-factor (Å$^2$) | | | |
| Protein | 13.83 | 19.76 | 25.39 |
| Water | 32.41 | 38.02 | 33.36 |
| Glycerol | N/A | 52.85 | N/A |
| Sulfate | N/A | 64.49 | N/A |
| Zinc | N/A | 33.63 | N/A |
| Total solvent | 32.41 | 40.70 | 33.36 |
| All atoms | 16.24 | 21.28 | 25.51 |
| Wilson B-factor (Å$^2$) | 14.66 | 23.66 | 25.87 |
| No. atoms | | | |
| Protein | 4,186 | 4,008 | 4,043 |
| Water | 625 | 260 | 61 |
| Glycerol | 0 | 48 | 0 |
| Sulfate | 0 | 5 | 0 |
| Zinc | 0 | 1 | 0 |
| Total solvent | 625 | 314 | 61 |
| All atoms | 4,811 | 4,322 | 4,104 |
| R.m.s. deviations | | | |
| Bond lengths (Å) | 0.007 | 0.006 | 0.006 |
| Bond angles (°) | 1.30 | 1.12 | 1.13 |
| Ramachandran plot (%) | | | |
| Favored | 98.9 | 97.7 | 97.5 |
| Allowed | 1.1 | 2.3 | 2.5 |
| Outliers | 0 | 0 | 0 |
| Rotamer outliers (%) | 1.25 | 0.91 | 0.89 |

Note:
*Values in parentheses are for highest-resolution shell.

The resolution for the 6E1.1.12 Fab-MICA*008 C273S α3 domain complex was called at 2.21 Å where completeness >50%, but data to 2.05 Å, where CC1/2>0.5, were used in refinement. Mean B-factors were calculated using Baverage in CCP4 and Wilson B-factors calculated using Xtriage in PHENIX. Ramachandran statistics and rotamer outliers were calculated using PDB Tools in PHENIX.

X-ray Structure Determination of Fab-MICA*008 α3 Domain Complexes

Data were integrated and scaled using HKL2000. The 1D5 Fab-MICA*008 crystal belonged to the P2$_1$ space group with one Fab-MICA complex in the asymmetric unit (ASU). The 13A9 Fab-MICA*008 crystal belonged to the P2$_1$2$_1$2$_1$ space group with one Fab-MICA complex in the ASU. The 6E1.1.12 Fab-MICA*008 C273S crystal was also found to be space group P2$_1$2$_1$2$_1$ with one Fab-MICA complex in the ASU (Table 11).

All structures were determined by molecular replacement using PHASER-MR in PHENIX. For each complex five sequential molecular replacement searches were performed with each of the Fab constant domains (CL and CH1), Fab variable domains (VL and VH), and the MICA α3 domain as individual search models as described below.

All of the Fabs used in this study contain human kappa CL and human IgG1 CH1 constant domains. The individual CL (residues 108-212 of chain A) and CH1 (residues 121-220 of chain B) domains from the Fab fragment of Herceptin (Protein Data Bank (PDB) accession 1NZ8) were used as search models.

The 1D5 Fab VL domain is derived from the murine IGKV4-91*01 germline gene and residues 1-108 of chain L from PBD accession 4M1G were used as a search model. The 1D5 Fab VH domain is derived from the murine IGHV1S135*01 germline gene and residues 1-113 of chain H from PDB accession 1F3D were used as a search model.

The 13A9 Fab VL domain is derived from the murine IGKV12-41*01 germline gene and residues 1-107 of chain A from PDB accession 1A2Y were used as a search model. The 13A9 Fab VH domain is derived from the murine IGHV1-54*02 germline gene and residues 2-113 of chain B from PDB accession 4J8R were used as a search model.

The 6E1.1.12 VL domain is derived from the murine IGKV1-117*01 germline gene and residues 1-107 of chain J from PDB accession 1F3D were used as a search model. The 6E1.1.12 Fab VH domain is derived from the murine IGHV1-84*01 germline gene and residues 1-113 of chain B from PDB accession 1CT8 were used as a search model.

For the 1D5 Fab-MICA*008 complex structure residues 181-274 of chain C from MICA*001 PDB accession 1HYR was used as a search model. For subsequent structures of the 13A9 Fab-MICA*008 and 6E1.1.12 Fab-MICA*008 complexes, residues 204-297 of MICA*008 from the 1D5 Fab-MICA*008 complex was used as a search model for the α3 domain.

Upon obtaining molecular replacement solutions, models were built using COOT and refined in REFMAC and PHENIX. Mean B-factors were calculated using Baverage in CCP4 and Wilson B-factors calculated using Xtriage in PHENIX. Ramachandran statistics and rotamer outliers were calculated using PDB Tools in PHENIX. Contacts were analyzed with Contact/NCONT and PISA in CCP4. All figures were generated with PYMOL.

The resolution of the 1D5 Fab-MICA*008 complex structure was 1.30 Å and the model was refined to an $R_{free}$ value of 20.5%. The final model contains residues 1-214 of the 1D5 LC, residues 2-216 of the 1D5 HC, and residues 204-297 of the MICA*008 α3 domain, with residues 215-220 of MICA*008 disordered in the structure. Ramachandran statistics indicate 98.9% of residues lie in favored regions, 1.1% in allowed regions, and there are no outliers (Table 11).

The resolution of the 13A9 Fab-MICA*008 complex structure was 1.90 Å and the model was refined to an $R_{free}$ lue of 24.7%. The final model contains residues 1-214 of the 13A9 LC, residues 1-217 of the 13A9 HC, and residues 204-297 of the MICA*008 α3 domain. Ramachandran statistics indicate 97.7% of residues lie in favored regions, 2.3% in allowed regions, and there are no outliers (Table 9).

The resolution of the 6E1.1.12 Fab-MICA*008 C273S complex structure was called at 2.21 Å where completeness was still above 50% (59.4%), however data to 2.05 Å resolution, ution, where CC1/2 was still greater than 0.5, were used in the refinement. The model was refined to an $R_{free}$ value of 27.5%. The final model contains residues 1-212 of the 6E1.1.12 LC, residues 2-214 of the 6E1.1.12 HC, and residues 204-297 of the MICA*008 α3 C273S domain. Ramachandran statistics indicate 97.5% of residues lie in favored regions, 2.5% in allowed regions, and there are no outliers (Table 11).

Structural Analysis of the 1D5 Fab-MICA*008 α3 Domain Complex

Figure 23A:
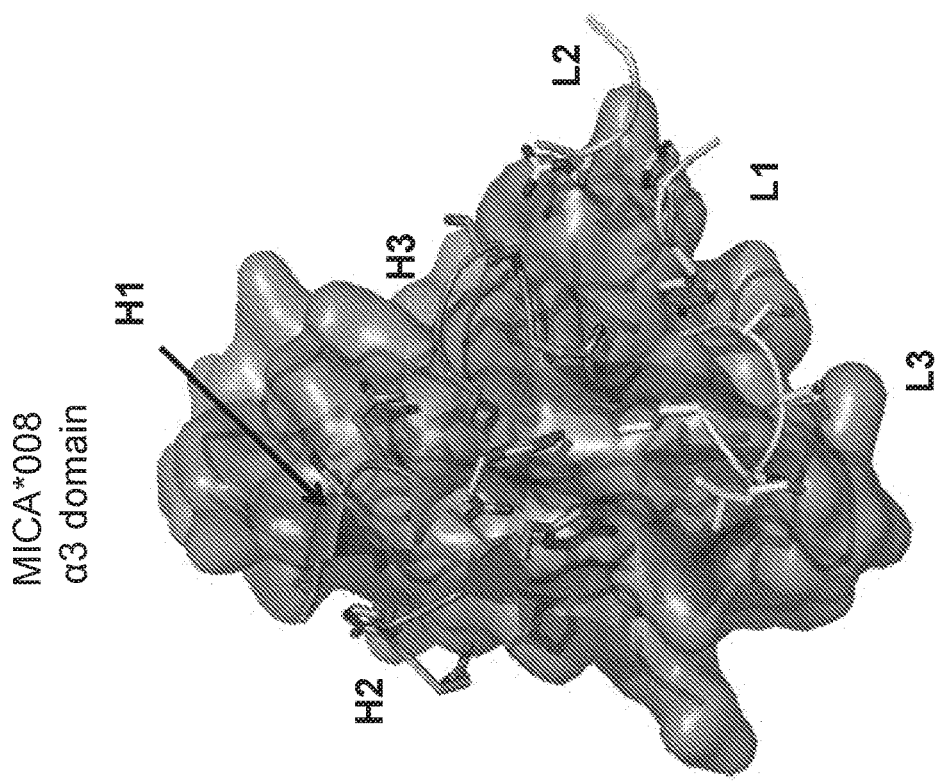
Figure 23B:
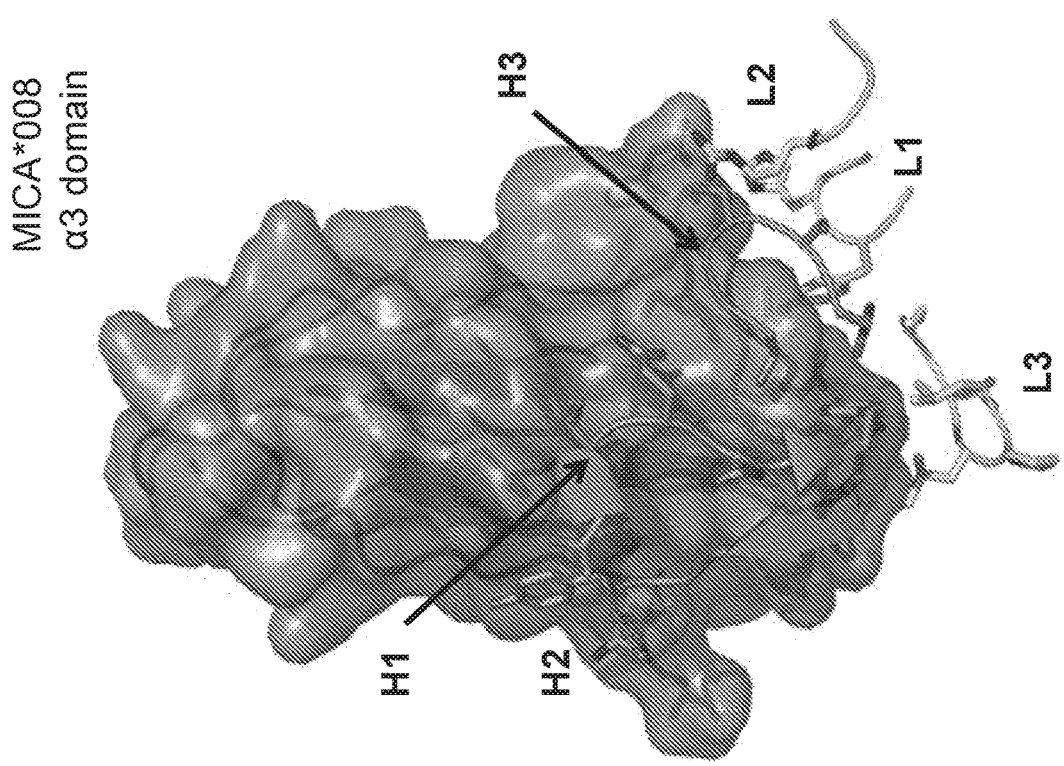
Figure 24A:
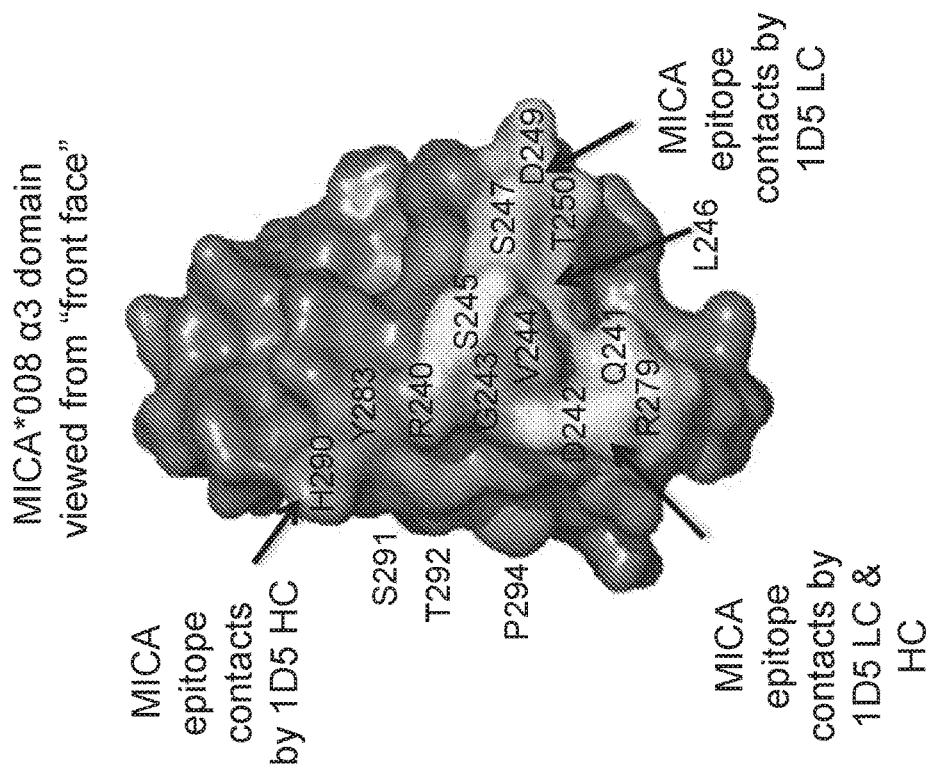
FIG. 24C and FIG. 24D are open book representations of the interface between the 1D5 Fab and the MICA*008 α3 domain, respectively, shown as ribbon diagrams. Residues in the 1D5 paratope, defined as being within 4.5 Å of the MICA*008 α3 domain, are highlighted in FIG. 24C with their residue numbers and have their side chains shown as sticks. MICA*008 α3 domain residues in the 1D5 epitope, defined as being within 4.5 Å of the 1D5 Fab, are highlighted in FIG. 24D with their residue numbers and have their side chains shown as sticks.
Figure 24B:
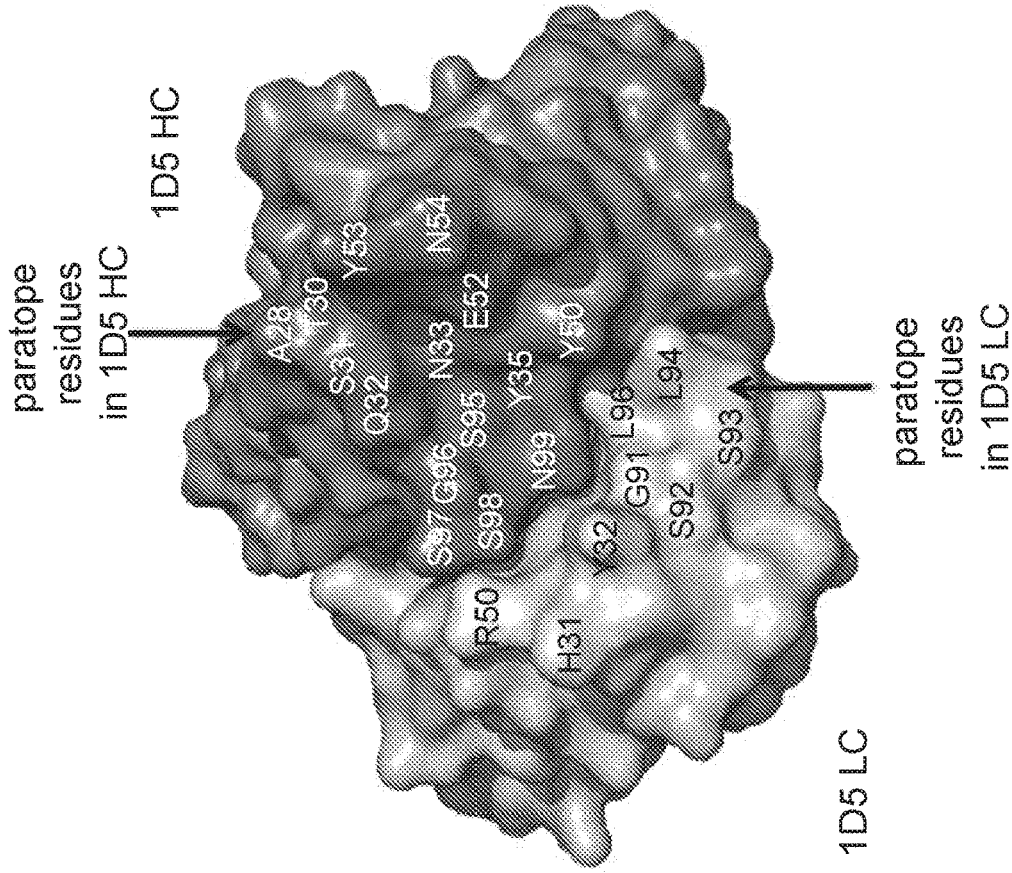
Figure 24D:
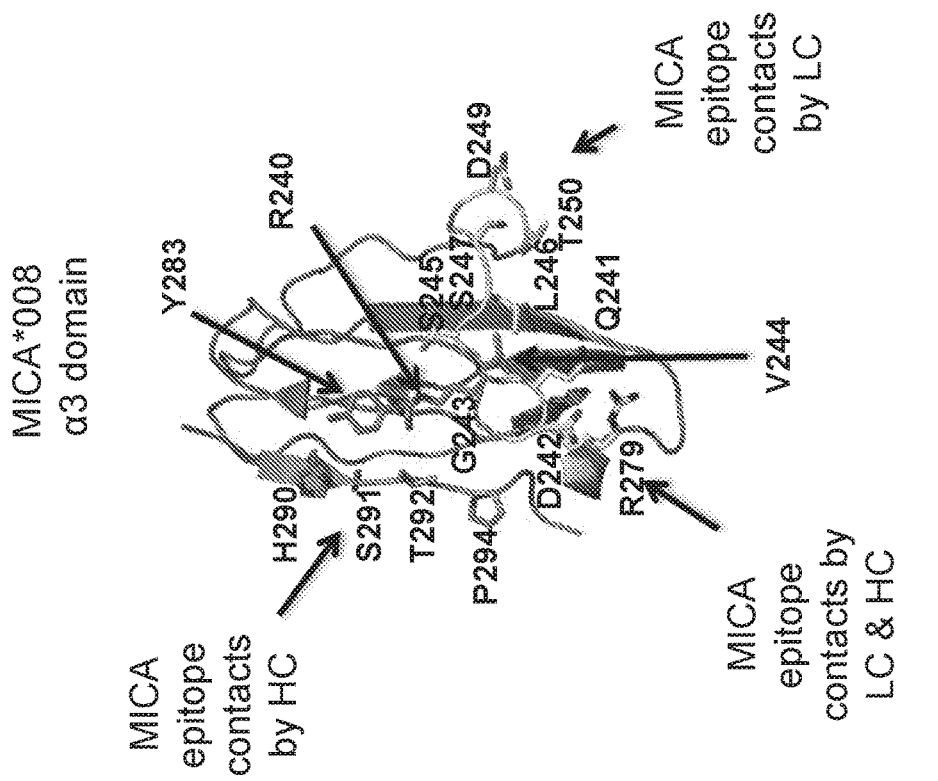
Figure 24C:
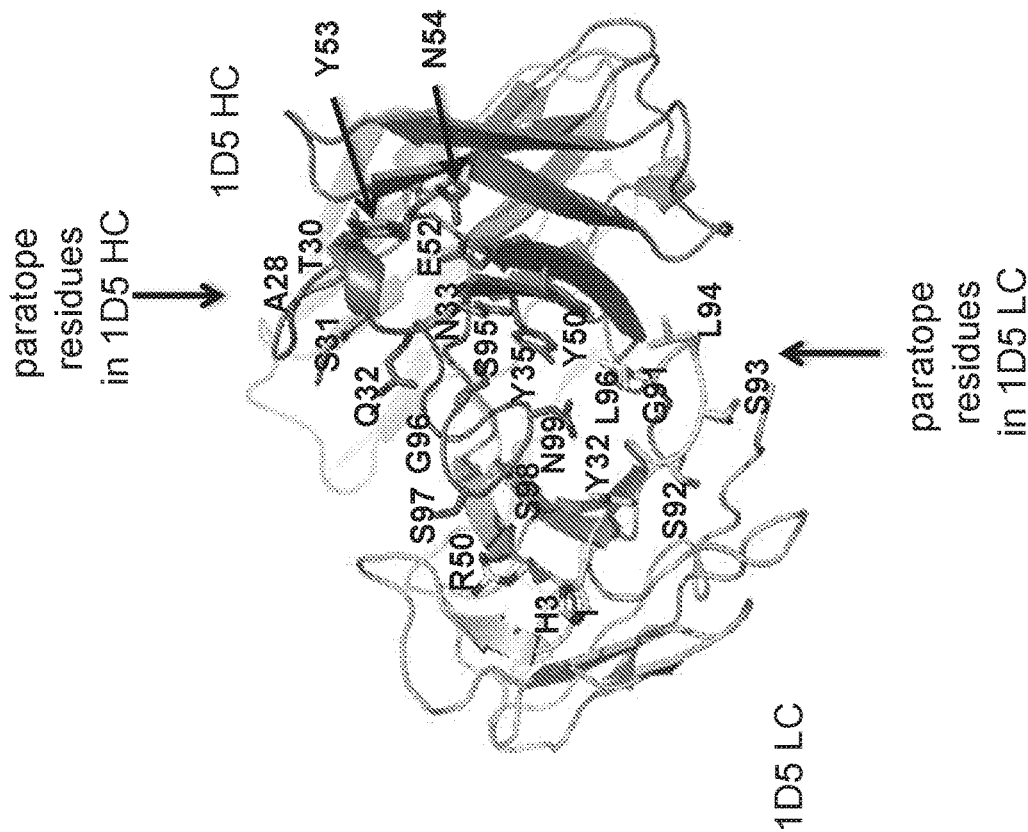

The structure of the 1D5 Fab in complex with the MICA*008 α3 domain reveals that 1D5 binds to the "front face" of the α3 domain, defined as the beta sheet of the immunoglobulin (Ig) domain containing the carboxy-terminal beta strand (FIG. 22A-FIG. 22D). Approximately 1526 Å$^2$ of surface area is buried at the interface of the 1D5 Fab and the MICA*008 α3 domain, 934 Å$^2$ of which comes from contacts with the HC and 526 Å$^2$ from the LC. Residues from all six CDRs make interactions with MICA*008, with the largest number of contacts coming from CDR H1 followed by CDRs L3 and H3 (FIG. 23A-FIG. 23B). The epitope of 1D5 is defined as residues of the MICA*008 α3 domain within 4.5 Å of the 1D5 Fab in the structure of the complex (Table 12 and FIG. 24A-FIG. 24D). Similarly the paratope of 1D5 is defined as residues of the 1D5 Fab within 4.5 Å of the MICA*008 α3 domain (Table 12 and FIG. 24A-FIG. 24D).

TABLE 12

Epitope residues of MICA*008 and their corresponding paratope residues of 1D5

| MICA*008α3 Epitope Residues | 1D5 LC Paratope Residues | 1D5 HC Paratope Residues |
|---|---|---|
| Arg240 | | Ser31, Gln32 |
| Gln241 | Tyr32, Gly91, Ser92 | |
| Asp242 | Gly91, Leu94, Leu96 | Asn33, Tyr35, Tyr50, Ser95, Asn99 |
| Gly243 | | Gln32, Asn33, Ser95, Gly96 |
| Val244 | | Tyr35, Ser95, Gly96, Ser97, Ser98, Asn99 |
| Ser245 | Arg50 | Gly96 |
| Leu246 | Tyr32 | |
| Ser247 | His31, Arg50 | |
| Asp249 | His31 | |

TABLE 12-continued

Epitope residues of MICA*008 and their corresponding paratope residues of 1D5

| MICA*008α3 Epitope Residues | 1D5 LC Paratope Residues | 1D5 HC Paratope Residues |
|---|---|---|
| Thr250 | His31 | |
| Arg279 | Gly91, Ser92, Ser93, Leu94 | Tyr50 |
| Tyr283 | | Ser31 |
| His290 | | Ala28, Thr30, Ser31, Tyr53 |
| Ser291 | | Tyr53 |
| Thr292 | | Thr30, Glu52, Tyr53, Asn54 |
| Pro294 | | Asn54 |

Note:
The 1D5 epitope was defined as MICA*008 α3 domain residues within 4.5 Å of the 1D5 Fab.
The 1D5 paratope was defined as 1D5 residues within 4.5 Å of the MICA*008 α3 domain.
Distances were calculated with Contact/NCONT in CCP4.

Figure 25A:
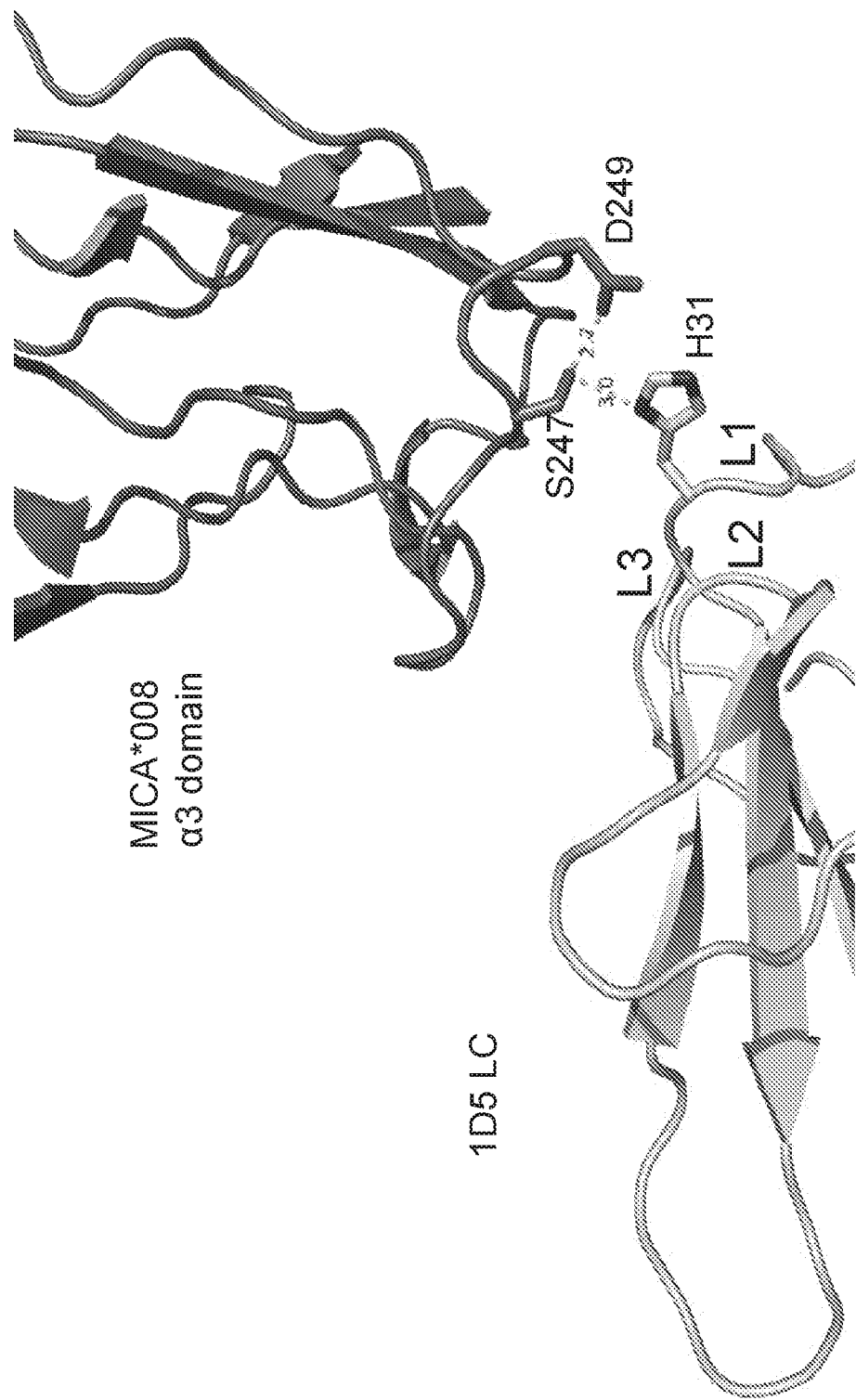
FIG. 25A and FIG. 25B highlight hydrogen bonds between residues of the LC of 1D5 and the MICA*008 α3 domain. The HC is not depicted for simplicity of viewing the LC interactions.
Figure 25B:
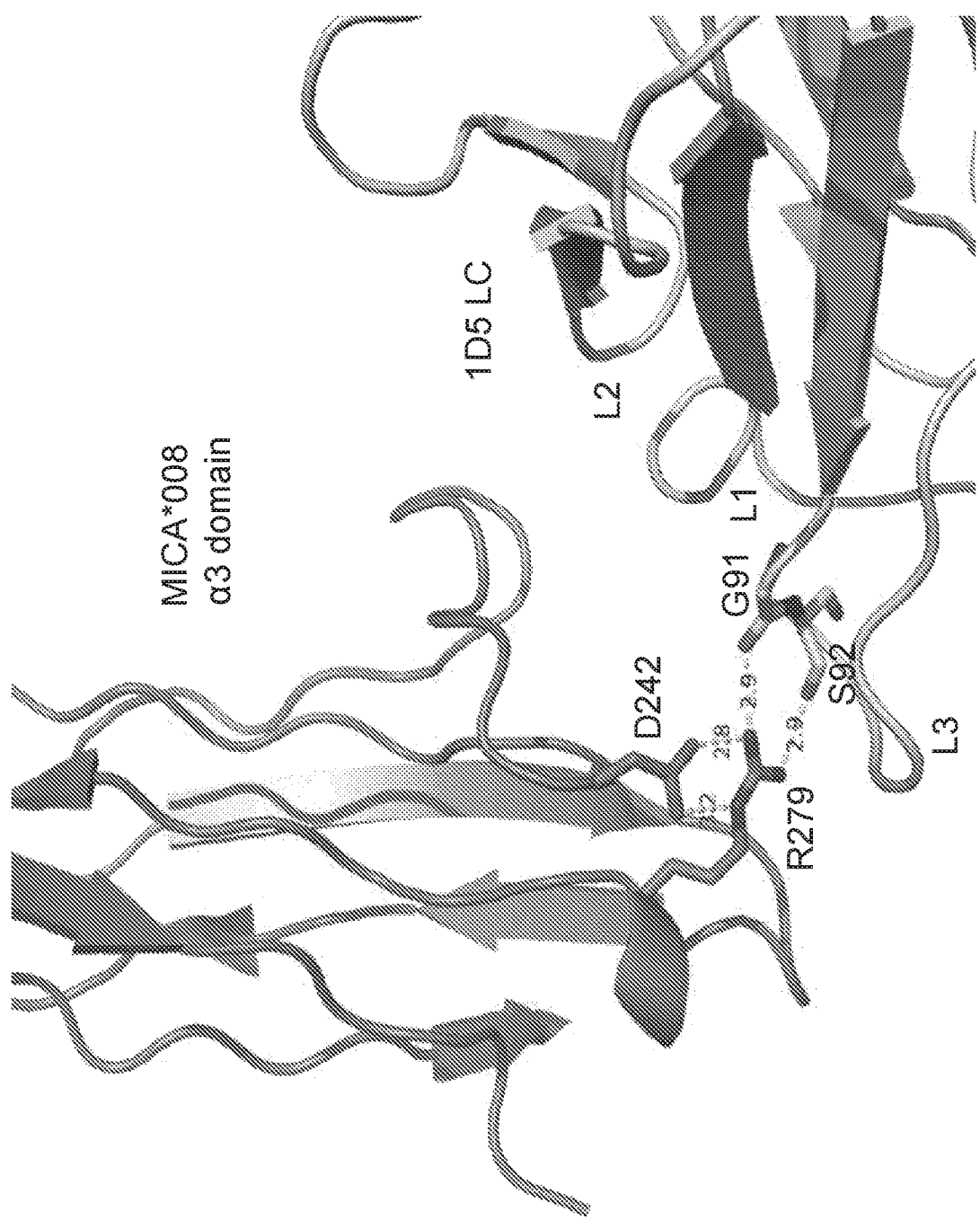
Figure 25C:
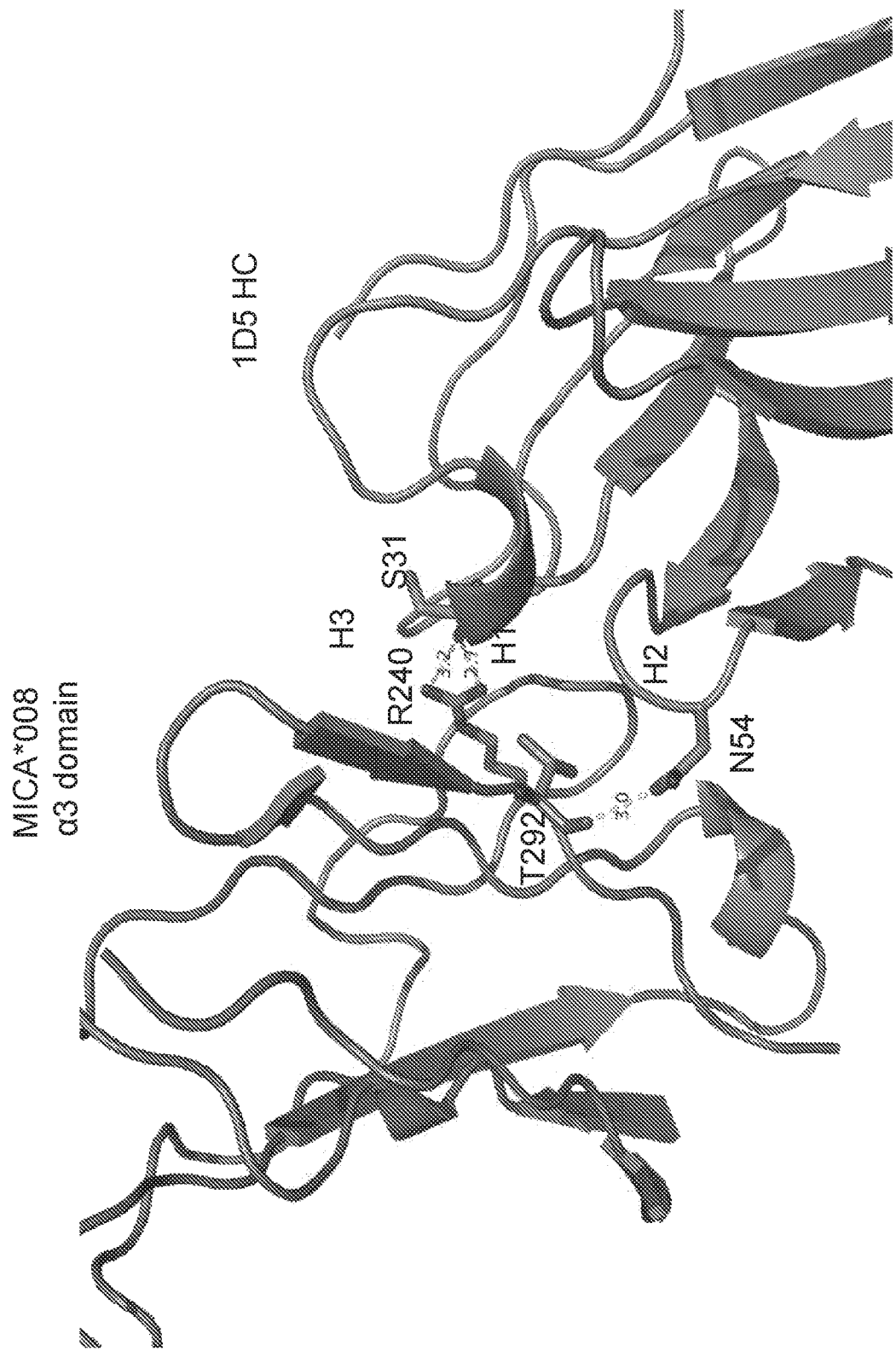
FIG. 25C and FIG. 25D highlight hydrogen bonds between residues of the HC of 1D5 and the MICA*008 α3 domain. The LC is not depicted for simplicity of viewing the HC interactions.
Figure 25D:
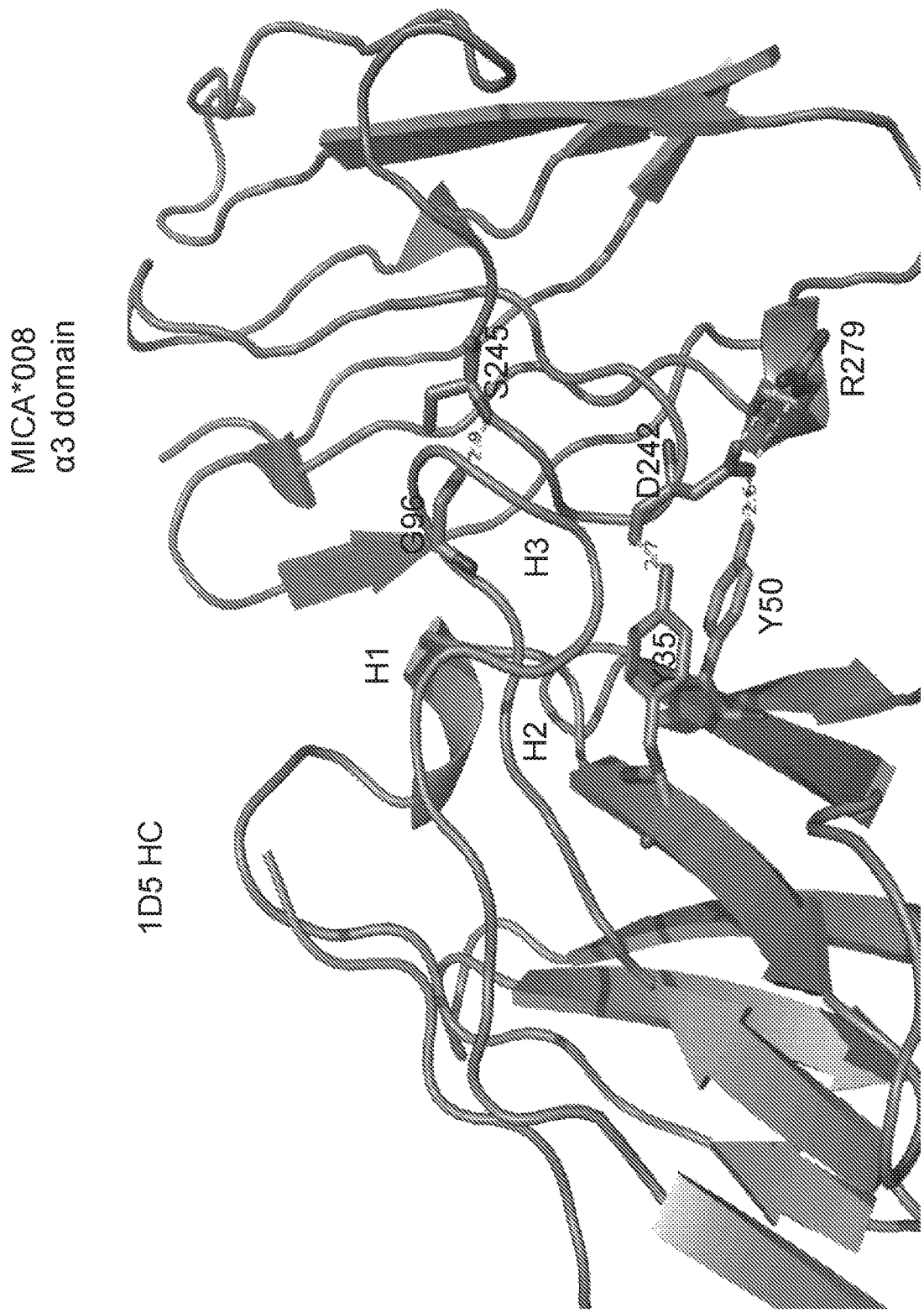
Figure 26B:
FIG. 26A and FIG. 26B are open book representations of the interface between the 1D5 Fab and the MICA*008 α3 domain, respectively, shown as surfaces with electrostatic surface potentials colored as calculated in Pymol. Residues in the 1D5 paratope, defined as being within 4.5 Å of the MICA*008 α3 domain, are highlighted in FIG. 26A with their residue numbers. MICA*008 α3 domain residues in the 1D5 epitope, defined as being within 4.5 Å of the 1D5 Fab, are highlighted in FIG. 26B with their residue numbers.
Figure 26A:
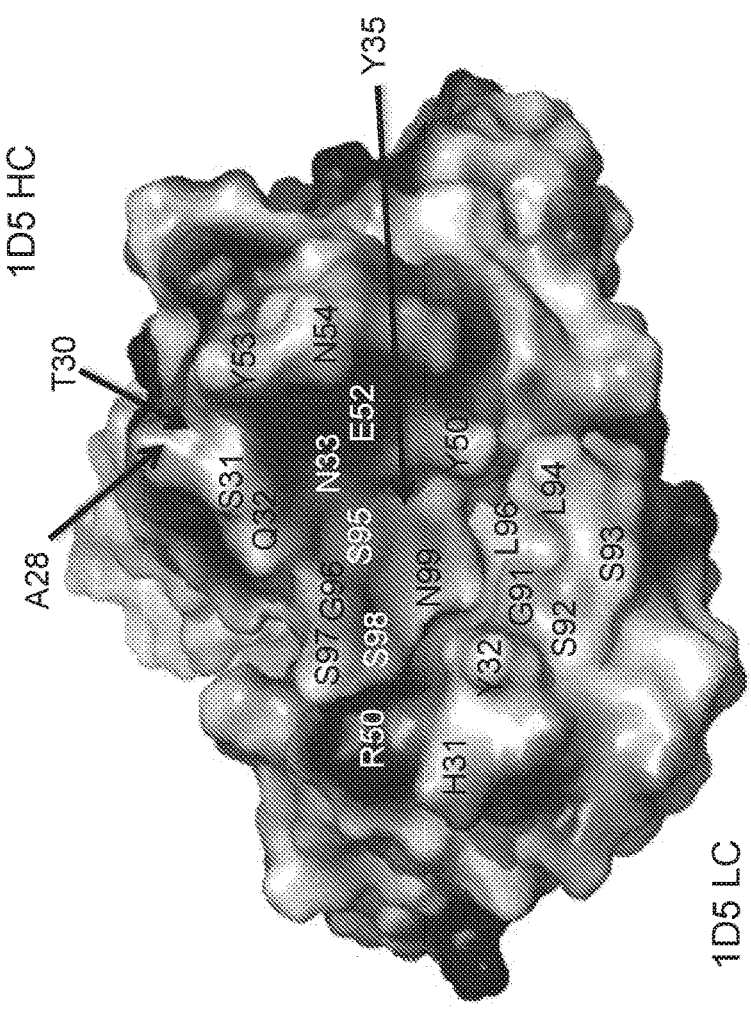
Figure 27D:
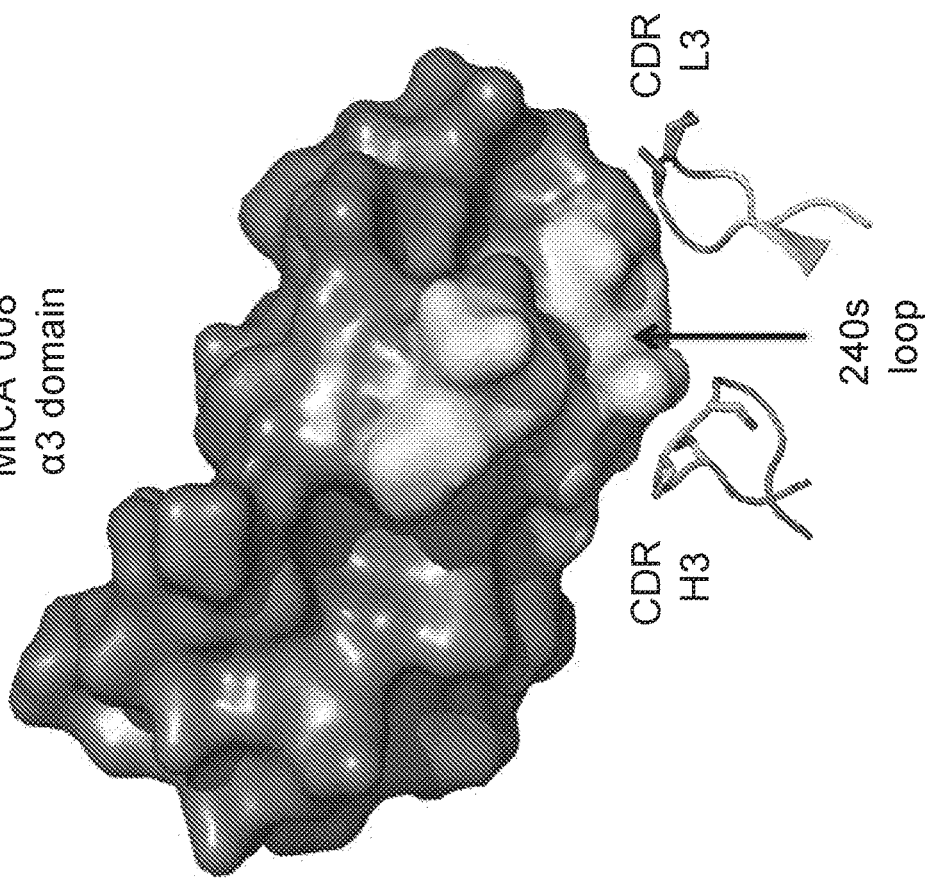
FIG. 27D-FIG. 27E are renderings of the crystal structure of the 1D5 Fab CDRs L3 and H3 bound to the MICA*008 α3 domain, shown from different angles to demonstrate the shape complementarity of the convex 240s loop of MICA*008 α3 domain and the concave surface created by the orientation and primary sequence of these CDRs. The MICA*008 α3 domain is depicted as a surface with the 240s loop highlighted and the L3 and H3 CDRs of the 1D5 Fab as ribbon diagrams. Serine residues within L3 and H3 defined as part of the 1D5 paratope (within 4.5 Å of the MICA*008 α3 domain) have their side chains shown as sticks.
Figure 27E:
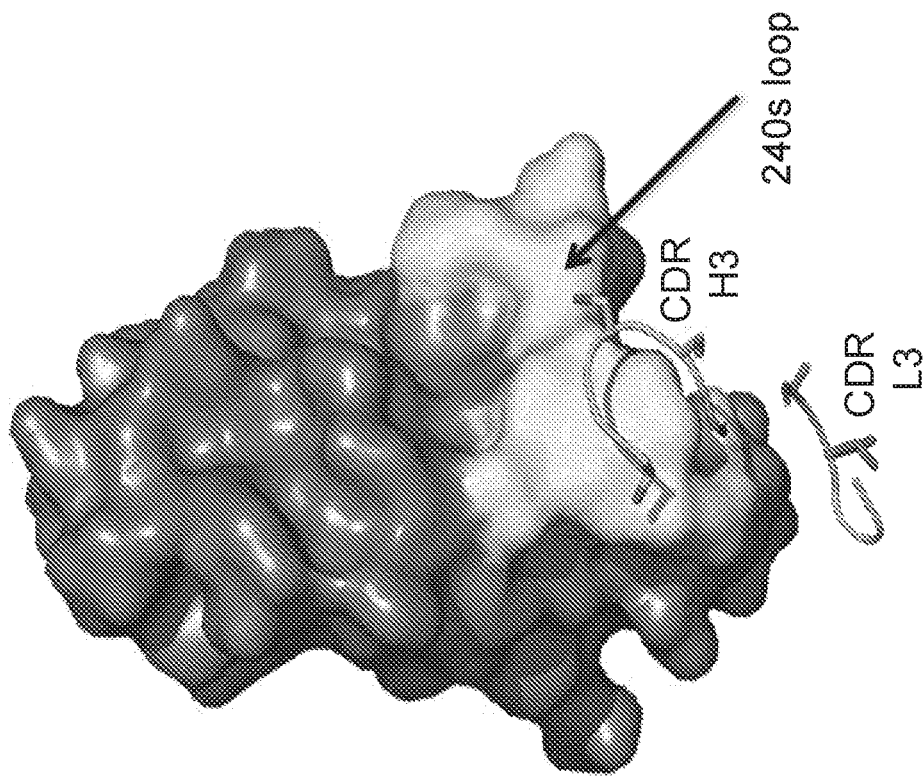
Figure 27G:
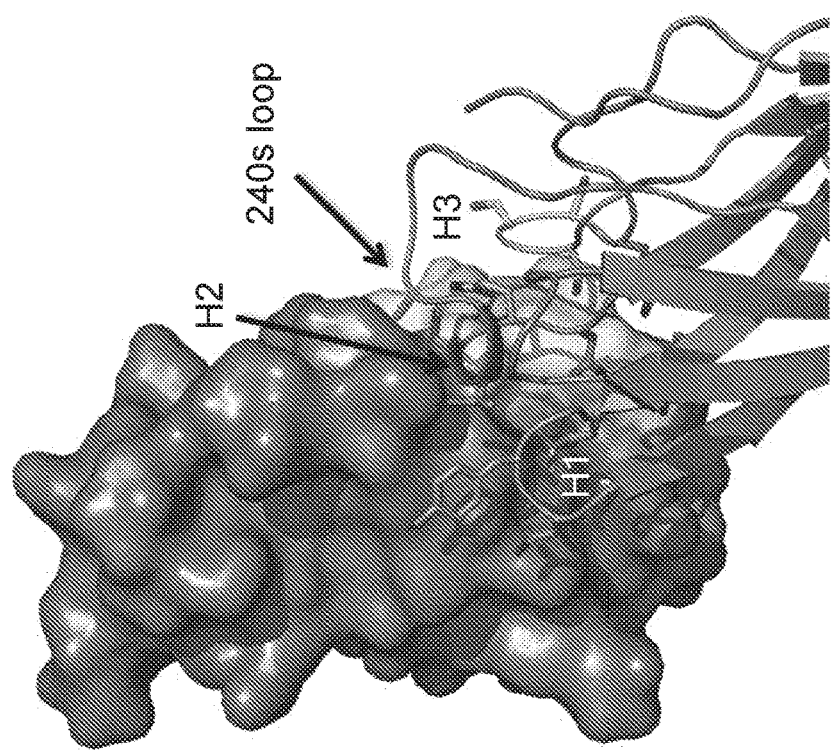
FIG. 27F and FIG. 27G are renderings of the crystal structure of the 1D5 Fab LC and HC bound to the MICA*008 α3 domain.
Figure 27F:
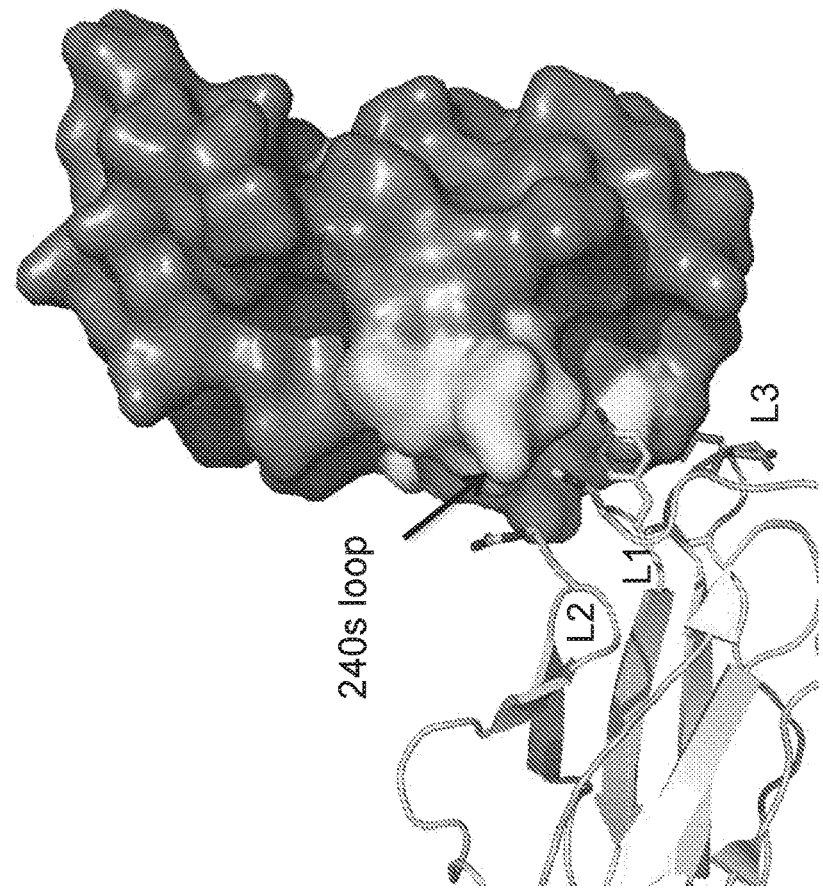
Figure 28C:
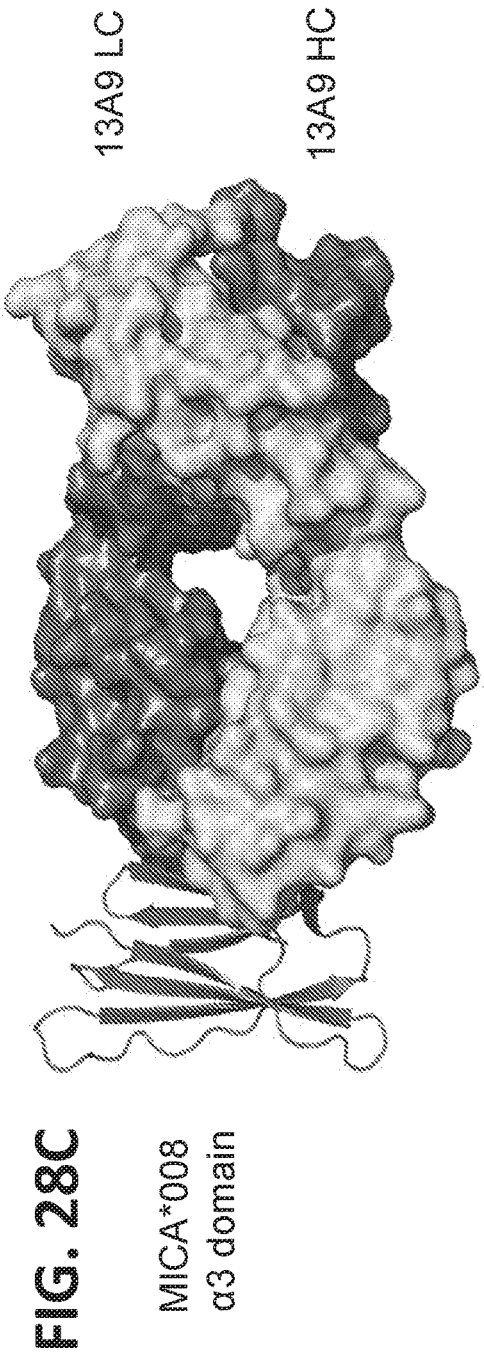
Figure 28D:
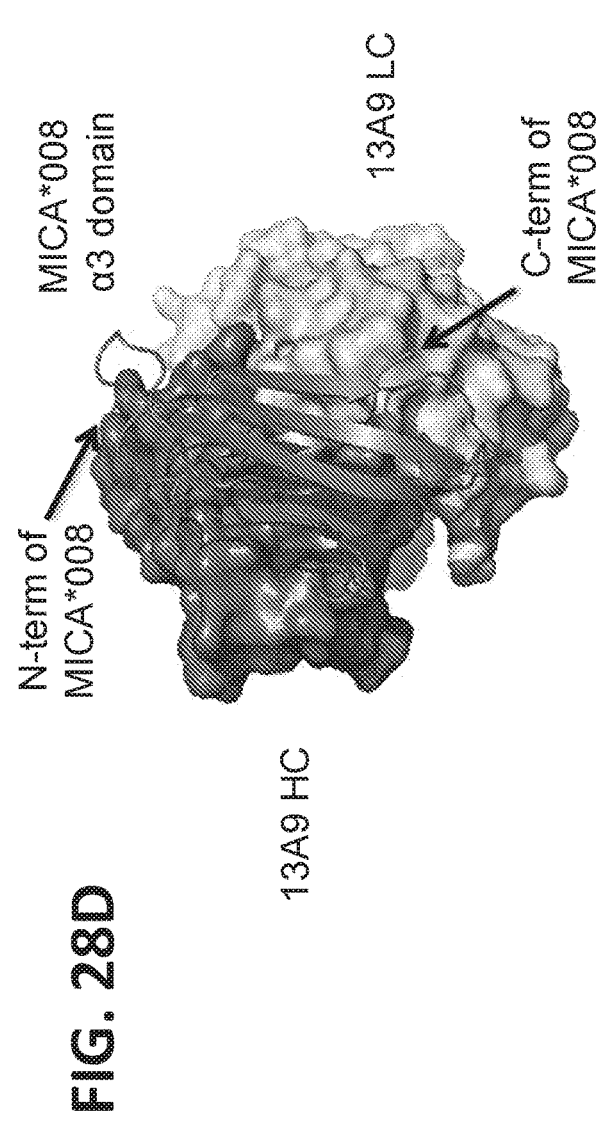

1D5 interacts with MICA*008 α3 domain using a combination of both polar and non-polar interactions. The polar interactions observed include both hydrogen bonds (FIG. 25A-FIG. 25D) and electrostatic interactions (FIG. 26A-FIG. 26B). The side chain of Ser247 of MICA*008 makes an intramolecular hydrogen bond with the side chain of Asp249 (FIG. 25A). This positions Asp249 to make an electrostatic interaction with His31 of CDR L1 (FIG. 26A-FIG. 26B). The 1D5 LC also contributes two hydrogen bonds with the main chain carbonyls of Gly91 and Ser92 of CDR L3 both forming hydrogen bonds with two amines from the guanidinium group of the side chain of Arg279 in MICA*008 (FIG. 25B). Several hydrogen bonds and polar interactions also come from the HC of 1D5. Two hydrogen bonds come from residues in CDR H1 with the main chain carbonyl of Ser31 of H1 forming a hydrogen bond with the side chain of Arg240 in MICA*008 (FIG. 25C) and the side chain hydroxyl of Tyr35 of H1 forming a hydrogen bond with the main chain carbonyl of Asp242 of MICA*008 (FIG. 25D). Tyr50 of CDR H2 also makes a hydrogen bond with the side chain carboxyl of Asp242 of MICA*008 (FIG. 25D). In addition the side chain carbonyl of Asn54 of CDR H2 forms a polar interaction with the main chain carbonyl of T292 of MICA*008 (FIG. 25C) and the main chain carbonyl of Gly96 of CDR H3 makes a hydrogen bond with the main chain amide of Ser245 of MICA*008 (FIG. 25D). The non-polar interactions observed include van der Waals interactions and shape complementarity. The 240s loop of MICA*008 protrudes out from the "front face" of the Ig domain creating a convex surface on the α3 domain (FIG. 27A-FIG. 27B). The 1D5 Fab uses shape complementarity at the interface of the LC and HC to accommodate this surface. Both CDRs L3 and H3 are involved in binding the 240s loop and both contain a string of residues with small side chains such as serine or no side chain such as glycine. These CDRs splay away from the LC/HC interface with the serine side chains pointed away from the MICA*008 interface creating a depression in which the convex surface of the MICA*008 binds (FIG. 27C-FIG. 27E). The nature of the CDR L3 and H3 amino acid composition as well as their conformations results in a concave surface that complements the convex nature of the 240 s loop. Whereas the side chains and overall loop conformations of CDRs L3 and H3 bend away from the MICA*008 interface, CDRs L1, L2, H1, and H2 and their side chains tend to point towards the interface filling in concave regions of the MICA*008 α3 domain surface (FIG. 27F-FIG. 27G).

Structural Analysis of the 13A9 Fab-MICA*008 α3 Domain Complex

The structure of the 13A9 Fab in complex with the MICA*008 α3 domain reveals that 13A9 binds to the "front face" of the α3 domain, defined as the beta sheet of the Ig domain containing the carboxy-terminal beta strand (FIG. 28A-FIG. 28D). Approximately 1750 Å$^2$ of surface area is buried at the interface of the 13A9 Fab and the MICA*008 α3 domain, 1086 Å$^2$ of which comes from contacts with the HC and 664 Å$^2$ from the LC. Residues from all six CDRs make interactions with MICA*008, with the largest number of contacts coming from CDR H2 followed by CDRs L3 and H3 (FIG. 29A-FIG. 29B). The epitope of 13A9 is defined as residues of the MICA*008 α3 domain within 4.5 Å of the 13A9 Fab in the structure of the complex (Table 13 and FIG. 30A-FIG. 30D). Similarly the paratope of 13A9 is defined as residues of the 13A9 Fab within 4.5 Å of the MICA*008 α3 domain (Table 13 and FIG. 30A-FIG. 30D). 13A9 interacts with MICA*008 α3 domain using a combination of both polar and non-polar interactions. The polar interactions observed include both hydrogen bonds (FIG. 31A-FIG. 31D) and electrostatic interactions (FIG. 32A-FIG. 32B). Residues from both the LC and HC form hydrogen bonds with MICA*008. Three hydrogen bonds come from CDR L1 of 13A9. The side chain of His30 makes a hydrogen bond with the main chain amide of Ser297, the main chain carbonyl group of Ser31 makes a hydrogen bond with the side chain of Gln278, and the side chain of Tyr32 forms a hydrogen bond with the main chain carbonyl of Val295 (FIG. 31A). An additional hydrogen bond from the LC comes from Tyr50 of CDR L2 where the side chain makes a hydrogen bond with the main chain carbonyl of Gln278 (FIG. 31A). A total of nine hydrogen bonds come from the HC of 13A9. The main chain carbonyl of Asn31 of CDR H1 forms a hydrogen bond with the side chain of Arg240 (FIG. 31B). CDR H2 forms five hydrogen bonds with the MICA*008 α3 domain (FIG. 31C). The side chain of Asn52 makes a hydrogen bond with the side chain of Tyr283. The side chain of Ser54 makes a hydrogen bond with the side chain of Glu285. The main chain carbonyl of Ala56 makes a hydrogen bond with the side chain of His290. Finally, Thr57 makes two hydrogen bonds with its main chain amide forming a bond with the main chain carbonyl of G288 and the main chain carbonyl of Thr57 making a hydrogen bond with the main chain amide of His290. CDR H3 of 13A9 makes three hydrogen bonds with MICA*008, but uses only a single residue to make these bonds (FIG. 31D). The side chain of Asn98 makes hydrogen bonds with the main chain carbonyls of Gln278 and of Phe280, as well as with the side chain of Thr281. The non-polar interactions of 13A9 and MICA*008 include van der Waals interactions and shape complementarity. The start of the 240s loop (residues 240-245), the end of the 270 s loop (residues 277-279), and the carboxy-terminal beta strand (residues 288-297) of the MICA*008 α3 domain protrude out from the "front face" of the Ig domain creating two ridges with a valley between them (FIG. 33A-FIG. 33B). 13A9 binds using all six of its CDRs to span the ridges and valley (FIG. 33C). Tyr32 of CDR L1, Tyr96 of CDR L3, Leu33 of CDR H1, Ala56 of CDR H2, and Phe95 and Asn98 of CDR H3 bind with their side chains pointing into the valley creating a complementary convex surface for recognition of the "front face" of the MICA*008 α3 domain (FIG. 33D-FIG. 33E). Side chains of residues such as His30 and Ser31 of CDR L1, Tyr50 of CDR L2, Trp92 and Thr94 of CDR L3, Asn31 and Tyr32 of CDR H1, Asn52, Ser54, and Asn58 of CDR H2, and Leu96 of CDR H3 fold over the ridges making significant van der Waals interactions with MICA*008 (FIG. 33D-FIG. 33E).

TABLE 13

Epitope residues of MICA*008 and the corresponding paratope residues of 13A9

| MICA*008 α3 Epitope Residues | 13A9 LC Paratope Residues | 13A9 HC Paratope Residues |
|---|---|---|
| Arg240 | | Asn31, Tyr32, Leu33, Asn52 |
| Asp242 | | Tyr32, Leu96, Gly97 |
| Gly243 | | Asn31, Tyr32, Phe95, Leu96, Gly97 |
| Val244 | | Asn31, Tyr32 |
| Glu277 | Tyr32 | |
| Gln278 | His30, Ser31, Tyr32, Tyr50 | Gly97, Asn98 |
| Arg279 | Tyr50 | Gly97, Asn98 |
| Phe280 | | Asn98 |
| Thr281 | | Phe95, Asn98 |
| Tyr283 | | Leu33, Asn52, Ser54, Ala56, |
| Glu285 | | Asn52, Ser54, Ala56 |
| Gly288 | | Ala56, Thr57 |
| Asn289 | | Ala56, Thr57 |
| His290 | | Leu33, Ala50, Ile51, Asn52, Ala56, Thr57, Asn58 |
| Ser291 | | Asn58 |
| Thr292 | Thr94, Tyr96 | Leu33, Asn58 |
| Pro294 | Tyr32, Phe91, Trp92 | Asn98 |
| Val295 | Tyr32, Trp92 | |
| Pro296 | His30, Trp92 | |
| Ser297 | His30 | |

Note:
The 13A9 epitope was defined as MICA*008 α3 domain residues within 4.5 Å of the 13A9 Fab.
The 13A9 paratope was defined as 13A9 residues within 4.5 Å of the MICA*008 α3 domain.
Distances were calculated with Contact/NCONT in CCP4.

Structural Analysis of the 6E1.1.12 Fab-MICA*008 C273S α3 Domain Complex

The structure of the 6E1.1.12 Fab in complex with the MICA*008 C273S α3 domain reveals that 6E1.1.12 binds to the "back face" of the α3 domain, defined as the beta sheet of the Ig domain containing the amino-terminal beta strand (FIG. 34A-FIG. 34D). Approximately 1416 Å$^2$ of surface area is buried at the interface of the 6E1.1.12 Fab and the MICA*008 α3 domain, 1046 Å$^2$ of which comes from contacts with the HC and 370 Å$^2$ from the LC. Residues from five of the six CDRs make interactions with MICA*008, with the largest number of contacts coming from CDR H3 followed by CDRs L1 and H2, and no contacts from CDR L3 (FIG. 35A-FIG. 35B). The epitope of 6E1.1.12 is defined as residues of the MICA*008 C273S α3 domain within 4.5 Å of the 6E1.1.12 Fab in the structure of the complex (Table 14 and FIG. 36A-FIG. 36D). Similarly the paratope of 6E1.1.12 is defined as residues of the 6E1.1.12 Fab within 4.5 Å of the MICA*008 C273S α3 domain (Table 14 and FIG. 36A-FIG. 36D).

TABLE 14

Epitope residues of MICA*008 C273S and the corresponding paratope residues of 6E1.1.12

| MICA*008 α3 Epitope Residues | 6E1.1.12 LC Paratope Residues | 6E1.1.12 HC Paratope Residues |
|---|---|---|
| Thr224 | | Tyr98 |
| Arg226 | | Asp31, Tyr98 |
| Arg233 | Ser27E, Asn28 | |
| Trp253 | | Ser100A |
| Gly254 | | Tyr97, Ser100A |

TABLE 14-continued

Epitope residues of MICA*008 C273S and the corresponding paratope residues of 6E1.1.12

| MICA*008 α3 Epitope Residues | 6E1.1.12 LC Paratope Residues | 6E1.1.12 HC Paratope Residues |
|---|---|---|
| Asp255 | Asn28, Asn30, Tyr32, Lys50 | Tyr97, Ser100A, Gly100B |
| Val256 | Asn28 | |
| Leu257 | His27D, Asn28, Tyr32 | Tyr33, His95, Tyr97, Trp100D |
| Pro258 | | Tyr33, Trp50 |
| Asp259 | | Trp50, Tyr52, Thr54, Gly56 |
| Gly260 | | Trp50, Gly56, Ser57 |
| Asn261 | | Thr54, Gly56 |
| Gln265 | | Tyr33, Tyr52, Tyr97 |
| Thr266 | | Tyr97 |
| Trp267 | | Tyr97, Tyr98, Ser100A |

Note:
The 6E1.1.12 epitope was defined as MICA*008 C273S α3 domain residues within 4.5 Å of the 6E1.1.12 Fab.
The 6E1.1.12 paratope was defined as 6E1.1.12 residues within 4.5 Å of the MICA*008 C273S α3 domain.
Distances were calculated with Contact/NCONT in CCP4.

6E1.1.12 interacts with MICA*008 α3 domain using a combination of both polar and non-polar interactions. The polar interactions observed include hydrogen bonds, salt bridges, pi-cation interactions, and electrostatic interactions (FIG. 37A-FIG. 37C, FIG. 38A-FIG. 38B). Residues from both the LC and HC form hydrogen bonds with MICA*008. Two residues in CDR L1 make hydrogen bonds with MICA*008. The side chain of Asn28 forms a hydrogen bond with the main chain carbonyl of Val256 of MICA*008 and the side chain of Tyr32 makes a hydrogen bond with the side chain of Asp255 of MICA*008 (FIG. 37A). The positively charged Lys50 of CDR L2 forms a salt bridge with the negatively charged Asp255 of MICA*008 (FIG. 37A). The negatively charged Asp31 of CDR H1 forms a salt bridge with the positively charged Arg226 of MICA*008 (FIG. 37B). The side chain of Tyr33 of CDR H1 forms a hydrogen bond with the side chain of Gln265 and with the main chain carbonyl of Pro258 of MICA*008 (FIG. 37B). The side chain of Thr54 makes a hydrogen bond with the main chain carbonyl of Asp259 (FIG. 37B). Tyr97 of CDR H3 makes three hydrogen bonds. The main chain carbonyl of Tyr97 forms a hydrogen bond with Trp267 of MICA*008 and the side chain of Tyr97 forms two hydrogen bonds with the main chain carbonyls of Asp255 and Gln265 of MICA*008 (FIG. 37C). The side chain of Ser100A of CDR H3 also forms a hydrogen bond with the main chain amide of Asp255. Finally Tyr98 forms a pi-cation interaction with Arg226 of MICA*008 (FIG. 37C). The non-polar interactions observed include van der Waals interactions and shape complementarity. CDR L1 of 6E1.1.12 has a five amino acid insertion after residue 27 (residues 27A-27E) creating a much longer L1 loop than typically found in most antibodies. This results in CDR L1 protruding out farther than all other CDRs of 6E1.1.12, which creates a groove between CDR L1 and CDR H3 (FIG. 39A-FIG. 39B). A longer CDR L1 is often seen in antibodies that bind peptide antigens, with the peptide binding in the cleft created by CDRs L1 and H3. The 250 s loop of MICA*008 (residues 254-260) creates a ridge across the "back face" of the α3 domain (FIG. 39C-FIG. 39D). The 250 s loop binds in the groove between CDR L1 and CDR H3 of 6E1.1.12 mimicking a peptide antigen (FIG. 39E-FIG. 39F). In particular the side chains of Asp255 and Leu257 point into the cleft and make interactions with residues from both CDRs L1 and H3. Leu257 binds in a hydrophobic pocket formed by residues His27D, Asn28, Tyr32 from the LC and Tyr33, His95, Tyr97, Trp100D from the HC (FIG. 39G). This pocket is heavily lined with aromatic residues. Asp255 binds into a pocket formed by residues Asn28, Asn30, Tyr32, Lys50 of the LC and Tyr97, Ser100A, Gly100B of the HC (FIG. 39H) and forms a hydrogen bond with Tyr32 and a salt bridge with Lys50 of the LC (FIG. 37A).

Comparison of the 1D5 Fab-MICA*008 α3 Domain, 13A9 Fab-MICA*008 α3 Domain, and 6E1.1.12 Fab-MICA*008 C273S α3 Domain Complex Structures Both 1D5 and 13A9 bind to the "front face" of MICA*008, as defined by the defined as the beta sheet of the Ig domain containing the carboxy-terminal beta strand, whereas 6E1.1.12 binds to the "back face" of MICA*008, defined as the beta sheet of the Ig domain containing the amino-terminal beta strand (FIG. 40A). Comparison of the epitopes (defined as residues within 4.5 Å of their respective Fabs) of 1D5 and 13A9 revealed that they have partially overlapping epitopes (FIG. 40B-FIG. 40C). Analysis of the reported MICA cleavage sites in the literature (*Cancer Res* (2008); 68: 6368 and BBRC (2009); 387: 476) revealed that all cleavage sites in the α3 domain mapped to the "front face" of the domain (FIG. 41A). Comparisons of the epitopes defined by crystallography with the reported cleavage sites demonstrated that the 1D5 and 13A9 epitopes overlapped with these cleavage sites found exclusively on the "front face" of the α3 domain (FIG. 41B). Binding of 1D5 or 13A9 to the MICA α3 domain may create steric hindrance and block access of proteases required for cleavage of MICA. In contrast, 6E1.1.12 binds on the "back face" of MICA and away from any reported cleavage sites (FIG. 41B). Defining the epitopes helps explain why 1D5 and 13A9 are potent blockers of MICA*008 cleavage and shedding, whereas 6E1.1.12 is a relatively weak blocker of cleavage and shedding.

MicA Oxidative Footprinting by Fast Photochemical Oxidation of Proteins (FPOP)

The epitope of the 1D5 Fab on MICA*008 was mapped by oxidative footprinting using the Fast Photochemical Oxidation of Proteins (FPOP) method. The 1D5 Fab was expressed and purified as described above for crystallography. The MICA*008 α3 domain (residues Thr204-Ser297) was expressed with a C-terminal His8 tag in CHO DP12 cells. The CHO DP12 cell line is a derivative of the CHO-K1 cell line (ATCC number CCL-61) selected for large-scale production. The MICA*008 α3 domain expression plasmid was transiently transfected using PEI as previously described (Wong, A. W. et al. (2010) Biotechnol Bioeng 106:751-763). Supernatants were harvested 14 days after transfection and the secreted MICA*008 α3 domain was purified over a Ni Sepharose Excel (GE Healthcare) column followed by a HiLoad Superdex 75 pg column (GE Healthcare) as described above for crystallography.

A 1.5:1 molar ratio of 1D5 Fab to MICA*008 α3 domain antigen was prepared in PBS with a total protein concentration of 2.35 mg/mL. The solution was incubated at 37° C. for 30 minutes. Size exclusion chromatography was performed to ensure complete complex formation. For the unbound MICA*008 α3 domain antigen a 2.35 mg/mL solution was prepared in 1 mL PBS. Scavenger Arginine was added at 30 mM final concentration to the protein solutions. The unbound MICA*008 α3 domain or the MICA*008 α3 domain:1D5 Fab complex were flow-mixed with 30 mM peroxide and labeling was performed using the fast photochemical oxidation of proteins (FPOP) methodology previously described (Zhang, Y., et al. (2015) J Am Soc Mass Spectrom 26:526-529; Zhang, Y., et al. (2017) J Am Soc Mass Spectrom 28:850-858; Li, J. et al. (2017) Anal Chem 89:2250-2258). Briefly, 15 µL/min of MICA solutions were mixed with 30 mM $H_2O_2$ at a rate of 7.5 µL/min through a micro-tee mixer (Cobert Associates Lab, St. Louis, Mo.) for rapid mixing prior to light exposure. The oxidation reaction was initiated by pulsing a focused 248 nm KrF excimer laser (GAM Laser Inc., Orlando, Fla.) at 70 mJ/pulse at a rate of 7 Hz through a 3.0 mm exposure window of 150 µm i.d. fused-silica tubing (Polymicro Technologies, Phoenix, Ariz.). Oxidized samples were collected in a tube containing a quench solution with Methionine (Sigma Aldrich) and catalase (Sigma Aldrich) in a final concentration of 40 mM and 1 µM, respectively. Samples were frozen and stored at −80° C. before proteolysis and mass spectrometry. To account for background oxidation, an unexposed sample was obtained and compared to three oxidized replicates for each protein state. The sequence and duration of sample collection for FPOP experiments is shown in Table 15.

TABLE 15

Time Table for Labeling Triplicate Samples

| Start Time (min) | End time (min) | Duration (min) | Action | Laser Status | Collection |
|---|---|---|---|---|---|
| 0 | 2 | 2 | Start Pump (Laser Off) | Off | Waste |
| 2 | 8 | 6 | Control (No Laser) | Off | Collection Vial |
| 8 | 10 | 2 | Turn on Laser | On | Waste |
| 10 | 16 | 6 | Sample 1 Collection | On | Collection Vial |
| 16 | 22 | 6 | Sample 2 Collection | On | Collection Vial |
| 22 | 28 | 6 | Sample 3 Collection | On | Collection Vial |
| 28 | End | | End of Run | Off | Waste |
| | | | Change Capillary Position | Off | Waste |

Upon thawing, samples were reduced, deglycosylated with PNGaseF, and alkylated with iodoacetamide then separated on SDS-PAGE (FIG. 42). The band at the 15 kDa region corresponding to the molecular weight of the MICA*008 α3 domain was excised from the MICA*008 α3 domain alone and the MICA*008:1D5 Fab complex samples, both unexposed and exposed. Samples were digested with trypsin and chymotrypsin at a 1:500 enzyme: substrate ratio. Digests were C18 stage tip cleaned, dried, and reconstituted in 100 uL of 0.1% Formic acid containing 2% acetonitrile. 1 uL was injected via auto-sampler onto a 75 µm×100 mm column (BEH, 1.7 micron, Waters Corp) at a flow rate of 1 µL/min using a NanoAcquity UPLC (Waters Corp). A gradient from 98% solvent A (water +0.1% formic acid) to 80% solvent B (acetonitrile +0.08% formic acid) was applied over 60 min. Samples were analyzed on-line via nanospray ionization into a hybrid Elite Orbitrap mass spectrometer (Thermo Fisher Scientific). Resultant spectra were interrogated against a theoretical tryptic and chymotryptic digestion of the protein sequence of the MICA*008 α3 domain construct used. Unmodified and oxidized species for each tryptic peptide were identified from the fragmentation spectra. Oxidation of Cysteine, Tryptophan, Tyrosine, Methionine, Phenylalanine, Histidine, Arginine, Leucine and Isoleucine were quantified by measuring areas under the curve of the matching modified ions versus total occurrence of a given peptide. Oxidation events for both the complex and the unbound MICA*008 α3 domain were then mapped onto the sequence of the MICA*008 α3 domain. Regions of protection were observed as having a significant change between the two values. Triplicate samples were averaged for the final percent oxidation and error bars represent the standard deviation of the three measurements.

A significant change in oxidation protection was observed for Trp239 within the MICA*008 α3 domain tryptic peptide containing residues Asn234-Arg240 and for residues Ile272 and Phe280 within the MICA*008 α3 domain chymotryptic peptide Val268-Phe280 (FIG. 43A-B, FIG. 44, FIG. 45).
Comparison of Epitope Mapping Results from Glycosylation Engineering, Alanine Scanning, FPOP, and X-ray Crystallography Comparison of the 1D5 epitope determined by glycosylation engineering, alanine scanning, FPOP and X-ray crystallography reveal consistent results between these methods.

The 1D5 antibody shows a complete loss in binding to the MICA*008 α3 domain containing either the glycosylation variant Glyco14 (G243N) or Glyco16 (R279N), but is unaffected by Glyco11 (R202N), Glyco12 (E215N), Glyco13 (I236T), Glyco15 (H248N), and Glyco17 (C-terminal addition of residues N298, G299, S300). Comparison of the epitope of 1D5 determined by X-ray crystallography with the location of the glycosylation site variants demonstrates that Glyco14 (G243N) and Glyco16 (R279N) are part of the 1D5 epitope, whereas Glyco11 (R202N), Glyco12 (E215N), Glyco13 (I236T), Glyco15 (H248N), and Glyco17 (carboxy-terminal addition of residues N298, G299, 5300) fall outside of the 1D5 epitope (FIG. 46A).

The 13A9 antibody shows a partial loss in binding to the MICA*008 α3 domain containing either the glycosylation variant Glyco14 (G243N) or Glyco16 (R279N), but is unaffected by Glyco11 (R202N), Glyco12 (E215N), Glyco13 (I236T), Glyco15 (H248N), and Glyco17 (C-terminal addition of residues N298, G299, S300). Comparison of the epitope of 13A9 determined by X-ray crystallography with the location of the glycosylation site variants demonstrates that Glyco14 (G243N) and Glyco16 (R279N) are part of the 13A9 epitope, whereas Glyco11 (R202N), Glyco12 (E215N), Glyco13 (I236T), Glyco15 (H248N), and Glyco17 (carboxy-terminal addition of residues N298, G299, S300) fall outside of the 13A9 epitope (FIG. 46A). Residues N298, G299, and S300 added to the carboxy-terminus are not present in the crystal structure therefore Glyco17 is indicated in FIG. 46A by highlighting the carboxy-terminal residue S297, immediately preceding the added glycoslation site. Glycosylation at N298 does not affect binding of 13A9.

The 6E1.1.12 antibody demonstrated no loss of binding to any of the glycosylation variants tested (Glyco11 (R202N), Glyco12 (E215N), Glyco13 (I236T), Glyco14 (G243N), Glyco15 (H248N), Glyco16 (R279N), or Glyco17 (carboxy-terminal addition of residues N298, G299, S300)). Comparison of the epitope of 6E1.1.12 determined by X-ray crystallography with the location of the glycosylation site variants demonstrates that all glycosylation variants (Glyco11 (R202N), Glyco12 (E215N), Glyco13 (I236T), Glyco14 (G243N), Glyco15 (H248N), Glyco16 (R279N), and Glyco17 (carboxy-terminal addition of residues N298, G299, S300) fall outside of the 6E1.1.12 epitope (FIG. 46A).

All of the epitopes determined by glycosylation engineering are consistent with the epitopes determined by X-ray crystallography. Moreover, glycosylation engineering can discriminate between subtle difference in epitopes such as those of 1D5 and 13A9. As indicated above, X-ray crystal structure analysis demonstrates that 1D5 and 13A9 contain partially overlapping epitopes (FIG. 40A-FIG. 40C). Binding of both antibodies was affected by the Glyco14 (G243N) and Glyco16 (R279N) variants, however to different extents. Whereas 1D5 binding was completely abolished by either the Glyco14 (G243N) or Glyco16 (R279N) variants, 13A9 demonstrated only a partial loss in binding to either of these two variants. Comparison of the X-ray crystal structures reveals that whereas the Glyco14 (G243N) and Glyco16 (R279N) variants are at the center of the binding interface with the 1D5 Fab, they are on the periphery of the binding interface with the 13A9 Fab (FIG. 46B). Glycosylation at positions 243 and 279 of MICA*008 would introduce a bulky sugar at the heart of the 1D5 epitope/paratope interaction that would disrupt binding, whereas the same sugars could potentially be accommodated by bending to the side of the 13A9 epitope/paratope away from the Fab, causing only a partial loss in binding.

Comparison of the epitope of 1D5 determined by FPOP to the epitope determined by the crystal structure reveals overlapping results (FIG. 46C). The FPOP epitope was defined by oxidation protection conferred to residue Trp239 in the tryptic peptide Asn234-Arg240 and Phe280 in the chymotryptic peptide Val268-Phe280 by binding of the 1D5 Fab to the MICA*008 α3 domain. These two FPOP peptides include residues Arg279 and Arg240 that are defined as part of the 1D5 epitope from the co-crystal structure (Table 10 and FIG. 24A-FIG. 24D).

Comparison of the epitope of 1D5 determined by alanine scanning to the epitope determined by the crystal structure also reveals highly overlapping results (FIG. 46C). Residues Arg240, Gln241, Val244, Ser245, Asp249, Thr250, Arg279, Tyr283, His290, and Thr292 identified as part of the 1D5 epitope by alanine scanning were also identified as part of the epitope in the crystal structure. Residues Asp242, Gly243, and Leu246 are part of the 1D5 epitope determined by the crystal structure, however they could not be tested in the alanine scan. These residues when mutated to alanine resulted in misfolded protein, as inferred by a lack of binding to these mutants by an antibody known to bind to the opposite face of the MICA*008 α3 domain (on the "back face"). Only three residues, Ser247, Ser291 and Pro294 identified as part of the epitope by the crystal structure were not part of the epitope determined by alanine scanning. All of these residues are on the periphery of the epitope in the crystal structure (FIG. 24A-FIG. 24D). Four additional residues, His248, Glu276, Glu285, and Ser287 were identified as part of the 1D5 epitope by alanine scanning that were not found in the epitope determine by the crystal structure. These residues are all found along the periphery of the epitope determined in the co-crystal structure (FIG. 46C).

While crystallography is the gold standard for epitope determination as it provides very high-resolution sequence information about the binding interface between two proteins, it is very labor intensive and low throughput. Alanine scanning, while also providing binding resolution at the level of individual residues, is only slightly less labor intensive than crystallography as many individual alanine point mutants must be expressed, purified and characterized. FPOP is still higher throughput yet, however the sequence resolution is compromised by the fact that binding residues are identified within linear peptides and the peptide fragments are determined by the presence or absence of protease cleavage sites in the primary amino acid sequence. Additionally, not all amino acids are equally susceptible to oxidation and side chains are more susceptible than the main chain peptide backbone. Therefore, not all contact residues in an epitope will be identified by FPOP as would be in a crystal structure.

Cross-blocking studies of pair-wise combinations of antibodies is the highest throughput method of epitope mapping but suffers from low-resolution sequence information. Glycosylation engineering combines the higher throughput of methods such as cross-blocking or FPOP with the high-resolution sequence information of alanine scanning and crystallography. Glycosylation engineering provides a rapid, high throughput method to map epitopes of large panels of antibodies with resolution at the individual residue level.

Comparison of the 1D5 and 13A9 Epitopes with Previously Described Epitopes

All of the previously described anti-MICA/B epitopes that block shedding map to the "back face" of MICA/B defined as the beta sheet of the Ig domain containing the amino-terminal beta strand. These include Dana Farber's CM33322 Ab4, CM33322 Ab28, and CM33322 Ab29, Innate Pharma's 16A8, and the University of Washington's H9 anti-MICA/B antibodies (FIG. 47A-FIG. 47B). This is in contrast to the 1D5 and 13A9 epitopes that map to the "front face" of MICA/B defined as the beta sheet of the Ig domain containing the carboxy-terminal beta strand (FIG. 47A-FIG. 47B).

Example 11

Biacore Anti-MICA/B Humanized Variants Kinetics

The binding kinetics of humanized variants of 1D5, 13A9, and 15F11 anti-MICA/B antibodies were measured using surface plasmon resonance (SPR) on a Biacore 8K instrument (GE Healthcare). A Protein A sensorchip (GE Healthcare) was used following manufacturer provided protocols to capture humanized anti-MICA/B antibodies. The MICA/B alleles were passed over. Antibody binding was measured to human MICA 002, 004, 008 and MICB 005 alpha 3 domains (His tagged, in-house). Sensograms for binding of MICA/B were recorded using an injection time of 2 minutes with a flow rate of 30 ml/min, at a temperature of 25° C., and with a running buffer of 10 mM HEPES, pH 7.4, 150 mM NaCl, 3 mM EDTA, and 0.005% Tween 20. After injection, disassociation of the alpha 3 domain from the antibody was monitored for 10 minutes in running buffer. The surface was regenerated between binding cycles with a 60 ul injection of 10 mM Glycine HCl pH 1.5. After subtraction of a blank which contained running buffer only, sensograms observed for MICA binding to anti-MICA/B antibody were analyzed using a 1:1 Langmuir binding model with software supplied by the manufacturer to calculate the kinetics and binding constants. The data was analyzed using a 1:1 binding model. Sensograms of MICA alleles binding to captured anti-MICA antibody were used to calculate the dissociation constant (Kd). Kinetic constants from these data are provided in Table 16.

TABLE 16

Kinetic Constants for Anti-MICA Antibodies Binding to its Ligands

| Clone | huMICA*002 alpha 3-his Kd (nM) | huMICA*004 alpha 3-his Kd (nM) | huMICA*008 alpha 3-his Kd (nM) | huMICB*005 alpha 3-his Kd (nM) |
|---|---|---|---|---|
| 1D5 | 0.83 | 0.63 | 0.61 | 0.95 |
| 1D5v1 | 1.4 | 1.17 | 0.96 | 1.96 |
| 1D5v2 | 1.69 | 1.34 | 0.89 | 2.69 |
| 1D5v3 | 1.21 | 0.96 | 0.85 | 1.78 |
| 1D5v4 | 6.63 | 6.20 | 7.45 | 16.19 |
| 1D5v5 | 2.59 | 2.13 | 1.64 | 3.99 |
| 1D5v6 | 3.69 | 2.91 | 2.61 | 6.15 |
| 1D5v7 | 2.21 | 1.67 | 1.70 | 3.31 |
| 1D5v8 | 11.33 | 9.41 | 9.08 | 18.82 |
| 1D5v9 | 1.31 | 0.95 | 0.87 | 1.51 |
| 1D5v10 | 1.44 | 1.08 | 1.05 | 1.98 |
| 1D5v11 | 1.09 | 0.83 | 0.78 | 1.38 |
| 1D5v12 | 4.64 | 3.91 | 3.66 | 9.16 |
| 1D5v13 | 1.20 | 0.91 | 0.85 | 1.48 |
| 1D5v14 | 1.62 | 1.23 | 1.16 | 2.14 |
| 1D5v15 | 1.06 | 0.81 | 0.76 | 1.26 |
| 1D5v16 | 4.09 | 3.42 | 3.21 | 8.37 |
| 1D5v17 | 0.91 | 0.68 | 0.64 | 1.01 |
| 1D5v18 | 1.04 | 0.79 | 0.75 | 1.41 |
| 1D5v19 | 1.16 | 0.88 | 0.83 | 1.51 |
| 1D5v20 | 1.14 | 0.88 | 0.83 | 1.57 |
| 1D5v21 | 1.35 | 1.08 | 0.99 | 1.98 |
| 1D5v22 | 6.46 | 5.45 | 4.98 | 13.25 |
| 1D5v23 | 1.11 | 0.90 | 0.58 | 1.65 |
| 1D5v24 | 1.21 | 0.90 | 1.41 | 1.62 |
| 1D5v25 | 1.22 | 0.96 | 0.93 | 1.84 |
| 1D5v26 | 3.90 | 3.17 | 3.12 | 7.15 |
| 1D5v27 | 1.85 | 1.52 | 1.44 | 3.31 |
| 1D5v28 | 1.19 | 0.87 | 0.84 | 1.49 |
| 1D5v29 | 2.01 | 1.58 | 1.65 | 3.86 |
| 13A9 | 4.82 | 6.77 | 2.35 | 2.35 |
| 13A9v1 | 5.87 | 8.37 | 5.60 | 5.12 |
| 13A9v2 | 4.44 | 5.32 | 2.56 | 3.15 |
| 13A9v3 | 4.97 | 4.79 | 3.85 | 3.15 |
| 13A9v4 | 3.93 | 3.69 | 2.72 | 2.40 |
| 13A9v5 | 4.27 | 5.52 | 3.68 | 3.17 |
| 13A9v6 | 3.94 | 3.77 | 2.80 | 2.45 |
| 15F11 | 2.21 | 1.31 | 0.79 | 2.28 |
| 15F11v1 | 12.80 | 5.96 | 6.52 | 16.10 |
| 15F11v2 | 5.05 | 2.74 | 3.17 | 6.71 |
| 15F11v3 | 12.74 | 5.70 | 5.56 | 14.10 |
| 15F11v4 | 4.75 | 2.58 | 2.58 | 5.72 |
| 15F11v5 | 6.05 | 3.11 | 3.20 | 7.80 |
| 15F11v6 | 5.47 | 2.91 | 2.94 | 6.62 |
| 6E1.1.12 | 1.49 | 3.95 | 3.72 | 2.96 |

Example 12

Anti-Alpha 3 MICAS Antibody Modulation of MIC-NKG2D Pathway in In Vivo Tumor Models This Example describes the effect of anti-MIC (1D5 antibody) modulation in in vitro and in vivo assays.

Introduction

MICA (MHC class I Chain Related Gene A) expression is induced in response to cellular stress and in tumor cells, MICA is induced by DNA damage. MICA binds to the activating receptor NKG2D on CD8+ T and NK cells. NKG2D engagement then induces cytolytic activity in NK cells and costimulates CD8+ T cells. Tumor cells cleave cell surface MICA and the reduced surface MIC expression impairs NKG2D-mediated tumor cell killing Shed MICA may interfere with NKG2D-mediated binding to tumor cells. A proposed hypothesis for the mechanism of action of anti-MIC antibodies is that anti-MIC antibodies prevent shedding, increasing surface expression and recognition by cytotoxic cells Results As described in Example 8, cell shedding assays were performed using various cell lines: MEL-JUSO, HCC1534, and PANC-1. Cells were incubated at 37° C. in medium containing anti-MIC 1D5 antibodies for 24 hours. Subsequently, cell supernatants were harvested and diluted (if needed), analyzed in the relevant ELISA format (MICA or MICB), and quantitated using the corresponding MIC ECD material. Percent shedding inhibition was calculated using the formula: 1-([sMIC] ab-treated cell sub)/([sMIC] untreated cells) where sMIC represented soluble MICA or soluble MICB. EC50 was also determined from these data. Table 17 displays antibody affinity, IC50 and percent maximum inhibition for each cell shedding assay.

TABLE 17

| 1D5 | MICA*008 MEL-JUSO cell shedding assay | MICB*005 HCC1534 cell shedding assay | MICA*002 PANC-1 cell shedding assay | MICA*004 HCC1534 cell shedding assay |
|---|---|---|---|---|
| Affinity (nM) | 0.54 | 2.28 | 0.82 | 0.56 |
| IC50 (mg/mL) | 0.008234 | 0.0293 | 0.02906 | 0.0247 |
| Max inhibition | 81% | 52% | 53% | 70% |

Next, MIC-NKG2D interactions were evaluated using NKG2D-Fc, anti-Fc antibodies, and anti-MIC antibodies. As shown in FIG. 48, blocking antibody 8C5 disrupted NKG2D binding in a dose-dependent manner whereas the 1D5 antibody did not interfere with MIC-NKG2D interactions.

The crystal structure of the 1D5 Fab bound to the MICA*008 α3 domain indicated that 1D5 binds to the "front face" of the α3 domain containing the C-terminal beta strand (FIG. 49A). Addionally, the epitope of 1D5, defined as MICA residues within 4.5 Å of the Fab, as well as reported cleavage sites were identified on the surface of the "front face" of the MICA*008 α3 domain (FIG. 49B). Taken together, these findings suggest an overlap in the 1D5 Fab-MICA*008 α3 Domain Complex of the 1D5 Epitope and MICA Cleavage Sites The anti-tumor effect of 1D5 treatment in xenograft tumor models propagated from HCC1534 cells in BALB/c SCID mice was then analyzed. As shown in FIG. 50A, 10 million HCC1534 were used for tumor inoculation in each mouse (n=10 mice/treatment group). Anti-MIC 1D5 IgG2a, Anti-MIC 1D5 IgG1, or anti-gp120 (control) were then administered TIW for four weeks to each group. Subsequently, PK samples were collected every 7 days for 21 days. Tumor volume by caliper measurement indicated prevention efficacy with anti-MIC 1D5 IgG2a treatment, but not 1D5 IgG1, suggesting antibody effector function is required. (FIG. 50B). Tumors were also harvested on day 7 post inoculation, processed, and stained with antibodies for FACS analysis, indicating that HCC1534 tumor growth inhibition was associated with increased NK cell numbers (FIG. 50C) and increased Granzyme B expression (FIG. 50D)

Figure 51B:
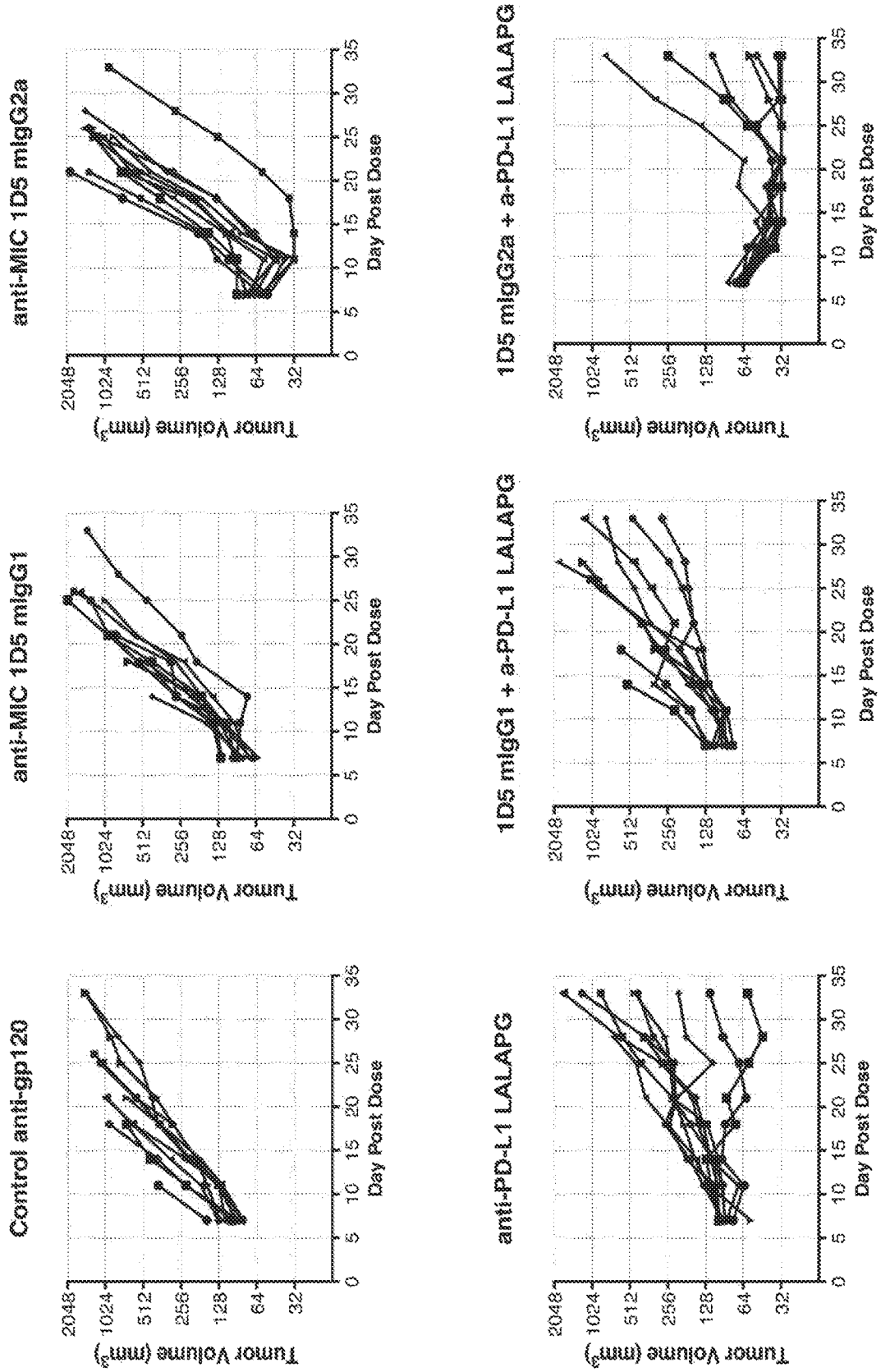

Next, $1 \times 10^4$ B16 cells engineered to express MICA (B16-MICA002) upon Doxicycline (dox) induction were plated per well with 1 ug/mL dox and 5 ug/mL antibody for 24 hours. Cells were then harvested and stained for MICA surface expression. 1D5 treatment was found to stabilize MICA surface expression in B16-MICA002 in a dox-dependent manner (FIG. 51A). The anti-tumor effect of 1D5 treatment in xenograft tumor models propagated from B16-MICA002 cells was then analyzed. As shown in FIG. 51B, tumor volume by caliper measurement indicated modest prevention efficacy with anti-MIC 1D5 IgG2a treatment and anti-PD-L1 when administered as single agents. However, a robust additive effect in the group receiving both anti-PDL1 and anti-MIC 1D5 IgG2a was observed. Tumor growth was not impacted by treatment with anti-MIC 1D5 IgG1, suggesting that ADCC may be an important mechanism.

CONCLUSION

Anti-MIC antibody,1D5, displayed cleavage inhibition in vitro, demonostrated broad activity against multiple alleles, and did not interfere with MIC-NKG2D interactions. Additonally, the crystal structure of the 1D5-MICA*008 complex revealed overlap of the 1D5 epitope with MICA cleavage sites.

Anti-tumor efficacy was observed with preventative antibody dosing of 1D5 in a mouse xenograft model, HCC1534, and was associated with an increased number of NK cells and increased granzyme B expression in NK cells.

Finally, in a B16.F10 MICA002 inducible over-expression model, 1D5 had both a single agent effect and robust additive effect when combined with anti-PDL1.

Example 13

Comparison of Epitopes Using Different Mapping Methods

This Example summarizes the epitopes determined for anti-MIC antibodies 1D5, 13A9, and 6E1.1.12 using various epitope mapping methods as shown in Table 18.

TABLE 18

Epitope Comparison.

| Antibody | Glyco-Engineering | Alanine Scanning | X-Ray Crystallography | FPOP |
|---|---|---|---|---|
| 1D5 | G243: R240, Q241, D242, V244, S245, R279, T281; R279: R240, Q241, D242, G243, E276, E277, N278, T281 | R240, Q241, V244, S245, H248, D249, T250, E276, R279, Y283, E285, S287, H290, T292 | R240, Q241, D242, G243, V244, S245, L246, S247, D249, T250, R279, Y283, H290, S291, T292, P294 | N234, I235, I236, L237, T238, W239, R240; V268, A269, T270, R271, I272, C273, R274, G275, E276, E277, Q278, R279, F280 |
| 13A9 | 'back & top': V205, P206, M208, T212, G219, T222, T224, R226, S228, Y231, P232, Q241, D242, G243, T250, D255-G262, Y264, Q265, W267, | N.D | R240, D242, G243, V244, E277, Q278, R279, F280, T281, Y283, E285, G288, N289, H290, S291, T292, P294, V295, P296, S297 | N.D |

TABLE 18-continued

Epitope Comparison.

| Antibody | Glyco-Engineering | Alanine Scanning | X-Ray Crystallography | FPOP |
|---|---|---|---|---|
| | R271, G275, E277, R279, G288, N289, H290 | | | |
| 6E1.1.12 | 'back and top': V205, P206, M208, T212, G219, T222, T224, R226, S228, Y231, P232, Q241, D242, T250, D255-G262, Y264, Q265, W267, R271, G275, E277, G288, N289, H290 | N.D | T224, R226, R233, W253, G254, D255, V256, L257, P258, D259, G260, N261, Q265, T266, W267 | N.D |
| 15F11 | G243: R240, Q241, D242, V244, S245, R279, T281; R279: R240, Q241, D242, G243, E276, E277, N278, T281 | N.D | N.D | N.D |
| 18G3 | G243: R240, Q241, D242, V244, S245, R279, T281 | N.D | N.D | N.D |
| 12H10 | G243: R240, Q241, D242, V244, S245, R279, T281 | N.D | N.D | N.D |

Note:
N.D. = not determined.

Example 14

MICA Shedding Inhibition and Interference Using Anti-MICAS Humanized Variants

This Example describes the testing of humanized anti-MIC antibodies for MIC shedding inhibition and interference in HEK293 and CHO cell lines.

Results

For variant samples, hIgG2a HEK293-derived material was used, which contained residual soluble MIC (sMICA at greater quantities than sMICB). This interference caused an over-recovery of sMIC in the samples, leading to decreased apparent shedding inhibition (Table 19). The sMIC co-diluted out with the antibody; therefore, less antibody showed less interference. Due to varying concentrations of antibodies, the amount of sMIC in samples varied with each antibody. Complicating the interference, there may have been artificial under-recovery of sMIC due to antibody interference that was observed regardless of purification method (CHO vs HEK293). As a result, reported data is from 0.625 ug/mL of MICA samples and 2.5 ug/mL for MICB, both for inhibition and interference; at these respective concentrations, many samples diluted out the majority of positive sMIC-related interference, but antibody effect was still observed. It should be noted that the observed antibody effect may not have reflected maximum potential inhibition.

Previous data have shown there to be some negative signal interference from antibodies on HCC1534 (MICA*004 and MICB*005) and much less on MEL-JUSO (MICA*008). Due to these two types of conflicting signal interference, some positive signal (MIC) and negative signal (Ab) interference on HCC1534 MICA*004, a predominantly positive signal (MIC) interference on MEL-JUSO MICA*008, and a predominantly negative signal (Ab) interference on HCC1534 MICB*005 were expected. For control antibodies, mIgG2a CHO-derived material was used; thus, the only significant interference observed was negative, possibly leading to more potent results than the true level of biological activity. Due to assay variation, absolute amounts of sMIC may have varied between the inhibition and interference assay.

There was insufficient sample in the following antibodies: 1D5v2, 1D5v15, 1D5v28, 13A9v1, and 15F11v1. Therefore, a previous antibody preparation was used. Due to automation errors, the accuracy of the aforementioned samples could not be guaranteed. 1D5v14 was able to be re-diluted, but the new sample preparation was slightly lower in concentration than intended. The original and possibly inaccurate sample dilution of 1D5v14 was also analyzed (Table 19).

Some interference samples were missing due to cold wells on an assay plate from clogged washer pins, notably HCC1534 A004: 13A9 v1; MEL-JUSO A008: 1D5v10, and 13A9v1; and HCC1534 B005: 1D5v3, 1D5v22, and 15F11v3. Thus, a 'ND' value was assigned since results could not be determined for each of these conditions (Table 19).

As shown in Table 20, positive cutoff was defined as the percent (%) inhibition determined by 3 times the standard deviation of all of the non-treated samples on the relevant plate. The average was determined using 3 assay plates.

MICA*004 Shedding Inhibition in HCC1534 Cells

All 1D5 variants (except for 1D5v28, which may have been compromised) showed inhibition activity approximately equivalent to the non-variant antibody (~50-60%), with some variance, and only minor interference (Table 19). In general, 13A9 variants showed minimal inhibition. 15F11 variants showed activity approximately similar to non-variant antibody (~50%) except for potentially compromised sample 15F11v1, and 15F11v4 and 15F11v6, which showed significant positive sMIC interference, which would have masked activity.

MICA*008 Shedding Inhibition in MEL-JUSO Cells

MEL-JUSO typically showed very little antibody interference with CHO samples. Thus, most interference was expected to be attributed to sMIC in these samples, and indeed the sMIC-increased effect is greater than on other cell lines.

All 1D5 variants, except for 1D5v28, which may have been compromised, showed inhibition activity approximately equivalent to the non-variant antibody (~60-70%), with some variance, and almost no antibody inhibition interference (but much more sMIC interference from the HEK293 material vs other cell lines and alleles) (Table 19). In general, 13A9 variants showed little to no inhibition. 15F11 variants showed activity approximately similar to non-variant antibody (~60%) except for potentially compromised sample 15F11v1, and 15F11v4 and 15F11v6, which showed significant positive sMIC interference, which would have masked activity.

MICB*005 Shedding Inhibition in HCC1534 Cells

Due to the higher-than expected variation on the interference plates, the positive cutoff was higher than the inhibition cutoff. All 1D5 variants (except for 1D5v28, which might have been compromised) showed some inhibition activity (~40-50%) approximately 10% lower than the non-variant antibody(~60%), with some variance, and varying degrees of negative signal (Ab) interference, likely attributed to the higher than expected variation on that assay (Table 19). In general, 13A9 variants showed significant inhibition approximately equivalent to non-variant 13A9, except for 13A9v1, which was possibly compromised. 15F11 variants showed activity approximately similar to non-variant antibody and 1D5 (~40%) except for potentially compromised sample 15F11v1, and 15F11v4 and 15F11v6, which showed significant positive sMIC interference, which would have masked activity.

TABLE 19

Percent Inhibition and Reduction due to Interference

| Clone | Cell Line | Fc | Conc. (mg/ml) | % Monomer | HCC1534 (MICA*004) % Inhibition | HCC1534 (MICA*004) % reduction due to interference | MEL-JUSO (MICA*008) % Inhibition | MEL-JUSO (MICA*008) % reduction due to interference | HCC1534 (MICA*005) % Inhibition | HCC1534 (MICA*005) % reduction due to interference |
|---|---|---|---|---|---|---|---|---|---|---|
| 13A9 | 293 | Hu IgG1 | 0.45 | 67.52 | 21% | 0% | −7% | −33% | 61% | 28% |
| 15F11 | 293 | Hu IgG1 | 1.06 | 96.2 | 54% | 13% | 50% | −8% | 43% | 16% |
| 1D5v1 | 293 | Hu IgG1 | 0.92 | 96.59 | 54% | 5% | 52% | −20% | 41% | 3% |
| 1D5v2 | 293 | Hu IgG1 | 0.83 | 96.62 | ^38% | ^15% | ^33% | ^7% | ^26% | ^15% |
| 1D5v3 | 293 | Hu IgG1 | 0.69 | 95.07 | 56% | 6% | 50% | −16% | 38% | ND |
| 1D5v4 | 293 | Hu IgG1 | 0.57 | 95.39 | 46% | 1% | 43% | −22% | 34% | 15% |
| 1D5v5 | 293 | Hu IgG1 | 0.26 | 95.56 | 39% | −39% | 36% | −92% | 32% | −5% |
| 1D5v6 | 293 | Hu IgG1 | 0.22 | 93.48 | 47% | −8% | 51% | −47% | 37% | 4% |
| 1D5v7 | 293 | Hu IgG1 | 0.31 | 92.59 | 48% | −2% | 51% | −33% | 42% | 9% |
| 1D5v8 | 293 | Hu IgG1 | 0.88 | 91.42 | 42% | 0% | 52% | −22% | 35% | 20% |
| 1D5v9 | 293 | Hu IgG1 | 0.96 | 98.35 | 53% | 7% | 49% | −8% | 41% | 9% |
| 1D5v10 | 293 | Hu IgG1 | 1.67 | 96.58 | 62% | 7% | 58% | NA | 43% | 17% |
| 1D5v11 | 293 | Hu IgG1 | 0.83 | 96.63 | 52% | 1% | 56% | −14% | 36% | 8% |
| 1D5v12 | 293 | Hu IgG1 | 0.51 | 96.59 | 50% | −5% | 44% | −18% | 27% | 1% |
| 1D5v13 | 293 | Hu IgG1 | 0.49 | 95.48 | 49% | −4% | 51% | −17% | 43% | 1% |
| 1D5v14 | 293 | Hu IgG1 | 0.46 | 96.07 | ^49% | ^8% | ^63% | ^−17% | ^43% | ^11% |
| 1D5v14 second data point | 293 | Hu IgG1 | 0.46 | 96.07 | ^^55% | ^^7% | ^^58% | ^^−3% | ^^31% | ^^23% |

TABLE 19-continued

Percent Inhibition and Reduction due to Interference

| Clone | Cell Line | Fc | Conc. (mg/ml) | % Monomer | HCC1534 (MICA*004) % Inhibition | HCC1534 (MICA*004) % reduction due to interference | MEL-JUSO (MICA*008) % Inhibition | MEL-JUSO (MICA*008) % reduction due to interference | HCC1534 (MICA*005) % Inhibition | HCC1534 (MICA*005) % reduction due to interference |
|---|---|---|---|---|---|---|---|---|---|---|
| 1D5v15 | 293 | Hu IgG1 | 1.29 | 96.16 | ^45% | ^14% | ^48% | ^13% | ^39% | ^13% |
| 1D5v16 | 293 | Hu IgG1 | 0.81 | 94.66 | 50% | −2% | 51% | −20% | 51% | 24% |
| 1D5v17 | 293 | Hu IgG1 | 2.02 | 98.79 | 52% | 12% | 68% | 2% | 50% | 21% |
| 1D5v18 | 293 | Hu IgG1 | 0.83 | 99.74 | 47% | 6% | 64% | −23% | 41% | 22% |
| 1D5v19 | 293 | Hu IgG1 | 0.04 | 98.81 | 44% | 4% | 57% | −27% | 40% | 34% |
| 1D5v20 | 293 | Hu IgG1 | 0.92 | 95.58 | 46% | 6% | 56% | −20% | 39% | 28% |
| 1D5v21 | 293 | Hu IgG1 | 2.38 | 98.89 | 55% | 16% | 62% | 13% | 25% | 28% |
| 1D5v22 | 293 | Hu IgG1 | 1.77 | 97.68 | 46% | 7% | 57% | 10% | 34% | *** |
| 1D5v23 | 293 | Hu IgG1 | 0.76 | 94.35 | 50% | 13% | 63% | −7% | 38% | 31% |
| 1D5v24 | 293 | Hu IgG1 | 2.48 | 89.01 | 50% | 20% | 65% | 17% | 43% | 28% |
| 1D5v25 | 293 | Hu IgG1 | 0.78 | 94.04 | 46% | 8% | 62% | −15% | 28% | 30% |
| 1D5v26 | 293 | Hu IgG1 | 0.79 | 92.31 | 37% | 0% | 50% | −19% | 42% | 33% |
| 1D5v27 | 293 | Hu IgG1 | 4.1 | ND | 53% | 11% | 69% | 3% | −8% | 13% |
| 1D5v28 | 293 | Hu IgG1 | 4.9 | ND | ^3% | ^−2% | ^0% | ^9% | ^36% | ^30% |
| 1D5v29 | 293 | Hu IgG1 | 2.4 | ND | 40% | 12% | 57% | −18% | −8% | 23% |
| 13A9v1 | 293 | Hu IgG1 | 3.08 | 97.25 | ^12% | ND | ^10% | ND | ^43% | ^36% |
| 13A9v2 | 293 | Hu IgG1 | 1.65 | 90.96 | 10% | 0% | 12% | −7% | 60% | 33% |
| 13A9v3 | 293 | Hu IgG1 | 0.83 | 99.51 | 25% | 1% | 2% | −19% | 42% | 0% |
| 13A9v4 | 293 | Hu IgG1 | 0.2 | 99.12 | −29% | −85% | −31% | −199% | 63% | 35% |
| 13A9v5 | 293 | Hu IgG1 | 1.41 | 91.8 | 9% | 3% | 4% | 0% | 63% | 37% |
| 13A9v6 | 293 | Hu IgG1 | 1.62 | 99.25 | 16% | 4% | 8% | −4% | 6% | 16% |
| 15F11v1 | 293 | Hu IgG1 | 2.18 | 98.07 | ^3% | ^3% | ^4% | ^7% | ^43% | ^26% |
| 15F11v2 | 293 | Hu IgG1 | 1.74 | 95.51 | 43% | 7% | 62% | −15% | 35% | 20% |
| 15F11v3 | 293 | Hu IgG1 | 3.97 | 99.42 | 39% | 13% | 50% | 0% | −49% | ND |
| 15F11v4 | 293 | Hu IgG1 | 0.18 | 98.47 | −34% | −91% | −19% | −383% | 44% | 9% |
| 15F11v5 | 293 | Hu IgG1 | 2.18 | 96.59 | 46% | 10% | 62% | −6% | −35% | 126% |
| 15F11v6 | 293 | Hu IgG1 | 0.2 | 98.55 | −14% | −91% | −8% | −300% | 59% | 33% |
| 1D5 | 293 | Hu IgG1 | 2.65 | 96.96 | 52% | 25% | 69% | 6% | 49% | 22% |
| 6E1 | 293 | Hu IgG1 | 0.8 | 98.65 | 34% | 13% | 31% | −9% | 58% | 34% |
| 1D5 | CHO | m IgG2a | 6.3 | ND | 59% | 34% | 74% | 18% | 76% | 38% |
| 13A9 | CHO | m IgG2a | 6 | ND | 34% | 32% | 29% | 9% | 60% | 24% |

TABLE 19-continued

Percent Inhibition and Reduction due to Interference

| Clone | Cell Line | Fc | Conc. (mg/ml) | % Monomer | HCC1534 (MICA*004) | | MEL-JUSO (MICA*008) | | HCC1534 (MICA*005) | |
|---|---|---|---|---|---|---|---|---|---|---|
| | | | | | % Inhibition | % reduction due to interference | % Inhibition | % reduction due to interference | % Inhibition | % reduction due to interference |
| 15F11 | CHO | m IgG2a | 4 | ND | 60% | 28% | 69% | 9% | 57% | 18% |
| 6E1 | CHO | m IgG2a | 4.3 | ND | 40% | 20% | 36% | 9% | 47% | 13% |

Note:
ND = not determined.
^= Out of sample on rerun; robot normalized sample loaded from an earlier run and may refer to correct antibody dilution, incorrect antibody dilution, or no antibody added.
^^= Diluted to slightly lower than intended concentration due to low volume.
Bolded and labeled "1D5v14 second data point" is a second data point collected for 1D5v14.

TABLE 20

Inhibtion and Interference Cutoff Values.

| | Positive Cutoff HCC1534 MICA*004 | Positive Cutoff HCC1534 MICB*005 |
|---|---|---|
| Inhibition Avg (3 plates) | 20% | 21% |
| Interference Avg (3 plates) | 19% | 32% |

Note:
Positive cutoff was defined as inhibition within 3 standard devations below non-treated samples.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

SEQUENCES

Hypervariable Region Sequences

| Ab | HVR H1 | HVR H2 | HVR H3 | HVR L1 | HVR L2 | HVR L3 |
|---|---|---|---|---|---|---|
| 3C9.10 | GSGVN (SEQ ID NO: 1) | MIWGDGNTDYNSALKS (SEQ ID NO: 2) | GAYYGKRWYFDV (SEQ ID NO: 3) | SASQGISNYLN (SEQ ID NO: 4) | YTSSLHS (SEQ ID NO: 5) | QQYSKLPPT (SEQ ID NO: 6) |
| 7D4.6 | SDYAWN (SEQ ID NO: 17) | YINYSGTTNYNPSLKS (SEQ ID NO: 18) | YRYDGAWFPY (SEQ ID NO: 19) | RASGNIHNYLA (SEQ ID NO: 20) | NAIMLAD (SEQ ID NO: 21) | QHFWSFPLT (SEQ ID NO: 22) |
| 6F8.7 | NDYYWN (SEQ ID NO: 33) | FISFGGSNNYNPSLKN (SEQ ID NO: 34) | YDGRGAWFAY (SEQ ID NO: 35) | RASGNIHNYLA (SEQ ID NO: 36) | DAITLAD (SEQ ID NO: 37) | QHFWSFPLT (SEQ ID NO: 38) |
| 32D2 | TFGMN (SEQ ID NO: 49) | YINSGSNTIYYADTVKG (SEQ ID NO: 50) | WEPVTGGFSY (SEQ ID NO: 51) | TASSSISSSYLH (SEQ ID NO: 52) | TTSNLAS (SEQ ID NO: 53) | HQHHRSPFT (SEQ ID NO: 54) |
| 3E11 | KYNIY (SEQ ID NO: 65) | YIDPYTGGTISNQKFTG (SEQ ID NO: 66) | PGSYWYFGV (SEQ ID NO: 67) | RSSQSIVYTNGNTNLE (SEQ ID NO: 68) | KVSNRFS (SEQ ID NO: 69) | FQASYVPFT (SEQ ID NO: 70) |
| 9C9.5.6 | GQGVN (SEQ ID NO: 81) | MIWGDGSTDYNSALKS (SEQ ID NO: 82) | GAHYGKRWYFDV (SEQ ID NO: 83) | SASQNINNYLN (SEQ ID NO: 84) | YTSSLPS (SEQ ID NO: 85) | QQYSKLPPT (SEQ ID NO: 86) |

| SEQUENCES | | | | | |
|---|---|---|---|---|---|
| 1E6.1.3 | GSGVN (SEQ ID NO: 97) | MIWGDGNTDYNSALKS (SEQ ID NO: 98) | GAHYGKRWYFDV (SEQ ID NO: 99) | SASQGINNYLN (SEQ ID NO: 100) | YTSTLPS (SEQ ID NO: 101) | QQYSKLPPT (SEQ ID NO: 102) |
| 7A3.1.9 | GSGVN (SEQ ID NO: 113) | MIWGDGNTDYNSALKS (SEQ ID NO: 114) | GAHYGKRWYFDV (SEQ ID NO: 115) | SASQGINNYLN (SEQ ID NO: 116) | YTSSLPS (SEQ ID NO: 117) | QQYSKLPPT (SEQ ID NO: 118) |
| 6E12.5 | DYYMY (SEQ ID NO: 129) | TISDGITYTYYSDSVRG (SEQ ID NO: 130) | GGGSTARGALDF (SEQ ID NO: 131) | HASQNIHVWLS (SEQ ID NO: 132) | GASHLHT (SEQ ID NO: 133) | LQGQSYPLT (SEQ ID NO: 134) |
| 20G11 | TFGIH (SEQ ID NO: 145) | YISYDSRTIYYADTVKG (SEQ ID NO: 146) | WAYEGGVNYFDN (SEQ ID NO: 147) | TATSGVSSSYLH (SEQ ID NO: 148) | SSSNLAS (SEQ ID NO: 149) | HQFHRSPLT (SEQ ID NO: 150) |
| 6E1.1.12 | DNYIS (SEQ ID NO: 161) | WIYAGTGGSSYNQKFRD (SEQ ID NO: 162) | HDYYGTSGAWFAY (SEQ ID NO: 163) | RSSQHIVHSNENTYLE (SEQ ID NO: 164) | KVSNRFS (SEQ ID NO: 165) | FQGSHVPWT (SEQ ID NO: 166) |
| 2E5.2.3 | DNYIS (SEQ ID NO: 177) | WIYAGTGGTSYNQKFTA (SEQ ID NO: 178) | HDYYGTSGAWFAY (SEQ ID NO: 179) | RSSQNIVHINGNTYLE (SEQ ID NO: 180) | KVSNRFS (SEQ ID NO: 181) | FQGSHVPWT (SEQ ID NO: 182) |

Framework Sequences

Light Chain Framework Sequences

| Ab | FR-L1 | FR-L2 | FR-L3 | FR-L4 |
|---|---|---|---|---|
| 3C9.10 | DIQMTQTTSSLSASLGDRVTISC (SEQ ID: 7) | WYQQKPDGTVKLLIY (SEQ ID: 8) | GVPSRFSGSGSGTDYS LTISNLEPEDIATYYC (SEQ ID: 9) | FGGGTKVEIK (SEQ ID: 10) |
| 7D4.6 | DIQMTQSPASLSASVGETVTITC (SEQ ID: 23) | WYQQKQGKSPQLLVY (SEQ ID: 24) | GVPSRFSASGSGTQYS LKINSLQPEDFGSYYC (SEQ ID: 25) | FGAGTKVEIK (SEQ ID: 26) |
| 6F8.7 | DIQMTQSPASLSASVGETVTITC (SEQ ID: 39) | WYQQKQGKSPQLLVY (SEQ ID: 40) | GVPSRFSGSGSGTQYS LKINSLQPEDFGNYYC (SEQ ID: 41) | FGAGTKVEIK (SEQ ID: 42) |
| 32D2 | QIVLTQSPAFKSSSLGERVTMTC (SEQ ID: 55) | WYQQKPGSSPKLWIY (SEQ ID: 56) | GVPARFSGSGSGTSYS LTISTMEAEDAATYYC (SEQ ID: 57) | FGSGTKVEIK (SEQ ID: 58) |
| 3E11 | DILMTQTPLSLPVSLGDQASISC (SEQ ID: 71) | WYLQKPGQSPKLLIY (SEQ ID: 72) | GVPDRFSGSGSGTDFT LKISRVEAEDLGVYYC (SEQ ID: 73) | FGSGTKVEIK (SEQ ID: 74) |
| 9C9.5.6 | DIQMTQTTSSLSASLGDRVTISC (SEQ ID: 87) | WYQQKPHGTVKLLIY (SEQ ID: 88) | GVPSRFSGSGSGTDYS LTISNLEPEDIASYYC (SEQ ID: 89) | FGGGTKVEIK (SEQ ID: 90) |
| 1E6.1.3 | DIQMTQTTFSLSASLGDRVTISC (SEQ ID: 103) | WYQQRPDGTVKLLIY (SEQ ID: 104) | GVPSRFSGSGSGTDYS LTISNLEPEDIASYYC (SEQ ID: 105) | FGGGTKVEIK (SEQ ID: 106) |
| 7A3.1.9 | DIQMTQTTSSLSASLGDRVTISC (SEQ ID: 119) | WYQQKPDGTVKLLIY (SEQ ID: 120) | GVPSRFSGSGSGTDYS LTISNLEPEDIATYYC (SEQ ID: 121) | FGGGTKVEIK (SEQ ID: 122) |
| 6E12.5 | DIQMNQSPSSLSASLGDTITITC (SEQ ID: 135) | WYQQKPGNIPKLLIY (SEQ ID: 136) | GVPSRFSGRGSGTGFT LTISSLQPEDIATYYC (SEQ ID: 137) | FGSGTKVEIK (SEQ ID: 138) |
| 20G11 | QIVLTQSPAIMSASLGERVTMTC (SEQ ID: 151) | WYQQKPGSSPKLWIY (SEQ ID: 152) | GVPARFSGSGSGTSYS LTIGSMEAEDAATYYC (SEQ ID: 153) | FGTGTKVEIK (SEQ ID: 154) |
| 6E1.1.12 | DVLMTQTPLSLPVSLGDQASISC (SEQ ID: 167) | WYLQKPGQSPKLLIY (SEQ ID: 168) | GVPDRFSGSGSGTDFT LKISRVEAEDLGVYYC (SEQ ID: 169) | FGGGTKVEIK (SEQ ID: 170) |

| | | SEQUENCES | | |
|---|---|---|---|---|
| 2E5.2.3 | DVLMTQTPLSLPVSLGDQASLSC (SEQ ID: 183) | WYLQKPGQSPKLLIY (SEQ ID: 184) | GVPDRFSGSGSGTDFT LKISRVEAEDLGVYYC (SEQ ID: 185) | FGGGTKVEIK (SEQ ID: 186) |

| Heavy Chain Framework Sequences | | | | |
|---|---|---|---|---|
| Ab | FR-H1 | FR-H2 | FR-H3 | FR-H4 |
| 3C9.10 | QVQLKESGPGLVAPSQSLSITC TVSGFSLT (SEQ ID: 11) | WVRQPPGKGLEWLG (SEQ ID: 12) | RLSISKDNSKSQIFLKMN SLQTDDTARYYCAR (SEQ ID: 13) | WGAGTTVTVSS (SEQ ID: 14) |
| 7D4.6 | DVQLQESGPGLVKPSQSLSLTC TVTGYSIT (SEQ ID: 27) | WIRQFPRNKLEWMG (SEQ ID: 28) | RISITRDTSKNQFFLQLI SVTTEDTATYYCSY (SEQ ID: 29) | WGQGTLVTVSA (SEQ ID: 30) |
| 6F8.7 | DVQLQGSGPGLVKPSQSLSLTC SVTGYSIT (SEQ ID: 43) | WIRQFPGNKLEWMG (SEQ ID: 44) | RISITRDTSKNQFFLKLS SVTTEDTATYYCAR (SEQ ID: 45) | WAQGTLVTVSA (SEQ ID: 46) |
| 32D2 | DVHLVESGGGLVQPGGSRKLS CAASGFTFN (SEQ ID: 59) | WVRQAPEKGLEWVA (SEQ ID: 60) | RFTISRDNPKNTLFLQMT SLRSEDTAMYYCTR (SEQ ID: 61) | WGQGTLVTVSA (SEQ ID: 62) |
| 3E11 | EIQLQQSGPELVKPGASVKVSC TASGYAFT (SEQ ID: 75) | WVKQSHGKSLEWIG (SEQ ID: 76) | RATLTVDKSSSTAYLHLN SLTSEDSAVYYCAR (SEQ ID: 77) | WGAGTTVTVSS (SEQ ID: 78) |
| 9C9.5.6 | QVQLKESGPGLVAPSQSLSITC TVSGFSLN (SEQ ID: 91) | WVRQPPGKGLEWLG (SEQ ID: 92) | RLSISKDNSRSQVFLKMN SLQTDDTARYYCAR (SEQ ID: 93) | WGAGTTVTVSS (SEQ ID: 94) |
| 1E6.1.3 | QVQLKESGPGLVAPSQSLSITC TVSGFSLT (SEQ ID: 107) | WVRQPPGQGLEWLG (SEQ ID: 108) | RLSISKDNSKSQVFLKMN SLQTDDTARYYCAR (SEQ ID: 109) | WGAGTTVTVSS (SEQ ID: 110) |
| 7A3.1.9 | QVQLKESGPGLVAPSQSLSITC TVSGFALT (SEQ ID: 123) | WVRQPPGKGLEWLG (SEQ ID: 124) | RLSISKDNSKSQIFLKMN SLQTDDTARYYCAR (SEQ ID: 125) | WGAGTTVTVSS (SEQ ID: 126) |
| 6E12.5 | EVQLVESGGGLVKPGGSLKLS CAASGFTFS (SEQ ID: 139) | WVRQTPEKRLEWVA (SEQ ID: 140) | RFTISRDNAENTLYLQMS SLKSEDTAMYYCSK (SEQ ID: 141) | WGQGTSVTVSS (SEQ ID: 142) |
| 20G11 | DVQLVESGGGLVQPGGSRKLS CAASGFTFS (SEQ ID: 155) | WVRQAPEKGLEWVA (SEQ ID: 156) | RFTISRDNPKNTLFLQMT SLRSEDTAMYYCAR (SEQ ID: 157) | WGQGTTLTVSS (SEQ ID: 158) |
| 6E1.1.12 | QGQMQQSGAELVKPGASVKL SCKTSGFTFS (SEQ ID: 171) | WLKQKPGQSLEWIA (SEQ ID: 172) | KAQLTVDTSSRTAYMQLS SLTTEDSAIYYCAR (SEQ ID: 173) | WGRGTLVTVSA (SEQ ID: 174) |
| 2E5.2.3 | QGQMQQSGAELVKPGASVKL SCKTSGFTFS (SEQ ID: 187) | WLKQKPGQSLEWIA (SEQ ID: 188) | KAQLTVDTSSTAYMQF SLTTEDSAIYYCARS (SEQ ID: 189) | WGQGTLVTVSA (SEQ ID: 190) |

| Variable Domain Sequences | | |
|---|---|---|
| Ab | VH | VL |
| 3C9.10 | QVQLKESGPGLVAPSQSLSITCTVSGFS LTGSGVNWVRQPPGKGLEWLGMIWDGN TDYNSALKSRLSISKDNSKSQIFLKMNS LQTDDTARYYCARGAYYGKRWYFDVWGA GTTVTVSS (SEQ ID NO: 15) | DIQMTQTTSSLSASLGDRVTISCSASQG ISNYLNWYQQKPDGTVKLLIYYTSSLHS GVPSRFSGSGSGTDYSLTISNLEPEDIA TYYCQQYSKLPPTFGGGTKVEIK (SEQ ID NO: 16) |

| SEQUENCES | | | |
|---|---|---|---|
| 7D4.6 | DVQLQESGPGLVKPSQSLSLTCTVTGYS ITSDYAWNWIRQFPRNKLEWMGYINYSG TTNYNPSLKSRISITRDTSKNQFFLQLI SVTTEDTATYYCSYYRYDGAWFPYWGQG TLVTVSA (SEQ ID NO: 31) | | DIQMTQSPASLSASVGETVTITCRASGN IHNYLAWYQQKGKSPQLLVYNAIMLAD GVPSRFSASGSGTQYSLKINSLQPEDFG SYYCQHFWSFPLTFGAGTKVEIK (SEQ ID NO: 32) |
| 6F8.7 | DVQLQGSGPGLVKPSQSLSLTCSVTGYS ITNDYYWNWIRQFPGNKLEWMGFISFGG SNNYNPSLKNRISITRDTSKNQFFLKLS SVTTEDTATYYCARYDGRGAWFAYWAQG TLVTVSA (SEQ ID NO: 47) | | DIQMTQSPASLSASVGETVTITCRASGN IHNYLAWYQQKGKSPQLLVYDAITLAD GVPSRFSGSGSGTQYSLKINSLQPEDFG NYYCQHFWSFPLTFGAGTKVEIK (SEQ ID NO: 48) |
| 32D2 | DVHLVESGGGLVQPGGSRKLSCAASGFT FNTFGMNWVRQAPEKGLEWVAYINSGSN TIYYADTVKGRFTISRDNPKNTLFLQMT SLRSEDTAMYYCTRWEPVTGGFSYWGQG TLVTVSA (SEQ ID NO: 63) | | QIVLTQSPAFKSSSLGERVTMTCTASSS ISSSYLHWYQQKPGSSPKLWIYTTSNLA SGVPARFSGSGSGTSYSLTISTMEAEDA ATYYCHQHRSPFTFGSGTKVEIK (SEQ ID NO: 64) |
| 3E11 | EIQLQQSGPELVKPGASVKVSCTASGYA FTKYNIYWVKQSHGKSLEWIGYIDPYTG GTISNQKFTGRATLTVDKSSSTAYLHLN SLTSEDSAVYYCARPGSYWYFGVWGAGT TVTVSS (SEQ ID NO: 79) | | DILMTQTPLSLPVSLGDQASISCRSSQS IVIYTNGNTNLEWYLQKPGQSPKLLIYK SNRFSGVPDRFSGSGSGTDFTLKISRVE AEDLGVYYCFQASYVPFTFGSGTKVEIK (SEQ ID NO: 80) |
| 9C9.5.6 | QVQLKESGPGLVAPSQSLSITCTVSGFS LNGQGVNWVRQPPGKGLEWLGMIWDGS TDYNSALKSRLSISKDNSRSQVFLKMNS LQTDDTARYYCARGAHYGKRWYFDVWGA GTTVTVSS (SEQ ID NO: 95) | | DIQMTQTTSSLSASLGDRVTISCSASQN INNYLNWYQQKPHGTVKLLIYYTSSLPS GVPSRFSGSGSGTDYSLTISNLEPEDIA SYYCQQYSKLPPTFGGGTKVEIK (SEQ ID NO: 96) |
| 1E6.1.3 | QVQLKESGPGLVAPSQSLSITCTVSGFS LTGSGVNWVRQPPGQGLEWLGMIWDGN TDYNSALKSRLSISKDNSKSQVFLKMNS LQTDDTARYYCARGAHYGKRWYFDVWGA GTTVTVSS (SEQ ID NO: 111) | | DIQMTQTTFSLSASLGDRVTISCSASQG INNYLNWYQQRPDGTVKLLIYYTSTLPS GVPSRFSGSGSGTDYSLTISNLEPEDIA SYYCQQYSKLPPTFGGGTKVEIK (SEQ ID NO: 112) |
| 7A3.1.9 | QVQLKESGPGLVAPSQSLSITCTVSGFA LTGSGVNWVRQPPGKGLEWLGMIWDGN TDYNSALKSRLSISKDNSKSQIFLKMNS LQTDDTARYYCARGAHYGKRWYFDVWGA GTTVTVSS (SEQ ID NO: 127) | | DIQMTQTTSSLSASLGDRVTISCSASQG INNYLNWYQQKPDGTVKLLIYYTSSLPS GVPSRFSGSGSGTDYSLTISNLEPEDIA TYYCQQYSKLPPTFGGGTKVEIK (SEQ ID NO: 128) |
| 6E12.5 | EVQLVESGGGLVKPGGSLKLSCAASGFT FSDYYMYWVRQTPEKRLEWVATISDGIT YTYYPDSVRGRFTISRDNAENTLYLQMS SLKSEDTAMYYCSKGGGSTARGALDFWG QGTSVTVSS (SEQ ID NO: 143) | | DIQMNQSPSSLSASLGDTITITCHASQN IHVWLSWYQQKPGNIPKLLIYGASHLHT GVPSRFSGRGSGTGFTLTISSLQPEDIA TYYCLQGQSYPLTFGSGTKVEIK (SEQ ID NO: 144) |
| 6E1.1.12 | QGQMQQSGAELVKPGASVKLSCKTSGFT FSDNYISWLKQPGQSLEWIAWIYAGTG GSSYNQKFRDKAQLTVDTSSRTAYMQLS SLTTEDSAIYYCARHDYYGTSGAWFAYW GRGTLVTVSA (SEQ ID NO: 159) | | DVLMTQTPLSLPVSLGDQASISCRSSQH IVHSNENTYLEWYLQKPGQSPKLLIYKV SNRFSGVPDRFSGSGSGTDFTLKISRVE AEDLGVYYCFQGSHVPWTFGGGTKVEIK (SEQ ID NO: 160) |
| 2E5.2.3 | QGQMQQSGAELVKPGASVKLSCKTSGFT FSDNYISWLKQPGQSLEWIAWIYAGTG GTSYNQKFTAKAQLTVDTSSSTAYMQFS SLTTEDSAIYYCARHDYYGTSGAWFAYW GQGTLVTVSA (SEQ ID NO: 175) | | DVLMTQTPLSLPVSLGDQASLSCRSSQN IVHINGNTYLEWYLQKPGQSPKLLIYKV SNRFSGVPDRFSGSGSGTDFTLKISRVE AEDLGVYYCFQGSHVPWTFGGGTKVEIK (SEQ ID NO: 176) |
| 20G11 | DVQLVESGGGLVQPGGSRKLSCAASGFT FSTFGIHWVRQAPEKGLEWVAYISYDSR TIYYADTVKGRFTISRDNPKNTLFLQMT SLRSEDTAMYYCARWAYEGGVNYFDNWG QGTTLTVSS (SEQ ID NO: 191) | | QIVLTQSPAIMSASLGERVTMTCTATSG VSSSYLHWYQQKPGSSPKLWIYSSSNLA SGVPARFSGSGSGTSYSLTIGSMEAEDA ATYYCHQFHRSPLTFGTGTKVEIK (SEQ ID NO: 192) |

Hypervariable region sequences, heavy chain and light chain framework sequences, and variable domain sequences for humanized variants of 1D5, 13A9, and 15F11 as well as for mouse chimeras 1D5, 13A9, 15F11, 18G3, and 12H10 are shown in the following tables (SEQ ID NO: 209 to SEQ ID NO: 440).

| Hypervariable Region Sequences | | | | | | |
|---|---|---|---|---|---|---|
| Ab | HVR H1 | HVR H2 | HVR H3 | HVR L1 | HVR L2 | HVR L3 |
| 1D5<br>1D5v1<br>1D5v2<br>1D5v3<br>1D5v4<br>1D5v5<br>1D5v6<br>1D5v7<br>1D5v8<br>1D5v9<br>1D5v10<br>1D5v11<br>1D5v12<br>1D5v13<br>1D5v14<br>1D5v15<br>1D5v16<br>1D5v17<br>1D5v18<br>1D5v19<br>1D5v20<br>1D5v21<br>1D5v22<br>1D5v23<br>1D5v24<br>1D5v25<br>1D5v26 | SQNIY<br>(SEQ ID<br>NO: 209) | YIEPYNVVPMYNPKFKG<br>(SEQ ID NO: 210) | SGSSNFDY<br>(SEQ ID<br>NO: 211) | SASSSISSHYLH<br>(SEQ ID NO: 212) | RTSNLASG<br>(SEQ ID<br>NO: 213) | QQGSSLPLT<br>(SEQ ID<br>NO: 214) |
| 1D5v27 | SQNIY<br>(SEQ ID<br>NO: 209) | YIEPYNVVPAYNPKFKG<br>(SEQ ID NO: 215) | SGSSNFDY<br>(SEQ ID<br>NO: 211) | SASSSISSHYLH<br>(SEQ ID NO: 212) | RTSNLASG<br>(SEQ ID<br>NO: 213) | QQGSSLPLT<br>(SEQ ID<br>NO: 214) |
| 1D5v28 | SQNIY<br>(SEQ ID<br>NO: 209) | YIEPYNVVPLYNPKFKG<br>(SEQ ID NO: 216) | SGSSNFDY<br>(SEQ ID<br>NO: 211) | SASSSISSHYLH<br>(SEQ ID NO: 212) | RTSNLASG<br>(SEQ ID<br>NO: 213) | QQGSSLPLT<br>(SEQ ID<br>NO: 214) |
| 1D5v29 | SQNIY<br>(SEQ ID<br>NO: 209) | YIEPYNVVPVYNPKFKG<br>(SEQ ID NO: 217) | SGSSNFDY<br>(SEQ ID<br>NO: 211) | SASSSISSHYLH<br>(SEQ ID NO: 212) | RTSNLASG<br>(SEQ ID<br>NO: 213) | QQGSSLPLT<br>(SEQ ID<br>NO: 214) |
| 13A9<br>13A9v1<br>13A9v2<br>13A9v3<br>13A9v4<br>13A9v5<br>13A9v6 | NYLIE<br>(SEQ ID<br>NO: 218) | AINPGSGATNYNEKFKD<br>(SEQ ID NO: 219) | FLGNYFDN<br>(SEQ ID<br>NO: 220) | RASGNIHSYLA<br>(SEQ ID NO: 221) | YAETLADG<br>(SEQ ID<br>NO: 222) | QQFWTTPYT<br>(SEQ ID<br>NO: 223) |
| 15F11<br>15F11v1<br>15F11v2<br>15F11v3<br>15F11v4<br>15F11v5<br>15F11v6 | SNNIY<br>(SEQ ID<br>NO: 224) | YIDPYIGRIIYNQQFKD<br>(SEQ ID NO: 225) | SGERSNFDY<br>(SEQ ID<br>NO: 226) | SASSSISSNYLH<br>(SEQ ID NO: 227) | RTSNLASG<br>(SEQ ID<br>NO: 228) | QQGGSLPLT<br>(SEQ ID<br>NO: 229) |
| 6E1.1.12 | DNYIS<br>(SEQ ID<br>NO: 230) | WIYAGTGGSSYNQKFRD<br>(SEQ ID NO: 231) | HDYYGTSGA<br>WFAY<br>(SEQ ID<br>NO: 232) | RSSQHIVHSNENTYLE<br>(SEQ ID NO: 233) | KVSNRFS<br>(SEQ ID<br>NO: 234) | FQGSHVPWT<br>(SEQ ID<br>NO: 235) |
| 18G3 | GDYAWN<br>(SEQ ID<br>NO: 236) | YIGYTGSTTYNPSLKS<br>(SEQ ID NO: 237) | WRNWAMDY<br>(SEQ ID<br>NO: 238) | RANQDISHYLN<br>(SEQ ID NO: 239) | YTSRIHSG<br>(SEQ ID<br>NO: 240) | QQGNTPPTT<br>(SEQ ID<br>NO: 241) |
| 12H10 | SNYAWN<br>(SEQ ID<br>NO: 242) | YISSSGITKSNPSLKS<br>(SEQ ID NO: 243) | WSNWSFDV<br>(SEQ ID<br>NO: 244) | RASQDIHNYFN<br>(SEQ ID NO: 245) | YTSRFHSG<br>(SEQ ID<br>NO: 246) | QQGNSLPPT<br>(SEQ ID<br>NO: 247) |

Framework Sequences

Light Chain Framework Sequences

| Ab | FR-L1 | FR-L2 | FR-L3 | FR-L4 |
|---|---|---|---|---|
| 1D5 | EIILTQSPTTMAASPGEKITITC (SEQ ID NO: 248) | WYQQKSGFSPKLLIY (SEQ ID NO: 249) | VPARFSGSGSGTSYSLT IGTMEAEDVATYYC (SEQ ID NO: 250) | FGAGTKVEIK (SEQ ID NO: 251) |
| 1D5v1 1D5v2 1D5v3 1D5v4 | EIVLTQSPDFQSVTPKEKVTITC (SEQ ID NO: 252) | WYQQKPDQSPKLLIY (SEQ ID NO: 253) | VPSRFSGSGSGTDYTLT INSLEAEDAATYYC (SEQ ID NO: 254) | FGQGTKVEIK (SEQ ID NO: 255) |
| 1D5v5 1D5v6 1D5v7 1D5v8 | EIVLTQSPDFQSVTPKEKVTITC (SEQ ID NO: 252) | WYQQKPDQSPKLLIK (SEQ ID NO: 256) | VPSRFSGSGSGTDFTLT INSLEAEDAATYYC (SEQ ID NO: 257) | FGQGTKVEIK (SEQ ID NO: 255) |
| 1D5v9 1D5v10 1D5v11 1D5v12 | DIQLTQSPSSLSASVGDRVTITC (SEQ ID NO: 258) | WYQQKPGKSPKLLIY (SEQ ID NO: 259) | VPSRFSGSGSGTDYTLT ISSLQPEDFATYYC (SEQ ID NO: 260) | FGQGTKVEIK (SEQ ID NO: 255) |
| 1D5v13 1D5v14 1D5v15 1D5v16 | DIQMTQSPSSLSASVGDRVTITC (SEQ ID NO: 261) | WYQQKPGKAPKLLIY (SEQ ID NO: 262) | VPSRFSGSGSGTDFTLT ISSLQPEDFATYYC (SEQ ID NO: 263) | FGQGTKVEIK (SEQ ID NO: 255) |
| 1D5v17 | DIQMTQSPSSLSASVGDRVTITC (SEQ ID NO: 261) | WYQQKPGKSPKLLIY (SEQ ID NO: 264) | VPSRFSGSGSGTDYTLT ISSLQPEDFATYYC (SEQ ID NO: 265) | FGQGTKVEIK (SEQ ID NO: 255) |
| 1D5v18 | DIQLTQSPSSLSASVGDRVTITC (SEQ ID NO: 266) | WYQQKPGKSPKLLIY (SEQ ID NO: 264) | VPSRFSGSGSGTDFTLT ISSLQPEDFATYYC (SEQ ID NO: 267) | FGQGTKVEIK (SEQ ID NO: 255) |
| 1D5v19 1D5v20 1D5v21 1D5v22 1D5v23 1D5v24 1D5v25 1D5v26 1D5v27 1D5v28 1D5v29 | DIQLTQSPSSLSASVGDRVTITC (SEQ ID NO: 266) | WYQQKPGKSPKLLIY (SEQ ID NO: 264) | VPSRFSGSGSGTDYTLT ISSLQPEDFATYYC (SEQ ID NO: 265) | FGQGTKVEIK (SEQ ID NO: 255) |
| 13A9 | DIQMTQSPASLSASVGETVTITC (SEQ ID NO: 268) | WYQQKQGKSPQLLVY (SEQ ID NO: 269) | VPSRFSGRGSGTQYSLK INSLQPEDEGSYFC (SEQ ID NO: 270) | FGGGTKVEIK (SEQ ID NO: 271) |
| 13A9v1 13A9v2 13A9v5 | DIQMTQSPSSLSASVGDRVTITC (SEQ ID NO: 272) | WYQQKPGKAPKLLIY (SEQ ID NO: 273) | VPSRFSGSGSGTDFTLT ISSLQPEDFATYYC (SEQ ID NO: 274) | FGQGTKVEIK (SEQ ID NO: 255) |
| 13A9v3 13A9v4 13A9v6 | DIQMTQSPSSLSASVGDRVTITC (SEQ ID NO: 272) | WYQQKPGKSPKLLVY (SEQ ID NO: 275) | VPSRFSGSGSGTDYTLT ISSLQPEDFATYFC (SEQ ID NO: 276) | FGQGTKVEIK (SEQ ID NO: 255) |
| 15F11 | EIVLTQSPTAMAASPGEKITITC (SEQ ID NO: 277) | WYQQKPGFSPKLLIY (SEQ ID NO: 278) | VPARFSGSGSGTSYSLT IGPMEAEDVATYYC (SEQ ID NO: 279) | FGAGTKVEIK (SEQ ID NO: 251) |
| 15F11v1 15F11v2 15F11v5 | EIVLTQSPATLSLSPGERATLSC (SEQ ID NO: 280) | WYQQKPGQAPRLLIY (SEQ ID NO: 281) | IPARFSGSGSGTDFTLT ISSLEPEDFAVYYC (SEQ ID NO: 282) | FGQGTKVEIK (SEQ ID NO: 255) |
| 15F11v3 15F11v4 15F11v6 | EIVLTQSPATLSLSPGERATLSC (SEQ ID NO: 280) | WYQQKPGQSPRLLIY (SEQ ID NO: 283) | VPARFSGSGSGTDYTLT ISSLEPEDFAVYYC (SEQ ID NO: 284) | FGQGTKVEIK (SEQ ID NO: 255) |
| 6E1.1.12 | DVLMTQTPLSLPVSLGDQASISC (SEQ ID NO: 285) | WYLQKPGQSPKLLIY (SEQ ID NO: 286) | GVPDRFSGSGSGTDFTL KISRVEAEDLGVYYC (SEQ ID NO: 287) | FGGGTKVEIK (SEQ ID NO: 271) |

| | | -continued | | |
|---|---|---|---|---|
| 18G3 | DIQMTQTPSSLSASLGDRVTISC (SEQ ID NO: 288) | WYQQKPDGAVKLLIY (SEQ ID NO: 289) | VPSRFSGSGSGTDYSLT IANLEQEDVATYFC (SEQ ID NO: 290) | FGGGTKVEIK (SEQ ID NO: 271) |
| 12H10 | DIQMTQTPSSLSVSLGDRVTINC (SEQ ID NO: 291) | WYQQKPDGTIKLLIY (SEQ ID NO: 292) | VPSRFSGSGSGTDYSLT ISNLEEEDIATYFC (SEQ ID NO: 293) | FGGGTKLEIK (SEQ ID NO: 294) |
| Heavy Chain Framework Sequences | | | | |
| Ab | FR-H1 | FR-H2 | FR-H3 | FR-H4 |
| 1D5 | EIQLQQSGPELVKPGASVKVSCK ASGYAFT (SEQ ID NO: 295) | WVKQSHGKSLEWIG (SEQ ID NO: 296) | KATLTVDKSSSSAYIHL NSLTSEDSAIYYCAR (SEQ ID NO: 297) | WGQGTTLTVSS (SEQ ID NO: 298) |
| 1D5v1 1D5v5 1D5v9 1D5v13 | EIQLVQSGAEVKKPGASVKVSCK ASGYAFT (SEQ ID NO: 299) | WVRQAPGQGLEWIG (SEQ ID NO: 300) | RATLTVDKSTSTAYMEL RSLRSDDTAVYYCAR (SEQ ID NO: 301) | WGQGTLVTVSS (SEQ ID NO: 302) |
| 1D5v2 1D5v6 1D5v10 1D5v14 | EVQLVQSGAEVKKPGASVKVSCK ASGYAFT (SEQ ID NO: 303) | WVRQAPGQGLEWMG (SEQ ID NO: 304) | RVTMTTDTSTSTAYMEL RSLRSDDTAVYYCAR (SEQ ID NO: 305) | WGQGTLVTVSS (SEQ ID NO: 302) |
| 1D5v3 1D5v7 1D5v11 1D5v15 1D5v17 1D5v18 1D5v27 1D5v28 1D5v29 | EIQLVQSGAEVKKPGASVKVSCK ASGYAFT (SEQ ID NO: 299) | WVRQAPGQGLEWIG (SEQ ID NO: 300) | RATLTVDKSTSTAYLEL SSLRSEDTAVYYCAR (SEQ ID NO: 306) | WGQGTLVTVSS (SEQ ID NO: 302) |
| 1D5v4 1D5v8 1D5v12 1D5v16 | EVQLVQSGAEVKKPGASVKVSCK ASGYAFT (SEQ ID NO: 303) | WVRQAPGQGLEWIG (SEQ ID NO: 300) | RVTITRDTSTSTAYLELS SLRSEDTAVYYCAR (SEQ ID NO: 307) | WGQGTLVTVSS (SEQ ID NO: 302) |
| 1D5v19 | EVQLVQSGAEVKKPGASVKVSCK ASGYAFT (SEQ ID NO: 303) | WVRQAPGQGLEWIG (SEQ ID NO: 300) | RATLTVDKSTSTAYLELS SLRSEDTAVYYCAR (SEQ ID NO: 306) | WGQGTLVTVSS (SEQ ID NO: 302) |
| 1D5v20 | EIQLVQSGAEVKKPGASVKVSCK ASGYAFT (SEQ ID NO: 299) | WVRQAPGQGLEWIG (SEQ ID NO: 300) | RVTLTVDKSTSTAYLELS SLRSEDTAVYYCAR (SEQ ID NO: 308) | WGQGTLVTVSS (SEQ ID NO: 302) |
| 1D5v21 | EIQLVQSGAEVKKPGASVKVSCK ASGYAFT (SEQ ID NO: 299) | WVRQAPGQGLEWIG (SEQ ID NO: 300) | RATITVDKSTSTAYLELS SLRSEDTAVYYCAR (SEQ ID NO: 309) | WGQGTLVTVSS (SEQ ID NO: 302) |
| 1D5v22 | EIQLVQSGAEVKKPGASVKVSCK ASGYAFT (SEQ ID NO: 299) | WVRQAPGQGLEWIG (SEQ ID NO: 300) | RATLTRDKSTSTAYLELS SLRSEDTAVYYCAR (SEQ ID NO: 310) | WGQGTLVTVSS (SEQ ID NO: 302) |
| 1D5v23 | EIQLVQSGAEVKKPGASVKVSCK ASGYAFT (SEQ ID NO: 299) | WVRQAPGQGLEWIG (SEQ ID NO: 300) | RATLTVDTSTSTAYLELS SLRSEDTAVYYCAR (SEQ ID NO: 311) | WGQGTLVTVSS (SEQ ID NO: 302) |
| 1D5v24 | EIQLVQSGAEVKKPGASVKVSCK ASGYAFT (SEQ ID NO: 299) | WVRQAPGQGLEWIG (SEQ ID NO: 300) | RVTITVDKSTSTAYLELS SLRSEDTAVYYCAR (SEQ ID NO: 312) | WGQGTLVTVSS (SEQ ID NO: 302) |
| 1D5v25 | EVQLVQSGAEVKKPGASVKVSCK ASGYAFT (SEQ ID NO: 303) | WVRQAPGQGLEWIG (SEQ ID NO: 300) | RVTITVDTSTSTAYLELS SLRSEDTAVYYCAR (SEQ ID NO: 313) | WGQGTLVTVSS (SEQ ID NO: 302) |
| 1D5v26 | EVQLVQSGAEVKKPGASVKVSCK ASGYAFT (SEQ ID NO: 303) | WVRQAPGQGLEWIG (SEQ ID NO: 300) | RVTITRDTSTSTAYLELS SLRSEDTAVYYCAR (SEQ ID NO: 314) | WGQGTLVTVSS (SEQ ID NO: 302) |
| 13A9 | QVQLQQSGAELVRPGTSVKVSCK ASGYAFT (SEQ ID NO: 315) | WVKQRPGQGLEWIG (SEQ ID NO: 316) | KARLTADKSSNTAYLQFS SLTSDDSAVYFCAR (SEQ ID NO: 317) | WGQGATLTVSS (SEQ ID NO: 318) |

-continued

| | | | | |
|---|---|---|---|---|
| 13A9v1 13A9v3 | EVQLVQSGAEVKKPGASVKVSCK ASGYAFT (SEQ ID NO: 319) | WVRQAPGQGLEWIG (SEQ ID NO: 320) | RVTITADTSTSTAYLELS SLRSEDTAVYYCAR (SEQ ID NO: 321) | WGQGTLVTVSS (SEQ ID NO: 302) |
| 13A9v2 13A9v4 | EVQLVQSGAEVKKPGASVKVSCK ASGYAFT (SEQ ID NO: 319) | WVRQAPGQGLEWIG (SEQ ID NO: 320) | RATLTADKSTNTAYLELS SLRSEDTAVYFCAR (SEQ ID NO: 322) | WGQGTLVTVSS (SEQ ID NO: 302) |
| 13A9v5 13A9v6 | EVQLVQSGAEVKKPGSSVKVSCK ASGYAFT (SEQ ID NO: 323) | WVRQAPGQGLEWIG (SEQ ID NO: 320) | RATLTADKSTNTAYMELS SLRSEDTAVYFCAR (SEQ ID NO: 324) | WGQGTLVTVSS (SEQ ID NO: 302) |
| 15F11 | EIQLQQSGPELVKPGASVRVSCK PSGYAFT (SEQ ID NO: 325) | WVKQSRRKSLEWIG (SEQ ID NO: 326) | KATLTVDKSSSTAYMHLN SLTSEDSAVYYCSR (SEQ ID NO: 327) | WGQGTTLTVSS (SEQ ID NO: 328) |
| 15F11v1 15F11v3 | EVQLVQSGAEVKKPGASVKVSCK ASGYAFT (SEQ ID NO: 329) | WVRQAPGQGLEWIG (SEQ ID NO: 320) | RVTITADTSTSTAYLELS SLRSEDTAVYYCSR (SEQ ID NO: 330) | WGQGTLVTVSS (SEQ ID NO: 302) |
| 15F11v2 15F11v4 | EIQLVQSGAEVKKPGASVKVSCK PSGYAFT (SEQ ID NO: 331) | WVRQAPGQGLEWIG (SEQ ID NO: 320) | RATLTVDKSTSTAYLELS SLRSEDTAVYYCSR (SEQ ID NO: 332) | WGQGTLVTVSS (SEQ ID NO: 302) |
| 15F11v5 15F11v6 | EIQLVQSGAEVKKPGSSVKVSCK PSGYAFT (SEQ ID NO: 333) | WVRQAPGQGLEWIG (SEQ ID NO: 320) | RATLTVDKSTSTAYMELS SLRSEDTAVYYCSR (SEQ ID NO: 334) | WGQGTLVTVSS (SEQ ID NO: 302) |
| 6E1.1.12 | QGQMQQSGAELVKPGASVKLSCK TSGFTFS (SEQ ID NO: 335) | WLKQKPGQSLEWIA (SEQ ID NO: 336) | KAQLTVDTSSRTAYMQLS SLTTEDSAIYYCAR (SEQ ID NO: 337) | WGRGTLVTVSA (SEQ ID NO: 338) |
| 18G3 | VQLQESGPGLVKPSQSLSLTCNV TGYSIT (SEQ ID NO: 339) | WIRQFPGNKLEWIG (SEQ ID NO: 340) | RVSITRDTSKNQFFLQLN SVTPEDTATYYCAR (SEQ ID NO: 341) | WGLGTSVTVSS (SEQ ID NO: 342) |
| 12H10 | DVQLQESGPGLVKPSQPLSLTCT VTGYSIT (SEQ ID NO: 343) | WIRQFPGDKLEWMG (SEQ ID NO: 344) | RISITRDTSKNQFFLQLN SLTTEDTATYYCSR (SEQ ID NO: 345) | WGAGTTVTVSS (SEQ ID NO: 346) |

| Variable Domain Sequences | | |
|---|---|---|
| Ab | VH | VL |
| 1D5 | EIQLQQSGPELVKPGASVKVSCKASGYAFTSQNI YWVKQSHGKSLEWIGYIEPYNVVPMYNPKFKGKA TLTDKSSSAYIHLNSLTSEDSAIYYCARSGSS NFDYWGQGTTLTVSS (SEQ ID NO: 347) | EIILTQSPTTMAASPGEKITITCSASSSISSHYLH WYQQKSGESPKLLIYRTSNLASGVPARFSGSGSGT SYSLTIGTMEAEDVATYYCQQGSSLPLTFGAGTKV EIK (SEQ ID NO: 348) |
| 1D5v1 | EIQLVQSGAEVKKPGASVKVSCKASGYAFTSQNI YWVRQAPGQGLEWIGYIEPYNVVPMYNPKFKGRA TLTVDKSTAYMELRSLRSDDTAVYYCARSGSS NFDYWGQGTLVTVSS (SEQ ID NO: 349) | EIVLTQSPDFQSVTPKEKVTITCSASSSISSHYLH WYQQKPDQSPKLLIYRTSNLASGVPSRFSGSGSGT DYTLTINSLEAEDAATYYCQQGSSLPLTFGQGTKV EIK (SEQ ID NO: 350) |
| 1D5v2 | EVQLVQSGAEVKKPGASVKVSCKASGYAFTSQNI YWVRQAPGQGLEWMGYIEPYNVVPMYNPKFKGRV TMTTDTSTSTAYMELRSLRSDDTAVYYCARSGSS NFDYWGQGTLVTVSS (SEQ ID NO: 351) | EIVLTQSPDFQSVTPKEKVTITCSASSSISSHYLH WYQQKPDQSPKLLIYRTSNLASGVPSRFSGSGSGT DYTLTINSLEAEDAATYYCQQGSSLPLTFGQGTKV EIK (SEQ ID NO: 352) |
| 1D5v3 | EIQLVQSGAEVKKPGASVKVSCKASGYAFTSQNI YWVRQAPGQGLEWIGYIEPYNVVPMYNPKFKGRA TLTVDKSTSTAYLELSSLRSEDTAVYYCARSGSS NFDYWGQGTLVTVSS (SEQ ID NO: 353) | EIVLTQSPDFQSVTPKEKVTITCSASSSISSHYLH WYQQKPDQSPKLLIYRTSNLASGVPSRFSGSGSGT DYTLTINSLEAEDAATYYCQQGSSLPLTFGQGTKV EIK (SEQ ID NO: 354) |
| 1D5v4 | EVQLVQSGAEVKKPGASVKVSCKASGYAFTSQNI YWVRQAPGQGLEWIGYIEPYNVVPMYNPKFKGRV TITRDTSTSTAYLELSSLRSEDTAVYYCARSGSS NFDYWGQGTLVTVSS (SEQ ID NO: 355) | EIVLTQSPDFQSVTPKEKVTITCSASSSISSHYLH WYQQKPDQSPKLLIYRTSNLASGVPSRFSGSGSGT DYTLTINSLEAEDAATYYCQQGSSLPLTFGQGTKV EIK (SEQ ID NO: 356) |

| | | |
|---|---|---|
| 1D5v5 | EIQLVQSGAEVKKPGASVKVSCKASGYAFTSQNI YWVRQAPGQGLEWIGYIEPYNVVPMYNPKFKGRA TLTVDKSTSTAYMELRSLRSDDTAVYYCARSGSS NFDYWGQGTLVTVSS (SEQ ID NO: 357) | EIVLTQSPDFQSVTPKEKVTITCSASSSISSHYLH WYQQKPDQSPKLLIKRTSNLASGVPSRFSGSGSGT DFTLTINSLEAEDAATYYCQQGSSLPLTFGQGTKV EIK (SEQ ID NO: 358) |
| 1D5v6 | EVQLVQSGAEVKKPGASVKVSCKASGYAFTSQNI YWVRQAPGQGLEWIGYIEPYNVVPMYNPKFKGRV TMTTDTSTSTAYMELRSLRSDDTAVYYCARSGSS NFDYWGQGTLVTVSS (SEQ ID NO: 359) | EIVLTQSPDFQSVTPKEKVTITCSASSSISSHYLH WYQQKPDQSPKLLIKRTSNLASGVPSRFSGSGSGT DFTLTINSLEAEDAATYYCQQGSSLPLTFGQGTKV EIK (SEQ ID NO: 360) |
| 1D5v7 | EIQLVQSGAEVKKPGASVKVSCKASGYAFTSQNI YWVRQAPGQGLEWIGYIEPYNVVPMYNPKFKGRA TLTVDKSTSTAYLELSSLRSEDTAVYYCARSGSS NFDYWGQGTLVTVSS (SEQ ID NO: 361) | EIVLTQSPDFQSVTPKEKVTITCSASSSISSHYLH WYQQKPDQSPKLLIKRTSNLASGVPSRFSGSGSGT DFTLTINSLEAEDAATYYCQQGSSLPLTFGQGTKV EIK (SEQ ID NO: 362) |
| 1D5v8 | EVQLVQSGAEVKKPGASVKVSCKASGYAFTSQNI YWVRQAPGQGLEWIGYIEPYNVVPMYNPKFKGRV TITRDTSTSTAYLELSSLRSEDTAVYYCARSGSS NFDYWGQGTLVTVSS (SEQ ID NO: 363) | EIVLTQSPDFQSVTPKEKVTITCSASSSISSHYLH WYQQKPDQSPKLLIKRTSNLASGVPSRFSGSGSGT DFTLTINSLEAEDAATYYCQQGSSLPLTFGQGTKV EIK (SEQ ID NO: 364) |
| 1D5v9 | EIQLVQSGAEVKKPGASVKVSCKASGYAFTSQNI YWVRQAPGQGLEWIGYIEPYNVVPMYNPKFKGRA TLTVDKSTSTAYMELRSLRSDDTAVYYCARSGSS NFDYWGQGTLVTVSS (SEQ ID NO: 365) | DIQLTQSPSSLSASVGDRVTITCSASSSISSHYLH WYQQKPGKSPKLLIYRTSNLASGVPSRFSGSGSGT DYTLTISSLQPEDFATYYCQQGSSLPLTFGQGTKV EIK (SEQ ID NO: 366) |
| 1D5v10 | EVQLVQSGAEVKKPGASVKVSCKASGYAFTSQNI YWVRQAPGQGLEWMGYIEPYNVVPMYNPKFKGRV TMTTDTSTSTAYMELRSLRSDDTAVYYCARSGSS NFDYWGQGTLVTVSS (SEQ ID NO: 367) | DIQLTQSPSSLSASVGDRVTITCSASSSISSHYLH WYQQKPGKSPKLLIYRTSNLASGVPSRFSGSGSGT DYTLTISSLQPEDFATYYCQQGSSLPLTFGQGTKV EIK (SEQ ID NO: 368) |
| 1D5v11 | EIQLVQSGAEVKKPGASVKVSCKASGYAFTSQNI YWVRQAPGQGLEWIGYIEPYNVVPMYNPKFKGRA TLTVDKSTSTAYLELSSLRSEDTAVYYCARSGSS NFDYWGQGTLVTVSS (SEQ ID NO: 369) | DIQLTQSPSSLSASVGDRVTITCSASSSISSHYLH WYQQKPGKSPKLLIYRTSNLASGVPSRFSGSGSGT DYTLTISSLQPEDFATYYCQQGSSLPLTFGQGTKV EIK (SEQ ID NO: 370) |
| 1D5v12 | EVQLVQSGAEVKKPGASVKVSCKASGYAFTSQNI YWVRQAPGQGLEWIGYIEPYNVVPMYNPKFKGRV TITRDTSTSTAYLELSSLRSEDTAVYYCARSGSS NFDYWGQGTLVTVSS (SEQ ID NO: 371) | DIQLTQSPSSLSASVGDRVTITCSASSSISSHYLH WYQQKPGKSPKLLIYRTSNLASGVPSRFSGSGSGT DYTLTISSLQPEDFATYYCQQGSSLPLTFGQGTKV EIK (SEQ ID NO: 372) |
| 1D5v13 | EIQLVQSGAEVKKPGASVKVSCKASGYAFTSQNI YWVRQAPGQGLEWIGYIEPYNVVPMYNPKFKGRA TLTVDKSTSTAYMELRSLRSDDTAVYYCARSGSS NFDYWGQGTLVTVSS (SEQ ID NO: 373) | DIQMTQSPSSLSASVGDRVTITCSASSSISSHYLH WYQQKPGKAPKLLIYRTSNLASGVPSRFSGSGSGT DFTLTISSLQPEDFATYYCQQGSSLPLTFGQGTKV EIK (SEQ ID NO: 374) |
| 1D5v14 | EVQLVQSGAEVKKPGASVKVSCKASGYAFTSQNI YWVRQAPGQGLEWMGYIEPYNVVPMYNPKFKGRV TMTTDTSTSTAYMELRSLRSDDTAVYYCARSGSS NFDYWGQGTLVTVSS (SEQ ID NO: 375) | DIQMTQSPSSLSASVGDRVTITCSASSSISSHYLH WYQQKPGKAPKLLIYRTSNLASGVPSRFSGSGSGT DFTLTISSLQPEDFATYYCQQGSSLPLTFGQGTKV EIK (SEQ ID NO: 376) |
| 1D5v15 | EIQLVQSGAEVKKPGASVKVSCKASGYAFTSQNI YWVRQAPGQGLEWIGYIEPYNVVPMYNPKFKGRA TLTVDKSTSTAYLELSSLRSEDTAVYYCARSGSS NFDYWGQGTLVTVSS (SEQ ID NO: 377) | DIQMTQSPSSLSASVGDRVTITCSASSSISSHYLH WYQQKPGKAPKLLIYRTSNLASGVPSRFSGSGSGT DFTLTISSLQPEDFATYYCQQGSSLPLTFGQGTKV EIK (SEQ ID NO: 378) |
| 1D5v16 | EVQLVQSGAEVKKPGASVKVSCKASGYAFTSQNI YWVRQAPGQGLEWIGYIEPYNVVPMYNPKFKGRV TITRDTSTSTAYLELSSLRSEDTAVYYCARSGSS NFDYWGQGTLVTVSS (SEQ ID NO: 379) | DIQMTQSPSSLSASVGDRVTITCSASSSISSHYLH WYQQKPGKAPKLLIYRTSNLASGVPSRFSGSGSGT DFTLTISSLQPEDFATYYCQQGSSLPLTFGQGTKV EIK (SEQ ID NO: 380) |
| 1D5v17 | EIQLVQSGAEVKKPGASVKVSCKASGYAFTSQNI YWVRQAPGQGLEWIGYIEPYNVVPMYNPKFKGRA TLTVDKSTSTAYLELSSLRSEDTAVYYCARSGSS NFDYWGQGTLVTVSS (SEQ ID NO: 381) | DIQMTQSPSSLSASVGDRVTITCSASSSISSHYLH WYQQKPGKSPKLLIYRTSNLASGVPSRFSGSGSGT DYTLTISSLQPEDFATYYCQQGSSLPLTFGQGTKV EIK (SEQ ID NO: 382) |

-continued

| | | |
|---|---|---|
| 1D5v18 | EIQLVQSGAEVKKPGASVKVSCKASGYAFTSQNI YWVRQAPGQGLEWIGYIEPYNVVPMYNPKFKGRA TLTVDKSTSTAYLELSSLRSEDTAVYYCARSGSS NFDYWGQGTLVTVSS (SEQ ID NO: 383) | DIQLTQSPSSLSASVGDRVTITCSASSSISSHYLH WYQQKPGKSPKLLIYRTSNLASGVPSRFSGSGSGT DFTLTISSLQPEDFATYYCQQGSSLPLTFGQGTKV EIK (SEQ ID NO: 384) |
| 1D5v19 | EVQLVQSGAEVKKPGASVKVSCKASGYAFTSQNI YWVRQAPGQGLEWIGYIEPYNVVPMYNPKFKGRA TLTVDKSTSTAYLELSSLRSEDTAVYYCARSGSS NFDYWGQGTLVTVSS (SEQ ID NO: 385) | DIQLTQSPSSLSASVGDRVTITCSASSSISSHYLH WYQQKPGKSPKLLIYRTSNLASGVPSRFSGSGSGT DYTLTISSLQPEDFATYYCQQGSSLPLTFGQGTKV EIK (SEQ ID NO: 386) |
| 1D5v20 | EIQLVQSGAEVKKPGASVKVSCKASGYAFTSQNI YWVRQAPGQGLEWIGYIEPYNVVPMYNPKFKGRV TLTVDKSTSTAYLELSSLRSEDTAVYYCARSGSS NFDYWGQGTLVTVSS (SEQ ID NO: 387) | DIQLTQSPSSLSASVGDRVTITCSASSSISSHYLH WYQQKPGKSPKLLIYRTSNLASGVPSRFSGSGSGT DYTLTISSLQPEDFATYYCQQGSSLPLTFGQGTKV EIK (SEQ ID NO: 388) |
| 1D5v21 | EIQLVQSGAEVKKPGASVKVSCKASGYAFTSQNI YWVRQAPGQGLEWIGYIEPYNVVPMYNPKFKGRA TITVDKSTSTAYLELSSLRSEDTAVYYCARSGSS NFDYWGQGTLVTVSS (SEQ ID NO: 389) | DIQLTQSPSSLSASVGDRVTITCSASSSISSHYLH WYQQKPGKSPKLLIYRTSNLASGVPSRFSGSGSGT DYTLTISSLQPEDFATYYCQQGSSLPLTFGQGTKV EIK (SEQ ID NO: 390) |
| 1D5v22 | EIQLVQSGAEVKKPGASVKVSCKASGYAFTSQNI YWVRQAPGQGLEWIGYIEPYNVVPMYNPKFKGRA TLTRDKSTSTAYLELSSLRSEDTAVYYCARSGSS NFDYWGQGTLVTVSS (SEQ ID NO: 391) | DIQLTQSPSSLSASVGDRVTITCSASSSISSHYLH WYQQKPGKSPKLLIYRTSNLASGVPSRFSGSGSGT DYTLTISSLQPEDFATYYCQQGSSLPLTFGQGTKV EIK (SEQ ID NO: 392) |
| 1D5v23 | EIQLVQSGAEVKKPGASVKVSCKASGYAFTSQNI YWVRQAPGQGLEWIGYIEPYNVVPMYNPKFKGRA TLTVDTSTSTAYLELSSLRSEDTAVYYCARSGSS NFDYWGQGTLVTVSS (SEQ ID NO: 393) | DIQLTQSPSSLSASVGDRVTITCSASSSISSHYLH WYQQKPGKSPKLLIYRTSNLASGVPSRFSGSGSGT DYTLTISSLQPEDFATYYCQQGSSLPLTFGQGTKV EIK (SEQ ID NO: 394) |
| 1D5v24 | EVQLVQSGAEVKKPGASVKVSCKASGYAFTSQNI YWVRQAPGQGLEWIGYIEPYNVVPMYNPKFKGRV TITVDKSTSTAYLELSSLRSEDTAVYYCARSGSS NFDYWGQGTLVTVSS (SEQ ID NO: 395) | DIQLTQSPSSLSASVGDRVTITCSASSSISSHYLH WYQQKPGKSPKLLIYRTSNLASGVPSRFSGSGSGT DYTLTISSLQPEDFATYYCQQGSSLPLTFGQGTKV EIK (SEQ ID NO: 396) |
| 1D5v25 | EVQLVQSGAEVKKPGASVKVSCKASGYAFTSQNI YWVRQAPGQGLEWIGYIEPYNVVPMYNPKFKGRV TITVDTSTSTAYLELSSLRSEDTAVYYCARSGSS NFDYWGQGTLVTVSS (SEQ ID NO: 397) | DIQLTQSPSSLSASVGDRVTITCSASSSISSHYLH WYQQKPGKSPKLLIYRTSNLASGVPSRFSGSGSGT DYTLTISSLQPEDFATYYCQQGSSLPLTFGQGTKV EIK (SEQ ID NO: 398) |
| 1D5v26 | EVQLVQSGAEVKKPGASVKVSCKASGYAFTSQNI YWVRQAPGQGLEWIGYIEPYNVVPMYNPKFKGRV TITRDKSTSTAYLELSSLRSEDTAVYYCARSGSS NFDYWGQGTLVTVSS (SEQ ID NO: 399) | DIQLTQSPSSLSASVGDRVTITCSASSSISSHYLH WYQQKPGKSPKLLIYRTSNLASGVPSRFSGSGSGT DYTLTISSLQPEDFATYYCQQGSSLPLTFGQGTKV EIK (SEQ ID NO: 400) |
| 1D5v27 | EIQLVQSGAEVKKPGASVKVSCKASGYAFTSQNI YWVRQAPGQGLEWIGYIEPYNVVPAYNPKFKGRA TLTVDKSTSTAYLELSSLRSEDTAVYYCARSGSS NFDYWGQGTLVTVSS (SEQ ID NO: 401) | DIQLTQSPSSLSASVGDRVTITCSASSSISSHYLH WYQQKPGKSPKLLIYRTSNLASGVPSRFSGSGSGT DYTLTISSLQPEDFATYYCQQGSSLPLTFGQGTKV EIK (SEQ ID NO: 402) |
| 1D5v28 | EIQLVQSGAEVKKPGASVKVSCKASGYAFTSQNI YWVRQAPGQGLEWIGYIEPYNVVPLYNPKFKGRA TLTVDKSTSTAYLELSSLRSEDTAVYYCARSGSS NFDYWGQGTLVTVSS (SEQ ID NO: 403) | DIQLTQSPSSLSASVGDRVTITCSASSSISSHYLH WYQQKPGKSPKLLIYRTSNLASGVPSRFSGSGSGT DYTLTISSLQPEDFATYYCQQGSSLPLTFGQGTKV EIK (SEQ ID NO: 404) |
| 1D5v29 | EIQLVQSGAEVKKPGASVKVSCKASGYAFTSQNI YWVRQAPGQGLEWIGYIEPYNVVPVYNPKFKGRA TLTVDKSTSTAYLELSSLRSEDTAVYYCARSGSS NFDYWGQGTLVTVSS (SEQ ID NO: 405) | DIQLTQSPSSLSASVGDRVTITCSASSSISSHYLH WYQQKPGKSPKLLIYRTSNLASGVPSRFSGSGSGT DYTLTISSLQPEDFATYYCQQGSSLPLTFGQGTKV EIK (SEQ ID NO: 406) |
| 13A9 | QVQLQQSGAELVRPGTSVKVSCKASGYAFTNYLI EWVKQRPGQGLEWIGAINPGSGATNYNEKFKDKA RLTADKSSNTAYLQFSSLTSDDSAVYFCARFLGN YFDNWGQGATLTVSS (SEQ ID NO: 407) | DIQMTQSPASLSASVGETVTITCRASGNIHSYLAW YQQKQGKSPQLLVYYAETLADGVPSRFSGRGSGTQ YSLKINSLQPEDEGSYFCQQFWTTPYTEGGGTKVE IK (SEQ ID NO: 408) |

| | | |
|---|---|---|
| 13A9v1 | EVQLVQSGAEVKKPGASVKVSCKASGYAFTNYLI EWVRQAPGQGLEWIGAINPGSGATNYNEKFKDRV TITADTSTSTAYLELSSLRSEDTAVYYCARFLGN YFDNWGQGTLVTVSS (SEQ ID NO: 409) | DIQMTQSPSSLSASVGDRVTITCRASGNIHSYLAW YQQKPGKAPKLLIYYAETLADGVPSRFSGSGSGTD FTLTISSLQPEDFATYYCQQFWTTPYTFGQGTKVE IK (SEQ ID NO: 410) |
| 13A9v2 | EVQLVQSGAEVKKPGASVKVSCKASGYAFTNYLI EWVRQAPGQGLEWIGAINPGSGATNYNEKFKDRA TLTADKSTNTAYLELSSLRSEDTAVYFCARFLGN YFDNWGQGTLVTVSS (SEQ ID NO: 411) | DIQMTQSPSSLSASVGDRVTITCRASGNIHSYLAW YQQKPGKAPKLLIYYAETLADGVPSRFSGSGSGTD FTLTISSLQPEDFATYYCQQFWTTPYTFGQGTKVE IK (SEQ ID NO: 412) |
| 13A9v3 | EVQLVQSGAEVKKPGASVKVSCKASGYAFTNYLI EWVRQAPGQGLEWIGAINPGSGATNYNEKFKDRV TITADTSTSTAYLELSSLRSEDTAVYYCARFLGN YFDNWGQGTLVTVSS (SEQ ID NO: 413) | DIQMTQSPSSLSASVGDRVTITCRASGNIHSYLAW YQQKPGKSPKLLVYYAETLADGVPSRFSGSGSGTD YTLTISSLQPEDFATYFCQQFWTTPYTFGQGTKVE IK (SEQ ID NO: 414) |
| 13A9v4 | EVQLVQSGAEVKKPGASVKVSCKASGYAFTNYLI EWVRQAPGQGLEWIGAINPGSGATNYNEKFKDRA TLTADKSTNTAYLELSSLRSEDTAVYFCARFLGN YFDNWGQGTLVTVSS (SEQ ID NO: 415) | DIQMTQSPSSLSASVGDRVTITCRASGNIHSYLAW YQQKPGKSPKLLVYYAETLADGVPSRFSGSGSGTD YTLTISSLQPEDFATYFCQQFWTTPYTFGQGTKVE IK (SEQ ID NO: 416) |
| 13A9v5 | EVQLVQSGAEVKKPGSSVKVSCKASGYAFTNYLI EWVRQAPGQGLEWIGAINPGSGATNYNEKFKDRA TLTADKSTNTAYMELSSLRSEDTAVYFCARFLGN YFDNWGQGTLVTVSS (SEQ ID NO: 417) | DIQMTQSPSSLSASVGDRVTITCRASGNIHSYLAW YQQKPGKAPKLLIYYAETLADGVPSRFSGSGSGTD FTLTISSLQPEDFATYYCQQFWTTPYTFGQGTKVE IK (SEQ ID NO: 418) |
| 13A9v6 | EVQLVQSGAEVKKPGSSVKVSCKASGYAFTNYLI EWVRQAPGQGLEWIGAINPGSGATNYNEKFKDRA TLTADKSTNTAYMELSSLRSEDTAVYFCARFLGN YFDNWGQGTLVTVSS (SEQ ID NO: 419) | DIQMTQSPSSLSASVGDRVTITCRASGNIHSYLAW YQQKPGKSPKLLVYYAETLADGVPSRFSGSGSGTD YTLTISSLQPEDFATYFCQQFWTTPYTFGQGTKVE IK (SEQ ID NO: 420) |
| 15F11 | EIQLQQSGPELVKPGASVRVSCKPSGYAFTSNNI YWVKQSRRKSLEWIGYIDPYIGRIIYNQQFKDKA TLTVDKSSSTAYMHLNSLTSEDSAVYYCSRSGER SNFDYWGQGTTLTVSS (SEQ ID NO: 421) | EIVLTQSPTAMAASPGEKITITCSASSSISSNYLH WYQQKPGFSPKLLIYRTSNLASGVPARFSGSGSGT SYSLTIGPMEAEDVATYYCQQGGSLPLTFGAGTKV EIK (SEQ ID NO: 422) |
| 15F11v1 | EVQLVQSGAEVKKPGASVKVSCKASGYAFTSNNI YWVRQAPGQGLEWIGYIDPYIGRIIYNQQFKDRV TITADTSTSTAYLELSSLRSEDTAVYYCSRSGER SNFDYWGQGTLVTVSS (SEQ ID NO: 423) | EIVLTQSPATLSLSPGERATLSCSASSSISSNYLH WYQQKPGQAPRLLIYRTSNLASGIPARFSGSGSGT DFTLTISSLEPEDFAVYYCQQGGSLPLTFGQGTKV EIK (SEQ ID NO: 424) |
| 15F11v2 | EIQLVQSGAEVKKPGASVKVSCKPSGYAFTSNNI YWVRQAPGQGLEWIGYIDPYIGRIIYNQQFKDRA TLTVDKSTSTAYLELSSLRSEDTAVYYCSRSGER SNFDYWGQGTLVTVSS (SEQ ID NO: 425) | EIVLTQSPATLSLSPGERATLSCSASSSISSNYLH WYQQKPGQAPRLLIYRTSNLASGIPARFSGSGSGT DFTLTISSLEPEDFAVYYCQQGGSLPLTFGQGTKV EIK (SEQ ID NO: 426) |
| 15F11v3 | EVQLVQSGAEVKKPGASVKVSCKASGYAFTSNNI YWVRQAPGQGLEWIGYIDPYIGRIIYNQQFKDRV TITADTSTSTAYLELSSLRSEDTAVYYCSRSGER SNFDYWGQGTLVTVSS (SEQ ID NO: 427) | EIVLTQSPATLSLSPGERATLSCSASSSISSNYLH WYQQKPGQSPRLLIYRTSNLASGVPARFSGSGSGT DYTLTISSLEPEDFAVYYCQQGGSLPLTFGQGTKV EIK (SEQ ID NO: 428) |
| 15F11v4 | EIQLVQSGAEVKKPGASVKVSCKPSGYAFTSNNI YWVRQAPGQGLEWIGYIDPYIGRIIYNQQFKDRA TLTVDKSTSTAYLELSSLRSEDTAVYYCSRSGER SNFDYWGQGTLVTVSS (SEQ ID NO: 429) | EIVLTQSPATLSLSPGERATLSCSASSSISSNYLH WYQQKPGQSPRLLIYRTSNLASGVPARFSGSGSGT DYTLTISSLEPEDFAVYYCQQGGSLPLTFGQGTKV EIK (SEQ ID NO: 430) |
| 15F11v5 | EIQLVQSGAEVKKPGSSVKVSCKPSGYAFTSNNI YWVRQAPGQGLEWIGYIDPYIGRIIYNQQFKDRA TLTVDKSTSTAYMELSSLRSEDTAVYYCSRSGER SNFDYWGQGTLVTVSS (SEQ ID NO: 431) | EIVLTQSPATLSLSPGERATLSCSASSSISSNYLH WYQQKPGQAPRLLIYRTSNLASGIPARFSGSGSGT DFTLTISSLEPEDFAVYYCQQGGSLPLTFGQGTKV EIK (SEQ ID NO: 432) |
| 15F11v6 | EIQLVQSGAEVKKPGSSVKVSCKPSGYAFTSNNI YWVRQAPGQGLEWIGYIDPYIGRIIYNQQFKDRA TLTVDKSTSTAYMELSSLRSEDTAVYYCSRSGER SNFDYWGQGTLVTVSS (SEQ ID NO: 433) | EIVLTQSPATLSLSPGERATLSCSASSSISSNYLH WYQQKPGQSPRLLIYRTSNLASGVPARFSGSGSGT DYTLTISSLEPEDFAVYYCQQGGSLPLTFGQGTKV EIK (SEQ ID NO: 434) |

| | | |
|---|---|---|
| 6E1.1.12 | QGQMQQSGAELVKPGASVKLSCKTSGEMDNYISW<br>LKQKPGQSLEWIAWIYAGTGGSSYNQKFRDKAQL<br>TVDTSSRTAYMQLSSLTTEDSAIYYCARHDYYGT<br>SGAWFAYWGRGTLVTVSA<br>(SEQ ID NO: 435) | DVLMTQTPLSLPVSLGDQASISCRSSQHIVHSNEN<br>TYLEWYLQKPGQSPKLLIYKVSNRFSGVPDRFSGS<br>GSGTDFTLKISRVEAEDLGVYYCFQGSHVPWTFGG<br>GTKVEIK<br>(SEQ ID NO: 436) |
| 18G3 | VQLQESGPGLVKPSQSLSLTCNVTGYSITGDYAW<br>NWIRQFPGNKLEWIGYIGYTGSTTYNPSLKSRVS<br>ITRDTSKNQFFLQLNSVTPEDTATYYCARWRNWA<br>MDYWGLGTSVTVSS<br>(SEQ ID NO: 437) | DIQMTQTPSSLSASLGDRVTISCRANQDISHYLNW<br>YQQKPDGAVKLLIYYTSRIHSGVPSRFSGSGSGTD<br>YSLTIANLEQEDVATYFCQQGNTPPTTFGGGTKVE<br>IK<br>(SEQ ID NO: 438) |
| 12H10 | DVQLQESGPGLVKPSQPLSLTCTVTGYSITSNYA<br>WNWIRQFPGDKLEWMGYISSSGITKSNPSLKSRI<br>SITRDTSKNQFFLQLNSLTTEDTATYYCSRWSNW<br>SFDVWGAGTTVTVSS<br>(SEQ ID NO: 439) | DIQMTQTPSSLSVSLGDRVTINCRASQDIHNYFNW<br>YQQKPDGTIKLLIYYTSRFHSGVPSRFSGSGSGTD<br>YSLTISNLEEEDIATYFCQQGNSLPPTFGGGTKLE<br>IK<br>(SEQ ID NO: 440) |

SEQ ID NOs: 193 through SEQ ID NO: 208
MICA *008 (with signal sequence)

SEQ ID NO: 193

MGLGPVFLLLAGIFPFAPPGAAAEPHSLRYNLTVLSWDGSVQSGFLAEVHLDGQPFLRYDR

QKCRAKPQGQWAEDVLGNKTWDRETRDLTGNGKDLRMTLAHIKDQKEGLHSLQEIRVCEIH

EDNSTRSSQHFYYDGELFLSQNLETEEWTVPQSSRAQTLAMNVRNFLKEDAMKTKTHYHAM

HADCLQELRRYLESGVVLRRTVPPMVNVTRSEASEGNITVTCRASSFYPRNIILTWRQDGV

SLSHDTQQWGDVLPDGNGTYQTWVATRICRGEEQRFTCYMEHSGNHSTHPVPSGKVLVLQS

HWQTFHVSAVAAGCCYFCYYYFLCPLL

Sequences for Constructs in Examples
>MICA008.muIgG2a (a3 domain in bold)

SEQ ID NO: 194

GSTVPPMVNVTRSEASEGNITVTCRASSFYPRNIILTWRQDGVSLSHDTQQWGDVLPDGN

GTYQTWVATRICRGEEQRFTCYMEHSGNHSTHPVPSGNSRAQVTDKKIEPRGPTIKPCPP

CKCPAPNLLGGPSVFIFPPKIKDVLMISLSPIVTCVVVDVSEDDPDVQISWFVNNVEVHT

AQTQTHREDYNSTLRVVSALPIQHQDWMSGKEFKCKVNNKDLPAPIERTISKPKGSVRAP

QVYVLPPPEEEMTKKQVTLTCMVTDFMPEDIYVEWTNNGKTELNYKNTEPVLDSDGSYFM

YSKLRVEKKNWVERNSYSCSVVHEGLHNHHTTKSFSRTPGK

>MICA008.His (a3 domain in bold)

SEQ ID NO: 195

GSTVPPMVNVTRSEASEGNITVTCRASSFYPRNIILTWRQDGVSLSHDTQQWGDVLPDGN

GTYQTWVATRICRGEEQRFTCYMEHSGNHSTHPVPSGNSHHHHHHHH

>MICA002.His (a3 domain in bold)

SEQ ID NO: 196

GSTVPPMVNVTRSEASEGNITVTCRASGFYPWNITLSWRQDGVSLSHDTQQWGDVLPDGN

GTYQTWVATRICQGEEQRFTCYMEHSGNHSTHPVPSGNSHHHHHHHH

>MICA004.His (a3 domain in bold)

SEQ ID NO: 197

GSVPPMVNVTRSEASEGNITVTCRASSFYPRNITLTWRQDGVSLSHDTQQWGDVLPDGNG

TYQTWVATRICQGEEQRFTCYMEHSGNHSTHPVPSGNSHHHHHHHH

>MICB005.His (a3 domain in bold)

SEQ ID NO: 198

GSTVPPMVNVTCSEVSEGNITVTCRASSFYPRNITLTWRQDGVSLSHNTQQWGDVLPDGN

GTYQTWVATRIRQGEEQRFTCYMEHSGNHGTHPVPSGNSHHHHHHHH

>MICA.008.a3.T204-S297.mIgG2a.Wild-type

SEQ ID NO: 199

TVPPMVNVTRSEASEGNITVTCRASSFYPRNIILTWRQDGVSLSHDTQQWGDVLPDGNGT

YQTWVATRICRGEEQRFTCYMEHSGNHSTHPVPS

| | |
|---|---|
| >MICA.008.a3.T204-S297.E215N.G243N.H248N.R279N.C-terminal insert of N298.G299.S300.mIgG2a.Glyco4 (Hypergylcosylated)<br><br>TVPPMVNVTRSNASEGNITVTCRASSFYPRNIILTWRQDNVSLSNDTQQWGDVLPDGNGT<br><br>YQTWVATRICRGEEQNFTCYMEHSGNHSTHPVPSNGS | SEQ ID NO: 200 |
| >MICA.008.a3.R202-S297.R202N mIgG2a.Glyco11<br><br>NRTVPPMVNVTRSEASEGNITVTCRASSFYPRNIILTWRQDGVSLSHDTQQWGDVLPDGN<br><br>GTYQTWVATRICRGEEQRFTCYMEHSGNHSTHPVPS | SEQ ID NO: 201 |
| >MICA.008.a3.T204-S297.E215N.mIgG2a.Glyco12<br><br>TVPPMVNVTRSNASEGNITVTCRASSFYPRNIILTWRQDGVSLSHDTQQWGDVLPDGNGT<br><br>YQTWVATRICRGEEQRFTCYMEHSGNHSTHPVPS | SEQ ID NO: 202 |
| >MICA.008.a3.T204-S297.I236T.mIgG2a.Glyco13<br><br>TVPPMVNVTRSEASEGNITVTCRASSFYPRNITLTWRQDGVSLSHDTQQWGDVLPDGNGT<br><br>YQTWVATRICRGEEQRFTCYMEHSGNHSTHPVPS | SEQ ID NO: 203 |
| >MICA.008.a3.T204-S297.G243N.mIgG2a.Glyco14<br><br>TVPPMVNVTRSEASEGNITVTCRASSFYPRNIILTWRQDNVSLSHDTQQWGDVLPDGNGT<br><br>YQTWVATRICRGEEQRFTCYMEHSGNHSTHPVPS | SEQ ID NO: 204 |
| >MICA.008.a3.T204-S297.H248N.mIgG2a.Glyco15<br><br>TVPPMVNVTRSEASEGNITVTCRASSFYPRNIILTWRQDGVSLSNDTQQWGDVLPDGNGT<br><br>YQTWVATRICRGEEQRFTCYMEHSGNHSTHPVPS | SEQ ID NO: 205 |
| >MICA.008.a3.T204-S297.R279N.mIgG2a.Glyco16<br><br>TVPPMVNVTRSEASEGNITVTCRASSFYPRNIILTWRQDGVSLSHDTQQWGDVLPDGNGT<br><br>YQTWVATRICRGEEQNFTCYMEHSGNHSTHPVPS | SEQ ID NO: 206 |
| >MICA.008.a3.T204-S297.C-terminal insert of N298.G299.S300.mIgG2a.Glyco17<br><br>TVPPMVNVTRSEASEGNITVTCRASSFYPRNIILTWRQDGVSLSHDTQQWGDVLPDGNGT<br><br>YQTWVATRICRGEEQRFTCYMEHSGNHSTHPVPSNGS | SEQ ID NO: 207 |
| >MILL1-MICA chimera.murine IgG2a Fc fusion<br><br>GSTVPPMVTVTSRNYPVGRVTLTCRASSPYPRNITLVWLQDGKPVQQKTFRSGDVLPDGN<br><br>GTYQTWVSIRVLPGQEPQFSCNLRHGNHSIMQTAVGNSRAQVTDKKIEPRGPTIKPCPPC<br><br>KCPAPNLLGGPSVFIFPPKIKDVLMISLSPIVTCVVVDVSEDDPDVQISWFVNNVEHTA<br><br>QTQTHREDYNSTLRVVSALPIQHQDWMSGKEFKCKVNNKDLPAPIERTISKPKGSVRAPQ<br><br>VYVLPPPEEEMTKKQVTLTCMVTDFMPEDIYVEWTNNGKTELNYKNTEPVLDSDGSYFMY<br><br>SKLRVEKKNWVERNSYSCSVVHEGLHNHHTTKSFSRTPGK | SEQ ID NO: 208 |

What is claimed is:

1. An antibody that specifically binds to human MICA*008, wherein the antibody comprises the following six hypervariable regions (HVRs):
   a HVR-H1 comprising the amino acid sequence of SEQ ID NO: 209;
   a HVR-H2 comprising the amino acid sequence of SEQ ID NO: 210;
   a HVR-H3 comprising the amino acid sequence of SEQ ID NO: 211;
   a HVR-L1 comprising the amino acid sequence of SEQ ID NO: 212;
   a HVR-L2 comprising the amino acid sequence of SEQ ID NO: 213; and
   a HVR-L3 comprising the amino acid sequence of SEQ ID NO: 214.

2. The antibody of claim 1, wherein the antibody comprises a VH sequence of SEQ ID NO: 369 and a VL sequence of SEQ ID NO: 370.

3. The antibody of claim 1, wherein the antibody is monoclonal.

4. The antibody of claim 1, wherein the antibody is humanized or chimeric.

5. The antibody of claim 1, wherein at least a portion of the framework sequence is a human consensus framework sequence.

6. The antibody of claim 1, wherein the antibody is a full-length antibody.

7. The antibody of claim 1, wherein the antibody is a fragment is selected from the group consisting of Fab, Fab', Fab'-SH, Fv, single chain variable fragment (scFv), and (Fab')$_2$ fragments.

8. The antibody of claim 1, wherein the antibody is an IgG class antibody.

9. The antibody of claim 8, wherein the IgG class antibody is an IgG1 subclass antibody.

10. An isolated nucleic acid encoding the antibody of claim 1.

11. A vector comprising the nucleic acid of claim 10.

12. A host cell comprising the vector of claim 11.

13. A method of producing an antibody, the method comprising culturing the host cell of claim 12 in a culture medium.

14. An immunoconjugate comprising the antibody of claim 1 and a cytotoxic agent.

15. A composition comprising the antibody of claim 1.

16. The composition of claim 15, wherein the composition further comprises a PD-1 axis binding antagonist or an additional therapeutic agent.

17. A kit comprising the antibody of claim 1 and a package insert comprising instructions for using the antibody for treating or delaying progression of a cancer in a subject.

18. A kit comprising the antibody of claim 1 and a package insert comprising instructions for using the antibody for treating or delaying progression of an immune related disease in a subject.

19. A kit comprising the antibody of claim 1 and a package insert comprising instructions for increasing, enhancing, or stimulating an immune response or function in a subject.

20. The antibody of claim 1, wherein the antibody is a bispecific antibody.

21. The antibody of claim 8, wherein the IgG class antibody is an IgG2 subclass antibody.

22. The antibody of claim 8, wherein the IgG class antibody is an IgG4 subclass antibody.

23. The antibody of claim 2, wherein the antibody is monoclonal.

24. The antibody of claim 2, wherein the antibody is humanized or chimeric.

25. The antibody of claim 2, wherein the antibody is a bispecific antibody.

26. The antibody of claim 2, wherein at least a portion of the framework sequence is a human consensus framework sequence.

27. The antibody of claim 2, wherein the antibody is a full-length antibody.

28. The antibody of claim 2, wherein the antibody is a fragment is selected from the group consisting of Fab, Fab', Fab'-SH, Fv, single chain variable fragment (scFv), and (Fab')$_2$ fragments.

29. The antibody of claim 2, wherein the antibody is an IgG class antibody.

30. The antibody of claim 29, wherein the IgG class antibody is an IgG1 subclass antibody.

31. The antibody of claim 29, wherein the IgG class antibody is an IgG2 subclass antibody.

32. The antibody of claim 29, wherein the IgG class antibody is an IgG4 subclass antibody.

* * * * *